Figure 1:
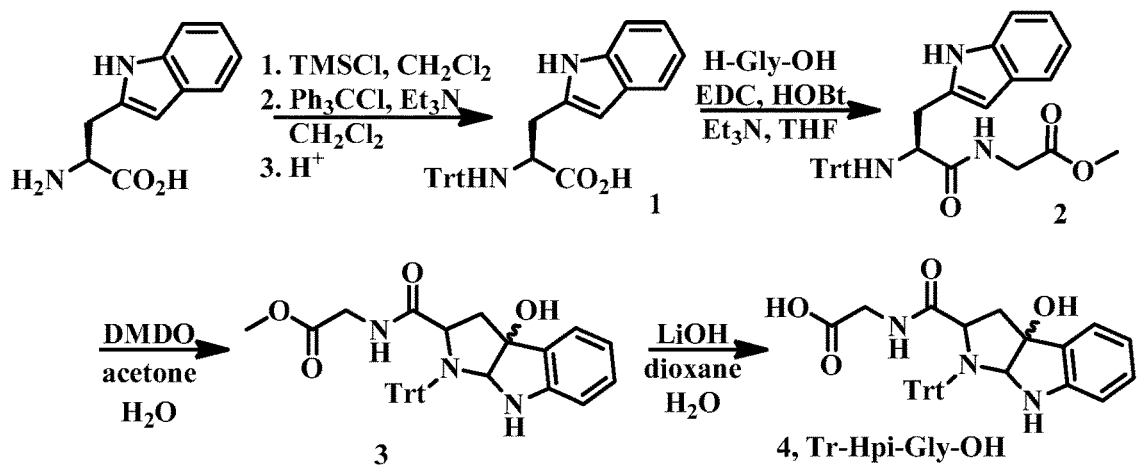
Figure 2:
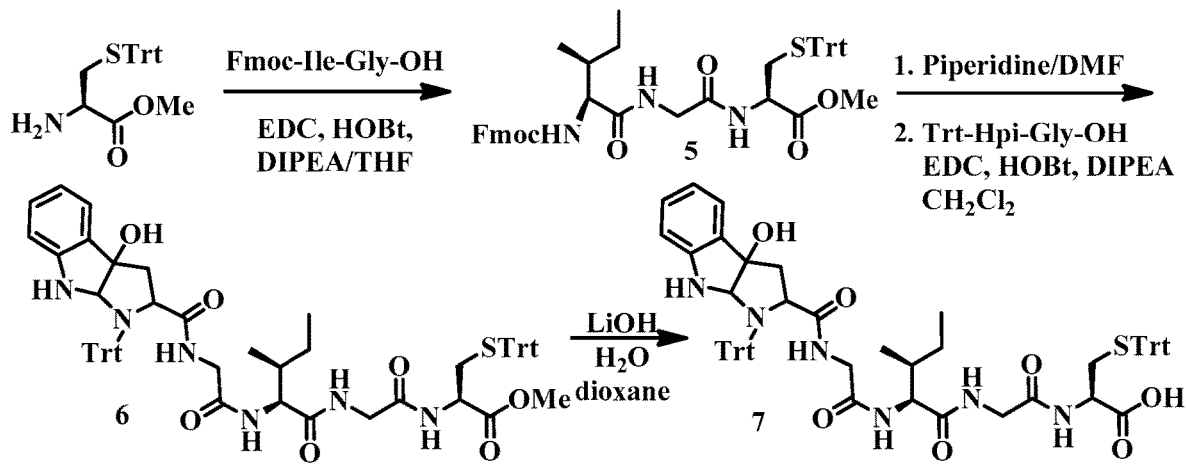
Figure 3:
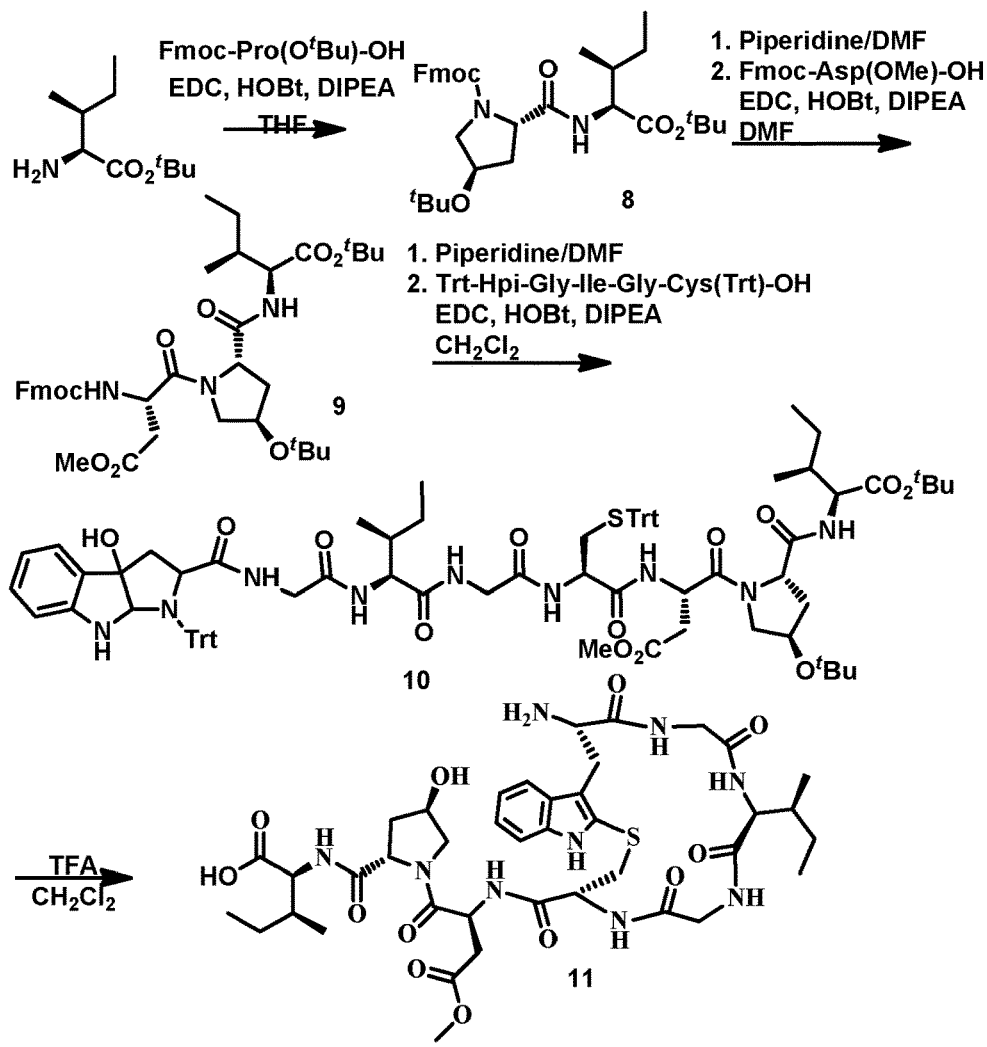
Figure 4:
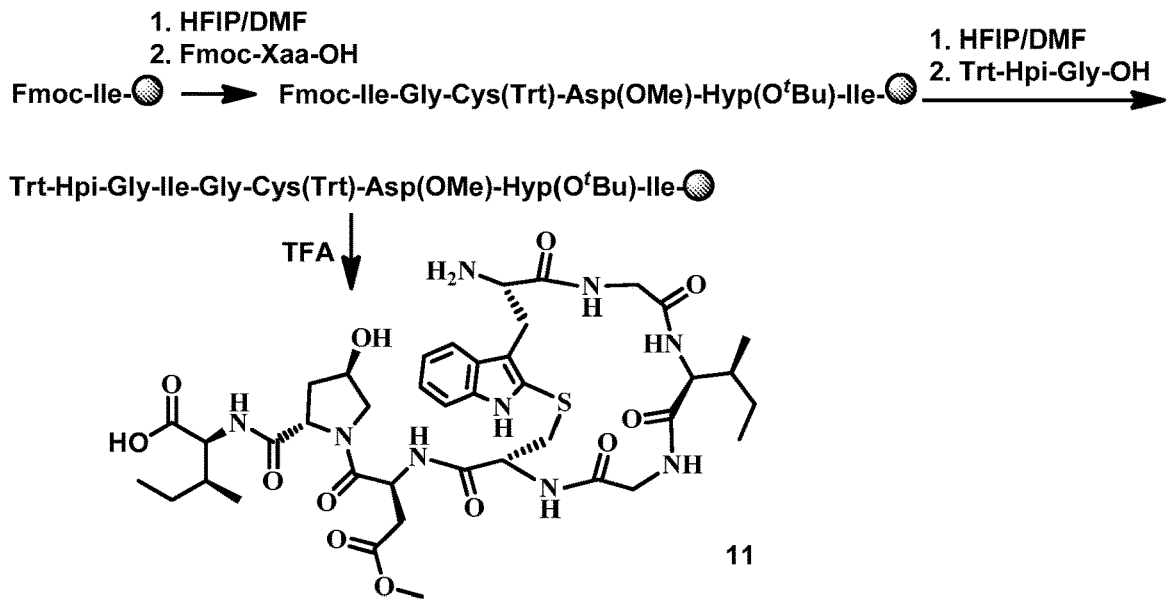
Figure 5:
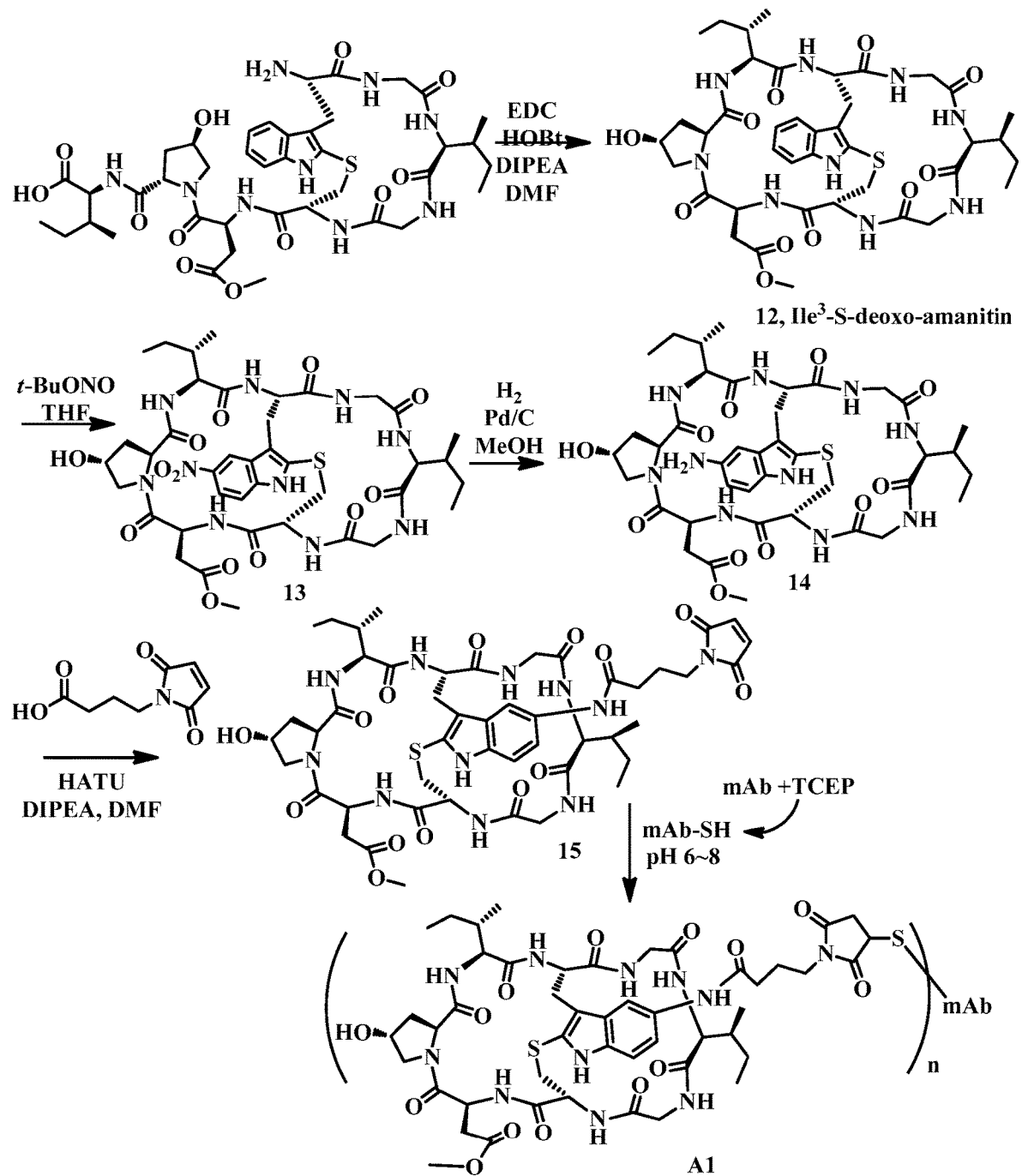

(12) United States Patent
Zhao et al.

(10) Patent No.: US 10,836,796 B2
(45) Date of Patent: Nov. 17, 2020

(54) **DERIVATIVES OF AMANITA TOXINS AND THEIR CONJUGATION TO A (III-1)

wherein the structure ![Y] is an IgG antibody.

(III-2)

wherein the structure ![Y] is an IgG antibody.

(III-3)

wherein the structure ⊻ is an IgG antibody.

(III-4)

wherein the structure ⊻ is an IgG antibody.

(III-5)

wherein the structure is an IgG antibody.

(III-6)

wherein the structure is an IgG antibody.

(III-7)

wherein the structure  is an IgG antibody.

(III-8)

wherein the structure  is an IgG antibody.

(III-9)

wherein the structure [Y] is an IgG antibody.

(III-10)

wherein the structure [Y] is an IgG antibody.

(III-11)

wherein the structure [Y] is an IgG antibody.

(III-12)

wherein the structure [Y] is an IgG antibody.

DERIVATIVES OF AMANITA TOXINS AND THEIR CONJUGATION TO A CELL BINDING MOLECULE

FIELD OF THE INVENTION

The present invention relates to novel cytotoxic agents, derivatives of *Amanita* toxins and their uses to specifically target cell population by chemically linking these derivatives to a cell binding agent.

BACKGROUND OF THE INVENTION

Antibody-drug conjugates (ADCs), which utilize the targeting ability of monoclonal antibodies (mAbs) to deliver highly toxic drugs to targeted tumor cells, have been proof that the products are technically feasible, therapeutically effective, and able to get regulatory approval after Seattle Genetics/Takeda's Brentuximab vedotin (Adcetris) and ImmunoGen/Roche's Trastuzumab emtansine (Kadcyla) are on the market (Sassoon, I. and Blanc, V. Laurent Ducry (ed.), Antibody-Drug Conjugates, Methods in Molecular Biology, vol. 1045, p 1-27). Currently there are more than 50 ADC drugs in the clinic trials according to www.clinictrails-.gov and many big pharmas and biotech firms, as well as plenty of small start-ups have a lot of incentives to invest in further development of this technology. Indeed, the complexity of antibody-drug conjugates with its four moving repertoires of cytotoxic agents, linker technologies, antibody properties, and conjugation methods makes this field incredibly challenging yet full of potential for innovation (Perez, H. L., et al. Drug Discovery Today, 2014, 19(7), 869-81). The development from novel targeting ligands to new site specific conjugation methods, from multiple payloads to changing the drug-antibody ratio, from functional linkers to homogeneous stoichiometry, are challenging the convention for the design and development of next-generation ADCs (Zhao, R. et al, PCT/182015/055051, PCT/IB2015/055264, introduction part). However, the important key factor in generating powerful ADCs is the cytotoxic agents (Bourchard, H., et al, Bioorg. Med. Chem. Lett. 2014, 24, 5357-63). One class of the highly potent cytotoxic agents that can be used for ADC is the Amanitins (Moldenhauer, G. et al, J Natl Cancer Inst 2012, 104 (8): 622-34; Flygare, J. A. et al, Chem. Biol. Drug. Des. 2013, 81, 113-121; WO2010/115629, WO2010/115630, WO2012041504, WO2012119787, WO2014/009025, WO2014135282, US pat appl 20120213805, 20120100161, 20130259880, 20140294865, 20150218220, EP2416805, EP1661584, EP1859811, EP2497499, EP2774624), which are highly toxic components of *Amanita* toxins (Vetter, J., Toxicon 1998, 36 (I): 13-24).

*Amanita* toxins are mainly cyclic octa- and heptapeptide toxins of *Amanita* mushrooms, which contain an unusual Trp-Cys crossbridge known as tryptathionine (Walton, J. D. et al. Biopolymers 2010; 94(5): 659-64). The major components of *amanita* toxins are amatoxins, phallotoxins, and virotoxins (Wieland, T., Faulstich, H., CRC Crit. Rev. Biochem. 1978, 5(3):185-260; Vetter, J., Toxicon 1998, 36 (1): 13-24; Weiland, T., and Faulstich, H. 1983. Peptide Toxins from *Amanita*. p. 585-635. In: Handbook of Natural Toxins, Volume I: Plant and Fungal Toxins. R. F. Keeler and A. T. Tu, Ed. Marcel Dekker, Inc. New York, N.Y., Wieland, T., Int J. Pept. Protein Res., 1983, 22, 257-76) and their collectively known structures are listed in Tables 1, 2 and 3 respectively below.

TABLE 1

Ten currently known structures of amatoxins

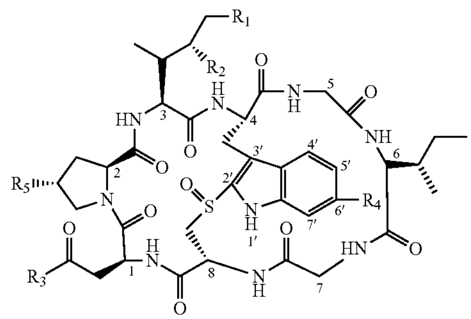

| Name | $R_1$ | $R_2$ | $R_3$ | $R_4$ | $R_5$ |
|---|---|---|---|---|---|
| α-Amanitin | OH | OH | $NH_2$ | OH | OH |
| β-Amanitin | OH | OH | OH | OH | OH |
| γ-Amanitin | H | OH | $NH_2$ | OH | OH |
| ε-Amanitin | H | OH | OH | OH | OH |
| Amanullin | H | H | $NH_2$ | OH | OH |
| Amanullinic acid | H | H | OH | OH | OH |
| Amaninamide | OH | OH | $NH_2$ | H | OH |
| Amanin | OH | OH | OH | H | OH |
| Proamanullin H | H | H | $NH_2$ | OH | H |

(The δ-Amanitin has been reported, but its chemical structure has not been determined)

TABLE 2

Structures of the Phallotoxins

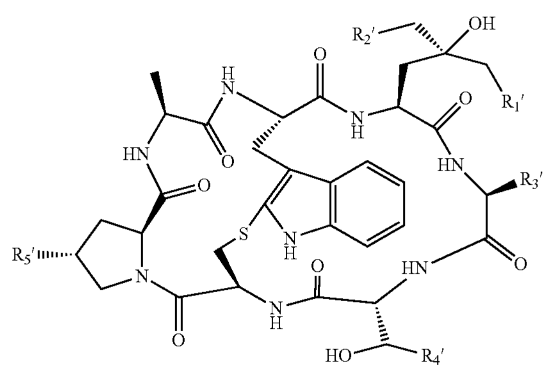

| Name | $R_1'$ | $R_2'$ | $R_3'$ | $R_4'$ | $R_5'$ |
|---|---|---|---|---|---|
| phalloidin | OH | H | $CH_3$ | $CH_3$ | OH |
| phalloin | H | H | $CH_3$ | $CH_3$ | OH |
| prophallin | H | H | $CH_3$ | $CH_3$ | H |
| phallisin | OH | OH | $CH_3$ | $CH_3$ | OH |
| phallacin | H | H | $CH(CH_3)_2$ | COOH | OH |
| phallacidin | OH | H | $CH(CH_3)_2$ | COOH | OH |
| phallisacin | OH | OH | $CH(CH_3)_2$ | COOH | OH |

TABLE 3

Structures of the Virotoxins

| Name | $R_1''$ | $R_2''$ | X |
|---|---|---|---|
| Viroidin | $CH_3$ | $CH(CH_3)_2$ | $S(O_2)$ |
| Desoxiviroidin | $CH_3$ | $CH(CH_3)_2$ | $S(O)$ |
| (Ala)viroidin | $CH_3$ | $CH_3$ | $S(O_2)$ |
| (Ala)desoxiviroidin | $CH_3$ | $CH_3$ | $S(O)$ |
| (Ala)viroisin | $CH_2OH$ | $CH(CH_3)_2$ | $S(O_2)$ |
| Desoxiviroisin | $CH_2OH$ | $CH(CH_3)_2$ | $S(O)$ |

Amatoxins which are a subgroup of at least ten toxic compounds originally found in several genera of poisonous mushrooms, most notably *Amanita phalloides* and several other mushroom species, are bicyclic octapeptides containing intra-annular tryptathionine crossbridge that is oxidatively formed from tryptophan and cysteine (Kaya, E., et al, Toxicon 2013, 76, 225-33).

Amatoxins are potent and selective inhibitors of RNA polymerase II (Pol II), a vital enzyme in the synthesis of messenger RNA (mRNA), microRNA, and small nuclear RNA (snRNA) (Karlson-Stiber C, Persson H. 2003 "Cytotoxic fungi—an overview", Toxicon 42 (4): 339-49). Thus Amatoxins kill cells by shutting down gene transcription and protein biosynthesis (Brodner, 0. G. and Wieland, T. 1976 Biochem., 15(16): 3480-4; Fiume, L., Curr Probl Clin Biochem, 1977, 7: 23-8; Karlson-Stiber C, Persson H. 2003, Toxicon 42(4): 339-49; Chafin, D. R., Guo, H. & Price, D. H. 1995 J. Biol. Chem. 270 (32): 19114-19; Wieland (1983) Int. J. Pept. Protein Res. 22(3): 257-76). So far ten known amatoxins, named α-Amanitin, β-Amanitin, γ-Amanitin, ε-Amanitin, Amanullin, Amanullinic acid, Amaninamide, Amanin, and Proamanullin are synthesized as 35-amino-acid proproteins, from which the final eight amino acids are cleaved by a prolyl oligopeptidase (Litten, W. 1975 Scientific American 232 (3): 90-101; H. E. Hallen, et al 2007 Proc. Nat. Aca. Sci. USA 104, 19097-101; K. Baumann, et al, 1993 Biochemistry 32 (15): 4043-50; Karlson-Stiber C, Persson H. 2003, Toxicon 42 (4): 339-49; Horgen, P. A. et al. 1978 Arch. Microbio. 118 (3): 317-9). Amatoxins can be produced from collected *Amanita phalloides* mushrooms (Yocum, R. R. 1978 Biochemistry 17(18): 3786-9; Zhang, P. et al, 2005, FEMS Microbiol. Lett. 252(2), 223-8), or from fermentation using a basidiomycete (Muraoka, S. and Shinozawa T., 2000 J. Biosci. Bioeng. 89(1): 73-6, US pat. Appl 20100267019) or from fermentation using A. fissa (Guo, X. W., et al, 2006 Wei Sheng Wu Xue Bao 46(3): 373-8), or from culturing *Galerina fasciculata* or *Galerina helvoliceps* (WO/1990/009799, JP11137291). However the yields from these isolation and fermentation were quite low (less than 5 mg/L culture). Several semi-chemical or synthetic preparations of amatoxins and their analogs have been reported in the past three decades (W. E. Savige, A. Fontana, Chem. Commun. 1976, 600-1; Zanotti, G., et al, Int J Pept Protein Res, 1981. 18(2): 162-8; Wieland, T., et al, Eur. J. Biochem. 1981, 117, 161-4; P. A. Bartlett, et al, Tetrahedron Lett. 1982, 23, 619-22; Zanotti, G., et al., Biochim Biophys Acta, 1986. 870 (3): 454-62; Zanotti, G., et al., Int. J. Peptide Protein Res. 1987, 30, 323-9; Zanotti, G., et al., Int. J. Peptide Protein Res. 1987, 30, 450-9; Zanotti, G., et al., Int J Pept Protein Res, 1988. 32(1): 9-20; G. Zanotti, T. et al, Int. J. Peptide Protein Res. 1989, 34, 222-8; Zanotti, G., et al., Int J Pept Protein Res, 1990. 35(3): 263-70; Mullersman, J. E. and J. F. Preston, 3rd, Int J Pept Protein Res, 1991. 37(6): 544-51; Mullersman, J. E., et al, Int J Pept Protein Res, 1991. 38(5): 409-16; Zanotti, G., et al, Int J Pept Protein Res, 1992. 40(6): 551-8; Schmitt, W. et al, J. Am, Chem. Soc. 1996, 118, 4380-7; Anderson, M. O., et al, J. Org. Chem., 2005, 70(12): 4578-84; J. P. May, et al, J. Org. Chem. 2005, 70, 8424-30; F. Brueckner, P. Cramer, Nat. Struct. Mol. Biol. 2008, 15, 811-8; J. P. May, D. M. Perrin, Chem. Eur. J. 2008, 14, 3404-9; J. P. May, et al, Chem. Eur. J. 2008, 14, 3410-17; Q. Wang, et al, Eur. J. Org. Chem. 2002, 834-9; May, J. P. and D. M. Perrin, Biopolymers, 2007. 88(5): 714-24; May, J. P., et al., Chemistry, 2008. 14(11): 3410-7; S. De Lamo Marin, et al, Eur. J. Org. Chem. 2010, 3985-9; Pousse, G., et al., Org Lett, 2010. 12(16): 3582-5; Luo, H., et al., Chem Biol, 2014. 21(12): 1610-7; Zhao, L., et al., Chembiochem, 2015. 16(10): 1420-5). Because of their extreme potency and unique mechanism of cytotoxicity, amatoxins have been used as payloads for conjugations (Fiume, L., Lancet, 1969. 2 (7625): 853-4; Barbanti-Brodano, G. and L. Fiume, Nat New Biol, 1973. 243(130): 281-3; Bonetti, E., M. et al, Arch Toxicol, 1976. 35(1): p. 69-73; Davis, M. T., Preston, J. F. Science 1981, 213, 1385-1388; Preston, J. F., et al, Arch Biochem Biophys, 1981. 209(1): 63-71; H. Faulstich, et al, Biochemistry 1981, 20, 6498-504; Barak, L. S., et al., Proc Natl Acad Sci USA, 1981. 78(5): 3034-8; Faulstich, H. and L. Fiume, Methods Enzymol, 1985. 112: 225-37; Zhelev, Z., A. et al, Toxicon, 1987. 25(9): 981-7; Khalacheva, K., et al, Eksp Med Morfol, 1990. 29(3): 26-30; U. Bermbach, H. Faulstich, Biochemistry 1990, 29, 6839-45; Mullersman, J. E. and J. F. Preston, Int. J. Peptide Protein Res. 1991, 37, 544-51; Mullersman, J. E. and J. F. Preston, Biochem Cell Biol, 1991. 69(7): 418-27; J. Anderl, H. Echner, H. Faulstich, Beilstein J. Org. Chem. 2012, 8, 2072-84; Moldenhauer, G., et al, J. Natl. Cancer Inst. 2012, 104, 622-34; A. Moshnikova, et al; Biochemistry 2013, 52, 1171-8; Zhao, L., et al., Chembiochem, 2015. 16(10): 1420-5; Zhou, B., et al., Biosens Bioelectron, 2015. 68: 189-96; WO2014/043403, US20150218220, EP 1661584).

The phallotoxins which are bicyclic heptapeptides, consist of at least seven compounds as shown in Table 2, were originally discovered from the death cap mushroom (*Amanita phalloides*) in 1937 by Feodor Lynen, Heinrich Wieland's student and son-in-law, and Ulrich Wieland of the University of Munich (Enjalbert, F., et al, Toxicon 1993, 31, 803-7). The phallotoxins, after i.p. administration, inhibit the conversion of actin-F into actin-G and disturb the dynamic equilibrium of these forms necessary for cell functions (Enjalbert, F., et al., C. R. Acad. Sci. Paris, Sciences de la vie/Life Sciences, 1999, 322, 855-62; Wieland, T., 50 Jahre Phalloidin, Naturwissenchaften 1987, 74, 367-73). There are six known structures of phallotoxins namely prophalloin, phalloin, phallisin, phallacidin, phallacin and phallisacin as shown in Table 2 (Yocum R. R., Simons M., Lloydia 1977, 40, 178-90; Enjalbert, F., et al., C. R. Acad. Sci. Paris, Sciences de la vie/Life Sciences, 1999, 322, 855-62; Schafer A. J., Faulstich H., Anal. Biochem. 1977, 83, 720-723). Though highly toxic to liver cells, phallotoxins have since been found to have little contribution to the death cap's toxicity because they are not absorbed through the gut. On average, the six structure known phallotoxins are about 5-10 times less toxic than (α-, β-, γ-, or ε-) amanitins (Vetter, J., Toxicon, 1998, 36, 13-24). Furthermore, phalloidin is also found in the edible Blusher (*Amanita rubescens*) (Litten, W., Scientific American 1975, 232, 90-101).

Virotoxins are monocyclic heptapeptides formed by at least five different compounds: alaviroidin, viroisin, deoxoviroisin, viroidin, and deoxoviroidin (Vetter, J., Toxicon, 1998, 36, 13-24) as shown in Table 3. The structure and biological activity of virotoxins are similar to those of phallotoxins, thus suggesting that virotoxins are biosynthetically derived from phallotoxins or share common precursor pathways (Wieland, T., Int J Pept Protein Res, 1983, 22, 257-76). However, differing from phallotoxins, virotoxins are monocyclic peptides and contain D-serine instead of L-cysteine, as well as have two unnatural amino acids: 2,3-trans-3,4-dihydroxy-L-proline and 2'-(methylsulfonyl)-L-tryptophan (Buku, A. et al, Proc Natl Acad Sci USA. 1980, 77(5), 2370-1). NMR studies revealed that D-configuration of serine is the structural element that maintains the phalloidin-like structure, while the hydroxy group does not contribute to conformational stability but is likely to be in contact with the actin surface (Zanotti, G., et al, Biochemistry. 1999, 38(33):10723-9). On the molecular level, the virotoxins behave similarly to the phallotoxins, e.g. the affinity of viroisin is very similar to that of phalloidin, with an apparent equilibrium dissociation constant $K_d$ approximately $2 \times 10^{-8} M$ (Faulstich, H., et al, Biochemistry, 1980, 19, 3334-43). However, the flexibility of the monocyclic structure and the presence of two additional hydroxy groups in the virotoxins suggest a different mode of interaction with actin. While there is proof that the bicyclic phallotoxins possess a rigid binding site, the virotoxins may adopt the biologically active conformation by an induced-fit mechanism upon contacting with actin (Faulstich, H., et al, Biochemistry, 1980, 19, 3334-43).

There are several methods disclosed so far in conjugation of amatoxins. Preston and his collegues used diazotization of p-aminobenzoylglycylglycine and then coupling the linker to a-amanitin at the 7'C position of Trptophan (Preston, J. F. et al, Arch. Biochem. Biophy. 1981, 209, 63-71; Davis, M-T. B. and Preston, J. F., Science, 1981, 213, 1385-7; Hencin, R. S. and Preston, J. F., Mol. Pharm., 1979, 16, 961-9). Heidelberg Pharma GMBH (WO2010/115629, WO2010115630, WO2012/041504, US20120100161, US20120213805) disclosed the conjugation of amatoxin via the oxygen atom as an ether linkage to the 6'C-atom of amino acid 4, or via the oxygen atom as an ester or a carbomate linkage to the SC-atom of amino acid 3, or via the nitrogen atom as an amide linkage to the γC-atom of amino acid 1. Heidelberg Pharma GMBH (EP2774624, WO2012119787, WO2014/135282, US20140294865, US20160002298) also disclosed the conjugation via position of 1'N-atom of indole of amatoxin. Agensys Inc (US20150218220) disclosed that through activation of the C7'-position of the indole group of a-amanitin with a reagent such as iodine, followed by coupling with a suitably substituted 2°-amino reagent to introduce a diamine spacer linkage, or introduce a carbon spacer (C—C bond of the C7-position of the indole) in front of a 2°-amino linkage in the presence of formaldehyde.

It is known that amatoxins are relatively non-toxic when coupled to large biomolecule carriers, such as antibody molecules, and that they exert their cytotoxic activity only after the biomolecule carrier is cleaved off. In light of the toxicity of amatoxins, particularly their notorious toxicity for liver cells (Zhou, P. et al, World J. Gastroenterology, 2012, 18(5), 435-4; Giannini, A., et al, Clin. Toxicology, 2007. 45(5), 539-42), it is of outmost importance that amatoxin conjugates for targeted tumour therapy remain highly stable after administration in plasma, and that the released the amatoxin would not run away from the target cells or damage liver cells when occurs after internalization in the target cells.

Here we disclose novel *amanita* toxin derivatives that first can be conjugated cell-binding molecule through stable amide bonds after simple nitrition, following by reduction and conjugation at the indole unit of the *amanita* toxin derivatives. Second, many of the *amanita* toxin derivatives of this invention have prodrug units on the indole units which can bring down the highly potency in vitro, but can be slowly transformed back the highly potent cytotoxicity in vivo after their extra prodrug units are removed by enzymes. Since amatoxins are notorious for their extremely toxic to hepatitis with centrolobular necrosis and hepatic steatosis, as well as acute tubulointerstitial nephropathy, which altogether induce a severe hepatorenal syndrome (Litten, W. 1975 Scientific American 232: 90-10; Karlson-Stiber C, Persson H. 2003 Toxicon 42 (4): 339-49). The slow conversion of the safer prodrugs to their mother toxins would minimize the severe side toxicity when the toxins are off-targets during the delivery. Thus these improvements of the conjugatable *amanita* toxin derivatives may have drastic consequences of wider therapeutic index windows and much more safety of the amatoxin conjugates for targeted therapeutic applications.

SUMMARY OF THE INVENTION

The first embodiment of this invention is to disclose potent cytotoxic agents, specifically, derivatives of amatoxins, phallotoxins or virotoxins which can be effectively used to block cell proliferation. In particular, this invention is to disclose novel *amanita* toxin derivatives, optionally linkable or linked to a cell binding agent to block cell proliferation. The novel cytotoxic agents and their conjugates to a cell binding agent of this invention are illustrated in the following formula (I):

(I)

or their pharmaceutically acceptable salts, hydrates, or hydrated salts; or the polymorphic crystalline structures of these compounds; or their optical isomers, racemates, diastereomers or enantiomers.

Wherein

---- represents a single bond that links any carbon position of the aromatic (indole) ring;

∿∿ represents an optional single bond or an absent bond.

$R_1$ and $R_2$ are independently selected from H, OH, $CH_2OH$, $CH(OH)CH_2OH$, $CH(CH_3)CH_2OH$, $CH(OH)CH_3$, $C_1$-$C_8$ alkyl, —$OR_{12}$ (ether), $C_2$-$C_8$ alkenyl, alkynyl, heteroalkyl, —$OCOR_{12}$ (ester), —$OC(=O)OR_{12}$-(carbonate), —$OC(=O)NHR_{12}$ (carbamate); $C_3$-$C_8$ aryl, heterocyclic, carbocyclic, cycloalkyl, heterocycloalkyl, heteroaralkyl, alkylcarbonyl.

$R_3$ and $R_4$ are independently selected from H, OH, —$OR_{12}$ (ether), —$OCOR_{12}$ (ester), —$OCOCH_3$ (acetate), —$OCOOR_{12}$ (carbonate), —$OC(=O)NHR_{12}$ (carbamate), —$OP(O)(OR_{12})(OR_{12}')$ (phosphate), $OP(O)(NHR_{12})(NHR_{12}')$ (phosphamide), O—$SO_3^-$, or O-glycoside;

$R_5$ is selected from H, OH, $NH_2$, NHOH, $NHNH_2$, —$OR_{12}$, —$NHR_{12}$, $NHNHR_{12}$, —$NR_{12}R_{12}'$, $N(H)(R_{12})R_{13}CO(Aa)_p$, (an amino acid or peptide, wherein Aa is an amino acid or a polypeptide, p represents 0-6);

$R_6$ is selected from H, OH, $CH_2OH$, $CH(OH)CH_2OH$, $CH(CH_2OH)_2$, $CH(CH_3)OH$, $CH_2CH_2OH$, PrOH, BuOH, $C_1$-$C_8$ alkyl, —$OR_{12}$ (ether), $C_2$-$C_8$ alkenyl, alkynyl, heteroalkyl, —$OCOR_{12}$ (ester); $C_3$-$C_8$ aryl, heterocyclic, or carbocyclic.

$R_7$, $R_8$ and $R_9$ are independently selected from H, OH, $CH_3$, $CH(CH_3)_2$, $CH(CH_3)CH_2CH_3$, $CH_2OH$, $CH(OH)CH_2OH$, $CH_2CH(OH)CH_2OH$, $CH(CH_2OH)_2$, $CH_2C(OH)(CH_2OH)_2$, $CH_2C(OH)(CH_3)(CH_2OH)$, $CH_2C(OH)(CH(CH_3)_2)(CH_2OH)$, $CH_2CH_2OH$, PrOH, BuOH, $CH_2COOH$, $CH_2CH_2COOH$, $CH(OH)COOH$, $CH_2CONH_2$, $CH_2CH_2CONH_2$, $CH_2CH_2CH_2CH_2NH_2$, $CH_2CH_2CH_2NHC(=NH)NH_2$, $C_1$-$C_8$ alkyl, $CH_2Ar$, $CH_2SH$, $CH_2SR_{12}$, $CH_2SSR_{12}$, $CH_2SSAr$, $CH_2CH_2SCH_3$, —$OR_{12}$ (ether), $C_2$-$C_8$ alkenyl, alkynyl, heteroalkyl, —$OCOR_{12}$ (ester); $C_3$-$C_8$ aryl, heterocyclic, or carbocyclic.

$R_{10}$ is selected from H, $NH_2$, OH, SH, $NO_2$, halogen, —NHOH, —$N_3$ (azido); —CN (cyano); $C_1$-$C_8$ alkyl, $C_2$-$C_8$ alkenyl, alkynyl, heteroalkyl; $C_3$-$C_8$ aryl, heterocyclic, or carbocyclic; —$OR_{12}$ (ether), —$OCOR_{12}$ (ester), —$OCOCH_3$ (acetate), —$OC(O)OR_{12}$ (carbonate), —$OC(O)CH(R_{12})NHAa$ (Aa is an amino acid group), —$NR_{12}R_{12}'$ (amine), —$NR_{12}COR_{12}'$(amine), —$NR_{12}NR_{12}'NR_{12}''$ (amine), —$OCONR_{12}R_{12}'$(carbamate); —$NR_{12}(C=NH)NR_{12}'R_{12}''$ (guanidinum); —$NR_{12}CO(Aa)_p$, (an amino acid or peptide, wherein Aa is an amino acid or a polypeptide, p represents 0-6); —$N(R_{12})CONR_{12}'R_{12}''$ (urea); —OCSNHR_{12}$ (thiocarbamate); —SH (thiol); —$SR_{12}$ (sulfide); —$S(O)R_{12}$ (sulfoxide); —$S(O_2)R_{12}$ (sulfone); —$SO_3$, $HSO_3$, $HSO_2$, or a salt of $HSO_3^-$, $SO_3^{2-}$ or —$HSO_2^-$ (sulphite); —$OSO_3^-$; —$N(R_{12})SOOR_{12}'$ (sulfonamide); $H_2S_2O_5$ or a salt of $S_2O_5^{2-}$ (metabisulfite); $PO_3SH_3$, $PO_2S_2H_2$, $POS_3H_2$, $PS_4H_2$ or a salt of $PO_3S^{3-}$, $PO_2S_2^{3-}$, $POS_3^{3-}$, $PS_4^{3-}$ (mono-, di-, tri-, and tetra-thiophosphate); $(R_{12}O)_2POSR_{12}'$ (thiophosphate ester); $HS_2O_3$ or a salt of $S_2O_3^{2-}$ (thiosulfate); $HS_2O_4$ or a salt of $S_2O_4^{2-}$ (dithionite); $(P(=S)(OR_{12})(S)(OH)$ or a salt formed with a cation (phosphorodithioate); —$N(R_{12})OR_{12}'$ (hydroxylamine derivative); $R_{12}C(=O)NOH$ or a salt formed with a cation (hydroxamic acid); $(HOCH_2SO_2^-$, or its salts (formaldehyde sulfoxylate); —$N(R_{12})COR_{12}'$ (amide); $R_{12}R_{12}'R_{12}''NPO_3H$ (trialkylphosphoramidate or phosphoramidic acid); or $ArAr'Ar''NPO_3H$ (triarylphosphonium); $OP(O)(OM_1)(OM_2)$, $OCH_2OP(O)(OM_1)(OM_2)$, $OSO_3M_1$; O-glycoside (glucoside, galactoside, mannoside, glucuronoside, alloside, fructoside, etc), NH-glycoside, S-glycoside or $CH_2$-glycoside; $M_1$ and $M_2$ are independently H, Na, K, Ca, Mg, $NH_4$, $NR_1'R_2'R_3'$; $R_1'$, $R_2'$ and $R_3'$ are independently H, $C_1$-$C_8$ alkyl; Ar, Ar', and Ar'' are $C_3$-$C_8$ aryl or heteroaromatic group.

$R_{11}$ is H, $C_1$-$C_8$ alkyl; $C_2$-$C_8$ alkenyl, alkynyl, heteroalkyl; $C_3$-$C_8$ aryl, heteroaoaryl.

$R_{12}$, $R_{12}'$, and $R_{12}''$ are independently selected from H, $C_1$-$C_8$ alkyl; $C_2$-$C_8$ alkenyl, alkynyl, heteroalkyl; $C_3$-$C_8$ aryl, heteroaoaryl, heterocyclic, or carbocyclic.

X is S, O, NH, SO, $SO_2$, or $CH_2$.

m is 0 or 1; n is 1, 2, 3, 4, 5, 6, 7, 8, 9, 10, 11, 12, 13, 14, 15, 16, 17, 18, 19, or 20.

L is a linker or a linker-cell-binding molecule (Q) covalently bound cluster, or a linker which has a functional group on the linker that enables linkage with a cell-binding agent (CBA). L is preferably a releasable linker, which has the formula of: -Ww-(Aa)r-Tt-; or -Ww-(Aa)r-Tt-Q; or Q-Ww-(Aa)r-Tt-; wherein W is a Stretcher unit; w is 0 or 1; Aa is an Amino Acid unit comprising independent amino acids; r is an integer ranging from 0 to 100. The Stretcher unit W may contain a self-immolative or a non-self-immolative component, peptidyl units, a hydrazone bond, a disulfide, an ester, an oxime, an amide, or a thioether bond. The self-immolative unit includes, but is not limited to, aromatic compounds that are electronically similar to the para-aminobenzylcarbamoyl (PAB) groups such as 2-aminoimidazol-5-methanol derivatives, heterocyclic PAB analogs, beta-glucuronide, and ortho or para-aminobenzylacetals. Preferably, the self-immolative linker component has one of the following structures:

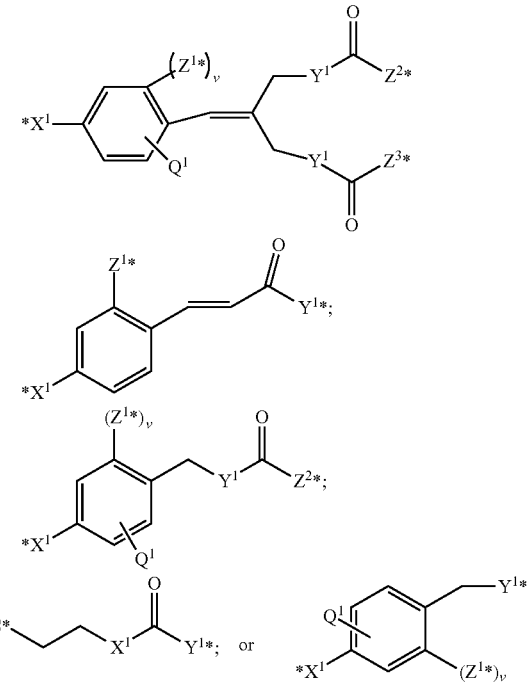

wherein the (*) atom is the point of attachment of additional spacer or releasable linker units, or the cytotoxic agent, and/or the binding molecule (CBA); $X^1$, $Y^1$, $Z^2$ and $Z^3$ are independently NH, O, or S; $Z^1$ is independently H, NH, O or S; v is 0 or 1; $Q^1$ is independently H, OH, $C_1$-$C_6$ alkyl, $(OCH_2CH_2)_n$, F, Cl, Br, I, $OR_{12}$, $SR_{12}$, $NR_{12}R_{12}'$, $N=NR_{12}$, $N=R_{12}$, $NR_{12}R_{12}'$, $NO_2$, $SOR_{12}R_{12}'$, $SO_2R_{12}$, $SO_3R_{12}$, $OSO_3R_{12}$, $PR_{12}R_{12}'$, $POR_{12}R_{12}'$, $PO_2R_{12}R_{12}'$, $OPO(OR_{12})(OR_{12}')$, or $OCH_2PO(OR_{12}(OR_{12}')$ wherein $R_{12}$ and $R_{12}'$ are as defined above; preferably $R_{12}$ and $R_{12}'$ are independently selected from H, $C_1$~$C_8$ alkyl; $C_2$~$C_8$ alkenyl, alkynyl, heteroalkyl; $C_3$~$C_8$ aryl, heterocyclic, carbocyclic, cycloalkyl, heterocycloalkyl, heteroaralkyl, alkylcarbonyl; or pharmaceutical cation salts.

The non-self-immolative linker component is one of the following structures:

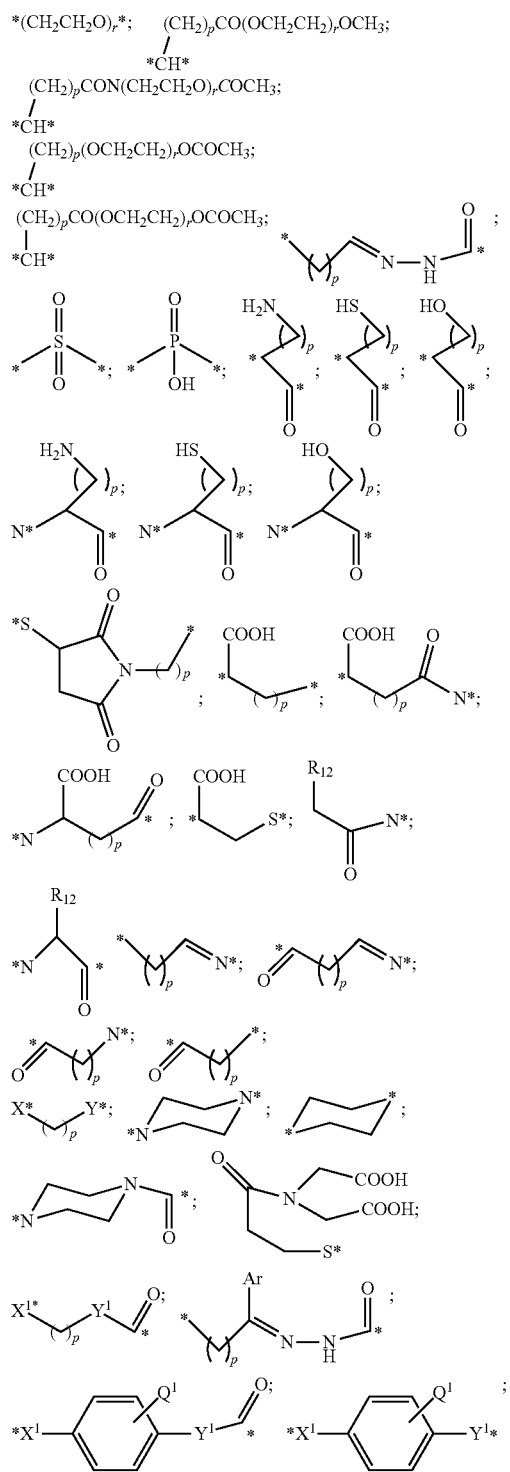
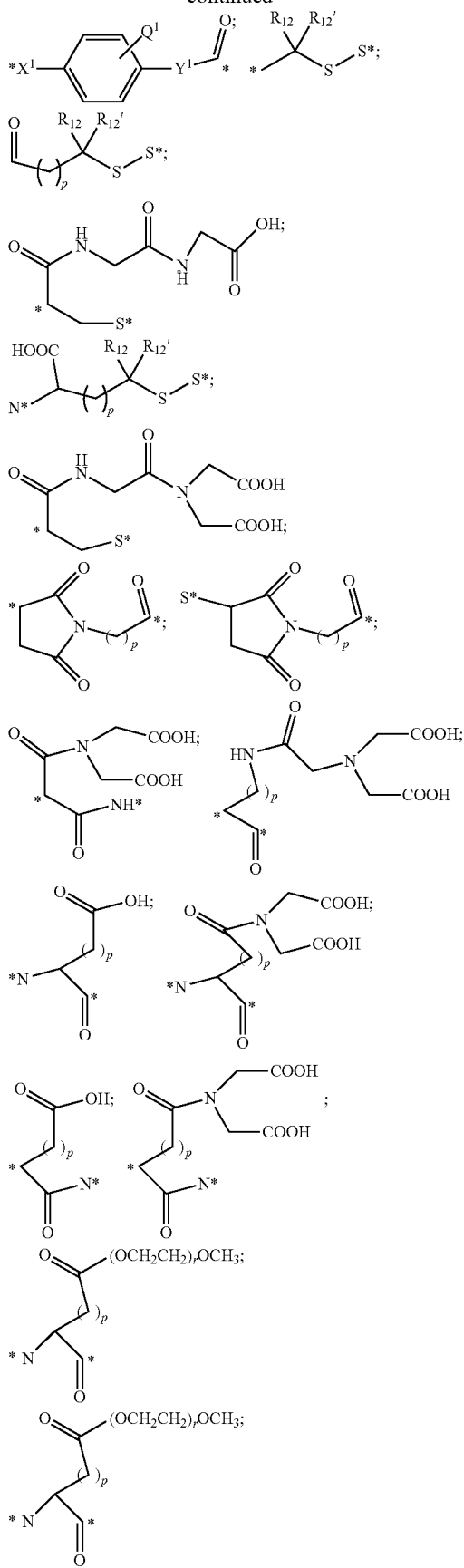

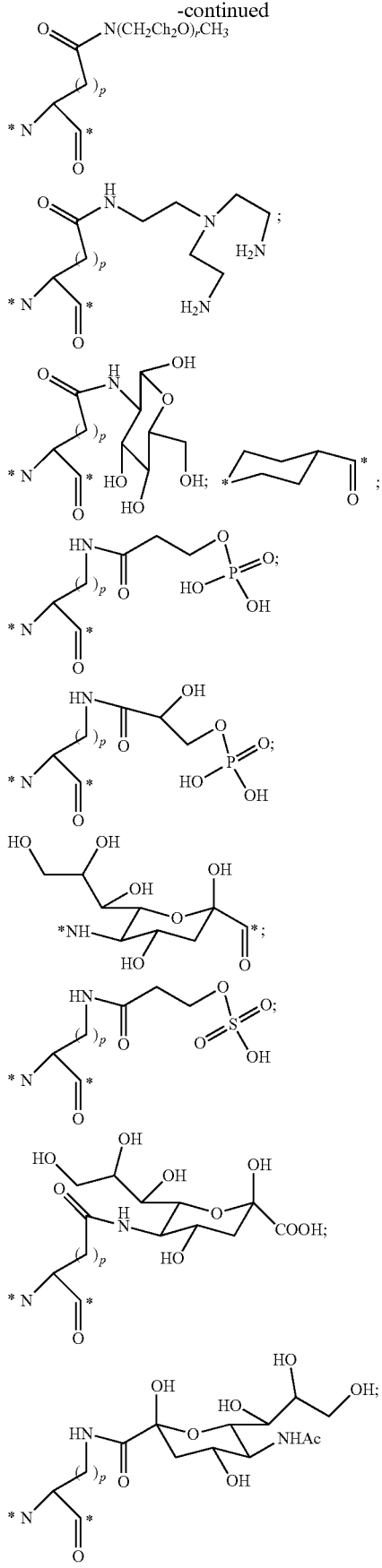
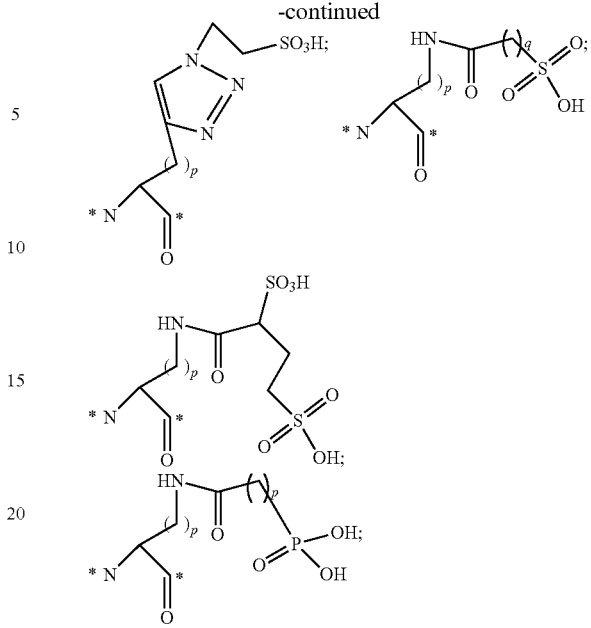

Wherein the (*) atom is the point of attachment of additional spacer or releasable linkers, the cytotoxic agents, and/or the binding molecules; $X^1$, $Y^1$, $Q^1$, $R_{12}$, $R_{12}'$ are defined as above; r is 0~100; p and q are 0~6 independently.

Spacer (T) is a linear, branched or cyclic alkyl, alkenyl, alkynyl or aryl having from 1 to 10 carbon atoms, or T can be a polyethylene glycol (—$CH_2CH_2O$—) spacer; t is 0, or 1~100. T can also undergo cyclization upon amide bond hydrolysis, such amides include substituted and unsubstituted 4-aminobutyric acid amides, appropriately substituted bicycle [2.2.1] and bicyclo[2.2.2] ring systems, and 2-aminophenylpropionic acid amides.

Figure 6:
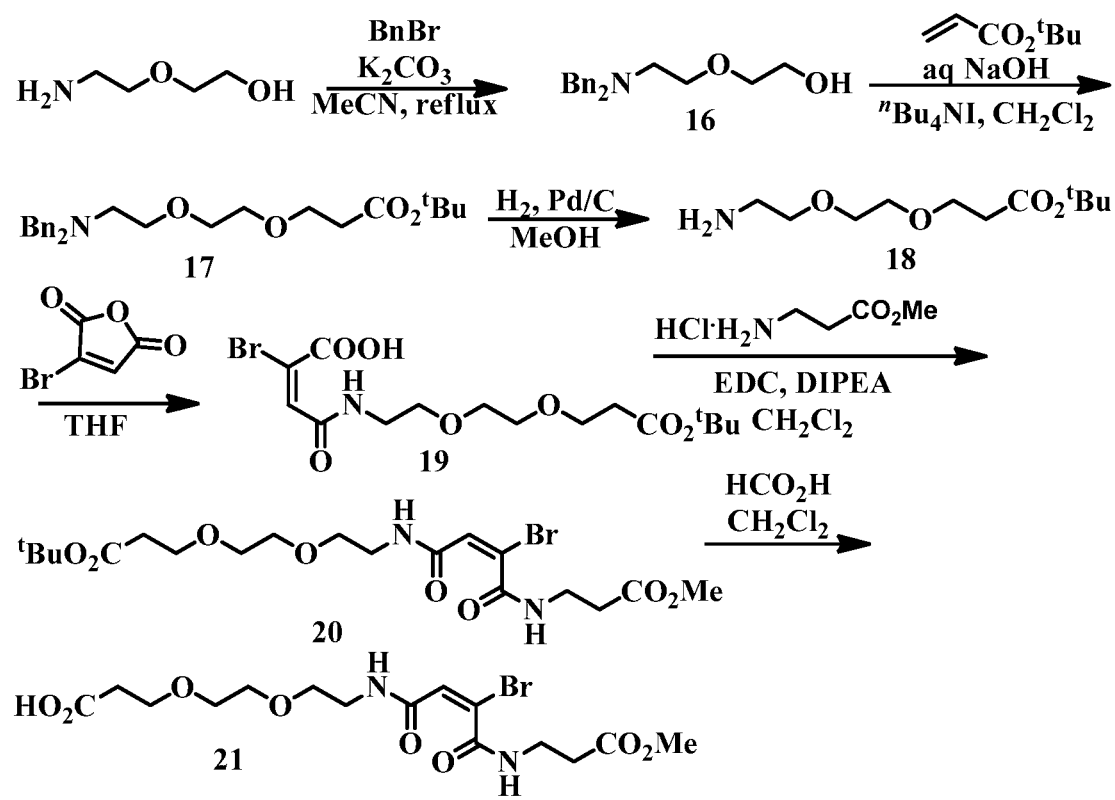

Q is a cell-binding agent/molecule (CBA), or a functional group that enables linkage with a cell-binding agent, or a functional group that enables linkage with a linker attached on a cell-binding agent. The function group is chosen from a thiol, an amine, a hydrazine, an alkoxylamino, a disulfide substituent, a maleimido, a haloacetyl group, a carboxy acid, an N-hydroxy succinimide ester, a ketone, an ester, an aldehyde, an alkynyl, an alkenyl, or a protected thiol or disulfide group, such as SAc, $SSR_1$ or SSAr. Ar is an aromatic group or hetero aromatic group.

In a further aspect, the present invention discloses a therapeutic composition comprising: (1). an effective amount of one or more derivatives of *amanita* toxins optionally linkable or linked to a cell binding agent, and (2). a pharmaceutically acceptable carrier, diluent, or excipient, of Formula (I) of the patent application, to kill target cells or tissues containing target cells.

BRIEF DESCRIPTION OF THE DRAWINGS

FIG. 1 shows the synthesis of dipeptide Tr-Hpi-Gly-OH.

FIG. 2 shows the solution phase synthesis of Ile-S-deoxo-amanitin_1.

FIG. 3 shows the solution phase synthesis of Ile-S-deoxo-amanitin_2.

FIG. 4 shows the solid phase synthesis of $Ile^3$-S-deoxo-amanitin precursor.

FIG. 5 shows the synthesis of $Ile^3$-S-deoxo-amanitin derivatives_1.

FIG. 6 shows the synthesis of linker_1 for the synthesis of *amanita* toxins.

Figure 7:
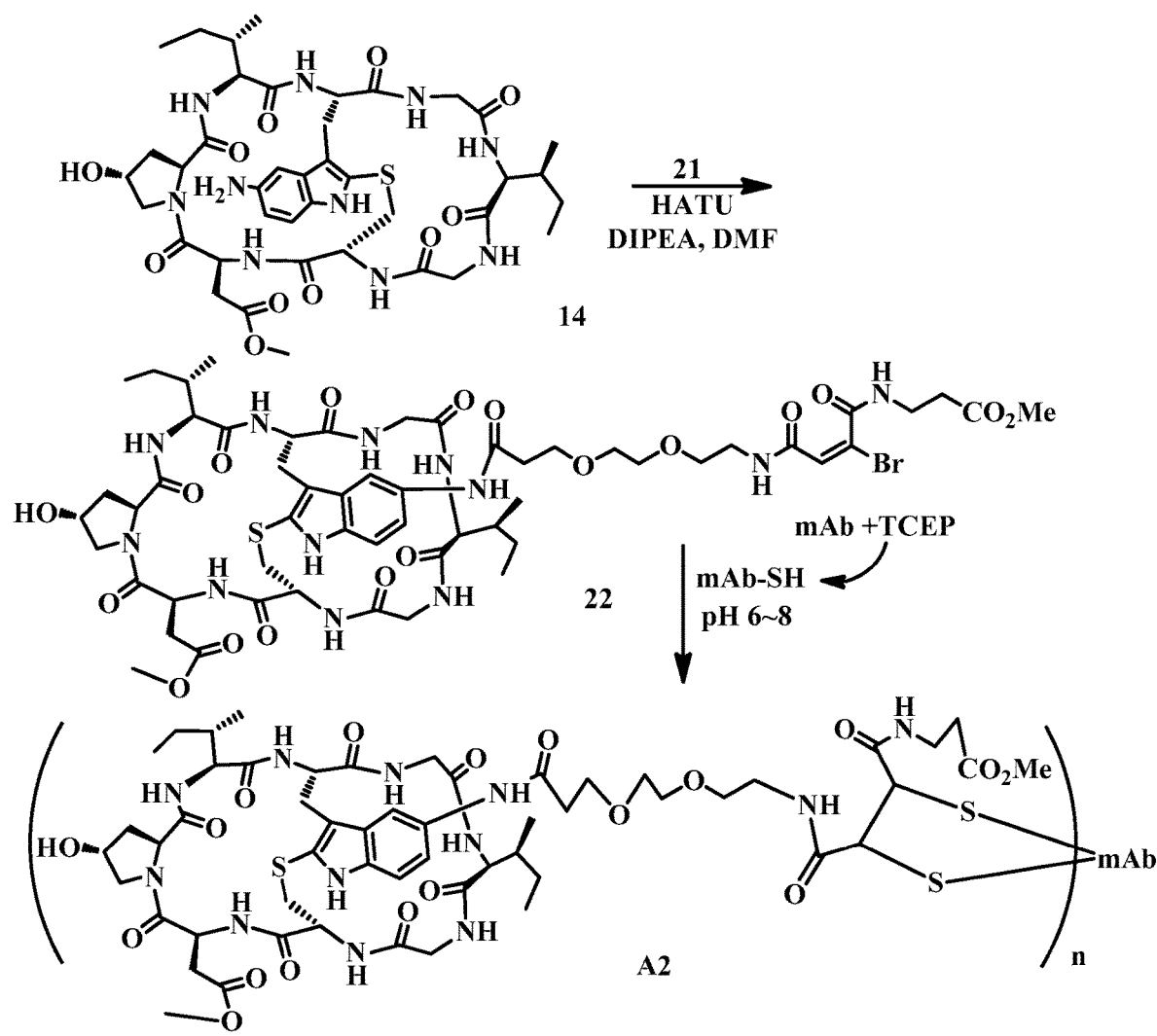
Figure 8:
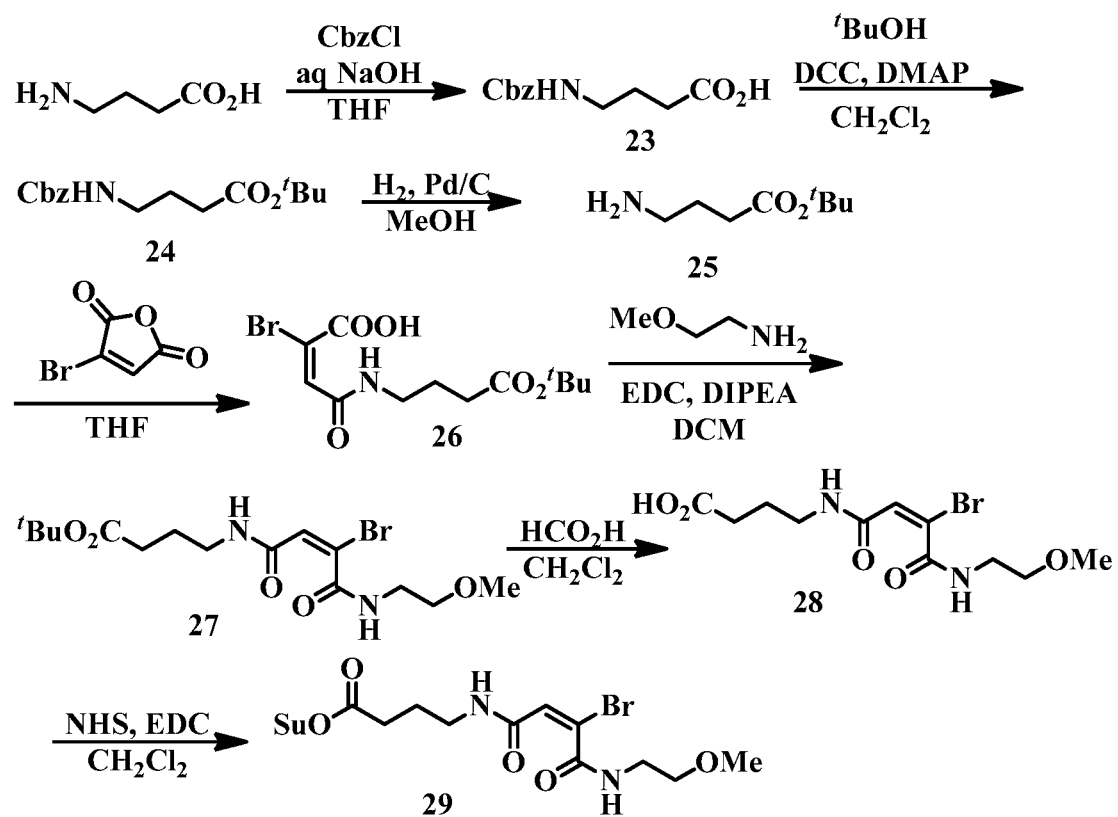
Figure 9:
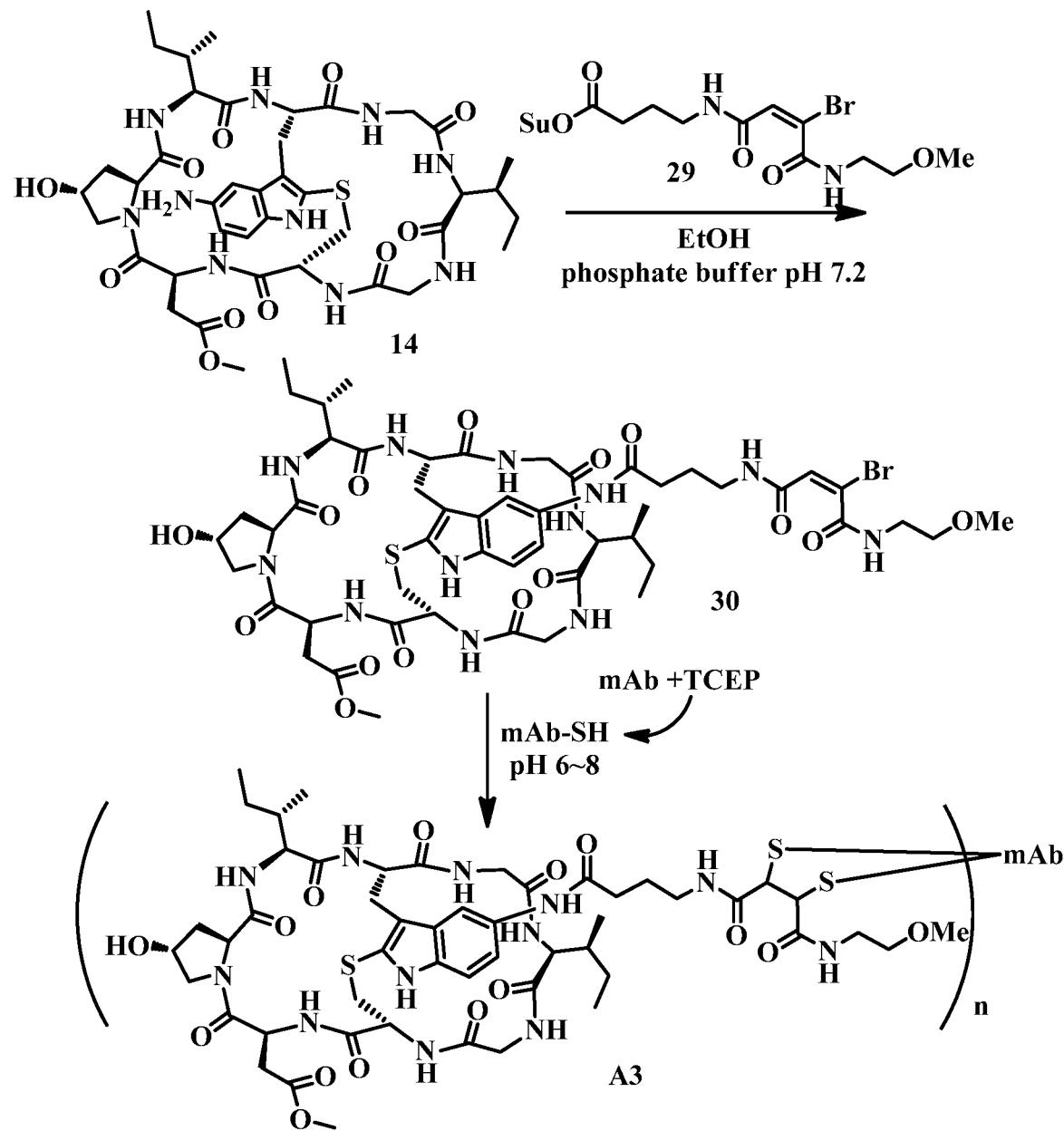
Figure 10:
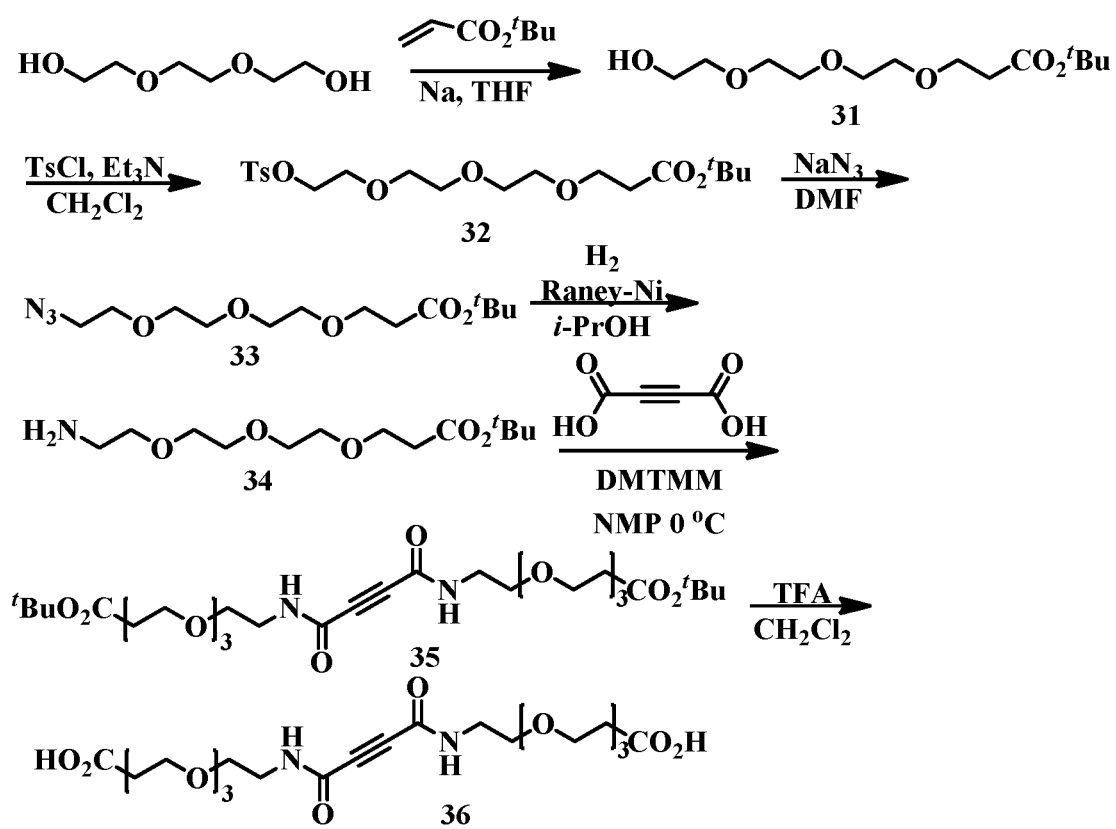
Figure 11:
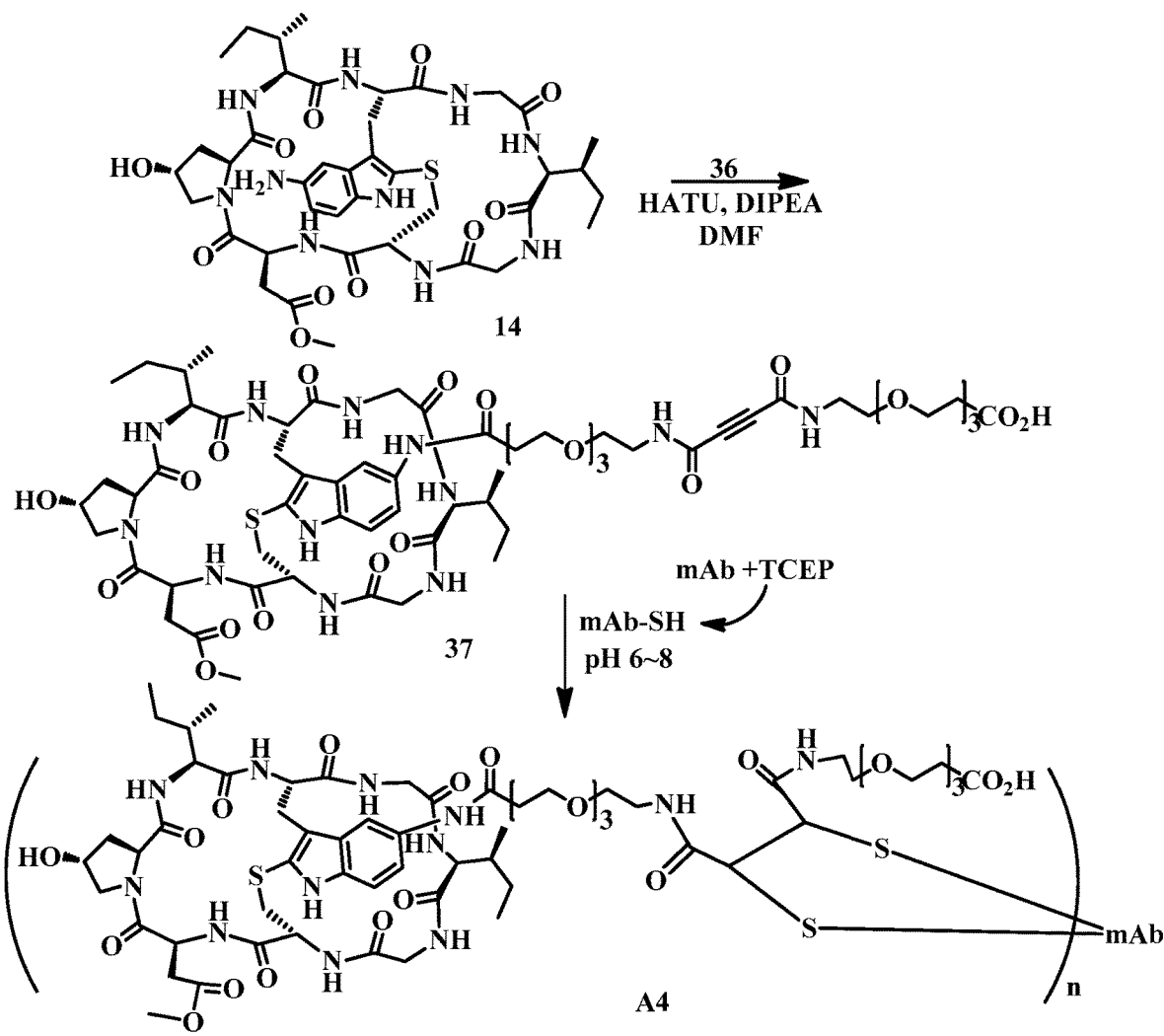
Figure 12:
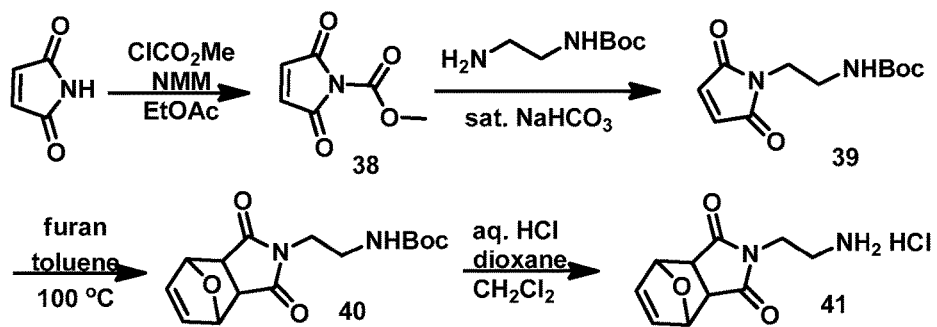
Figure 13:
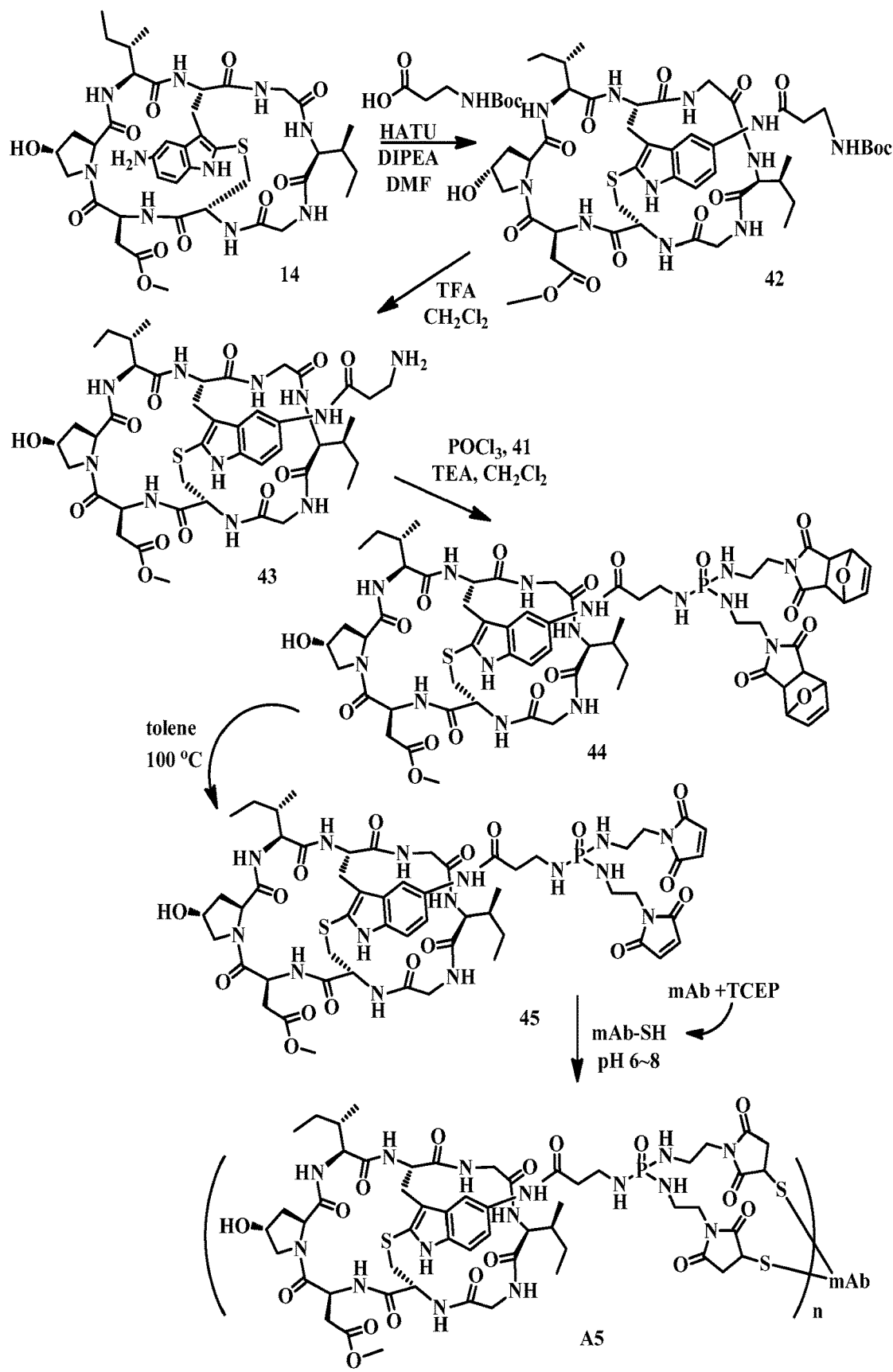
Figure 14:
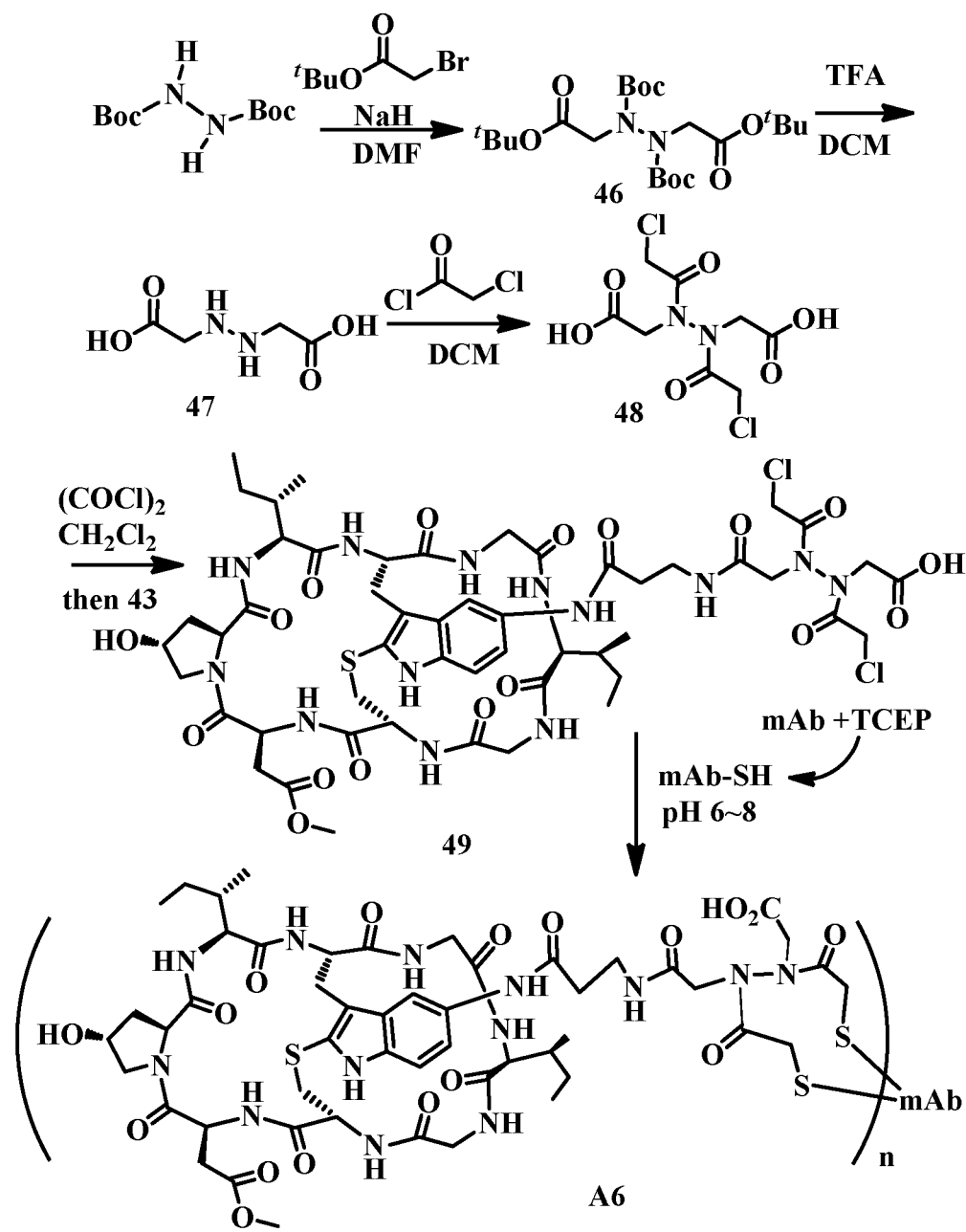
Figure 15:
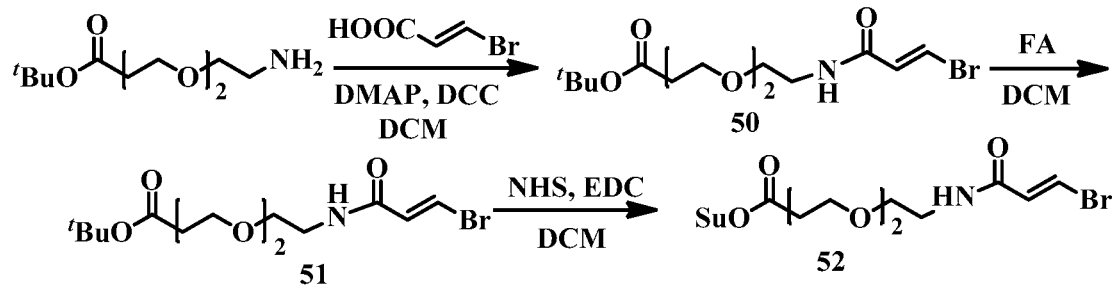
Figure 16:
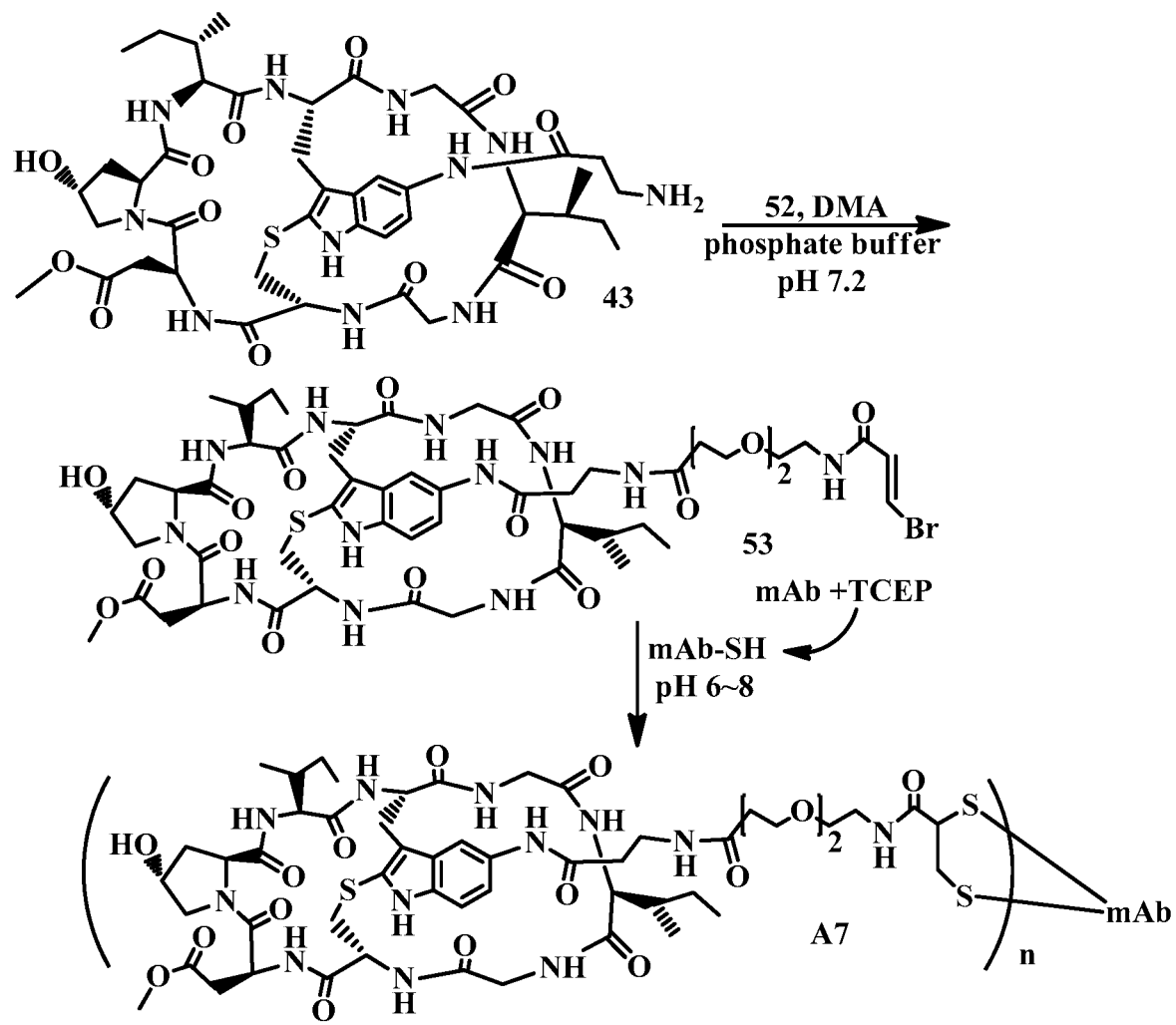
Figure 17:
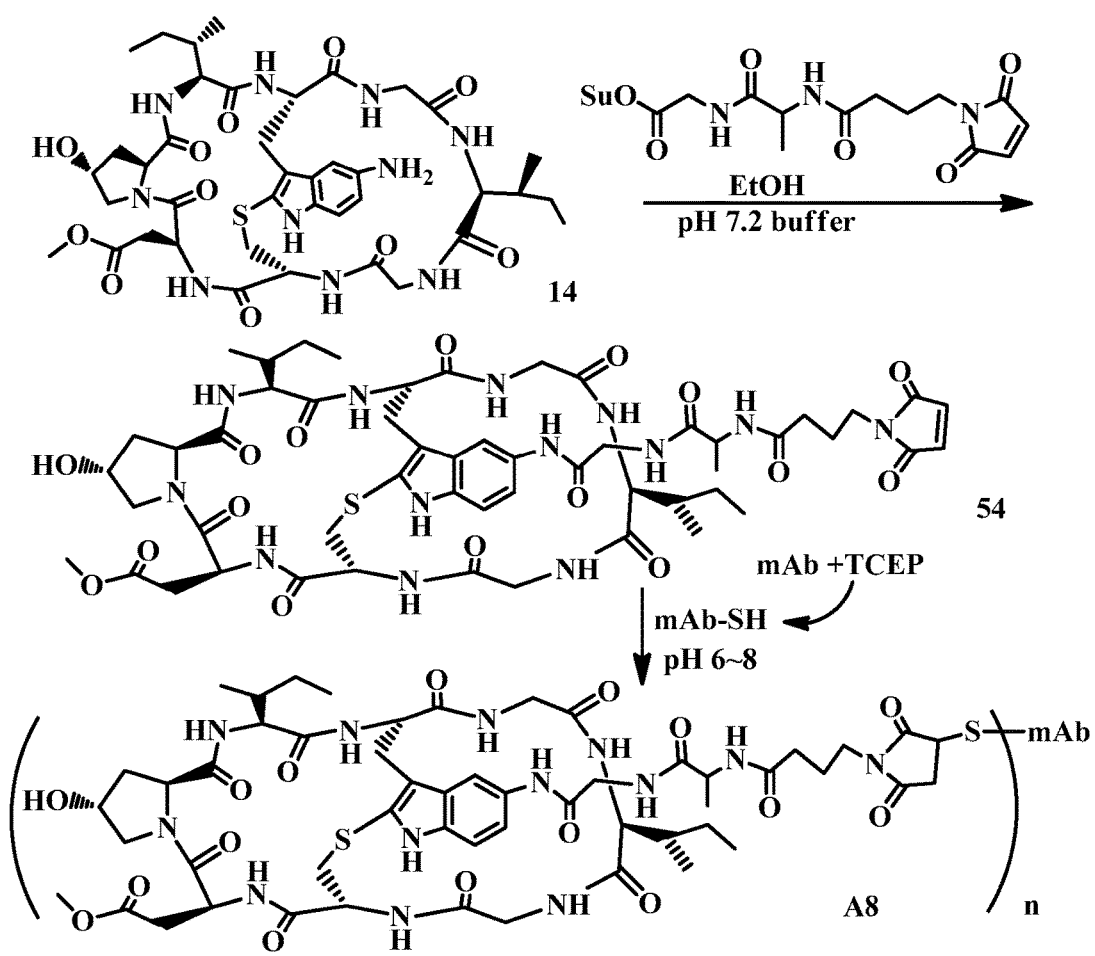
Figure 18:
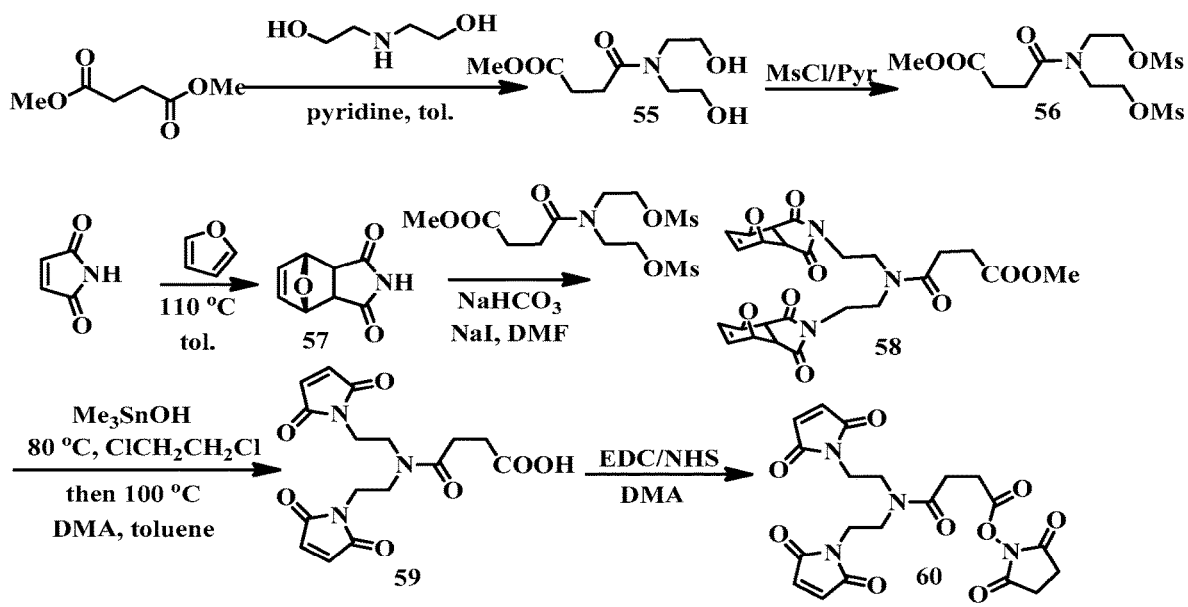
Figure 19:
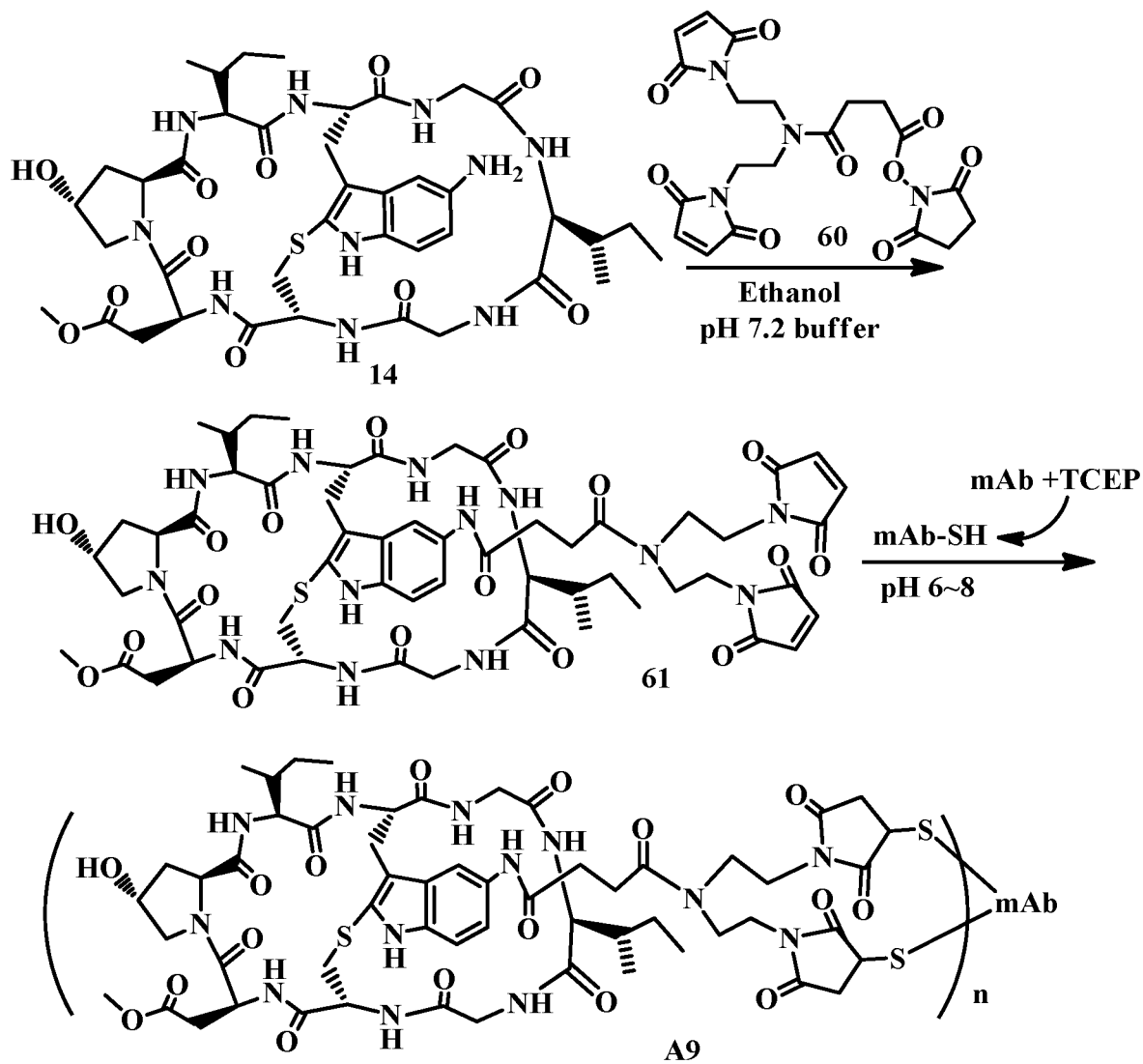
Figure 20:
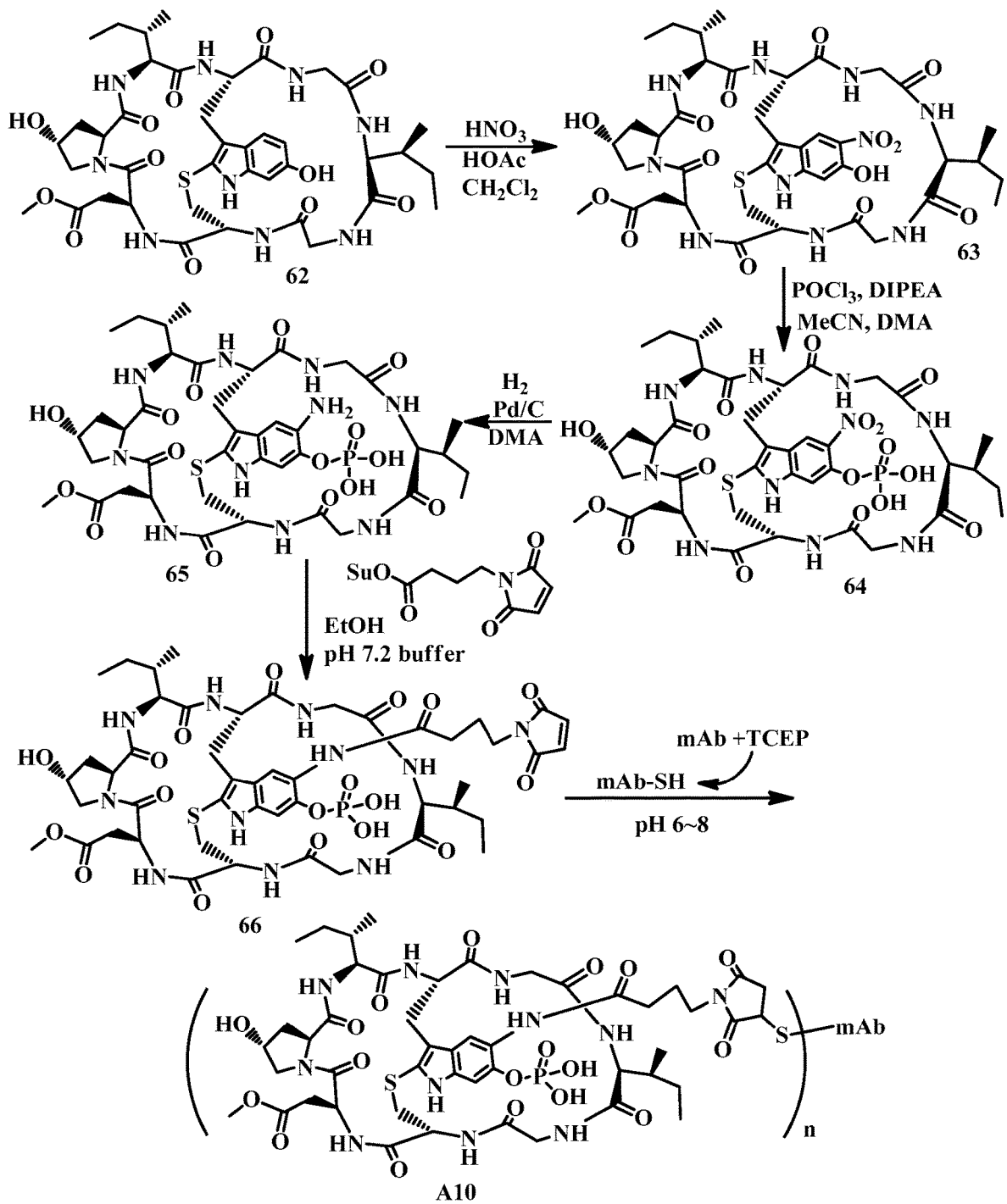
Figure 21:
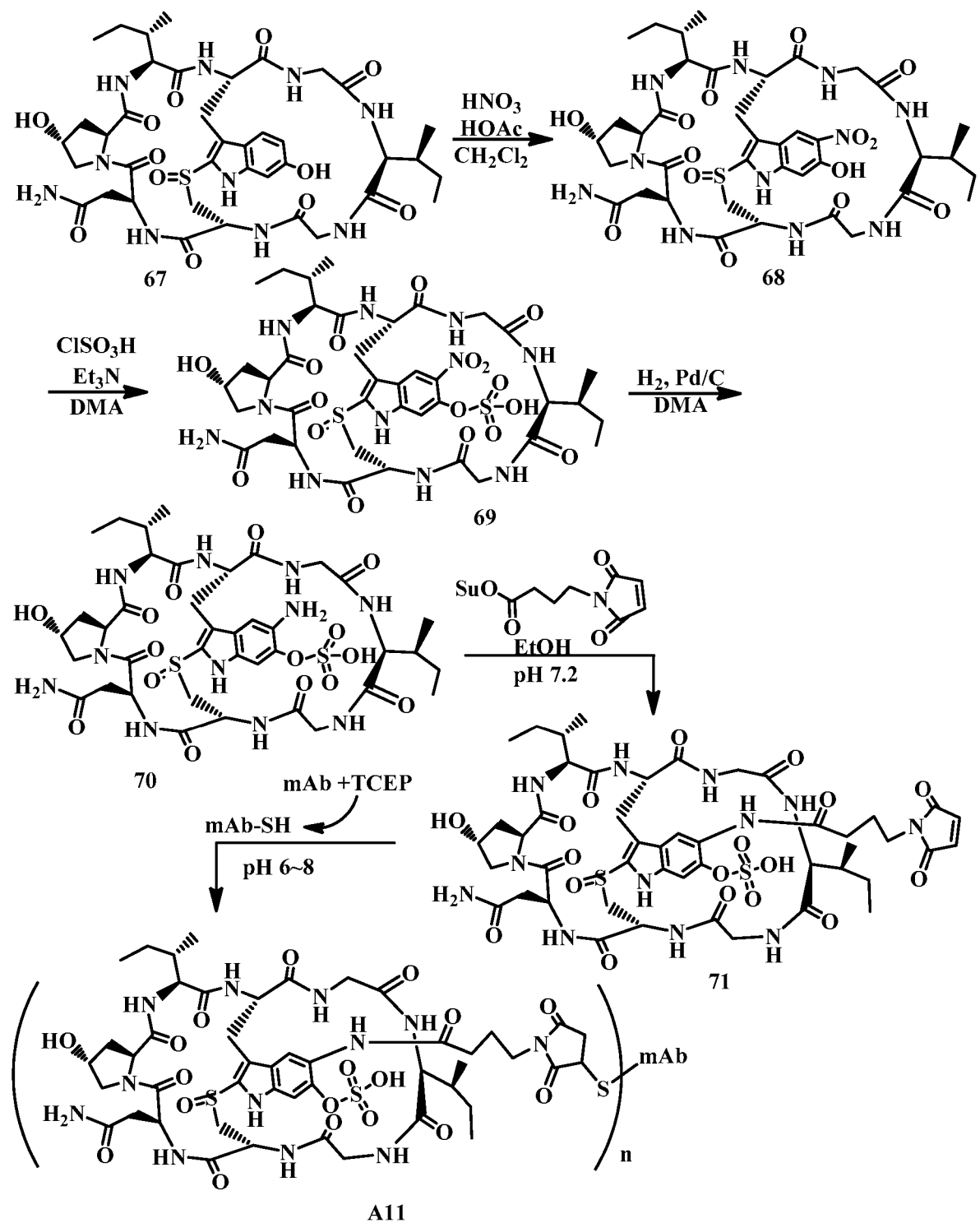
Figure 22:
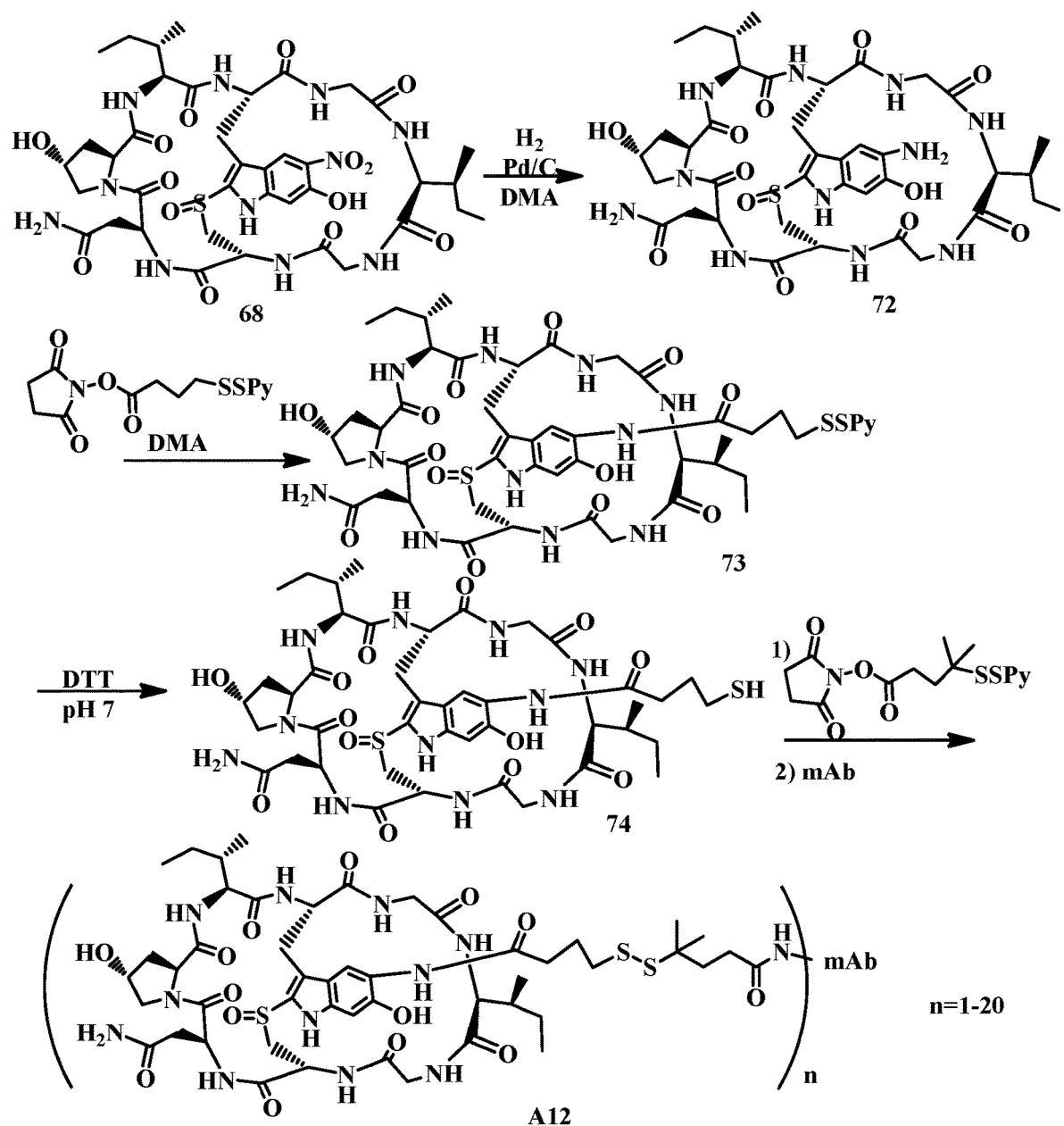
Figure 23:
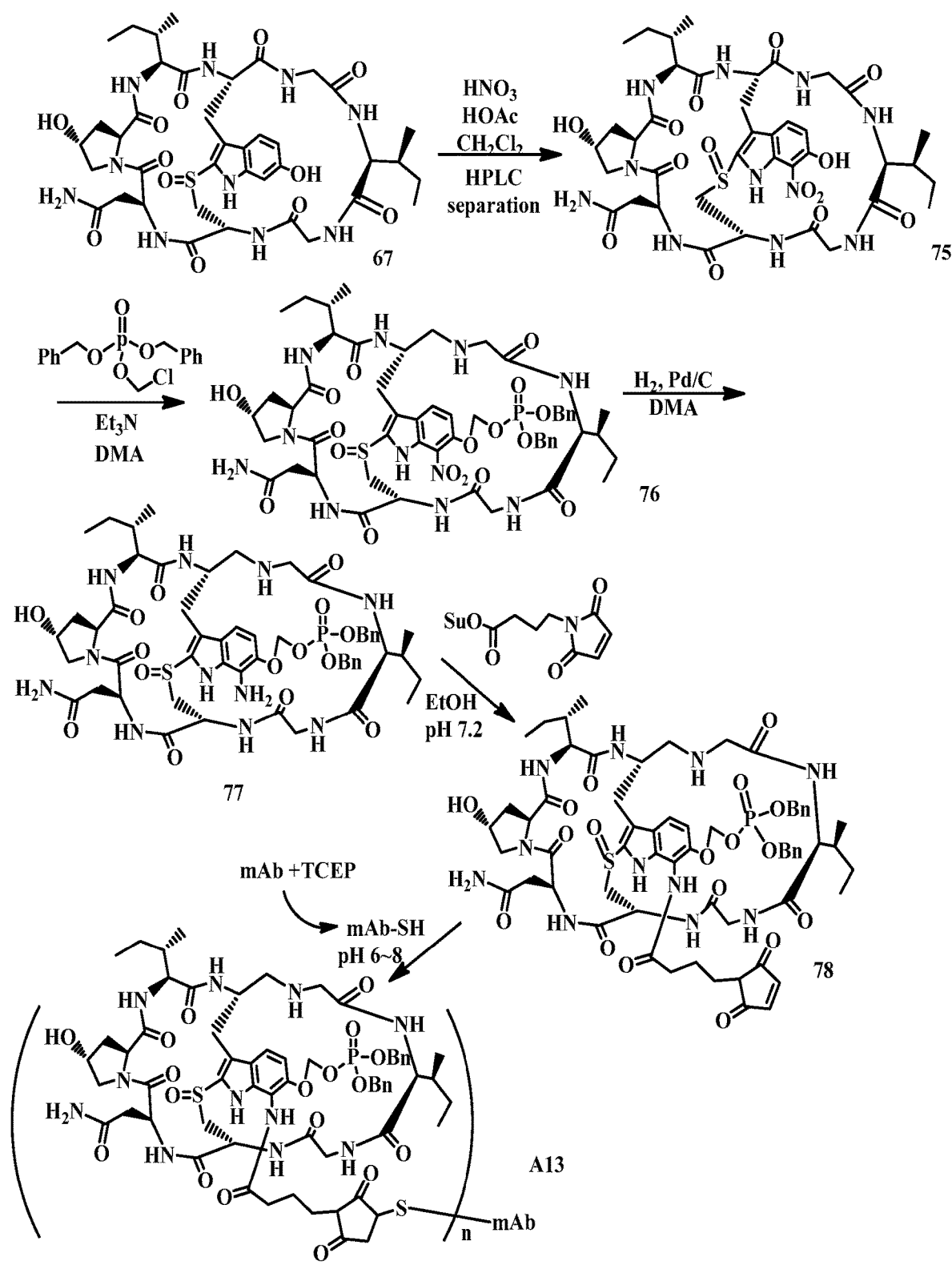
Figure 24:
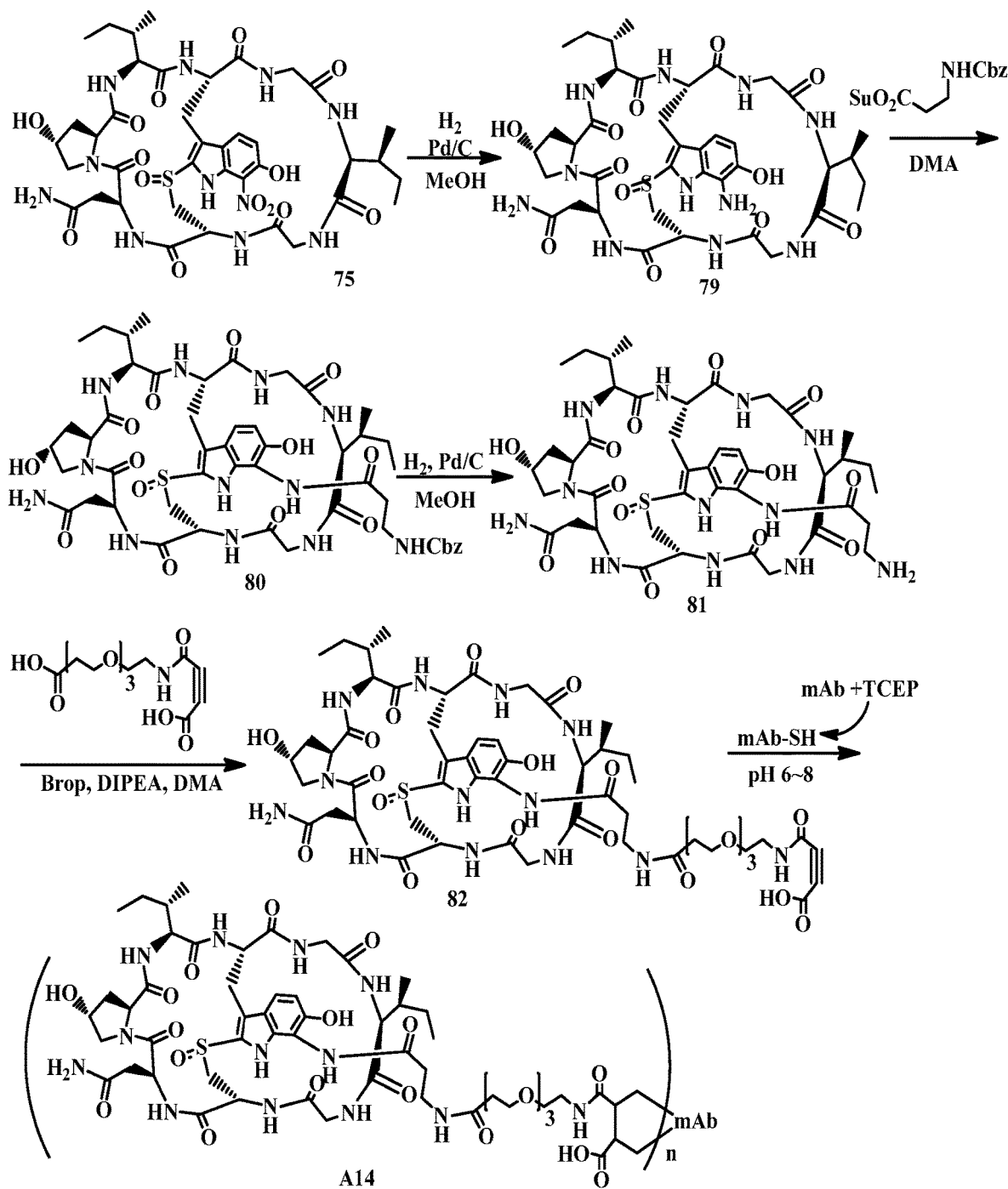
Figure 25:
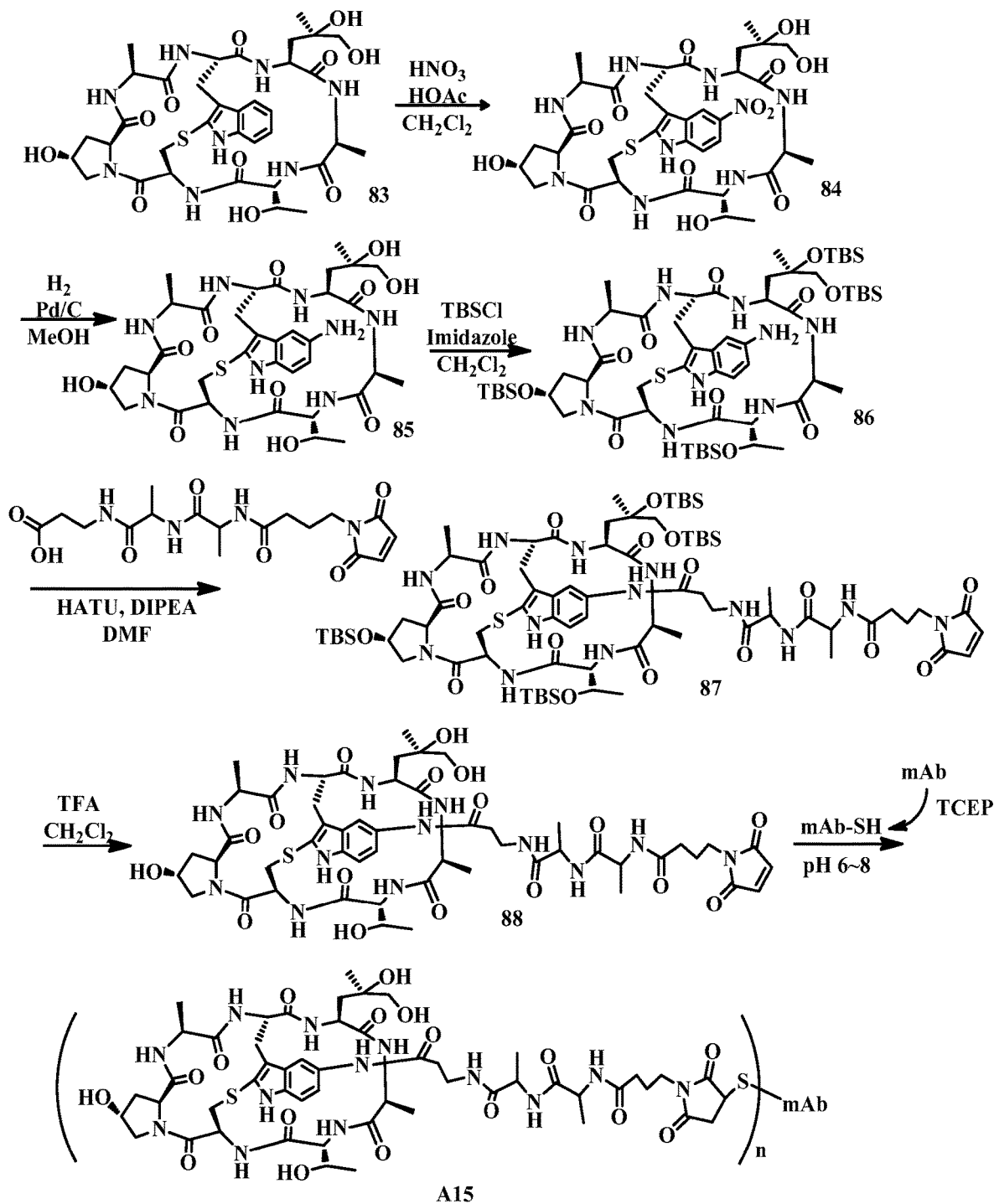
Figure 26:
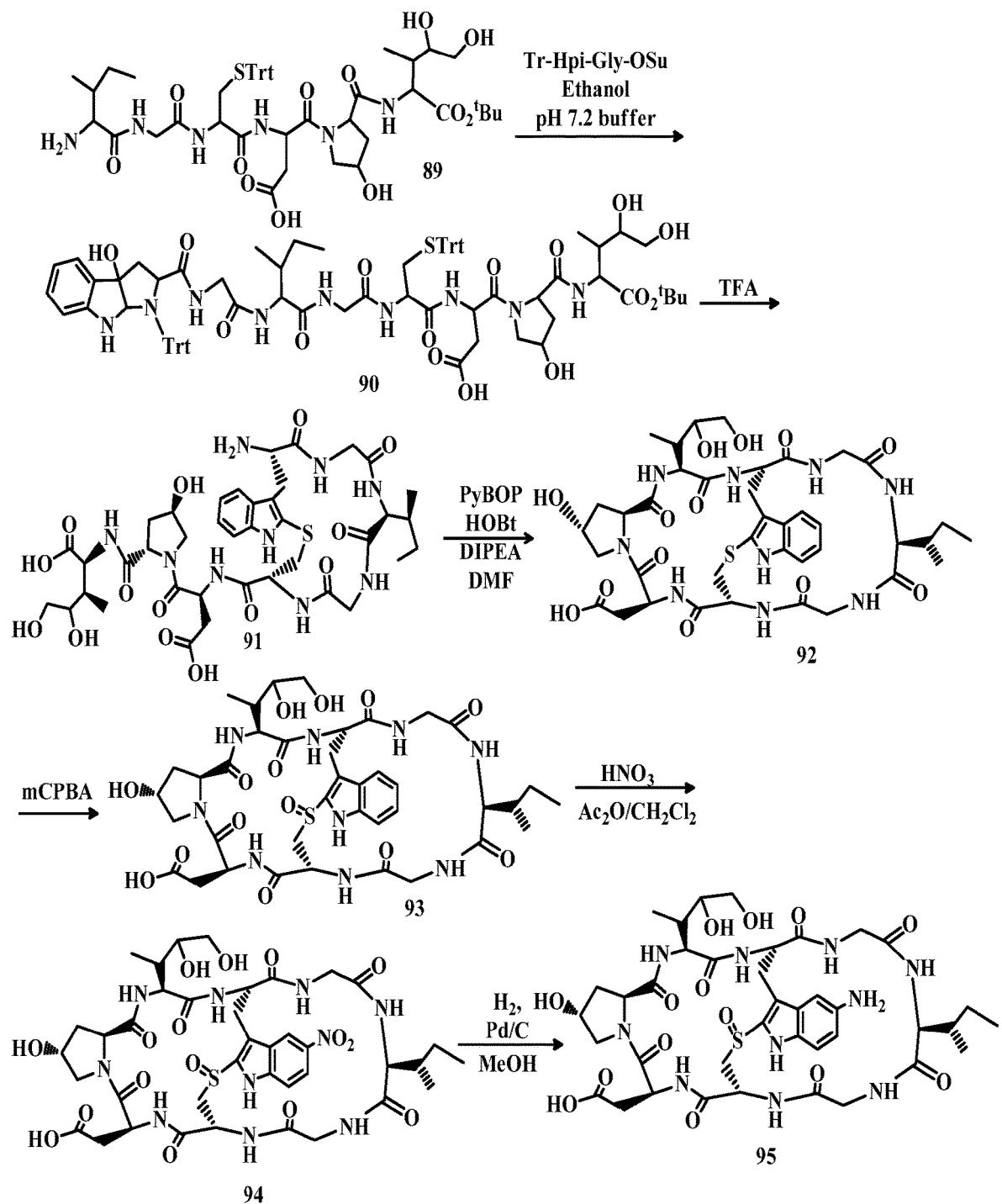
Figure 27:
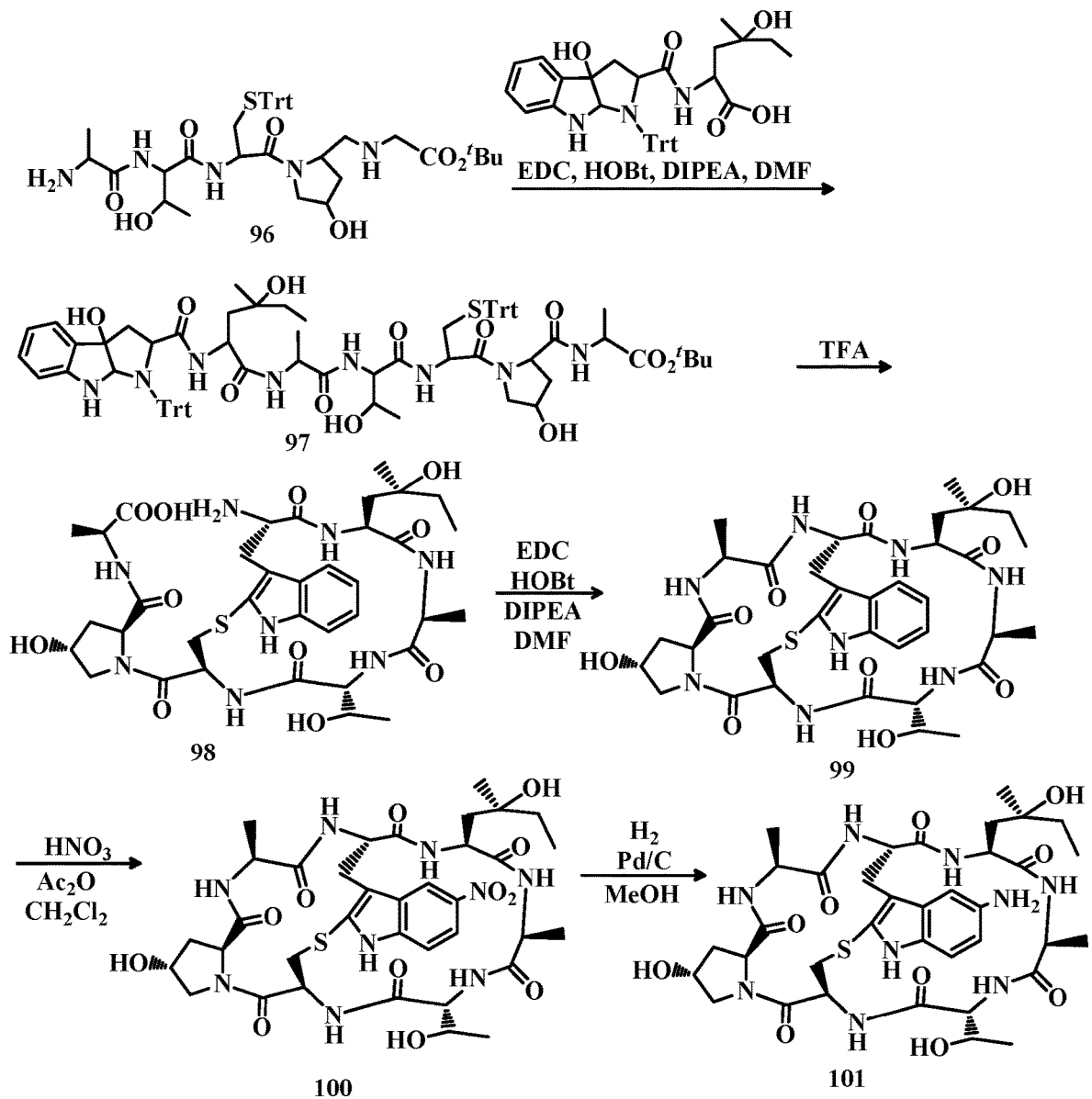
Figure 28:
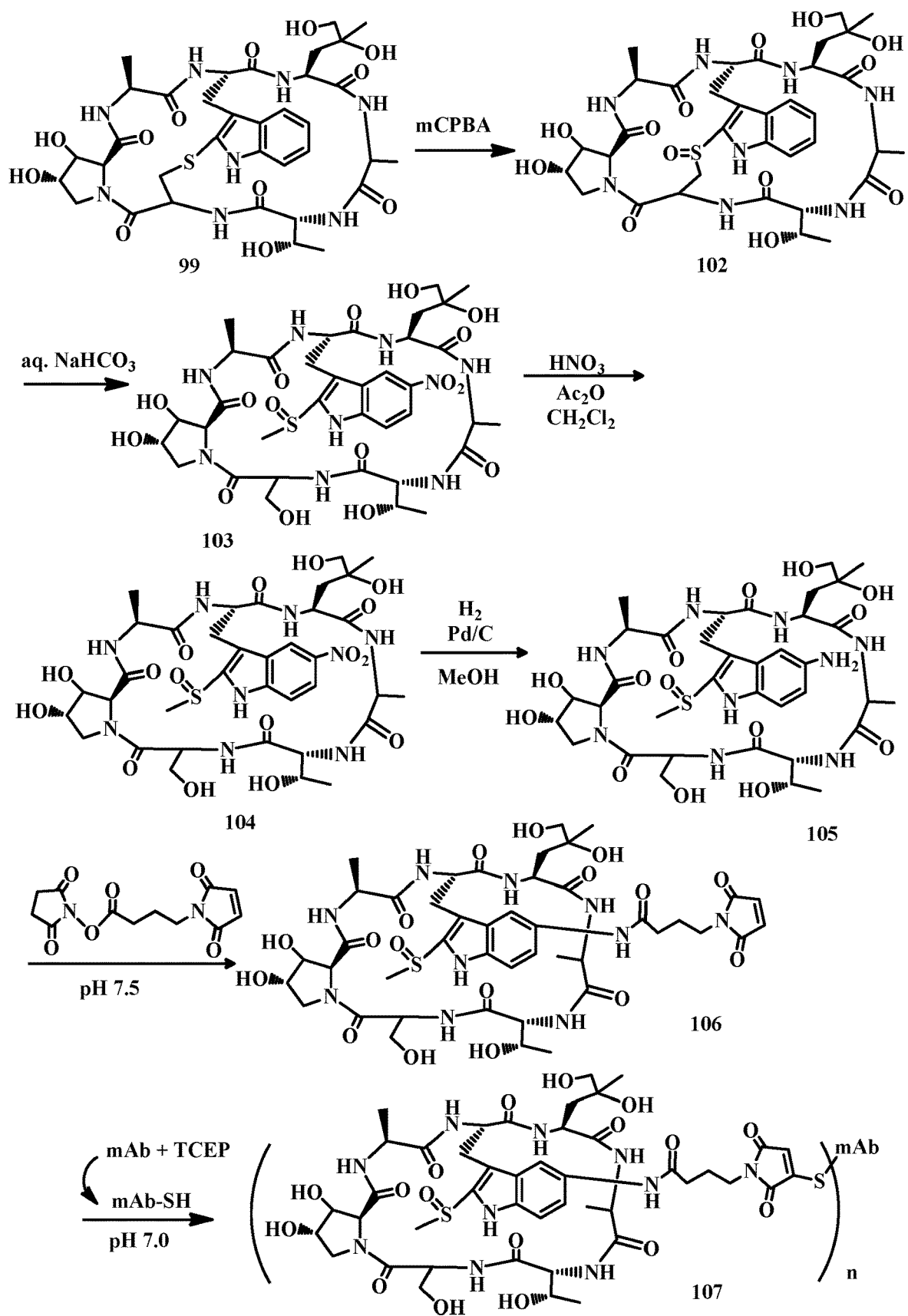

FIG. 7 shows the synthesis of $Ile^3$-S-deoxo-amanitin derivatives and conjugates_2.

FIG. 8 shows the synthesis of linker_2 for the synthesis of *amanita* toxins.

FIG. 9 shows the synthesis of $Ile^3$-S-deoxo-amanitin derivatives and conjugates_3.

FIG. 10 shows the synthesis of linker_3 for the synthesis of *amanita* toxins.

FIG. 11 shows the synthesis of $Ile^3$-S-deoxo-amanitin derivatives and conjugates_4.

FIG. 12 shows the synthesis of Synthesis of linker_4 of *amanita* toxins.

FIG. 13 shows the synthesis of $Ile^3$-S-deoxo-amanitin derivatives and conjugates_5

FIG. 14 shows the synthesis of $Ile^3$-S-deoxo-amanitin derivatives and conjugates_6.

FIG. 15 shows the synthesis of linker_5 of *amanita* toxins.

FIG. 16 shows the synthesis of $Ile^3$-S-deoxo-amanitin derivatives and conjugates_7.

FIG. 17 shows the synthesis of $Ile^3$-S-deoxo-amanitin derivatives and conjugates_8.

FIG. 18 shows the synthesis of linker_6 for *amanita* toxins.

FIG. 19 shows the synthesis of $Ile^3$-S-deoxo-amanitin derivatives and conjugates_9.

FIG. 20 shows the synthesis of $Ile^3$-S-deoxo-amanitin derivatives and conjugates_10.

FIG. 21 shows the synthesis of conjugates of amanitin derivatives_1.

FIG. 22 shows the synthesis of conjugates of amanitin derivatives_2.

FIG. 23 shows the synthesis of conjugates of amanitin derivatives_3.

FIG. 24 shows the synthesis of conjugates of amanitin derivatives_4.

FIG. 25 shows the synthesis of conjugates of phalloidin derivatives_1.

FIG. 26 shows the synthesis Solution phase synthesis of amatoxin and derivatives.

FIG. 27 shows the solution phase synthesis of phallotoxin and derivatives.

FIG. 28 shows the solution phase synthesis of virotoxin and derivatives.

FIG. 29 shows the comparison of the anti-tumor effect of conjugate compounds A1, A2, A3, A5, A6, A7, A9, and A10 with T-DM1 using human gastric tumor N87 cell model at dosing of 6 mg/kg, i.v., one injection. It shows all the conjugates did not cause the animal body weight loss FIG. 30 shows the comparison of the anti-tumor effect of conjugate compounds A1, A2, A3, A5, A6, A7, A9, and A10 with T-DM1 using human gastric tumor N87 cell model at dosing of 6 mg/kg, i.v., one injection. The animals at control group were sacrificed at day 45. All the 8 conjugate compounds (A1, A2, A3, A5, A6, A7, A9, and A10) had better in vivo activity than T-DM1.

FIGS. 31A to 31F are exemplary ADCs.

DETAILED DESCRIPTION OF THE INVENTION

Definitions

"Alkyl" means an aliphatic hydrocarbon group which may be straight or branched having 1 to 8 carbon atoms in the chain or cyclic. "Branched" means that one or much lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methyl hexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$~$C_8$ alkyl, —O—($C_1$~$C_8$ alkyl), -aryl, —C(O)R', —OC(O)R', —C(O)OR', —$C(O)NH_2$, —C(O)NHR', —$C(O)N(R')_2$—NHC(O)R', —$S(O)_2R'$, —S(O)R', —OH, -halogen (F, Cl, Br or I), —$N_3$, —$NH_2$, —NH(R'), —N(R') 2 and —CN; where each R' is independently selected from —$C_1$~$C_8$ alkyl and aryl.

A "cyclic alkyl", "cycloalkyl" and "$C_3$~$C_8$ carbocycle" can be used interchangeably. They mean a 3-, 4-, 5-, 6-, 7- or 8-membered saturated or unsaturated non-aromatic carbocyclic ring. Representative $C_3$~$C_8$ carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl. A $C_3$~$C_8$ carbocycle group can be unsubstituted or substituted with one or more groups including, but not limited to, —$C_1$~$C_8$ alkyl, —$OR_5$, -aryl, —$C(O)R_5$, —$OC(O)R_5$, —$C(O)OR_5$, —$C(O)NH_2$, —$C(O)NHR_5$, —$C(O)NR_5R_{5'}$—$NHC(O)R_5$, —$S(O)_2R_5$, —$S(O)R_5$, —OH, -halogen, —$N_3$, —$NH_2$, —$NHR_5$, —$NR_5R_{5'}$ and —CN; wherein $R_5$ and $R_{5'}$ are independently H; $C_1$~$C_8$ of alkyl, alkenyl, alkynyl, heteroalkyl, aryl, arylalkyl, or carbonylalkyl; or pharmaceutical salts. $R_5$ and $R_{5'}$ can further be substituted with at least one substituent selected from ~$N(R_5)(R_5)$, —$CO_2H$, —$SO_3H$, —$OR_5$, —$CO_2R_5$, —CONKS, and —$PO_3H$.

A "$C_3$~$C_8$ carbocyclo" refers to a $C_3$~$C_8$ carbocycle group defined above wherein one of hydrogen atoms on the carbocycle is replaced with a bond.

Alkenyl refers to an aliphatic hydrocarbon group containing a carbon-carbon double bond and which may be straight or branched having 2 to 8 carbon atoms in the chain. The alkenyl double bond may have "cis" and "trans" orientations, or alternatively, "E" and "Z" orientations. Exemplary alkenyl groups include, but are not limited to, ethylenyl or vinyl, propenyl or allyl, n-butenyl, i-butenyl, 3-methylbut-2-enyl, n-pentenyl, hexylenyl, heptenyl, octenyl.

"Alkynyl" or "alkinyl" means an aliphatic hydrocarbon group containing a carbon-carbon triple bond and which may be straight or branched having 2 to 8 carbon atoms in the chain. Exemplary alkynyl groups include ethynyl, propynyl, n-butynyl, 2-butynyl, 3-methylbutynyl, pentynyl, n-pentynyl, hexylynyl, heptynyl, and octynyl.

"Heteroalkyl" is $C_2$~$C_8$ alkyl in which one to four carbon atoms are independently replaced with a heteroatom from the group consisting of O, S and N.

"Heterocycle" refers to an aromatic or non-aromatic $C_3$~$C_{14}$ carbocycle in which one to four of the ring carbon atoms are independently replaced with a heteroatom from the group of O, N, P, S and Se. Preferable heteroatoms are oxygen, nitrogen and sulphur. Suitable heterocyclics are also disclosed in The Handbook of Chemistry and Physics, $76^{th}$ Edition, CRC Press, Inc., 1995-1996, p 2-25 to 2-26, the disclosure of which is hereby incorporated by reference. Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrmidinyl, dihydrothiopyranyl, azepanyl, as well as the fused systems resulting from the condensation with a phenyl group.

"Aryl" or Ar refers to an aromatic or hetero aromatic group, composed of one or several rings, comprising three to fourteen carbon atoms, preferentially six to ten carbon atoms. The term of hetero aromatic group refers one or several carbon on aromatic group, preferentially one, two, three or four carbon atoms are replaced by O, N, Si, Se, P or S, preferentially by O, S, N. The term aryl or Ar also refers to a aromatic group, wherein one or several H atoms are replaced independently by alkyl, F, Cl, Br, I, $OR_5$, or $SR_5$, $NR_5R_{5'}$, $N=NR_5$, $N=R_5$, $NR_5R_{5'}$, $NO_2$, $SOR_5R_{5'}$, $SO_2R_5$, $SO_3R_5$, $OSO_3R_5$, $PR_5R_{5'}$, $POR_5R_{5'}$, $PO_5R_{5'}$, $OPO_3R_5R_{5'}$, or $PO_3R_5R_{5'}$ wherein $R_5$ and $R_{5'}$ are independently H, alkyl, alkenyl, alkinyl, heteroalkyl, aryl, arylalkyl, carbonyl, or pharmaceutical salts.

The term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Halogen atom" refers to fluorine, chlorine, bromine or iodine atom; preferably bromine and chlorine atom.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, triethanolamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared by reaction of the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, Pa., 1985, p 1418, the disclosure of which is hereby incorporated by reference.

The term "compound", "cytotoxic agent", "cytotoxic compound," "cytotoxic dimer" and "cytotoxic dimer compound" are used interchangeably. They are intended to include compounds for which a structure or formula or any derivative of thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

"Cell binding agents" or "Cell binding molecules" may be of any kind presently known, or those become known, and include peptides and non-peptides. Generally, these can be antibodies (especially monoclonal antibodies) or a fragment of an antibody that contains at least one binding site, lymphokines, hormones, growth factors, nutrient-transport molecules (such as transferrin), or any other cell binding molecule or substance (such as vitamins).

More specific examples of cell binding agents that can be used include:

monoclonal antibodies (mAb);

single chain antibodies;

fragments of antibodies such as Fab, Fab', F(ab')$_2$, F$_v$, (Parham, J. Immunol. 131, 2895-2902 (1983); Spring et al, J. Immunol. 113, 470-478 (1974); Nisonoff et al, Arch. Biochem. Biophys. 89, 230-244 (1960)), fragments produced by a Fab expression library, anti-idiotypic (anti-Id) antibodies, CDR's, and epitope-binding fragments of any of the above which immunospecifically bind to cancer cell antigens, viral antigens or microbial antigens.

interferons;

peptides; or conjugated proteins or peptides;

lymphokines such as IL-2, IL-3, IL-4, IL-5, IL-6;

hormones such as insulin, TRH (thyrotropin releasing hormones), MSH (melanocyte-stimulating hormone), steroid hormones, such as androgens and estrogens;

growth factors and colony-stimulating factors such as EGF, TGFα, insulin like growth factor (IGF-I, IGF-II) G-CSF, M-CSF and GM-CSF (Burgess, Immunology Today 5, 155-158 (1984)); vitamins, such as folate and transferrin (O'Keefe et al, J. Biol. Chem. 260, 932-937 (1985)).

Monoclonal antibodies (mAb), mAb single chain or fragments can be produced in the well known state of art technology. The technology permits the production of extremely selective cell binding agents in the form of specific monoclonal antibodies. The well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins.

Selection of appropriate cell binding agents is a matter of choice that depends upon the particular cell population that is to be targeted, but in general monoclonal antibodies are preferred if an appropriate one is available.

For example, an anti-CD20 antigen monoclonal antibody, known as Rituximab is a chimeric (mouse/human) monoclonal antibody and it was the first therapeutic antibody approved by the United States Food and Drug Administration for treatment of relapsed or refractory low-grade or follicular NHL (Leonard, J. P. et al., Clin. Canc. Res. 10:5327-5334 (2004)). Another anti-CD20 antibody, known as Ofatumumab, is a human monoclonal antibody targeting an epitope different from that of rituximab and most other CD20 directed antibodies. It was approved by US FDA for treating chronic lymphocytic leukemia and has also shown potential in treating Follicular non-Hodgkin's lymphoma, Diffuse large B cell lymphoma, rheumatoid arthritis and relapsing remitting multiple sclerosis (Coiffier, B. et al Blood 111: 1094-100 (2008); Zhang, B. MAbs 1 (4): 326-31 (2009)). A third-generation, humanized and glyco-engineered anti-CD20 mAb for the treatment of B-cell lymphoid malignancies named Afutuzumab (now called obinutuzumab) has been developed (Robak, T (2009) Current opinion in investigational drugs (London, England: 2000) 10 (6): 588-96). Obinutuzumab is fully humanized IgG1 type II anti-CD20 antibody and it selectivity binds to the extracellular domain of the human CD20 antigen on malignant human B cells. Similarly, an anti-CD19 antigen monoclonal antibody B4 is a murine $IgG_1$, that binds to the CD19 antigen on B cells (Nadler et al, 131 J. Immunol. 244-250 (1983)) and can be used if the target cells are B cells or diseased cells that express CD19 antigen such as in non-Hodgkin's lymphoma or chronic lymphoblastic leukemia. In addition, the anti-CD22 antibodies that include RFB4 (Mansfield, E. et al., Blood 90:2020-2026 (1997)), CMC-544 (DiJoseph, J. F., Blood 103:1807-1814 (2004)) and LL2 (Pawlak-Byczkowska, E. J. et al., Cancer Res. 49:4568-4577 (1989)) can be used as potential therapies for B cell cancers and other B cell proliferative diseases. The LL2 antibody (formerly called HPB-2) is an IgG2a mouse monoclonal antibody directed against the CD22 antigen (Pawlak-Byczkowska, E. J. et al. (1989), supra). Furthermore, the anti CD33 antigen monoclonal antibody, named Gemtuzumab was first monoclonal antibody conjugated with a cytotoxic drug to treat acute myelogenous leukemia (AML) (P. F. Bross et al Clin Cancer Res 7 (6): 1490-6). A similar anti CD33 antigen antibody, named My9-6 is a murine $IgG_1$ antibody that binds specifically to the CD33 Antigen (J. D. Griffin et al 8 Leukemia Res., 521 (1984)) and can be used to target cells express CD33 as in the disease of acute myelogenous leukemia (AML). Additionally, GM-CSF antibody which binds to myeloid cells can be used as a cell binding agent to diseased cells from acute myelogenous leukemia. IL-2 antibody, which binds to activated T-cells, can be used for prevention of transplant graft rejection, for therapy and prevention of graft-versus-host disease, and for the treatment of acute T-cell leukemia. MSH antibody, which binds to melanocytes, can be used for the treatment of melanoma.

Novel Cytotoxic Agents and their Conjugation of the Invention.

The novel *amanita* toxin derivatives according to the present invention comprises one or more derivatives of amatoxins, phallotoxins or virotoxins, optionally linkable or linked to a cell binding agent via a linking group. The linking group is part of a chemical moiety that is covalently bound to *amanita* toxin derivatives through conventional methods.

The *amanita* toxin derivatives disclosed in the present invention have the formula (I) shown below:

(I)

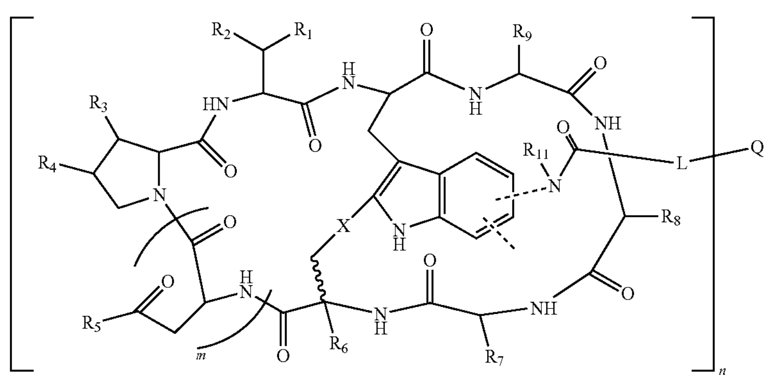

or their pharmaceutically acceptable salts, hydrates, or hydrated salts; or the polymorphic crystalline structures of these compounds; or their optical isomers, racemates, diastereomers or enantiomers.

Wherein

---- represents a single bond that links any carbon position of the aromatic (indole) ring;

$\sim\!\!\sim\!\!\sim$ represents an optional single bond or an absent bond.

$R_1$ and $R_2$ are independently selected from H, OH, $CH_2OH$, $CH(OH)CH_2OH$, $CH(CH_3)CH_2OH$, $CH(OH)CH_3$, $C_1$-$C_8$ alkyl, —$OR_{12}$ (ether), $C_2$-$C_8$ alkenyl, alkynyl, heteroalkyl, —$OCOR_{12}$ (ester), —$OC(=O)OR_{12}$-(carbonate), —$OC(=O)NHR_{12}$(carbamate); $C_3$-$C_8$ aryl, heterocyclic, carbocyclic, cycloalkyl, heterocycloalkyl, heteroaralkyl, alkylcarbonyl.

$R_3$ and $R_4$ are independently selected from H, OH, —$OR_{12}$ (ether), —$OCOR_{12}$ (ester), —$OCOCH_3$ (acetate), —$OCOOR_{12}$ (carbonate), —$OC(=O)NHR_{12}$(carbamate), —$OP(O)(OR_{12})(OR_{12}')$ (phosphate), $OP(O)(NHR_{12})(NHR_{12}')$ (phosphamide), O—$SO_3^-$, or O-glycoside.

$R_5$ is selected from H, OH, $NH_2$, —$OR_{12}$, —$NHR_{12}$, —$NR_{12}R_{12}'$, $N(H)(R_{12})R_{13}CO(Aa)_p$, (an amino acid or peptide, wherein Aa is an amino acid or a polypeptide, p represents 0-6).

$R_6$ is selected from H, OH, $CH_2OH$, $CH(OH)CH_2OH$, $CH(CH_2OH)_2$, $CH(CH_3)OH$, $CH_2CH_2OH$, PrOH, BuOH, $C_1$~$C_8$ alkyl, —$OR_{12}$ (ether), $C_2$~$C_8$ alkenyl, alkynyl, heteroalkyl, —$OCOR_{12}$ (ester); $C_3$~$C_8$ aryl, heterocyclic, or carbocyclic.

$R_7$, $R_8$ and $R_9$ are independently selected from H, OH, $CH_3$, $CH(CH_3)_2$, $CH(CH_3)CH_2CH_3$, $CH_2OH$, $CH(OH)CH_2OH$, $CH_2CH(OH)CH_2OH$, $CH(CH_2OH)_2$, $CH_2C(OH)(CH_2OH)_2$, $CH_2C(OH)(CH_3)(CH_2OH)$, $CH_2C(OH)(CH(CH_3)_2)(CH_2OH)$, $CH_2CH_2OH$, PrOH, BuOH, $CH_2COOH$, $CH_2CH_2COOH$, $CH(OH)COOH$, $CH_2CONH_2$, $CH_2CH_2CONH_2$, $CH_2CH_2CH_2CH_2NH_2$, $CH_2CH_2CH_2NHC(=NH)NH_2$, $C_1$~$C_8$ alkyl, $CH_2Ar$, $CH_2SH$, $CH_2SR_{12}$, $CH_2SSR_{12}$, $CH_2SSAr$, $CH_2CH_2SCH_3$, —$OR_{12}$ (ether), $C_2$~$C_8$ alkenyl, alkynyl, heteroalkyl, —$OCOR_{12}$ (ester); $C_3$~$C_8$ aryl, heterocyclic, or carbocyclic.

$R_{10}$ is selected from H, $NH_2$, OH, SH, $NO_2$, halogen, —NHOH, —$N_3$ (azido); —CN (cyano); $C_1$~$C_8$ alkyl, $C_2$~$C_8$ alkenyl, alkynyl, heteroalkyl; $C_3$~$C_8$ aryl, heterocyclic, or carbocyclic; —$OR_{12}$ (ether), —$OCOR_{12}$ (ester), —$OCOCH_3$ (acetate), —$OC(O)OR_{12}$ (carbonate), —$OC(O)CH(R_{12})NHAa$ (Aa is an amino acid group), —$NR_{12}R_{12}'$ (amine), —$NR_{12}COR_{12}'$(amine), —$NR_{12}NR_{12}'NR_{12}''$ (amine), —$OCONR_{12}R_{12}'$(carbamate); —$NR_{12}(C=NH)NR_{12}'R_{12}''$ (guanidinum); —$NR_{12}CO(Aa)_p$, (an amino acid or peptide, wherein Aa is an amino acid or a polypeptide, p represents 0-6); —$N(R_{12})CONR_{12}'R_{12}''$ (urea); —OC-SNHR$_{12}$ (thiocarbamate); —SH (thiol); —$SR_{12}$ (sulfide); —$S(O)R_{12}$ (sulfoxide); —$S(O_2)R_{12}$ (sulfone); —$SO_3$, $HSO_3$, $HSO_2$, or a salt of $HSO_3^-$, $SO_3^{2-}$ or —$HSO_2^-$ (sulphite); —$OSO_3^-$; —$N(R_{12})SOOR_{12}'$ (sulfonamide); $H_2S_2O_5$ or a salt of $S_2O_5^{2-}$ (metabisulfite); $PO_3SH_3$, $PO_2S_2H_2$, $POS_3H_2$, $PS_4H_2$ or a salt of $PO_3S^{3-}$, $PO_2S_2^{3-}$, $POS_3^{3-}$, $PS_4^{3-}$ (mono-, di-, tri-, and tetra-thiophosphate); $(R_{12}O)_2POSR_{12}'$ (thiophosphate ester); $HS_2O_3$ or a salt of $S_2O_3^{2-}$ (thiosulfate); $HS_2O_4$ or a salt of $S_2O_4^{2-}$ (dithionite); $(P(=S)(OR_{12})(S)(OH)$ or a salt formed with a cation (phosphorodithioate); —$N(R_{12})OR_{12}'$ (hydroxylamine derivative); $R_{12}C(=O)NOH$ or a salt formed with a cation (hydroxamic acid); $(HOCH_2SO_2')$, or its salts (formaldehyde sulfoxylate); —$N(R_{12})COR_{12}'$ (amide); $R_{12}R_{12}'R_{12}''NPO_3H$ (trialkylphosphoramidate or phosphoramidic acid); or $ArAr'Ar''NPO_3H$ (triarylphosphonium); $OP(O)(OM_1)(OM_2)$, $OCH_2OP(O)(OM_1)(OM_2)$, $OSO_3M_1$; O-glycoside (glucoside, galactoside, mannoside, glucuronoside, alloside, fructoside, etc), NH-glycoside, S-glycoside or $CH_2$-glycoside; $M_1$ and $M_2$ are independently H, Na, K, Ca, Mg, $NH_4$, $NR_1'R_2'R_3'$; $R_1'$, $R_2'$ and $R_3'$ are independently H, $C_1$~$C_8$ alkyl; Ar, Ar', and Ar'' are $C_3$~$C_8$ aryl or heteroaromatic group.

$R_{11}$ is H, $C_1$~$C_8$ alkyl; $C_2$~$C_8$ alkenyl, alkynyl, heteroalkyl; $C_3$~$C_8$ aryl, heteroaoaryl.

$R_{12}$, $R_{12}'$, and $R_{12}''$ are independently selected from H, $C_1$~$C_8$ alkyl; $C_2$~$C_8$ alkenyl, alkynyl, heteroalkyl; $C_3$~$C_8$ aryl, heteroaoaryl, heterocyclic, or carbocyclic.

X is S, O, NH, SO, $SO_2$, or $CH_2$.

m is 0 or 1, n is 1, 2, 3, 4, 5, 6, 7, 8, 9, 10, 11, 12, 13, 14, 15, 16, 17, 18, 19, or 20.

L is a linker or a linker-cell-binding molecule (Q) covalently bound cluster, or a linker which has a functional group on the linker that enables linkage with a cell-binding agent (CBA). L is preferably a releasable linker, which has the formula of: -Ww-(Aa)r-Tt-; or -Ww-(Aa)r-Tt-Q; or Q-Ww-(Aa)r-Tt-; wherein W is a Stretcher unit; w is 0 or 1; Aa is an Amino Acid unit comprising independent amino acids; r is an integer ranging from 0 to 100. The Stretcher unit W may contain a self-immolative or a non-self-immolative component, peptidyl units, a hydrazone bond, a disulfide, an ester, an oxime, an amide, or a thioether bond. The self-immolative unit includes, but is not limited to, aromatic compounds that are electronically similar to the para-aminobenzylcarbamoyl (PAB) groups such as 2-aminoimidazol-5-methanol derivatives, heterocyclic PAB analogs, beta-glucuronide, and ortho or para-aminobenzylacetals. Preferably, the self-immolative linker component has one of the following structures:

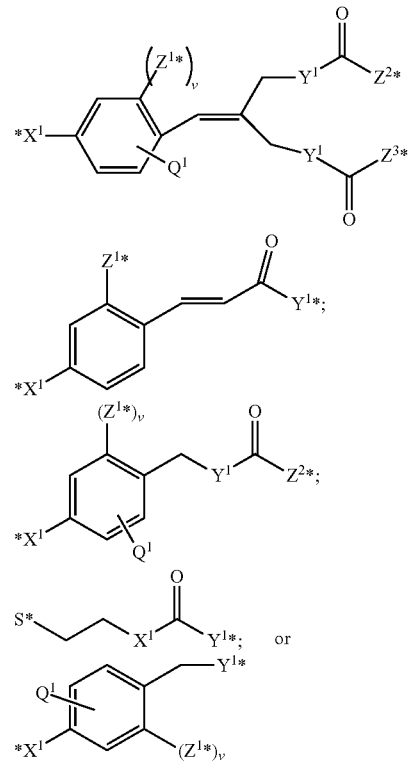

wherein the (*) atom is the point of attachment of additional spacer or releasable linker units, or the cytotoxic agent, and/or the binding molecule (CBA); $X^1$, $Y^1$, $Z^2$ and $Z^3$ are independently NH, O, or S; $Z^1$ is independently H, NH, O or S; v is 0 or 1; Q' is independently H, OH, $C_1$~$C_6$ alkyl, $(OCH_2CH_2)_n$, F, Cl, Br, I, $OR_{12}$, $SR_{12}$, $NR_{12}R_{12}'$, $N=NR_{12}$, $N=R_{12}$, $NR_{12}R_{12}'$, $NO_2$, $SOR_{12}R_{12}'$, $SO_2R_{12}$, $SO_3R_{12}$, $OSO_3R_{12}$, $PR_{12}R_{12}'$, $PO_2R_{12}R_{12}'$, $OPO(OR_{12})(OR_{12}')$, or $OCH_2PO(OR_{12}(OR_{12}')$ wherein $R_{12}$ and $R_{12}'$ are as defined above; preferably $R_{12}$ and $R_{12}'$ are independently selected from H, $C_1\sim C_8$ alkyl; $C_2\sim C_8$ alkenyl, alkynyl, heteroalkyl; $C_3\sim C_8$ aryl, heterocyclic, carbocyclic, cycloalkyl, heterocycloalkyl, heteroaralkyl, alkylcarbonyl; or pharmaceutical cation salts.

The non-self-immolative linker component is one of the following structures:

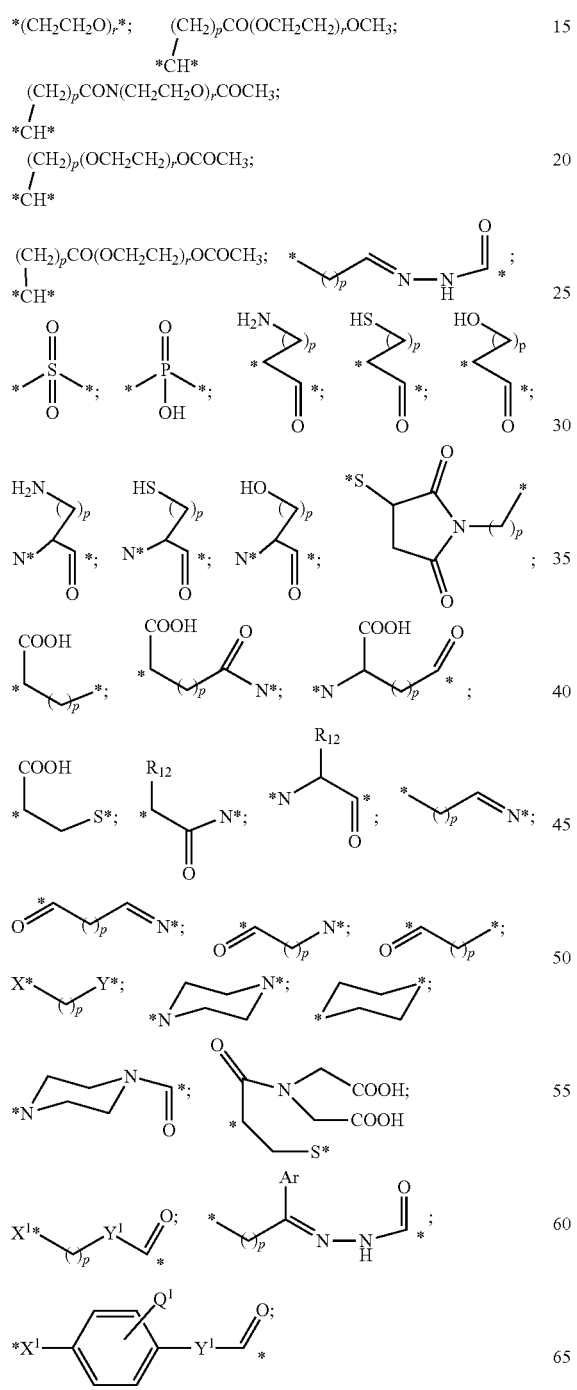
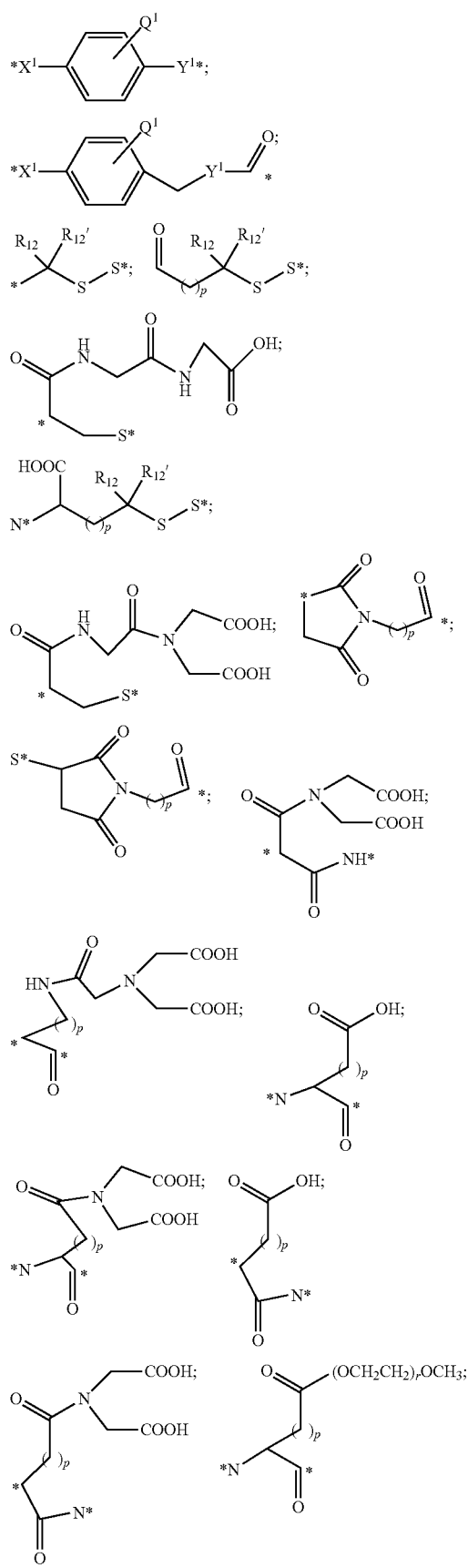

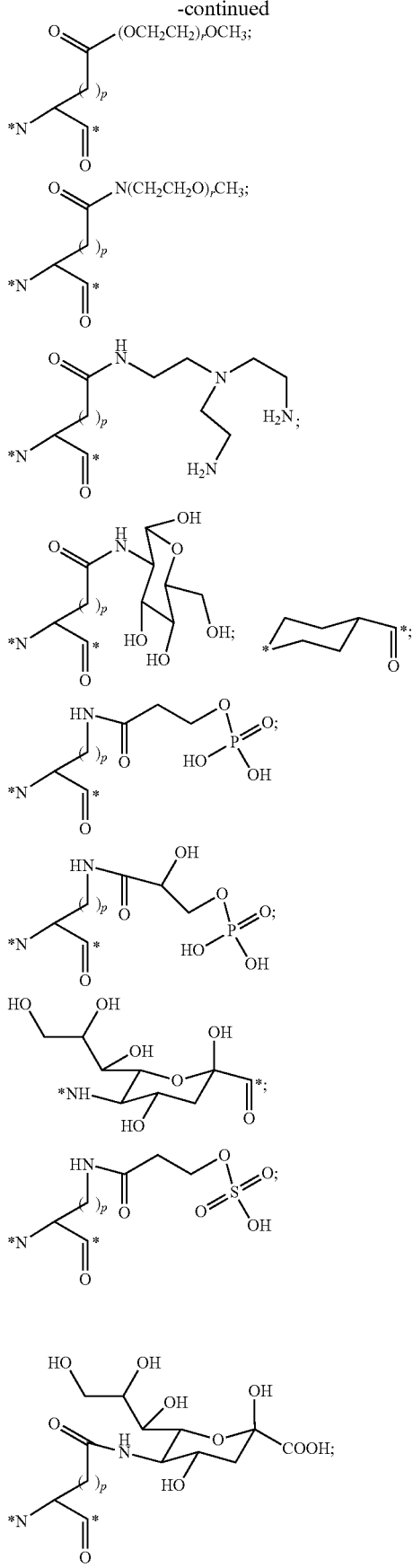
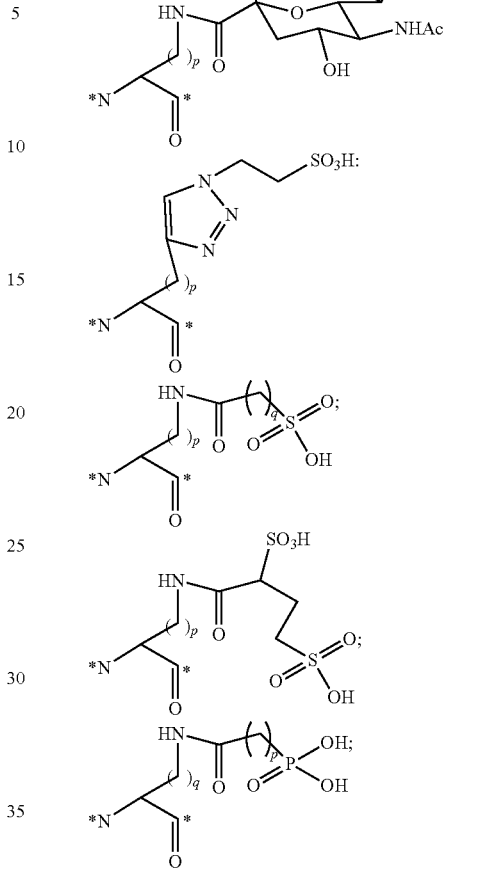

Wherein the (*) atom is the point of attachment of additional spacer or releasable linkers, the cytotoxic agents, and/or the binding molecules; $X^1$, $Y^1$, $Q^1$, $R_{12}$, $R_{12}'$ are defined as above; r is 0~100; p and q are 0~6 independently.

Spacer (T) is a linear, branched or cyclic alkyl, alkenyl, alkynyl or aryl having from 1 to 10 carbon atoms, or T can be a polyethylene glycol (—$CH_2CH_2O$—) spacer; t is 0, or 1~100. T can also undergo cyclization upon amide bond hydrolysis, such amides include substituted and unsubstituted 4-aminobutyric acid amides, appropriately substituted bicycle [2.2.1] and bicycle [2.2.2] ring systems, and 2-aminophenylpropionic acid amides.

The linker L can be also selected from the group consisting of: $R_{12}$, $OR_{12}$, $OR_{12}O$, $NHR_{12}$, $NHR_{12}NH$, $NR_{11}R_{12}$, $SR_{12}S$, $OR_{12}NH$, $OR_{12}Ar$, $NHR_{12}Ar$, —$(CR_{11}R_{14}$-$(Aa)_r$$(CR_{12}'R_{12}')_q(OCH_2CH_2)_r$, —$(CR_{11}R_{12})_p(CR_{12}'R_{12}")_q(Aa)_r$$(OCH_2CH_2)_r$—, -$(Aa)_r$-$(CR_{11}R_{12})_p(CR_{12}'R_{12}")_q$—$(OCH_2CH_2)_r$, —$(CR_{11}R_{12})_p(CR_{12}'R_{12}")_n(OCH_2CH_2)_t$$(Aa)_r$-, —$(CR_{11}R_{12})_p(CH=CH)(CR_{12}'R_{12}")_q(Aa)_r$$(OCH_2CH_2)_r$, —$(CR_{11}R_{12})_p(NR_{12}CO)(Aa)_r(CR_{12}'R_{12}")_q$—$(OCH_2CH_2)_r$, —$(CR_{11}R_{12})_p(Aa)_r(NHCO)(CR_{12}'R_{12}")_q$—$(OCH_2CH_2)_r$—, $(CR_{11}R_{12})_p(OCO)(Aa)_r$-$(CR_{12}'R_{12}")_q$—$(OCH_2CH_2)_r$, —$(CR_{11}R_{12})_p(OCNR_7)(Aa)_r(CR_{12}'R_{12}")$$(OCH_2CH_2)_r$, —$(CR_{11}R_{12})_p$—$(CO)$-$(Aa)_r(CR_{12}'R_{12}")_q$$(OCH_2CH_2)_r$, —$(CR_{11}R_{12})_p(NR_{11}CO)(Aa)_r(CR_{12}'R_{12}")_q$$(OCH_2CH_2)_r$, —$(CR_{11}R_{12})_p$—$(OCO)(Aa)_r(CR_{12}'R_{12}")_q$—$(OCH_2CH_2)_r$, —$(CR_{11}R_{12})_p(OCNR_7)(Aa)_r(CR_{12}'R_{12}")_q$—$(OCH_2CH_2)_r$, —$(CR_{11}R_{12})_p(CO)(Aa)_r(CR_{12}'R_{12}")_q$ (OCH$_2$CH$_2$)$_t$, —(CR$_{11}$R$_{12}$)$_p$-phenyl-CO-(Aa)$_r$(CR$_{12}$'R$_{12}$')$_q$, —(CR$_{11}$R$_{12}$)$_p$-furyl-CO-(Aa)$_r$(CR$_{12}$'R$_{12}$")$_q$, —(CR$_{11}$R$_{12}$)$_p$-oxazolyl-CO-(Aa)$_r$(CR$_{12}$'R$_{12}$")$_q$, —(CR$_{11}$R$_{12}$)$_p$-thiazolyl-CO-(Aa)$_r$(CR$_{12}$'R$_{12}$")$_q$, —(CR$_{11}$R$_{12}$)$_p$-thienyl-CO—(CR$_{12}$'R$_{12}$")$_q$, —(CR$_{11}$R$_{12}$)$_p$-imidazolyl-CO—(CR$_{12}$'R$_{12}$")$_q$—, —(CR$_{11}$R$_{12}$)$_p$-morpholino-CO-(Aa)$_r$(CR$_{12}$'R$_{12}$")$_q$—, —(CR$_{11}$R$_{12}$)$_p$-piperazino-CO(Aa)$_r$-(CR$_{12}$'R$_{12}$")$_q$—, —(CR$_{11}$R$_{12}$)$_p$—N-methyl-piperazin-CO(Aa)$_r$(CR$_{12}$'R$_{12}$")$_q$—, —(CR$_{11}$R$_{12}$)$_p$(Aa)$_r$-phenyl-, —(CR$_{11}$R$_{12}$)$_p$-(Aa)$_r$-furyl-, —(CR$_{11}$R$_{12}$)$_p$-oxazolyl(Aa)$_r$-, —(CR$_{11}$R$_{12}$)$_p$-thiazolyl-(Aa)$_r$-, —(CR$_{11}$R$_{12}$)$_p$-thienyl-(Aa)$_r$-, —(CR$_{11}$R$_{12}$)$_p$-imidazolyl(Aa)$_r$-, —(CR$_{11}$R$_{12}$)$_p$-morpholino-(Aa)$_r$-, —(CR$_{11}$R$_{12}$)$_p$-piperazino-(Aa)$_r$-, —(CR$_{11}$R$_{12}$)$_p$—N-methylpiperazino-(Aa)$_r$-, —K(CR$_{11}$R$_{12}$)$_p$-(Aa)$_r$(CR$_{12}$'R$_{12}$")$_q$(OCH$_2$CH$_2$)$_t$—, —K(CR$_{11}$R$_{12}$)$_p$(CR$_{12}$'R$_{12}$")$_q$(Aa)$_r$(OCH$_2$CH$_2$)$_t$—, —K(Aa)$_r$(CR$_{11}$R$_{12}$)$_p$(CR$_{12}$'R$_{12}$")$_q$—(OCH$_2$CH$_2$)$_t$—, —K(CR$_{11}$R$_{12}$)$_p$(CR$_{12}$'R$_{12}$")$_q$(OCH$_2$CH$_2$)$_t$(Aa)$_r$, —K(CR$_{11}$R$_{12}$)$_p$(CR$_7$=CR$_8$)(CR$_{12}$'R$_{12}$")$_q$-(Aa)$_r$(OCH$_2$CH$_2$)$_t$—, —K(CR$_{11}$R$_{12}$)$_p$(NR$_7$CO)(Aa)$_r$(CR$_{12}$'R$_{12}$")$_q$(OCH$_2$CH$_2$)$_t$, —K(CR$_{11}$R$_{12}$)$_p$-(Aa)$_r$(NR$_7$—CO)(CR$_{12}$'R$_{12}$")$_q$(OCH$_2$CH$_2$)$_t$, —K(CR$_{11}$R$_{12}$)$_p$(OCO)(Aa)$_r$(CR$_{12}$'R$_{12}$")$_q$(OCH$_2$CH$_2$)$_t$—, —K(CR$_{11}$R$_{12}$)$_p$(OCNR$_7$)(Aa)$_r$(CR$_{12}$'R$_{12}$")$_q$(OCH$_2$CH$_2$)$_t$—, —K(CR$_{11}$R$_{12}$)$_p$(CO)(Aa)$_r$(CR$_{12}$'R$_{12}$")$_q$—(OCH$_2$CH$_2$)$_t$, —K(—CR$_{11}$R$_{12}$)$_p$(NR$_{11}$CO)(Aa)$_r$(CR$_{11}$'R$_{12}$")$_q$(OCH$_2$CH$_2$)$_t$, —K(CR$_{11}$R$_{12}$)$_p$(OCO)-(Aa)$_r$(CR$_{12}$'R$_{12}$")$_q$(OCH$_2$CH$_2$N, —K(CR$_{11}$R$_{12}$)$_p$(OCNR$_7$)(Aa)$_r$(CR$_{12}$'R$_{12}$")$_q$(OCH$_2$CH$_2$)$_t$, R$_{12}$)$_p$(CO)(Aa)$_r$-, —K(CR$_{12}$'R$_{12}$")$_q$(OCH$_2$CH$_2$)$_r$Q, —K(CR$_{11}$R$_{12}$)$_p$-phenyl-CO-(Aa)$_r$(CR$_{12}$'R$_{12}$")$_q$—, —K(CR$_{11}$R$_{12}$)$_p$-furyl-CO(Aa)$_r$-(CR$_{12}$'R$_{12}$")$_q$, —K(C$_{11}$R$_{12}$)$_p$-oxazolyl-CO(Aa)$_r$(CR$_{12}$'R$_{12}$")$_q$—, —K(CR$_{11}$R$_{12}$)$_p$-thiazolyl-CO(Aa)$_r$-(CR$_{12}$'R$_{12}$")$_q$, —K(CR$_{11}$R$_{12}$)$_p$-thienyl-CO(CR$_{12}$'R$_{12}$")$_q$—, —K(CR$_{11}$R$_{12}$)$_p$-imidazolyl-CO—(CR$_{12}$'R$_{12}$")$_q$, —K(CR$_{11}$R$_{12}$)$_p$-morpholino-CO(Aa)$_r$(CR$_{12}$'R$_{12}$")$_q$—, —K(C$_{11}$R$_{12}$)$_p$-piperazino-CO-(Aa)$_r$(CR$_{12}$'R$_{12}$")$_q$, —K(CR$_{11}$R$_{12}$)$_p$—N-methylpiperazin-CO(Aa)$_r$-(CR$_{12}$'R$_{12}$")$_q$, —K(CR$_{11}$R$_{12}$)$_p$-(Aa)$_r$-phenyl-, —K(CR$_{11}$R$_{12}$)$_m$(Aa)$_r$-furyl-, —K(CR$_{11}$R$_{12}$)$_p$-oxazolyl(Aa)$_r$-, —K(CR$_{11}$R$_{12}$)$_m$-thiazolyl-(Aa)$_r$-, —K(CR$_{11}$R$_{12}$)$_p$-thienyl-(Aa)$_r$, —K(CR$_{11}$R$_{12}$)$_p$-imidazolyl(Aa)$_r$-, —K((CR$_{11}$R$_{12}$)$_m$-morpholino-(Aa)$_r$, —K(CR$_{11}$R$_{12}$)$_p$-piperazino-(Aa)$_r$-, —K(CR$_{11}$R$_{12}$)$_m$N-methylpiperazino-(Aa)$_r$.

Wherein Aa, r, n, p, q, t, R$_7$, R$_{11}$, R$_{12}$, R$_{12}$', R$_{12}$" are as defined above. K is NR$_{12}$, O, S, Se, B, C$_3$~C$_{10}$ of Ar or Heterocyclic.

Q is a cell-binding molecule (CBA), or a functional group that enables linkage with a cell-binding agent, or a functional group that enables linkage with a linker attached on a cell-binding agent. The function group is chosen from a thiol, an amine, a hydrazine, an alkoxylamino, a disulfide substituent, a maleimido, a haloacetyl group, a carboxy acid, an N-hydroxy succinimide ester, a ketone, an ester, an aldehyde, an alkynyl, an alkenyl, or a protected thiol or disulfide group, such as SAc, SSR$_1$ or SSAr. Ar is an aromatic group or hetero aromatic group.

The compounds of the general formula (I) having geometrical and stereoisomers are also a part of the invention.

In certain embodiments, the *amanita* toxin derivatives are presented by the following formula (Ia) (Ib), and (Ic), wherein an amide linker linked to C-5 position of the indole unit.

Wherein "----", "∽∽∽", R$_1$, R$_2$, R$_4$, R$_5$, R$_7$, R$_8$, R$_9$, R$_{10}$, L and Q are defined the same as in Formula (I).

In certain embodiments, the *amanita* toxin derivatives are presented by the following formula (Id), wherein an amide linker linked to C-7 position of the indole unit.

Wherein R$_1$, R$_2$, R$_4$, R$_5$, R$_{10}$, L and Q are defined the same as in Formula (I).

In certain embodiments, the *amanita* toxin derivatives of formula (Ia), (Ib), and (Ic) are represented by the following formulas (Ia-1), (Ia-2), (Ia-3), (Ia-4), (Ia-5), (Ia-6), (Ia-7), (Ia-8), (Ia-9), (Ia-10), (Ia-11), (Ia-12), (Ia-13), (Ia-14), (Ia-15), (Ia-16), (Ia-17), (Ia-18), (Ia-19), (Ia-20), (Ia-21), (Ia- 22), (Ia-23), (Ia-24), (Ib-1), (Ib-2), (Ib-3), (Ib-4), (Ib-5), (Ib-6), (Ib-7), (Ic-1), (Ic-2), (Ic-3), (Ic-4), (Ic-5), and (Ic-6):
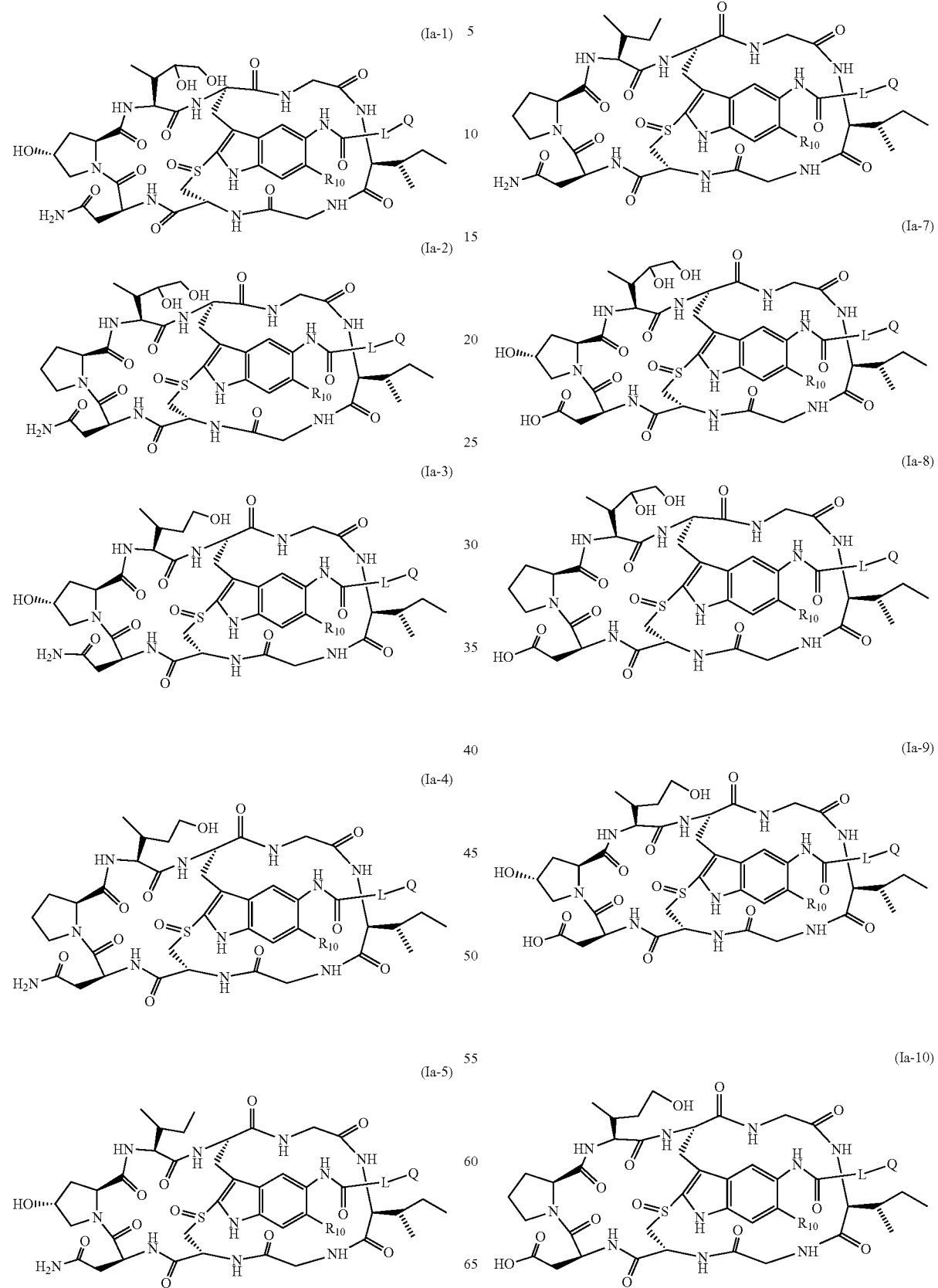

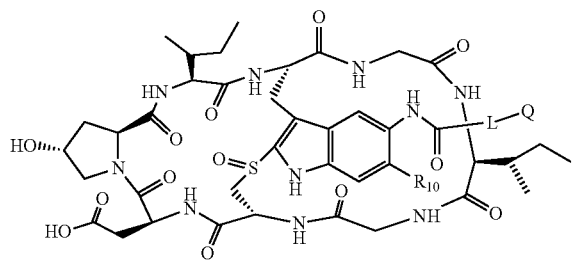
(Ia-11)
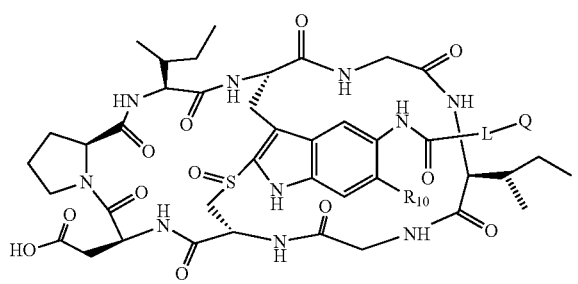
(Ia-12)
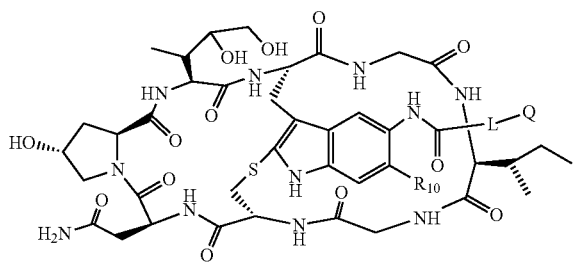
(Ia-13)
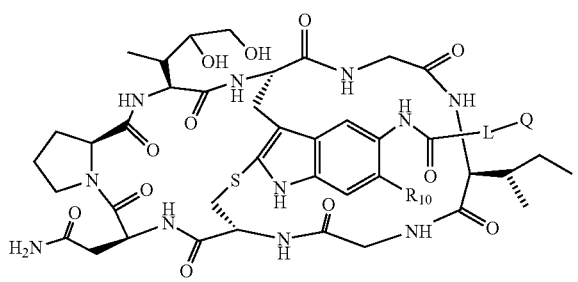
(Ia-14)
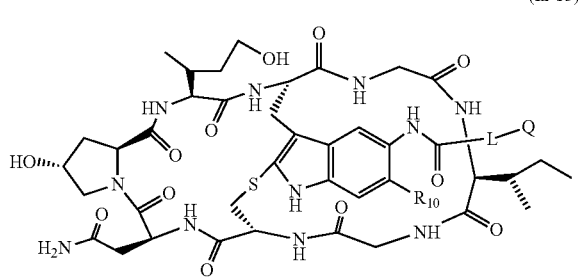
(Ia-15)
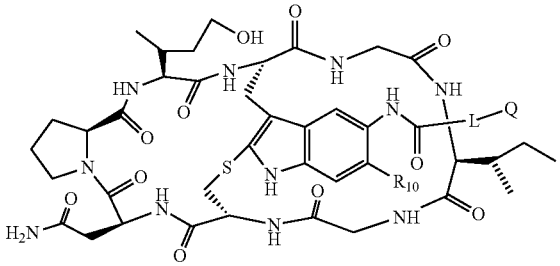
(Ia-16)
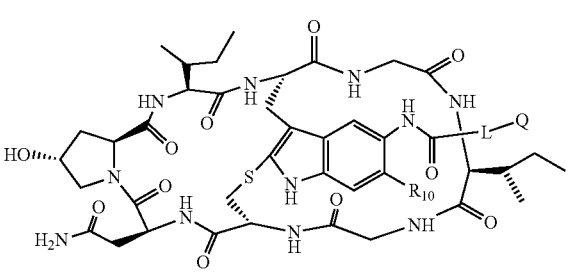
(Ia-17)
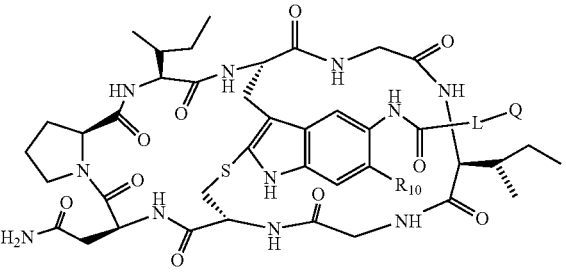
(Ia-18)
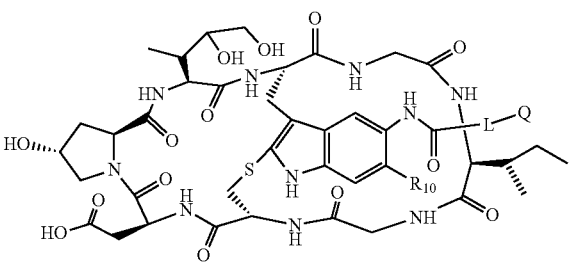
(Ia-19)
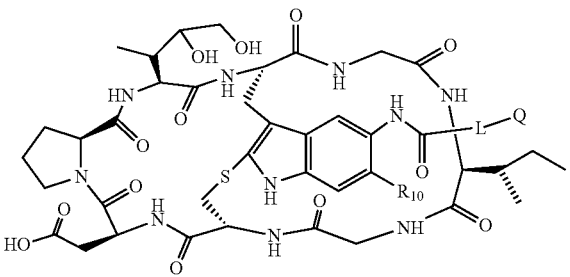
(Ia-20)

-continued
(Ia-21)
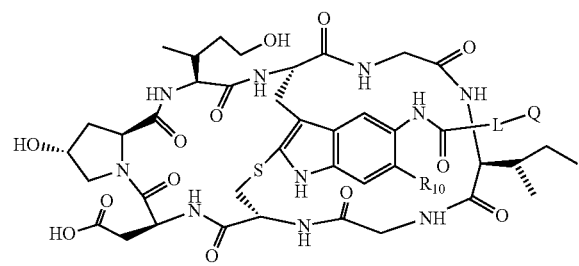
(Ia-22)
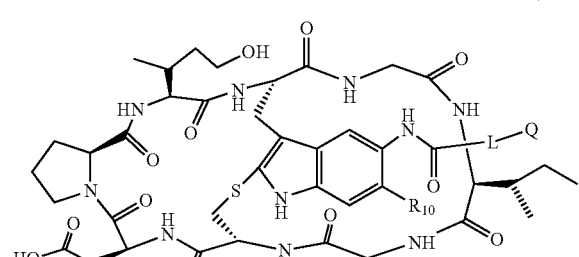
(Ia-23)
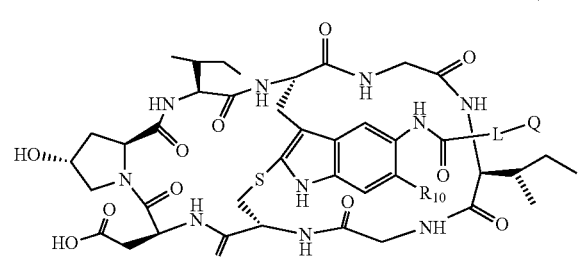
(Ia-24)
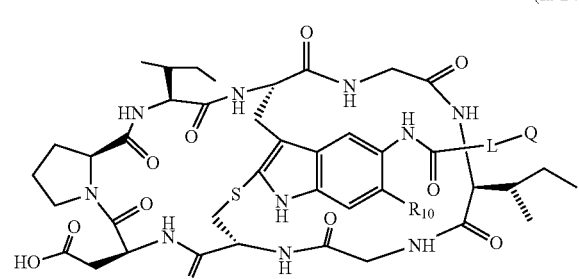
(Ib-1)
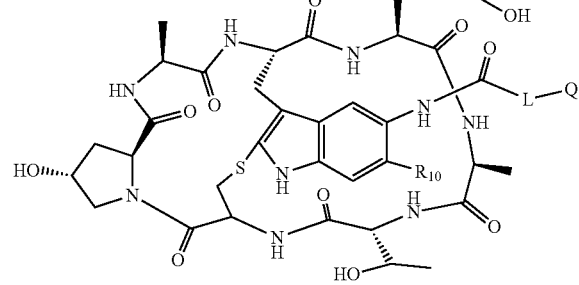
-continued
(Ib-2)
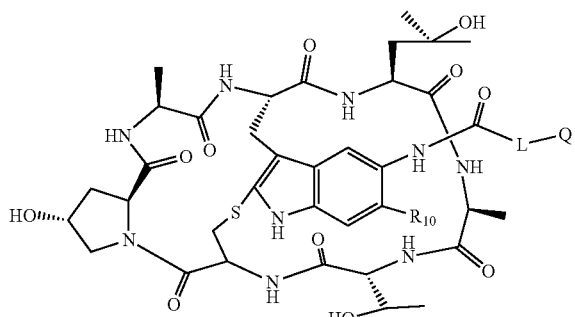
(Ib-3)
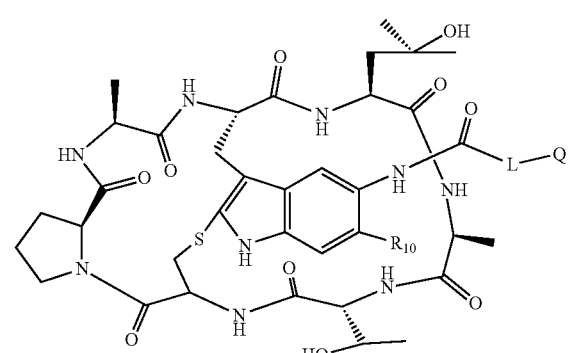
(Ib-4)
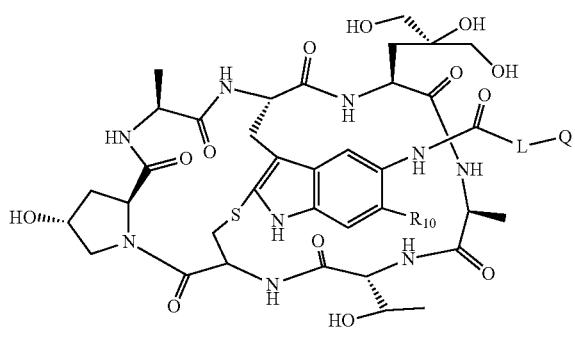
(Ib-5)
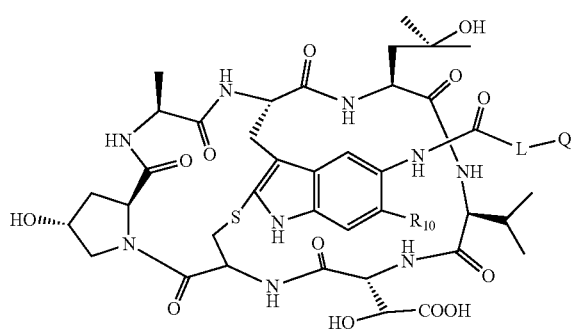

33
-continued
(Ib-6)
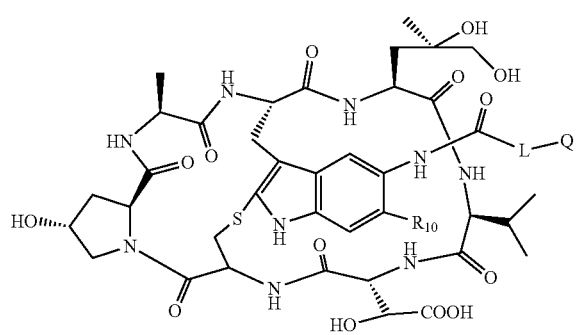
(Ib-7)
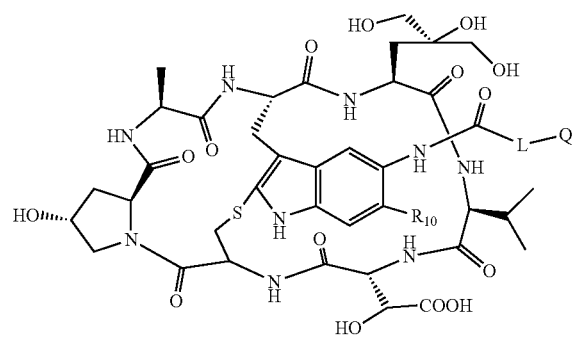
(Ic-1)
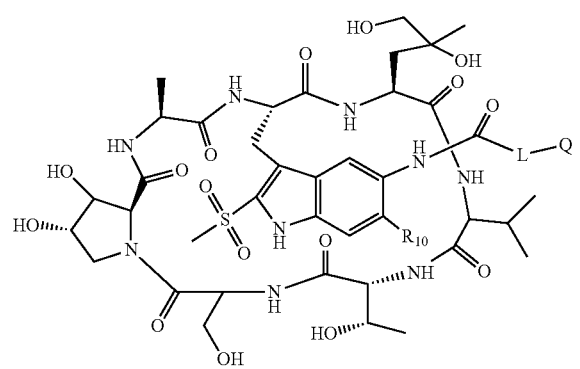
(Ic-2)
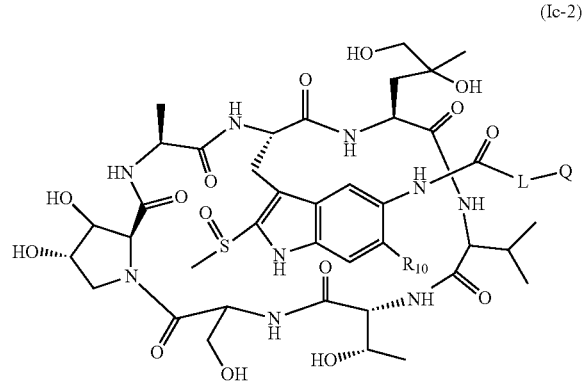
34
-continued
(Ic-3)
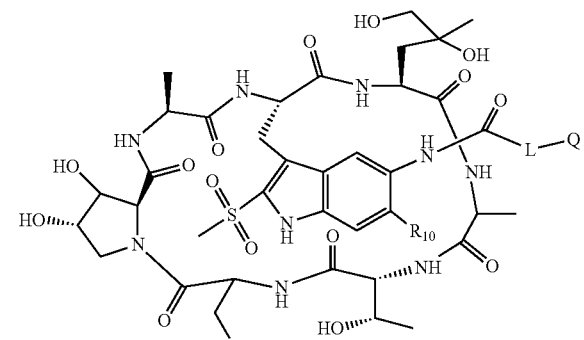
(Ic-4)
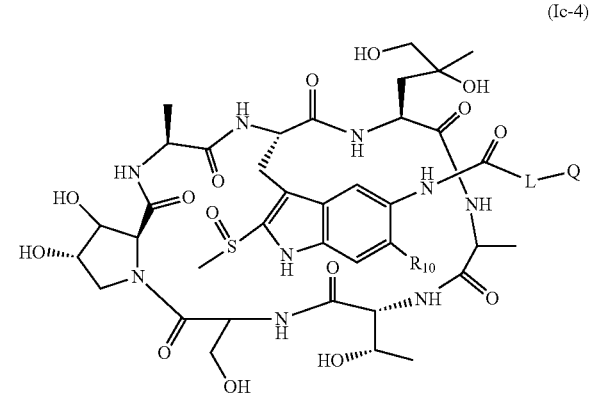
(Ic-5)
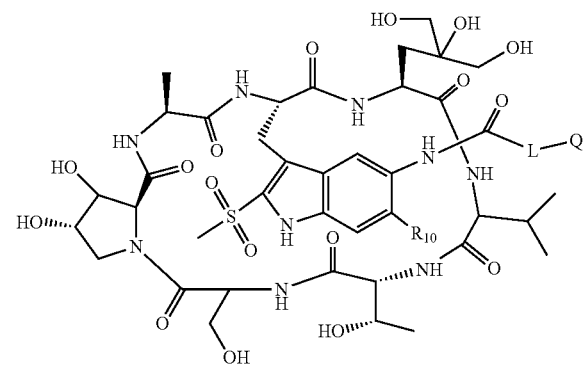
(Ic-6)
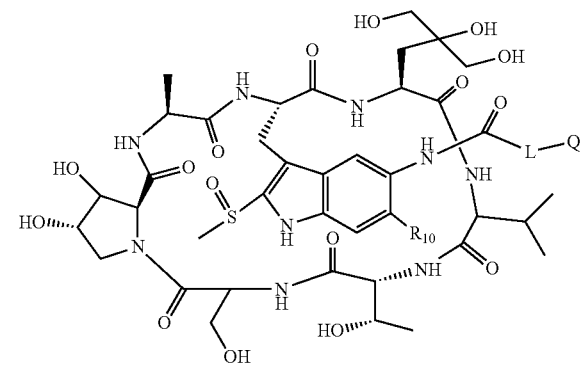
Wherein $R_{10}$, L and Q are defined the same as in Formula (I).
In certain embodiments, the *amanita* toxin derivatives of formula (Id) are represented by the following formulas (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), and (Id-21):
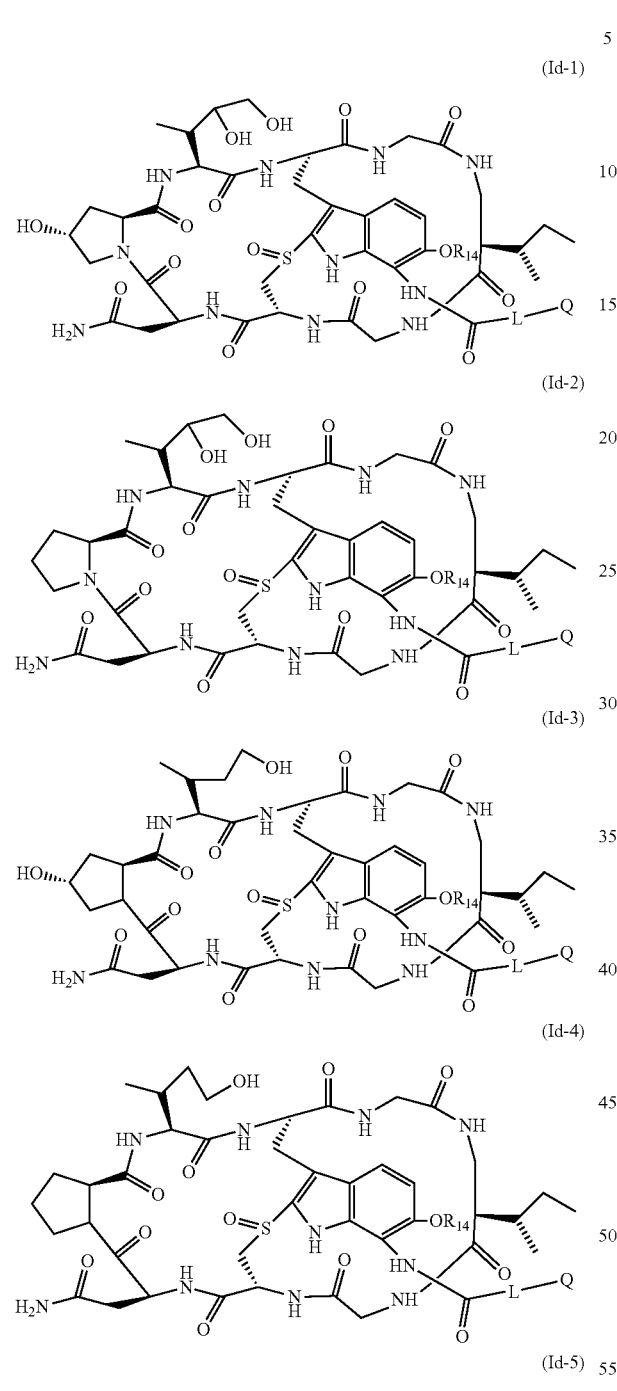
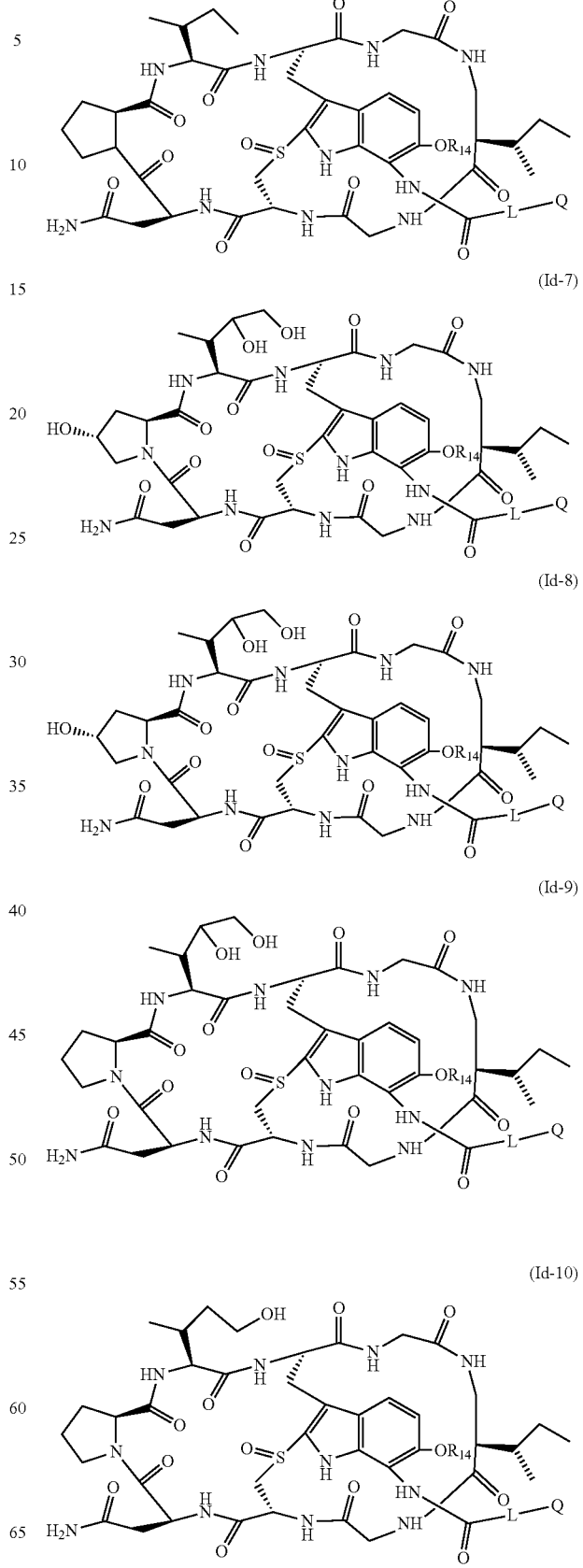

(Id-11)
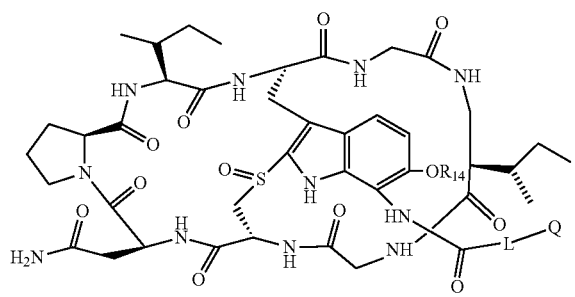
(Id-12)
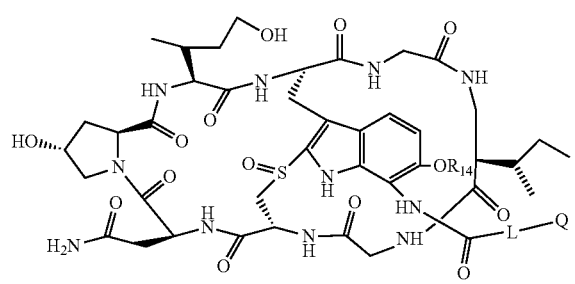
(Id-13)
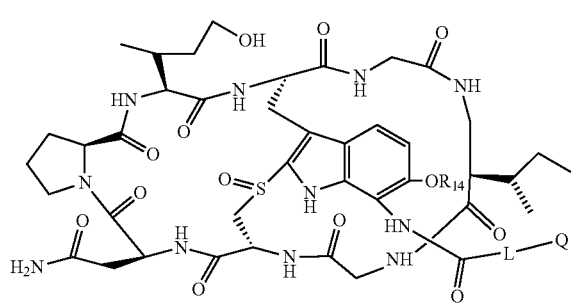
(Id-14)
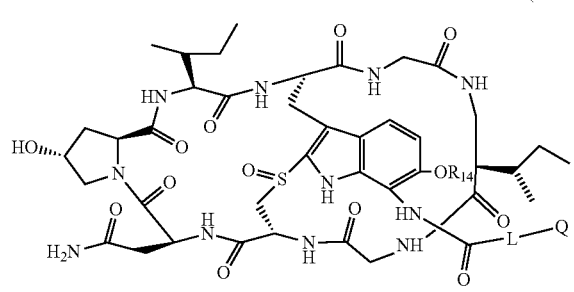
(Id-15)
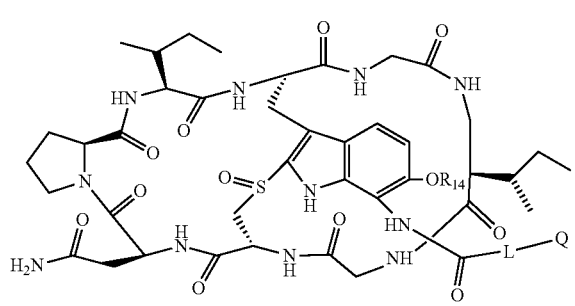
(Id-16)
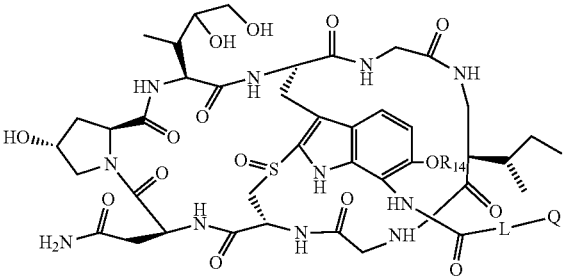
(Id-17)
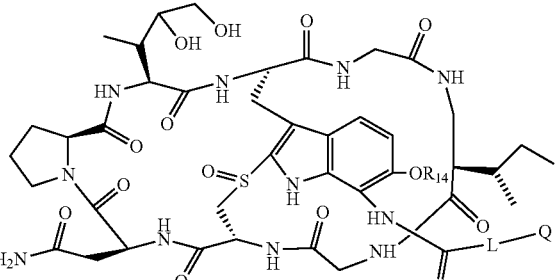
(Id-18)
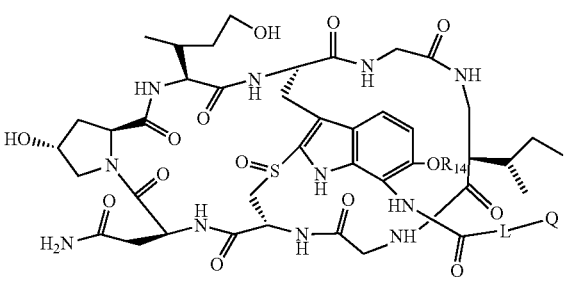
(Id-19)
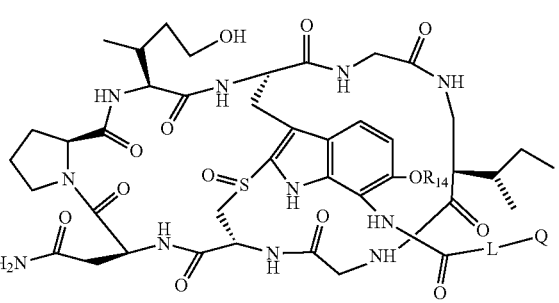
(Id-20)
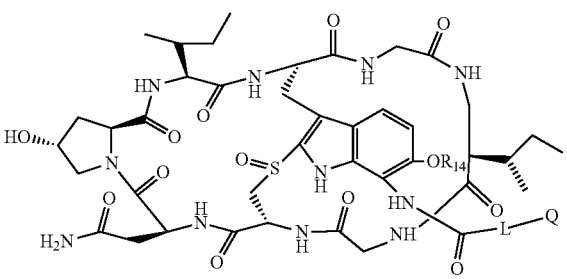

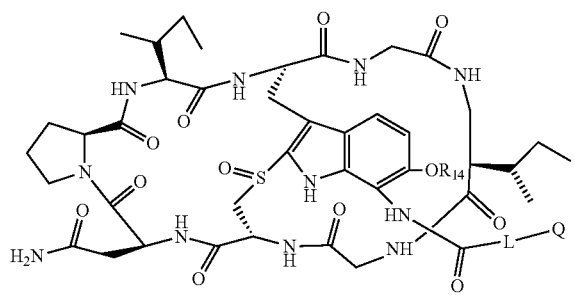

(Id-21)

Wherein $R_{14}$ is H, $PO_3^{2-}$, $SO_3^-$, $R_{12}$, —$COR_{12}$, —$COCH_3$, —$COOR_{12}$, —$CONR_{12}R_{12}'$, —$C(=O)R_{12}NH(Aa)_t$, (an amino acid or peptide, wherein Aa is an amino acid or a polypeptide, t represents 0-100); —$CSNHR_{12}$ (thiocarbamate); —$SOR_{12}$ (sulfoxide); —$SO_2R_{12}$ (sulfone); —$SO_3^-$, $HSO_3$, $HSO_2$, or a salt of $HSO_3^-$, $SO_3^{2-}$ or —$HSO_2^-$ (sulphite); $P(O)(OM_1)(OM_2)$, $CH_2OP(O)(OM_1)(OM_2)$, $SO_3M_1$; glycoside (glucoside, galactoside, mannoside, glucuronoside, alloside, fructoside, etc), $M_1$ and $M_2$ are independently H, Na, K, Ca, Mg, $NH_4$, $NR_1'R_2'R_3'$; $R_1'$, $R_2'$ and $R_3'$, are independently H, $C_1\sim C_8$ alkyl.

In further embodiments, the cytotoxic agent and its conjugate of this invention are preferred one of the following structures:

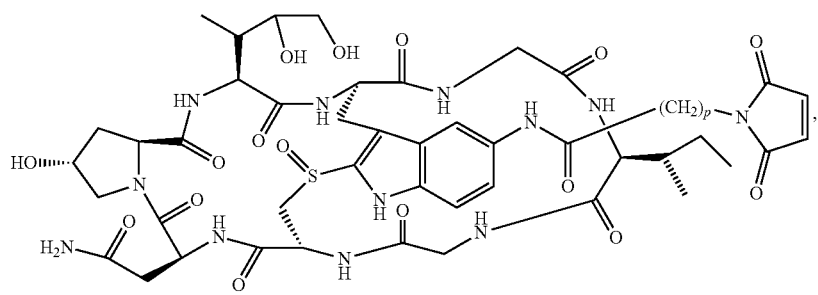

(I-1)

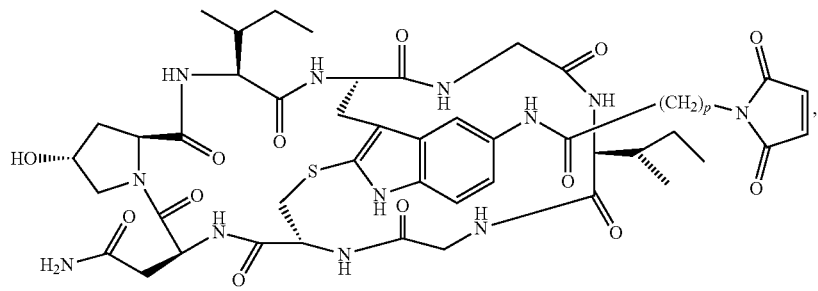

(I-2)

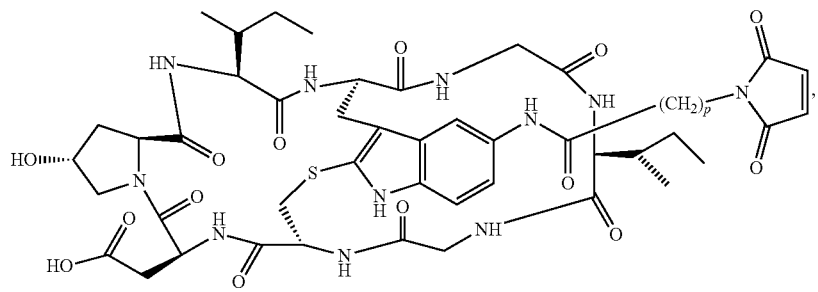

(I-3)

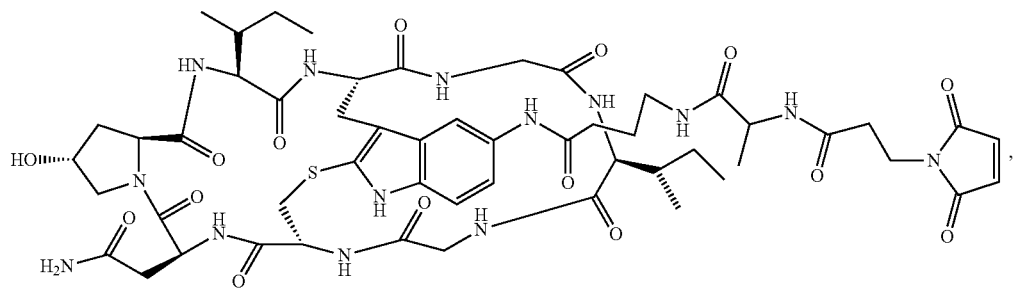

(I-4)

-continued
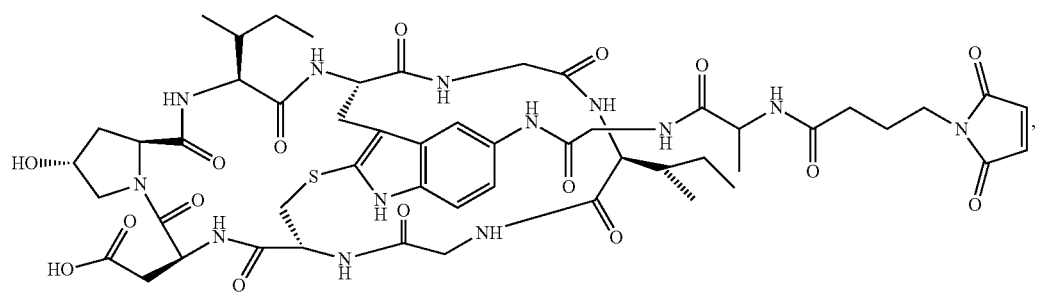
(I-5)
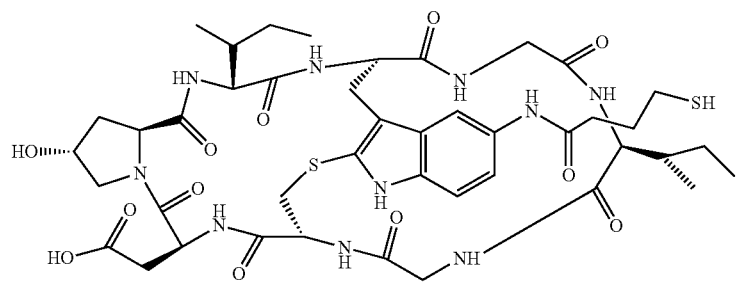
(I-6)
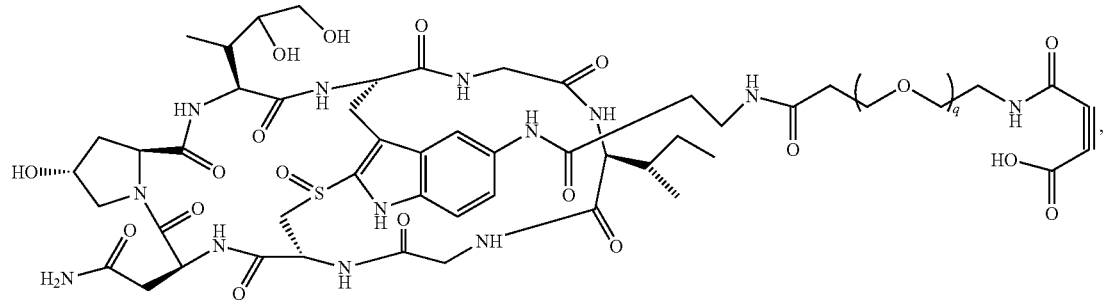
(I-7)
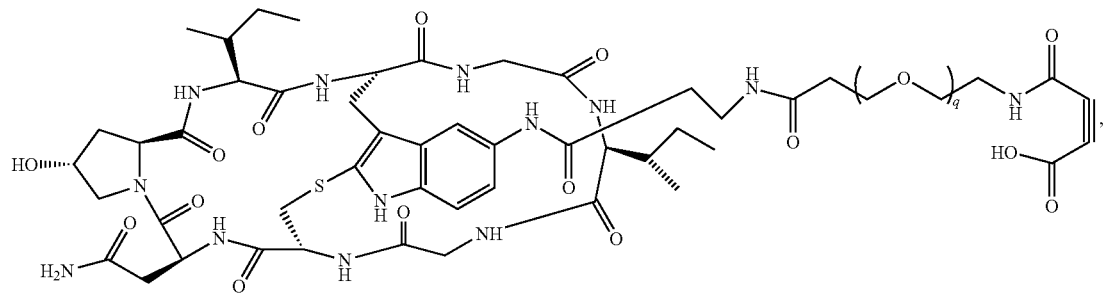
(I-8)
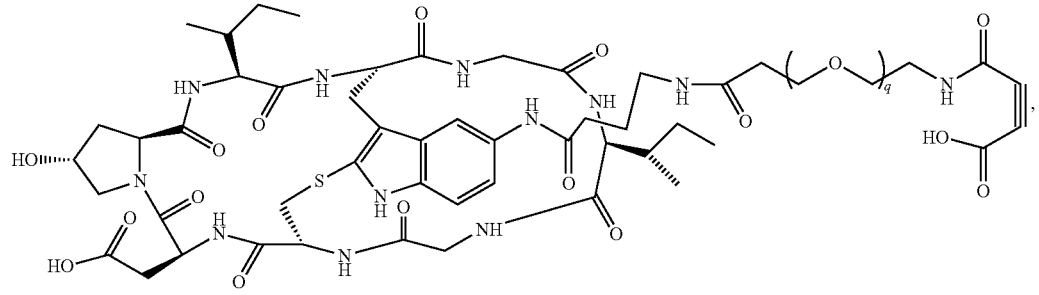
(I-9)

-continued
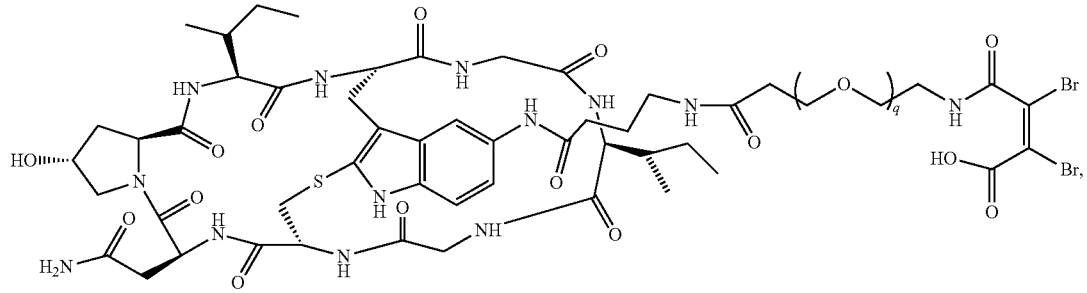
(I-10)
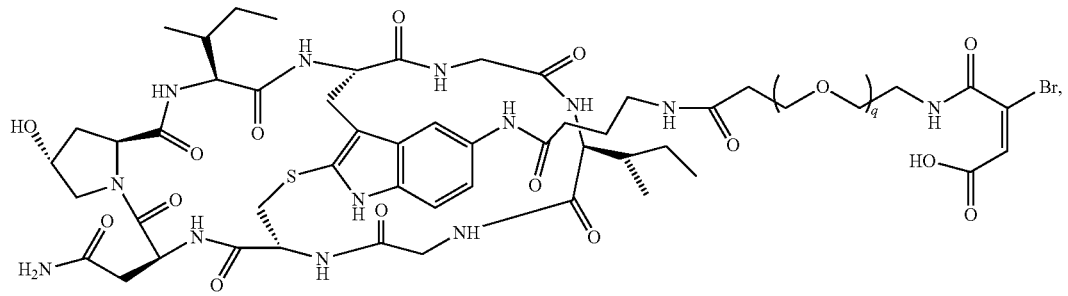
(I-11)
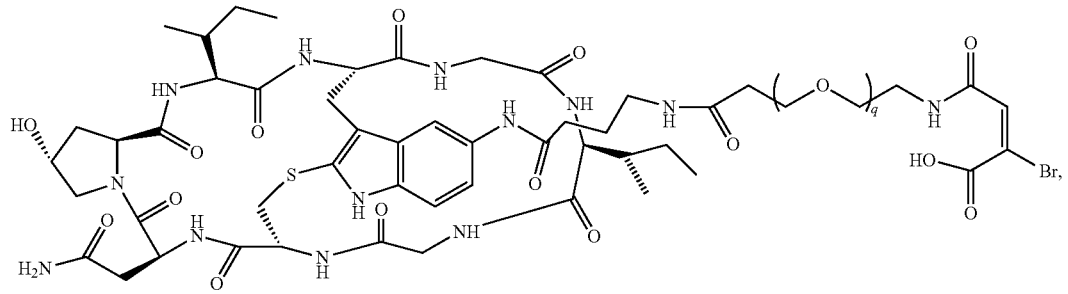
(I-12)

(I-13)
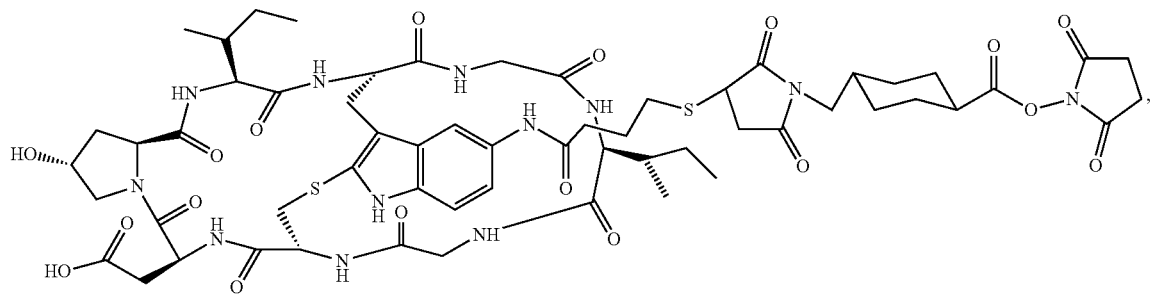
(I-14)

-continued
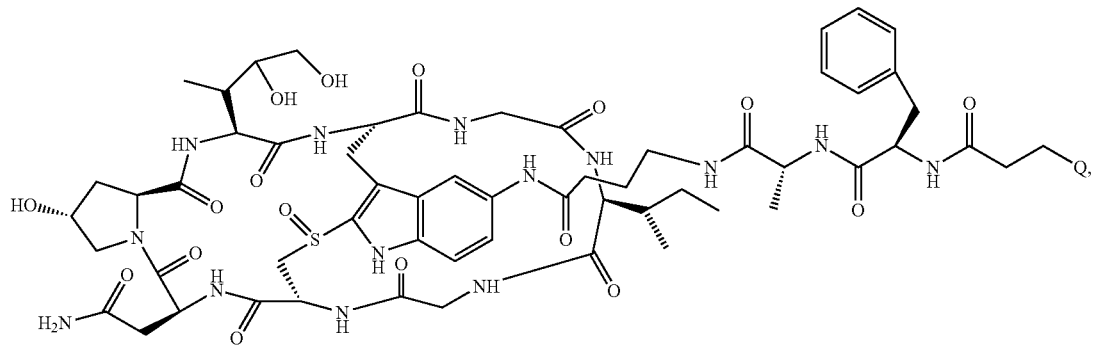
(I-15)
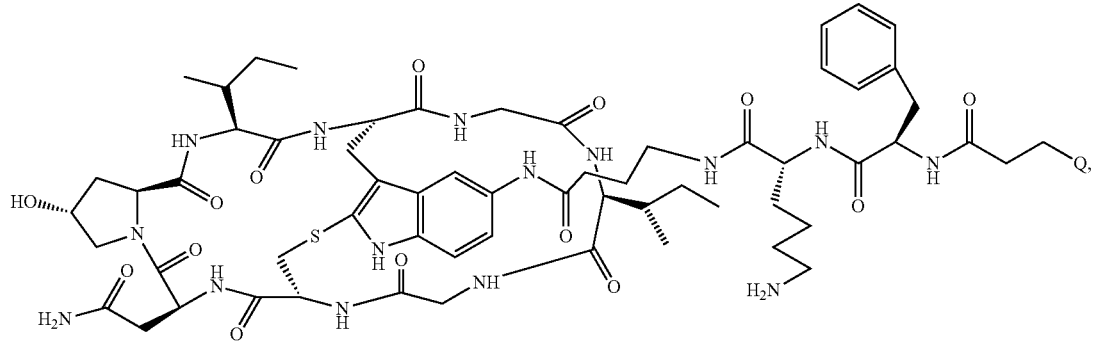
(I-16)
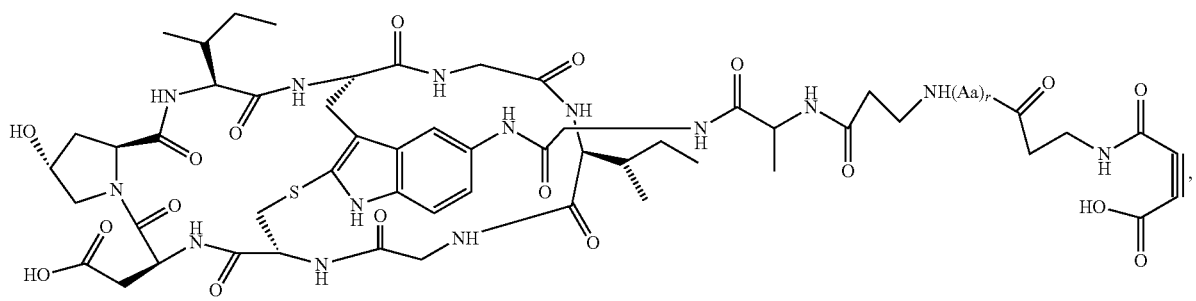
(I-17)
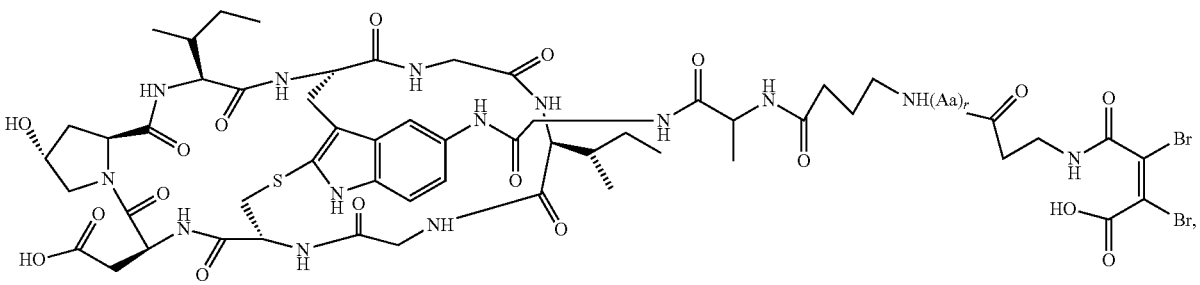
(I-18)
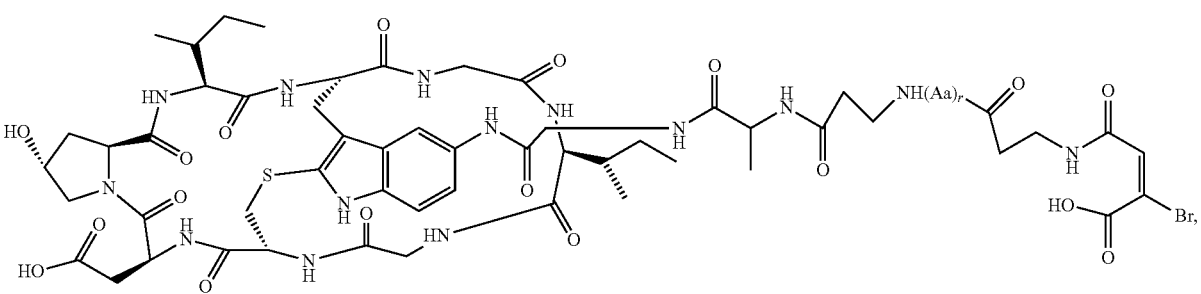
(I-19)

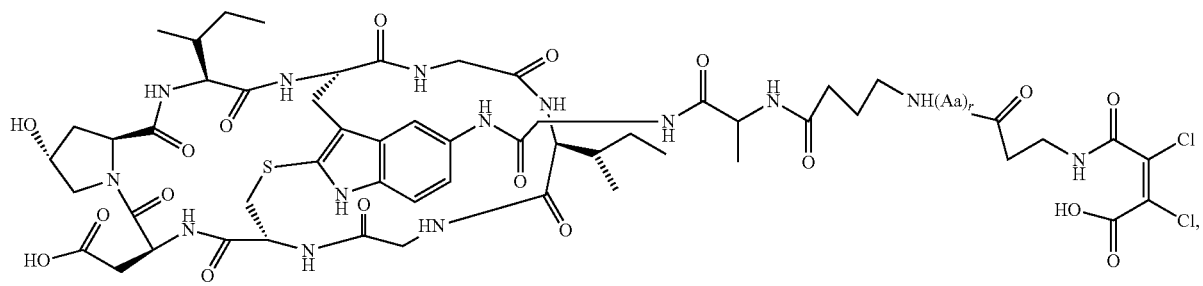
(I-20)
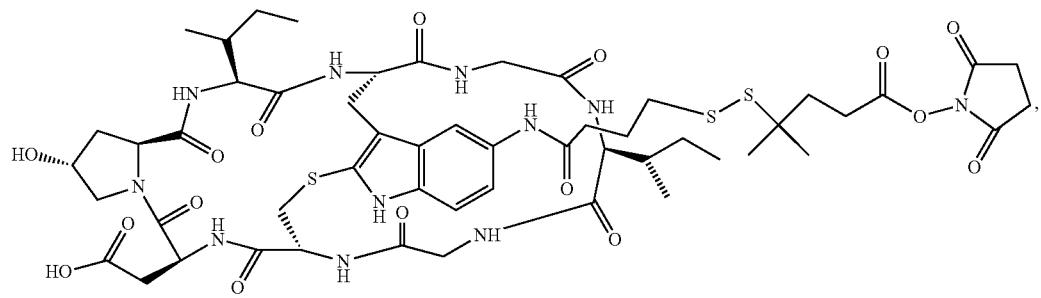
(I-21)
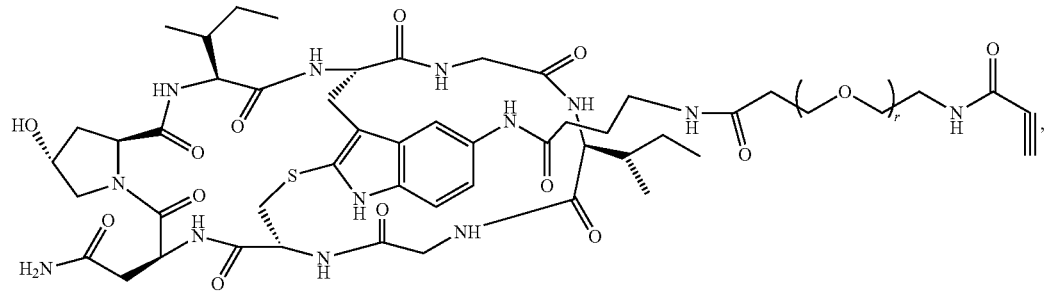
(I-22)
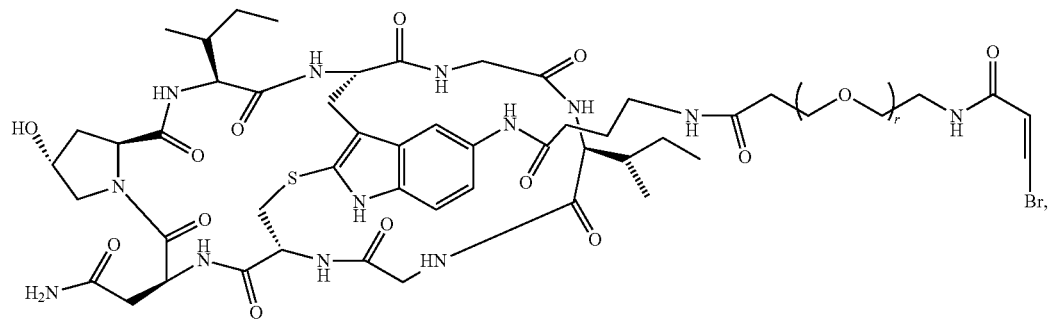
(I-23)
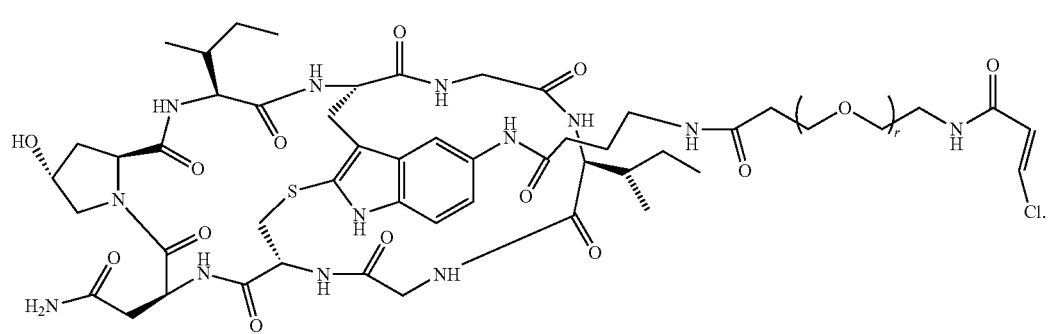
(I-24)

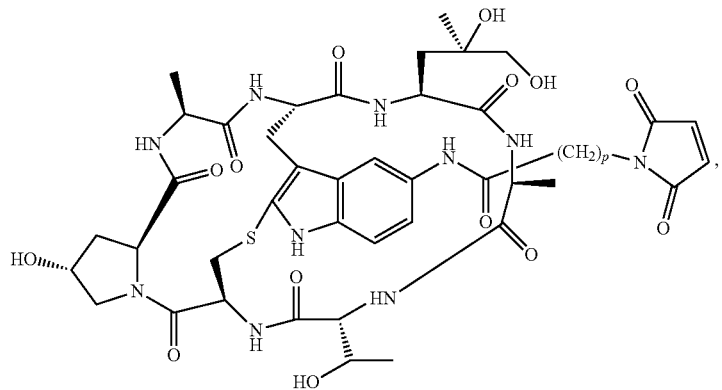
(I-25)
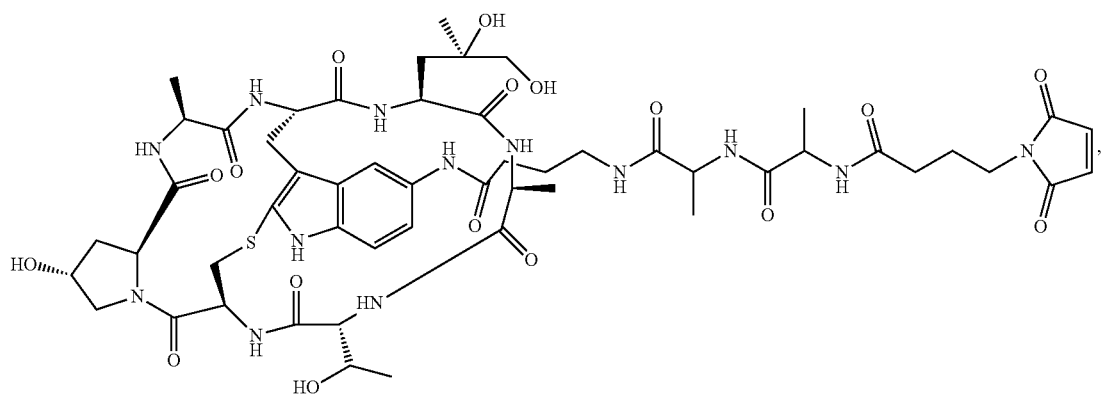
(I-26)
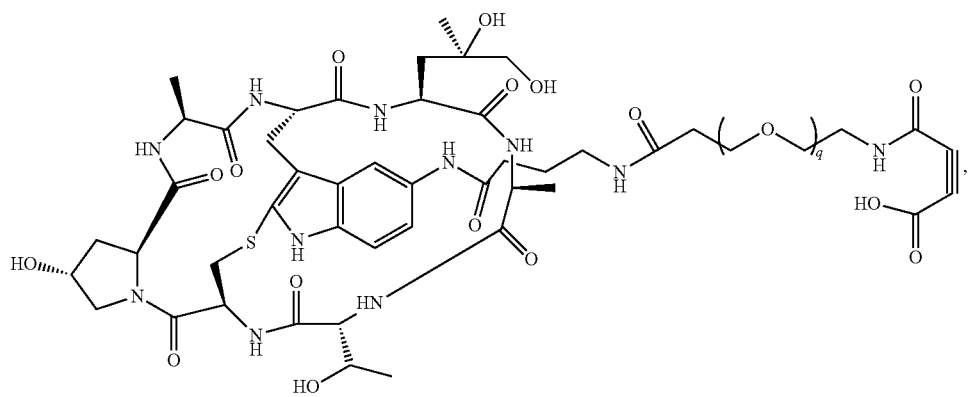
(I-27)
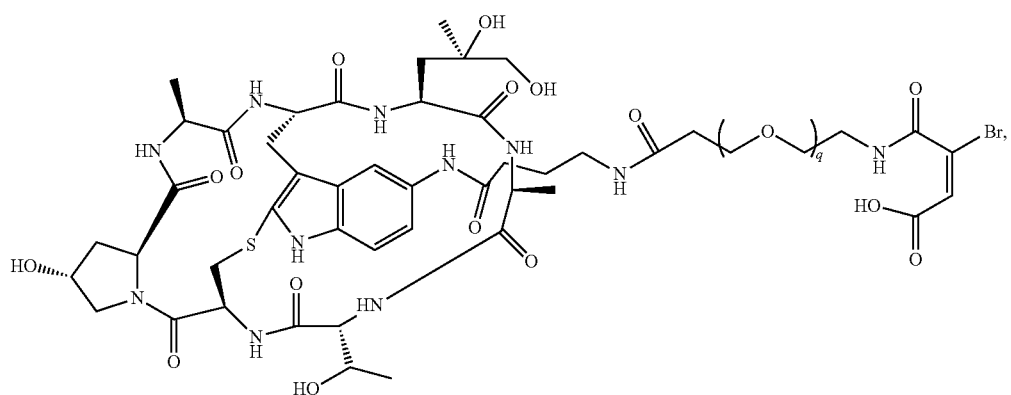
(I-28)

-continued
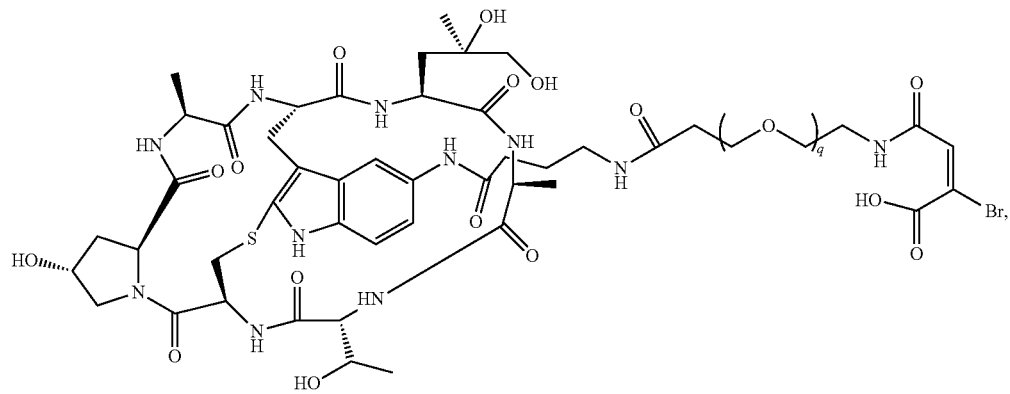
(I-29)
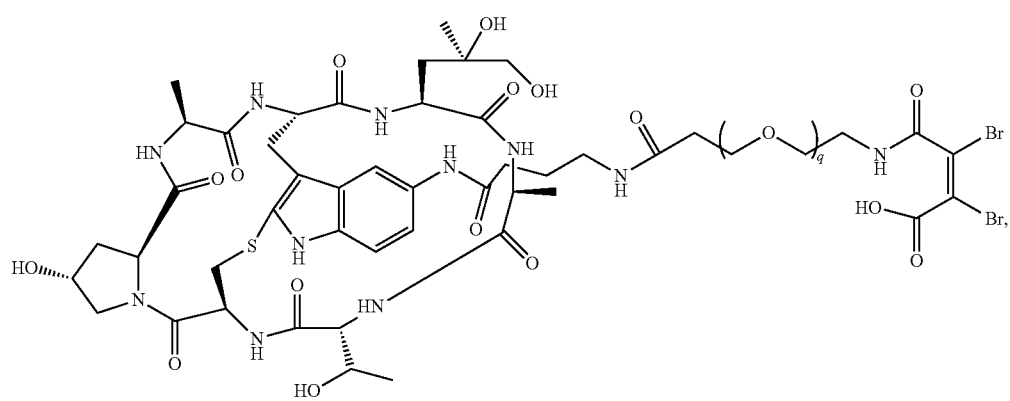
(I-30)
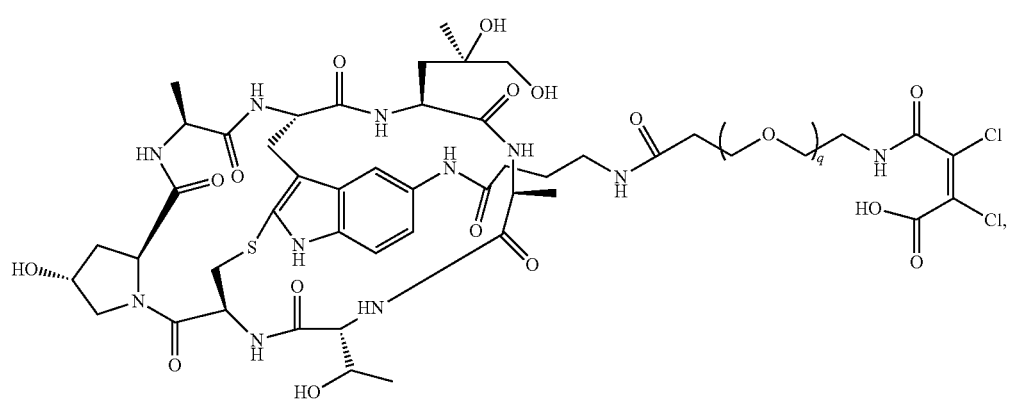
(I-31)
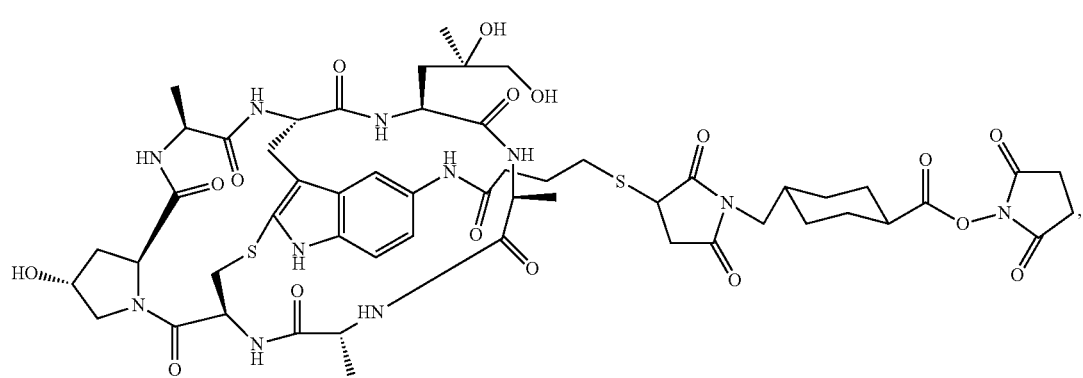
(I-32)

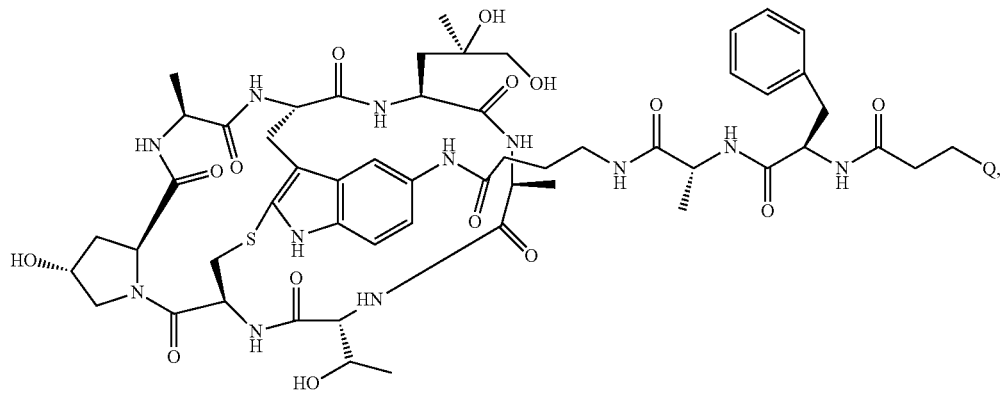
(I-33)
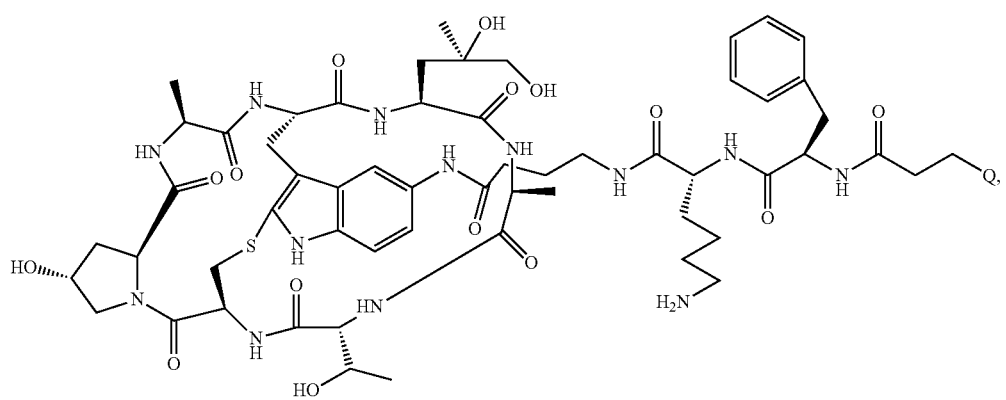
(I-34)
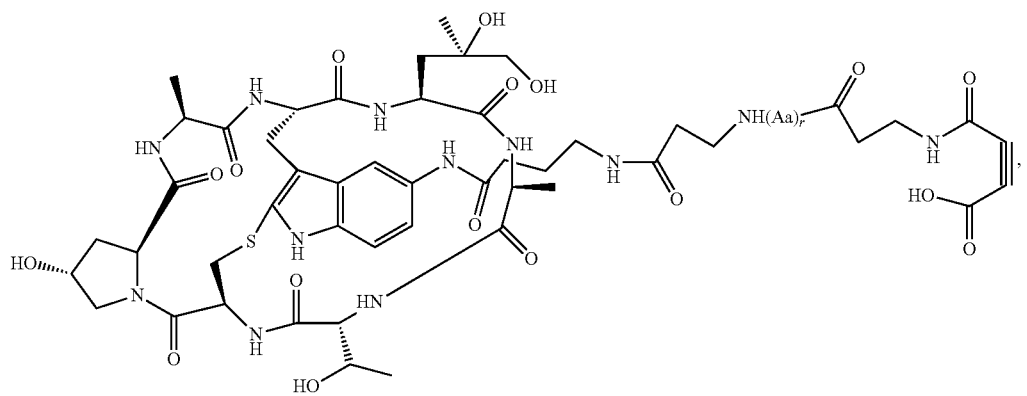
(I-35)
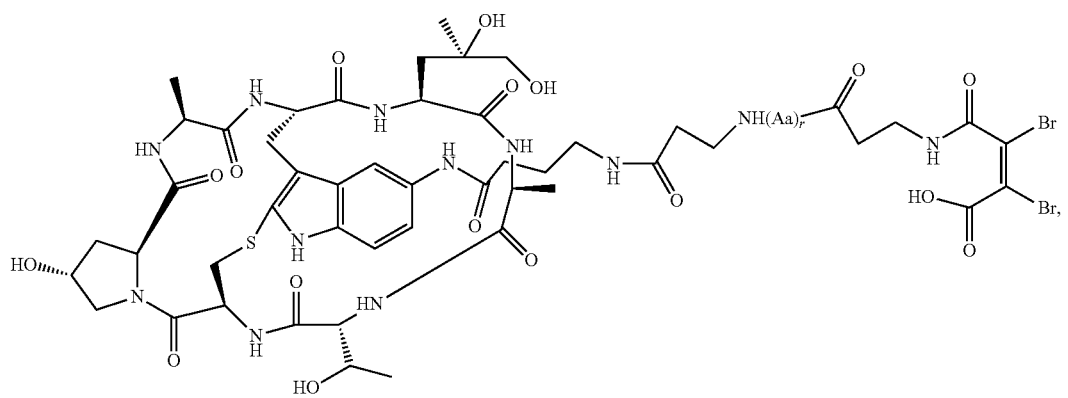
(I-36)

-continued
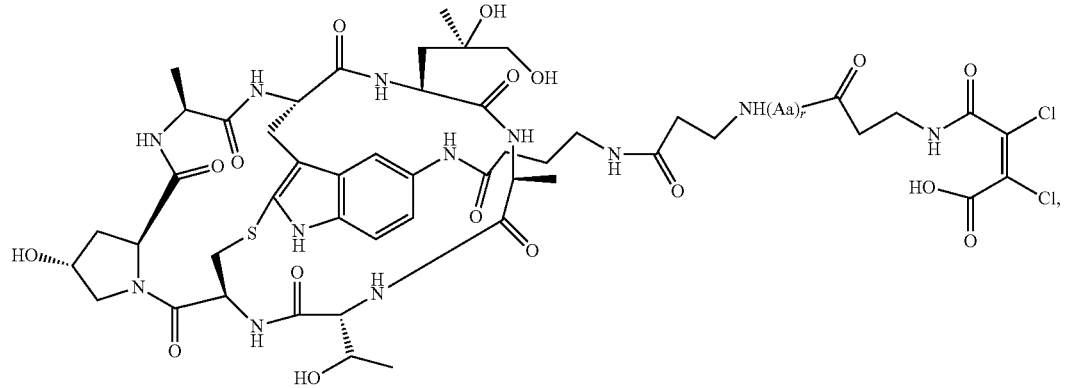
(I-37)
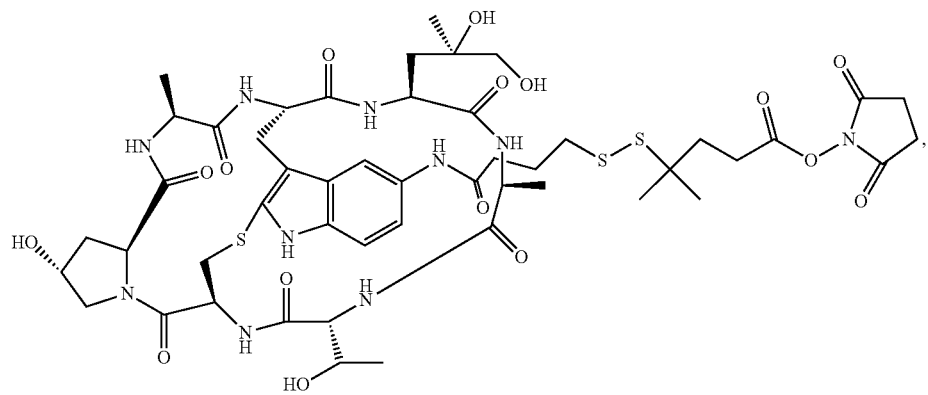
(I-38)
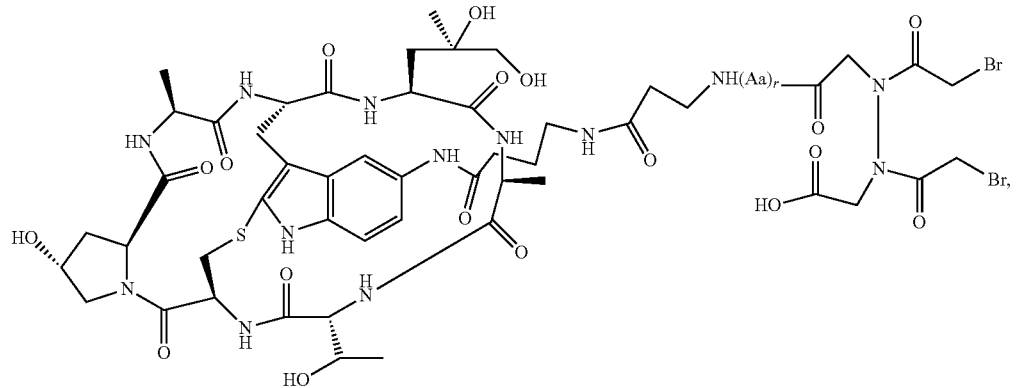
(I-39)
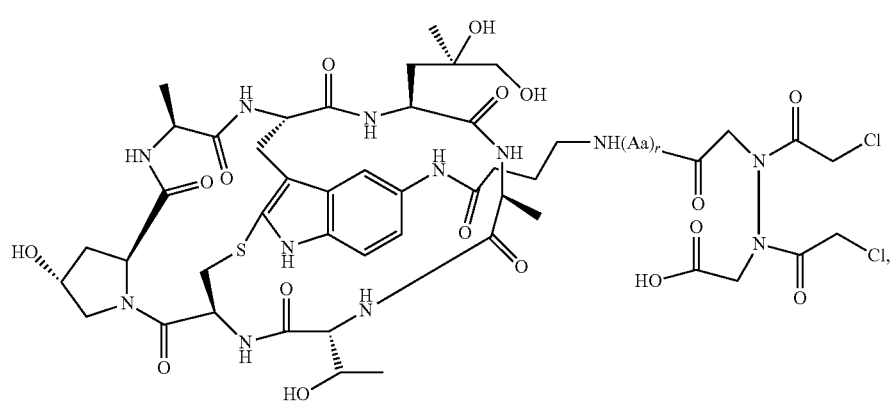
(I-40)

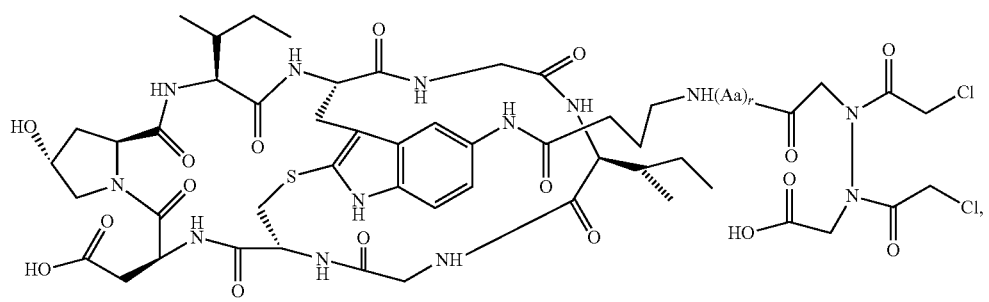
(I-41)
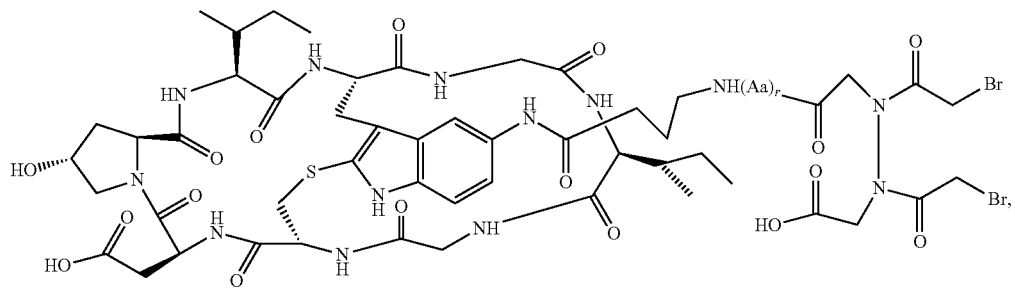
(I-42)
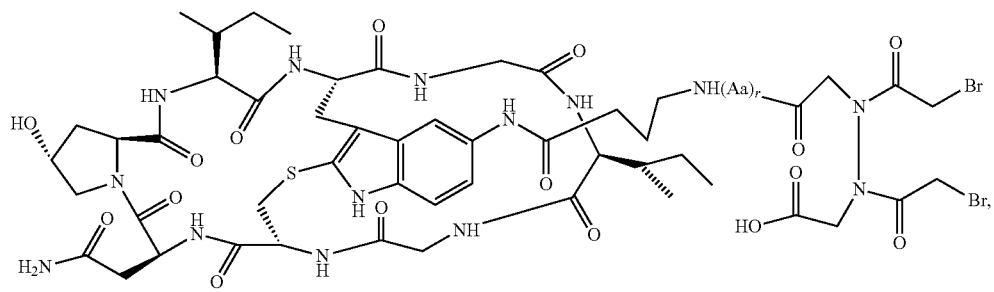
(I-43)
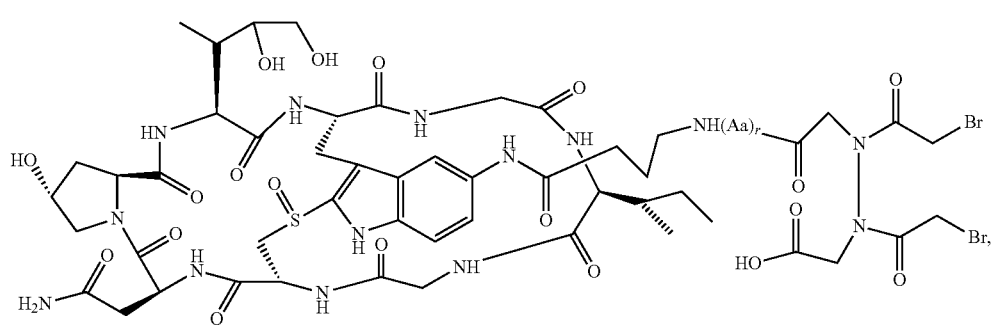
(I-44)
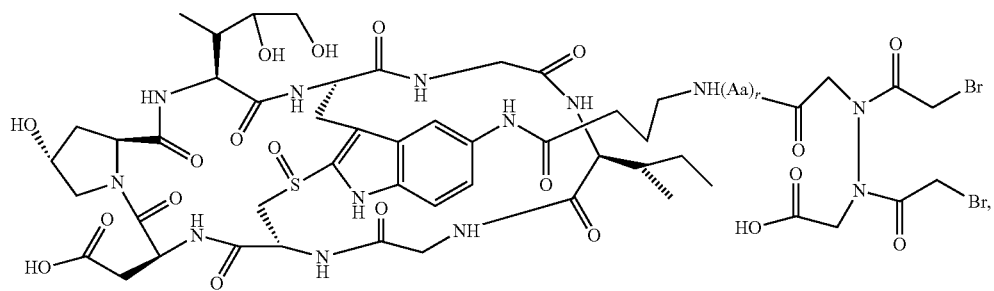
(I-45)

-continued
(I-46)
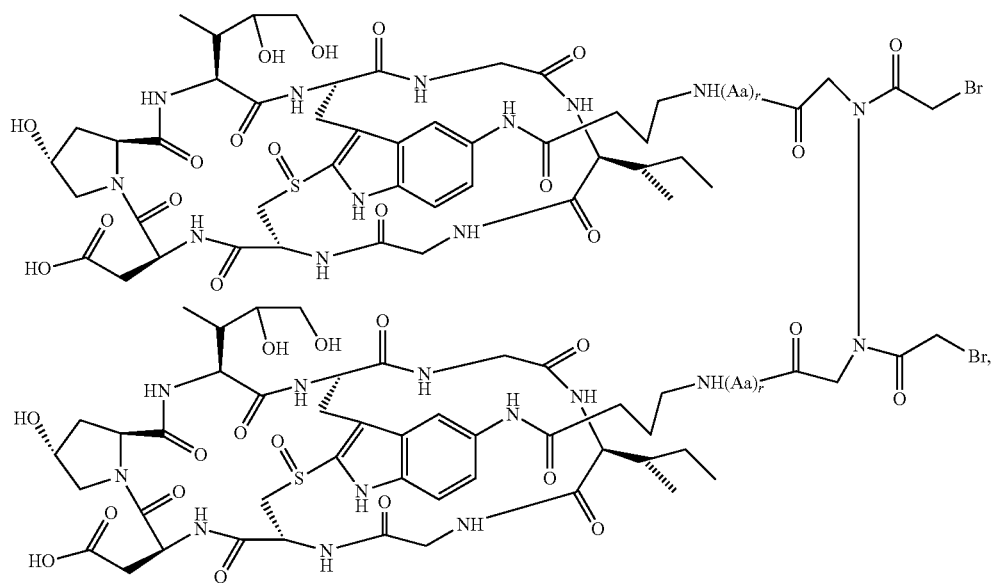
(I-47)
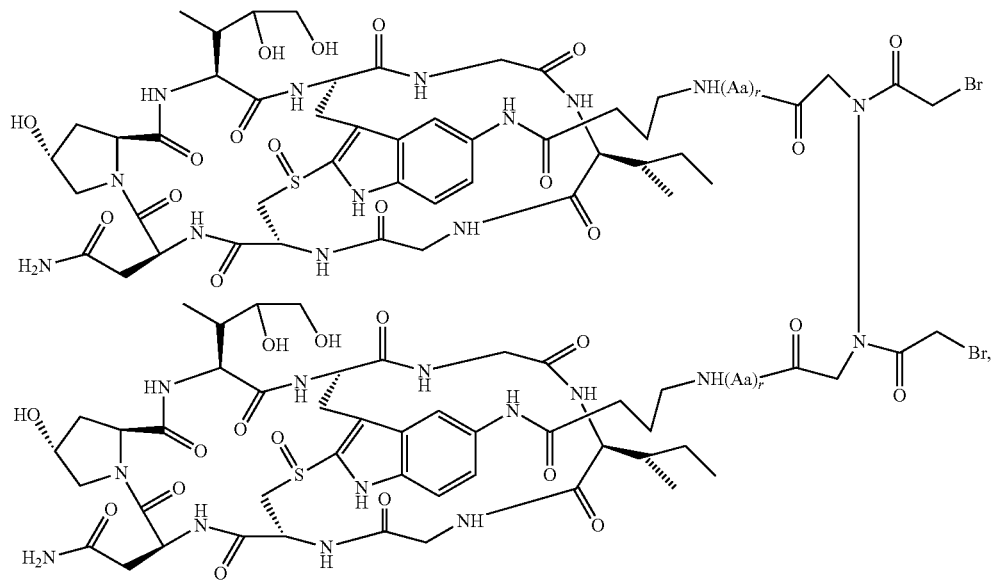

-continued
(I-48)
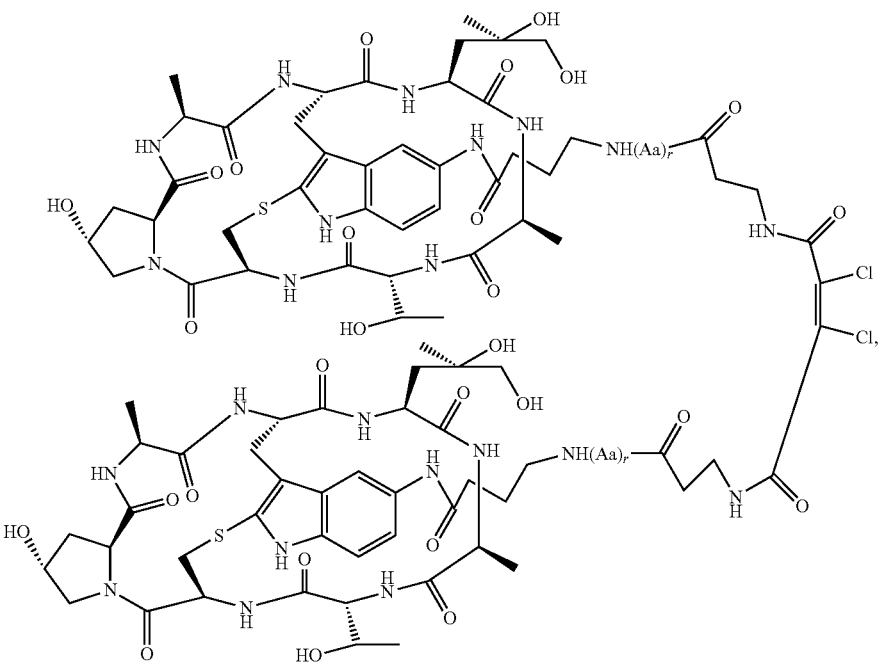
(I-49)
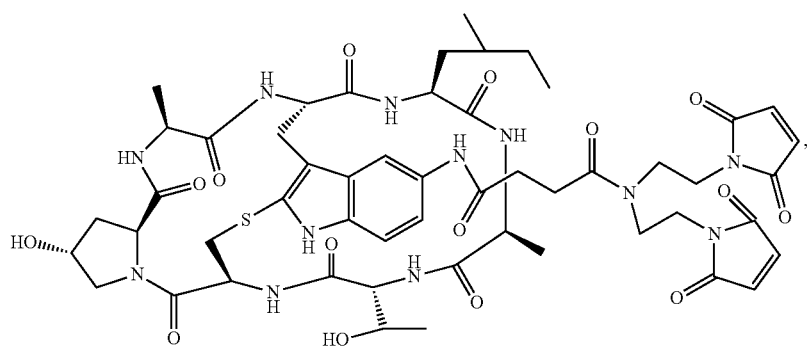
(I-50)
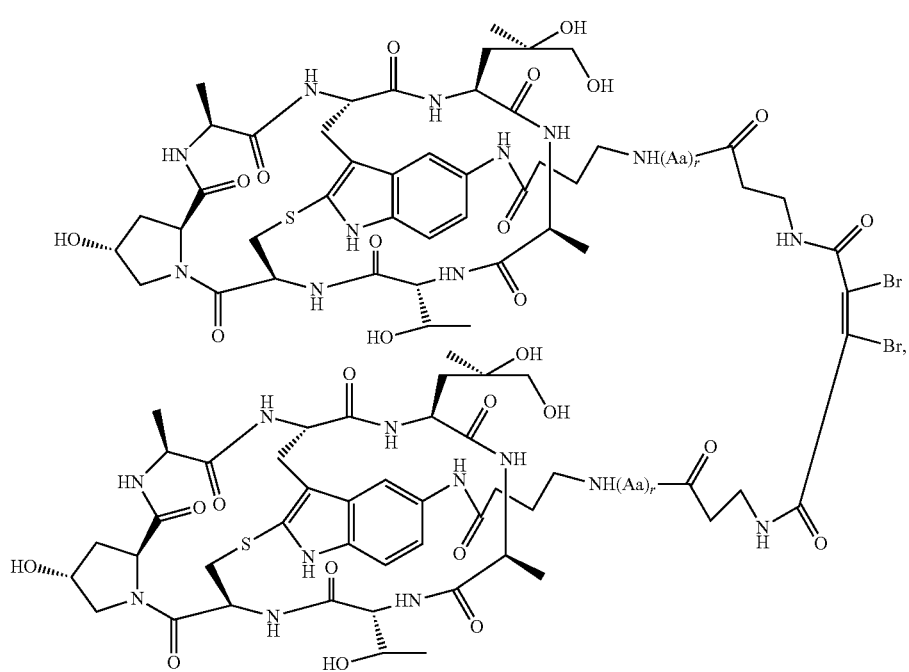

(I-51)
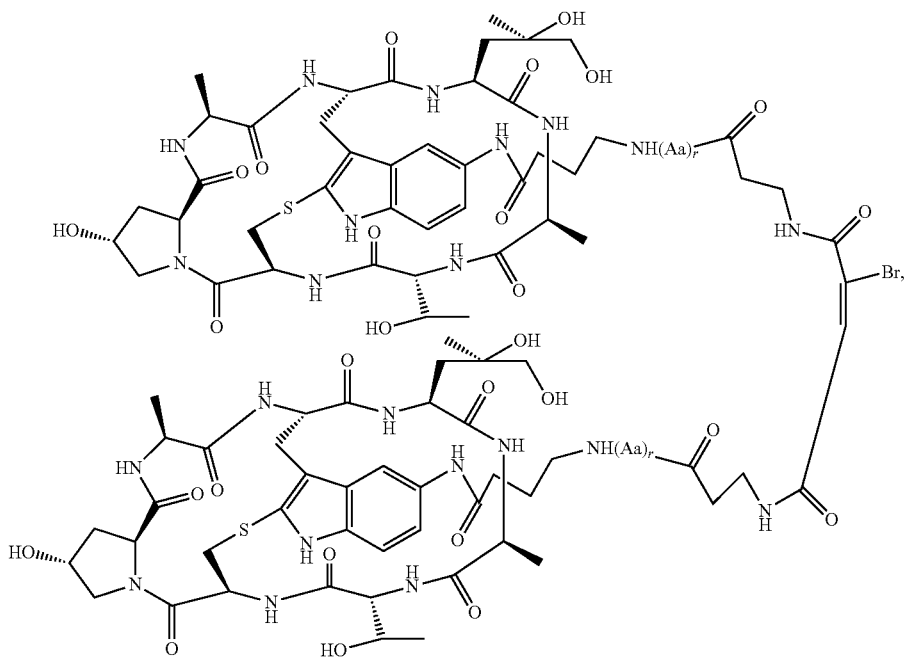
(I-52)
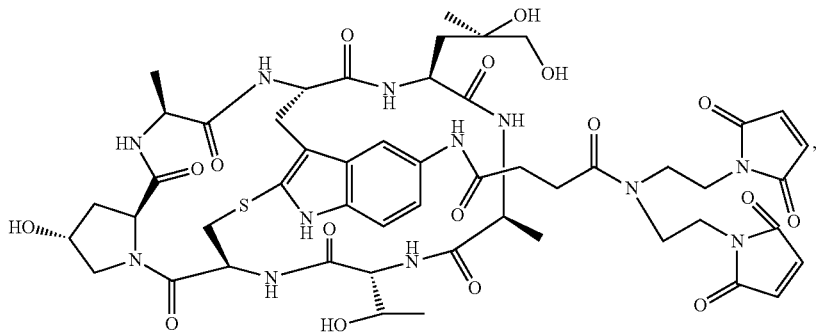
(I-53)
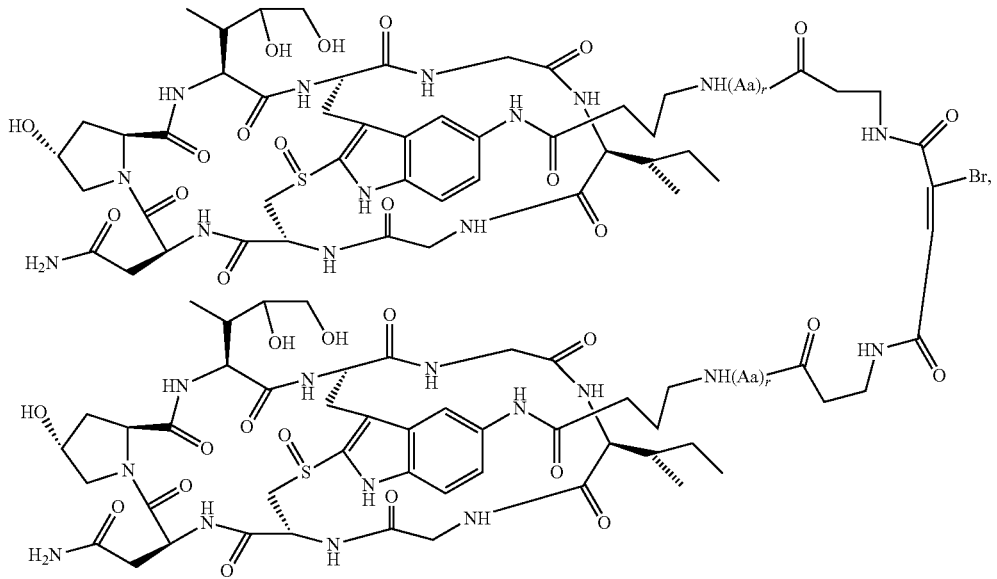

(I-54)
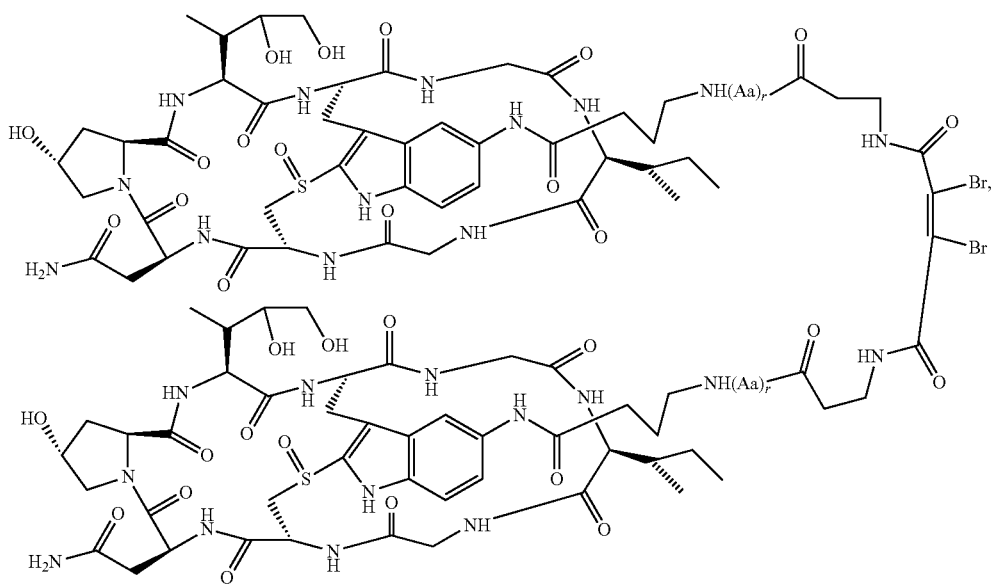
(I-55)
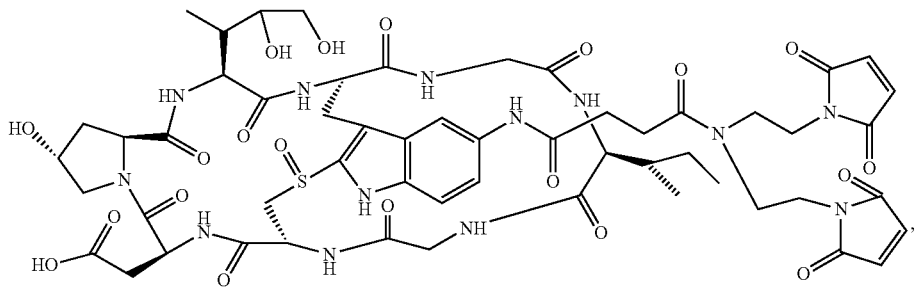
(I-56)
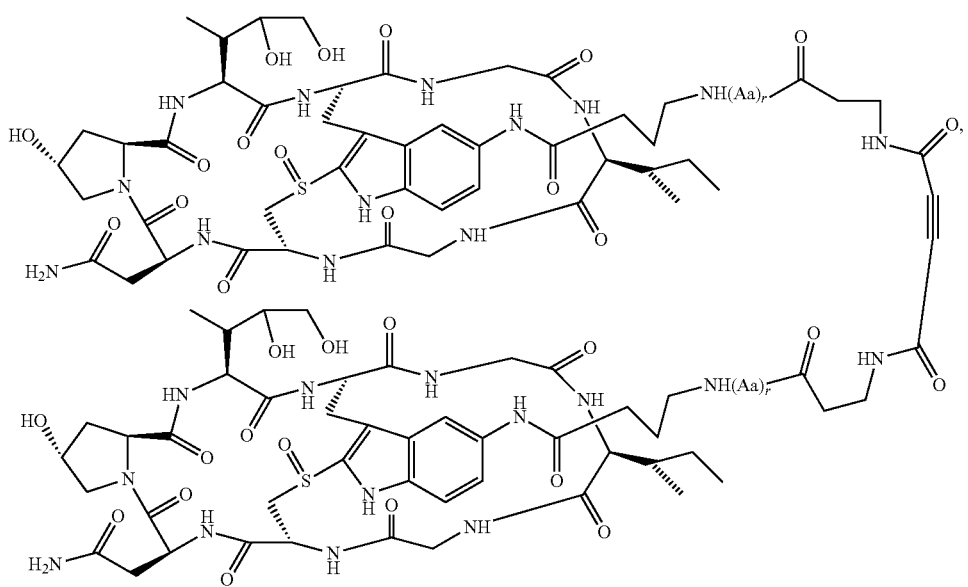

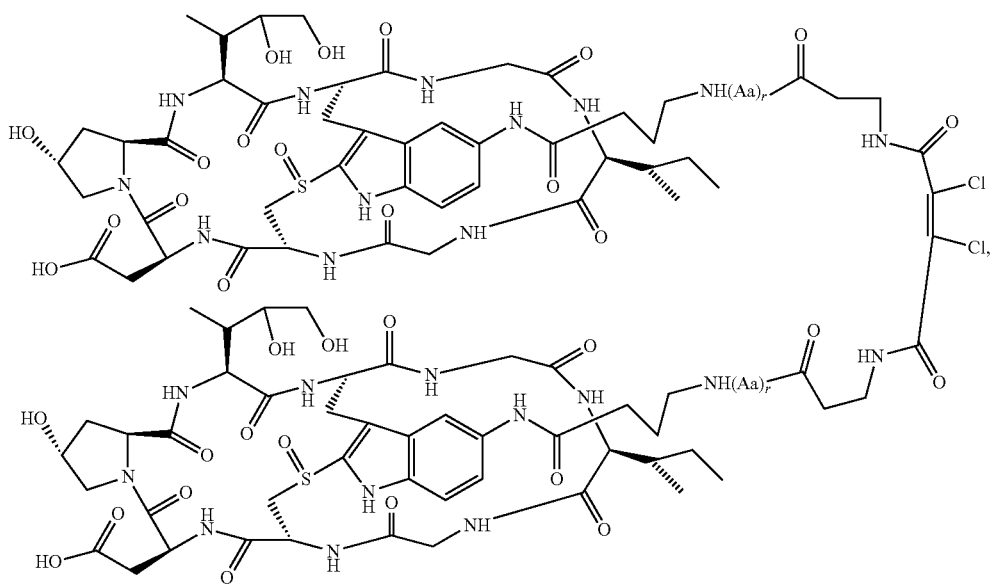
(I-57)
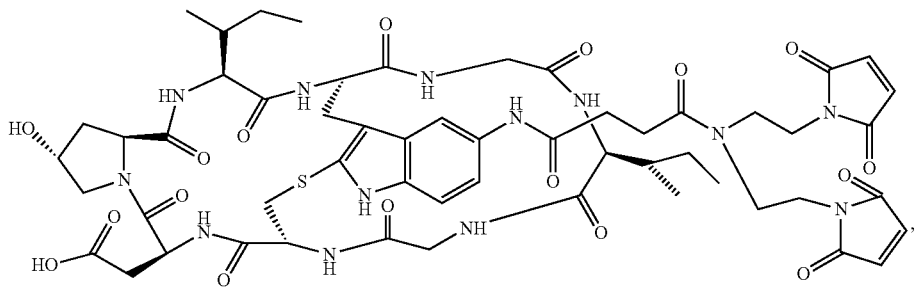
(I-58)
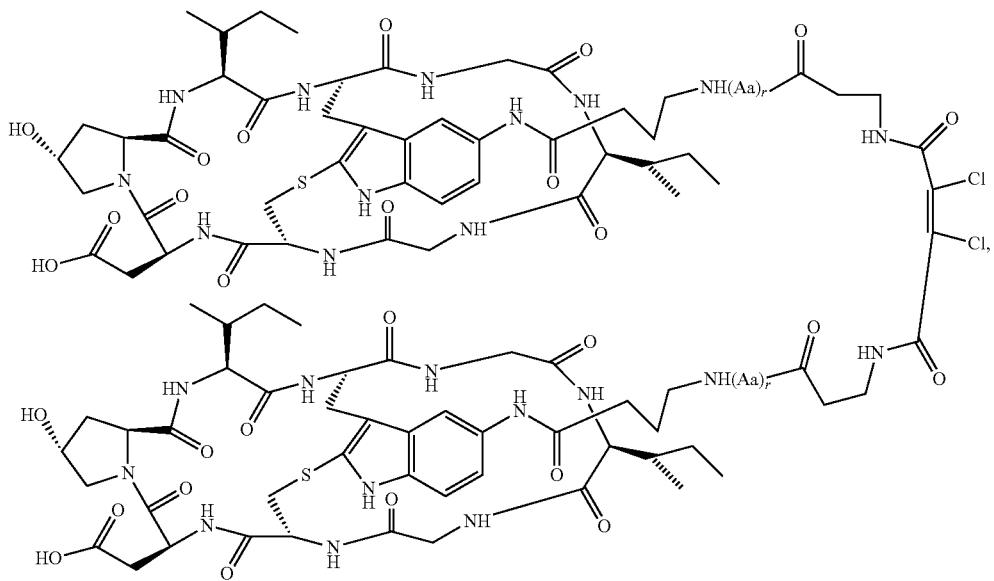
(I-59)

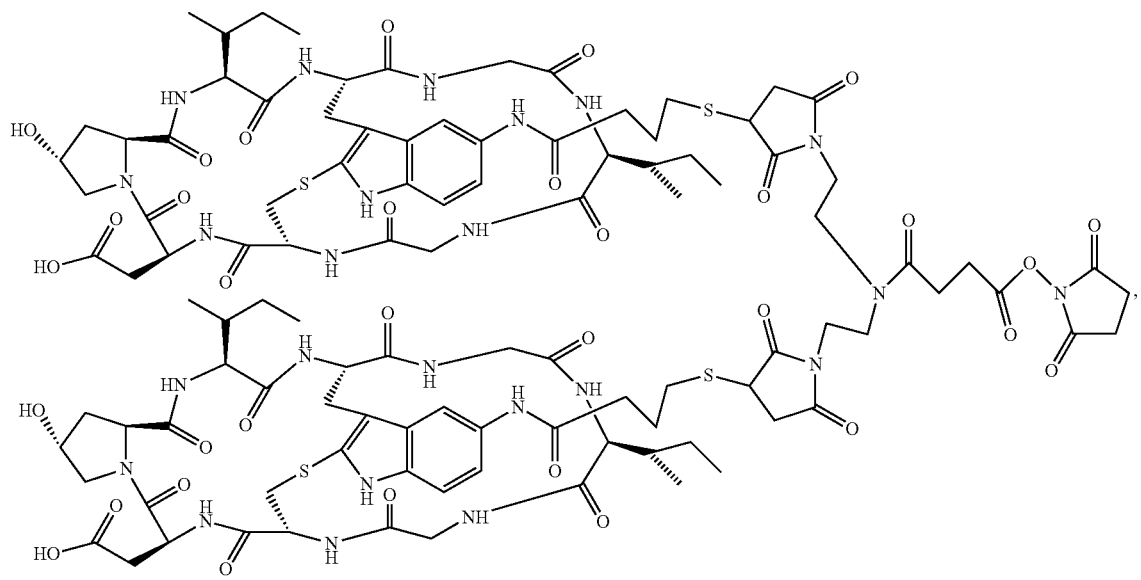
(I-60)
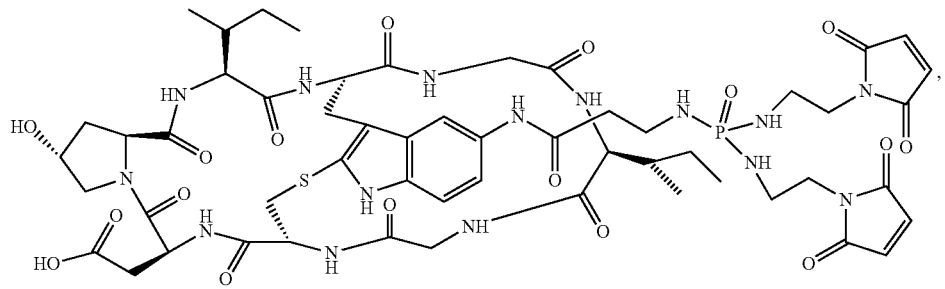
(I-61)
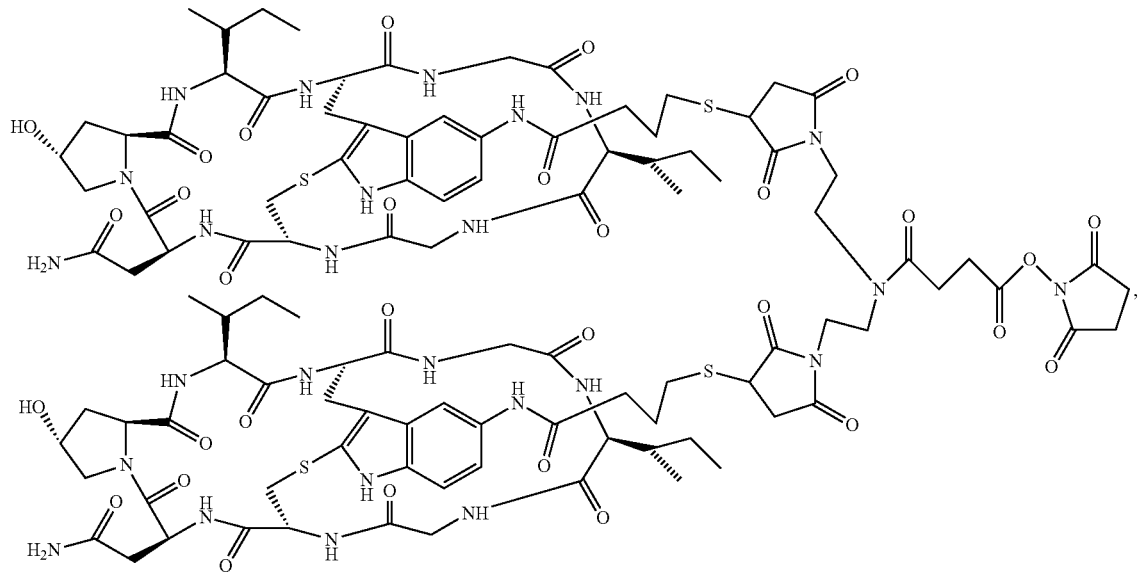
(I-62)

-continued
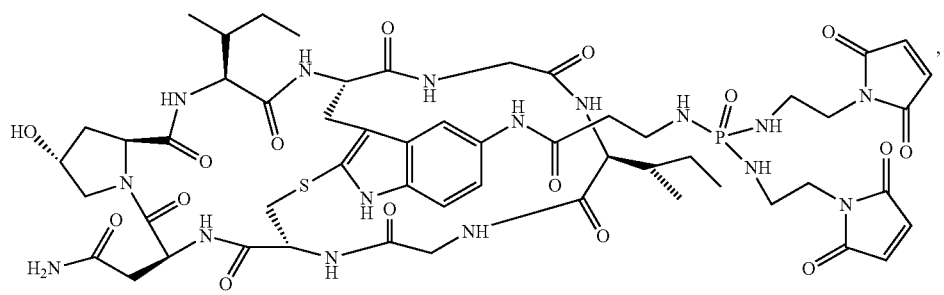
(I-63)

(I-64)

(I-65)

(I-66)
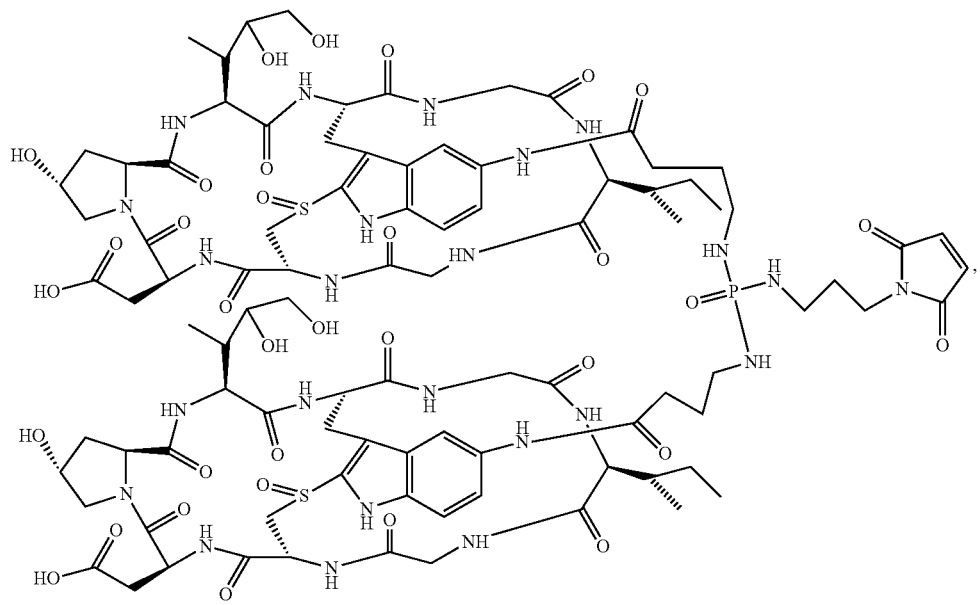
(I-67)
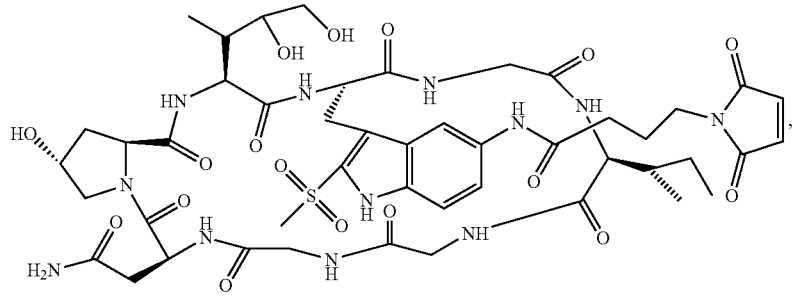
(I-68)
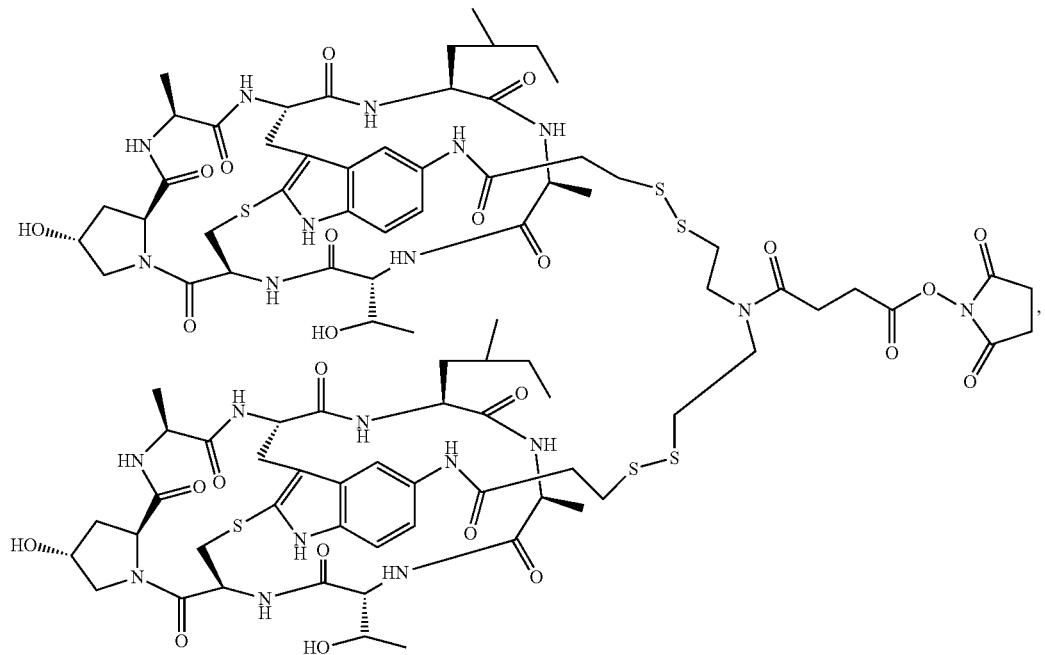

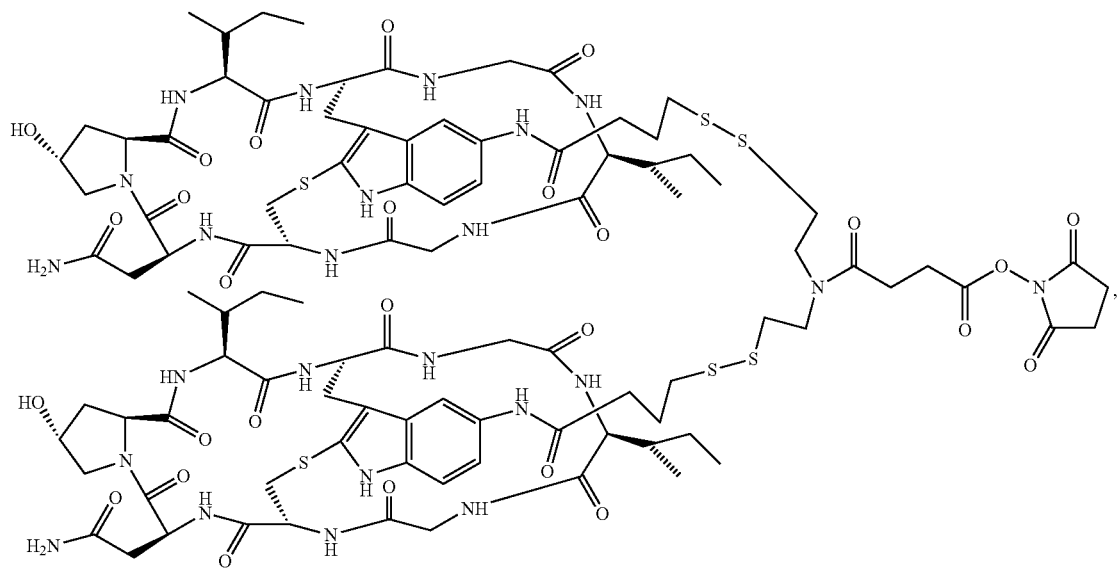
(I-69)
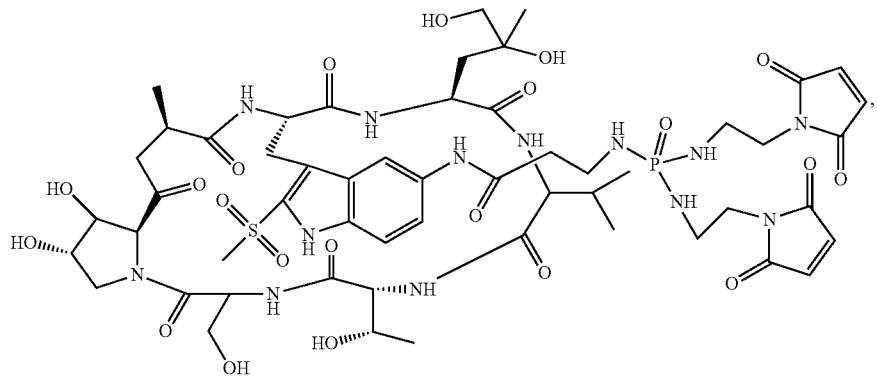
(I-70)
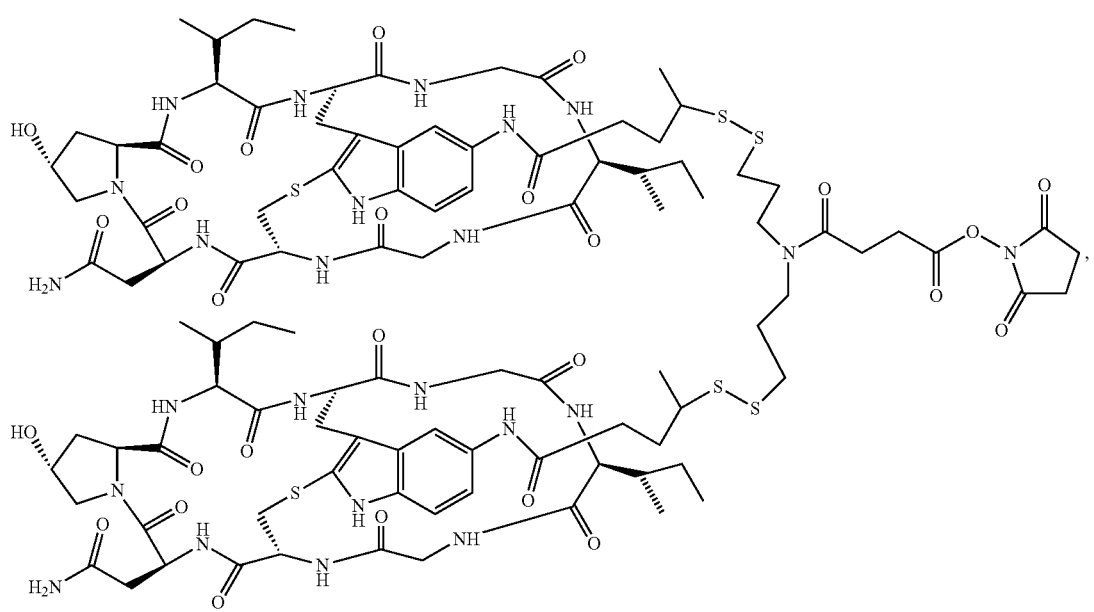
(I-71)

(I-72)
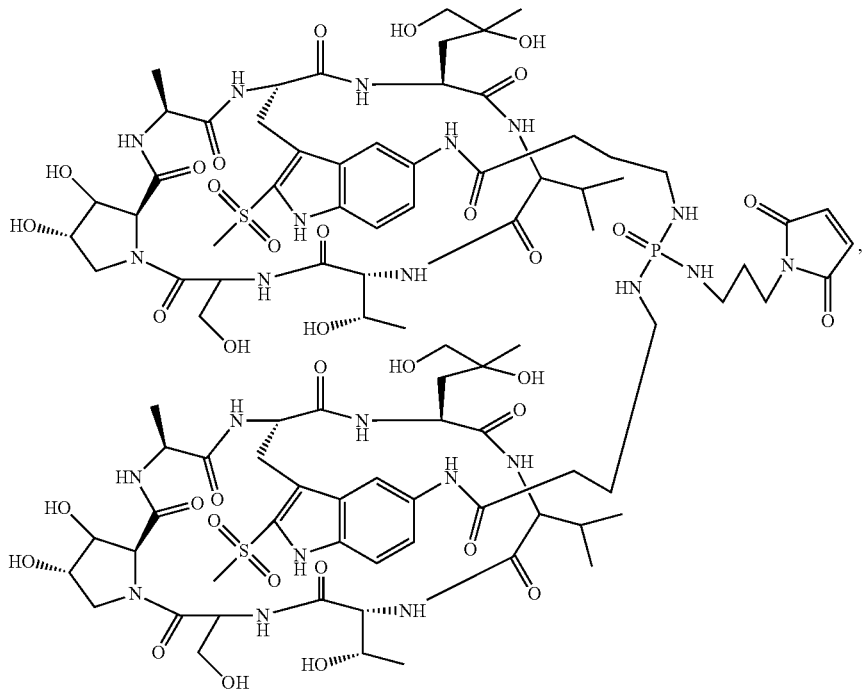
(I-73)
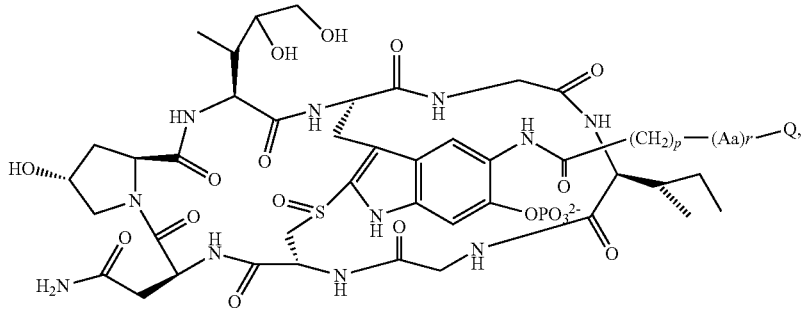
(I-74)
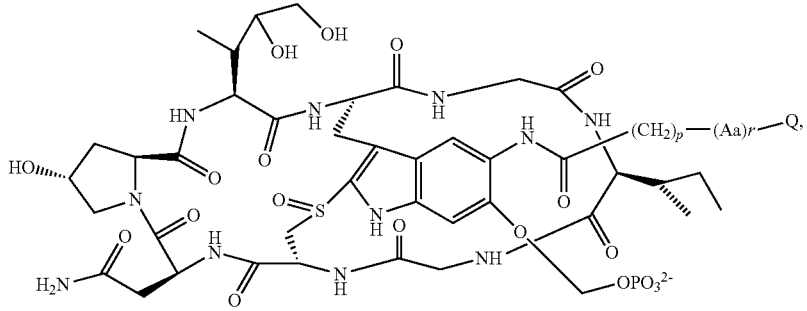
(I-75)
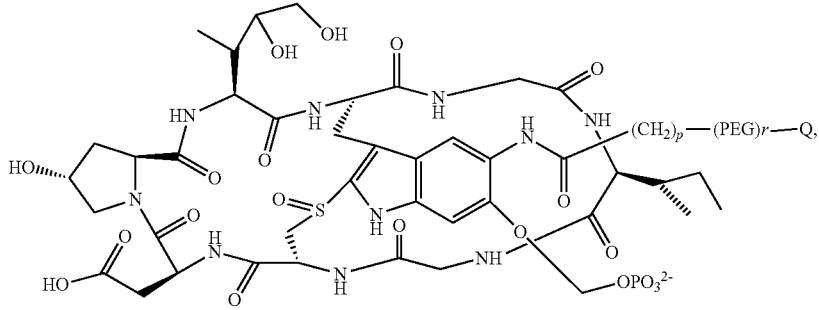

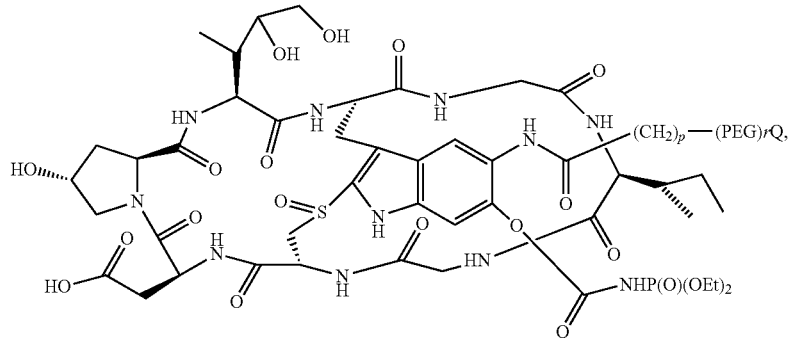
(I-76)
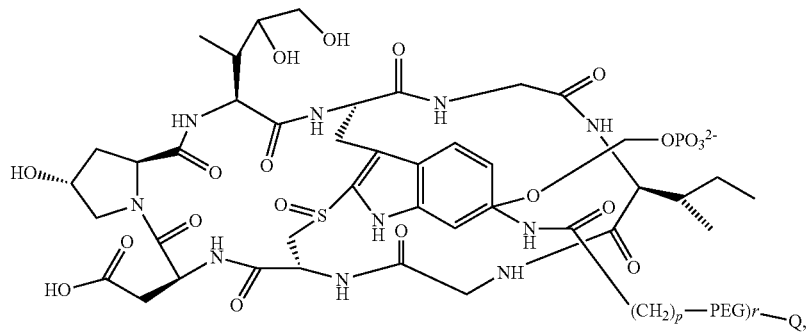
(I-77)
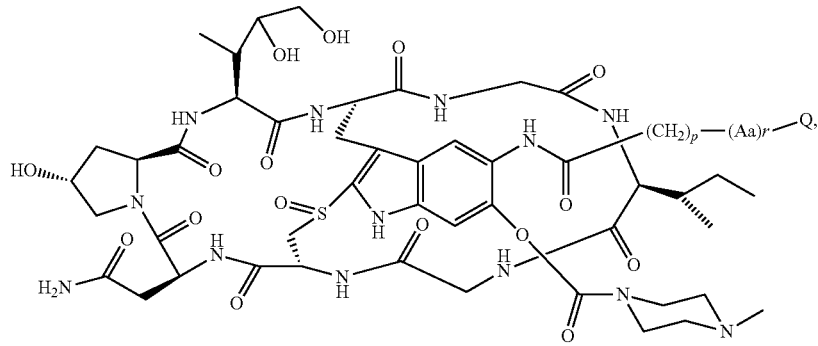
(I-78)
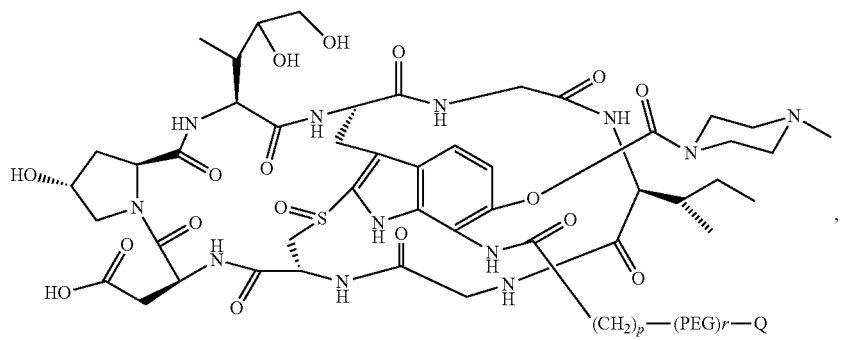
(I-79)

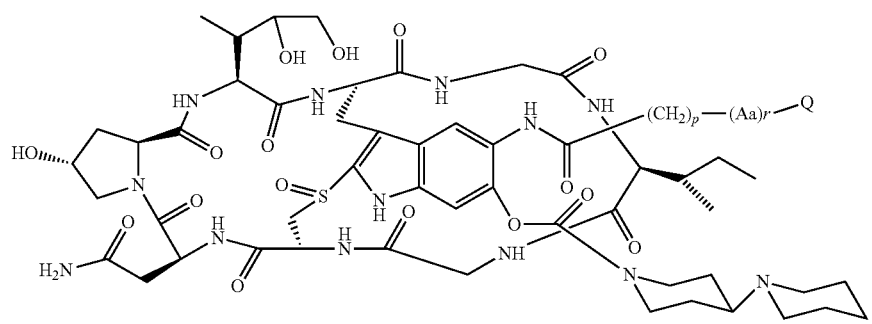
(I-80)
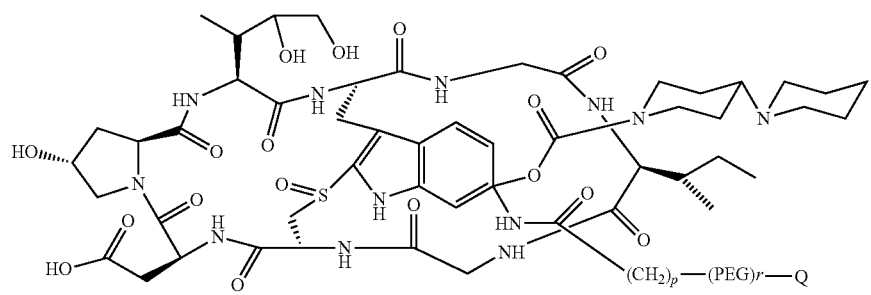
(I-81)
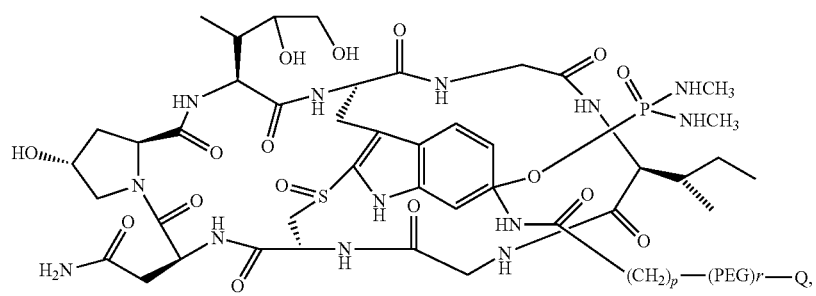
(I-82)
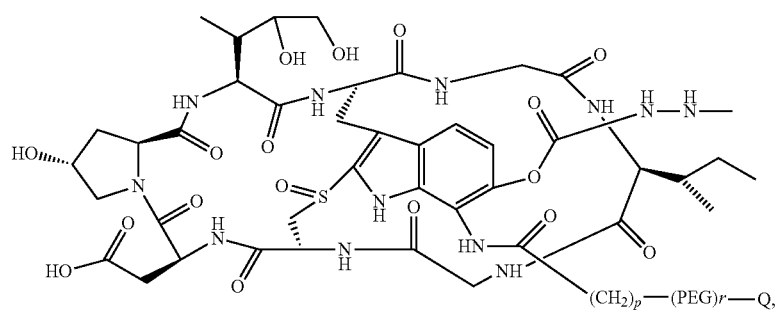
(I-83)
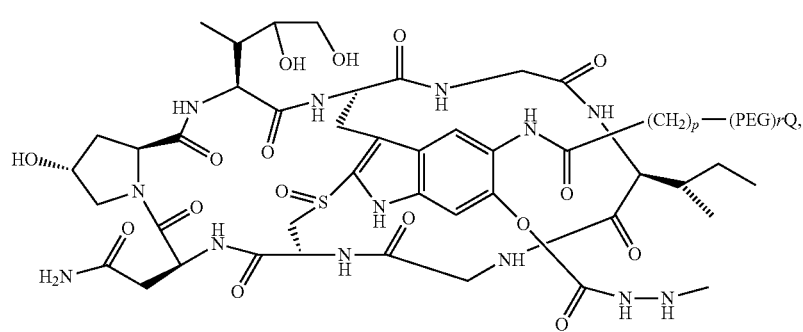
(I-84)

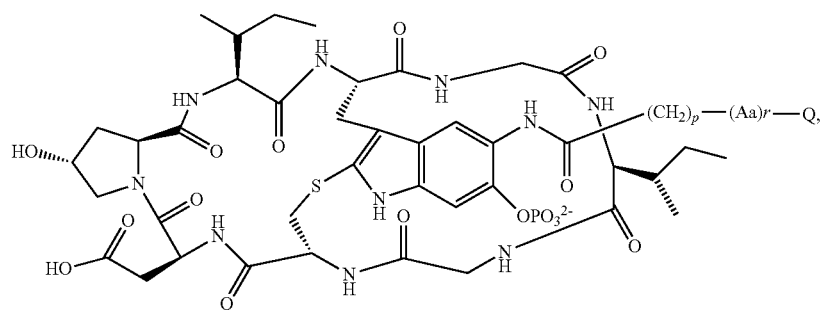
(I-85)
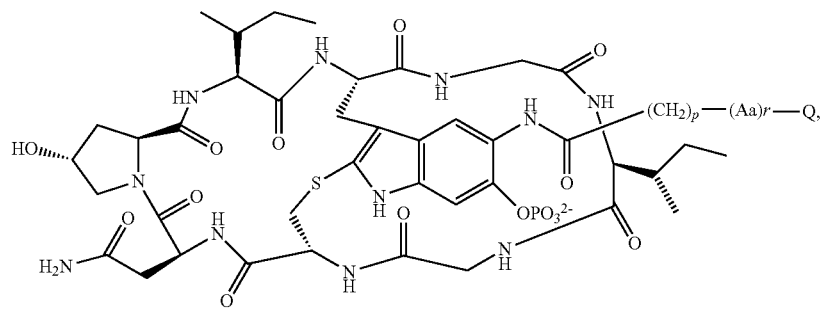
(I-86)
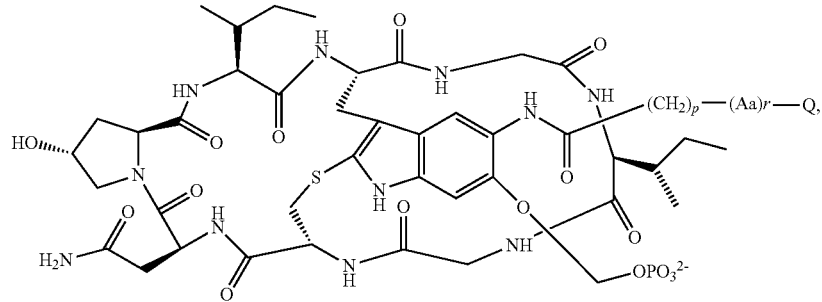
(I-87)
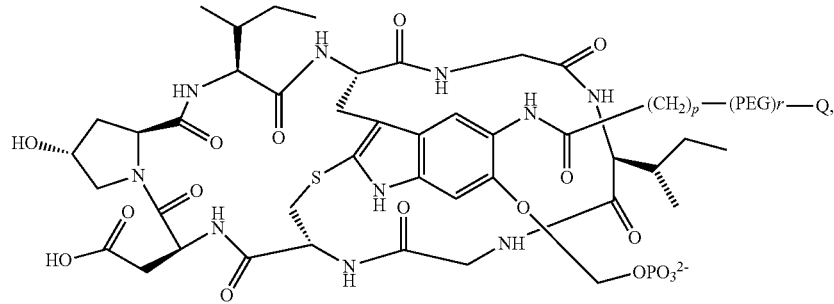
(I-88)
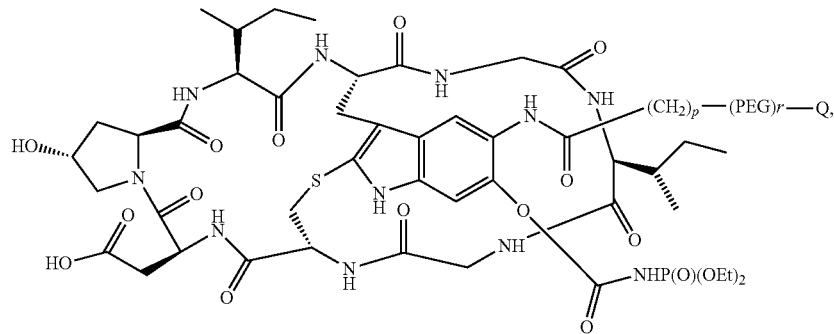
(I-89)

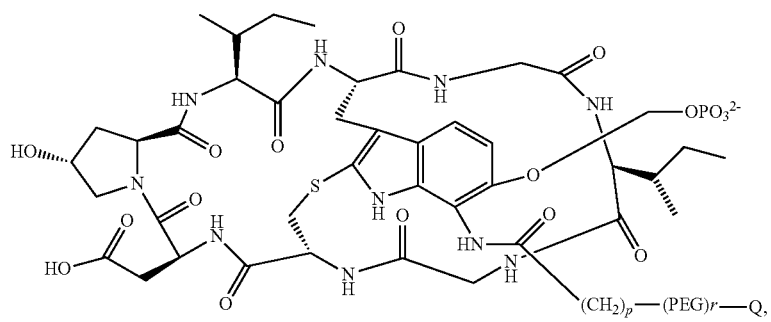
(I-90)
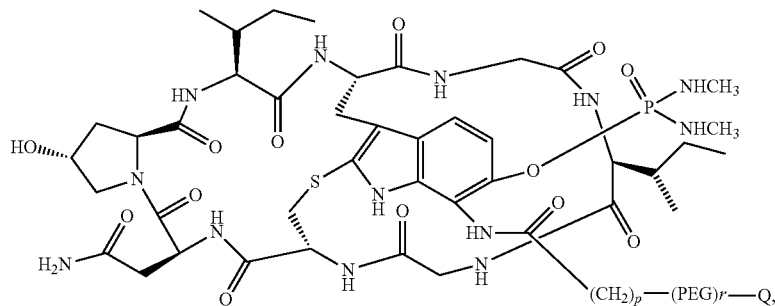
(I-91)
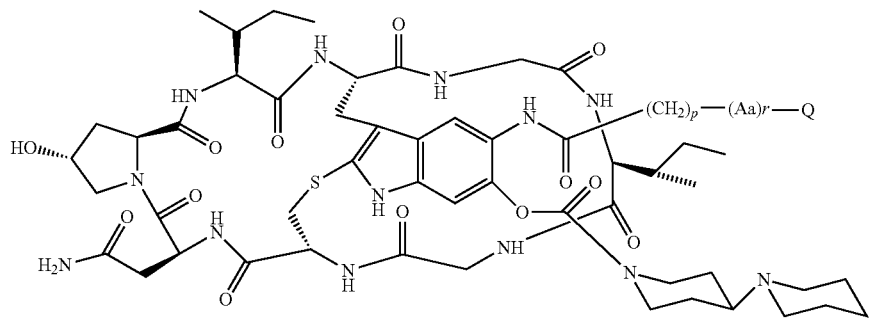
(I-92)
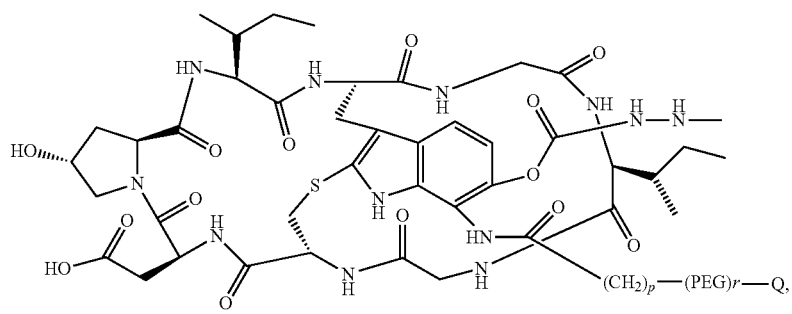
(I-93)
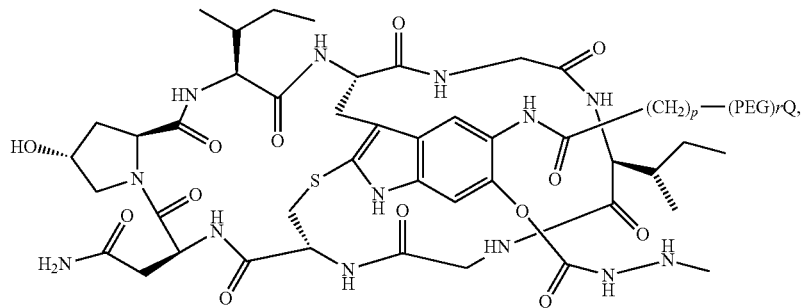
(I-94)

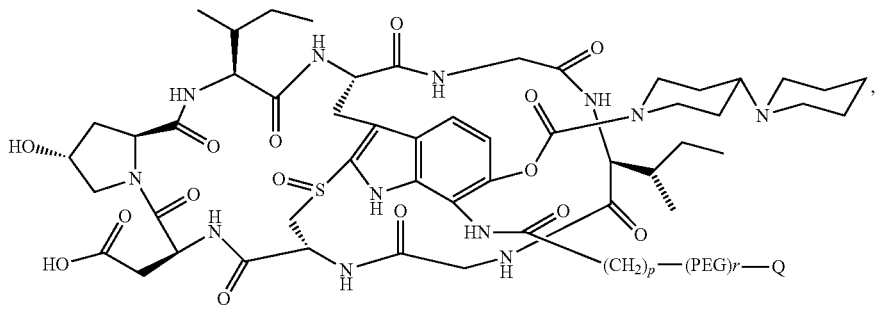

(I-95)

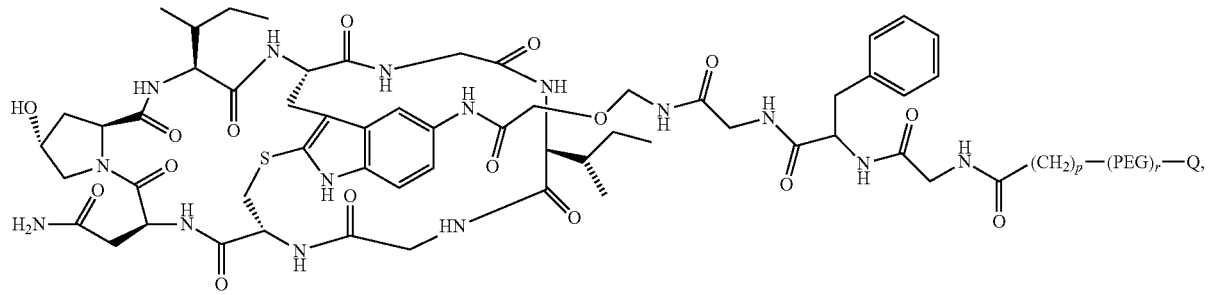

(I-96)

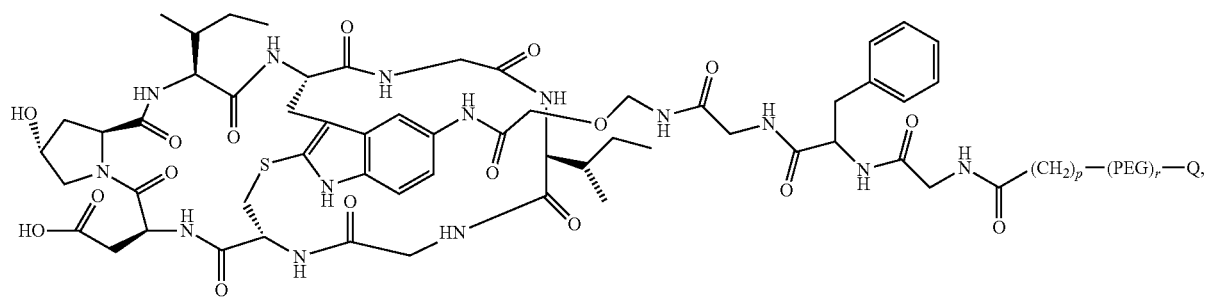

(I-97)

or a pharmaceutically acceptable salt, hydrates, or hydrated salt, or the polymorphic crystalline structure of the compounds thereof, or the optical isomers, racemates, diastereomers or enantiomers.

Wherein Aa, r, n, L and Q are the same in the Formula (I). PEG is polyethylene glycol with the formula of —OCH$_2$CH$_2$. Preferably, Q is H, C$_1$–C$_8$ of alkyl, alkenyl, alkinyl, aryl, cyclic, cyclohetero, haloalkyl, alkoxy, haloalkoxy alkylamino; or halogen; or —NO$_2$; or —CN; —SH; —SSCH$_3$; —SSAc; —SSAr; —SS-Pyridine; —SS-Ar(NO$_2$); —S-cell binding agent; or a function group of NHS ester, pentafluorophenyl ester; alkyloxyamine; aldehyde; ketone; carboxyl acid; hydrazine; amine; or thiolactone; or linked a cell binding agent via Stretcher units (Ww) or via Spacer units (Tt), wherein W, w, T, and t are as defined in Formula (I); or Q is selected from any one of the following formulas:

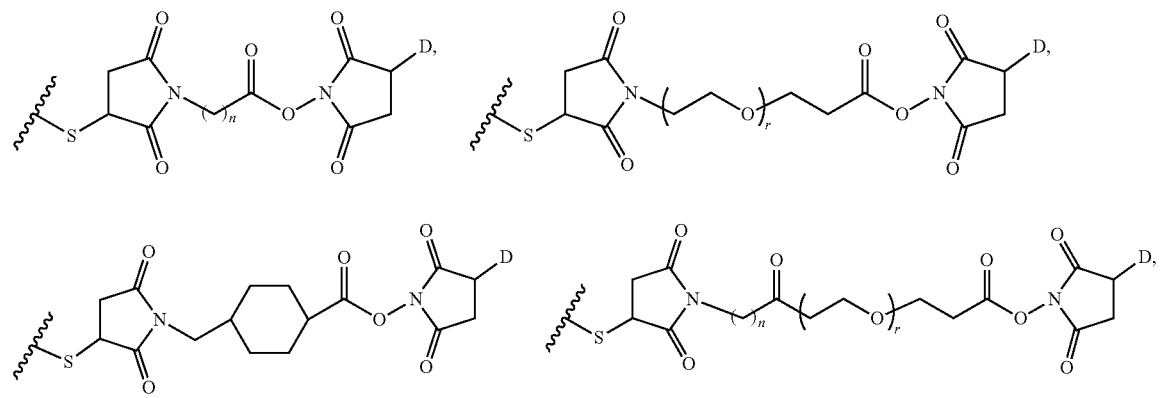

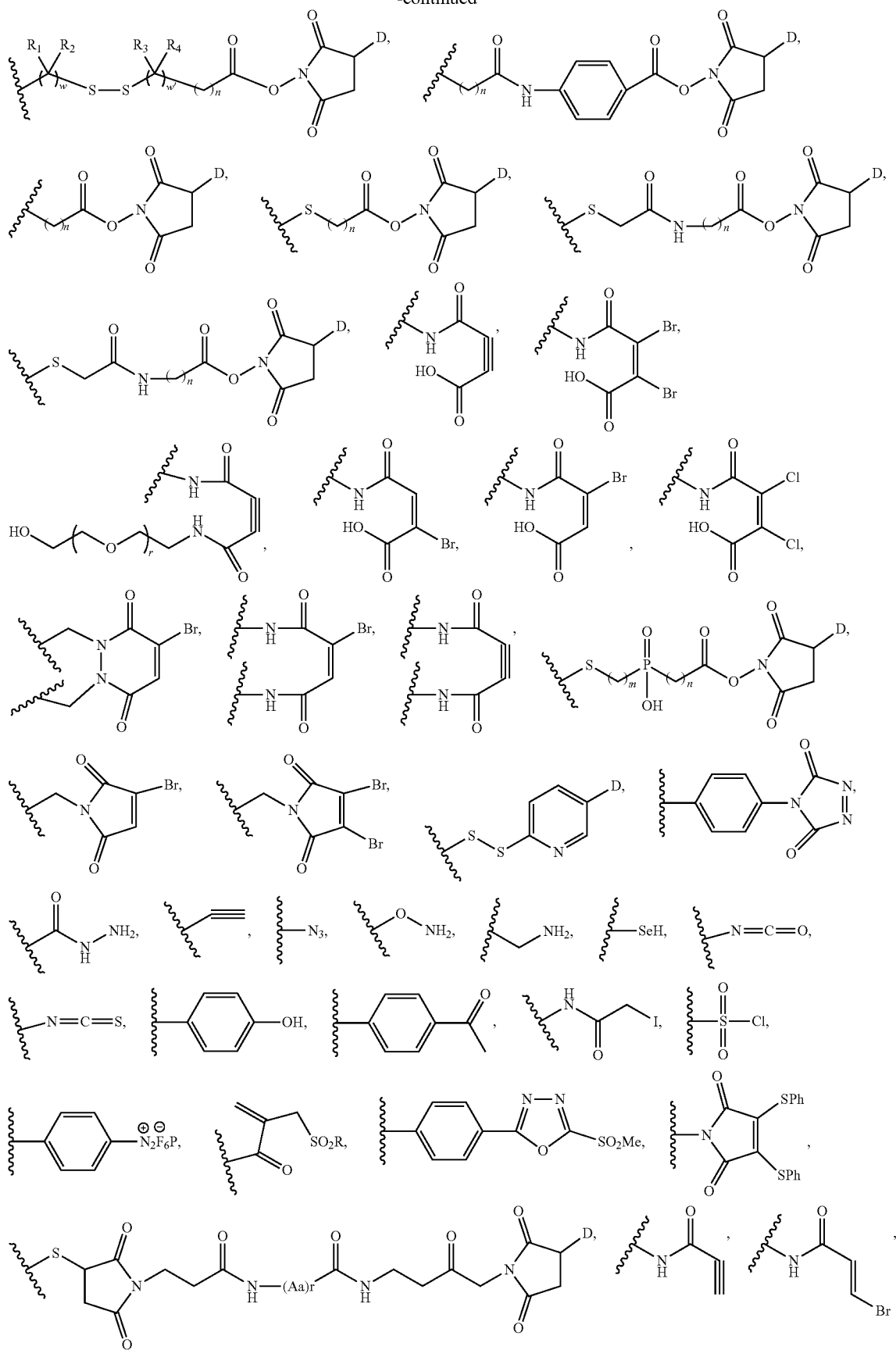

-continued

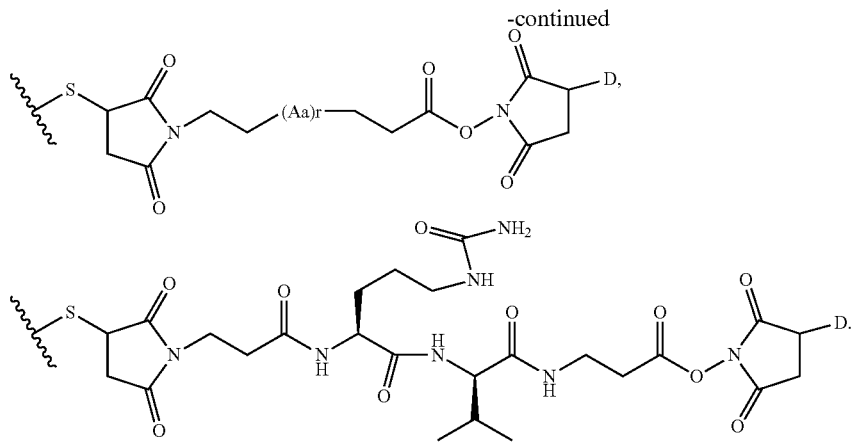

Wherein D is H, —$NO_2$, $SO_3^-$, CN, or F; $R_1$, $R_2$, $R_3$, $R_4$, r, m, and n are described in Formula (I); w and w' are 0 or 1 independently.

Synthesis of the Derivatives of *Amanita* Toxins as Cytotoxic Agents.

The compounds and process of the present invention can be prepared in a number of ways well known to those skilled in the art. The compounds can be synthesized, for example, by application or adaptation of the methods described in the examples, or variations thereon as appreciated by the skilled artisan. The appropriate modifications and substitutions will be readily apparent and well known or readily obtainable from the scientific literature to those skilled in the art. In particular, such methods can be found in Richard C. Larock, "Comprehensive Organic Transformations, A Guide to Functional Group Preparations", Two Volume Set, 2nd Edition, Wiley Publishers, 2010.

One preferred aspect of preparation of theses derivatives of *Amanita* toxins of the invention is semi-synthesis. Thus, the core structure compounds of theses derivatives of *Amanita* toxins are isolated from theses derivatives-containing mushroom species from the genera *Amanita, Galerina* and *Lepiota*, in particular, *A. bisporigera, A. visosa, A. suballiacea, A. phalloides* and allied species (Hallen, H. E. et al, 2007 Proc. Nat. Acad. Sci. USA, 104, 19097-101), or isolated from fermentation using a basidiomycete, or using A. fissa (Guo, X. W., et al, 2006 Wei Sheng Wu Xue Bao 46(3): 373-8). The isolated toxin compounds are sequentially undergone aromatic nitration of the indole units, followed by reduction of the nitro group to an amine, and then the produced amine compounds are condensated with a linker having a reactive or a reactable carboxylic group to form an amide linkage. An illustration of the semi-synthesis steps are shown below:

-continued

Wherein $R_{10}$, L and Q are defined the same in the Formula (I). Wherein Lv is leaving group selected from OH, halogen, NHS (N-hydroxyl succinimide), nitrophenol, pentalfluorophenol, etc.

The nitrition above can be using nitric acid, or mixture of nitric acid and sulfuric acids, or mixture of nitric acid and acetic acid optionally containing acetic anhydride, or tert-Butyl nitrite (TBN), or nitrosonium salts ($NO^+BF_4^-$, $NO^+ClO_4$, $NO^+PF^-_6$, $NO^+AsF^-_6$, $NO^+SbF^-_6$), or nitronium salts ($NO^{2+}BF^{4-}$, $NO^{2+}ClO^{4-}$, $NO^{2+}BF^{-6}$, $NO^{2+}AsF^{-6}$, $NO^{2+}SbF^{-6}$) The reduction of the nitro group to the amine can be by many different ways, such as catalytic hydrogenation reduction using palladium-on-carbon, platinum(IV) oxide, or Raney nickel; or direct reduction by using iron in acidic media, sodium hydrosulfite; sodium sulfide (or hydrogen sulfide and base), tin(II) chloride, titanium(III) chloride, triphenylphosphine, trialkylphosphine, zinc, or samarium. The final condensation of the amino group to the linker L containing a carboxylic acid derivative, —C(O)-Lv. Wherein Lv can be selected from F, Cl, Br, I, nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride. When Lv is OH group, then the condensation with the amino group is through a coupling reagent, such as a peptide coupling agent, or coupling agent for Mitsunobu reaction. These coupling reagents are, but not limited: N-(3-dimethylaminopropyl)-N'-ethylcarbodiimide (EDC), dicyclohexyl-carbodiimide(DCC), N,N'-diisopropyl-carbodiimide (DIC), N-cyclohexyl-N'-(2-morpholinoethyl)carbodiimide metho-p-toluenesulfonate (CMC, or CME-CDI), 1,1'-carbonyldiimidazole (CDI), O-(benzotriazol-1-yl)-N,N,N',N'-tetramethyluronium tetrafluoroborate (TBTU), N,N,N',N'-tetramethyl-O-(1H-benzotriazol-1-yl)uronium hexafluorophosphate (HBTU), benzotriazol-1-yloxy)tris(dimethyl-amino)phosphonium hexafluorophosphate (BOP), (benzotriazol-1-yloxy)tripyrrolidinophosphonium hexafluorophosphate (PyBOP), diethyl cyanophosphonate (DEPC), chloro-N,N,N',N'-tetramethylformamidinium hexafluorophosphate, 1-[bis(dimethylamino)-methylene]-1H-1,2,3-triazolo[4,5-b]pyridinium 3-oxid hexafluorophosphate (HATU), 1-[(dimethylamino)(morpholino) methylene]-1H-[1,2,3]triazolo[4,5-b]pyridine-1-ium 3-oxide hexafluorophosphate (HDMA), 2-chloro-1,3-di methyl imidazolidinium hexafluorophosphate (CIP), chlorotripyrrolidinophosphonium hexafluorophosphate (PyCloP), fluoro-N,N,N',N'-bis(tetramethylene)formamidinium hexafluorophosphate (BTFFH), N,N,N',N'-tetramethyl-S-(1-oxido-2-pyridyl)thiuronium hexafluorophosphate, O-(2-oxo-1(2H)pyridyl)-N,N,N',N'-tetramethyluronium tetrafluoroborate (TPTU), S-(1-oxido-2-pyridyl)-N,N,N',N'-tetramethylthiuronium tetrafluoroborate, O-[(ethoxycarbonyl) cyano-methylenamino]-N,N,N,N'-tetramethyluronium hexafluorophosphate (HOTU), (1-cyano-2-ethoxy-2-oxoethylidenaminooxy) dimethylamino-morpholino-carbenium hexafluorophosphate(COMU), O-(benzotriazol-1-yl)-N,N,N',N'-bis(tetramethylene)uronium hexafluorophosphate (HBPyU), N-benzyl-N'-cyclohexylcarbodiimide (with, or without polymer-bound), dipyrrolidino(N-succinimidyloxy)carbenium hexafluorophosphate (HSPyU), chlorodipyrrolidinocarbenium hexafluorophosphate (PyClU), 2-chloro-1,3-dimethylimidazolidinium tetrafluoroborate(CIB), (benzotriazol-1-yloxy) dipiperidinocarbenium hexafluorophosphate (HBPipU), O-(6-chlorobenzotriazol-1-yl)-N,N,N',N'-tetramethyluronium tetrafluoroborate (TCTU), bromotris(dimethylamino)-phosphonium hexafluorophosphate (BroP), propylphosphonic anhydride (PPACA, 2-morpholinoethyl isocyanide (MEI), N,N,N',N'-tetramethyl-O—(N-succinimidyl)uronium hexafluorophosphate (HSTU), 2-bromo-1-ethyl-pyridinium tetrafluoroborate (BEP), O-[(ethoxycarbonyl)cyanomethylenamino]-N,N,N',N'-tetramethyl-uronium tetrafluoroborate (TOTU), 4-(4,6-dimethoxy-1,3,5-triazin-2-yl)-4-methyl-morpholinium chloride (MMTM, DMTMM), N,N,N',N-tetram ethyl-O—(N-succinimidyl)-uronium tetrafluoroborate (TSTU), O-(3,4-dihydro-4-oxo-1,2,3-benzotriazin-3-yl)-N,N,N',N'-tetramethyluronium tetrafluoro-borate (TDBTU), 1,1'-(azodicarbonyl)dipiperidine (ADD), di-(4-chlorobenzyl) azodicarboxylate (DCAD), di-tert-butyl azodicarboxylate (DBAD), diisopropyl azodicarboxylate (DIAD), diethyl azodicarboxylate (DEAD).

Another aspect of the invention provides a chemical synthetic preparation of derivatives of *amanita* toxins of Formula (I) which are illustrated in FIGS. 1-28. The synthetic preparations can be in solid phase, solution phase or combination of solid and solution phases.

Because the cytotoxic agents of formula (I) of the present invention contain asymmetrically substituted carbon atoms, and may be isolated in optically active or racemic forms, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The cytotoxic agents of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the synthetic reactions of the cytotoxic agents of the present invention, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see Peter G. M. Wuts, Theodora W. Greene in "Greene's Protective Groups in Organic Synthesis", 4th Edition, John Wiley and Sons, 2006; Ian T. Harrison, Shuyen Harrison in "Compendium of Organic Synthetic Methods", Vol 1, 2 Vols. 1& 2 By Ian T. Harrison & Shuyen Harrison, Vols 3~5 by Louis S. Hegedus, Leroy Wade Vols 6~Vol 12 by Michael B. Smith, John Wiley and Sons, 2006-2012.

Normally the synthetic reactions are carried out in suitable solvents, temperatures and time. A variety of solvents which have no adverse effect on the reaction or on the reagents involved can be used in a synthetic reaction of the cytotoxic agent. Examples of suitable solvents include: hydrocarbons, which may be aromatic, aliphatic or cycloaliphatic hydrocarbons, such as hexane, cyclohexane, benzene, toluene and xylene; hydrocarbons containing halogens, such as chloroform, dichloromethane, dichloroethane; amides, such as dimethylactamide or dimethylformamide; alcohols such as propanol, ethanol or methanol, and ethers, such as diethyl ether, tetrahydrofuran, or dioxane. The reactions can take place over a wide range of temperatures, from −100° C.~300° C., preferably from 0° C. to 100° C. The time required for the synthetic reaction may also vary widely, depending on many factors, notably the reaction temperature and the nature of the reagents and can be from 5 second to 4 weeks, more preferably from 10 min to 20 hours. In addition, the cytotoxic agents prepared may be isolated or purified from the reaction mixture by conventional means, such as evaporating or distilling off the solvent from the reaction mixture, or after distilling off the solvent from the reaction mixture, pouring the residue into water followed by extraction with a water-immiscible organic solvent and then distilling off the solvent from the extract. It may also involve various well known techniques, such as re-crystallization, re-precipitation or the various chromatography techniques, notably column chromatography, preparative thin layer chromatography, or high performance liquid chromatography.

Some of the synthetic reactions of the cytotoxic agents and their conjugates to a cell binding agent are further exampled but not restricted in the FIGS. 1-28 and in the examples 1~70 of the description, The Conjugates of Cell-Binding Agent—Cytotoxic Agent The present invention also provides a conjugate molecule comprising at least one derivative of *amanita* toxins covalently linked to a cell binding agent (CBA) through the linking group of the crosslinker (L). Preferably said conjugate comprises one to twenty molecules of derivatives of *amanita* toxins according to the invention covalently linked to a cell binding agent through the linking group of the linker of the derivatives of *amanita* toxins.

As stated above, the conjugates of a cell surface binding molecule—cytotoxic agent are illustrated in the Formula (I).

(I)

or their pharmaceutically acceptable salts, hydrates, or hydrated salts; or the polymorphic crystalline structures of these compounds; or their optical isomers, racemates, diastereomers or enantiomers.

wherein $R_1$, $R_2$, $R_3$, $R_4$, $R_5$, $R_6$, $R_7$, $R_8$, $R_9$, $R_{10}$, $R_{11}$, L, m, n and Q are described the same as early in Formula (I). L is preferred a linker-cell binding molecule covalently bound cluster.

In certain embodiments, the conjugates of the invention are illustrated in the following formula:

(II-1)

(II-2)

(II-3)
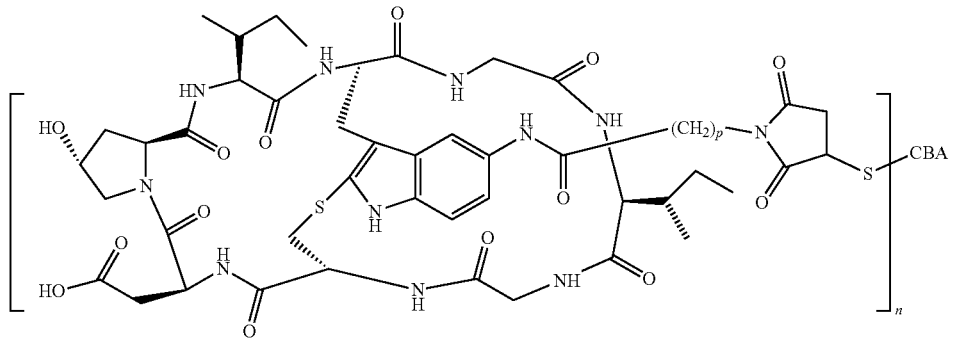
(II-4)
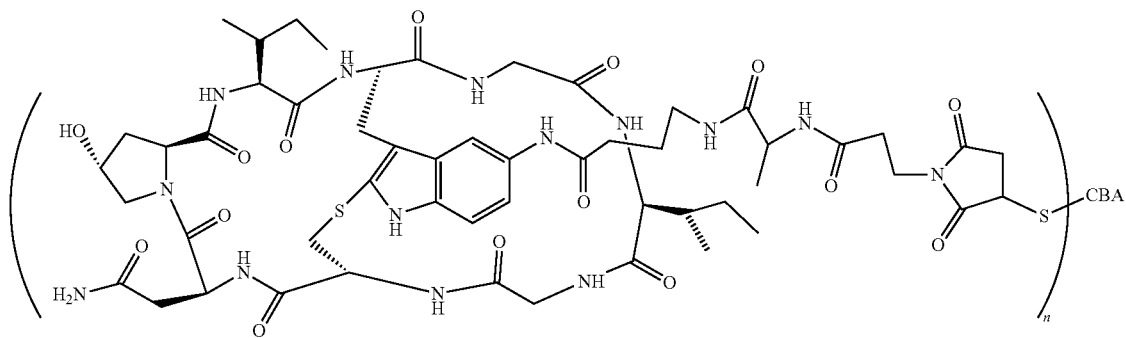
(II-5)
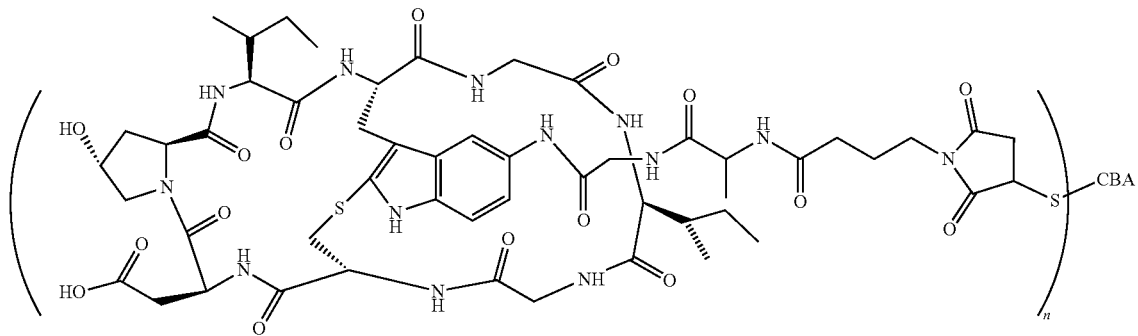
(II-6)
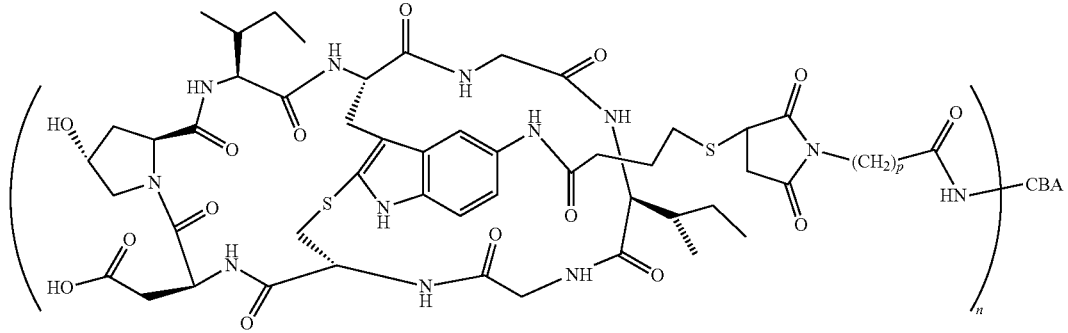

(II-7)
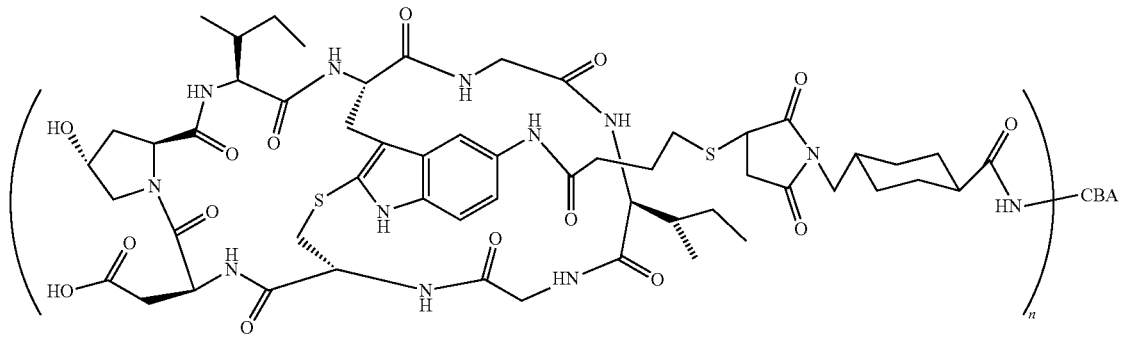
(II-8)
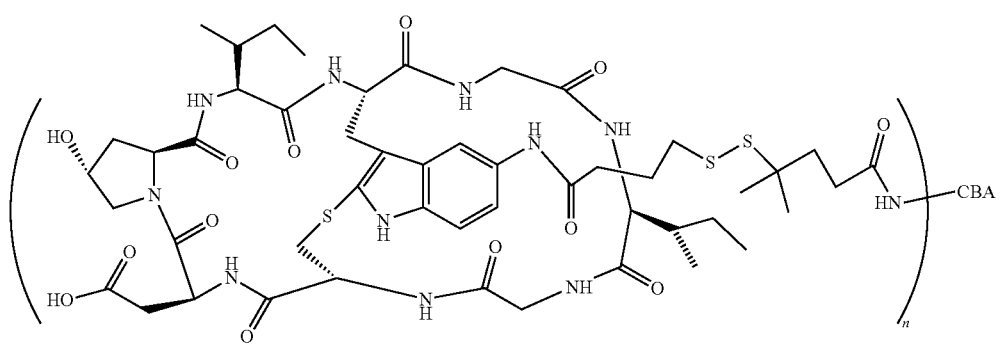
(II-9)
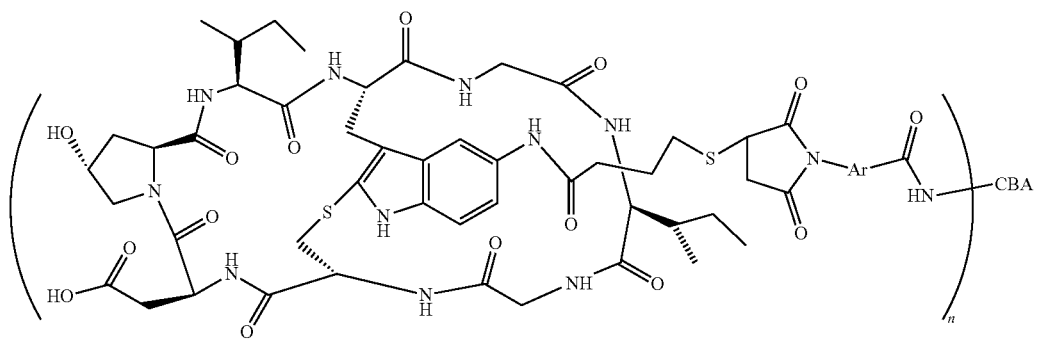
(II-10)
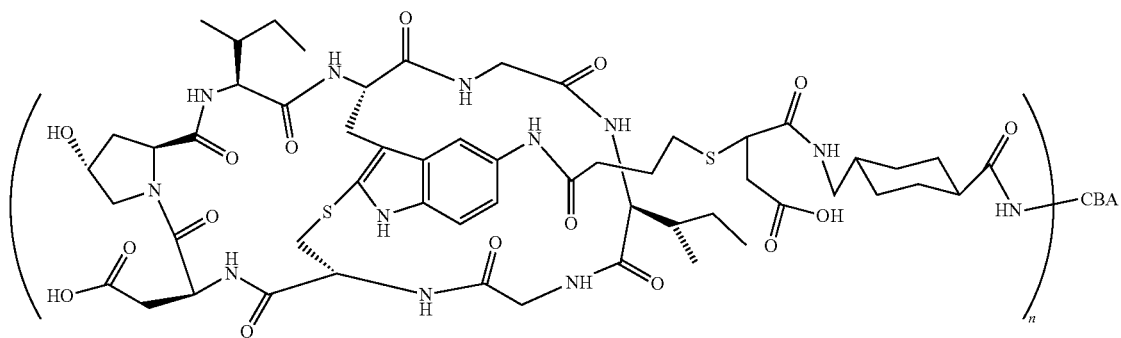

(II-11)

(II-12)

(II-13)
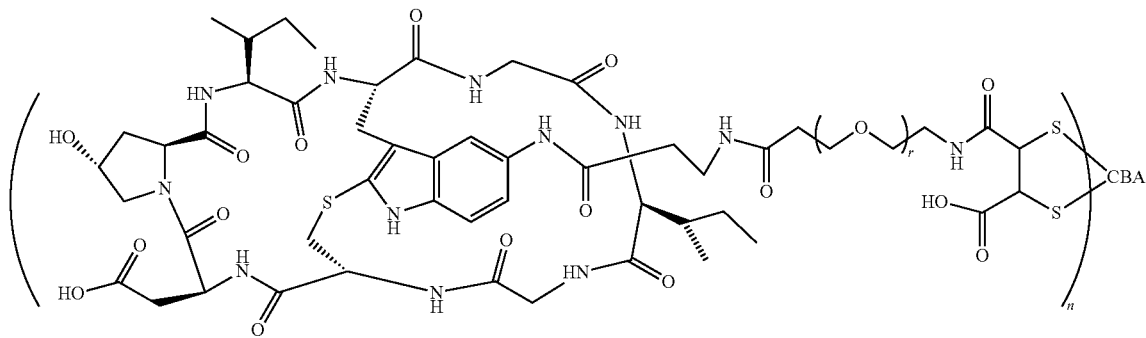
(II-14)
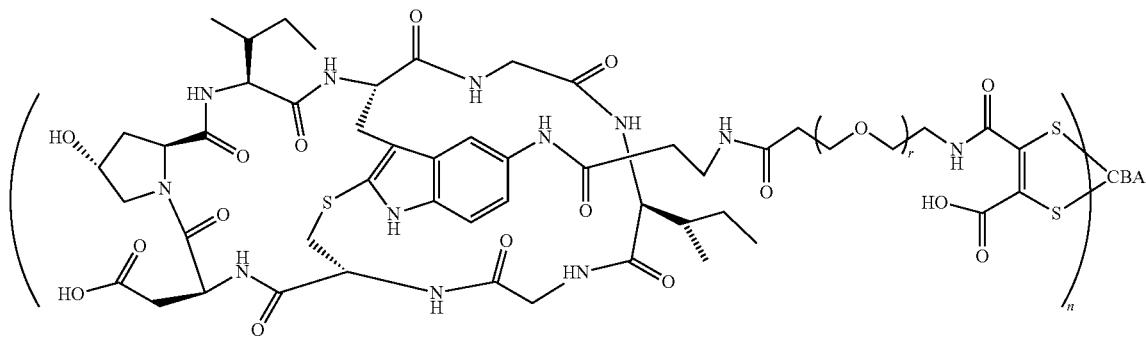

(II-15)
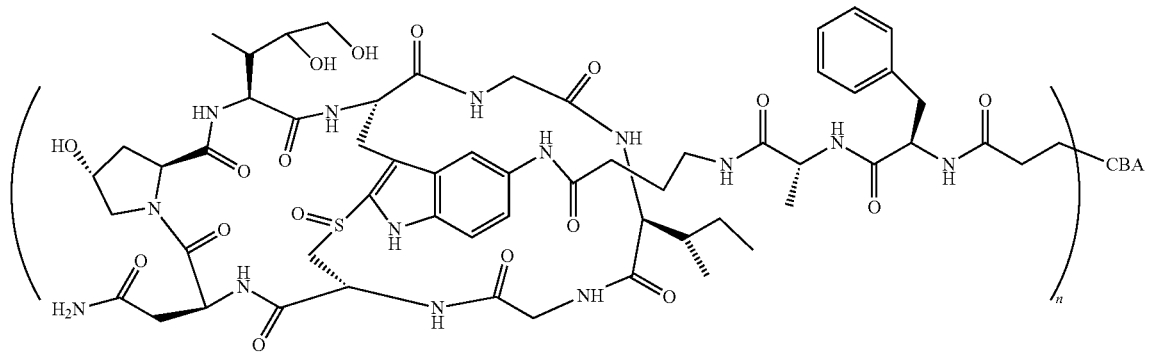
(II-16)
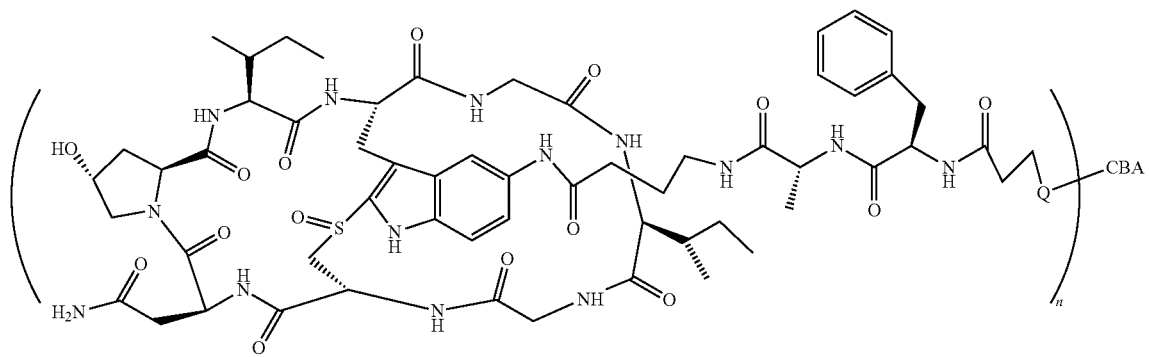
(II-17)
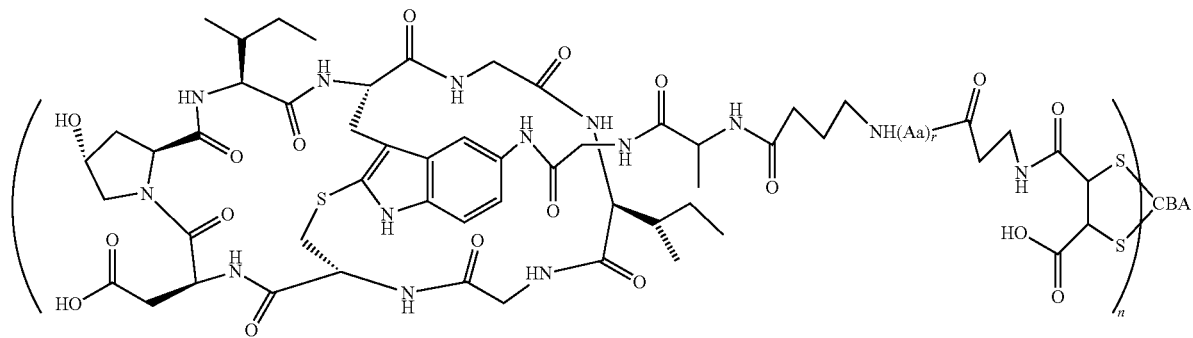
(II-18)
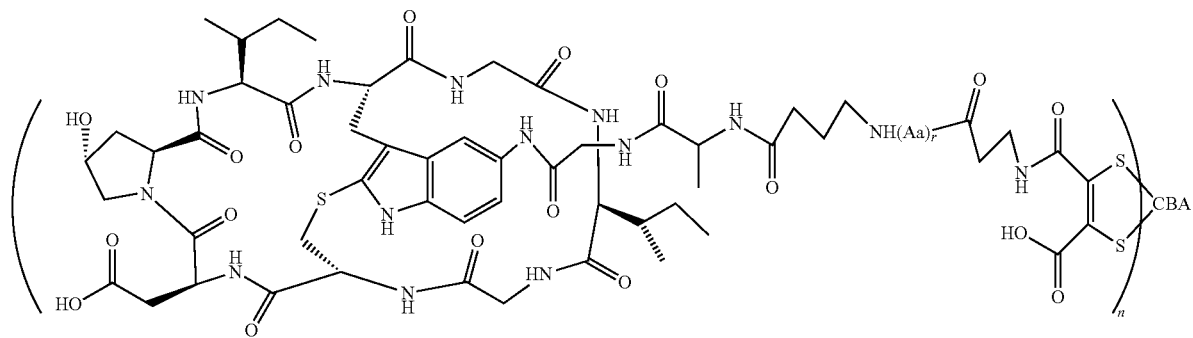

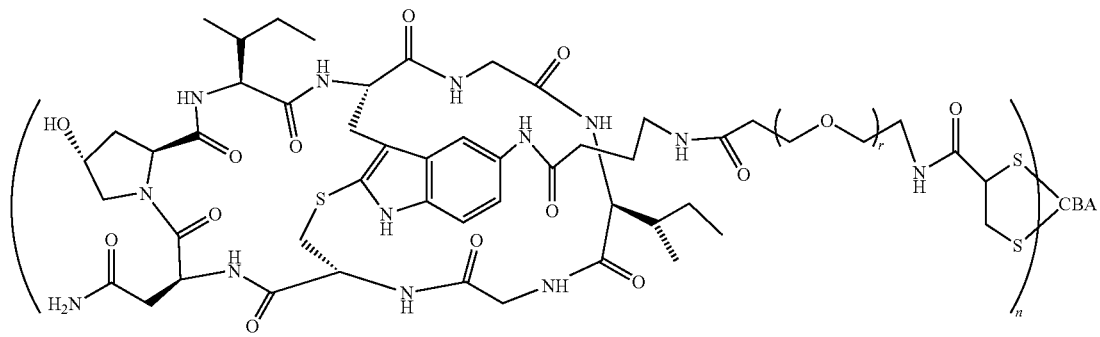
(II-19)
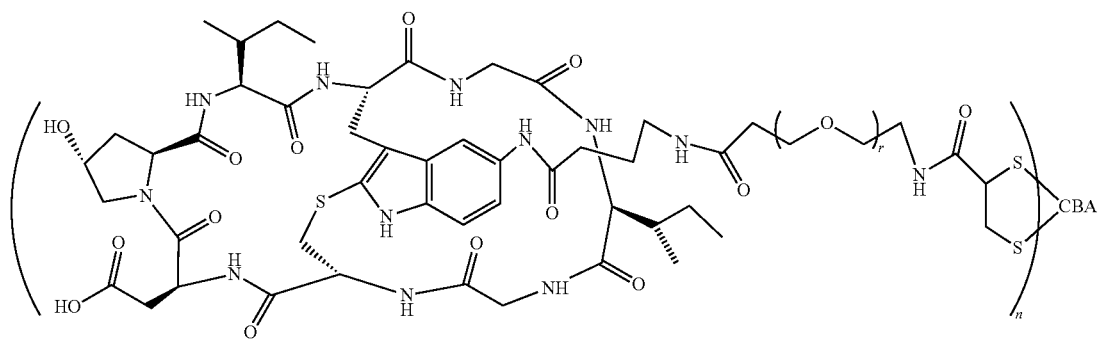
(II-20)
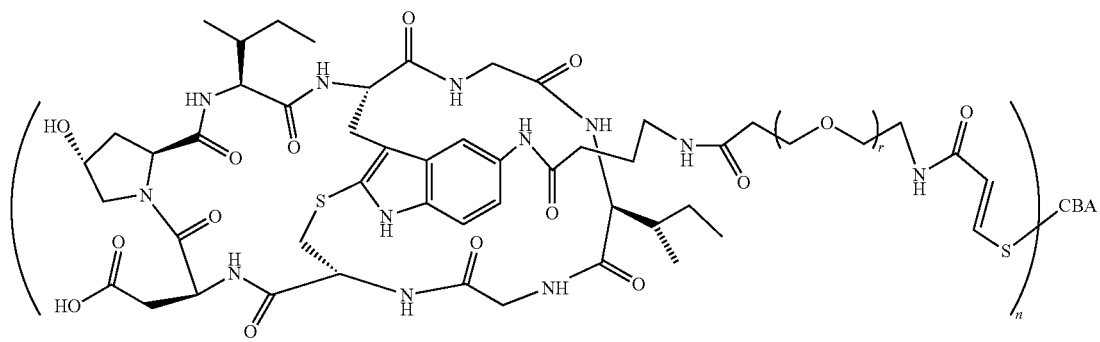
(II-21)
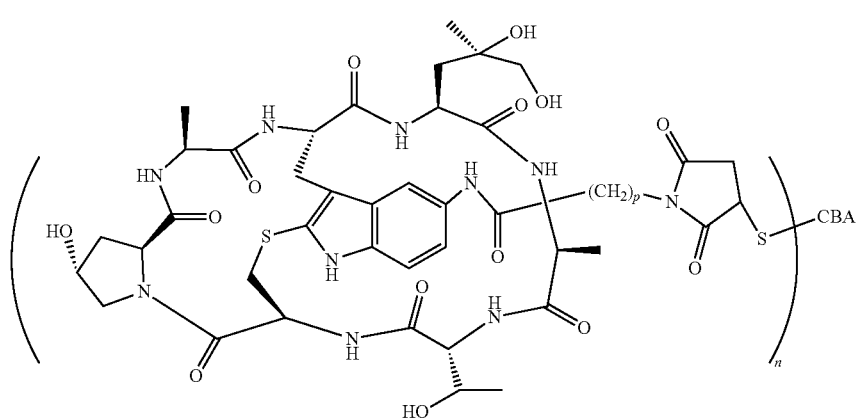
(II-22)

(II-23)
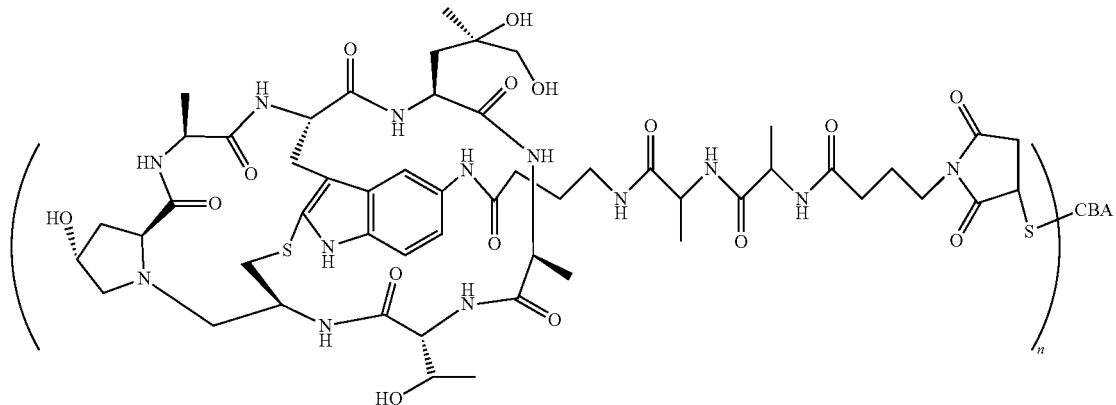
(II-24)
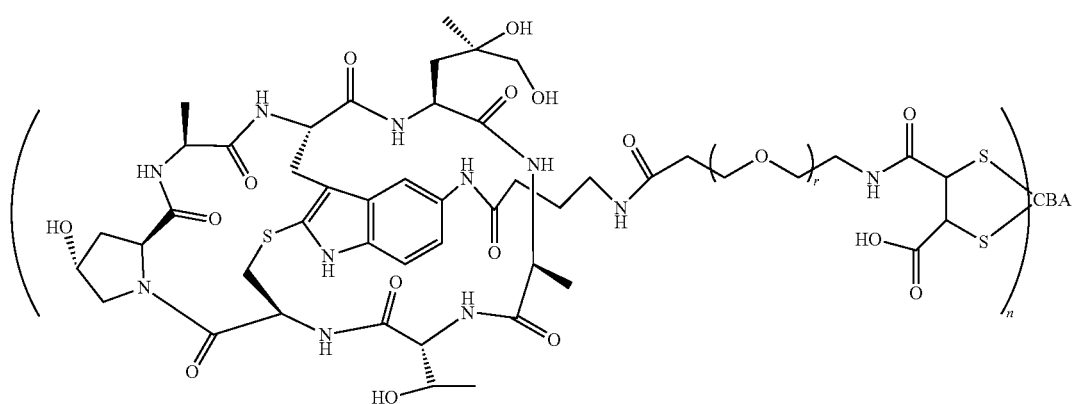
(II-25)
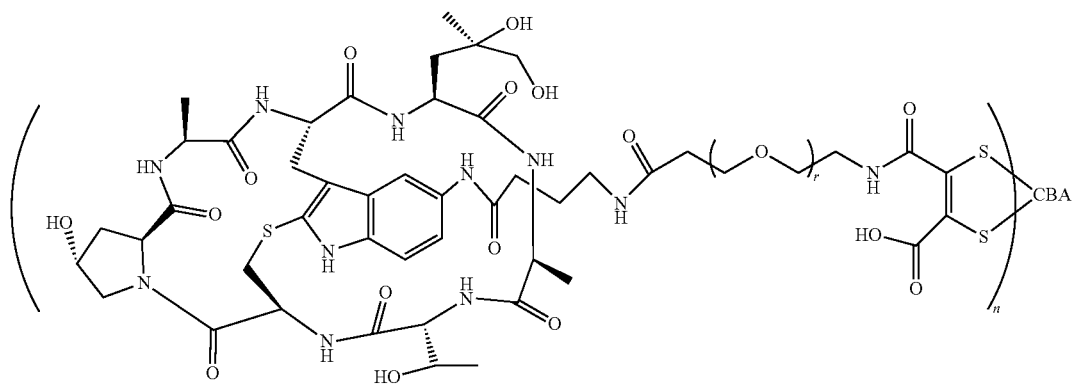
(II-26)
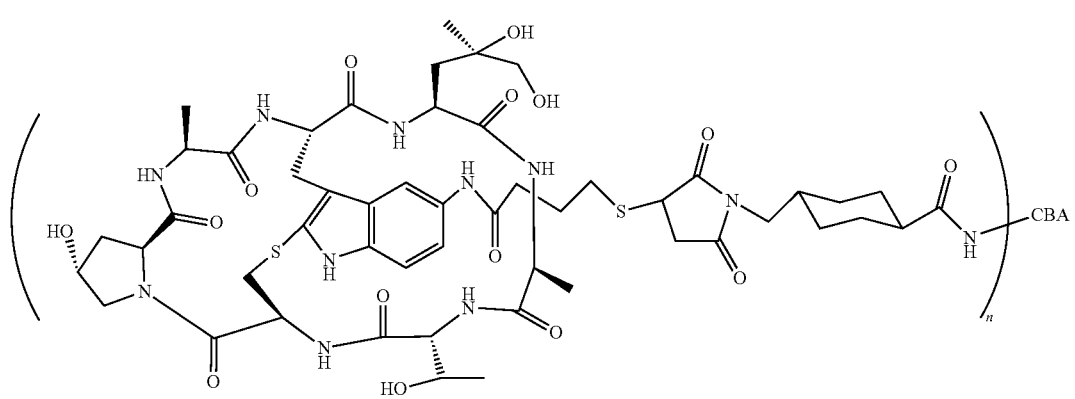

(II-27)
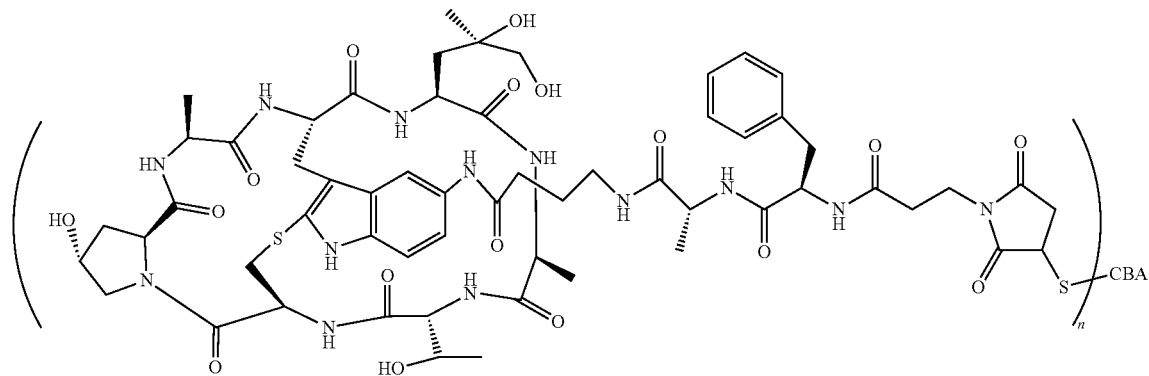
(II-28)
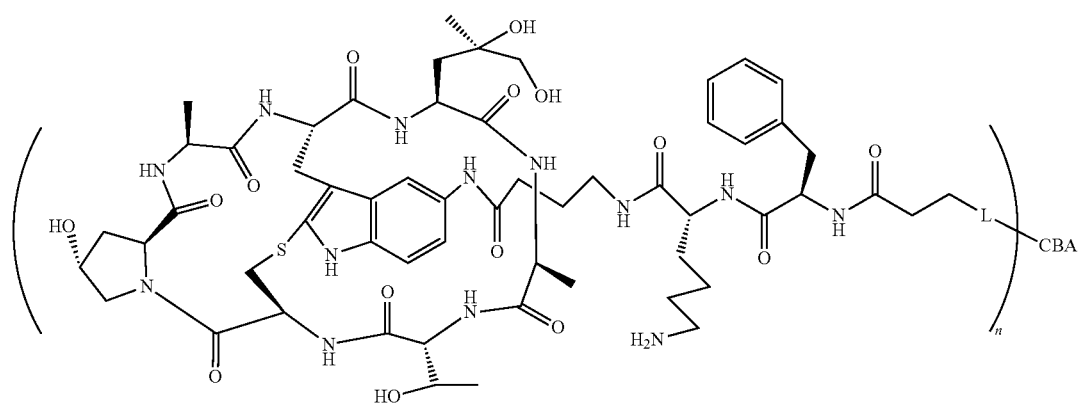
(II-29)
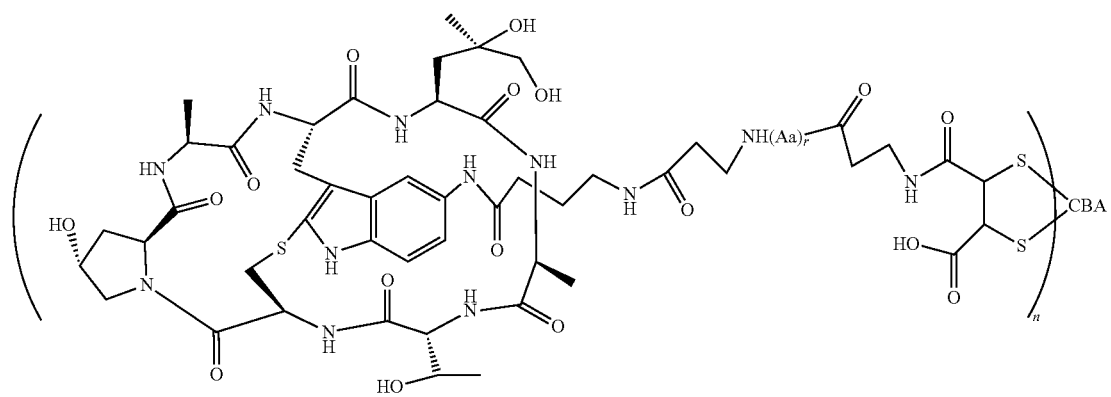
(II-30)
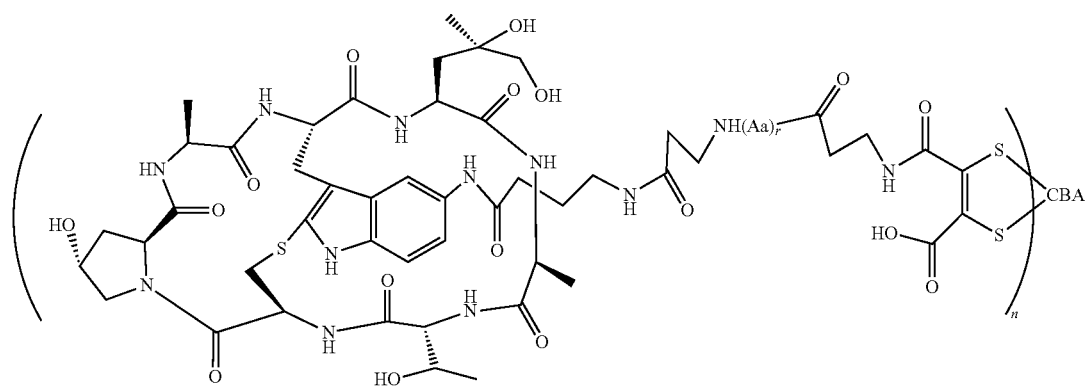

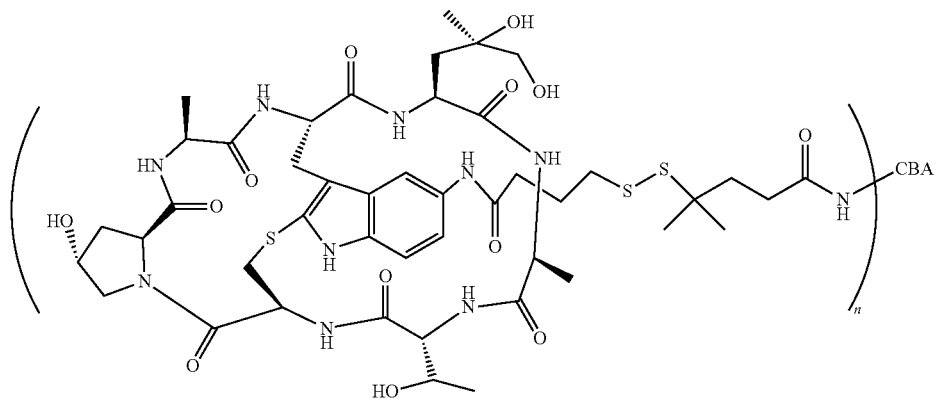
(II-31)
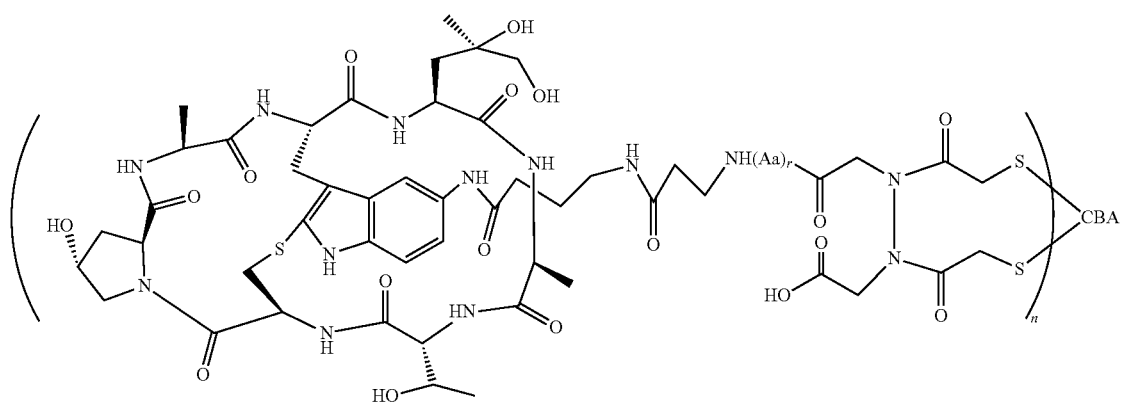
(II-32)

(II-33)

(II-34)

-continued
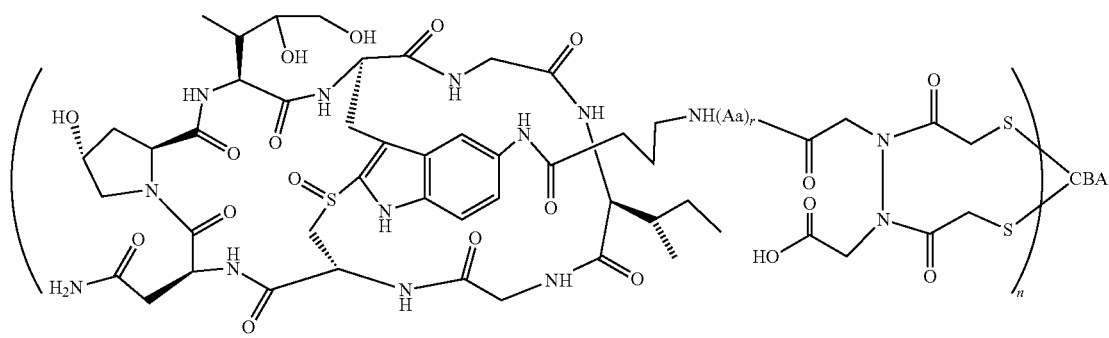
(II-35)

(II-36)

(II-37)
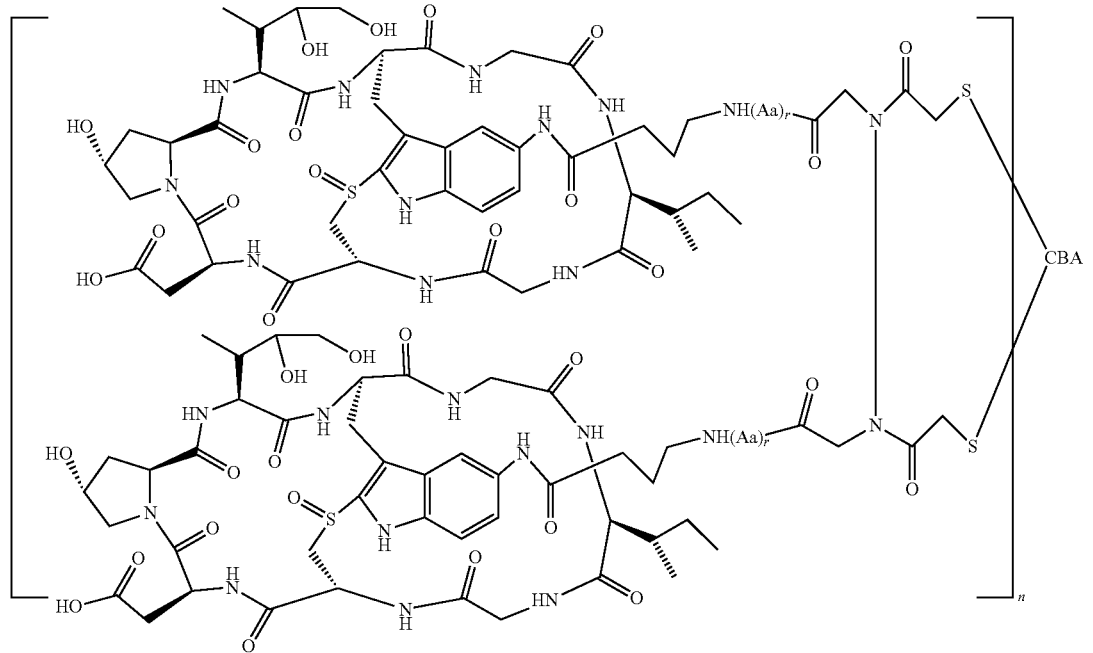
(II-38)

-continued
(II-39)
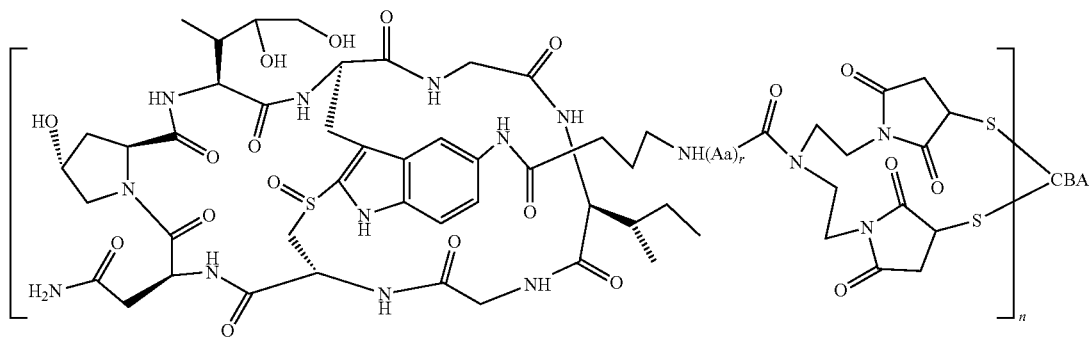
(II-40)
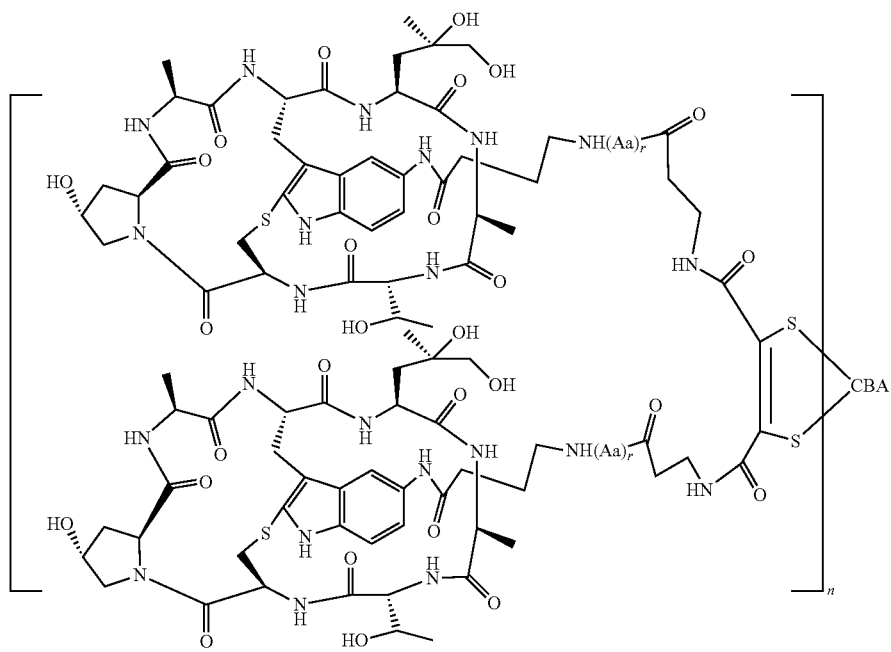
(II-41)
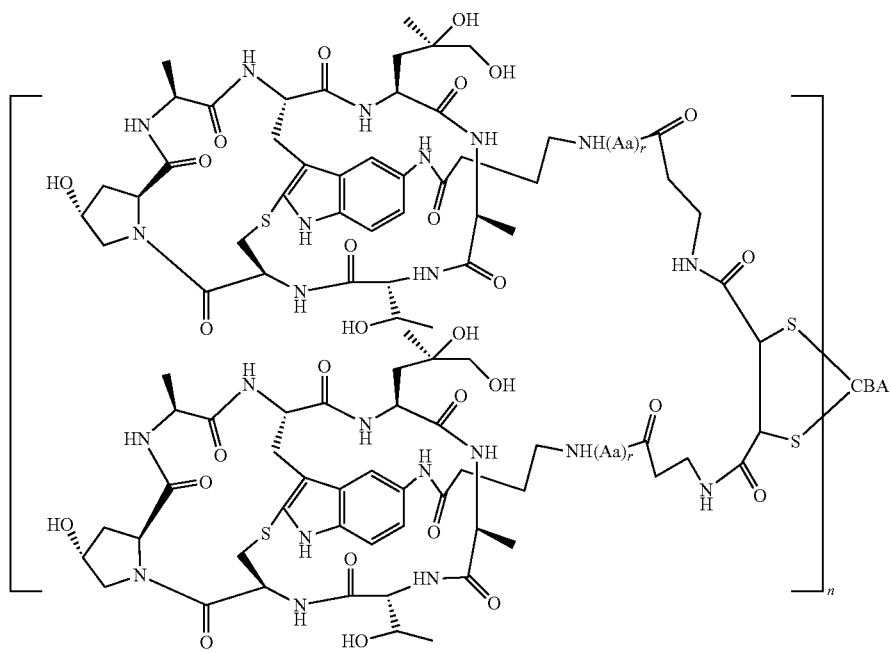

(II-42)
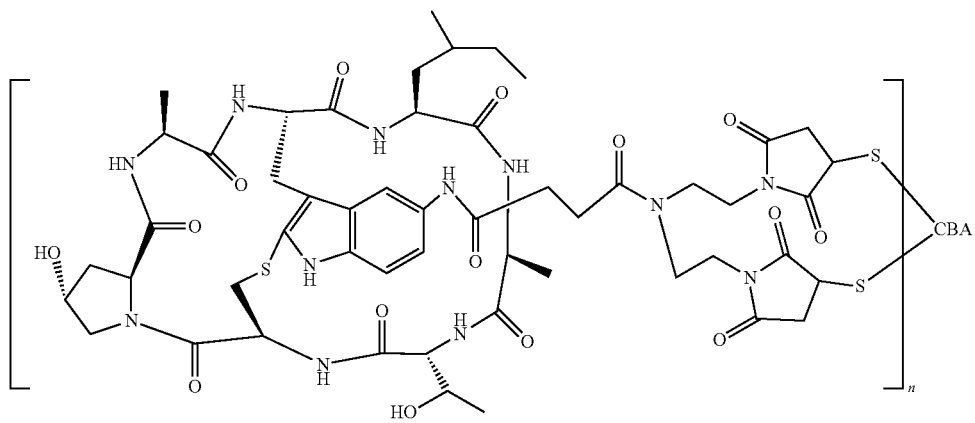
(II-43)
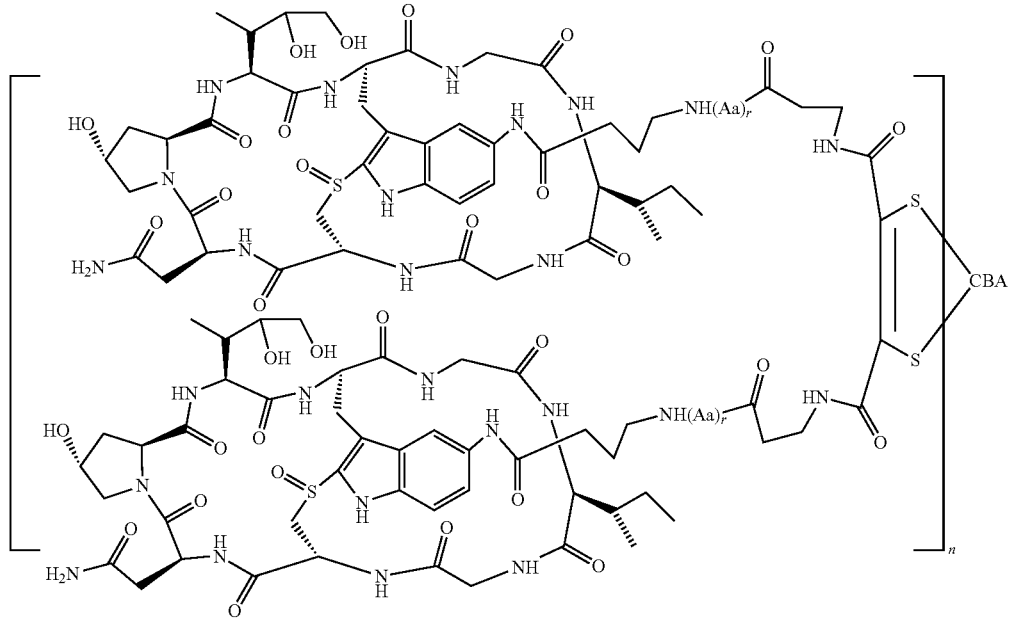
(II-44)
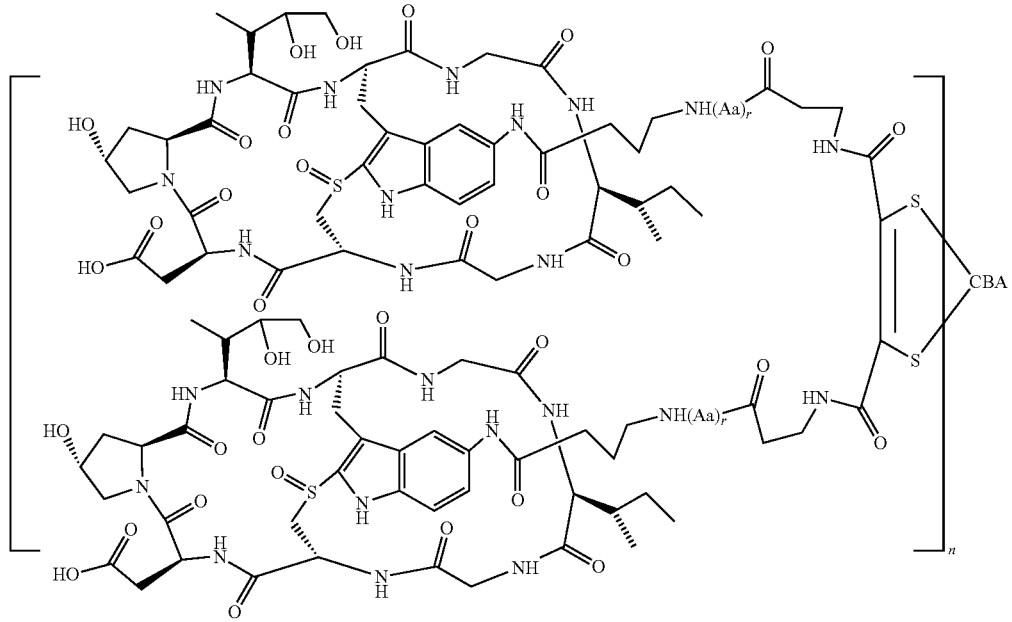

-continued
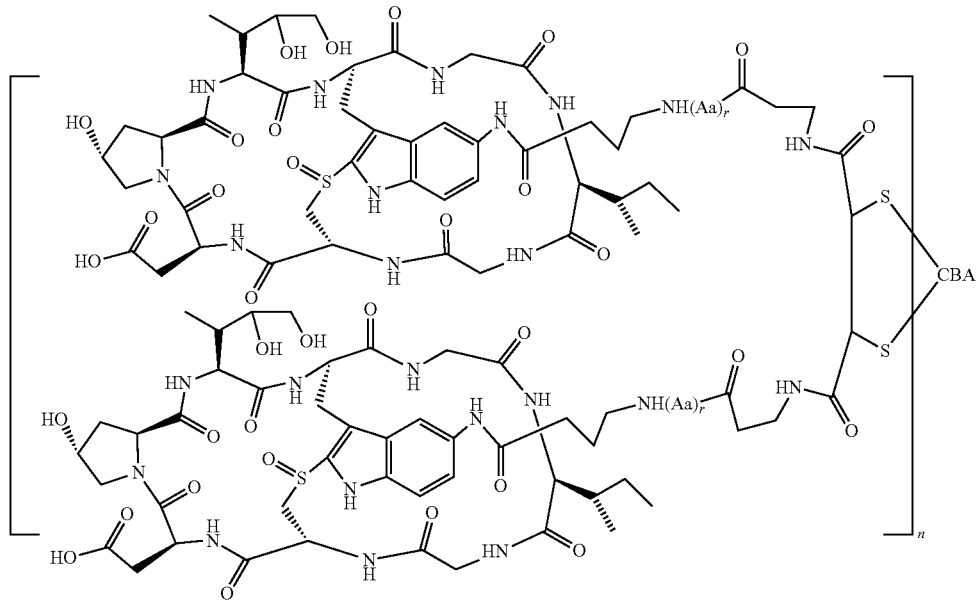
(II-45)
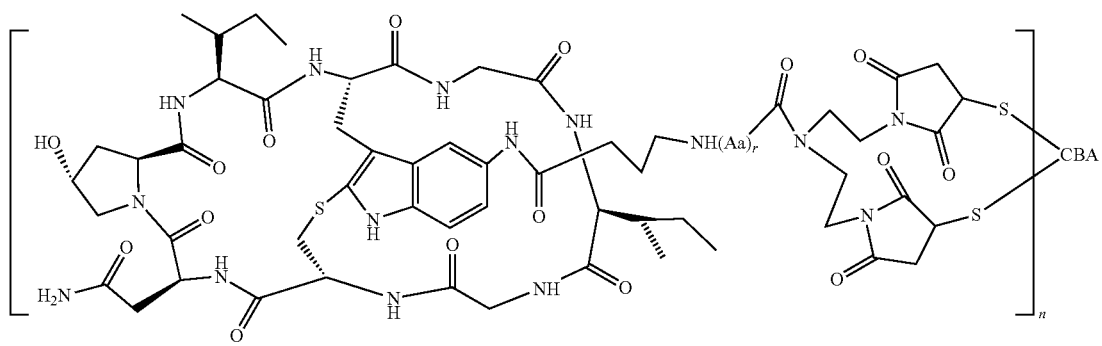
(II-46)
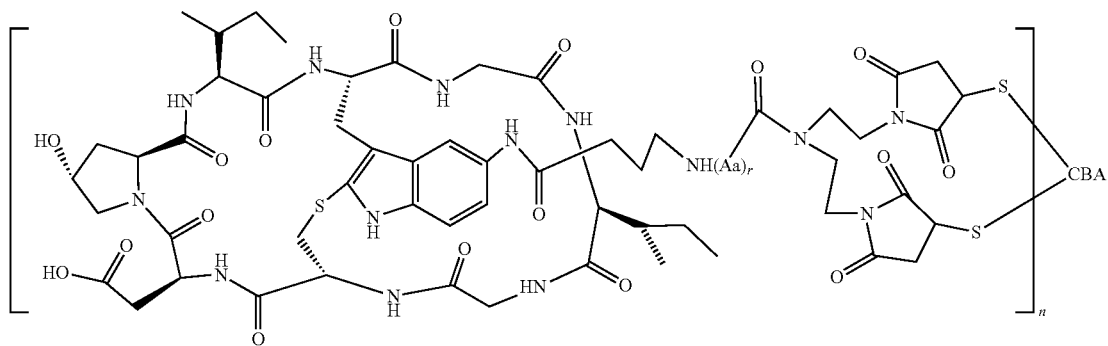
(II-47)

-continued
(II-48)
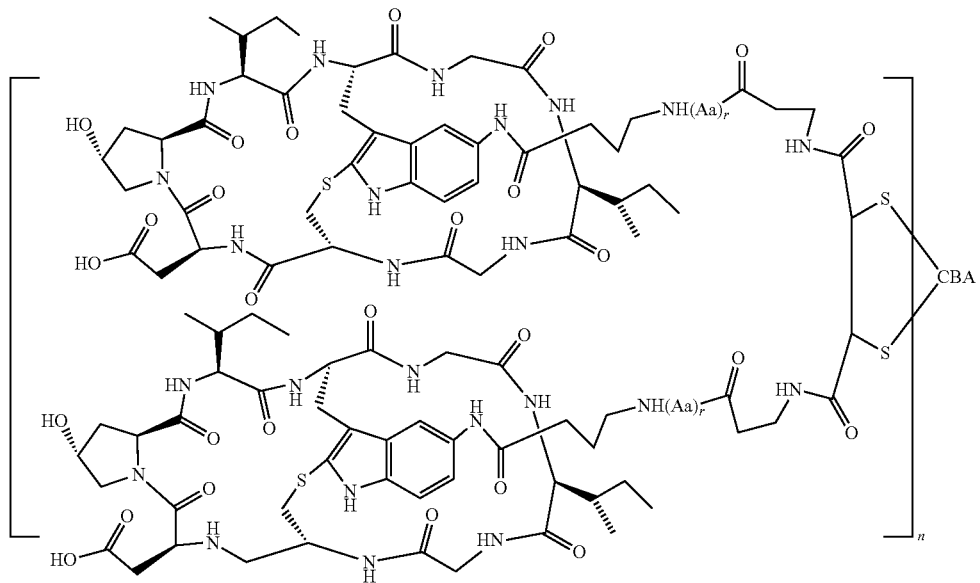
(II-49)
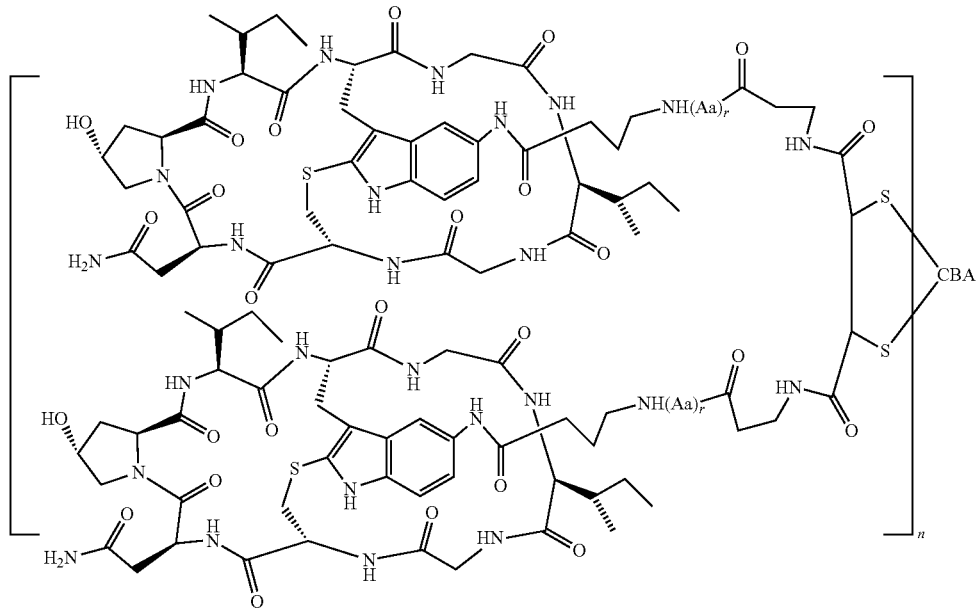
(II-50)
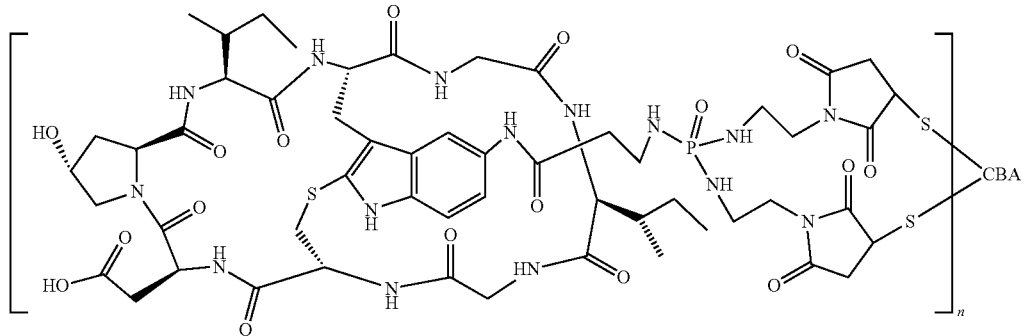

(II-51)
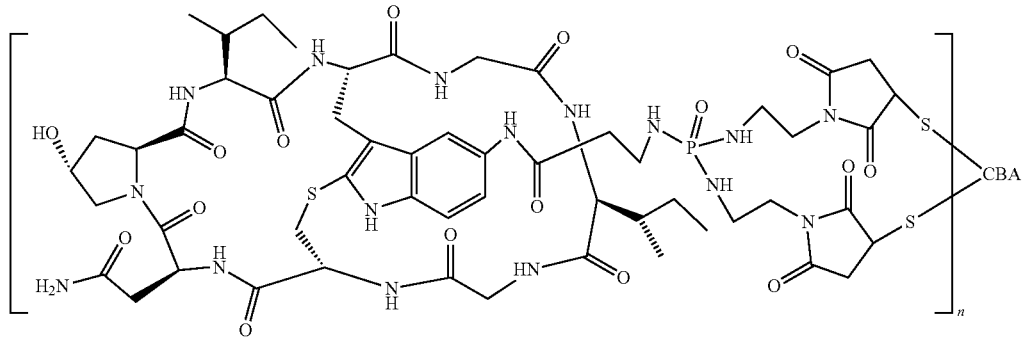
(II-52)
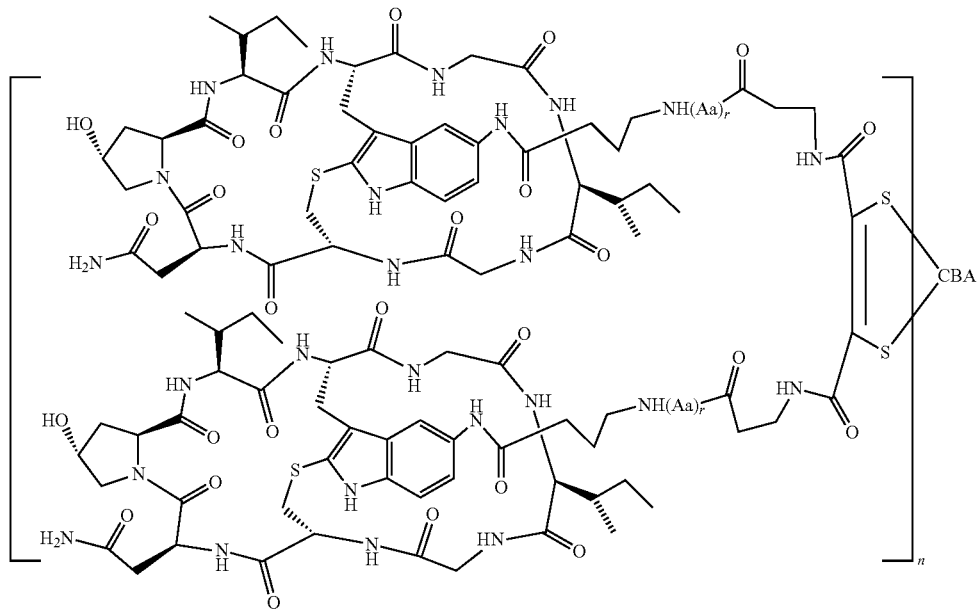
(II-53)
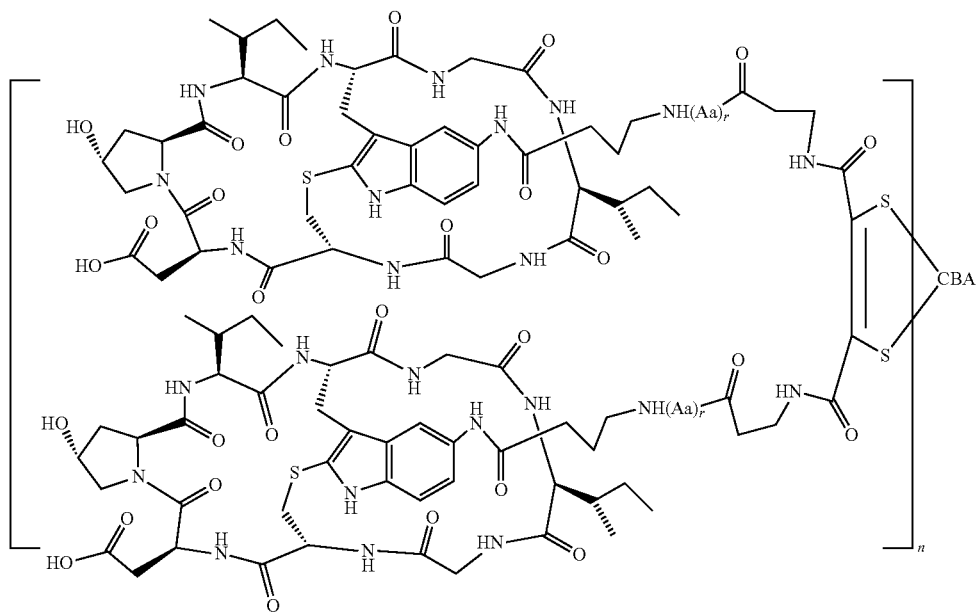

(II-54)
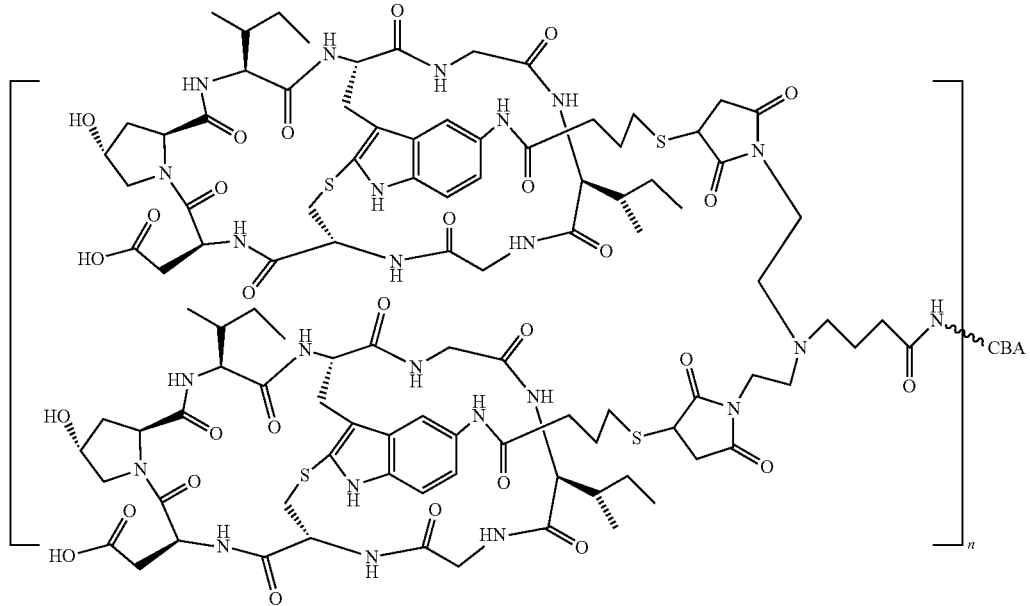
(II-55)
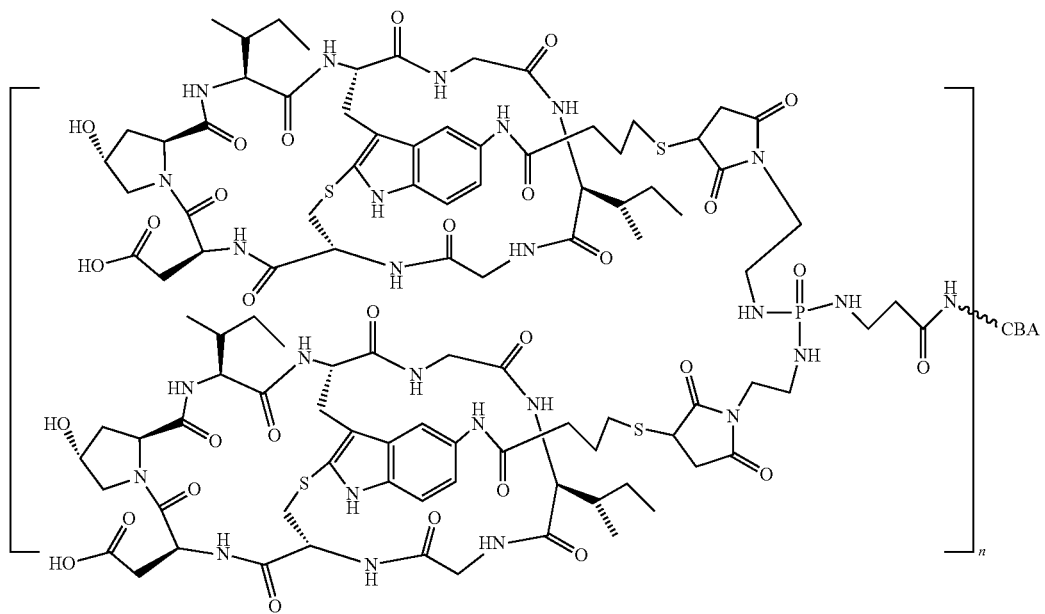

(II-56)
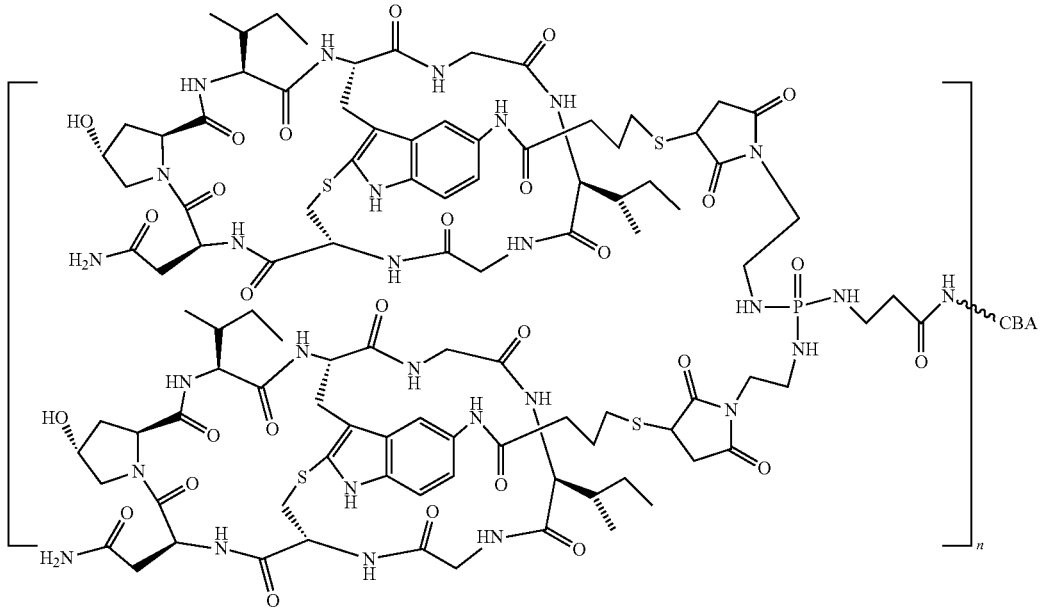
(II-57)
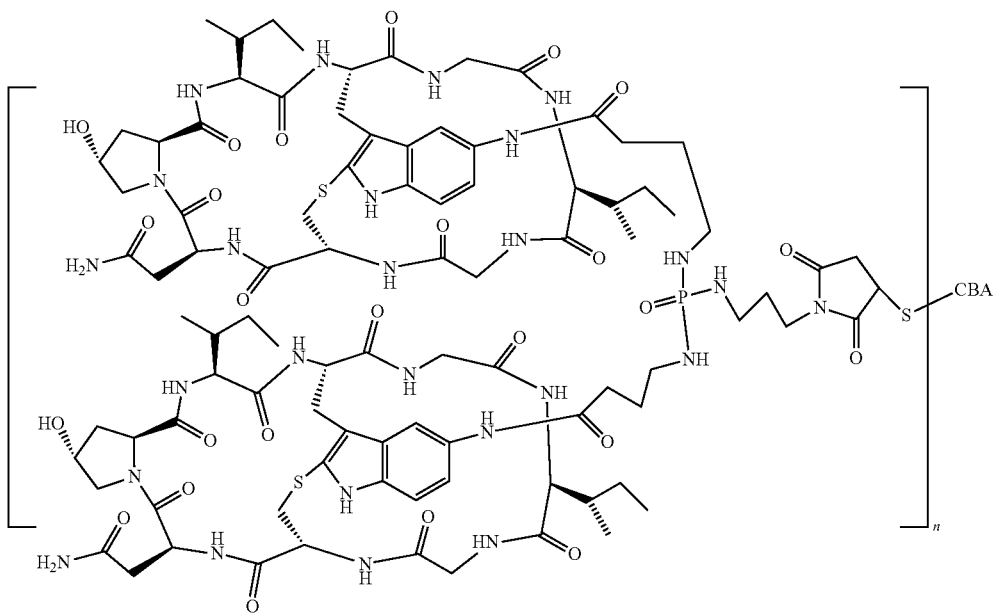

-continued
(II-58)
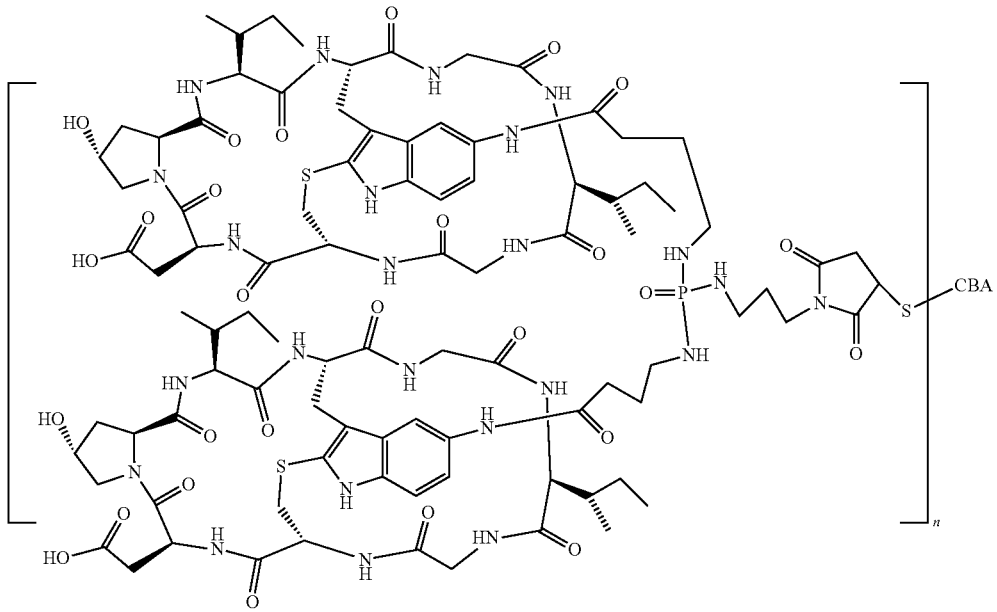
(II-59)
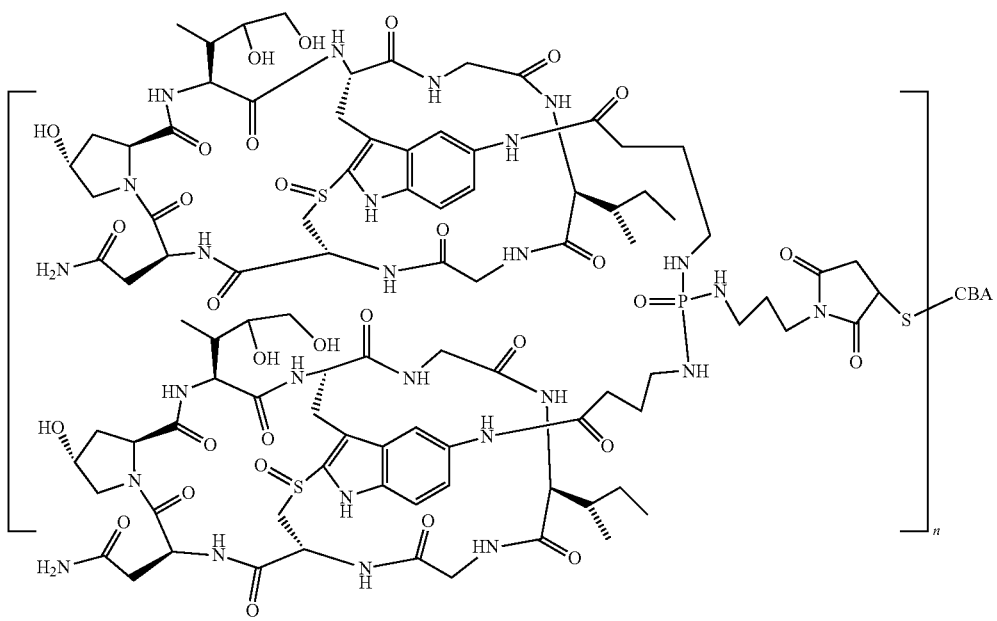
(II-60)
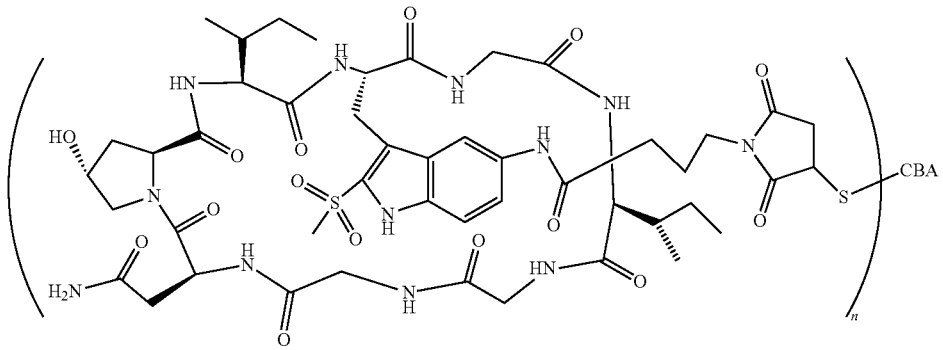

(II-61)
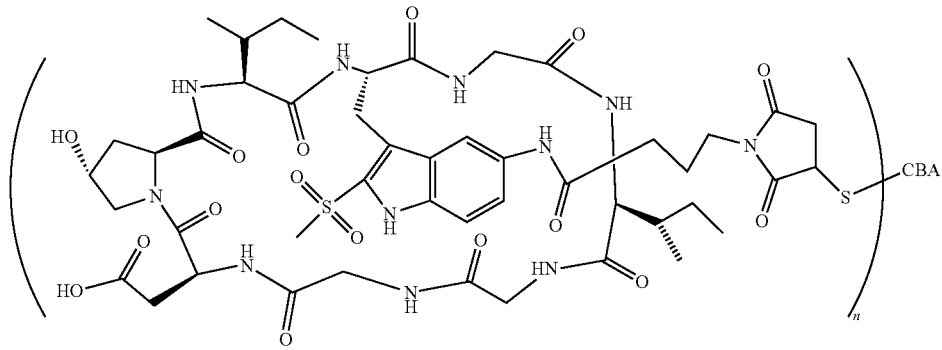
(II-62)
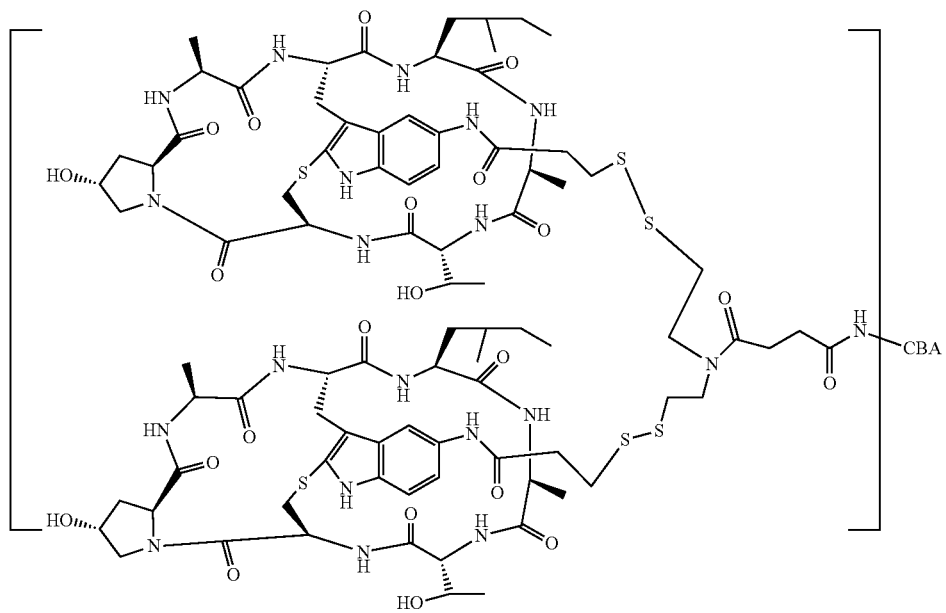
(II-63)
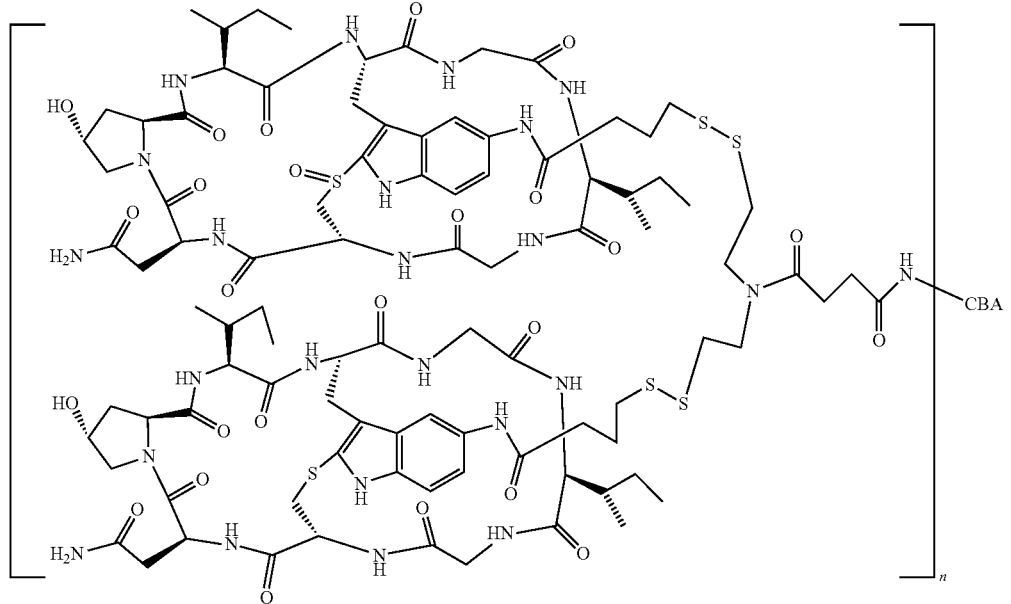

(II-64)
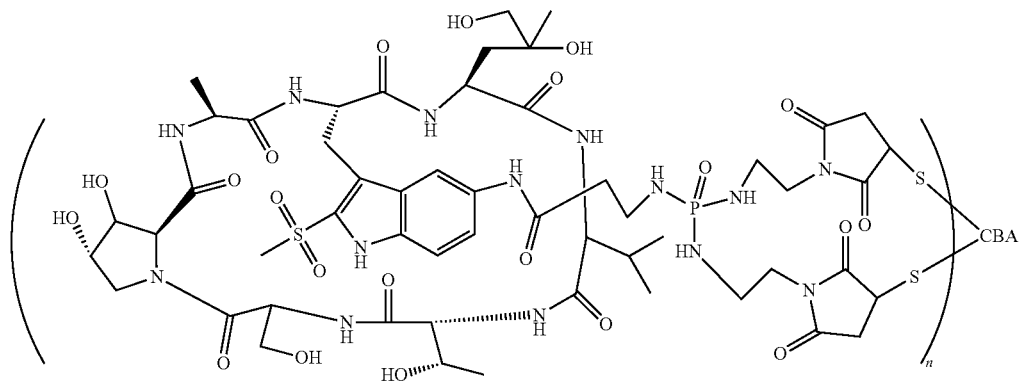
(II-65)
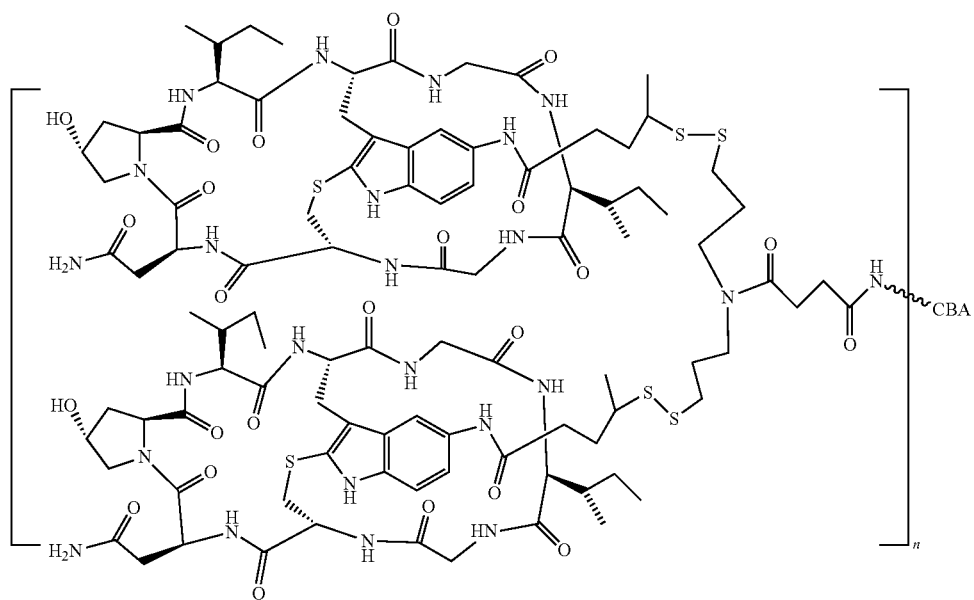
(II-66)
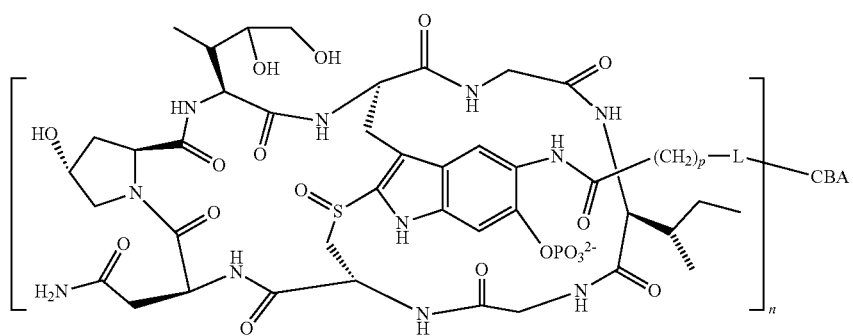

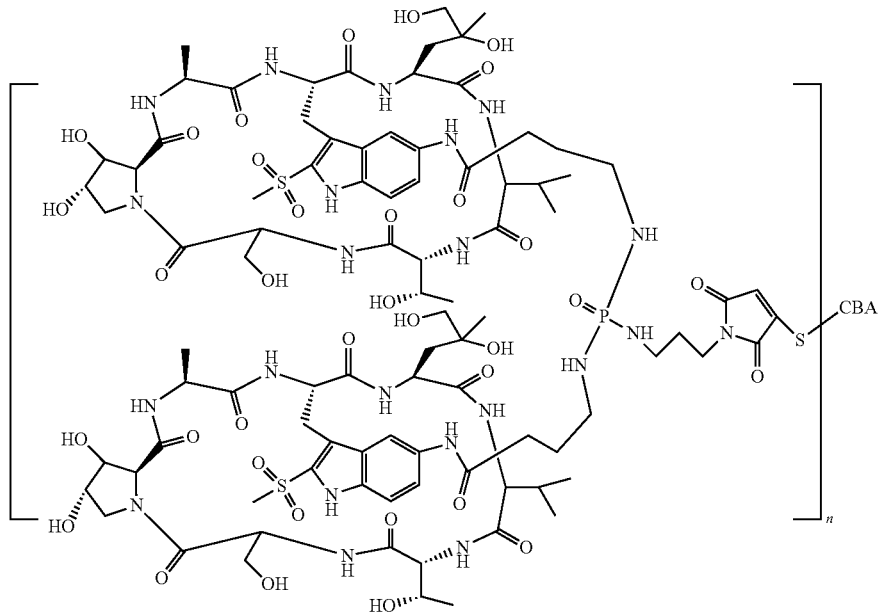
(II-67)
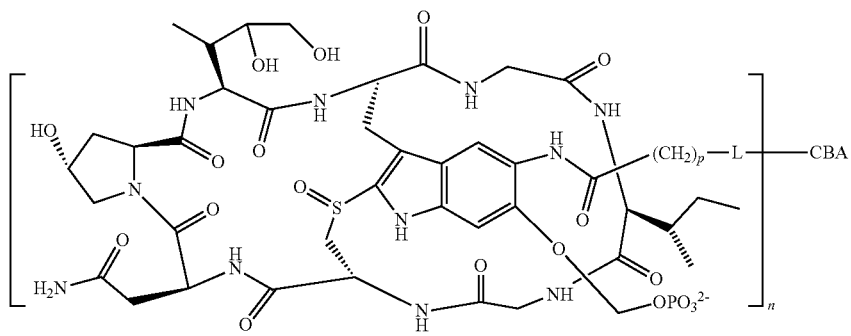
(II-68)
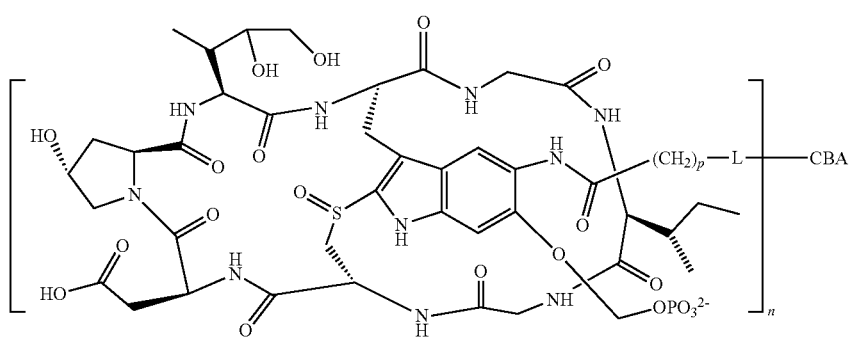
(II-69)

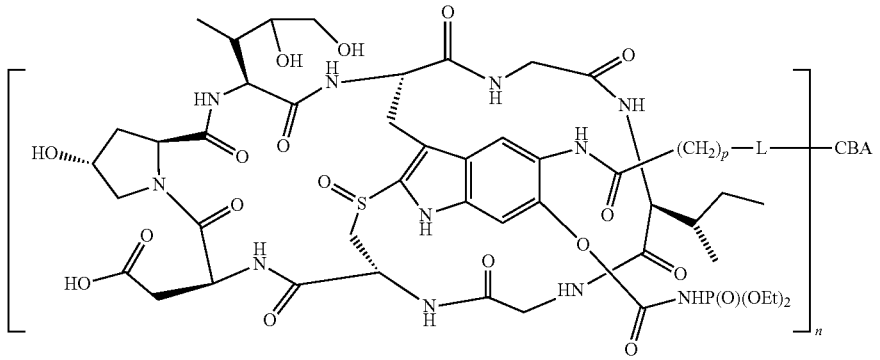
(II-70)
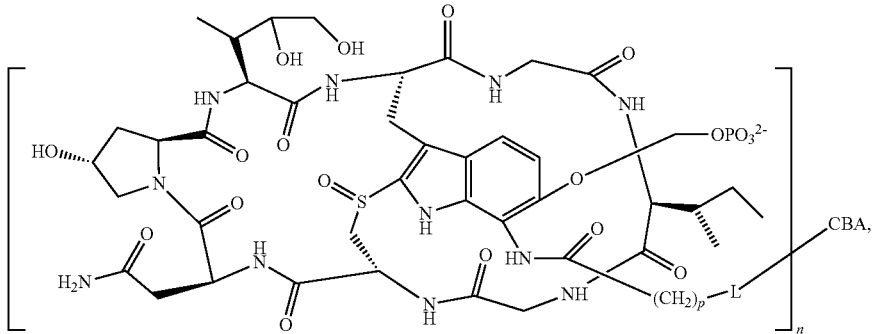
(II-71)
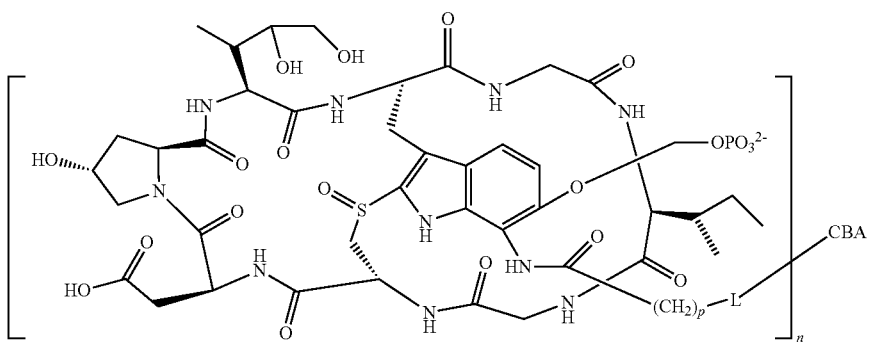
(II-72)
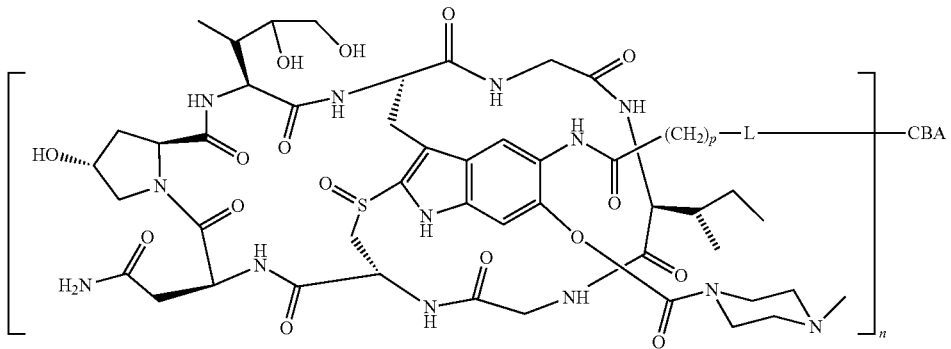
(II-73)

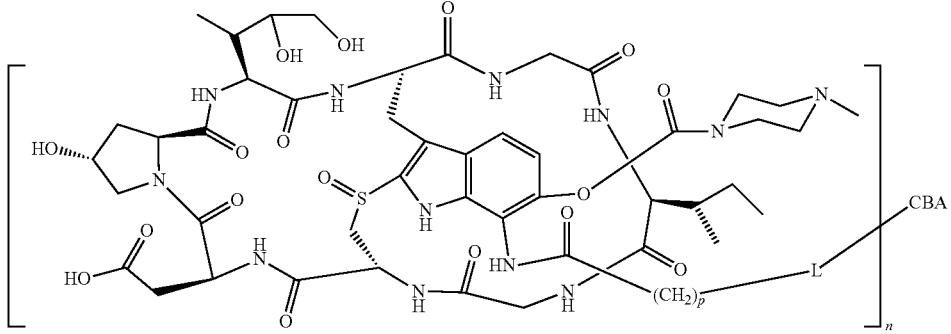
(II-74)
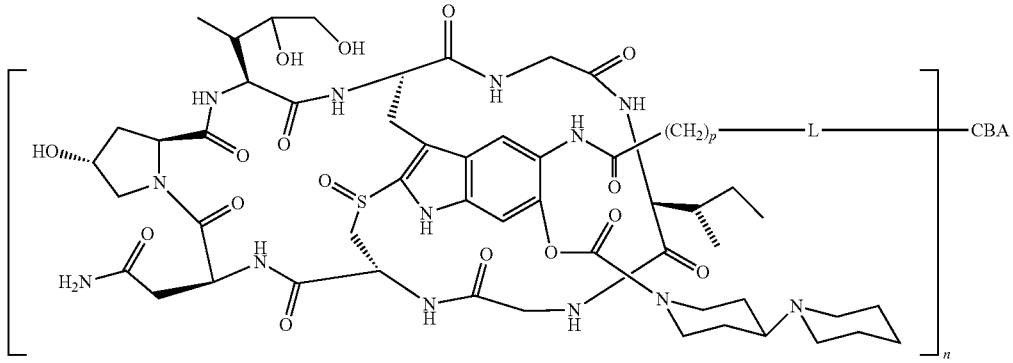
(II-75)
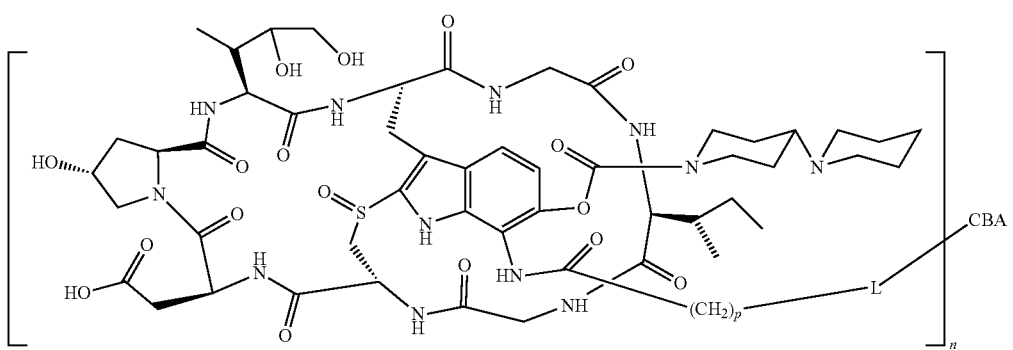
(II-76)
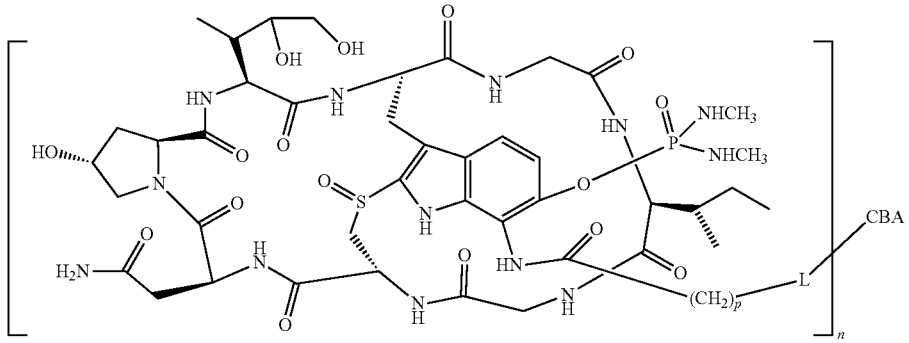
(II-77)

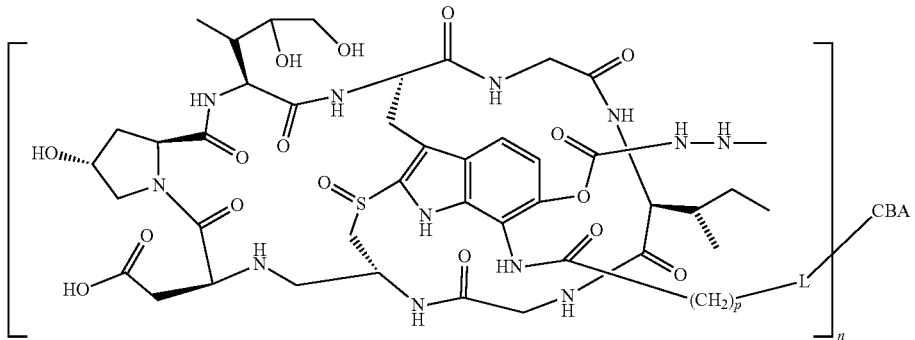
(II-78)
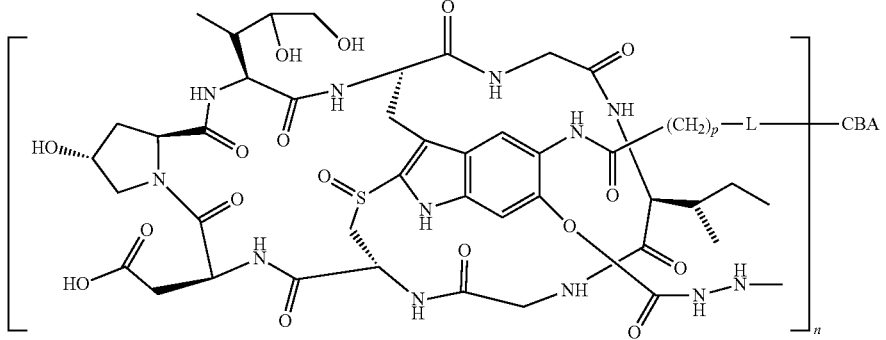
(II-79)
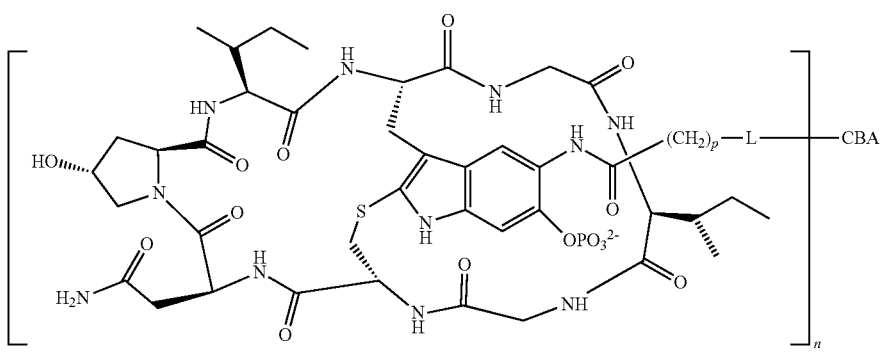
(II-80)
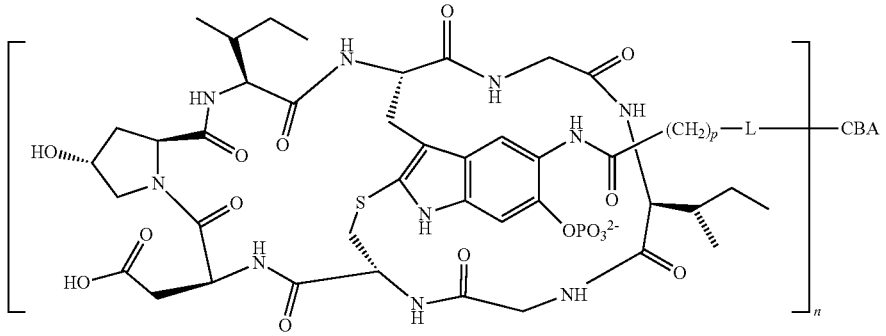
(II-81)

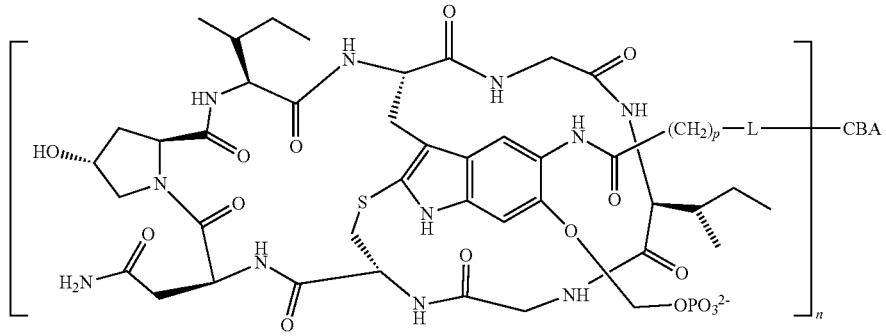
(II-82)
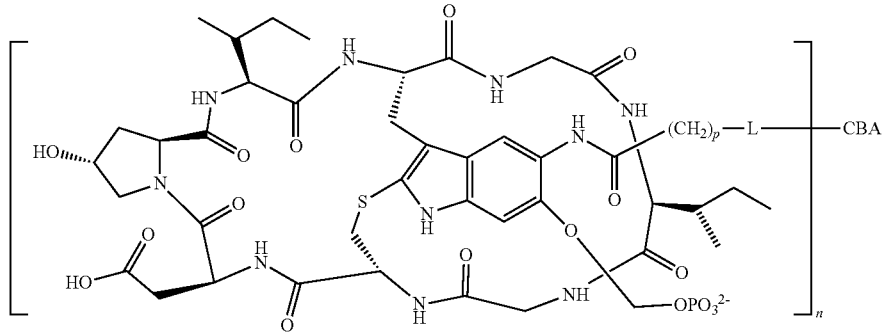
(II-83)
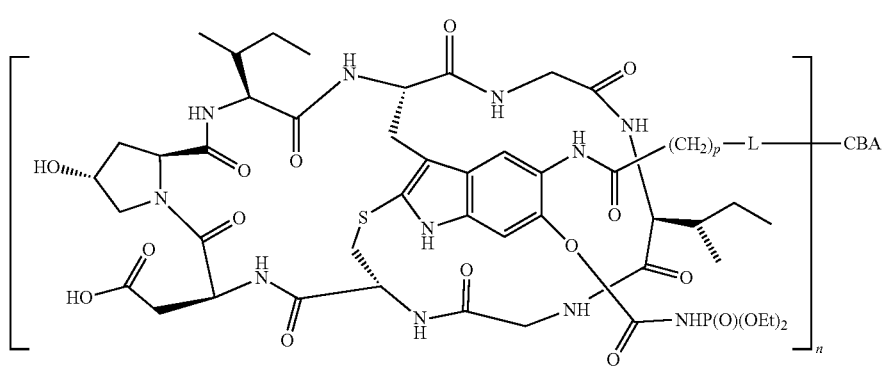
(II-84)
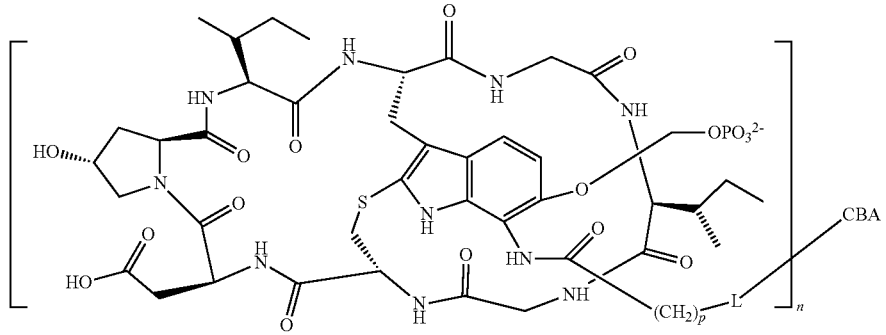
(II-85)

-continued
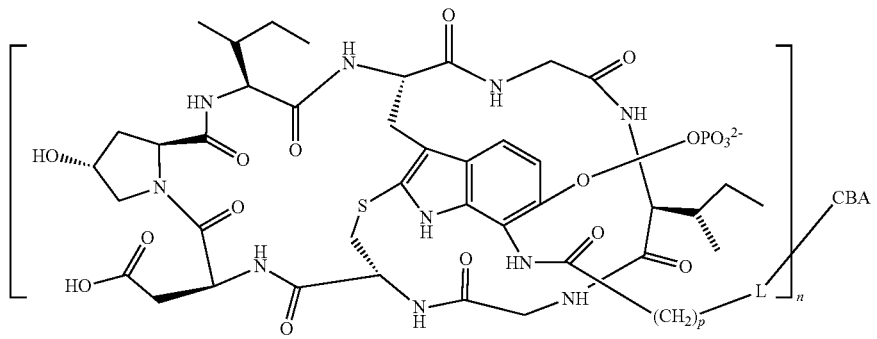
(II-86)
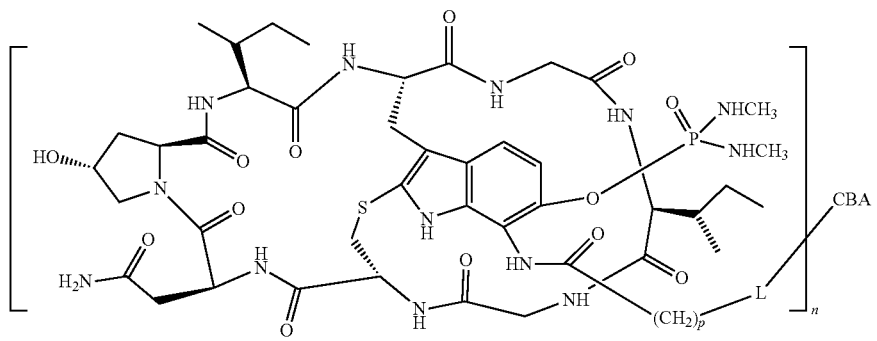
(II-87)
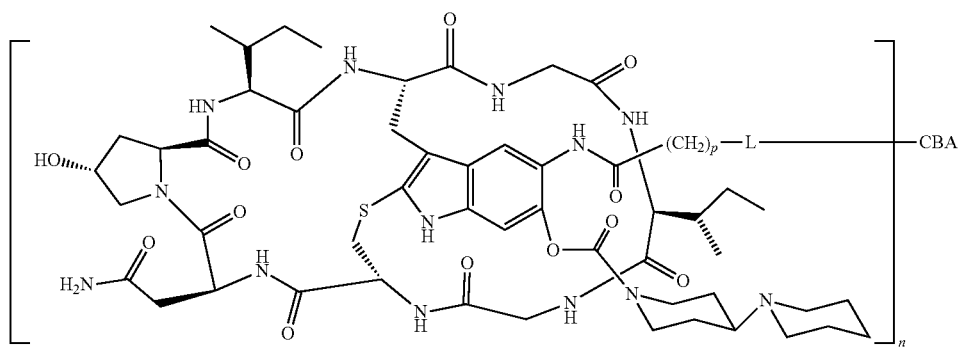
(II-88)
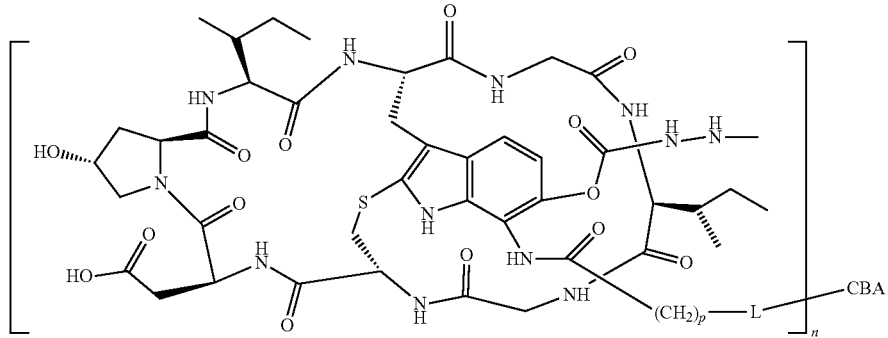
(II-89)

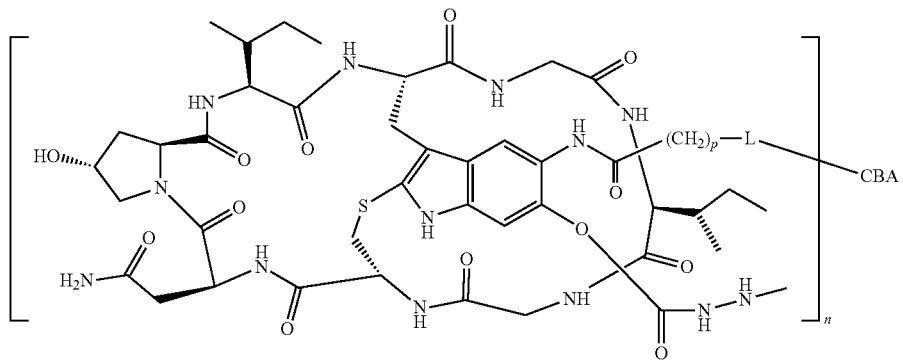

(II-90)

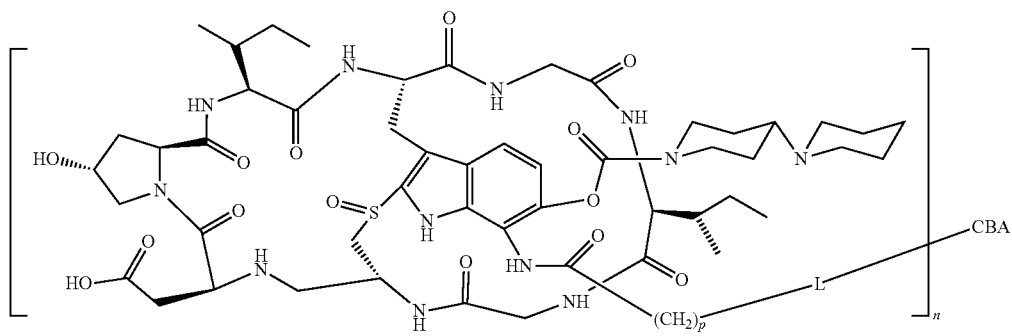

(II-91)

Wherein Aa, L, m, n, p, Q, r, $R_1$, and $R_2$, are described above in Formula (I). CBA is a Cell binding agent.

Drug loading (DAR) of the conjugates may range from 1 to 20 drug moieties (D) per cell binding agent and is preferred the average number of 2-8 drug moieties per cell binding agent in a molecule of Formula (II-1)-(II-91). When CBA is antibody in preparations of ADC, the preferred drug loading is 3~6 drug per antibody and the average number of drug moieties per antibody from conjugation reactions may be characterized by conventional means such as mass spectroscopy (HPLC-MS, UPLC-QTOF, HPLC-MS/MS), ELISA assay, and HPLC (SEC-HPLC, HIC-HPLC). The quantitative distribution of the conjugates in terms of the drug loading may also be determined. In some instances, separation, purification, and characterization of homogeneous the conjugates where drug loading is a certain value from the conjugates with the drug loadings may be achieved by means such as reverse phase HPLC or electrophoresis.

The Cell binding agents (CBA) may be of any kind and include peptides and non-peptides. Generally, the cell binding agents include, but are not limited to, large molecular weight proteins such as, for example, full-length antibodies (polyclonal and monoclonal antibodies); single chain antibodies; fragments of antibodies such as Fab, Fab', F(ab')$_2$, F$_v$, [Pharma, J. Immunol. 131, 2895-2902 (1983)], fragments produced by a Fab expression library, anti-idiotypic (anti-Id) antibodies, CDR's, and epitope-binding fragments of any of the above which immuno-specifically bind to cancer cell antigens, viral antigens or microbial antigens; antibody mimetic, such as an affibody; domain antibodies (dAb); nanobodies; unibodies; DARPins; anticalins; versabodies; duocalins; lipocalins; vimers; interferons (such as type I, II, III); peptides; lymphokines such as IL-2, IL-3, IL-4, IL-5, IL-6, GM-CSF, interferon-gamma (ITN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-158 (1984)]; vaccinia growth factors (VGF); fibroblast growth factors (FGFs); smaller molecular weight proteins, poly-peptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin {O'Keefe et al, 260 J. Biol. Chem. 932-937 (1985)}; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61) or a polymer having a cell binding agent on its surface; dendrimers (Lee, et al, Nat. Biotechnol. 2005, 23, 1517-26; Almutairi, et al; Proc. Natl. Acad. Sci. 2009, 106, 685-90) or a dendrimer containing a cell binding agent; nanoparticles (Liong, et al, ACS Nano, 2008, 19, 1309-12; Medarova, et al, Nat. Med. 2007, 13, 372-7; Javier, et al, Bioconjugate Chem. 2008, 19, 1309-12) or a nanoparticles having a cell binding agent on its surface; liposomes (Medinai, et al, Curr. Phar. Des. 2004, 10, 2981-9) or a liposome having a cell binding agent; viral capsides (Flenniken, et al, Viruses Nanotechnol. 2009, 327, 71-93). In general monoclonal antibodies are preferred as a cell-surface binding agent if an appropriate one is available.

The linker used for the conjugation of this invention includes, but not limited to, a disulfide linker, a thioether linker, an amide bonded linker, a peptidase-labile linker, a photolabile linker, an acid-labile linkers (such as hydrazone liner), an esterase-labile linker, an oxidatively labile linker, a metabolically labile linker, a biochemically labile linker.

Preferably, the linker is linked to the cell binding agent via a function reactive towards for instance thiol and amino functions of the cell binding agent coming from reduced disulfide bonds and lysine residues respectively. More particularly, said derivative is linked through the —CO— group to the amino function of the lysine residue of said cell binding agent, so as to form an amide bond.

In addition, the linker may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), glycine-glycine, a nature peptides containing up to 6 the same or different aminoacides (dipeptide, tripeptide, tetrapeptide, pentapeptide, hexapeptide), p-aminobenzyloxycarbonyl ("PAB"), N-succinimidyl 4-(2-pyridyl-thio)pentanoate ("SPP"), N-succinimidyl 4-(N-maleimidomethyl)cyclohexane-1 carboxylate ("SMCC"), N-Succinimidyl (4-iodo-acetyl)aminobenzoate ("STAB"), ethyleneoxy (—$CH_2CH_2O$—) as one or up to 100 repeating units ("EO" or "PEO"). The linker may be a "cleavable linker," facilitating release of a drug in the cell. Additional linker components are known in the art and some are illustrated below:

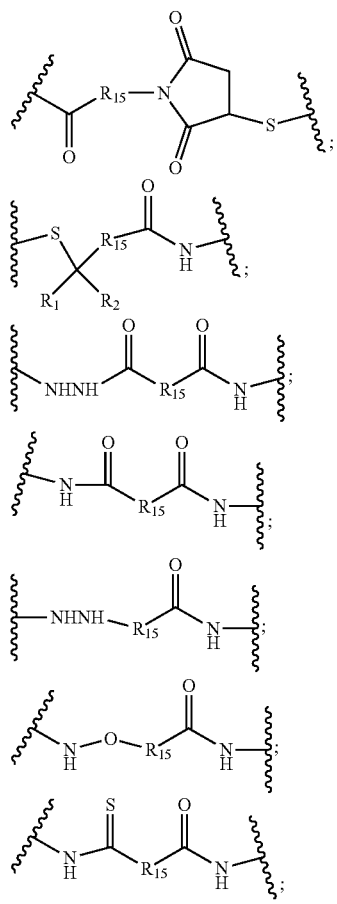

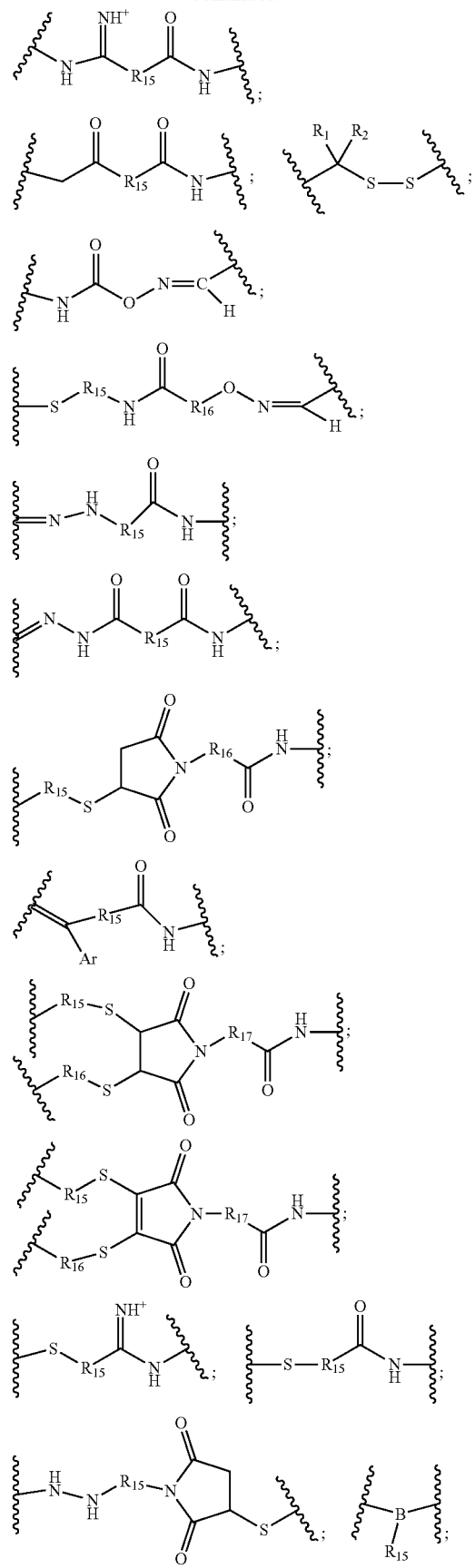

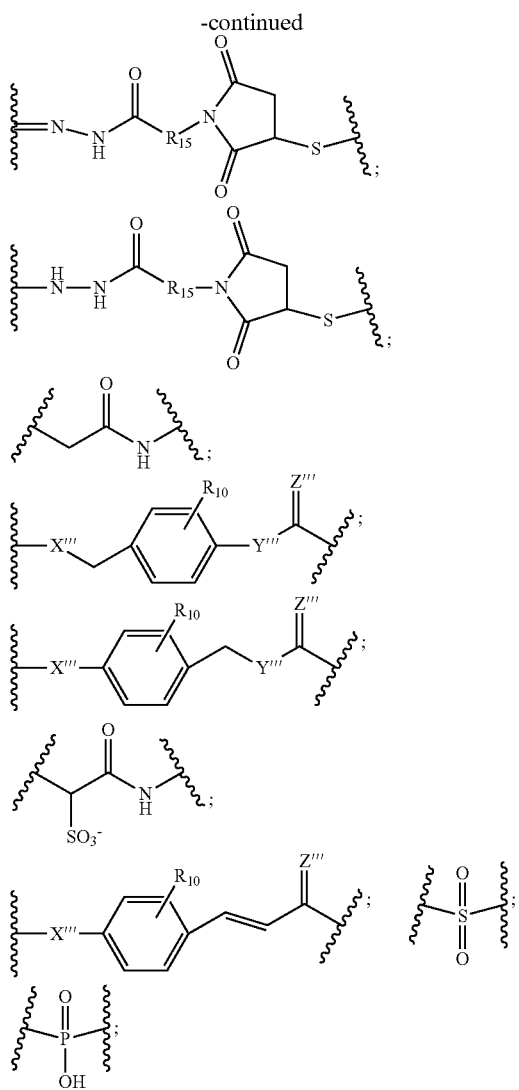

Wherein $R_{10}$ is defined in Formula (I) above. Wherein $R_{15}$, $R_{16}$ and $R_{17}$ are independently selected from —$C_1$~$C_8$ alkyl or alkylene-, —$C_1$~$C_7$ carbocyclo-, alkyl)-, —NH—($C_1$~$C_8$ alkyl)-, -arylene-, —$C_1$~$C_5$ alkylene-arylene-, -arylene, —$C_1$~$C_8$ alkylene-, —$C_1$~$C_8$ alkylene-($C_1$~$C_8$ carbocyclo)-, —($C_3$~$C_7$ carbocyclo)-$C_1$~$C_8$ alkylene-, —$C_3$~$C_8$ heterocyclo-, —$C_1$~$C_8$ alkylene-($C_3$~$C_8$ heterocyclo)-, —($C_3$~$C_8$ heterocyclo)-$C_1$~$C_9$ alkylene-, —($CH_2CH_2O)_k$—, —($CH(CH_3)CH_2O)_k$—, and —($CH_2CH_2O)_k$—$CH_2$—; k is an integer ranging from 1-30; X''', Y''' and Z''' are independently selected from NH, O or S.

In a preferred embodiment, conjugates of the invention are antibody/cytotoxic agent, antibody fragment/cytotoxic agent, diabody/cytotoxic agent, tri(a)body/cytotoxic agent, epidermal growth factor (EGF)/cytotoxic agent, prostate specific membrane antigen (PSMA) inhibitor/cytotoxic agent, melanocyte stimulating hormone (MSH)/cytotoxic agent, thyroid stimulating hormone (TSH)/cytotoxic agent, polyclonal antibody/cytotoxic agent, somatostatin/cytotoxic agent, folate/cytotoxic agent, matriptase inhibitor/cytotoxic agent, estrogen/cytotoxic agent, estrogen analogue/cytotoxic agent, designed ankyrin repeat proteins (DARPins)/cytotoxic agent, androgen/cytotoxic agent, and androgen analogue/cytotoxic agent.

In a more preferred embodiment, conjugates of the invention are monoclonal antibody/cytotoxic agent. Examples of antibodies used for conjugation of cyotoxic agents in this prevention include, but are not limited to, 3F8 (anti-GD2), Abagovomab (anti CA-125), Abciximab (anti CD4l (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (α chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (a chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-C5), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $α_vβ_3$), Exbivirumab (anti-hepatitis B surface antigen), Fanolesomab (NeutroSpec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Inflixinnab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R$_2$), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C$_{242}$), Naptumomab (anti-5T4), Natalizumab (Tysabri, anti-integrin α4), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-Rα), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab Rovelizumab (LeukArrest, anti-CD11, CD18), Rupluzumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) MI95 (anti-CD33), Solanezumab (anti-beta amyloid), Sonepcizumab (anti-sphingosine-1-phosphate), Sontuzumab (anti-episialin), Staniulumab (anti-myostatin), Sulesomab (LeukoScan, (anti-NCA-90 (granulocyte antigen), Tacatuzumab (anti-alpha-fetoprotein), Tadocizumab (anti-integrin α$_{11b}$β$_3$), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R$_2$), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin α$_4$β$_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin α$_5$β$_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.28S [anti-HMW-MAA (High molecular weight-melanoma-associated antigen), Sorin Radiofarmaci S. R. L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRαβ (T cell receptor alpha/beta), complex, from MedImmune Inc for Graft-versus-host disease], RING SCAN [anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; LymphoCide (Immunomedics, NJ), Smart IDIO (Protein Design Labs), Oncolym (Techniclone Inc, CA), Allomune (BioTransplant, CA), anti-VEGF (Genentech, CA); CEAcide (Immunomedics, NJ), IMC-1C11 (ImClone, NJ) and Cetuximab (ImClone, NJ).

Other antibodies as binding ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (A-like-4), EGFR (Epidermal Growth Factor Receptor, various cancers), CTLA4 (melanoma), CXCR4 (CD184, Hemeoncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins ($\alpha v \beta 3$, $\alpha 5 \beta 1$, $\alpha 6 \beta 4$, $\alpha 11 \beta 3$, $\alpha 5 \beta 5$, $\alpha v \beta 5$, for various cancers), MAGE-1 (carcinomas), MAGE-2 (carcinomas), MAGE-3 (carcinomas), MAGE 4 (carcinomas), anti-transferrin receptor (carcinomas), p 97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-N-glycolylneuraminic acid (Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-$R_1$ (Tumor necrosis apoprosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother. 54(3), 187-207 (2005). Franke, et al, Cancer Biother Radiopharm. 2000, 15, 459-76). Examples of these antigens that antibodies against are: Many other Cluster of Differentiations (CD4, CD5, CD6, CD7, CD8, CD9, CD10, CD11a, CD11b, CD11c, CD12w, CD14, CD15, CD16, CDw17, CD18, CD20, CD21, CD22, CD23, CD24, CD25, CD26, CD27, CD28, CD29, CD30, CD31, CD32, CD34, CD35, CD36, CD37, CD38, CD41, CD42, CD43, CD44, CD45, CD46, CD47, CD48, CD49b, CD49c, CD53, CD54, CD55, CD56, CD58, CD59, CD61, CD62E, CD62L, CD62P, CD63, CD68, CD69, CD70, CD71, CD72, CD79, CD81, CD82, CD83, CD86, CD87, CD88, CD89, CD9O, CD91, CD95, CD96, CD100, CD103, CD105, CD106, CD109, CD117, CD120, CD125, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), Annexin A1, Nucleolin, Endoglin (CD105), ROBO4, Amino-peptidase N, A-like-4 (DLL4), VEGFR-2 (CD309), CXCR4 9CD184), Tie2, B7-H3, WT1, MUC1, LMP2, HPV E6 E7, EGFRvIII, HER-2/neu, Idiotype, MAGE A3, p53 nonmutant, NY-ESO-1, GD2, CEA, MelanA/MARTI, Ras mutant, gp100, p53 mutant, Proteinase3 (PR1), bcr-abl, Tyrosinase, Survivin, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-$\beta$, MAD-CT-2, Fos-related antigen 1.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Kohler, G.; Milstein, C. (1975). Nature 256: 495-497). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A, or protein-G affinity chromatography; anion, cation, hydrophobic, or size exclusive chromatographies (particularly by affinity for the specific antigen after Protein A or G, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8:396 (1959)) supplemented with 4.5 gm/l glucose, 20 mm glutamine, 20% fetal calf serum and with an anti-foaming agent, such as polyoxyethylene-polyoxypropylene block copolymer.

In addition, antibody-producing cell lines can also be created by techniques other than cell fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-4953 (1983); Geysen et al., Proc. Natl. Acad. Sci. USA, 82: 178-182 (1985); Lei et al. Biochemistry 34(20): 6675-6688, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3):539-55 (1994); Clackson et al., Nature 352: 264-268 (1991); Huse et al., Science 246:1275-1281 (1989), Hoogenboom et al. in Methods in Molecular Biology 178: 1-37 (2001) (O'Brien et al., ed., Human Press, Totowa, N.J.), and in certain embodiments, in Lee et al. J. Mol. Biol. 340:1073-1093 (2004).

Moncolonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859,205 and 6,797,492; Liu et al, Immunol Rev. 222:9-27 (2008); Almagro et al, Front Biosci. 1; 13:1619-33 (2008); Lazar et al, Mol Immunol. 44(8):1986-98 (2007); Li et al, Proc. Natl. Acad. Sci. USA. 103(10):3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse (Abgenix/Amgen.), the HuM Ab-Mouse (Medarex/BMS), the VelociMouse (Regeneron), see also U.S. Pat. Nos. 6,596,541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26: 39-60 (2004); Houdebine, Curr Opin Biotechnol. 13: 625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3: 964-70, (2002)); Adams et al, J Immunol Methods. 231: 249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immunospecific for a malignant cell antigen can be obtained commercially, e.g., from the GenBank database or a database like it, the literature publications, or by routine cloning and sequencing.

DNA encoding hybridoma-derived monoclonal antibodies or phage display Fv clones of the antibody can be readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells (Skerra et al., Curr. Opinion in Immunol., 5: 256 (1993) and Pluckthun, Immunol. Revs, 130: 151 (1992)). Antibodies can also be produced by using an expression system in which the quantitative ratio of expressed polypeptide components can be modulated in order to maximize the yield of secreted and properly assembled antibodies. Such modulation is accomplished at least in part by simultaneously modulating translational strengths for the polypeptide components. After the fermentation which is known in the art, the produced antibody protein is further purified to obtain preparations that are substantially homogeneous for further assays and uses. Standard protein purification methods known in the art can be employed. The exemplary purification procedures: fractionation on immunoaffinity (such as Protein A columns) or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immunoglobulin family. These peptides can be isolated by similar techniques as for phage display antibodies (Szardenings, J Recept Signal Transduct Res. 23(4): 307-49, 2003). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, as long as such attachment permits the peptide or protein to retain its antigen binding specificity.

Any one of several different reactive groups on a cell binding agent, preferably on an antibody, can be a conjugation site, such as c-amino groups in lysine residues, pendant carbohydrate moieties, carboxylic acid groups, disulfide groups, and thiol groups. For reviews on antibody reactive groups suitable for conjugation, see, e.g., Hermanson, G. T. (2008). Bioconjugate Techniques, Academic Press; Garnett, Adv. Drug Delivery Rev. 53 (2001), 171-216 and Dubowchik and Walker, Pharmacology & Therapeutics 83 (1999), 67-123, the disclosures of which are incorporated herein by reference.

The cytotoxic agents of this invention can be directly conjugated (linked) to a cell binding agent, or via a bifunctional linker or a crosslinking agent to a cell binding agent. The bifunctional linker possess two reactive groups; one of which is capable of reacting with a cell binding agent while the other one reacts with one or more molecules of cytotoxic agent of the invention. The bifunctional crosslinkers are well known in the art (see, for example, U.S. Pat. No. 5,208,020; Isalm and Dent in "Bioconjugation" chapter 5, p 218-363, Groves Dictionaries Inc. New York, 1999). Examples of bifunctional linker are: N-succinimidyl-3-(2-pyridyldithio) propionate (SPDP), N-succinimidyl-4-(2-pyridyldithio)butyrate (SPDB), N-succinimidyl-4-(2-pyridyldithio)pentanoate (SPP), N-succinimidyl-3-(2-pyridyldithio)-butyrate (SDPB), 2-iminothiolane, N-succinimidyl-4-(5-nitro-2-pyridyldithio) butyrate (SNPB), N-succinimidyl 4-(5-nitro-2-pyridyldithio)-pentanoate (SNPP), N-sulfosuccinimidyl- 4-(5-nitro-2-pyridyldithio) butyrate (SSNPB), N-succinimidyl-4-methyl-4-(5-nitro-2-pyridyldithio)pentanoate (SMNP), N-sulfosuccinimidyl 4-(5-nitro-2-pyridyldithio)-pentanoate (SSNPP), 4-succinimidyl-oxycarbonyl-a-methyl-a-(2-pyridyldithio)-toluene (SMPT), N-sulfosuccinimidyl-4-methyl-4-(5-nitro-2-pyridyldithio) pentanoate (SSNMP); N-succinimidyl-4-methyl-4-(2-pyridyldithio)pentanoate (SMPDP), N-succinimidyl-4-(5-N,N-dimethyl-carboxamido-2-pyridyldithio) butyrate (SCPB), N-sulfosuccinimidyl-4-(5-N,N-dimethyl-carboxamido-2-pyridyldithio) butyrate (SSCPB), N-succinimidyl-4,4-dimethyl-4-(2-pyridyldithio)pentanoate (SDMPDP), succinimidyl-4-(N-maleimidomethyl)cyclohexane-1-carboxylate (SMCC), N-succinimidyl-4-(iodoacetyl)-aminobenzoate (SIAB), bis-maleimidopolyethyleneglycol (BMPEG), BM(PEG)$_{1-20}$, N-(β-maleimidopropyloxy)-succinimide ester (BMPS), iminothiolane (IT), dimethyl adipimidate HCl or derivatives of imidoesters, active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene), gamma-maleimidobutyric acid N-succinimidyl ester (GMBS), E-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate) (a "long chain" analog of SMCC (LC-SMCC)), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), kappa-maleimidoundecanoic acid N-succinimidyl ester (KMUA), N-succinimidyl 4-(p-maleimidophenyl)-butyrate (SMPB), succinimidyl-6-(beta-maleimidopropionamido)-hexanoate (SMPH), succinimidyl-(4-vinylsulfonyl) benzoate (SVSB), dithiobis-maleimidoethane (DTME), 1,4-bis-maleimidobutane (BMB), 1,4 bismaleimidyl-2,3-di hydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(gamma-maleimidobutryloxy)sulfo-succinimdeester (sulfo-GMBS), N-(epsilon-maleimidocaproyloxy)sulfosuccimido ester (sulfo-EMCS), N-(kappa-maleimidoundecanoyloxy)sulfosuccinimide ester (sulfo-KMUS), and sulfosuccinimidyl 4-(p-maleimidophenyl) butyrate (sulfo-SMPB); or the commercially available linkers (such as from Thermo Scientific's Pierce: Imidoester Crosslinkers: DMA (Dimethyl adipimidate.2 HCl), DMP (Dimethyl pimelimidate.2 HCl), DMS (Dimethyl Suberimidate.2 HCl), DTBP (Dimethyl 3,3'-dithiobispropionimidate.2 HCl), NHS-ester Crosslinkers-Amine Reactive: BS(PEG)$_5$ (Bis(succinimidyl) penta(ethylence glycol), BS(PEG)$_9$ (Bis(succinimidyl) nona(ethylence glycol), BS$^3$ (Bis[sulfosuccinimidyl] suberate), BSOCOES (Bis[2-(succinimidooxycarbonyloxy)ethyl]sulfone), DSG (Disuccinimidyl glutarate), DSP (Dithiobis[succinimidyl propionate]), DSS (Disuccinimidyl suberate), DST (Disuccinimidyl tartarate), DTSSP (3,3'-Dithiobis[sulfosuccinimidylpropionate]), EGS (Ethylene glycol bis[succinimidylsuccinate]), Sulfo-EGS (Ethylene glycol bis[sulfosuccinimidylsuccinate]), TSAT (Tris-succinimidyl aminotriacetate), DFDNB (1,5-Difluoro-2,4-dinitrobenzene); Amine-to-Sulfhydryl Crosslinkers: Sulfo-SIAB (Sulfosuccinimidyl (4-iodoacetyl) aminobenzoate), SLAB (Succinimidyl (4-iodoacetyl)aminobenzoate), SBAP(Succinimidyl 3-(bromoacetamido)propionate), SIA (Succinimidyl iodoacetate), Sulfo-SMCC (Sulfosuccinimidyl-4-(N-maleimidomethyl)-cyclohexane-1-carboxylate), SM(PEG)n (NHS-PEG-Maleimide Crosslinkers: Succinimidyl-([N-maleimidopropionamido])-#-ethyleneglycol)ester, #=1, 2, 3, 4, 5, 6, 7, 8, 9, 10, 11, 12, 13, 14, 15, 16, 18, 20, 22, 24), LC-SMCC (Succinimidyl 4-(N-maleimidomethyl) cyclohexane-1-carboxy-(6-amido-caproate)), Sulfo-EMCS (N-epsilon-Maleimidocaproyl-oxysulfosuccinimide ester), EMCS (N-epsilon-Malemidocaproyl-oxysuccinimide ester), Sulfo-GMBS (N-gamma-Maleimidobutyryl-oxysulfosuccinimide ester), GMBS (N-gamma-Maleimidobutyryl-oxysuccinimide ester), Sulfo-KMUS (N-kappa-Maleimidoundecanoyl-oxysulfosuccinimide ester), Sulfo-MBS (m-Maleimidobenzoyl-N-hydroxysulfosuccinimide ester), MBS (m-Maleimidobenzoyl-N-hydroxysuccinimide ester), Sulfo-SMPB ((Sulfosuccinimidyl 4-(p-maleii midophenyl)butyrate), SMPB (Succinimidyl 4-(p-maleimidophenyl)butyrate), AMAS N-(a-Maleimidoacetoxy) succinimide ester), BMPS (N-beta-Maleimidopropyl-oxysuccinimide ester), SMPH (Succinimidyl 6-[(beta-maleimidopropionamido)hexanoate]), PEG12-SPDP (2-Pyridyldithiol-tetraoxaoctatriacontane-N-hydroxysuccinimide), PEG4-SPDP (2-Pyridyldithiol-tetraoxatetradecane-N-hydroxysuccinimide), Sulfo-LC-SPDP (Sulfosuccinimidyl 6-[3'-(2-pyridyldithio) propionamido]hexanoate), LC-SPDP (Succinimidyl 6-[3-(2-pyridyldithio)propionamido]hexanoate), SMPT (4-Succinimidyloxycarbonyl-alpha-methyl-alpha(2-pyridyl-dithio)toluene); Carboxyl-to-Amine Crosslinkers: DCC (Dicyclohexylcarbodiimide), EDC (1-Ethyl-3-(3-dimethylaminopropyl) carbodiimide); Photoreactive Crosslinkers: ANB-NOS (N-5-Azido-2-nitrobenzoyloxysuccinimide), NHS-Diazirine (SDA) Crosslinkers: SDA (NHS-Diazirine) (Succinimidyl 4,4'-azipentanoate), LC-SDA (NHS-LC-Diazirine) (Succinimidyl 6-(4,4'-azipentanamido)hexanoate), SDAD (NHS-SS-Diazirine) (Succinimidyl 2-([4,4'-azipentanamido]ethyl)-1,3'-dithiopropionate), Sulfo-SDA (Sulfo-NHS-Diazirine) (Sulfosuccinimidyl 4,4'-azipentanoate), Sulfo-LC-SDA (Sulfo-NHS-LC-Diazirine) (Sulfosuccinimidyl 6-(4,4'-azipentanamido)hexanoate), Sulfo-SDAD (Sulfo-NHS-SS-Diazifine) (Sulfosuccinimidyl 2-([4,4'-azipentanamido]ethyl)-1,3'-dithiopropionate), Sulfo-SANPAH (Sulfosuccinimidyl 6-(4'-azido-2'-nitrophenylamino)-hexanoate), SPB (Succinimidyl-[4-(psoralen-8-yloxy)]-butyrate); Sulfhydryl-to-Carbohydrate Crosslinkers: BMPH (N-beta-Mal eimidopropionic acid hydrazide-TFA), EMCH (N-epsilon-Maleimidocaproic acid hydrazide-TFA), KMUH (N-kappa-Maleimidoundecanoic acid hydrazide-TFA), MPBH (4-(4-N-Maleimidophenyl)butyric acid hydrazide-HCl), PDPH (3-(2-Pyridyldithio)propionyl hydrazide); Sulfhydryl-to-Hydroxyl Crosslinkers: PMPI (p-Maleimidophenyl isocyanate); Sulfhydryl-to-Sulfhydryl Crosslinkers: BM(PEG)$_2$ (1,8-Bismaleimido-diethyleneglycol), BM(PEG)3 (1,11-Bismaleimido-triethyleneglycol), BMB (1,4-Bismaleimidobutane), BMDB (1,4-Bismaleimidyl-2,3-dihydroxybutane), BMH (Bismaleimidohexane), BMOE (Bismaleimidoethane), DTME (Dithiobismaleimido-ethane), TMEA (Ths(2-maleimidoethyl)amine) and SVSB (succinimidyl-(4-vinylsulfone)benzoate).

The bis-maleimide or bis-2-pyridyldithiol reagents allow the attachment of the thiol group of a thiol-containing cell binding agent (such as antibody) to a thiol-containing drug moiety, label, or linker intermediate, in a sequential or concurrent fashion. Other functional groups besides maleimide and pyridyldithiol, which are reactive with a thiol group of a cell binding agent, drug moiety, label, or linker intermediate include iodoacetamide, bromoacetamide, vinyl pyridine, disulfide, pyridyl disulfide, isocyanate, and isothiocyanate.

In additional embodiments, the linker may be composed of one or more linker components. The exemplary linker components are:

1. The self-immolative linker components:

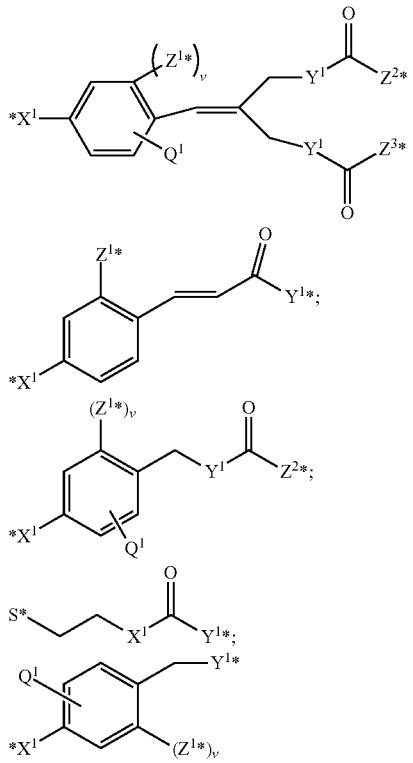

wherein the (*) atom is the point of attachment of additional spacer or releasable linker units, or the cytotoxic agent, and/or the binding molecule (CBA); $X^1$, $Y^1$, $Z^2$ and $Z^3$ are independently NH, or O, or S; $Z^1$ is H, or NH, or O or S independently. v is 0 or 1; $Q^1$ is independently H, OH, $C_1$~$C_6$ alkyl, $(OCH_2CH_2)_nF$, Cl, Br, I, $OR_5$, or $SR_5$, $NR_5R_5'$, N=$NR_5$, N=$R_5NR_5R_5'$, $NO_2$, $SOR_5R_5'$, $SO_2R_5$, $SO_3R_5$, $OSO_3R_5$, $PR_5R_5'$, $POR_5R_5'$, $PO_2R_5R_5'$, $OPO(OR_5)(OR_5')$, or $OCH_2PO(OR_5(OR_5'))$ wherein $R_5$ and $R_5'$ are described in the Formula (I), preferably $R_5$ and $R_5'$ are independently selected from H, $C_1$~$C_8$ of alkyl; $C_2$~$C_8$ of alkenyl, alkynyl, heteroalkyl; $C_3$~$C_8$ of aryl, heterocyclic, carbocyclic, cycloalkyl, heterocycloalkyl, heteroaralkyl, alkylcarbonyl; or pharmaceutical cation salts 2. The examples of non-self-immolative linker components:

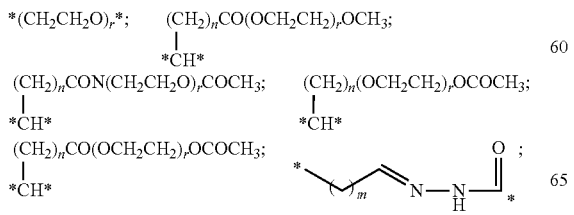

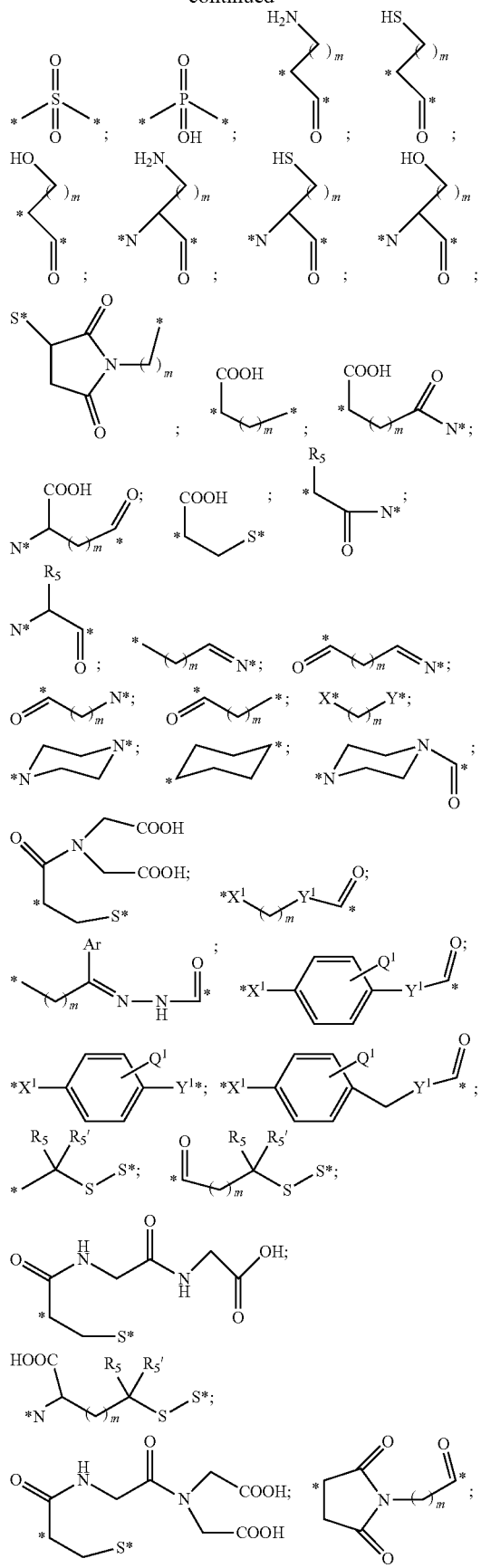

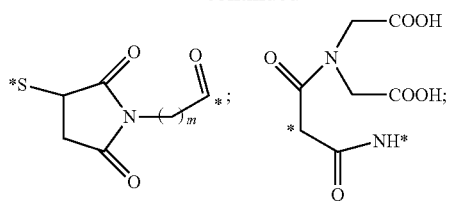
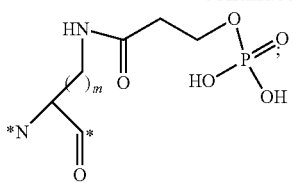

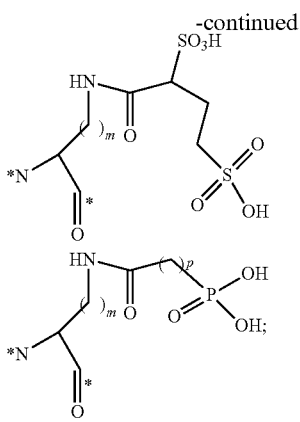

Wherein the (*) atom is the point of attachment of additional spacer or releaseable linkers, the cytotoxic agents, and/or the binding molecules; $X^1$, $Y^1$, $Q^1$, $R_5$, $R_{5'}$ and r are as defined in Formula (I), m, n and p are 0~6.

3. Exemplary linker components may include 6-maleimidocaproyl ("MC"), maleimidopropanoyl ("MP"), valine-citrulline ("val-cit" or "vc"), alanine-phenylalanine ("ala-phe" or "af"), p-aminobenzyloxy-carbonyl ("PAB"), N-succinimidyl 4-(2-pyridylthio)pentanoate ("SPP"), N-succinimidyl 4-(N-maleimidomethyl)cyclohexane-1 carboxylate ("SMCC"), N-Succinimidyl (4-iodo-acetyl)aminobenzoate ("SIAB"), ethyleneoxy (—$CH_2CH_2O$—) as one or more repeating units ("EO" or "PEO"). Additional linker components are known in the art and some are described through this patent application.

In additional embodiments, the linker may comprise amino acid residues. Exemplary amino acid linker components include a dipeptide, a tripeptide, a tetrapeptide or a pentapeptide. Exemplary dipeptides include: valine-citrulline (VC or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by particular enzymes, for example, a tumor-associated protease, cathepsin B, C and D, or a plasmin protease.

In the cell-binding agent—drug conjugates of the invention, cell-binding agent (CBA) is conjugated to one or more drug moieties (Drug, or PBD derivatives), e.g. about 1 to about 20 drug moieties per cell-binding agent, through a bifunctional linker (L). The conjugate of Formula (II-1)-(II-91) may be prepared by several routes, employing organic chemistry reactions, conditions, and reagents known to those skilled in the art, including: (1) the first modification of cell-binding agent (CBA) with a crosslinker (L) in an aqueous buffer pH 3~9 having optionally 0~30% organic co-solvents to introduce reactive disulfide, maleimido, haloacetyl, hydrazide, nitrile, alkynyl, alkyloxyamino or aldehyde groups on the cell-binding agent, to form a covalent bonded CBA-L. The CBA-L molecule then reacts with a drug moiety (Drug) of formula (I) to generate a cell binding agent—drug conjugate; or (2) the first modification of drug moiety (Drug) of the formula (I) with a crosslinker (L) in organic media or in an aqueous buffer pH 3~9 having optionally 0~99% organic co-solvents to introduce a reactive disulfide, maleimido, haloacetyl, hydrazide, nitrile, alkynyl, alkyloxyamino, aldehyde, N-hydroxysuccinimide (NHS) or pentafluorophenyl ester group on the drug moiety (a covalent bonded Drug-L molecule). The Drug-L molecule then reacts with a cell binding agent (CBA), or pre-modified CBA to generate a cell binding agent—drug conjugate; or (3) directly through reaction of a cell—binding agent with drug moieties of formula (I) bearing reactive function groups of disulfide, maleimido, haloacetyl, hydrazide, nitrile, alkynyl, alkyloxyamino, aldehyde, N-hydroxysuccinimide (NHS) or pentafluorophenyl esters in an aqueous buffer pH 3~9 having optionally 0~30% organic co-solvents.

The thiol or amine groups on a cell-binding agents, such as an antibody, are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Nucleophilic groups on antibodies or proteins can react to electrophilic groups on a function linker following by reaction with a cytotoxic agent, or directly react to a linker-cytotoxic agent moiety to form covalent bond conjugate of a cell binding agent-cytotoxic agent. Nucleophilic groups on antibodies or proteins include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker-cytotoxic agent moieties including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges which may be made reactive by treatment with a reducing agent such as DTT (dithiothreitol), L-glutathione (GSH), dithioerythritol (DTE), 2-mercaptoethylamine (β-MEA), beta mercaptoethanol (β-ME, 2-ME), or tricarbonylethylphosphine (TCEP) (Getz et al (1999) Anal. Biochem. Vol 273:73-80; Soltec Ventures, Beverly, Mass.). Each cysteine bridge will thus form, theoretically, two reactive thiol nucleophiles. Alternatively, sulfhydryl groups can be introduced into antibodies through modification of lysine residues, e.g., by reacting lysine residues with 2-iminothiolane (Tract's reagent), resulting in conversion of an amine into a thiol. Reactive thiol groups may be introduced into an antibody by introducing one, two, three, four, or more cysteine residues (e.g., by preparing variant antibodies comprising one or more non-native cysteine amino acid residues). Thus free thiol on the cell binding agents can be conjugated to the thiol-reactive groups, such as, a maleimide, an iodoacetamide, a pyridyl disulfide, or other thiol-reactive groups on the cytotoxic agents, or linker-cytotoxic agent intermediates of the invention. Some unconjugated free thiols on the antibodies can be reoxidized to reform interchain and intrachain disulfide bonds.

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with a drug moiety or linker nucleophile.

Examples of the general conjugations which a linker reacts to a drug to form a linker-drug intermediate first, following by conjugation reaction with a cell-binding molecule are depicted below:

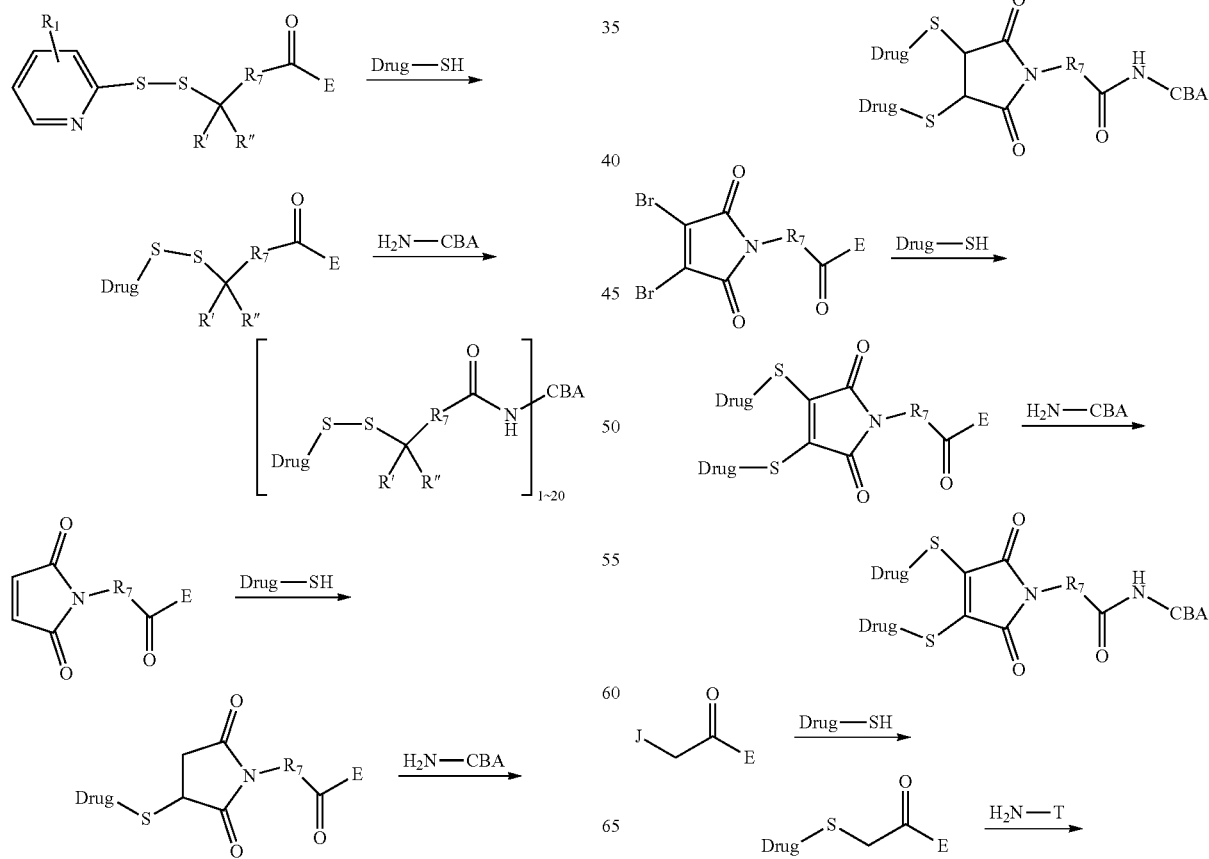

-continued

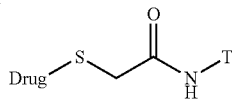

wherein E includes, but is not limited to, such as hydroxysuccinimidyl esters (NHS, Sulfo-NHS, etc), 4-nitrophenyl esters, pentafluorophenyl esters, tetrafluorophenyl (includes sulfo-tetrafluorophenyl) esters, anhydrides, acid chlorides, sulfonyl chlorides, isocyanates and isothiocyanates. R' and R" are independently H or $CH_3$, or $C_2H_5$; J is F, Cl, Br, I, tosylate (TsO), mesylate (MsO), nitrophenol, dinitrophenol, or pentafluorophenol; wherein Drug is a compound of the Formula (I), (Ia), (Ib), (Ic) or (Id) of this invention.

It is to be understood that where more than one nucleophilic group on the cell binding agents, such as an antibody, reacts with a drug-linker intermediate or linker reagent followed by drug moiety reagent, then the resulting product is a mixture of the cell binding agent-cytoxic agent conjugates with a distribution of one or more drug moieties attached to an antibody. The average number of drugs per antibody may be calculated from the mixture by a dual ELISA antibody assay, which is specific for antibody and specific for the drug. Individual conjugate molecules may be identified in the mixture by mass spectroscopy and separated by HPLC, e.g. hydrophobic interaction chromatography. In certain embodiments, a homogeneous conjugate with a single loading value may be isolated from the conjugation mixture by electrophoresis or chromatography.

In yet another embodiment, when an IgG antibody conjugated with one, or two, or more the same or different of derivatives of *amanita* toxins of Formula (I), (Ia), (Ib), (Ic) or (Id), optionally together with other different function molecules or cytotoxic agents, through a pair of thiols on the IgG antibody, as exampled in formula (II-11), (II-12), (II-13), (II-14), (II-17), (II-18), (II-19), (II-20), (II-24), (II-25), (II-29), (II-30), (II-32), (II-33), (II-34), (II-35), (H-36), (II-37), (II-38), (II-39), (II-40), (II-41), (II-42), (II-43), (II-44), (II-45), (II-46), (II-47), (II-48), (II-49), (II-50), (II-51), (II-52), (II-53), and (II-64), the ADCs containing an *amanita* toxin of Formula (I), (Ia), (Ib), (Ic) or (Id) are preferred to be formed via a bridge linker specifically at the pair of thiols (through reduction of the disulfide bonds) between the light chain and heavy chain, or/and the upper disulfide bonds between the two heavy chains, or/and the lower disulfide bonds between the two heavy chains. The ADCs containing one, or two, or more the same or different of derivatives of *amanita* toxins of Formula (I), (Ia), (Ib), (Ic) or (Id) with a bridge linker are preferrably having the formula of (III-1), (III-2), (III-3), (III-4), (III-5), (III-6), (III-7), (III-8), (III-9), (III-10), (III-11), or (III-12) illustrated in FIGS. 31A to 31F.

In formulae of (III-1), (III-2), (III-3), (III-4), (III-5), (III-6), (III-7), (III-8), (III-9), (III-10), (III-11), and (III-12), the IgG antibody is, preferably IgG1, IgG2, IgG3 or IgG4 antibody; "---=" represents either a single bond or a double bond; $L_1$ and $L_2$ are, the same or deferent, independently defined the same as L in Formula (I); $X_1$ and $X_2$, are, the same or deferent, independently selected from NH, $N(R_1)$, O, S, $CH_2$, or Ar, wherein $R_1$ is $C_1$-$C_6$ alkyl, Ar is aromatic or heteroaromatic ring; wherein $Drug_1$ and $Drug_2$ are the same or deferent, a derivative of *amanita* toxins of Formula (I), (Ia), (Ib), (Ic) or (Id). In addition, either $Drug_1$ or $Drug_2$ can be absent, but not be absent at the same time. When any single one of $Drug_1$ or $Drug_2$ is a derivative of *Amanita* toxin of Formula (I), (Ia), (Ib), (Ic) or (Id), the other one of either $Drug_1$ or $Drug_2$ can be selected from $(OCH_2CH_2)_rOR_{10}$, or $(OCH_2CH(CH_3))_pOR_{10}$, or $NH(CH_2CH_2O)_rR_{10}$, or $NH(CH_2CH(CH_3)O)_pR_{10}$, or $N[(CH_2CH_2O)_pR_{10}][(CH_2CH_2O)_rR_5]$, or $(OCH_2CH_2)_pCOOR_{10}$, or $CH_2CH_2(OCH_2CH_2)_pCOOR_{10}$, wherein p, r, $R_{10}$ are described in many embodiments throughout this patent application. In further addition, $Drug_2$ and $L_2$ can be absent, thus $X_2$ is $NH_2$ or OH.

In yet another embodiment, when an IgG antibody conjugated with one derivative of *amanita* toxins of Formula (I), (Ia), (Ib), (Ic) or (Id) through a pair of thiols of an IgG antibody, the ADCs containing an *amanita* toxin of Formula (I), (Ia), (Ib), (Ic) or (Id) are also preferred to be formed via a bridge linker specifically at the pair of thiols of IgG antibody (through reduction of the disulfide bonds) between the light chain and heavy chain, the upper disulfide bonds between the two heavy chains, and the lower disulfide bonds between the two heavy chains. The bridge linkage is preferred having the following structures of (IV-1), (IV-2), (IV-3), (IV-4), (IV-5), and (IV-6):

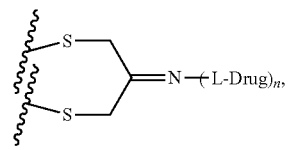
(IV-1)

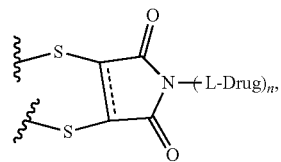
(IV-2)

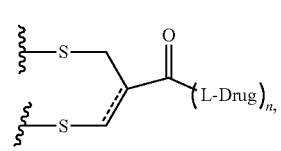
(IV-3)

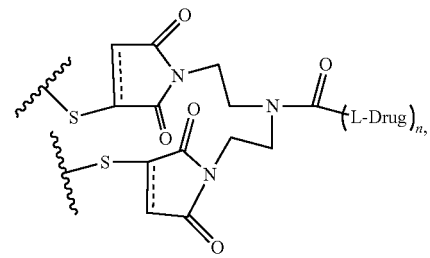
(IV-4)

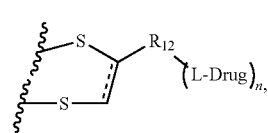
(IV-5)

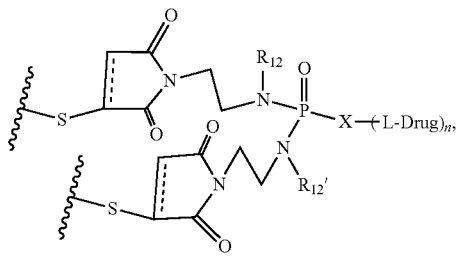

-continued (IV-6)

wherein"=" represents either a single bond or a double bond; Drug is a derivative of *Amanita* toxin of Formula (I), (Ia), (Ib), (Ic) or (Id);

represents the sites on an antibody; L, X, n and $R_{12}$ are defined the same as in Formula (I).

The pairs of thiols on the antibody are preferred to be reduced by a reducing agent selected from dithiothreitol (DTT), dithioerythritol (DTE), L-glutathione (GSH), tris (2-carboxyethyl) phosphine (TCEP), 2-mercaptoethylamine (β-MEA), or/and beta mercaptoethanol (β-ME, 2-ME). More preferably, these reducing agents are loaded or covalently bonded to a solid polymer or a solid particle. The polymer or the particle can be polyethene, polyacrylate, silican, crossed-linked silica (e.g. 2-mercaptoethyl)silica, (aminoethyl)silica, (aminopropyl)silica), polyethylene terephthalate, polyethylene glycol, polystyrene, poly(isopropyl acrylate), dextrans (e.g. sephadex, cross-linked dextran), isopropylacrylamide butyl methacrylate copolymer, polysaccharide polymer (e.g. agarose, agar, agaropectin, sepharose). Under the reduction of the polymer bonded reducing agents, the pairs of disulfide bonds can be selectively reduced at a certain position, for instance, at the hinge region of IgG1, IgG2, IgG3 or IgG4 antibody, or disulfide bonds between heavy chain and the light chain of the IgG1, IgG2, IgG3 or IgG4 antibody, or the certain outer surfaces of a protein or a cell binding molecule. Thus the loading ratios as well as the postions of derivatives of *amanita* toxins conjugated on the cell binding molecules are controlled.

In addition, when any single one of either $Drug_1$ or $Drug_2$ of Formula (III-1), (III-2), (III-3), (III-4), (III-5), (III-6), (III-7), (III-8), (III-9), (III-10), (III-11), or (III-12), is a derivative of *Amanita* toxin of Formula (I), the other one of either $Drug_1$ or $Drug_2$ can be selected from a protein, an antibody, antibody dimers, antibody multimers, a bispecific or trispecific antibody, a single chain antibody, an antibody fragment that binds to the target cell, a monoclonal or polyclonal antibody, a chromophore molecule, a tubulysin derivative, a maytansinoid, a taxanoid (taxane), a CC-1065 analog, a daunorubicin or doxorubicin compound, a benzodiazepine dimer (e.g., dimers of pyrrolobenzodiazepine (PBD), tomaymycin, anthramycin, indolinobenzodiazepines, imidazobenzothiadiazepines, or oxazolidinobenzodiazepines), a calicheamicin or the enediyne antibiotic, an actinomycin, an azaserine, a bleomycin, a epirubicin, a tamoxifen, a idarubicin, a dolastatins, an auristatin derivative (e.g. monomethyl auristatin E, MMAE, MMAF, auristatin PYE, auristatin TP, Auristatins 2-AQ, 6-AQ, EB (AEB), and EFP (AEFP)), a duocarmycin, a thiotepa, a vincristine, a hemiasterlin, a nazumamide, a microginin, a radiosumins, an alterobactin, a microsclerodermin, a theonellamide, an esperamicin, a PNU-159682, a geldanamycin, a methotrexate, a vindesines, a siRNA, a nucleolytic enzyme. The examples of the preferred structures of some of these function molecules or cytotoxic drugs are illustrated below:

V-1, an antibody, (V-2, a chromophore molecule)

(V-3, a chromophore molecule)

(V-4, a calicheamicin)

-continued
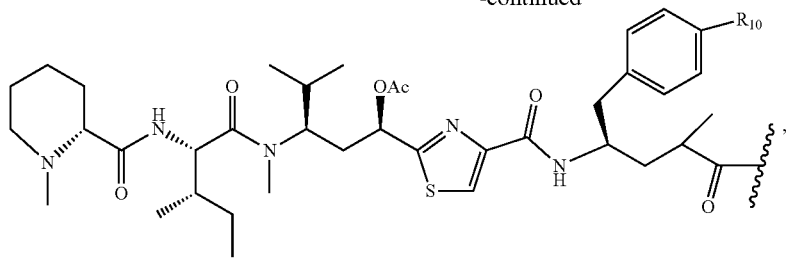
(V-5, a tubulysin derivative)
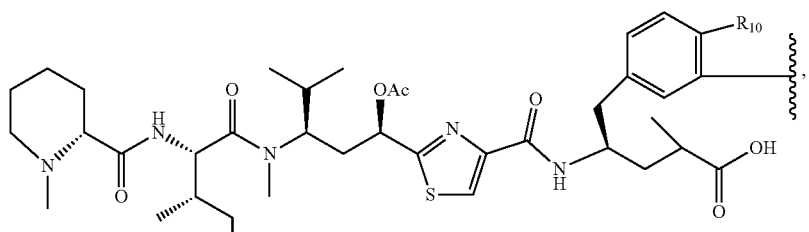
(V-6, a tubulysin derivative)
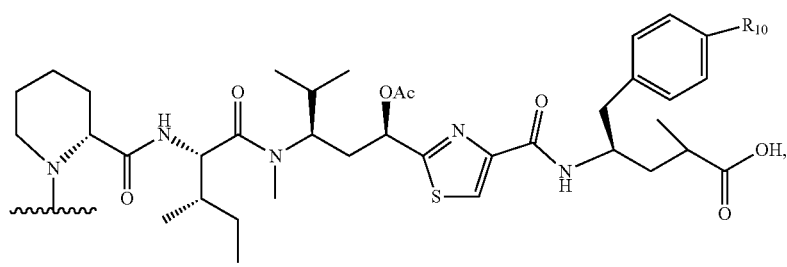
(V-7, a tubulysin derivative)
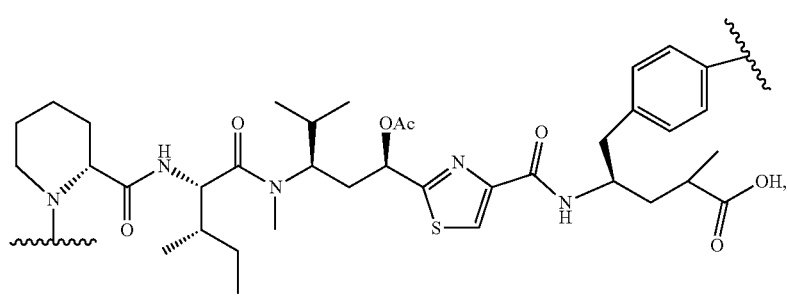
(V-8, a tubulysin derivative)
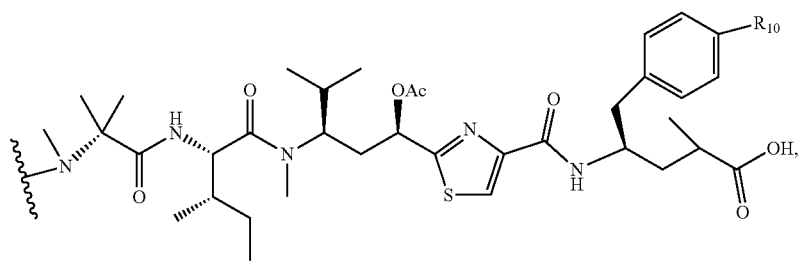
(V-9, a tubulysin derivative)

-continued
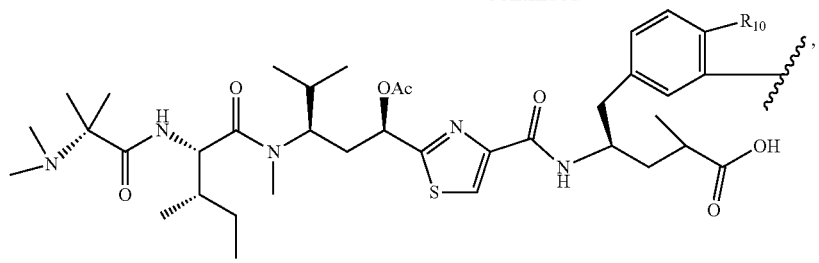
(V-10, a tubulysin derivative)
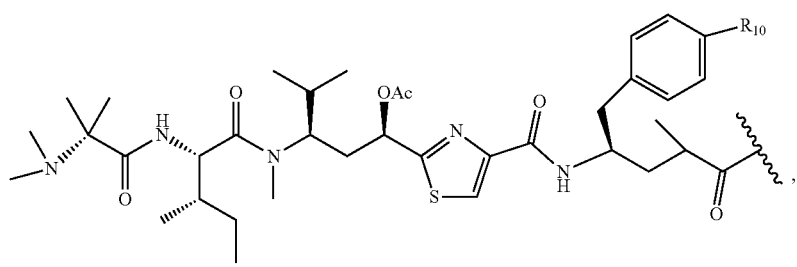
(V-11, a tubulysin derivative)
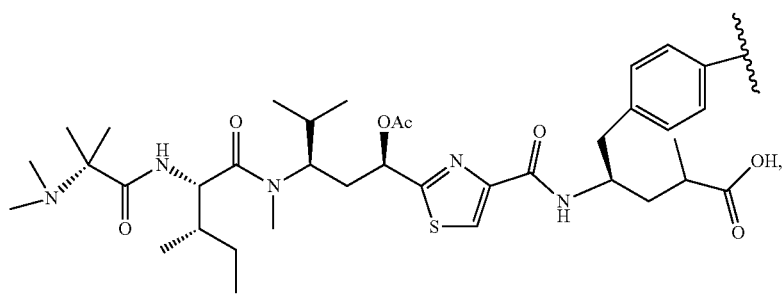
(V-12, a tubulysin derivative)
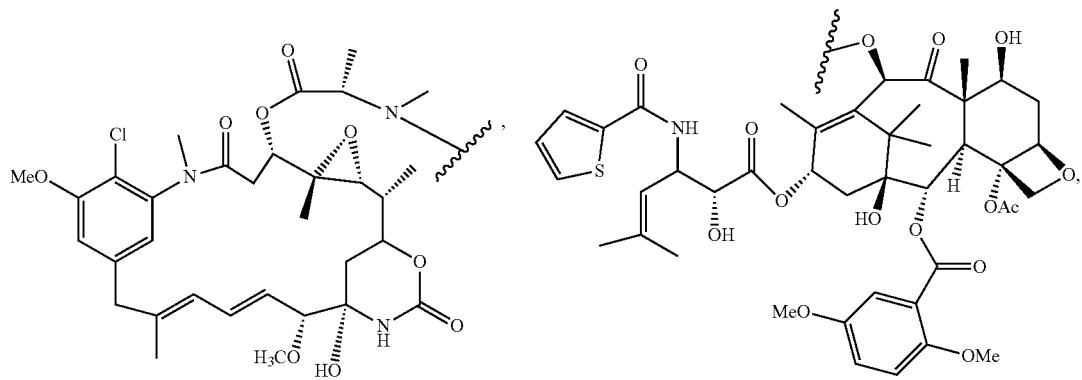
(V-13, a maytansinoid)   (V-14, a taxanoids)
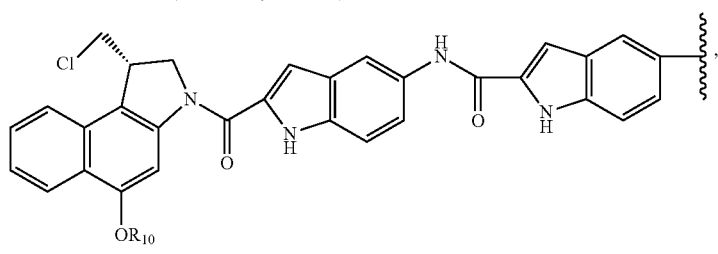
(V-15, a CC-1065 analog)

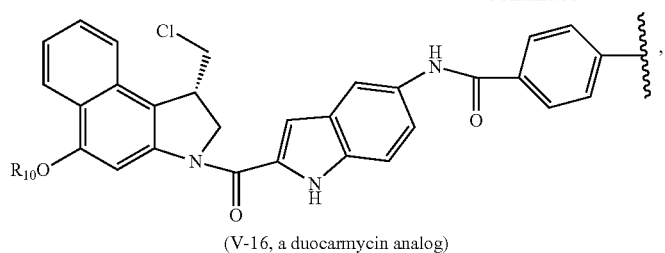
(V-16, a duocarmycin analog)
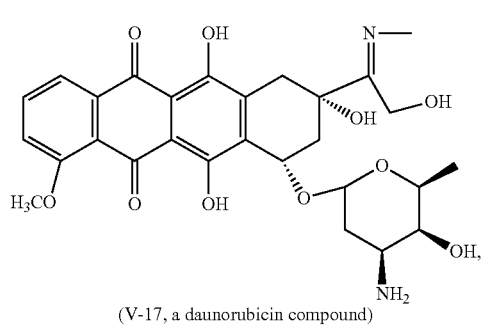
(V-17, a daunorubicin compound)
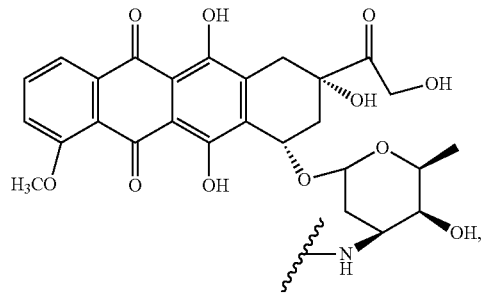
(V-18, a doxorubicin compound)
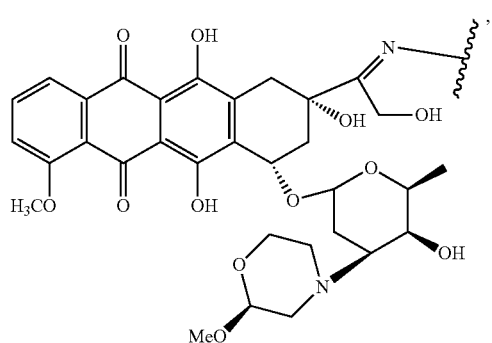
(V-19, a daunorubicin compound)
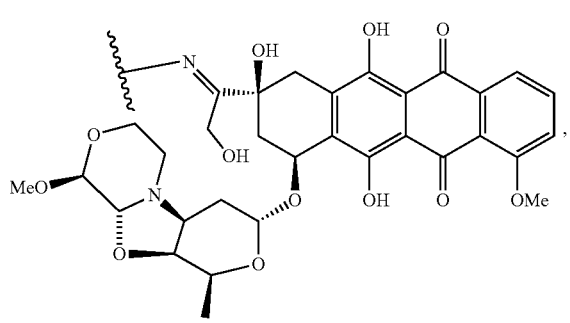
(V-20, a daunorubicin or doxorubicin compound)
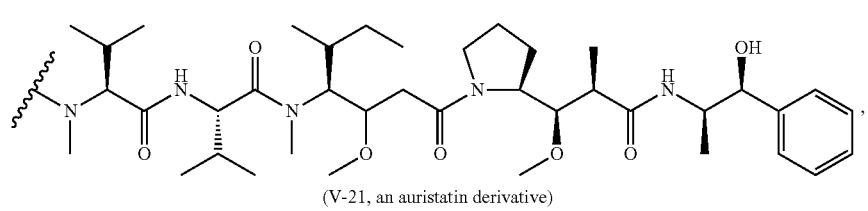
(V-21, an auristatin derivative)
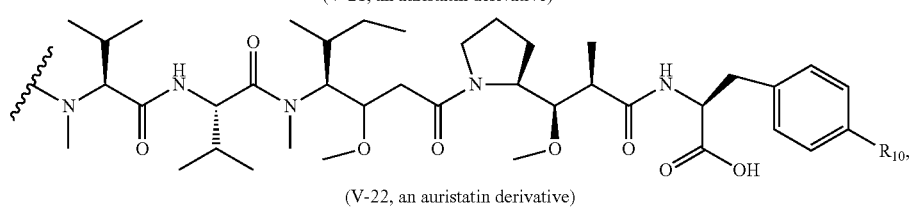
(V-22, an auristatin derivative)
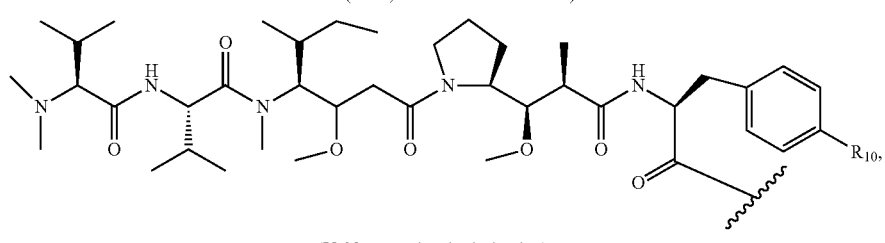
(V-23, an auristatin derivative)

-continued
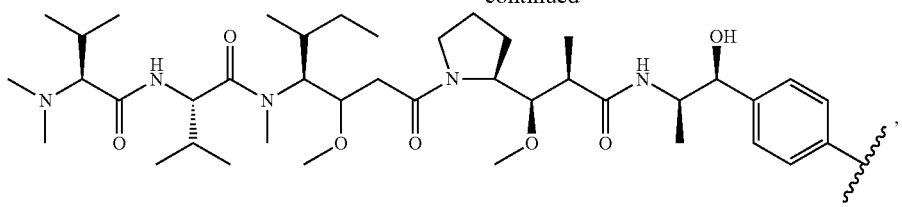
(V-24, a dolastatin or an auristatin derivative (MMAE)),
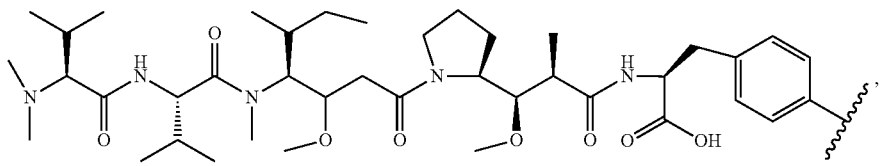
(V-25, a dolastatin or an auristatin derivative),
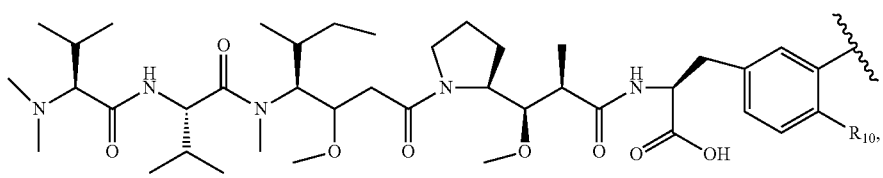
(V-26, an auristatin derivative),
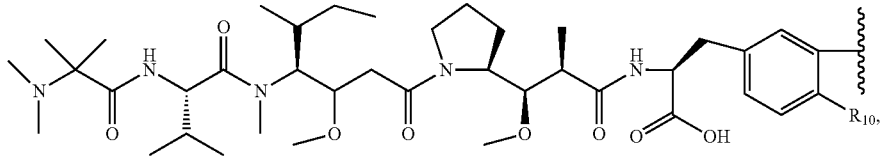
(V-27, an auristatin derivative),
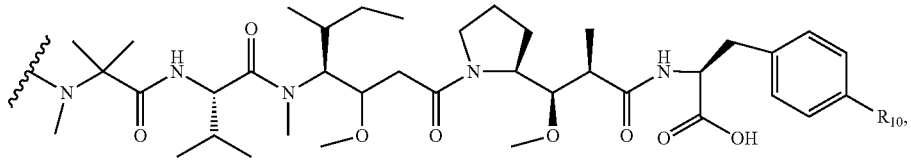
(V-28, an auristatin derivative),
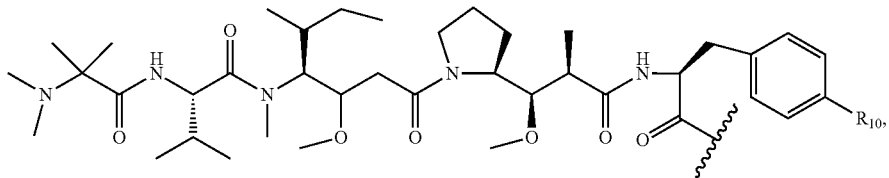
(V-29, an auristatin derivative),
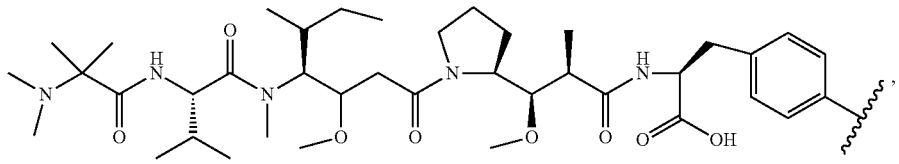
(V-30, an auristatin derivative),
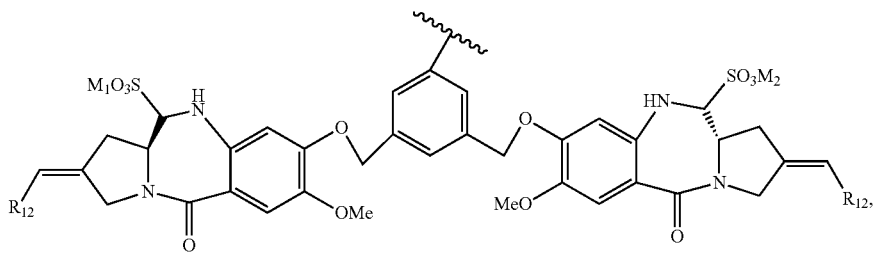
(V-31, an benzodiazepine dimer)

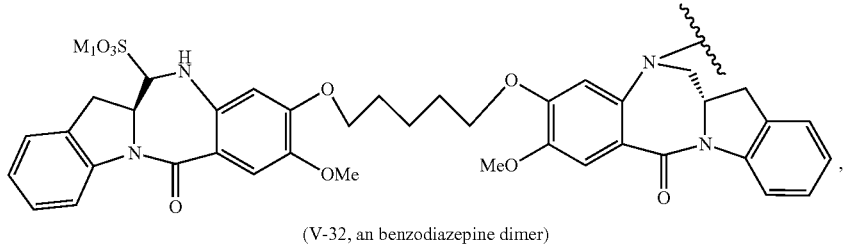

(V-32, an benzodiazepine dimer)

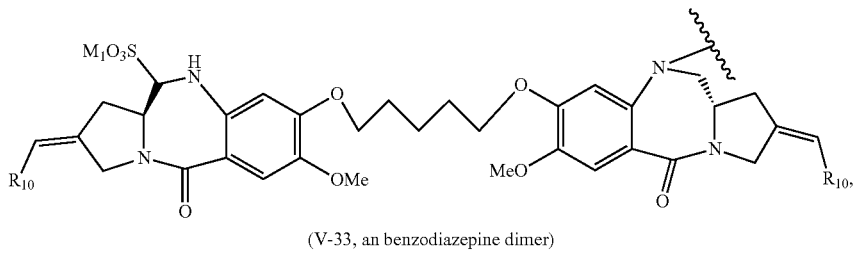

(V-33, an benzodiazepine dimer)

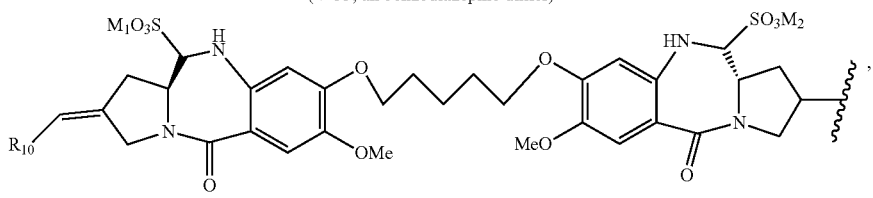

(V-34, an benzodiazepine dimer)

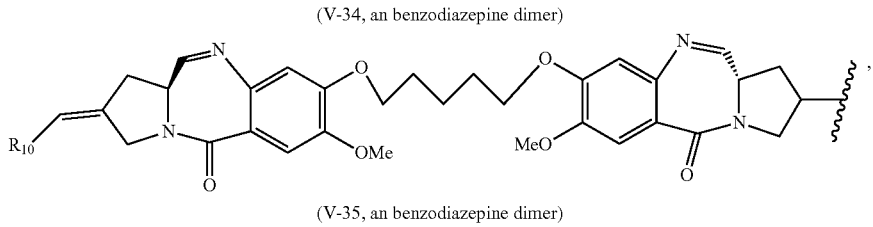

(V-35, an benzodiazepine dimer)

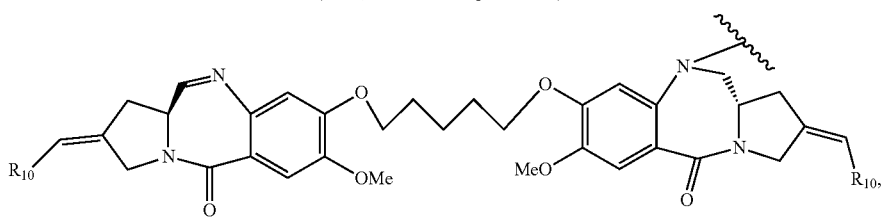

(V-36, an benzodiazepine dimer)

V-37, a siRNA, V-38, an enzyme or protein linked from N-terminal, V-39, an enzyme or protein linked from C-terminal.

wherein $R_{10}$ are described in Formula (I),

is the site to link either linker $L_1$ or linker $L_2$.

In conjugation, the loading (drug/antibody ratio) and/or position of an ADC with these derivatives of *amanita* toxins of this invention can be controlled in other different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of lysine, carbohydrate, serine, tyrosine, glutamine, histidine, cysteine or the residues is modified, or unnatural amino acids are inserted to the antibody sequences. These engineering methods are, but not limited, thioMab, thioFab, thiocarbohydrate, selenocysteine, cell-based approach of unnatural amino acids, open cell-free synthesis (OCFS) of unnatural amino acids, oxidation or chemo-enzymatic modification of glycans, Formylglycine generating enzyme (FGE), Sortase or Transglutaminases, Conjugation via Fc-Binding Domains (FcBD) or via the Nucleotide Binding Site, or Catalytic antibodies) (Dennler, P. et al, Antibodies 2015, 4, 197-224)

Other further examplary methods for preparing ADC of these derivatives of *amanita* toxins are described in FIGS. 1-28 and examples 1-70 in the description of the patent.

Treatments of Cell-Binding Agent-Drug Conjugates of these Derivatives of *Amanita* Toxins It is contemplated that the cell-binding agent—drug conjugate, preferably antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune disorders.

In specific embodiment, the conjugates of the invention are used in accordance with the compositions and methods of the invention for the treatment of cancers. The cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproliferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell. Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor In another specific embodiment, the compounds and the conjugates of the invention are used in accordance with the compositions and methods of the invention for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoiminune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo di sease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barré syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Meniere's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis *nodosa*, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulotnatosis, Wilson's syndrome, Wiskott-Aldrich syndrome In another specific embodiment, a binding molecule used for the conjugate for the treatment or prevention of an autoimmune disease includes, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial(M2) antibody; Rheumatoid factor antibody; Anti-MCV antibody; Anti-topoisomerase antibody; Anti-neutrophil cytoplasmic (cANCA) antibody.

In certain preferred embodiments, the binding molecule for the conjugate in the present invention, can bind to either a receptor or a receptor complex expressed on an activated lymphocyte which is associated with an autoimmune disease. The receptor or receptor complex can comprise an immunoglobulin gene superfamily member (e.g. CD2, CD3, CD4, CD8, CD19, CD20, CD22, CD28, CD30, CD33, CD37, CD38, CD56, CD70, CD79, CD90, CD152/CTLA-4, PD-1, or ICOS), a TNF receptor superfamily member (e.g. CD27, CD40, CD95/Fas, CD134/OX40, CD137/4-IBB, INF-R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuraminidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g. a bacteria, fungi, pathogenic protozoa, or yeast polypeptide including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PRO542 which is a CD4 fusion antibody for the treatment of HIV infection; Ostavir which is a human antibody for the treatment of hepatitis B virus; PROTVIR which is a humanized lgG.sub.1 antibody for the treatment of cytomegalovirus; and anti-LPS antibodies.

The binding molecules-cytotoxic agent conjugates of this invention can be used in the treatment of infectious diseases. These infectious diseases include, but are not limited to, *Acinetobacter* infections, Actinomycosis, African sleeping sickness (African trypanosomiasis), AIDS (Acquired immune deficiency syndrome), Amebiasis, Anaplasmosis, Anthrax, Arcanobacterium *haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, *Baylisascaris* infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioidomycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, *Enterovirus* infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, *Fusobacterium* infection, Gas gangrene (Clostridial myonecrosis), Geotrichosis, Gerstmann-Straussler-Scheinker syndrome, Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, *Kingella kingae* infection, *Kuru*, Lassa fever, Legionellosis (Legionnaires' disease), Legionellosis (Pontiac fever), Leishmaniasis, Leprosy, Leptospirosis, Listeriosis, Lyme disease (Lyme borreliosis), *Lymphatic filariasis* (Elephantiasis), *Lymphocytic choriomeningitis*, Malaria, Marburg hemorrhagic fever, Measles, Melioidosis (Whitmore's disease), Meningitis, Meningococcal disease, Metagonimiasis, Microsporidiosis, *Molluscum contagiosum*, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis* pneumonia, Pneumonia, Poliomyelitis, *Prevotella* infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever, Rocky mountain spotted fever, Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (*Pityriasis versicolor*), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White *piedra* (Tinea blanca), *Yersinia pseudotuberculosis* infection, Yersiniosis, Yellow fever, Zygomycosis.

The binding molecules, more preferred antibodies described in this patent that are against pathogenic strains include, but are not limit, *Acinetobacter baumannii, Actinomyces israelii, Actinomyces gerencseriae* and *Propionibacterium propionicus, Trypanosoma brucei,* HIV (Human immunodeficiency virus), *Entamoeba histolytica, Anaplasma* genus, *Bacillus anthracis, Arcanobacterium haemolyticum, Junin virus, Ascaris lumbricoides, Aspergillus* genus, Astroviridae family, *Babesia* genus, *Bacillus cereus,* multiple bacteria, *Bacteroides* genus, *Balantidium coli, Baylisascaris* genus, BK virus, *Piedraia hortae, Blastocystis hominis, Blastomyces dermatitides*, Machupo virus, *Borrelia* genus, *Clostridium botulinum*, Sabia, *Brucella* genus, usually *Burkholderia cepacia* and other *Burkholderia* species, *Mycobacterium ulcerans, Caliciviridae family, Campylobacter* genus, usually *Candida albicans* and other *Candida* species, *Bartonella henselae*, Group A *Streptococcus* and *Staphylococcus, Trypanosoma cruzi, Haemophilus ducreyi, Varicella zoster* virus (VZV), *Chlamydia trachomatis, Chlamydophila pneumoniae, Vibrio cholerae, Fonsecaea pedrosoi, Clonorchis sinensis, Clostridium difficile, Coccidioides immitis* and *Coccidioides posadasii*, Colorado tick fever virus, rhinoviruses, coronaviruses, CJD prion, Crimean-Congo hemorrhagic fever virus, *Cryptococcus neoformans, Cryptosporidium genus, Ancylostoma braziliense*; multiple parasites, *Cyclospora cayetanensis, Taenia solium*, Cytomegalovirus, Dengue viruses (DEN-1, DEN-2, DEN-3 and DEN-4)—Flaviviruses, *Dientamoeba fragilis, Corynebacterium diphtheriae, Diphyllobothrium, Dracunculus medinensis*, Ebolavirus, *Echinococcus* genus, *Ehrlichia* genus, *Enterobius vermicularis, Enterococcus* genus, *Enterovirus* genus, *Rickettsia prowazekii*, Parvovirus B19, Human herpesvirus 6 and Human herpesvirus 7, *Fasciolopsis buski, Fasciola hepatica* and *Fasciola gigantica*, FFI prion, Filarioidea superfamily, *Clostridium perfringens, Fusobacterium genus, Clostridium perfringens*; other *Clostridium* species, *Geotrichum candidum*, GSS prion, Giardia intestinalis, *Burkholderia mallei, Gnathostoma spinigerum* and *Gnathostoma hispidum, Neisseria gonorrhoeae, Klebsiella granulomatis, Streptococcus pyogenes, Streptococcus agalactiae, Haemophilus influenzae*, Enteroviruses, mainly Coxsackie A virus and *Enterovirus* 71, Sin Nombre virus, *Helicobacter pylori, Escherichia coli* O157: H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum, Ancylostoma duodenale* and *Necator americanus, Hemophilus influenzae*, Human bocavirus, *Ehrlichia ewingii, Anaplasma phagocytophilum*, Human metapneumovirus, *Ehrlichia chaffeensis*, Human papillomavirus, Human parainfluenza viruses, *Hymenolepis nana* and *Hymenolepis diminuta*, Epstein-Barr Virus, Orthomyxoviridae family, *Isospora belli, Kingella kingae, Klebsiella pneumoniae, Klebsiella ozaenas, Klebsiella rhinoscleromotis, Kuru prion*, Lassa virus, *Legionella pneumophila, Legionella pneumophila, Leishmania genus, Mycobacterium leprae* and *Mycobacterium lepromatosis, Leptospira* genus, *Listeria monocytogenes, Borrelia burgdorferi* and other *Borrelia* species, *Wuchereria bancrofti* and *Brugia malayi, Lymphocytic choriomeningitis* virus (LCMV), *Plasmodium* genus, Marburg virus, Measles virus, *Burkholderia pseudomallei, Neisseria meningitides, Metagonimus yokagawai, Microsporidia phylum, Molluscum contagiosum* virus (MCV), Mumps virus, *Rickettsia typhi, Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus, Paracoccidioides brasiliensis, Paragonimus westermani* and other *Paragonimus* species, *Pasteurella* genus, *Pediculus humanus capitis, Pediculus humanus corporis, Phthinis pubis, Bordetella pertussis, Yersinia pestis, Streptococcus pneumoniae, Pneumocystis jirovecii*, Poliovirus, *Prevotella* genus, *Naegleria fowleri*, JC virus, *Chlamydophila psittaci, Coxiella burnetii*, Rabies virus, *Streptobacillus monilifonnis* and Spirillum minus, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei, Schistosoma genus, Shigella* genus, *Varicella zoster* virus, Variola major or Variola minor, *Sporothrix schenckii, Staphylococcus genus, Staphylococcus genus, Staphylococcus aureus, Streptococcus pyogenes, Strongyloides stercoralis, Treponema pallidum, Taenia genus, Clostridium tetani, Trichophyton genus, Trichophyton tonsurans, Trichophyton genus, Epidermophyton floccosum, Trichophyton rubrum*, and *Trichophyton mentagrophytes, Trichophyton rubrum, Hortaea werneckii, Trichophyton genus, Malassezia genus, Toxocara canis* or *Toxocara cati, Toxoplasma gondii, Trichinella spiralis, Trichomonas vaginalis, Trichuris trichiura, Mycobacterium tuberculosis, Francisella tularensis, Ureaplasma urealyticum*, Venezuelan equine encephalitis virus, *Vibrio colerae*, Guanarito virus, West Nile virus, *Trichosporon beigelii, Yersinia pseudotuberculosis, Yersinia enterocolitica*, Yellow fever virus, Mucorales order (Mucormycosis) and Entomophthorales order (Entomophthoramycosis), *Pseudomonas aeruginosa, Campylobacter* (*Vibrio*) fetus, *Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, Mycoplasma* spp., *Rickettsia prowazeki, Rickettsia tsutsugumushi, Clamydia* spp.; pathogenic fungi (*Aspergillus furnigatus, Candida albicans, Histoplasma capsulatum*); protozoa (*Entomoeba histolytica, Trichomonas tenas, Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmo-

*dium malaria*); or Helminiths (*Schistosoma japonicum, Schistosoma mansoni, Schistosoma haematobium*, and hookworms).

Other antibodies as a binding ligand in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (*Lymphocytic choriomeningitis*), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further embodiment, the present invention also concerns pharmaceutical compositions comprising the conjugate of the invention together with a pharmaceutically acceptable carrier for treatment of cancer and autoimmune disorders. The method for treatment of cancer, autoimmune disorders, infectious diseases or viral disease can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cell binding agent-cytotoxic agent conjugates of this invention will be supplied as solutions or as a lyophilized solid that can be redissolved in sterile water for injection. Examples of suitable protocols of conjugate administration are as follows. Conjugates are given weekly, biweekly, triweekly or monthly for 4-24 weeks or until disease progression or unacceptable toxicity as an i.v. bolus. Bolus doses are given in 10 to 500 ml of normal saline to which human serum albumin (e.g. 0.5 to 1 mL of a concentrated solution of human serum albumin, 100 mg/mL) can be added. Dosages will be about 50 μs to 20 mg/kg of body weight weekly, biweekly, triweekly or monthly i.v. (range of 10 μg to 200 mg/kg per injection). 4-24 weeks after treatment, the patient may receive a second course of treatment. Specific clinical protocols with regard to route of administration, excipients, diluents, dosages, times, etc., can be determined by the skilled clinicians. For example, the simple excipients can be 0.002%-0.5% polysorbate (polysorbate 20, polysorbate 40, polysorbate 60, or polysorbate 80) or the other pharmaceutical acceptable sururfactant, such as sodium lauryl sulfate, triton X-100, 0.1%~10% of binders, such as saccharides and their derivatives (disaccharides: sucrose, lactose, trehalose or maltose), sugar alcohols such as xylitol, sorbitol or maltitol, or polyethylene glycol, and 0.1%~10% of pharmaceutical buffering agents such as citrate, succinate acetate, phosphate, or borate with a certain pH in the range of pH 4.5-9.5. In certain applications, or a dose formula can contain other excipients, such as polysaccharides and their derivatives: starches, cellulose or modified cellulose such as microcrystalline cellulose and cellulose ethers such as hydroxypropyl cellulose (HPC), hypromellose (hydroxypropyl methylcellulose (HPMC)) or Hydroxypropyl cellulose; a protein such as gelatin, or albumin; Synthetic polymers: polyvinylpyrrolidone (PVP), polyethylene glycol (PEG); Antioxidants like vitamin A, vitamin E, vitamin C, retinyl palmitate, and selenium; The amino acids such cysteine, tyrosine or methionine; Synthetic preservatives like the parabens: methyl paraben and propyl paraben.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the cell binding agent-cytotoxic agent conjugates of this invention may be provided in an aqueous physiological buffer solution containing 0.1 to 10% w/v conjugates for parenteral administration. Typical dose ranges are from 1 mg/kg to 0.1 g/kg of body weight per day, per three-days, weekly, bi-weekly, tri-weekly or once per four weeks. A preferred dose range is from 0.01 mg/kg to 20 mg/kg of body weight weekly, bi-weekly, tri-weekly or monthly, or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The cell binding agent-cytotoxic agent conjugates of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably the unit dose range is from 0.1 to 500 mg administered one to three times a day, weekly, bi-weekly, tri-weekly or monthly, and even more preferably from 1 mg to 500 mg, weekly, bi-weekly, or tri-weekly, Conjugatess provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches. The compositions may conveniently be administered in unit dosage form and may be prepared by any of the methods well known in the pharmaceutical art, for example, as described in Remington: The Science and Practice of Pharmacy, $21^{th}$ ed.; Lippincott Williams & Wilkins: Philadelphia, Pa., 2005. Preferred formulations include pharmaceutical compositions in which a compound of the present invention is formulated for oral or parenteral administration. For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination. Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

In a specific embodiment, the cell binding agent-cytotoxic agent conjugates of this invention are administered concurrently with the other known or will be known therapeutic agents such as the chemotherapeutic agent, the radiation therapy, immunotherapy agents, autoimmune disorder agents, anti-infectious agents or the other antibody-drug conjugates, resulting in a synergistic effect. In another specific embodiment, the synergistic drugs or radiation therapy are administered prior or subsequent to administration of a conjugate, in one aspect at least an hour, 12 hours, a day, a week, bi-week, tri-week, a month, in further aspects several months, prior or subsequent to administration of a conjugate of the invention.

In other embodiments, the synergistic drugs include, but not limited to:

1). Chemotherapeutic agents: a). Alkylating agents: such as [Nitrogen mustards: (chlorambucil, cyclophosphamide, ifosfamide, mechlorethamine, melphalan, trofosfamide); Nitrosoureas: (carmustine, lomustine); Alkyl sulphonates: (busulfan, treosulfan); Triazenes: (dacarbazine); Platinum containing compounds: (carboplatin, cisplatin, oxaliplatin)]; b). Plant Alkaloids: such as [*Vinca* alkaloids: (vincristine, vinblastine, vindesine, vinorelbine); Taxoids: (paclitaxel, docetaxol)]; c). DNA Topoisomerase Inhibitors: such as

[Epipodophyllins: (9-aminocamptothecin, camptothecin, crisnatol, etoposide, etoposide phosphate, irinotecan, teniposide, topotecan,); Mitomycins: (mitomycin C)]; d). Antimetabolites: such as {[Anti-folate: DHFR inhibitors: (methotrexate, trimetrexate); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (5-Fluorouracil, doxifluridine, floxuridine, ratitrexed(Tomudex)); Cytosine analogs: (cytarabine, cytosine arabinoside, fludarabine); Purine analogs: (azathioprine, mercaptopurine, thioguanine)]}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). Others: such as gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), vismodegib, Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A. More detail lists of known and will be known anti-cancer drugs that can be used as a combination therapy (a synergistic effect) with the compounds and conjugates of the invention can be seen in National Cancer Institute (US) website (www.cancer.gov; www.cancer.gov/cancertopics/druginfo/alphalist), American Cancer Society (www.cancer.org/treatment/index) and Cancer Research UK (www.cancerrearchuk.org; (www.cancerresearchuk.org/cancer-help/about-cancer/treatment/cancer-drugs/)

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; I). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethylpenicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g. tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensirnycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides & nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2', 3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), l-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). Other itnmunotheraphy drugs: e.g. imiquimod, interferons (e.g. α, β), granulocyte colony-stimulating factors, cytokines, Interleukins (IL-1~IL-35), antibodies (e. g. trastuzumab, pertuzumab, bevacizumab, cetuximab, panitumumab, infliximab, adalimumab, basiliximab, daclizumab, omalizumab), Protein-bound drugs (e.g., Abraxane), an antibody conjugated with drugs selected from calicheamicin derivative, of maytansine derivatives (DM1 and DM4), CC-1065 and duocarmycin minor groove binders, potent taxol derivatives, doxorubicin, auristatin antimitotic drugs (e. g. Trastuzumab-DM1, Inotuzumab ozogamicin, Brentuximab vedotin, Glembatumumab vedotin, lorvotuzumab mertansine, AN-152 LMB2, TP-38, VB4-845, Cantuzumab mertansine, AVE9633, SAR3419, CAT-8015 (anti-CD22), IMGN388, milatuzumab-doxorubicin, SGN-75 (anti-CD70), Anti-CD22-MCC-DM1, IMGN853, Anti-CD22-MMAE, Anti-CD22-IVIMAF, Anti-CD22-calicheamicin.

The invention is further illustrated but not restricted by the description in the following examples.

EXAMPLES

Example 1. Synthesis of (S)-3-(1H-indol-2-yl)-2-(tritylamino)propanoic Acid (1)

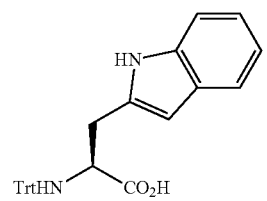

Chlorotrimethylsilane (3.4 mL, 26.9 mmol) was added slowly to a suspension of L-tryptophan (5.00 g, 24.5 mL) in methylene chloride (40 mL) at r.t. The mixture was continuously stirred for 4.5 h and triethylamine (6.8 mL, 49.0 mmol) was added, followed by a solution of triphenylmethyl chloride (7.17 g, 25.7 mmol) in methylene chloride (20 mL). The mixture was stirred at r.t. for 20 h and then quenched with methanol (25 mL). The reaction was concentrated to near dryness and re-dissolved in methylene chloride, washed with 5% citric acid solution (3×) and brine. The organic phase was dried over anhydrous sodium sulfate, filtered and concentrated. The residue was further dissolved in methylene chloride and filtered over a celite pad and the filtrate was concentrated to give a pale white foam (11.8 g), which was used directly in the next step. ESI MS m/z 446.5 ([M+H]$^+$).

Example 2. Synthesis of (S)-methyl 2-(3-(1H-indol-2-yl)-2-(tritylamino)propan amido)acetate (2)

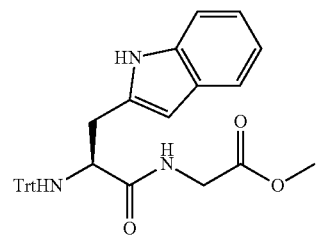

To a solution of acid (9.27 g, 30.7 mmol) in THF (30 mL) was added glycine methyl ester hydrochloride (2.85 g, 22.8 mmol) and HOBt (3.08 g, 22.8 mmol). The mixture was cooled to 0° C. and triethylamine (7.4 mL, 51.9 mmol) was added, followed by EDC.HCl (4.38 g, 22.8 mmol) in portions. The mixture was allowed to warm to r.t. and stirred for 20 h and then concentrated and redissolved in methylene chloride and washed with 5% citric acid solution (3×) and brine. The organic phase was dried over anhydrous sodium sulfate, filtered and concentrated. The residue was triturated with ethyl acetate and a white solid was collected by filtration (6.46 g, 65% yield over two steps). ESI MS m/z 518.2 ([M+H]+).

Example 3. Synthesis of dimethyldioxirane (DMDO)

Distilled water (20 mL), acetone (30 mL), and NaHCO$_3$ (24 g, 0.285 mol) were combined in a 1-L round-bottomed flask and chilled in an ice/water bath with magnetic stirring for 20 min. After 20 min, stirring was halted and Oxone (25 g, 0.0406 mol) was added in a single portion. The flask was loosely covered and the slurry was stirred vigorously for 15 min while still submerged in the ice bath. The flask containing the reaction slurry was then attached to a rotary evaporator with a bath at room temperature. The bump bulb (250 mL) was chilled in a dry ice/acetone bath and a vacuum of 165 mtor was applied via a benchtop diaphragm pump. After 15 min, the bath temperature was raised to 40° C. over 10 min. When the bath reached 40° C., the distillation was halted immediately via releasing the vacuum and raising the flask from the heated water bath. The pale yellow acetone solution of DMDO was decanted from the bump bulb directly into a graduated cylinder to measure the total volume of the solution (about 25 mL) and then the solution was dried over Na2SO4.

The $Na_2SO_4$ is removed by filtration and rinsed with 5 mL of acetone. Titration of the obtained DMDO solution is then performed according to the procedure of Adam, et al (Adam, W.; Chan, Y. Y.; Cremer, D.; Gauss, J.; Scheutzow, D.; Scheutzow, D.; Schindler, M. J. Org. Chem. 1987, 52, 2800-2803). Results consistently showed 2.1-2.3 mmol of DMDO in the solution. The DMDO solution was used immediately following titration.

Example 4. Synthesis of methyl 2-(3a-hydroxy-1-trityl-1,2,3,3a,8,8a-hexahydro pyrrolo[2,3-b]indole-2-carboxamido)acetate (3)

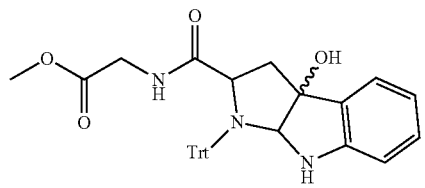

To a solution of Trt-Trp-Gly-OMe (0.80 g, 1.54 mmol) in methylene chloride (20 mL) at −78° C. was added a solution of DMDO in acetone (2.25 mmol). After 1 h the mixture was concentrated to dryness under reduced pressure at room temperature. The crude material was purified by column chromatography (hexanes/EtOAc/Et3N 70:30:1 to 30:70:1) to give a light yellow foam, the mixture of two diastereomers (0.58 g, 70% yield). ESI MS m/z 534.22 ([M+H]+).

Example 5. Synthesis of 2-(3a-hydroxy-1-trityl-1,2,3,3a,8,8a-hexahydropyrrolo [2,3-b]indole-2-carboxamido)acetic Acid (4)

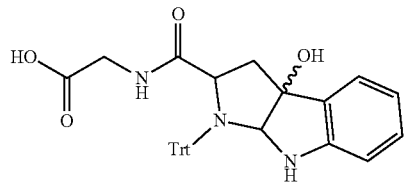

To a solution of Tr-Hpi-Gly-OMe (mixture of diastereomers) (0.80 g, 1.50 mmol) in dioxane/water (30 mL, v/v 2:1) was added LiOH (0.63 g, 15.0 mmol) and the reaction was stirred at r.t. for 30 min (following consumption of the starting material by TLC ($CH_2Cl_2$/MeOH, 9:1)). The reaction mixture was evaporated to dryness and the residue was purified by a short silica gel plug, eluting with $CH_2Cl_2$/MeOH/$Et_3N$ (90:10:1). Fractions were combined to yield a light yellow solid as the triethylamine salt of the two diastereomers (0.89 g, 95% yield).

Example 6. Synthesis of (5S,11R)-methyl 5-((S)-sec-butyl)-1-(9H-fluoren-9-yl)-3,6,9-trioxo-11-((tritylthio)methyl)-2-oxa-4,7,10-triazadodecan-12-oate (5)

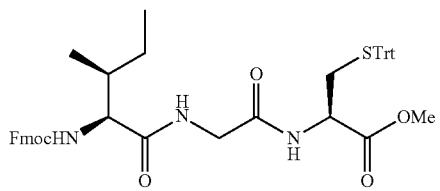

To a solution of Fmoc-Ile-Gly-OH (2.50 g, 6.09 mmol), H-Cys(Trt)-OMe (2.76 g, 7.30 mmol), HOBt (1.11 g, 7.30 mmol) in THF (40 mL) was added DIPEA (2.6 mL, 15.3 mmol) at 0° C., followed by EDC.HCl (1.40 g, 7.30 mmol) in portions. The reaction was warmed to r.t. and stirred for 16 h. The reaction was concentrated to dryness and diluted with ethyl acetate and washed with 5% citric acid (3×), saturated $NaHCO_3$(3×) and brine. The organic phase was dried over anhydrous $Na_2SO_4$ and concentrated. The residue was purified by column chromatography (0-20% ethyl acetate/hexanes) to give a white solid (4.45 g, 95% yield). ESI MS m/z 770.2 ([M+H]$^T$).

Example 7. Synthesis of (6S,12R)-methyl 6-((S)-sec-butyl)-1-(3a-hydroxy-1- trityl-1,2,3,3 a,8,8a-hexahydropyrrolo[2,3-b]indol-2-yl)-1,4,7,10-tetraoxo-12-((tritylthio)methyl)-2,5,8,11-tetraazatridecan-13-oate (6)

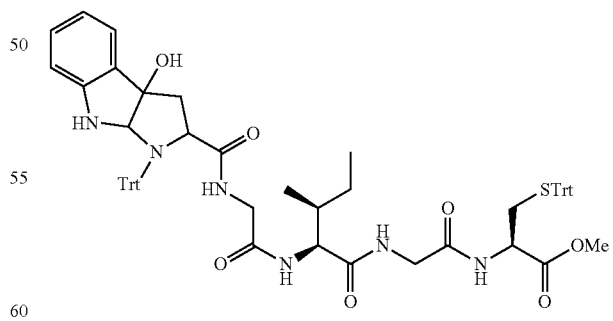

Fmoc-Ile-Gly-Cys(Trt)-OMe (4.45 g, 5.78 mmol) was mixed with piperidine/DMF (20%, 10 mL) and stirred at r.t. for 30 min. The reaction mixture was diluted with dichloromethane (50 mL) and washed with water and brine. The organic phase was dried over anhydrous $Na_2SO_4$ and concentrated. The residue was purified by column chromatography (0-10% MeOH/CH₂Cl₂ with 1% Et₃N) to give a white solid (3.12 g, 99% yield). ESI MS m/z 548.2 ([M+H]⁺).

The above solid (1.04 g, 1.90 mmol) was mixed with Trt-Hpi-Gly-OH.NEt₃ (0.98 g, 1.58 mmol) in CH₂Cl₂ (10 mL), to which HOBt (0.29 g, 1.90 mmol) and DIPEA (0.7 mL, 4.00 mmol) were added at 0° C. EDC.HCl (0.36 g, 1.90 mmol) was added at last in portions. The reaction was warmed to r.t. and stirred for 16 h and then diluted with ethyl acetate and washed with 5% citric acid (3×), saturated NaHCO₃ (3×) and brine. The organic phase was dried over anhydrous Na₂SO₄ and concentrated. The residue was purified by column chromatography (20-70% ethyl acetate/hexanes) to give a white solid (0.75 g, 45% yield). ESI MS m/z 1049.4 ([M+H]⁺).

Example 8. Synthesis of (6S,12R)-6-((S)-sec-butyl)-1-(3a-hydroxy-1-trityl-1,2,3,3a,8,8a-hexahydropyrrolo[2,3-b]indol-2-yl)-1,4,7,10-tetraoxo-12-(((tritylthio)methyl)-2,5,8,11-tetraazatridecan-13-oic Acid (7)

7

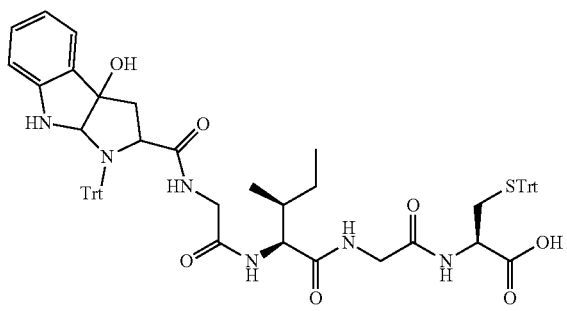

Trt-Hpi-Gly-Ile-Gly-Cys(Trt)-OMe (0.75 g, 0.71 mmol) was dissolved in dioxane/water (v/v 2:1, 30 mL) and treated with LiOH.H₂O (0.30 g, 7.1 mmol) at r.t. for 30 min. The reaction mixture was evaporated to dryness and the residue was purified by a short silica gel plug, eluting with CH₂Cl₂/MeOH/Et₃N (90:10:1). Fractions were combined to yield a white solid as the triethylamine salt of Trt-Hpi-Gly-Ile-Gly-Cys(Trt)-OH (0.77 g, 95% yield).

Example 9. Synthesis of (2S,4R)-(9H-fluoren-9-yl) methyl 4-(tert-butoxy)-2-(((2S,3S)-1-(tert-butoxy)-3-methyl-1-oxopentan-2-yl)carbamoyl)pyrrolidine-1-carboxylate (8)

8

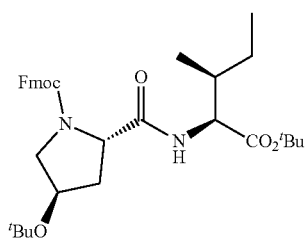

To a solution of Fmoc-Pro(OᵗBu)-OH (2.50 g, 6.10 mmol), H-Ile-OᵗBu (1.37 g, 7.32 mmol), HOBt (1.12 g, 7.32 mmol) in THF (40 mL) was added DIPEA (2.6 mL, 15.3 mmol) at 0° C., followed by EDC.HCl (1.40 g, 7.32 mmol) in portions. The reaction was warmed to r.t. and stirred for 16 h. After concentration, the residue was diluted with ethyl acetate and washed with 5% citric acid (3×), saturated NaHCO₃ (3×) and brine. The organic phase was dried over anhydrous Na₂SO₄ and concentrated. The residue was purified by column chromatography (0-20% ethyl acetate/hexanes) to give a white solid (2.55 g, 85% yield). ESI MS m/z 579.3 ([M+H]⁺).

Example 10. Synthesis of (2S,3S)-tert-butyl 2-(2S,4R)-1-((S)-2-((((9H-fluoren-9-yl)methoxy)carbonyl) amino)-4-methoxy-4-oxobutanoyl)-4-(tert-butoxy) pyrrolidine-2-carboxamido)-3-methylpentanoate (9)

9

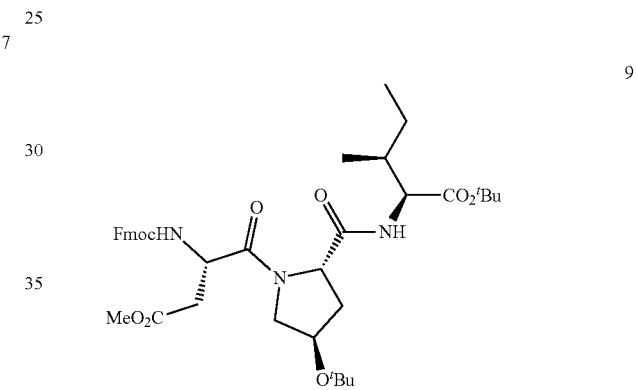

Fmoc-Pro(OᵗBu)-Ile-OᵗBu (2.55 g, 4.40 mmol) was treated with 20% piperidine in DMF (20 mL) for 30 min. The reaction mixture was concentrated and purified by column chromatography (0-10% MeOH/CH₂Cl₂ with 1% Et₃N) to give a white solid (1.41 g, 90% yield). ESI MS m/z 357.2 ([M+H]⁺).

The above solid (1.41 g, 3.96 mmol) was mixed with Fmoc-Asp(OMe)-OH (1.22 g, 3.30 mmol) in DMF (20 mL), to which HOBt (0.61 g, 3.96 mmol) and DIPEA (1.4 mL, 8.25 mmol) were added at 0° C. EDC.HCl (0.76 g, 3.96 mmol) was added at last in portions. The reaction was warmed to r.t. and stirred for 16 h and then diluted with ethyl acetate and washed with H₂O, 5% citric acid (3×), saturated NaHCO₃ (3×) and brine. The organic phase was dried over anhydrous Na₂SO₄ and concentrated. The residue was purified by column chromatography (20-70% ethyl acetate/hexanes) to give a white solid (1.78 g, 76% yield). ESI MS m/z 708.4 ([M+H]⁺).

Example 11. Synthesis of ((6S,12R,15S)-methyl 15-((2S,4R)-4- (tert-butoxy)-2-(((2S,3S)-1-(tert-butoxy)-3-methyl-1-oxopentan-2-yl)carbamoyl)pyrrolidine-1-carbonyl)-6-((S)-sec-butyl)-1-(3a-hydroxy-1-trityl-1,2,3,3a,8,8a-hexahydropyrrolo[2,3-b]indol-2-yl)-1,4,7,10,13-pentaoxo-12-((tritylthio)methyl)-2,5,8,11,14-pentaazaheptadecan-17-oate (10)

Trt-Hpi-Gly-Ile-Gly-Cys(Trt)-Asp(OMe)-Pro(O'Bu)-Ile-O'Bu (0.50 g, 0.33 mmol) was treated with neat TFA at r.t. for 5 h. Methanol was added and the reaction was concentrated. This was repeated twice and the residue was purified by prep-HPLC (H₂O/MeCN) to afford a white solid (99.6 mg, 34% yield).

Fmoc-Ile-OH was attached on the 2-chlorotrityl chloride resin according to the following protocol:

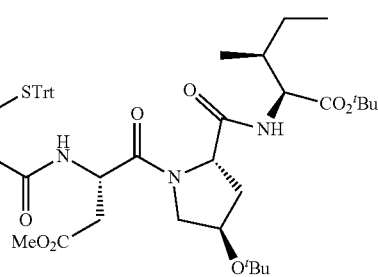

Fmoc-Asp(OMe)-Pro(O'Bu)-Ile-O'Bu (0.59 g, 0.90 mmol) was mixed with piperidine/DMF (20%, 10 mL) and stirred at r.t. for 30 min. The reaction mixture was diluted with dichloromethane (50 mL) and washed with water and brine. The organic phase was dried over anhydrous Na₂SO₄ and concentrated. The residue was purified by column chromatography (0-10% MeOH/CH₂Cl₂ with 1% Et₃N) to give a white solid (0.43 g, 99% yield). ESI MS m/z 486.6 ([M+H]⁺).

The above solid (0.43 g, 0.89 mmol) was mixed with Trt-Hpi-Gly-Ile-Gly-Cys(Trt)-OH.NEt₃ (0.77 g, 0.67 mmol) in CH₂Cl₂ (5 mL), to which HOBt (0.12 g, 0.80 mmol) and DIPEA (0.33 mL, 1.88 mmol) were added at 0° C. EDC.HCl (0.15 g, 0.80 mmol) was added at last in portions. The reaction was warmed to r.t. and stirred for 18 h and then diluted with ethyl acetate and washed with 5% citric acid (3×), saturated NaHCO₃ (3×) and brine. The organic phase was dried over anhydrous Na₂SO₄ and concentrated. The residue was purified by column chromatography (30-80% ethyl acetate/hexanes) to give a white solid (0.50 g, 50% yield). ESI MS m/z 1502.7 ([M+H]⁺).

Example 12. Synthesis of (2S,3S)-2-((2S,4R)-1-((S)-2-((3R,9S,15S)-15-amino-9-((S)-sec-butyl)-5,8,11,14-tetraoxo-2,3,4,5,6,7,8,9,10,11,12,13,14,15,16,21-hexadecahydro-[1,4,7,10,13]thiatetraazacyclooctadecino[18,17-b]indole-3-carboxamido)-4-methoxy-4-oxobutanoyl)-4-hydroxypyrrolidine-2-carboxamido)-3-methylpentanoic acid (11)

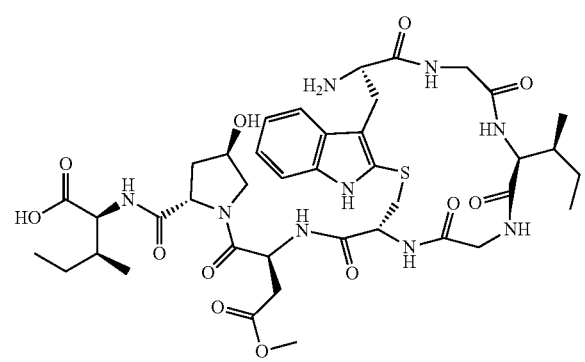

Fmoc-Ile-OH (0.35 g, 1.0 mmol) and DIPEA (0.70 mL, 4.0 mmol) were dissolved in dry methylene chloride (10 mL). The resulting solution was added to chlorotrityl resin (1.0 g, 0.911 mmol/g, GL Biochem) and the mixture was shaken under nitrogen for 1.5 h. Subsequently methanol (2 mL) was added and shaking continued for 30 min. The liquid was drained under vacuum and resin washed with methylene chloride (15 mL), DMF (10 mL) and methanol (10 mL) and dried under vacuum.

Coupling was Performed According to the Following Protocol:

Resin was placed in a column and swollen in DMF (10 mL) for 30 min. The solvent was drained under vacuum and the N-terminal Fmoc protecting group was cleaved by shaking with 20% piperidine in DMF for 30 min. Following deprotection, the resin was washed with DMF (3×10 mL), followed by CH₂Cl₂ (3×10 mL) and again with DMF (3×10 mL). The next Fmoc protected amino acid (Fmoc-Xaa-OH, 5 eq.) was coupled to the resin with coupling reagent HBTU (5 eq.) and DIPEA (10 eq.) in DMF (10 mL) with shaking for 2 h. The resin was then washed extensively with DMF (3×10 mL), followed by CH₂Cl₂ (3×10 mL) and DMF (3×10 mL). A small sample was taken and treated with hexafluoroisopropanol (HFIP) in CH₂Cl₂ for 5 min to cleave the peptide from the resin and checked by mass spectrometry. In case of coupling of non-commercially available amino acid, such as Trt-Hpi-Gly-OH, fewer equivalents (3 eq.) and longer time (3 h) were employed.

When all the couplings were completed, the resin-bounded peptide was transferred to a round bottom flask and TFA (10 mL) was added and stirred at r.t. for 5 h. The acid labile protecting groups were concomitantly removed during TFA treatment. The resin was filtered and washed with CH₂Cl₂ (10 mL) and methanol (10 mL). The filtrate was concentrated and partitioned between water and ethyl acetate. The aqueous layer was purified by prep-HPLC (H₂O/MeCN) to yield a white solid of monocyclic octapeptide (40.3 mg, 5% yield). ESI MS m/z 888.38 ([M+H]⁺).

Example 13. Synthesis of Ile³-S-deoxo-amanitin (12)

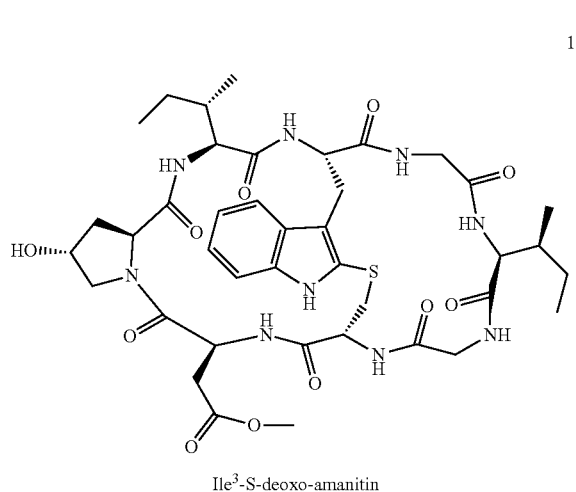

Ile³-S-deoxo-amanitin

To a solution of monocyclic octapeptide (25.7 mg, 0.0289 mmol) in dry DMF (5 mL) was added EDC.HCl (27.7 mg, 0.145 mmol), HOBt (39.0 mg, 0.289 mmol) and DIPEA (0.025 mL, 0.145 mmol). The reaction was stirred at r.t. for 20 h and then concentrated and purified by prep-HPLC ($H_2O$/MeCN) to give a white solid compound 12 (9.0 mg, 36% yield). ESI MS m/z 870.40 ([M+H]⁺).

Example 14. Synthesis of Compound 13

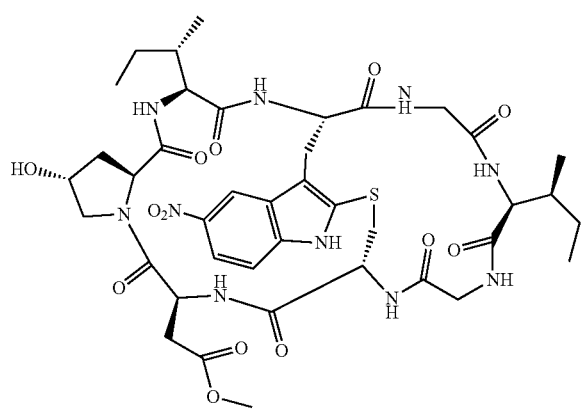

To a solution of compound 12 (5.0 mg, 0.00575 mmol, 1.0 eq.) in THF (1 mL) was added t-BuONO (7 µL, 0.0575 mmol) at 0° C. The reaction was stirred at 0° C. for 1 h then room temperature 20 h. After water (5 mL) was added, the reaction mixture was concentrated and purified by prep-HPLC ($H_2O$/MeCN) to give a white solid (2.6 mg, 50% yield). ESI MS m/z 915.38 ([M+H]⁺).

Example 15. Synthesis of Compound 14

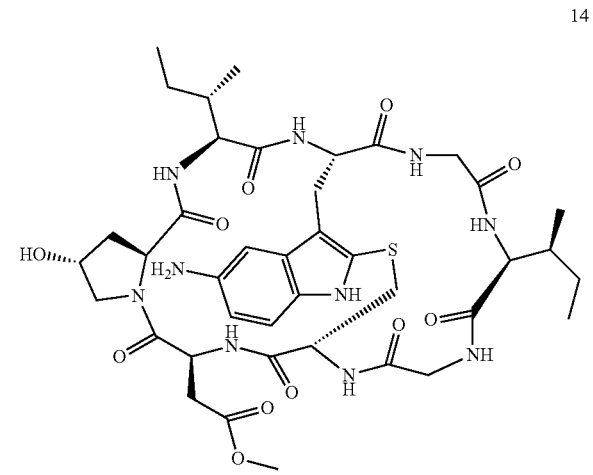 [SMILES: CC[C@H](C)[C@@H]1NC(=O)CNC(=O)[C@@H]2Cc3c([nH]c4ccc(N)cc34)SC[C@H](NC(=O)CNC1=O)C(=O)N[C@@H](CC(=O)OC)C(=O)N1C[C@H](O)C[C@H]1C(=O)N[C@@H]([C@@H](C)CC)C(=O)N2]

A mixture of nitro compound (2.6 mg, 0.00284 mmol) and Pd/C (10 wt %, 10 mg) in methanol (2 mL) was hydrogenated (1 atm $H_2$) at r.t. for 1 h, and then filtered through Celite (filter aid). The filtrate was concentrated to afford a white solid (2.5 mg, 99% yield). ESI MS m/z 885.38 ([M+1-1]⁺).

Example 16. Synthesis of Compound 15

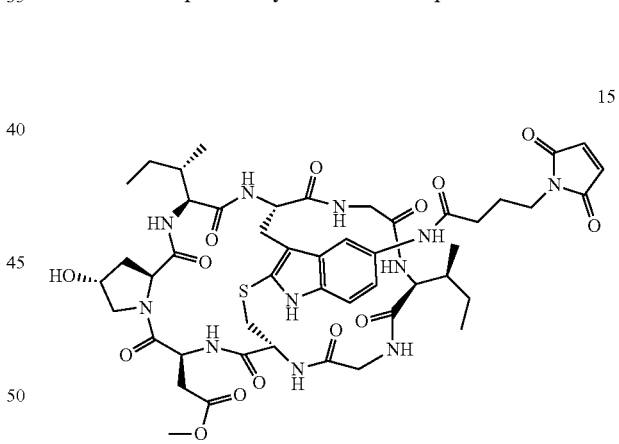

To a solution of compound 14 (2.5 mg, 0.00283 mmol) and 4-(2,5-dioxo-2,5-dihydro-1H-pyrrol-1-yl)butanoic acid (2.6 mg, 0.0141 mmol) in dry DMF (1 mL) was added HATU (5.4 mg, 0.0141 mmol) and DIPEA (0.05 mL, 0.283 mmol). The reaction was stirred at r.t. for 20 h and then diluted with ethyl acetate and washed with brine. The organic phase was concentrated and purified by prep-HPLC ($H_2O$/MeCN) to give a white solid Ile³-S-deoxo-amanitin (1.7 mg, 56% yield). ESI MS m/z 1050.41 ([M+H]⁺).

Example 17. Synthesis of 2-(2-(dibenzylamino)ethoxy)ethanol (16)

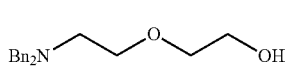

16

2-(2-aminoethoxy)ethanol (21.00 g, 200 mmol, 1.0 eq.) and $K_2CO_3$ (83.00 g, 600 mmol, 3.0 eq.) in acetonitrile (350 mL) was added BnBr(57.0 mL, 480 mmol, 2.4 eq.). The mixture was refluxed overnight. Water (1 L) was added and extracted with EtOAc (3×300 mL). The combined organic layers were washed with brine (1000 mL), dried over anhydrous $Na_2SO_4$, filtered, concentrated and purified by $SiO_2$ column chromatography (4:1 hexanes/EtOAc) to give a colorless oil (50.97 g, 89.2% yield). MS ESI m/z $[M+Na]^+$ 309.1967.

Example 18. Synthesis of tert-butyl 3-(2-(2-(dibenzylamino)ethoxy)ethoxy) propanoate (17)

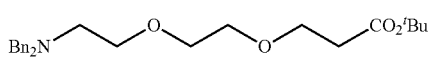

17

To a mixture of 2-(2-(dibenzylamino)ethoxy)ethanol (47.17 g, 165.3 mmol, 1.0 eq.), tert-butyl acrylate (72.0 mL, 495.9 mmol, 3.0 eq.) and n-Bu$_4$NI (6.10 g, 16.53 mmol, 0.1 eq.) in DCM (560 mL) was added sodium hydroxide solution (300 mL, 50%). The mixture was stirred overnight. The organic layer was separated and the water layer was extracted with EtOAc (3×100 mL). The organic layers were washed with water(3×300 mL) and brine (300 mL), dried over anhydrous $Na_2SO_4$, filtered, concentrated and purified by $SiO_2$ column chromatography (7:1 hexanes/EtOAc) to give a colorless oil (61.08 g, 89.4% yield). MS ESI m/z $[M+H]^+$ 414.2384.

Example 19. Synthesis of tert-butyl 3-(2-(2-aminoethoxy)ethoxy)propanoate (18)

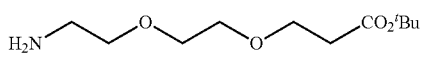

18

To a solution of tert-butyl 3-(2-(2-(dibenzylamino)ethoxy)ethoxy) propanoate (20.00 g, 48.36 mmol, 1.0 eq.) in THF (30 mL) and MeOH (60 mL) was added Pd/C (2.00 g, 10 wt %, 50% wet) in a hydrogenation bottle. The mixture was shaken overnight, filtered through Celite (filter aid), and the filtrate was concentrated to afford a colorless oil (10.58 g, 93.8% yield). MS ESI m/z $[M+H]^+$ 234.1810.

Example 20. Synthesis of (E)-16-bromo-2,2-dimethyl-4,14-dioxo-3,7,10-trioxa-13-azaheptadec-15-en-17-oic Acid (19)

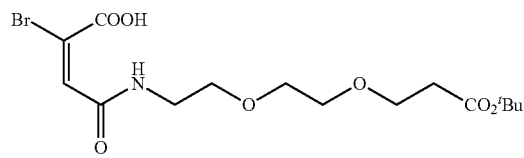

19

To a solution of 3-bromofuran-2,5-dione (89 mg, 0.5 mmol) in THF (5 mL), tert-butyl 3-(2-(2-aminoethoxy)ethoxy)propanoate (117 mg, 0.5 mmol) was added. The resulting solution was stirred at r.t. for 4 h. The solvent was removed under vacuum to afford compound 19 (205 mg, theoretical yield). MS ESI m/z $[M+H]^-$ 410.03.

Example 21. Synthesis of (E)-1-tert-butyl 18-methyl 13-bromo-11,14-dioxo-4,7-dioxa-10,15-diazaoctadec-12-ene-1,18-dioate (20)

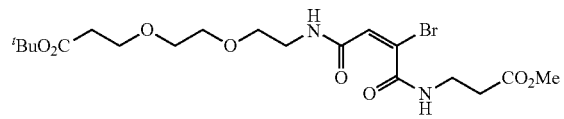

20

Compound 19 (205 mg, 0.5 mmol) and methyl 3-aminopropanoate hydrochloride (70 mg, 0.5 mmol) were dissolved in DCM (20 mL), to which DIPEA (0.26 mL, 1.5 mmol) and EDC.HCl (144 mg, 0.75 mmol) were added. The resulting solution was stirred at r.t. overnight, and then washed with brine (50 mL), dried over anhydrous $Na_2SO_4$. Concentration and purification by column chromatography (0 to 10% MeOH/DCM) yielded compound 20 (88 mg, 36% yield). MS ESI m/z $[M+H]^+$ 495.25.

Example 22. Synthesis of (E)-8-bromo-3,7,10-trioxo-2,14,17-trioxa-6,11-diazaicos-8-en-20-oic Acid (21)

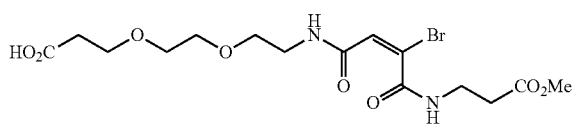

21

Compound 20 (88 mg, 0.18 mmol) in DCM (3 mL) was treated with formic acid (6 ml) at 38° C. overnight. All volatiles were removed under vacuum to yield compound 21 (78 mg, theoretical yield).

Example 23. Synthesis of Compound 22

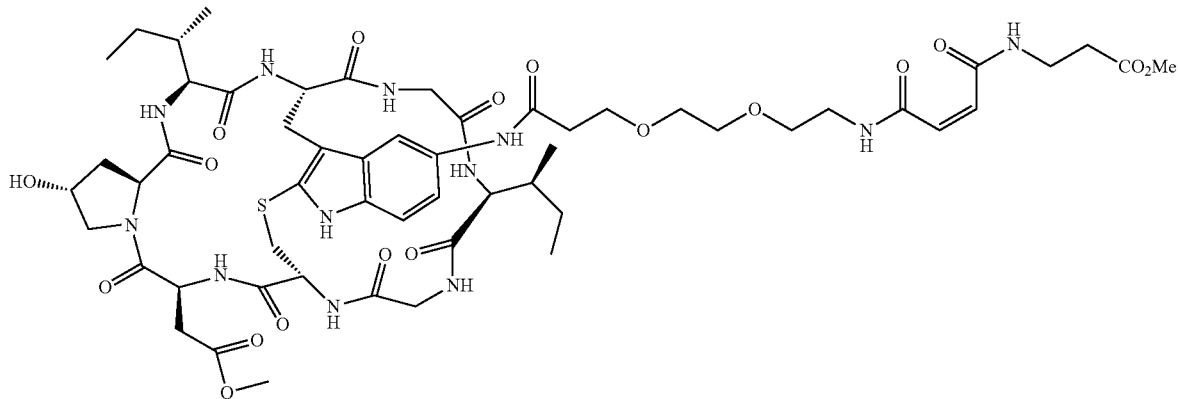

22

Compound 14 (2.0 mg, 0.00226 mmol) and compound 21 (5.0 mg, 0.0113 mmol) were dissolved in DMF (1 mL), to which HATU (4.3 mg, 0.0113 mmol) and DIPEA (2.0 µL, 0.0113 mmol) were added. The resulting solution was stirred at r.t. overnight, diluted with ethyl acetate and then washed with brine, dried over anhydrous $Na_2SO_4$. Concentration and purification by prep-HPLC ($H_2O$/MeCN) gave a white solid (1.2 mg, 44% yield). MS ESI m/z [M+H]$^+$1227.50.

Example 24. Synthesis of 4-(((benzyloxy)carbonyl)amino)butanoic Acid (23)

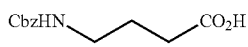

23

A solution of 4-aminobutyric acid (7.5 g, 75 mmol) and NaOH (6 g, 150 mmol) in $H_2O$ (40 mL) was cooled to 0° C. and treated with a solution of CbzCl (16.1 g, 95 mmol) in THF (32 ml) dropwise. After 1 h, the reaction was allowed to warm to r.t. and stirred for 3 h. THF was removed under vacuum, the pH of the aqueous solution was adjusted to 1.5 by addition of 6 N HCl. Extracted with ethyl acetate, and the organic layer was washed with brine, dried and concentrated to give compound 23 (16.4 g, 92% yield). MS ESI m/z [M+H]$^+$ 238.08.

Example 25. Synthesis of tert-butyl 4-(((benzyloxy)carbonyl)amino)butanoate (24)

24

DMAP (0.8 g, 6.56 mmol) and DCC (17.1 g, 83 mmol) were added to a solution of 4-(((benzyloxy)carbonyl)amino) butanoic acid (16.4 g, 69.2 mmol) and t-BuOH (15.4 g, 208 mmol) in DCM (100 mL). After stirring at r.t. overnight, the reaction was filtered and filtrate concentrated. The residue was dissolved in ethyl acetate and the washed with 1N HCl, brine and dried over $Na_2SO_4$. Concentration and purification by column chromatography (10 to 50% EtOAc/hexanes) yielded compound 24 (7.5 g, 37% yield). MS ESI m/z [M+Na]$^+$ 316.13.

Example 26. Synthesis of tert-butyl 4-aminobutanoate (25)

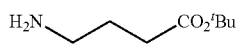

25 tert-Butyl 4-(((benzyloxy)carbonyl)amino)butanoate (560 mg, 1.91 mmol) was dissolved in MeOH (50 mL), and mixed with Pd/C catalyst (10 wt %, 100 mg) then hydrogenated (1 atm) at r.t. for 3 h. The catalyst was filtered off and all volatiles were removed under vacuum to afford compound 25 (272 mg, 90% yield). MS ESI m/z [M+H]$^+$ 160.13.

Example 27. Synthesis of (E)-2-bromo-4-((4-(tert-butoxy)-4-oxobutyl)amino)-4-oxobut-2-enoic Acid (26)

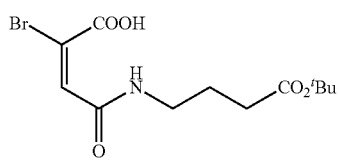

26

3-Bromofuran-2,5-dione (300 mg, 1.71 mmol) was dissolved in THF (20 mL), to which tert-butyl 4-aminobutanoate (272 mg, 1.71 mmol) was added and the resulting solution was stirred at r.t. for 3 h. The solvent was removed under vacuum to afford compound 26 (572 mg, theoretical yield). MS ESI m/z [M+H]$^+$ 338.04.

Example 28. Synthesis of (E)-tert-butyl 4-(3-bromo-4-((2-methoxyethyl) amino)-4-oxobut-2-enamido)butanoate (27)

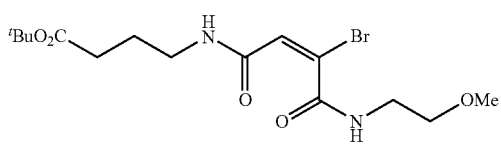

27

2-Bromo-4((4-(tert-butoxy)-4-oxobutyl)amino)-4-oxobut-2-enoic acid(286 mg, 0.85 mmol) and 2-methoxyethanamine (128 mg, 1.7 mmol) were dissolved in DCM (40 mL), to which DIPEA (329 mg, 2.55 mmol) and EDC.HCl (490 mg, 2.55 mmol) were added. The resulting solution was stirred at r.t. for 24 h and then washed with brine, dried over Na$_2$SO$_4$. Concentration and purification by column chromatography (0 to 10% MeOH/DCM) yielded compound 27 (102 mg, 31% yield). MS ESI m/z [M+H]$^+$ 393.11.

Example 29. Synthesis of (E)-4-(3-bromo-4-((2-methoxyethyl)amino)-4-oxobut-2-enamido)butanoic acid (28)

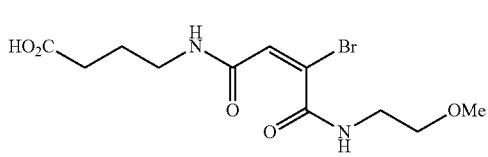

28

Compound 27 (52 mg, 0.132 mmol) was dissolved in DCM (3 mL), to which formic acid (6 ml) was added. The resulting solution was stirred at 38° C. overnight then concentrated to afford compound 28 (45 mg, theoretical yield). MS ESI m/z [M+H]$^+$ 339.05.

Example 30. Synthesis of (E)-2,5-dioxopyrrolidin-1-yl 4-(3-bromo-4-((2-methoxyethyl)amino)-4-oxobut-2-enamido)butanoate (29)

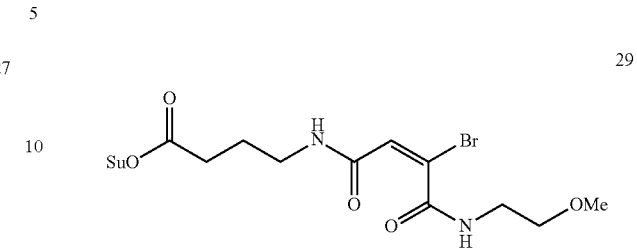

29

To a solution of compound 28 (45 mg, 0.132 mmol) in DCM (10 mL) NHS (23 mg, 0.199 mmol) and EDC.HCl (38 mg, 0.199 mmol) were added. After stirring at r.t. for 3 h, the reaction was concentrated and purified by column chromatography (10 to 50% EtOAc/hexanes) to yield compound 29 (57 mg, 99% yield). MS ESI m/z [M+H]$^+$ 436.06.

Example 31. Synthesis of Compound 30

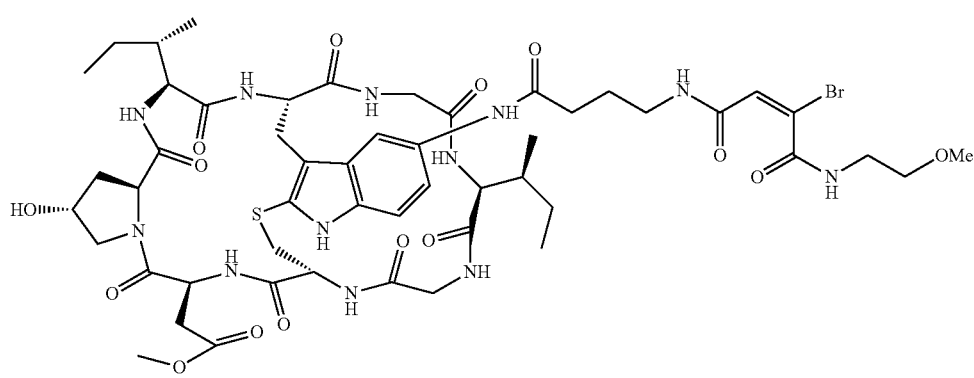

30

To a solution of compound 14 (2.0 mg, 0.00226 mmol) in ethanol (1 mL) and phosphate buffer solution (pH 7.2, 1 mL) was added compound 29 (4.9 mg, 0.0113 mmol) in ethanol (1 mL) over 30 min. After stirring at r.t. for 3 h, the reaction was concentrated and purified by prep-HPLC (H$_2$O/MeCN) to yield compound 30 (2.7 mg, 30% yield). MS ESI m/z [M+H]$^+$ 1203.40.

Example 32. Synthesis of tert-butyl 3-(2-(2-(2-hydroxyethoxy)ethoxy)ethoxy) propanoate (31)

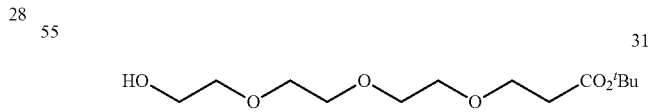

31

To a solution of 2,2'-(ethane-1,2-diylbis(oxy))diethanol (55.0 mL, 410.75 mmol, 3.0 eq.) in anhydrous THF (200 mL) was added sodium (0.1 g). The mixture was stirred until Na disappeared and then tert-butyl acrylate (20.0 mL, 137.79 mmol, 1.0 eq.) was added dropwise. The mixture was stirred overnight and then quenched by HCl solution (20.0 mL, 1 N) at 0° C. THF was removed by rotary evaporation, brine (300 mL) was added and the resulting mixture was extracted with EtOAc (3×100 mL). The organic layers were washed with brine (3×300 mL), dried over anhydrous Na₂SO₄, filtered and concentrated to afford a colorless oil (30.20 g, 79.0% yield), which was used without further purification. MS ESI m/z [M+H]⁺ 278.17.

Example 33. Synthesis of tert-butyl 3-(2-(2-(2-(tosyloxy)ethoxy)ethoxy)ethoxy) propanoate (32)

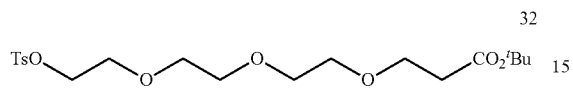

32

To a solution of tert-butyl 3-(2-(2-(2-hydroxyethoxy)ethoxy)ethoxy) propanoate (30.20 g, 108.5 mmol, 1.0 eq.) and TsCl (41.37 g, 217.0 mmol, 2.0 eq.) in anhydrous DCM (220 mL) at 0° C. was added TEA (30.0 mL, 217.0 mmol, 2.0 eq.). The mixture was stirred at room temperature overnight, and then washed with water (3×300 mL) and brine (300 mL), dried over anhydrous Na₂SO₄, filtered, concentrated and purified by SiO₂ column chromatography (3:1 hexanes/EtOAc) to give a colorless oil (39.4 g, 84.0% yield). MS ESI m/z [M+H]⁺ 433.28.

Example 34. Synthesis of tert-butyl 3-(2-(2-(2-azidoethoxy)ethoxy)ethoxy) propanoate (33)

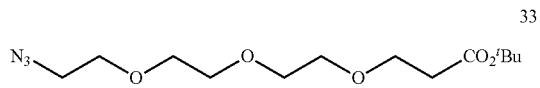 [SMILES: CC(C)(C)OC(=O)CCOCCOCCOCCN=[N+]=[N-]]

33

To a solution of tert-butyl 3-(2-(2-(2-(tosyloxy)ethoxy)ethoxy)ethoxy) propanoate (39.4 g, 91.1 mmol, 1.0 eq.) in anhydrous DMF(100 mL) was added NaN₃ (20.67 g, 316.6 mmol, 3.5 eq.). The mixture was stirred at room temperature overnight. Water (500 mL) was added and extracted with EtOAc (3×300 mL). The combined organic layers were washed with water (3×900 mL) and brine (900 mL), dried over anhydrous Na₂SO₄, filtered, concentrated and purified by SiO₂ column chromatography (5:1 hexanes/EtOAc) to give a light yellow oil (23.8 g, 85.5% yield). MS ESI m/z [M+Na] 326.20.

Example 35. Synthesis of tert-butyl 3-(2-(2-(2-aminoethoxy)ethoxy)ethoxy) propanoate (34)

34

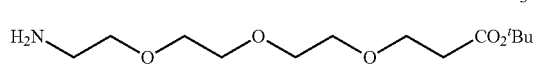

Raney-Ni (7.5 g, suspended in water) was washed with water (three times) and isopropyl alcohol (three times) and mixed with compound 33 (5.0 g, 16.5 mmol) in isopropyl alcohol. The mixture was stirred under a H₂ balloon at r.t. for 16 h and then filtered over a Celite pad, with washing of the pad with isopropyl alcohol. The filtrate was concentrated and purified by column chromatography (5-25% MeOH/DCM) to give a light yellow oil (2.60 g, 57% yield). MS ESI m/z [M+H]⁺ 279.19.

Example 36. Synthesis of di-tert-butyl 14,17-dioxo-4,7,10,21,24,27-hexaoxa-13,18-diazatriacont-15-yne-1,30-dioate (35)

35

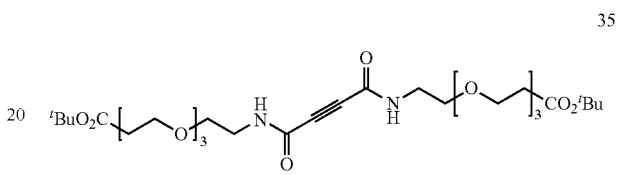

Acetylenedicarboxylic acid (0.35 g, 3.09 mmol, 1.0 eq.) was dissolved in NMP (10 mL) and cooled to 0° C., to which compound 34 (2.06 g, 7.43 mmol, 2.4 eq.) was added, followed by DMTMM (2.39 g, 8.65 mmol, 2.8 eq.) in portions. The reaction was stirred at 0° C. for 6 h and then diluted with ethyl acetate and washed with water and brine. The organic solution was concentrated and triturated with a mixture solvent of ethyl acetate and petroleum ether. The solid was filtered off and the filtrate was concentrated and purified by column chromatography (80-90% EA/PE) to give a light yellow oil (2.26 g, >100% yield), which was used without further purification. MS ESI m/z [M+H]⁺ 633.30.

Example 37. Synthesis of 14,17-dioxo-4,7,10,21,24,27-hexaoxa-13,18-diaza triacont-15-yne-1,30-dioic acid (36)

36

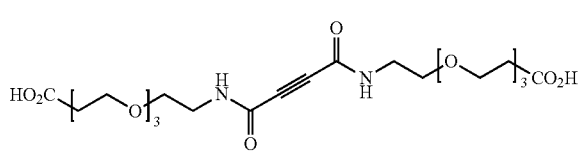

Compound 35 (2.26 g) was dissolved in dichloromethane (15 mL) and cooled to 0° C. then treated with TFA (15 mL). The reaction was warmed to r.t. and stirred for 45 min, and then the solvent and residual TFA was removed on rotovap. The crude product was purified by column chromatography (0-15% MeOH/DCM) to give a light yellow oil (1.39 g, 86% yield for two steps). MS ESI m/z [M+H]+ 521.24.

Example 38. Synthesis of Compound 37

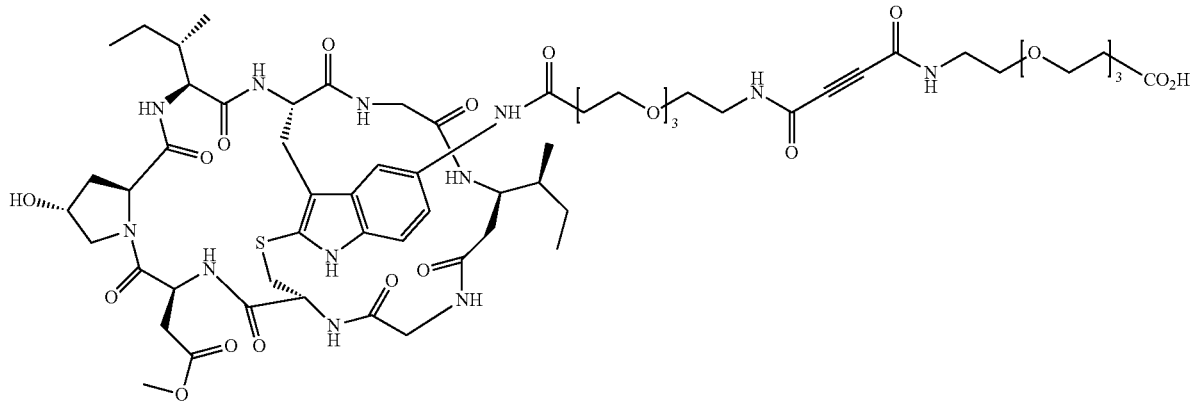

37

Compound 14 (2.0 mg, 0.00226 mmol) and compound 36 (5.9 mg, 0.0113 mmol) were dissolved in DMF (1 mL), to which HATU (4.3 mg, 0.0113 mmol) and DIPEA (2.0 µL, 0.0113 mmol) were added. The resulting solution was stirred at r.t. overnight, and then concentrated and purified by prep-HPLC (H$_2$O/MeCN) to give a white solid (0.94 mg, 30% yield). MS ESI m/z [M+H]$^+$ 1387.50.

Example 39. Synthesis of methyl 2,5-dioxo-2,5-dihydro-1H-pyrrole-1-carboxylate (38)

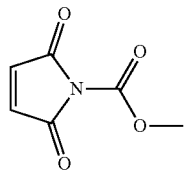

38

To a solution of maleimide (6.35 g, 65.4 mmol) in ethyl acetate (120 mL) at 0° C. was added NMM (8.6 mL, 78.5 mmol), followed by methyl chloroformate (6.0 mL, 78.5 mmol). The reaction was stirred at 0° C. for 30 min and r.t. 1 h. The solid was filtered off and filtrate was concentrated. The residue was dissolved in methylene chloride and filtered through a silica gel plug and eluted with methylene chloride to remove the red color. After concentration, the solid was triturated with ethyl acetate and petroleum ether to give a white solid (9.0 g, 88% yield).

Example 40. Synthesis of tert-butyl (2-(2,5-dioxo-2,5-dihydro-1H-pyrrol-1-yl) ethyl)carbamate (39)

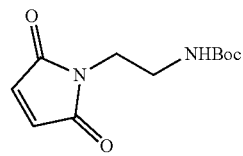

39

A mixture of tert-butyl (2-aminoethyl)carbamate (11.2 mL) and saturated NaHCO$_3$ (120 mL) was stirred vigorously at 0° C., to which compound 38 (10.0 g, 64.4 mmol) was added in portions. After stirring at 0° C. for 30 min the reaction was warmed to r.t. and stirred for 1.0 h. The solid was then collected by vacuum filtration and then dissolved in ethyl acetate and washed with brine, dried over anhydrous Na$_2$SO$_4$, filtered and concentrated to give a white foam (13.6 g, 87% yield).

Example 41. Synthesis of tert-butyl (2-(1,3-dioxo-3a,4,7,7a-tetrahydro-1H-4,7-epoxyisoindol-2(3H)-yl)ethyl)carbamate (40)

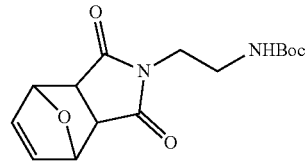

40

A mixture of compound 39 (6.0 g, 25.0 mmol) and furan (18 mL) in toluene (120 mL) was heated to 100° C. in a high pressure flask. The reaction was stirred for 16 h and then the solvent removed. A solid was formed which was triturated with ethyl ether to give a white solid (6.5 g, 84% yield).

Example 42. Synthesis of 2-(2-aminoethyl)-3a,4,7,7a-tetrahydro-1H-4,7-epoxyisoindole-1,3(2H)-dione hydrochloride (41)

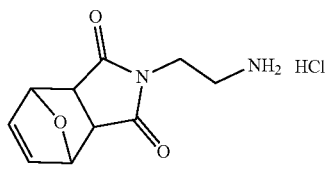

41

To an ice cooled solution of compound 40 (7.90 g, 25.6 mmol) in methylene chloride (60 mL) was added HCl/dioxane (10 mL of concentrated HCl dissolved in 30 mL of dioxane) slowly. The reaction mixture was then warmed to r.t. and stirred for 2 h. The process of reaction was monitored by TLC. Once completed, the reaction was concentrated and triturated with ethyl acetate. A white solid was collected (6.32 g, theoretical yield) by vacuum filtration.

Example 43. Synthesis of Compound 42

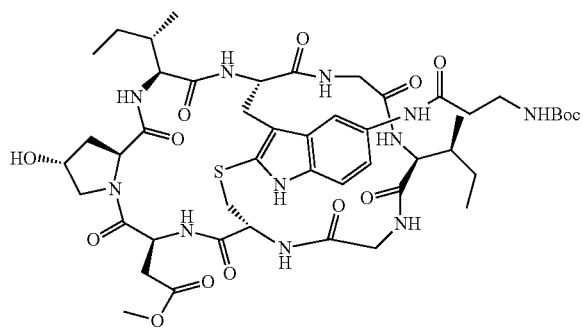

42

Compound 14 (2.0 mg, 0.00226 mmol) and 3-((tert-butoxycarbonyl)amino) propanoic acid (2.1 mg, 0.0113 mmol) were dissolved in DMF (1 mL), to which HATU (4.3 mg, 0.0113 mmol) and DIPEA (2.0 µL, 0.0113 mmol) were added. The resulting solution was stirred at r.t. overnight, and then concentrated and purified by prep-HPLC (H$_2$O/MeCN) to give a white solid (1.8 mg, 62% yield). MS ESI m/z [M+H]$^+$ 1156.50.

Example 44. Synthesis of Compound 43

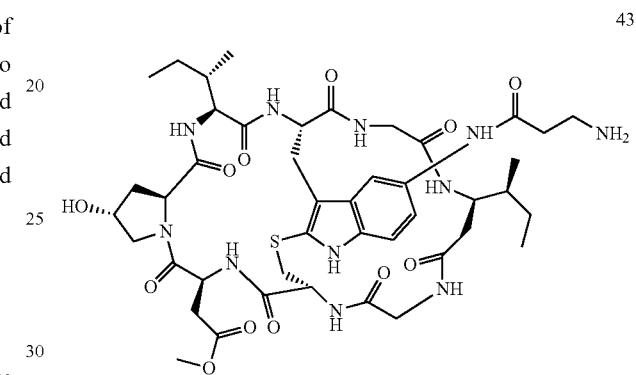

43

Compound 42 (1.8 mg, 0.0016 mmol) was dissolved in CH$_2$Cl$_2$ (2 mL) and cooled to 0° C., TFA (0.5 mL) was added dropwise. The reaction was stirred at 0° C. for 5 h then diluted with CH$_2$Cl$_2$ and concentrated. The residue was purified by prep-HPLC (H$_2$O/MeCN) to give a white solid (1.1 mg, 75% yield) as TFA sat. MS ESI m/z [M+H]$^+$ 956.40.

Example 45. Synthesis of Compound 44

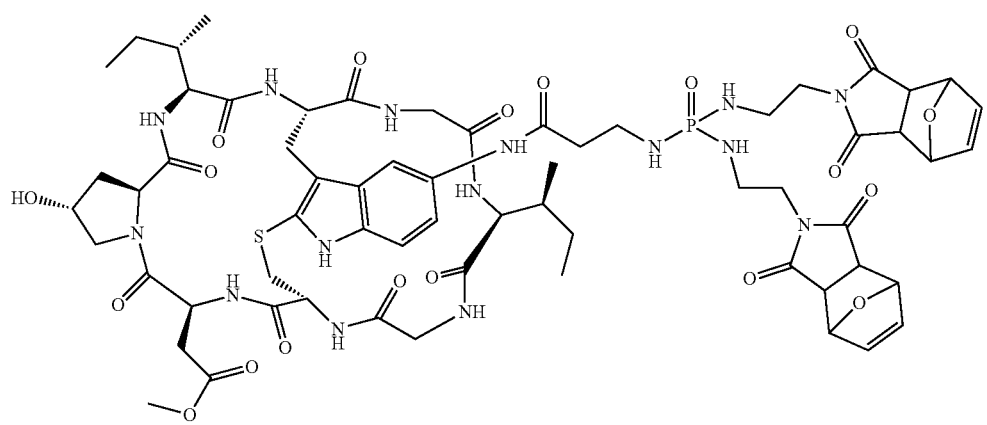

44

Compound 41 (0.40 g, 1.64 mmol) was suspended in methylene chloride (2.5 mL) and cooled to 0° C. Phosphoryl trichloride (0.75 mL, 0.82 mmol) was added dropwise, followed by triethylamine (0.69 mL) slowly. The reaction was stirred at 0° C. for 1 h and filtered over a celite pad. The filtrate was used immediately.

Compound 43 (1.1 mg, 0.00115 mmol) was dissolved in methylene chloride (0.5 mL) and cooled to 0 C, the above solution was added slowly. After stirring for 2 h, the reaction was concentrated and purified by prep-HPLC (H$_2$O/MeCN) to give a white solid (1.0 mg, 60% yield). MS ESI m/z [M+H]$^+$ 1416.54.

Example 46. Synthesis of Compound 45

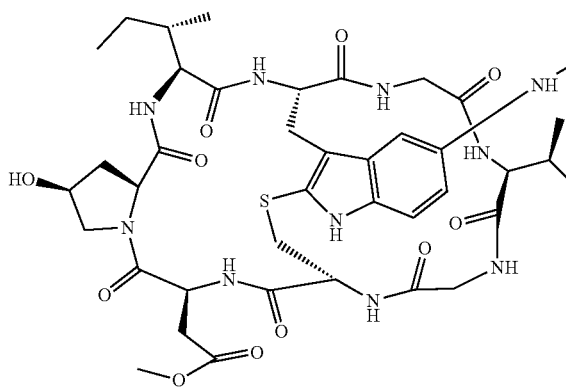

Compound 44 (1.0 mg, 0.000706 mmol) was dissolved in toluene (2 mL) and heated at 100° C. for 16 h. The solvent was then removed under vacuum to give a white solid (0.85 mg, 95% yield). MS ESI m/z [M+H]$^+$ 1280.48.

Example 47. Synthesis of Compound di-tert-butyl 1,2-bis(2-(tert-butoxy)-2-oxoethyl)hydrazine-1,2-dicarboxylate (46)

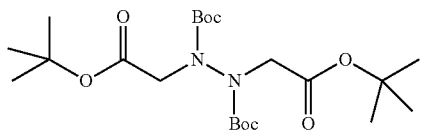

To a suspension of NaH (0.259 g, 6.48 mmol, 3.0 eq.) in anhydrous DMF (2 mL) at room temperature was added di-tert-butyl hydrazine-1,2-dicarboxylate (0.50 g, 2.16 mmol, 1.0 eq.) in anhydrous DMF (8 mL) in 10 minutes under nitrogen. The mixture was stirred at room temperature for 10 minutes and then cooled to 0° C. To which tert-butyl 2-bromoacetate(1.4 mL, 8.61 mmol, 4.0 eq.) was added dropwise. The resulting mixture was allowed to warm to room temperature and stirred overnight. Saturated ammonium chloride solution (100 mL) was added. The organic layer was separated and the aqueous layer was extracted with EtOAc (3×50 mL). The combined organic solution was washed with water and brine, dried over anhydrous Na$_2$SO$_4$, concentrated and purified by SiO$_2$ column chromatography (10:1 hexanes/EtOAc) to give compound 46 as a colorless oil (0.94 g, 99.6% yield). ESI MS m/z [M+Na]+483.4.

Example 48. Synthesis of Compound 2,2'-(hydrazine-1,2-diyl)diacetic Acid (47)

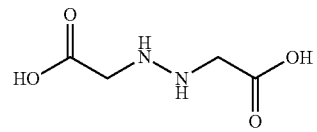

To a solution of compound 46 (0.94 g, 2.04 mmol) in DCM (4 mL) at 0° C. was added TFA (4 mL). The reaction was stirred for 30 minutes and then warmed to room temperature and stirred overnight. The mixture was concentrated, diluted with DCM, and concentrated. This operation was repeated for three times to give a white solid. Trituration with DCM and a white solid was collected by filtration (0.232 g, 76.8% yield). ESI MS m/z [M+H]$^+$ 149.2.

Example 49. Synthesis of Compound 2,2'-(1,2-bis(2-chloroacetyl)hydrazine-1,2-diyl)diacetic Acid (48)

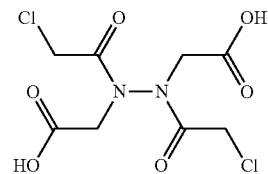

To a solution of compound 47 (0.232 g, 1.57 mmol, 1.0 eq.) in anhydrous THF (10 mL) at 0° C. was added 2-chloroacetyl chloride (0.38 mL, 4.70 mmol, 3.0 eq.) in 10 minutes. The reaction was warmed to room temperature and stirred overnight and concentrated. The residue was co-evaporated with THF for three times to give a white solid (0.472 g, theoretical yield). ESI MS m/z [M+H]$^+$ 301.1.

Example 50. Synthesis of Compound 49

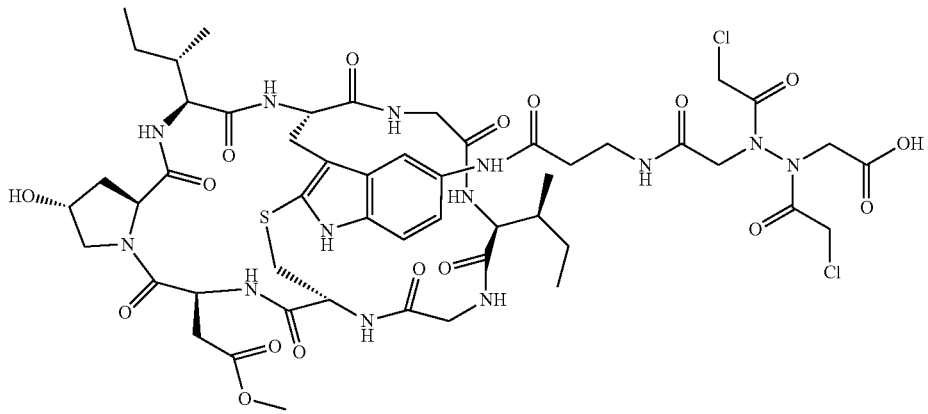

49

To a solution of compound 48 (0.0245 g, 0.0814 mmol) in anhydrous DCM (3 mL) at 0° C. was added oxalyl dichloride (0.07 mL, 0.814 mmol) in 10 minutes, followed by a drop of anhydrous DMF. The mixture was stirred for 30 minutes before warmed to room temperature and stirred for 1.5 h. At last, the mixture was concentrated and co-evaporated with DCM for three times to give a yellow oil, which was used directly.

To a solution of compound 43 (2.0 mg, 0.00209 mmol) in anhydrous DCM (1 mL) was added one fourth of the above yellow oil in DCM (1 mL) at 0° C. The mixture was stirred for 2 h and then concentrated and purified by prep-HPLC (H$_2$O/MeCN) to give a colorless oil (1.3 g, 48% yield), which was used directly in the next step. ESI MS m/z [M+H]$^+$ 1238.40.

Example 51. Synthesis of (E)-tert-butyl 3-(2-(2-(3-bromoacrylamido)ethoxy) ethoxy)propanoate (50)

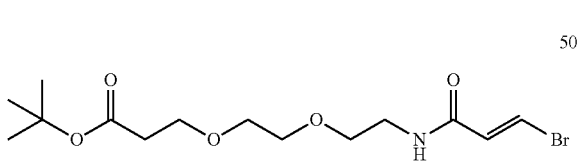 [SMILES: CC(C)(C)OC(=O)CCOCCOCCNC(=O)/C=C/Br]

50

To a solution or (E)-3-bromoacrylic acid (0.15 g, 1 mmol), DMAP (0.15 g, 1.2 mmol) and DCC (0.21 g, 1 mmol) in DCM (10 ml) at 0° C., tert-butyl 3-(2-(2-aminoethoxy)ethoxy)propanoate (0.23 g, 1 mmol) were added. The reaction mixture was allowed to warm to r.t. and stirred overnight. The crude product was concentrated and purified by SiO$_2$ column chromatography with a gradient of EA/DCM to give the title product 50 (0.31 g, 85% yield). ESI MS m/z [M+H]$^+$ 366.08.

Example 52. Synthesis of (E)-3-(2-(2-(3-bromoacrylamido)ethoxy)ethoxy) propanoic Acid (51)

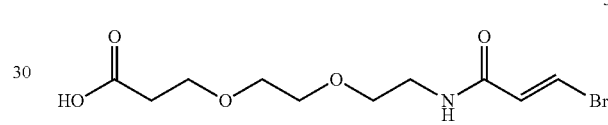

51

Compound 50 (0.31 g, 0.84 mmol) was dissolved in formic acid (4 ml) at 0° C. then H$_2$O (2 ml) was added. The reaction mixture was allowed to warm to r.t. and stirred at r.t. overnight. The crude product was concentrated and used for the next step without further purification. ESI MS m/z [M+H]$^+$ 310.03.

Example 53. Synthesis of (E)-2,5-dioxopyrrolidin-1-yl 3-(2-(2-(3-bromoacryl amido)ethoxy)ethoxy) propanoate (52)

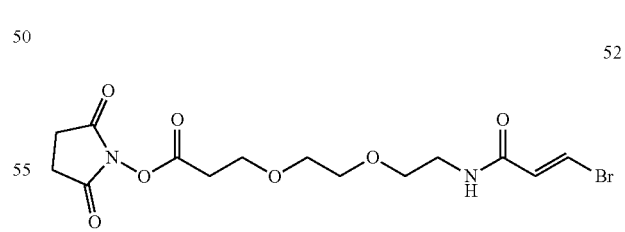

52

Compound 51 (0.12 g, 0.39 mmol), NHS (0.067 g, 0.58 mmol) and EDC (0.11 g, 0.58 mmol) were dissolved in DCM (10 ml), the mixture was stirred at r.t. overnight, concentrated and purified by SiO$_2$ column chromatography to give the title product 52 (0.13 g, 82% yield). ESI MS m/z [M+H]$^+$ 407.04.

Example 54. Synthesis of Compound 53

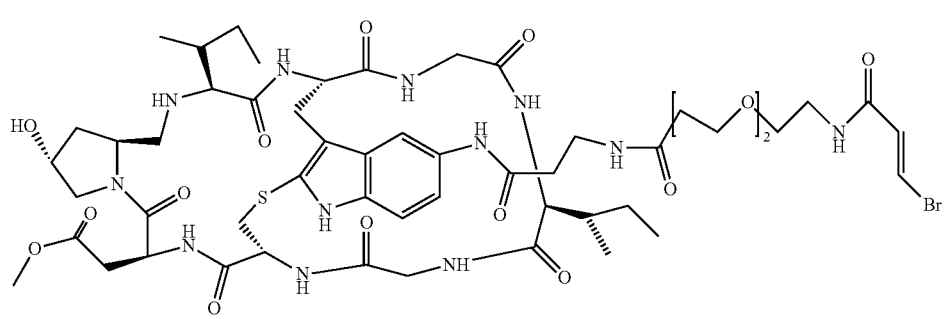

53

Compound 43 (2.0 mg, 0.00209 mmol), compound 52 (4.2 mg, 0.0105 mmol) were dissolved in DMA (1 ml), then phosphate buffer solution (pH 7.2, 1 mL) was added. The mixture was stirred at r.t. overnight, concentrated and purified by reverse phase HPLC with a gradient of MeCN/H$_2$O to give the title product 53 (0.9 mg, 33% yield). ESI MS m/z [M+H]$^+$ 1248.40.

Example 55. Synthesis of Compound 54

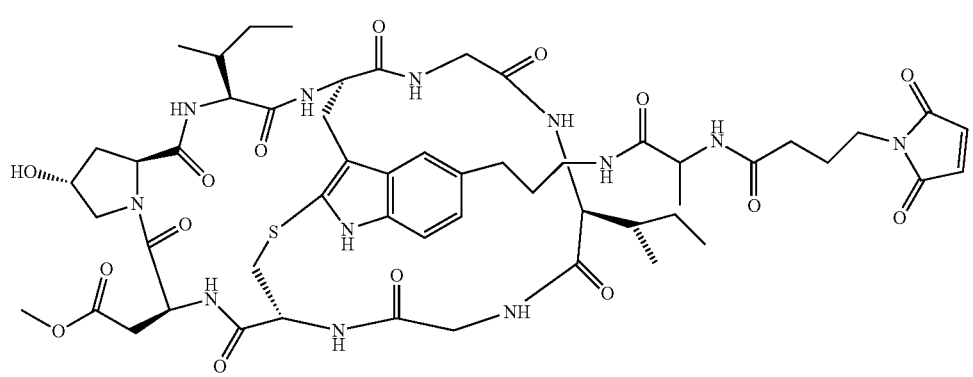

54

To a solution of compound 14 (2.0 mg, 0.00226 mmol) in ethanol (1 mL) and phosphate buffer solution (pH 7.2, 1 mL) was added 2,5-dioxopyrrolidin-1-yl 2-(2-(4-(2,5-dioxo-2,5-dihydro-1H-pyrrol-1-yl)butanamido)propanamido)acetate (4.6 mg, 0.0113 mmol) in ethanol (1 mL) over 30 min. After stirring at r.t. for 3 h, the reaction was concentrated and purified by prep-HPLC (H$_2$O/MeCN) to yield compound 54 (1.1 mg, 41% yield). MS ESI m/z [M+H]+ 1178.48.

Example 56. Synthesis of methyl 4-(bis(2-hydroxyethyl)amino)-4-oxobutanoate (55)

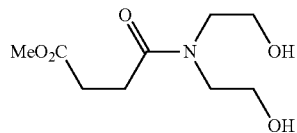

55

Dimethyl succinate (20.0 g, 136.9 mmol) and dihydroxyethylamine (7.20 g, 68.7 mmol) in the mixture of anhydrous toluene (500 ml) and pyridine (50 ml) were refluxed at 150° C. for 28 h. The mixture was concentrated and purified on SiO$_2$ column eluted with EtOAc/DCM (5%~25% EtOAc) to afford the title compound (12.5 g, 83% yield). ESI MS m/z [M+Na]$^+$ 242.4.

Example 57. Synthesis of methyl 4-(bis(2-((methyl sulfonyl)oxy)ethyl) amino)-4-oxobutanoate (56)

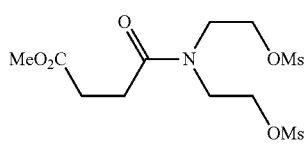

56

Methyl 4-(bis(2-hydroxyethyl)amino)-4-oxobutanoate (12.0 g, 49.56 mmol) in anhydrous pyridine (350 ml) was added methanesulfonyl chloride (20.0 g, 175.4 mmol). After stirred overnight the mixture was concentrated, diluted with EtOAc (350 ml), washed with cold 1 M NaH$_2$PO$_4$ (2×300 ml), dried over MgSO$_4$, filtered and evaporated to afford crude product (~18.8 g, >100% yield). The crude product was used for next step without further purification.

Example 58. Synthesis of 3,6-endoxo-Δ-tetrahydrophthalimide (57)

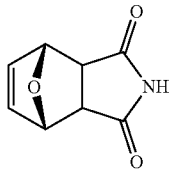

Maleimide (10.0 g, 103.0 mmol) in toluene (200 ml) was added furan (10.0 ml, 137.4 mmol). The mixture was heated inside a 1 L of autoClave bomb at 100° C. for 8 h. The bomb was cooled to room temperature, and the inside solid was rinsed with methanol, concentrated and crystallized in ethyl acetate/hexane to afford 16.7 g (99%) of the title compound. 1H NMR (CDCl$_3$): 11.12 (s, 1H), 6.68-6.64 (m, 2H), 5.18-5.13 (m, 2H), 2.97-2.92 (m, 2H). ESI MS m/z [M+Na]$^+$ 188.04.

Example 59. Synthesis of Methyl 4-((2-((3aR,4R,7S,7aS)-1,3-dioxo-3a,4,7,7a-tetrahydro-1H-4,7-epoxyisoindol-2(3H)-yl)ethyl)(2-((4R,7S,7aS)-1,3-dioxo-3a,4,7,7a-tetrahydro-1H-4,7-epoxyisoindol-2(3H)-yl)ethyl)amino)-4-oxobutanoate (58)

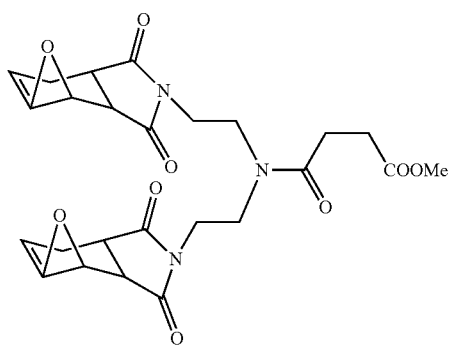

Methyl 4-(bis(2-((methylsulfonyl)oxy)ethyl)amino)-4-oxobutanoate (56, fresh made, 90% pure, 8.5 g, ~20 mmol) in DMA (350 ml) was added 3,6-endoxo-Δ-tetrahydrophthalimide (10.2 g, 61.8 mmol), sodium carbonate (8.0 g, 75.5 mmol) and sodium iodide (0.3 g, 2.0 mmol). The mixture was then stirred at room temperature overnight, concentrated, diluted with EtOAc (350 ml), washed with sat'ed NaHCO$_3$ solution (300 ml), sat'ed NaCl solution (300 ml) and 1 M NaH$_2$PO$_4$ (300 ml). The organic layer was dried over Na$_2$SO$_4$, filtered, evaporated, loaded on SiO$_2$ column and eluted with EtOAc/hexane (10%~30% EtOAc) to afford the title compound (7.9 g, 77% yield). ESI MS m/z [M+Na]$^+$ 536.4.

Example 60. Synthesis of 4-(bis(2-(2,5-dioxo-2,5-dihydro-1H-pyrrol-1-yl)ethyl)amino)-4-oxobutanoic Acid (59)

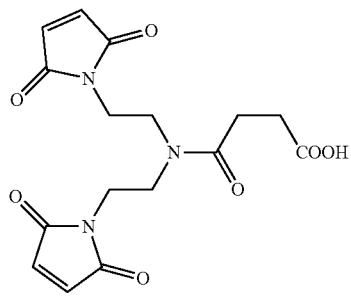

Compound 58 (3.0 g, 5.8 mmol) and trimethylstannanol (4.8 g, 26.4 mmol) in 1,2-dichloroethane (150 ml) was refluxed at 80° C. for 8 h. It was cooled to room temperature and the residue was passed a short silica gel column and eluted with dichloromethane/methanol to remove the extra trimethyltin hydroxide. Then the pooled fractions were combined, concentrated and diluted with DMA and toluene, refluxed at 120° C. overnight, loaded on SiO$_2$ column and eluted with MeOH/DCM (5%~10% MeOH) to afford the title compound (1.62 g, 76% yield). ESI MS m/z [M+Na]$^+$ 386.2.

Example 61. Synthesis of 2,5-dioxopyrrolidin-1-yl 4-(bis(2-(2,5-dioxo-2,5-dihydro-1H-pyrrol-1-yl)ethyl)amino)-4-oxobutanoate (60)

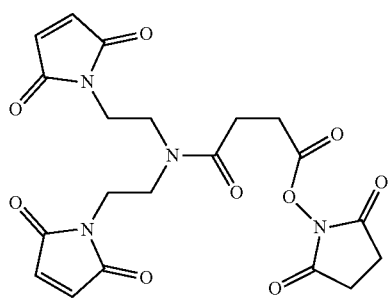

To a solution or compound 59 (1.60 g, 4.4 mmol) in DMA (100 ml) was added NHS (0.76 g, 6.61 mmol) and EDC (1.70 g, 8.90 mmol). The mixture was stirred overnight, evaporated and purified on SiO$_2$ column, eluted with EtOAc/DCM (5% to 15% EtOAc) to afford the title product (1.72 g, 85.0% yield). ESI MS m/z [M+Na]$^+$483.2.

Example 62. Synthesis of Compound 61

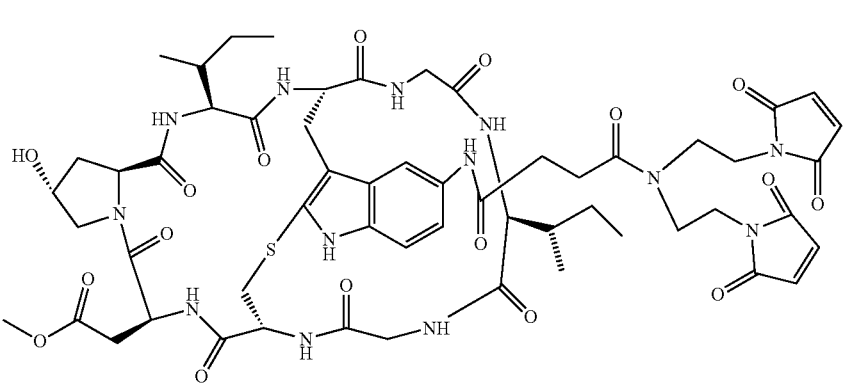
61

To a solution of compound 14 (2.0 mg, 0.00226 mmol) in ethanol (1 mL) and phosphate buffer solution (pH 7.2, 1 mL) was added compound 60 (5.2 mg, 0.0113 mmol) in ethanol (1 mL) over 30 min. After stirring at r.t. for 3 h, the reaction was concentrated and purified by prep-HPLC (H$_2$O/MeCN) to yield compound 61 (1.2 mg, 45% yield). MS ESI m/z [M+H]$^+$1230.48.

Example 63. Synthesis of Compound 63

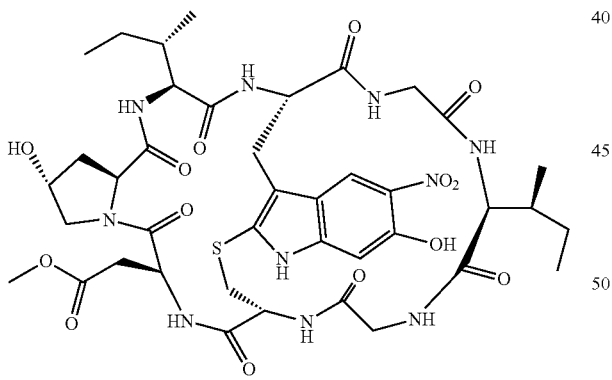
63

To a solution of compound 62 (5.0 mg, 0.00563 mmol, 1.0 eq.) in acetic acid (1 mL) and CH$_2$Cl$_2$ (1 mL) was added 70% HNO$_3$ (0.5 mL) at 0° C. The reaction was stirred at 0° C. for 1 h then room temperature 2 h. After water (5 mL) was added, the reaction mixture was concentrated and purified by prep-HPLC (H$_2$O/MeCN) to give a light yellow solid (2.4 mg, 46% yield). ESI MS m/z 931.34 ([M+H]$^+$).

Example 64. Synthesis of Compound 64

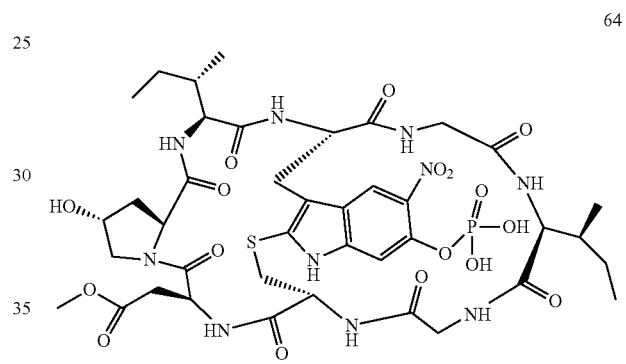
64

Compound 63 (2.4 mg, 0.00257 mmol) in a mixture of CH$_3$CN (2 ml) and DMA (1 ml) was added DIPEA (9 µl, 0.0524 mmol) at 0° C. After stirred for 2 min, POCl$_3$ (2.4 µl, 0.0262 mmol) was added dropwise at 0° C. The mixture was stirred at r.t. for 2 h, and quenched with slowly addition of sat'ed NaHCO$_3$ solution at 0° C. The mixture was concentrated and purified prep-HPLC (H$_2$O/MeCN) to give a white solid (2.0 mg, 77% yield). ESI MS m/z 1011.28 ([M+H]$^+$).

Example 65. Synthesis of Compound 65

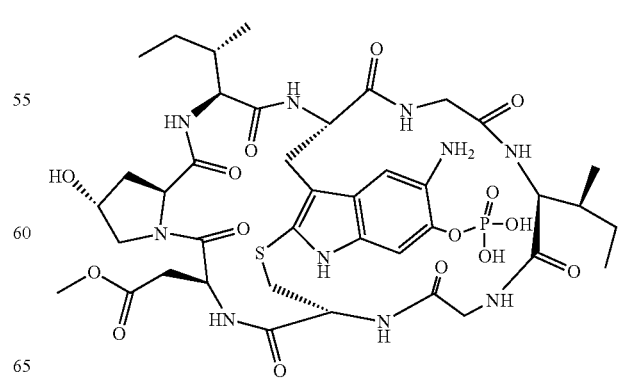
65

A mixture of compound 64 (2.0 mg, 0.00197 mmol) and Pd/C (10 wt %, 5 mg) in methanol (2 mL) was hydrogenated (1 atm $H_2$) at r.t. for 1 h, and then filtered through Celite (filter aid). The filtrate was concentrated to afford a white solid (1.8 mg, 93% yield). ESI MS m/z 981.33 ([M+H]$^+$).

Example 66. Synthesis of Compound 66

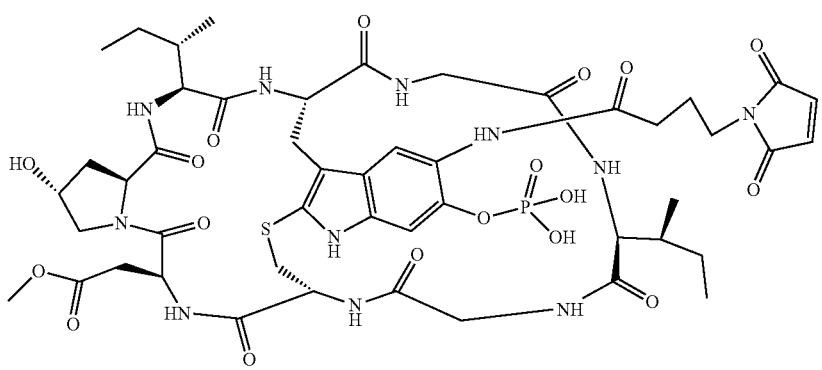

66

To a solution of compound 14 (1.8 mg, 0.00183 mmol) in ethanol (1 mL) and phosphate buffer solution (pH 7.2, 1 mL) was added 2,5-dioxopyrrolidin-1-yl 4-(2,5-dioxo-2,5-dihydro-1H-pyrrol-1-yl)butanoate (2.6 mg, 0.0930 mmol) in ethanol (1 mL) over 10 min. After stirring at r.t. for 3 h, the reaction was concentrated and purified by prep-HPLC ($H_2O$/MeCN) to yield compound 30 (1.3 mg, 62% yield). MS ESI m/z [M+H]$^+$ 1146.45.

Example 67. General Method of Conjugation of Compound 15, 22, 30, 37, 45, 49, 53, 54, 61, or 66 Independently to a Her2 Antibody (Herceptin)

To a mixture of 2.0 mL of 10 mg/ml Herceptin in pH 6.0~8.0, were added of 0.70~2.0 mL PBS buffer of 100 mM $NaH_2PO_4$, pH 6.5~8.5 buffers, TCEP (14-35 µL, 20 mM in water) and the compound 15, 22, 30, 37, 45, 49, 53, 54, 61, or 66 (14-28 µL, 20 mM in DMA). The mixture was incubated at RT for 4~16 h, then DHAA (135 µL, 50 mM) was added in. After continuous incubation at RT overnight, the mixture was purified on G-25 column eluted with 100 mM $NaH_2PO_4$, 50 mM NaCl pH 6.0~7.5 buffer to afford 12.0~18.4 mg of the conjugate compound A1, A2, A3, A4, A5, A6, A7, A8, A9, or A10 (68%~83% yield) accordingly in 13.0~15.8 ml buffer. The drug/antibody ratio (DAR) was 1.9~4.0, which was determined via UPLC-QTOF mass spectrum. It was 94~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Example 68. General Method of Conjugation of Compound 22, 30, 37, 45, 49, 54 or 61 Independently to Herceptin (a Her2 Antibody)

To a mixture of 2.0 mL of 10 mg/ml Herceptin in pH 6.0-8.0, 0.70-2.0 mL of 100 mM $NaH_2PO_4$, 1 mM $Na_2SO_3$, pH 6.5~8.5 buffer, and the compound 22, 30, 37, 45, 49, 54 or 61 independently (21-24 µL, 20 mM in DMA) incubated for 1 h, was added TCEP (14-23 µL, 20 mM in water). After the mixture was continued to incubate at RT for 8~24 h, DHAA (135 µL, 50 mM) was added in. And the solution was continuously incubated for another 12 h. then purified on G-25 column eluted with 100 mM $NaH_2PO_4$, 50 mM NaCl pH 6.0~7.5 buffer to afford 13.8~17.6 mg of the conjugate compound A2, A3, A4, A5, A6, A7 or A9 respectively (63%~87% yield) in 13.6~15.7 ml buffer. The drug/antibody ratio (DAR) was 1.9~3.8, which was determined via UPLC-QTOF mass spectrum. It was 96~99% monomer analyzed by SEC HPLC (Tosoh Bioscience, Tskgel G3000SW, 7.8 mm ID×30 cm, 0.5 ml/min, 100 min) and a single band measured by SDS-PAGE gel or two bands when a reduce reagent DTT was in the SDS Page.

Example 69. In Vitro Cytotoxicity Evaluation of Conjugates A1, A2, A3, A4, A5, A6, A7, A8, A9, and A10 in Comparison with T-DM1

The cell line used in the cytotoxicity assays was NCI-N87, a human gastric carcinoma cell line; The cells were grown in RPMI-1640 with 10% FBS. To run the assay, the cells (180 µl, 6000 cells) were added to each well in a 96-well plate and incubated for 24 hours at 37° C. with 5% $CO_2$. Next, the cells were treated with test compounds (20 µl) at various concentrations in appropriate cell culture medium (total volume, 0.2 mL). The control wells contain cells and the medium but lack the test compounds. The plates were incubated for 120 hours at 37° C. with 5% $CO_2$. MTT (5 mg/ml) was then added to the wells (200) and the plates were incubated for 1.5 hr at 37° C. The medium was carefully removed and DMSO (180 µl) was added afterward. After it was shaken for 15 min, the absorbance was measured at 490 nm and 570 nm with a reference filter of 620 nm. The inhibition % was calculated according to the following equation: inhibition %=[1-(assay-blank)/(control-blank)]×100.

The cytotoxicity results:

| | DAR (drug ratio) | N87 cell (Ag+) $IC_{50}$ (nM) |
|---|---|---|
| Conjugate A1 | 3.8 | 1.19 nM |
| Conjugate A2 | 2.9 | 3.32 nM |
| Conjugate A3 | 2.8 | 17.33 nM |
| Conjugate A4 | 2.7 | 69.24 nM |
| Conjugate A5 | 3.2 | 3.13 nM |
| Conjugate A6 | 2.7 | 53.3 nM |
| Conjugate A7 | 2.9 | 5.53 nM |
| Conjugate A8 | 3.2 | 48.13 nM |

-continued

| | DAR (drug ratio) | N87 cell (Ag+) IC$_{50}$ (nM) |
|---|---|---|
| Conjugate A9 | 2.3 | 5.71 nM |
| Conjugate A10 | 2.8 | 3.63 nM |
| T-DM1 | 3.5 | 0.19 nM |

The conjugates with the bridge linkers were less potent than T-DM1 in vitro.

Example 70. Antitumor Activity In Vivo

The in vivo efficacy of conjugates A1, A2, A3, A5, A6, A7, A9, and A10 along with T-DM1 were evaluated in a human gastric carcinoma N-87 cell line tumorxenograft models. Five-week-old female BALB/c Nude mice (60 animals) were inoculated subcutaneously in the area under the right shoulder with N-87 carcinoma cells ($5 \times 10^6$ cells/mouse) in 0.1 mL of serum-free medium. The tumors were grown for 8 days to an average size of 123 mm$^3$. The animals were then randomly divided into 10 groups (6 animals per group). The first group of mice served as the control group and was treated with the phosphate-buffered saline vehicle. The remaining 9 groups were treated with conjugates A1, A2, A3, A5, A6, A7, A9, and A10 and T-DM1 respectively at dose of 6 mg/Kg administered intravenously. Three dimensions of the tumor were measured every 4 days and the tumor volumes were calculated using the formula tumor volume=1/2 (length×width×height). The weight of the animals was also measured at the same time. A mouse was sacrificed when any one of the following criteria was met: (1) loss of body weight of more than 20% from pretreatment weight, (2) tumor volume larger than 1500 mm$^3$, (3) too sick to reach food and water, or (4) skin necrosis. A mouse was considered to be tumor-free if no tumor was palpable.

Figure 29:
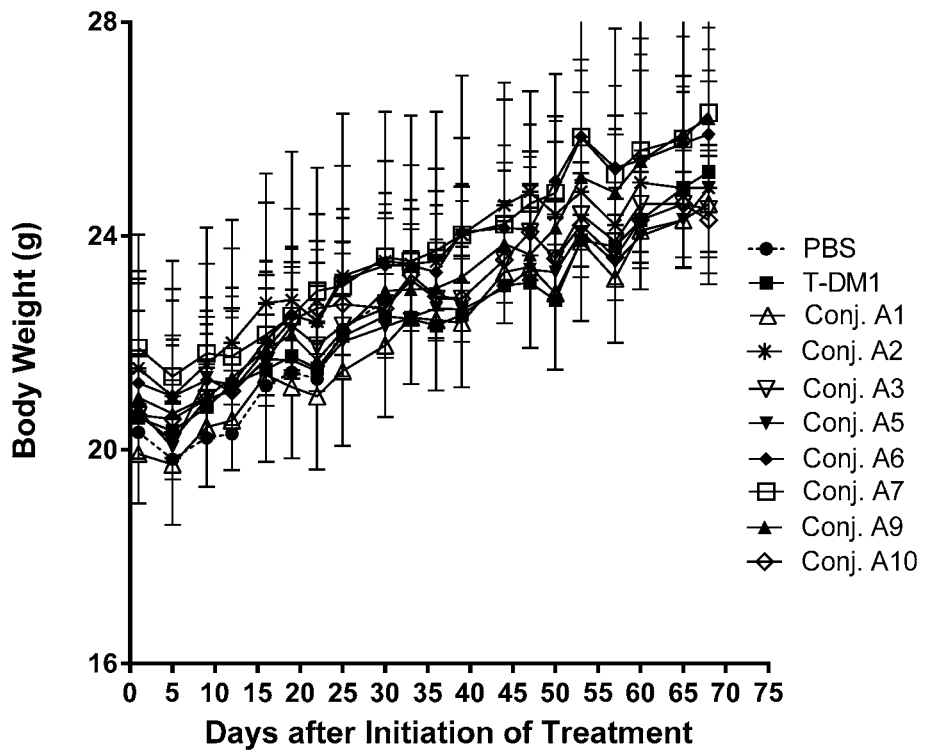
Figure 30:
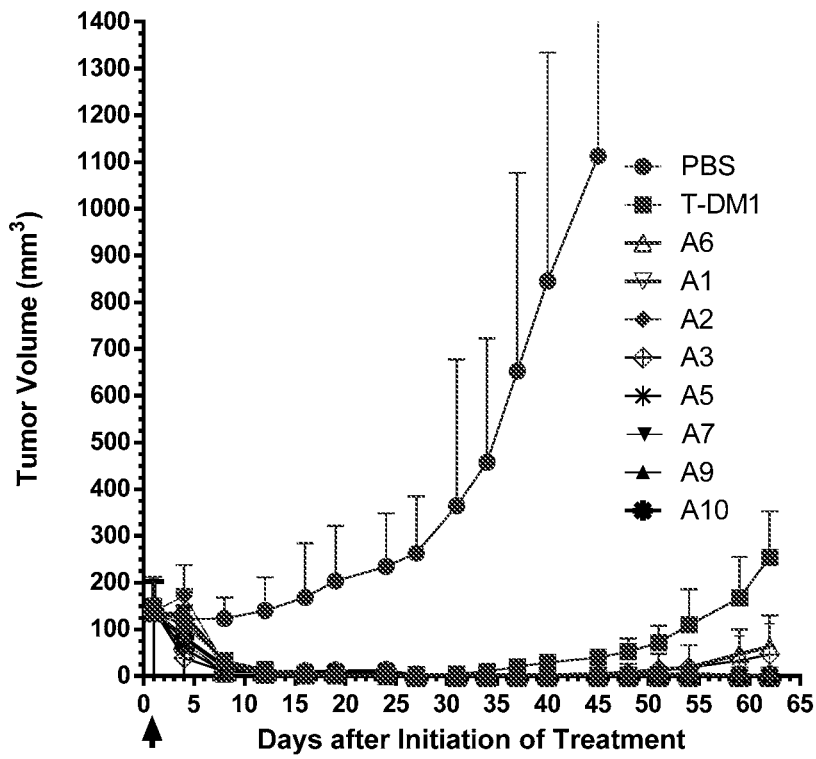
Figure 31A:
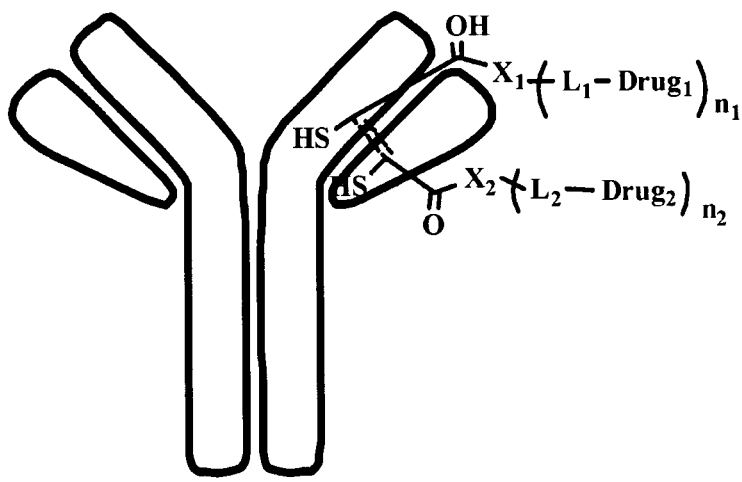
Figure 31A:
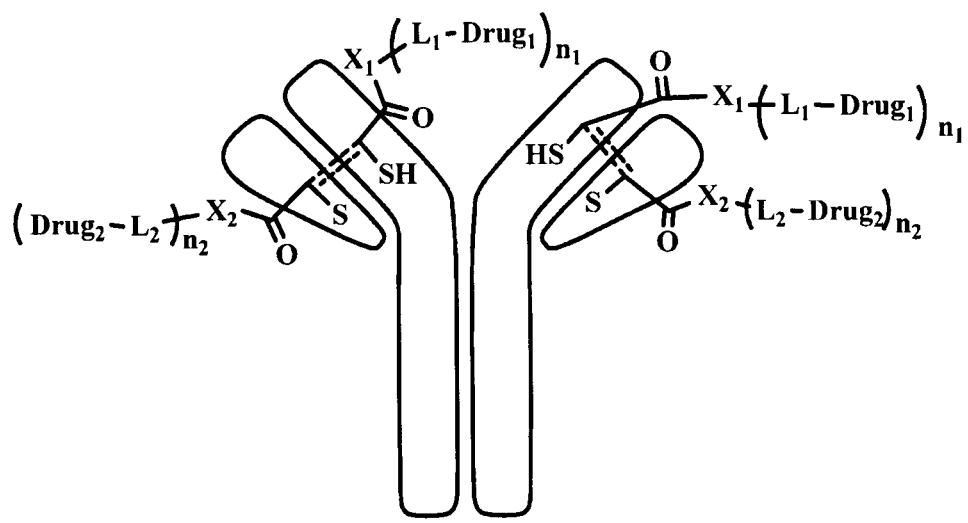
Figure 31B:
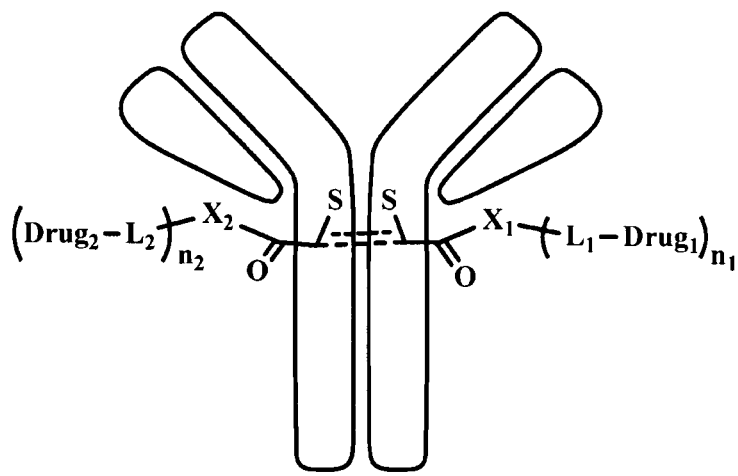
Figure 31B:
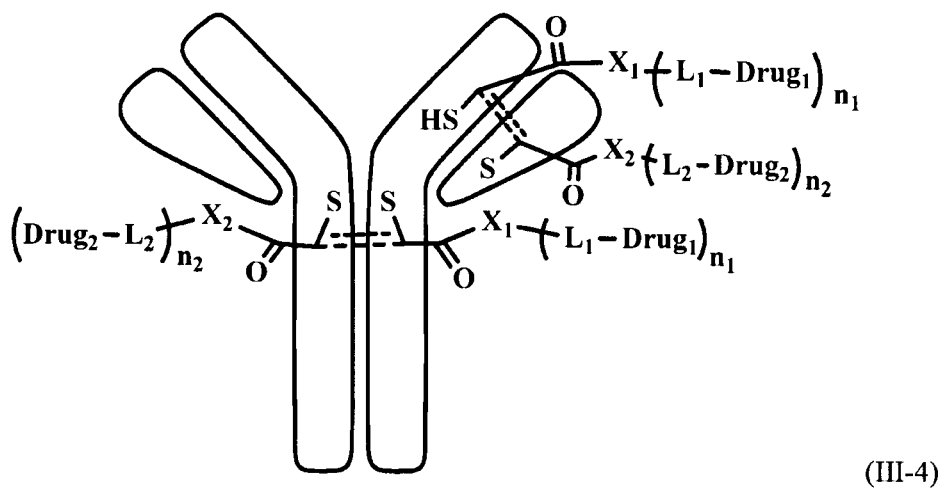
Figure 31C:
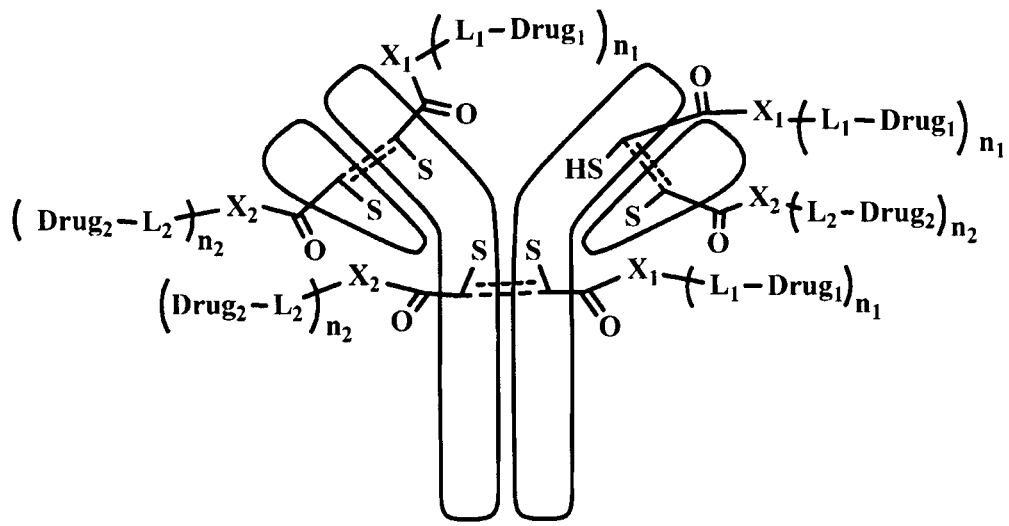
Figure 31C:
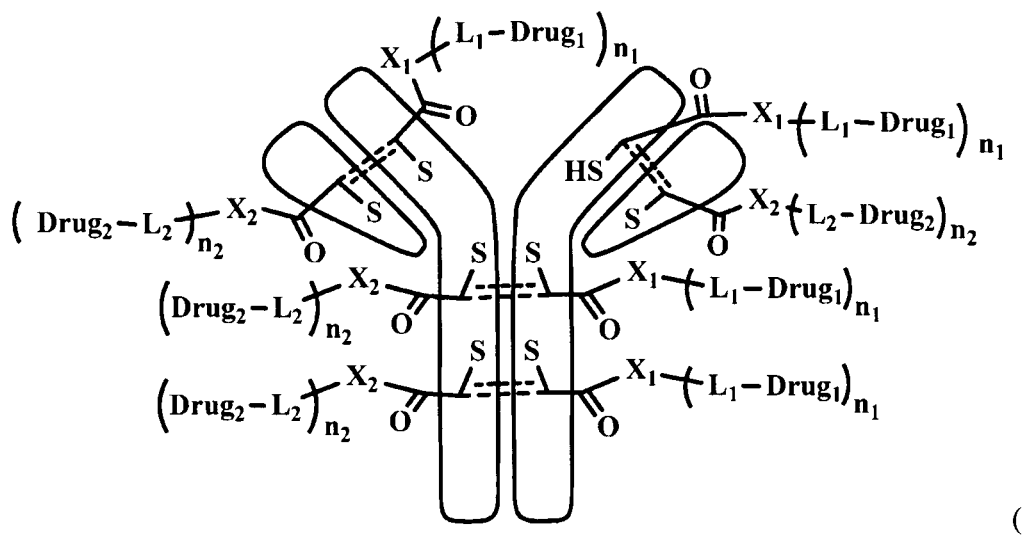
Figure 31D:
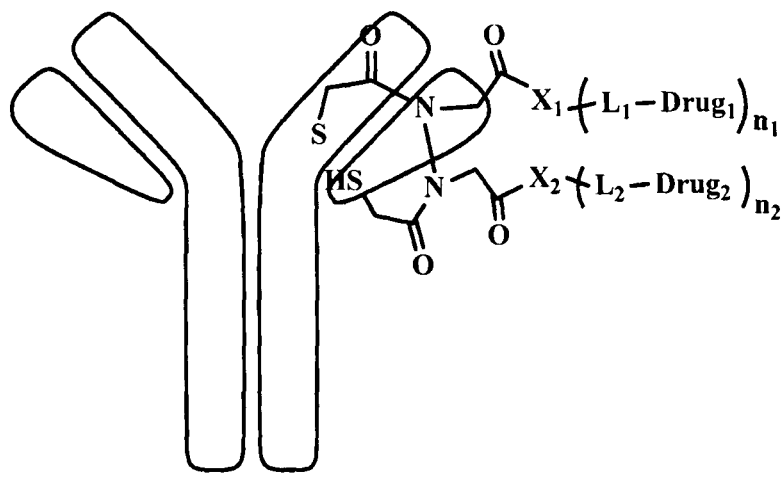
Figure 31D:
Figure 31D:
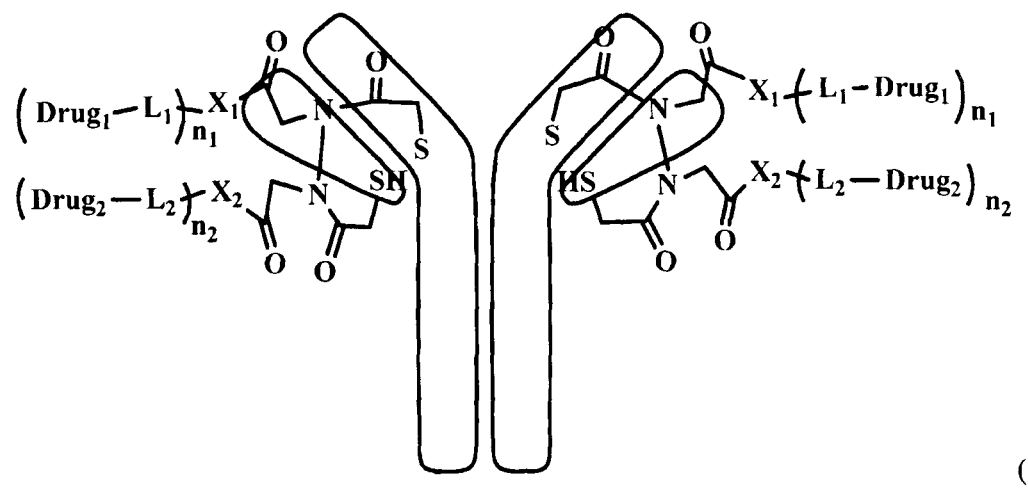
Figure 31D:
Figure 31E:
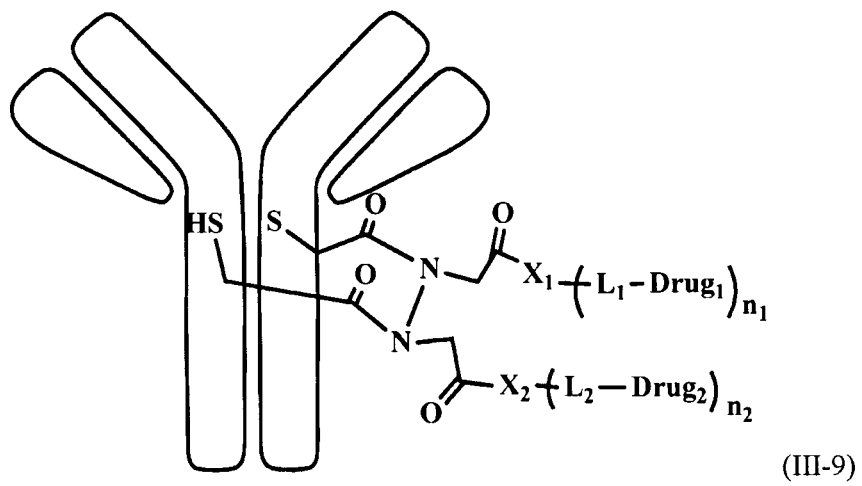
Figure 31E:
Figure 31E:
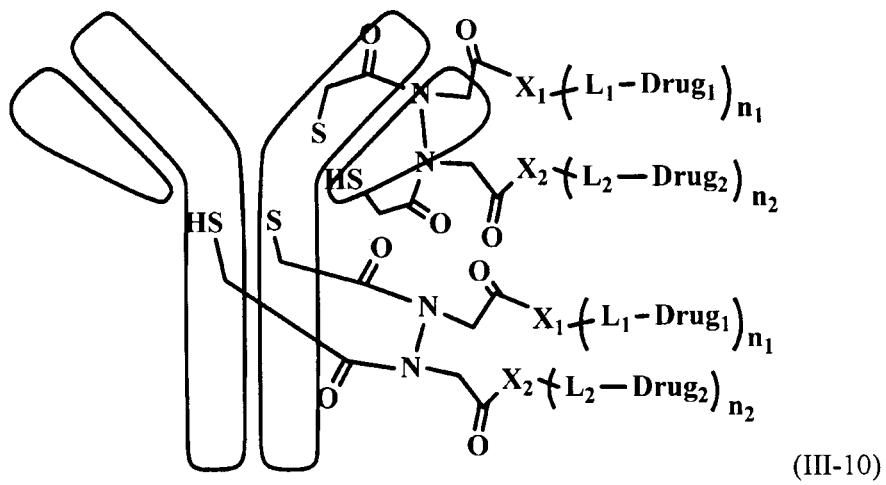
Figure 31E:
Figure 31F:
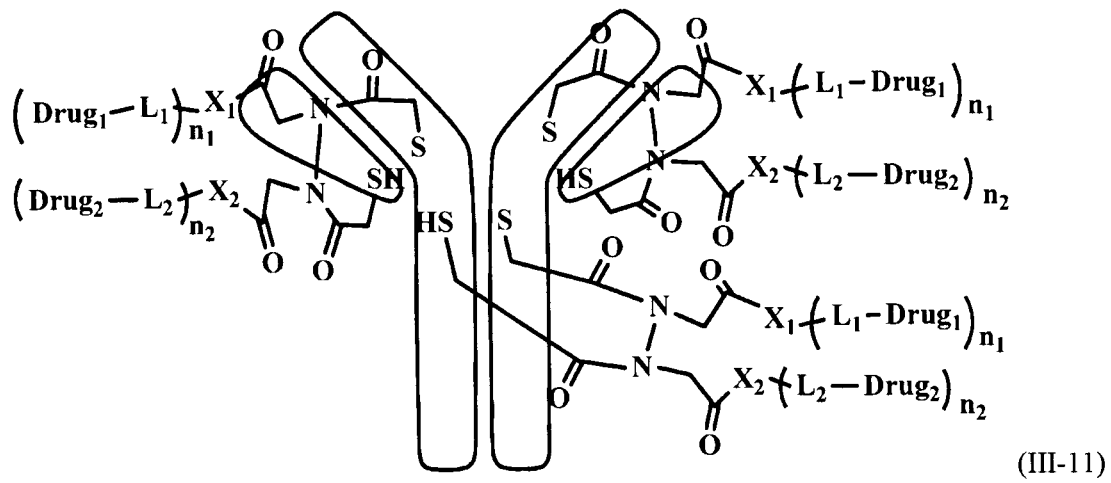
Figure 31F:
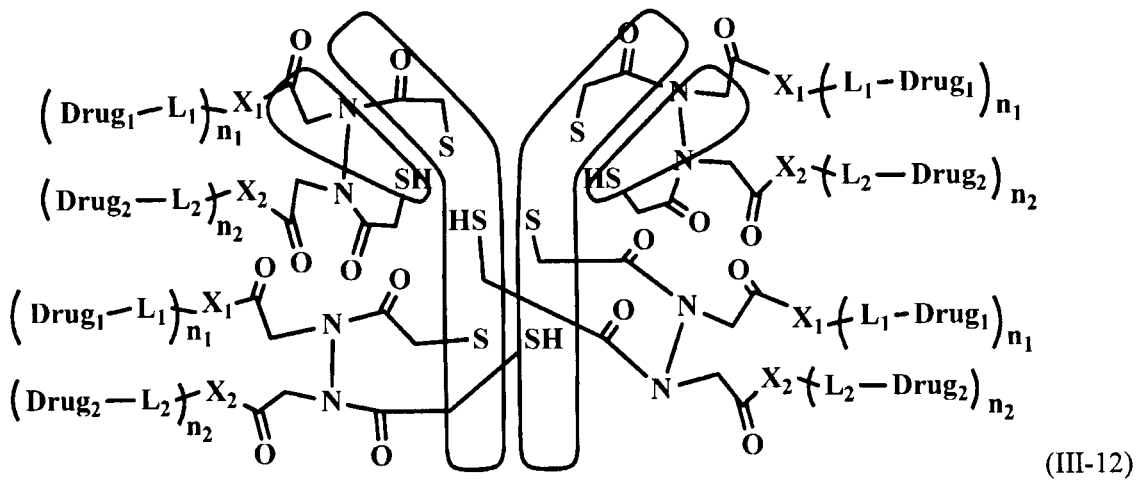

The results were plotted in FIG. 29. All the 9 conjugates did not cause the animal body weight loss. And the animals at control group were sacrificed at day 30 due to the tumor volume larger than 1200 mm$^3$ and they were too sick. In FIG. 30. All 6/6 animals at the groups of compounds A2, A5, A7, A9 and A10 had completely no tumor measurable at day 16 till day 62 (the end of experiment). In contrast T-DM1 at dose of 6 mg/Kg was not able to eliminate the tumors completely and it only inhibited the tumor growth for 37 days. Conjugate compounds A1, A3, and A6 also did not eradicate the tumor completely at dose of 6 mg/Kg, but had better antitumor activity than T-DM1. More importantly, all animals treated with conjugate compounds A1, A2, A3, A5, A6, A7, A9, and A10 had no or less liver toxicities than the animals treated with T-DM1 when measured levels of alanine aminotransferase (ALT) and aspartame aminotransferase (AST) in serum at the end of experiment (data not shown). This demonstrates that the conjugates of this patent application would have broader therapeutical applications than the traditional conjugates.

The invention claimed is:
1. A compound of Formula (I)

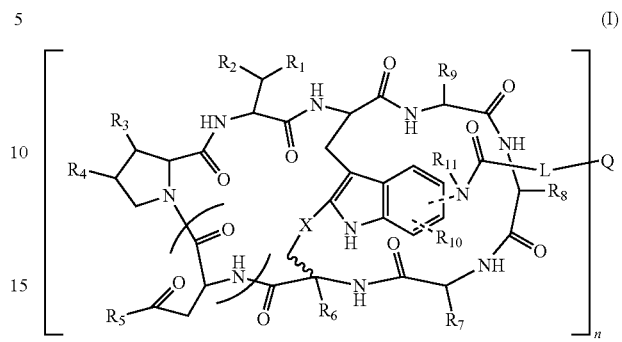

or a pharmaceutically acceptable salt, hydrate, or hydrated salt thereof; or a polymorphic crystalline structures thereof; or an optical isomer, racemate, diastereomer or enantiomer thereof, wherein ----- represents a single bond that links any carbon position of the aromatic (indole) ring;

∿∿∿ represents an optional single bond or an absent bond;

R$_1$ and R$_2$ are independently selected from the group consisting of H, OH, CH$_2$OH, CH(OH)CH$_2$OH, CH(CH$_3$)CH$_2$OH, CH(OH)CH$_3$, C$_1$-C$_8$ alkyl, —OR$_{12}$ (ether), C$_2$-C$_8$ alkenyl, alkynyl, heteroalkyl, —OCOR$_{12}$ (ester), —OC(=O)OR$_{12}$ (carbonate), —OC(=O)NHR$_{12}$ (carbamate); C$_3$-C$_8$ aryl, heterocyclic, carbocyclic, cycloalkyl, heterocycloalkyl, heteroaralkyl, and alkylcarbonyl;

R$_3$ and R$_4$ are independently selected from the group consisting of H, OH, —OR$_{12}$ (ether), —OCOR$_{12}$ (ester), —OCOCH$_3$ (acetate), —OCOOR$_{12}$ (carbonate), —OC(=O)NHR$_{12}$ (carbamate), —OP(O)(OR$_{12}$)(OR$_{12}$') (phosphate), OP(O)(NHR$_{12}$)(NHR$_{12}$') (phosphamide), O—SO$_3^-$, and O-glycoside;

R$_5$ is selected from the group consisting of H, OH, NH$_2$, NHOH, NHNH$_2$, —OR$_{12}$, —NHR$_{12}$, NHNHR$_{12}$, —NR$_{12}$R$_{12}$', and N(H)(R$_{12}$)R$_{13}$CO(Aa)$_p$, wherein Aa is an amino acid or a polypeptide, p represents 0-6;

R$_6$ is selected from the group consisting of H, OH, CH$_2$OH, CH(OH)CH$_2$OH, CH(CH$_2$OH)$_2$, CH(CH$_3$) OH, CH$_2$CH$_2$OH, PrOH, BuOH, C$_1$~C$_8$ alkyl, —OR$_{12}$ (ether), C$_2$~C$_8$ alkenyl, alkynyl, heteroalkyl, or —OCOR$_{12}$ (ester); and C$_3$~C$_8$ aryl, heterocyclic, or carbocyclic;

R$_7$, R$_8$ and R$_9$ are independently selected from the group consisting of H, OH, CH$_3$, CH(CH$_3$)$_2$, CH(CH$_3$) CH$_2$CH$_3$, CH$_2$OH, CH(OH)CH$_2$OH, CH$_2$CH(OH) CH$_2$OH, CH(CH$_2$OH)$_2$, CH$_2$C(OH)(CH$_2$OH)$_2$, CH$_2$C (OH)(CH$_3$)(CH$_2$OH), CH$_2$C(OH)(CH(CH$_3$)$_2$) (CH$_2$OH), CH$_2$CH$_2$OH, PrOH, BuOH, CH$_2$COOH, CH$_2$CH$_2$COOH, CH(OH)COOH, CH$_2$CONH$_2$, CH$_2$CH$_2$CONH$_2$, CH$_2$CH$_2$CH$_2$CH$_2$NH$_2$, CH$_2$CH$_2$CH$_2$NHC(=NH)NH$_2$, C$_1$~C$_8$ alkyl, CH$_2$Ar, CH$_2$SH, CH$_2$SR$_{12}$, CH$_2$SSR$_{12}$, CH$_2$SSAr, CH$_2$CH$_2$SCH$_3$, —OR$_{12}$ (ether), C$_2$~C$_8$ alkenyl, alkynyl, heteroalkyl, or —OCOR$_{12}$ (ester); and C$_3$~C$_8$ aryl, heterocyclic, or carbocyclic;

R$_{10}$ is selected from the group consisting of H, NH$_2$, OH, SH, NO$_2$, halogen, —NHOH, —N$_3$ (azido); —CN (cyano); $C_1$~$C_8$ alkyl, $C_2$~$C_8$ alkenyl, alkynyl, heteroalkyl; $C_3$~$C_8$ aryl, heterocyclic, or carbocyclic; —$OR_{12}$ (ether), —$OCOR_{12}$ (ester), —$OCOCH_3$ (acetate), —$OC(O)OR_{12}$ (carbonate), —$OC(O)CH(R_{12})$ NHAa (Aa is an amino acid group), —$NR_{12}R_{12}'$ (amine), —$NR_{12}COR_{12}'$ (amine), —$NR_{12}NR_{12}'NR_{12}''$ (amine); —$OCONR_{12}R_{12}'$(carbamate); —$NR_{12}$ (C=NH)$NR_{12}'R_{12}''$ (guanidinum); —$NR_{12}CO(Aa)_p$, (an amino acid or peptide, wherein Aa is an amino acid or a polypeptide, p represents 0-6); —$N(R_{12})$ $CONR_{12}'R_{12}''$ (urea); —$OCSNHR_{12}$ (thiocarbamate); —SH (thiol); —$SR_{12}$ (sulfide); —$S(O)R_{12}$ (sulfoxide); —$S(O_2)R_{12}$ (sulfone); —$SO_3$, $HSO_3$, $HSO_2$, or a salt of $HSO_3^-$, $SO_3^{2-}$ or —$HSO_2^-$(sulphite), —$OSO_3^-$; —$N(R_{12})SOOR_{12}'$ (sulfonamide); $H_2S_2O_5$ or a salt of $S_2O_5^{2-}$ (metabisulfite); $PO_3SH_3$, $PO_2S_2H_2$, $POS_3H_2$, $PS_4H_2$ or a salt of $PO_3S^{3-}$, $PO_2S_2^{3-}$, $POS_3^{3-}$, $PS_4^{3-}$ (mono-, di-, tri-, and tetra-thiophosphate); $(R_{12}O)_2$ $POSR_{12}'$ (thiophosphate ester); $HS_2O_3$ or a salt of $S_2O_3^{2-}$ (thiosulfate); $HS_2O_4$ or a salt of $S_2O_4^{2-}$ (dithionite); (P(=S)($OR_{12}$)(S)(OH) or a salt formed with a cation (phosphorodithioate); —$N(R_{12})OR_{12}'$ (hydroxylamine derivative); $R_{12}C(=O)NOH$ or a salt formed with a cation (hydroxamic acid); ($HOCH_2SO_2^-$, or its salt (formaldehyde sulfoxylate); —$N(R_{12})COR_{12}'$ (amide); $R_{12}R_{12}'R_{12}''NPO_3H$ (trialkylphosphor-amidate or phosphoramidic acid); ArAr'Ar"$NPO_3H$ (triarylphosphonium); $OP(O)(OM_1)(OM_2)$, $OCH_2OP(O)$ $(OM_1)(OM_2)$, $OSO_3M_1$; O-glycoside (glucoside, galactoside, mannoside, glucuronoside, alloside, fructoside), NH-glycoside, S-glycoside and $CH_2$-glycoside; $M_1$ and $M_2$ are independently H, Na, K, Ca, Mg, $NH_4$, or $NR_1'R_2'R_3'$; $R_1'$, $R_2'$ and $R_3'$ are independently H, or alkyl; and Ar, Ar', and Ar" are $C_3$-$C_8$ aryl or heteroaromatic group;

$R_{11}$ is H, $C_1$~$C_8$ alkyl; $C_2$~$C_8$ alkenyl, alkynyl, or heteroalkyl; or $C_3$~$C_8$ aryl or heteroaryl;

$R_{12}$, $R_{12}'$, and $R_{12}''$ are independently selected from the group consisting of H, $C_1$~$C_8$ alkyl; $C_2$~$C_8$ alkenyl, alkynyl, heteroalkyl; $C_3$~$C_8$ aryl, heteroaryl, heterocyclic, and carbocyclic;

X is S, O, NH, SO, $SO_2$, or $CH_2$;

m is 0 or 1; n is 1, 2, 3, 4, 5, 6, 7, 8, 9, 10, 11, 12, 13, 14, 15, 16, 17, 18, 19, or 20;

L is a releasable linker having the formula of: -Ww-(Aa)r-Tt-; or -Ww-(Aa)r-Tt-Q; or Q-Ww-(Aa)r-Tt-; wherein W is a Stretcher unit; w is 0 or 1; Aa is an amino acid unit comprising independent amino acids; r is an integer ranging from 0 to 100, the Stretcher unit W comprises a self-immolative or a non-self-immolative component, peptidyl unit, a hydrazone bond, a disulfide, an ester, an oxime, an amide, or a thioether bond, the self-immolative component comprises a 2-aminoimidazol-5-methanol compound, heterocyclic PAB analog, beta-glucuronide, and ortho or para-aminobenzylacetal; the non-self-immolative component is one of the following structures:

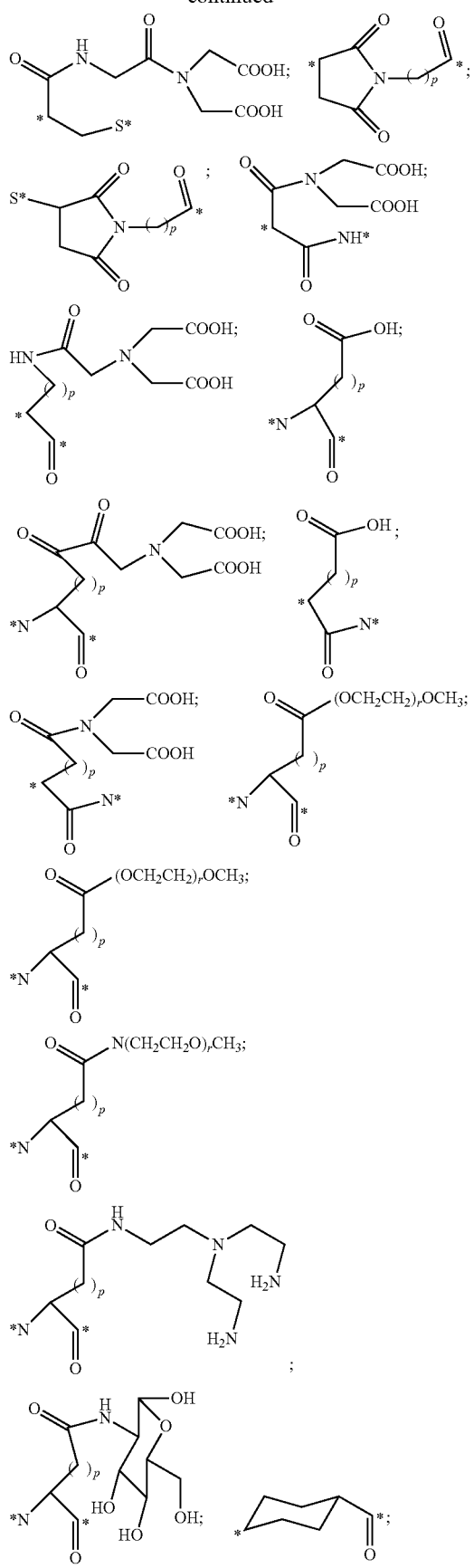
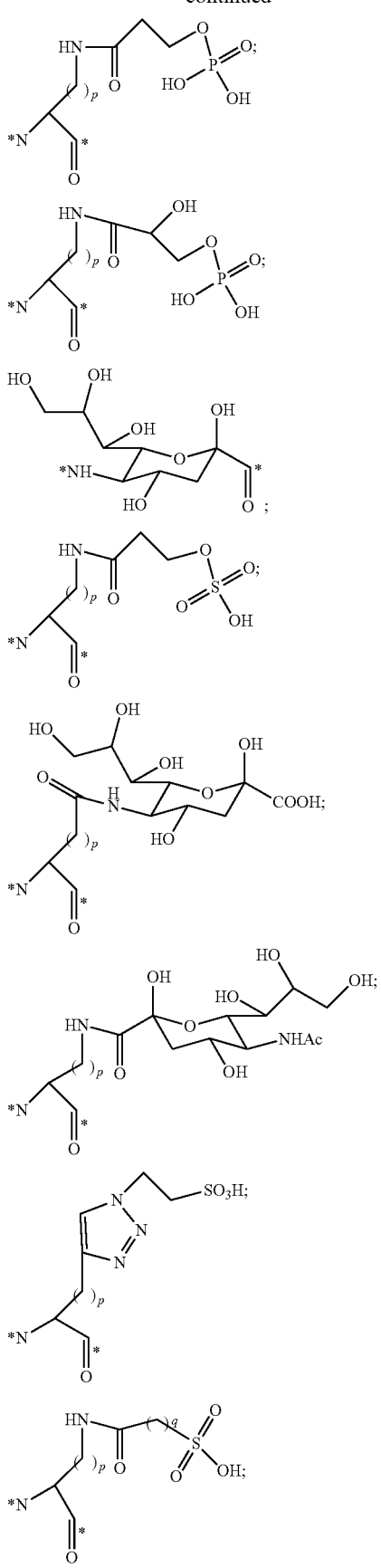

-continued

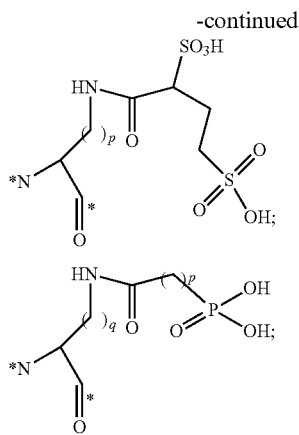

wherein the (*) atom is a point of attachment of additional spacer or releasable linker, a cytotoxic agent, or a cell-binding agent; $X^1$, $Y^1$, $Q^1$, $R_{12}$, $R_{12}'$ are defined as above; r is 0~100; p and q is independently 0, 1, 2, 3, 4, 5 or 6;

Spacer (T) is a linear, branched or cyclic alkyl, alkenyl, alkynyl or aryl having from 1 to 10 carbon atoms, or a polyethylene glycol ($-CH_2CH_2O-$) spacer; t is 0, or 1~100, or T undergoes cyclization upon amide bond hydrolysis, of a substituted and unsubstituted 4-aminobutyric acid amide, substituted bicycle [2.2.1] and bicycle [2.2.2] ring systems or 2-aminophenylpropionic acid amide;

Q is a cell-binding agent or a functional group that enables the compound of Formula (I) to link with a cell-binding agent, or a functional group that enables the compound of Formula (I) to link with a linker attached on a cell-binding agent, the function group being selected from the group consisting of a thiol, an amine, a hydrazine, an alkoxylamino, a disulfide substituent, a maleimido, a haloacetyl group, a carboxy acid, an N-hydroxy succinimide ester, a ketone, an ester, an aldehyde, an alkynyl, an alkenyl, and a protected thiol or disulfide group: $SAr$, $SSR_1$ or $SSAr$, wherein Ar is an aromatic group or hetero aromatic group, the cell-binding agent being selected from the group consisting of antibodies and fragments each containing at least one binding site, lymphokines, hormones, growth factors, nutrient-transport molecules and vitamins.

2. The compound according to claim 1 having the following Formula (Ia) (Ib), or (Ic):

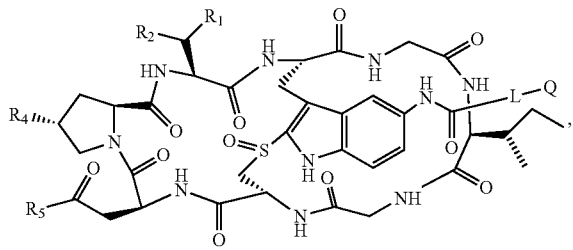

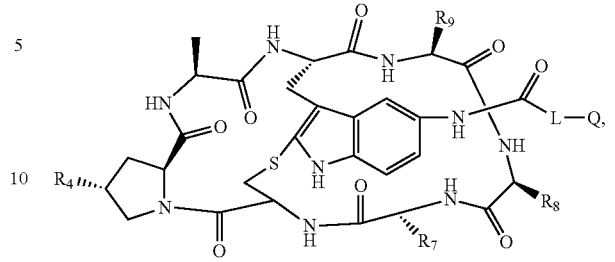

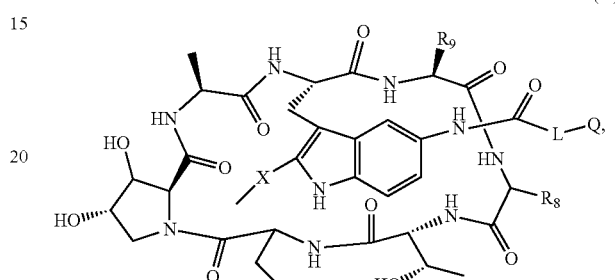

or a pharmaceutically acceptable salt, hydrate, hydrated salt, or polymorphic crystalline structure thereof, or an optical isomer, racemate, diastereomer or enantiomer thereof, wherein $R_1$, $R_2$, $R_4$, $R_5$, $R_7$, $R_8$, $R_9$, $R_{10}$, L and Q are defined the same as in claim 1.

3. The compound according to claim 1 having the following Formula (Id):

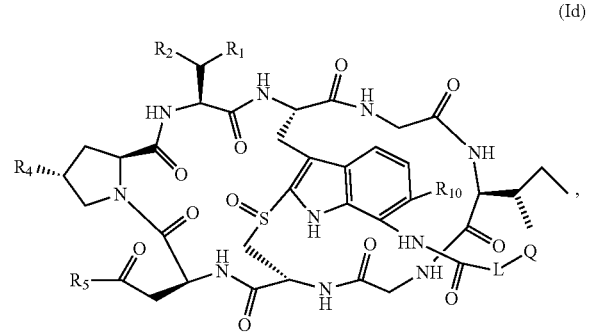

or a pharmaceutically acceptable salt, hydrate, hydrated salt, or polymorphic crystalline structure thereof, or an optical isomer, racemate, diastereomer or enantiomer thereof;

wherein $R_1$, $R_2$, R-4, $R_5$, $R_{10}$, L and Q are defined the same as in claim 1.

4. The compound according to claim 1 having the following Formula (Ia-1), (Ia-2), (Ia-3), (Ia-4), (Ia-5), (Ia-6), (Ia-7), (Ia-8), (Ia-9), (Ia-10), (Ia-11), (Ia-12), (Ia-13), (Ia-14), (Ia-15), (Ia-16), (Ia-17), (Ia-18), (Ia-19), (Ia-20), (Ia-21), (Ia-22), (1a-23), (Ia-24), (Ib-1), (Ib-2), (Ib-3), (Ib-4), (Ib-5), (Ib-6), (Ib-7), (Ic-1), (Ic-2), (Ic-3), (Ic-4), (Ic-5), or (Ic-6):

(Ia-1)
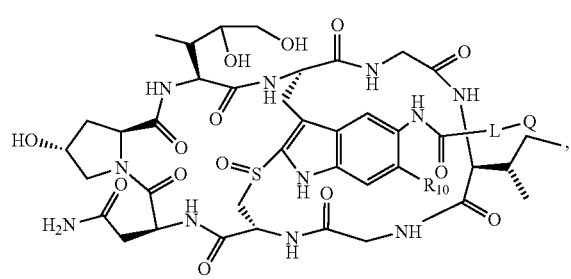
(Ia-2)
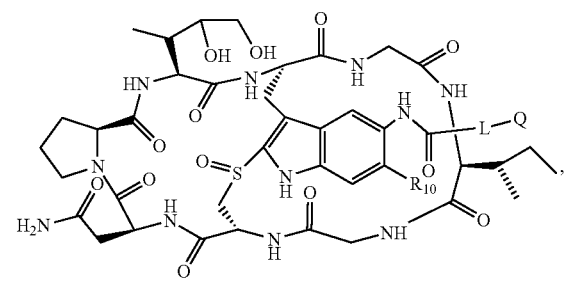
(Ia-3)
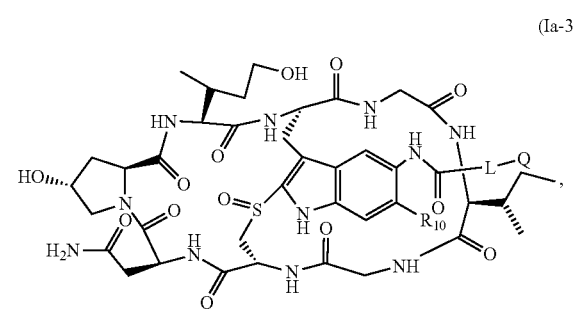
(Ia-4)
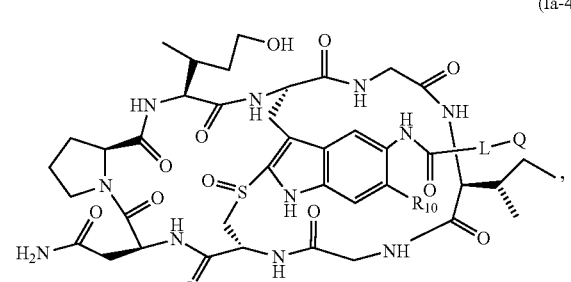
(Ia-5)
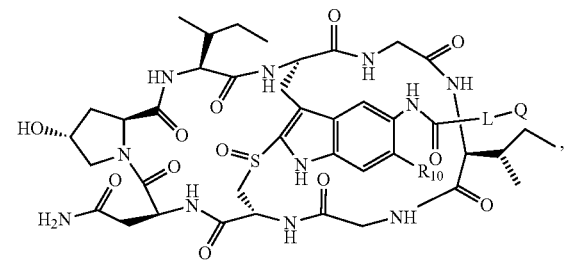
-continued
(Ia-6)
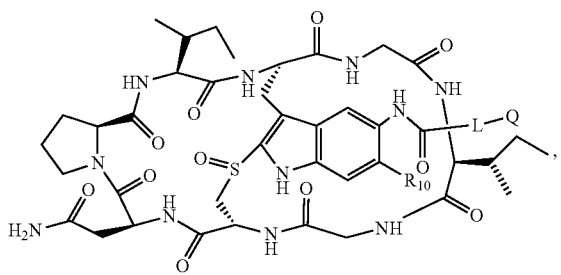
(Ia-7)
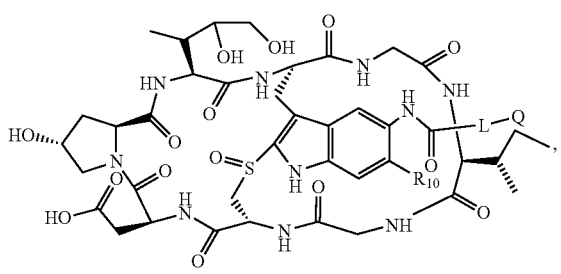
(Ia-8)
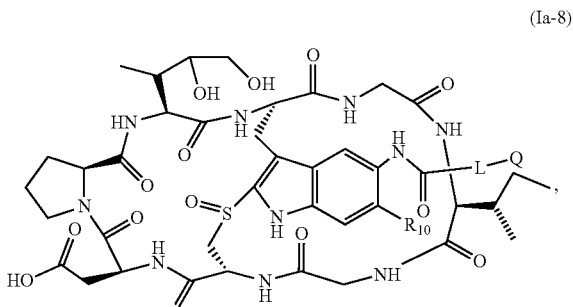
(Ia-9)
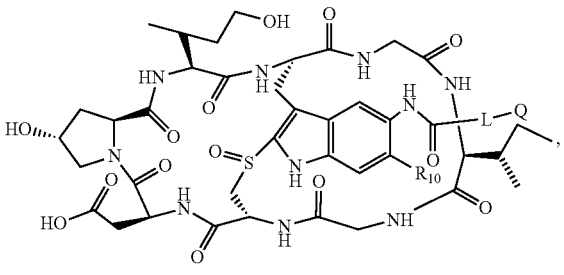
(Ia-10)
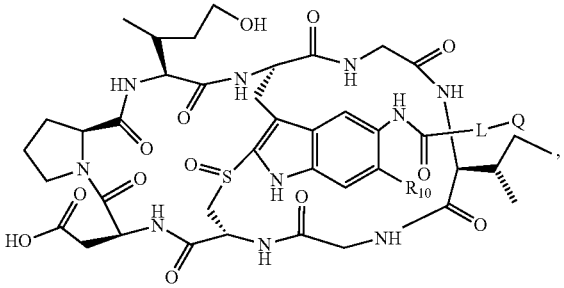

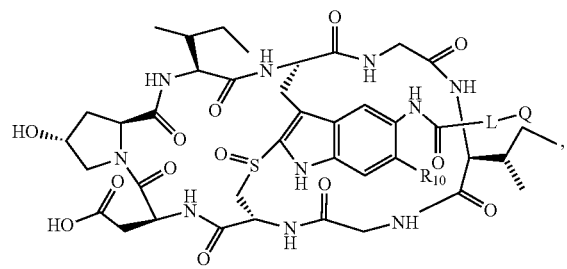
(Ia-11)
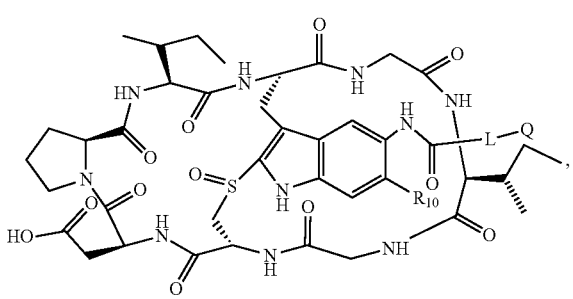
(Ia-12)
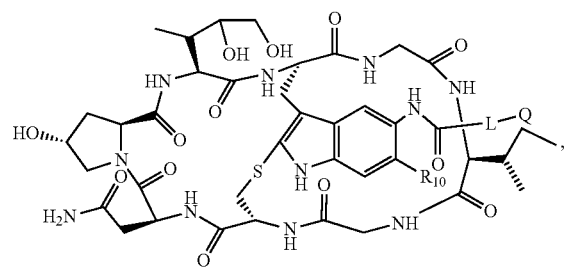
(Ia-13)
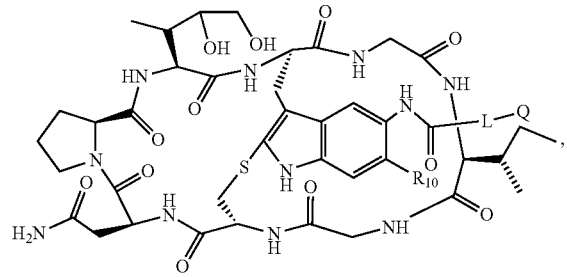
(Ia-14)
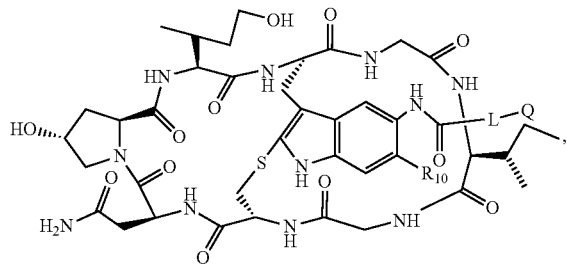
(Ia-15)
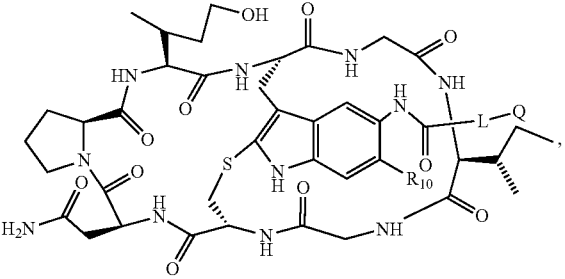
(Ia-16)
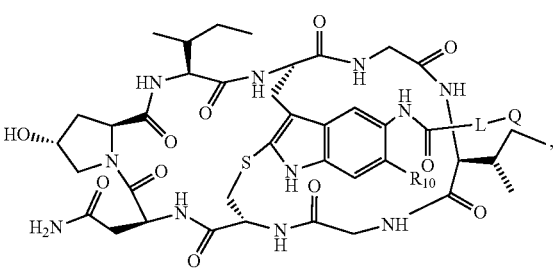
(Ia-17)
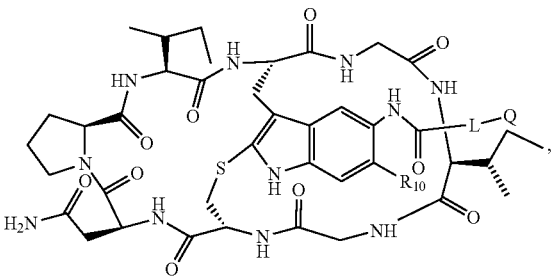
(Ia-18)
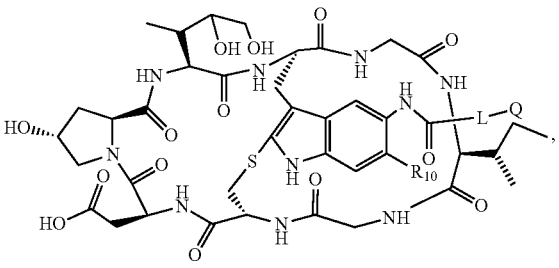
(Ia-19)
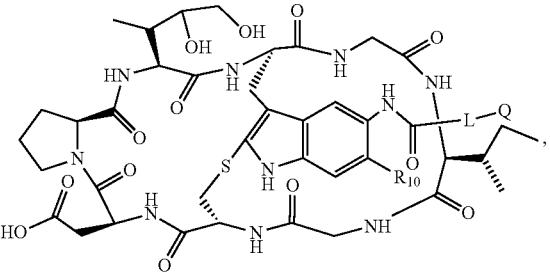
(Ia-20)

241
-continued
(Ia-21)
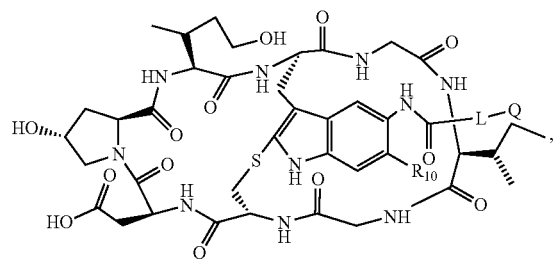
(Ia-22)
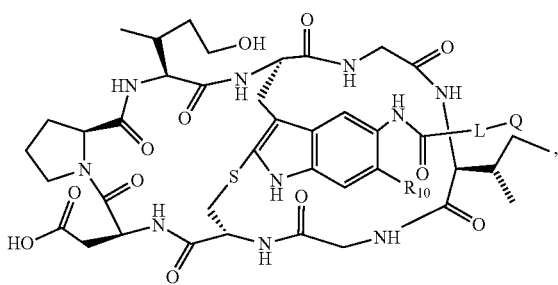
(Ia-23)
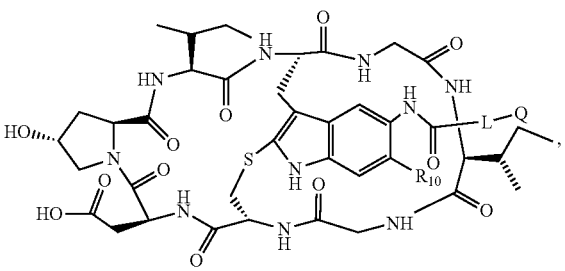
(Ia-24)
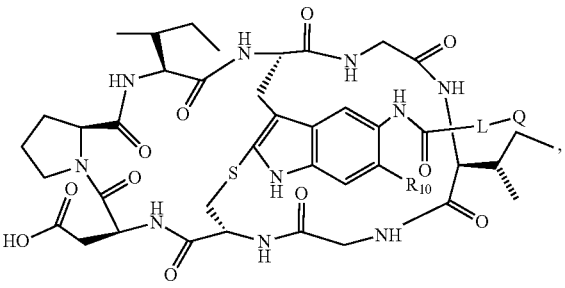
(Ib-1)
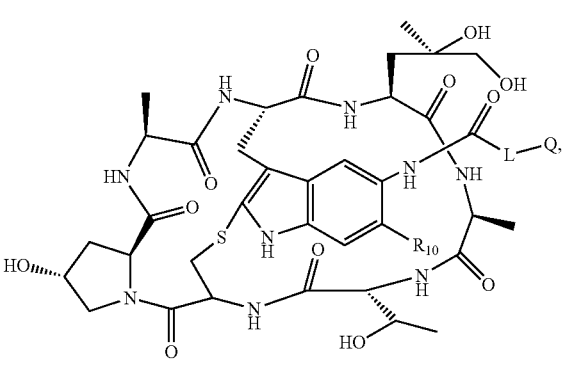
242
-continued
(Ib-2)
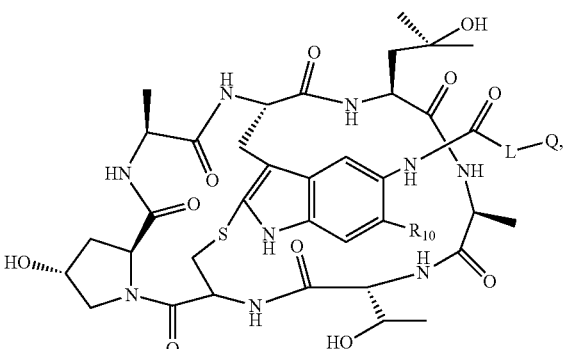
(Ib-3)
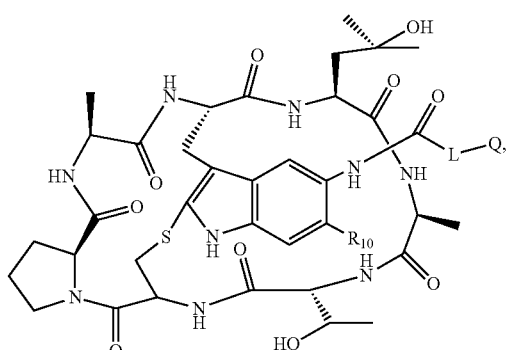
(Ib-4)
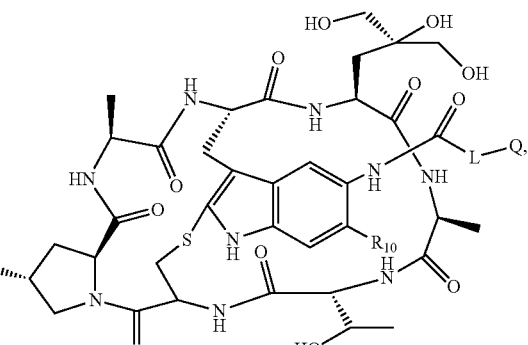
(Ib-5)
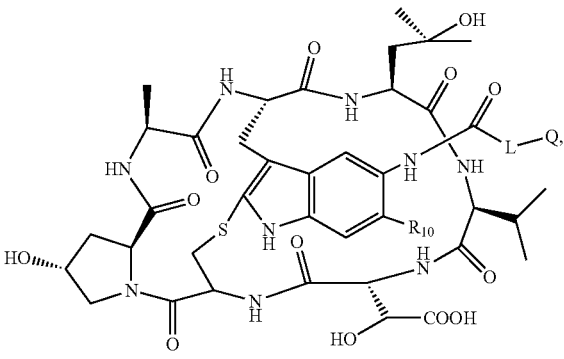

-continued
(Ib-6)
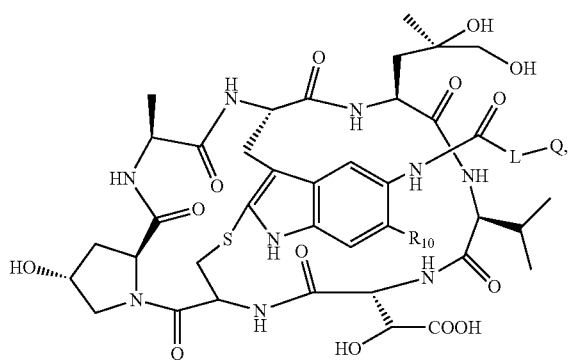
(Ic-3)
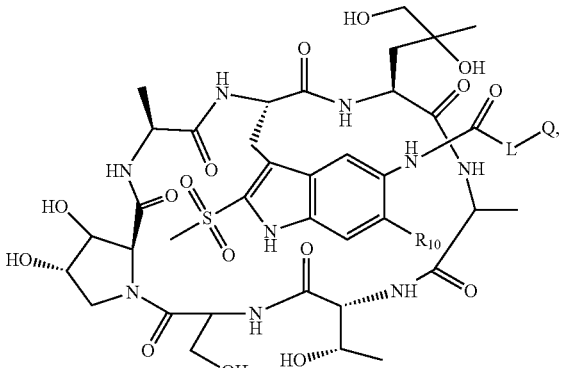
(Ib-7)
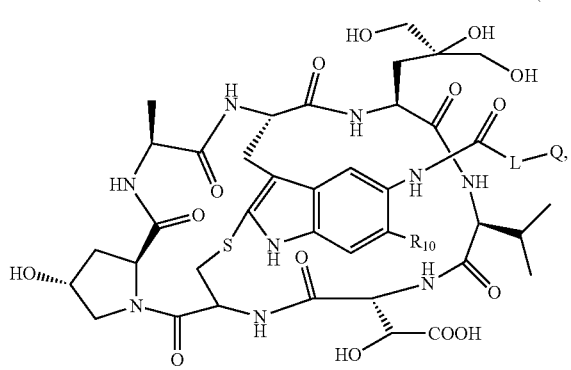
(Ic-4)
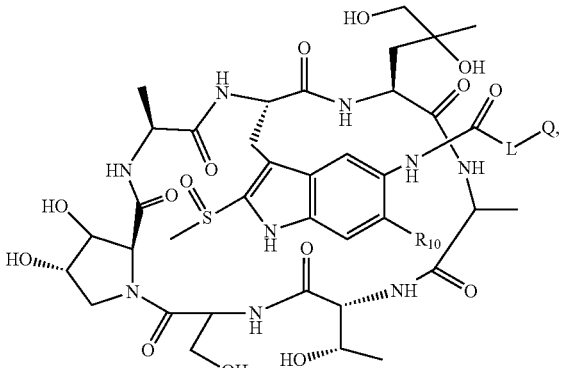
(Ic-1)
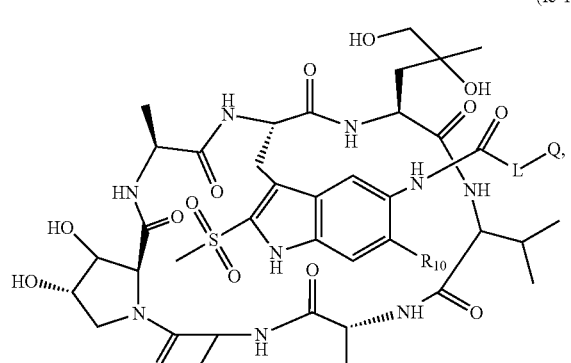
(Ic-5)
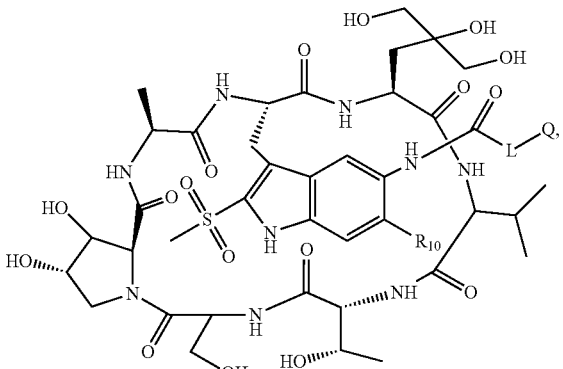
(Ic-2)
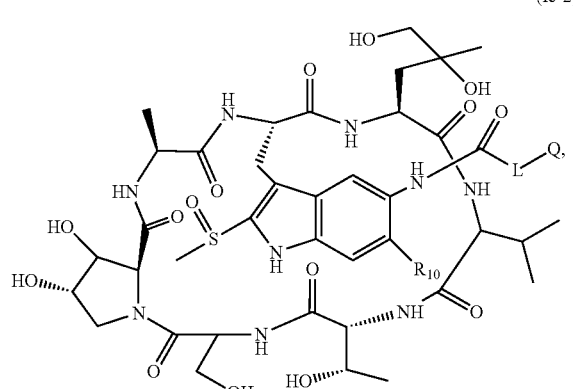
(Ic-6)
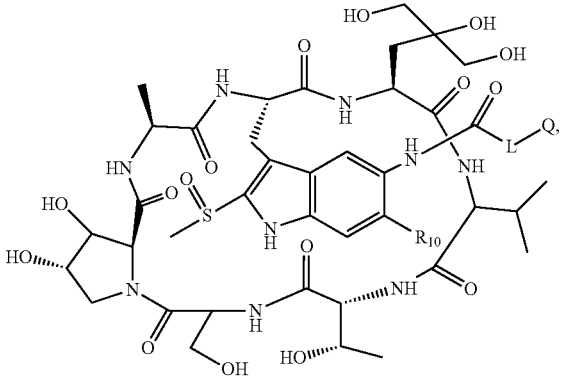

or a pharmaceutically acceptable salt, hydrate, hydrated salt, or polymorphic crystalline structure thereof, or an optical isomer, racemate, diastereomer or enantiomers thereof;

wherein $R_{10}$, L and Q are defined the same as in claim 1.

5. The compound according to claim 1 having the following Formula (Id-1), (Id-2), (Id-3), (Id-4), (Id-5), (Id-6), (Id-7), (Id-8), (Id-9), (Id-10), (Id-11), (Id-12), (Id-13), (Id-14), (Id-15), (Id-16), (Id-17), (Id-18), (Id-19), (Id-20), or (Id-21):

(Id-1)

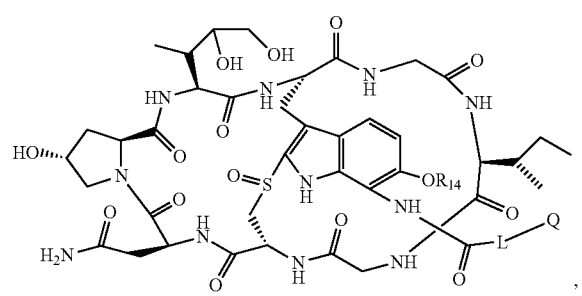

, (Id-2)

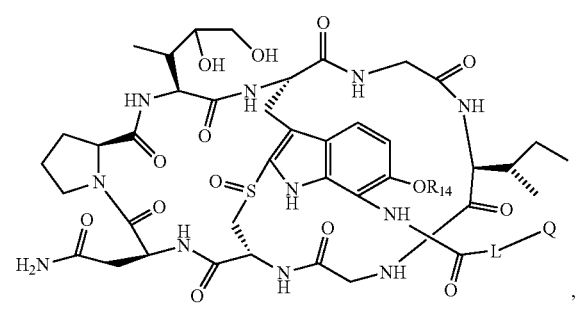

, (Id-3)

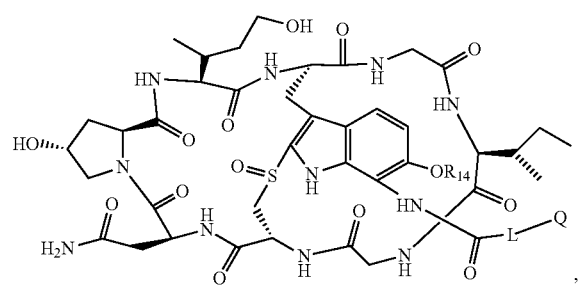

, (Id-4)

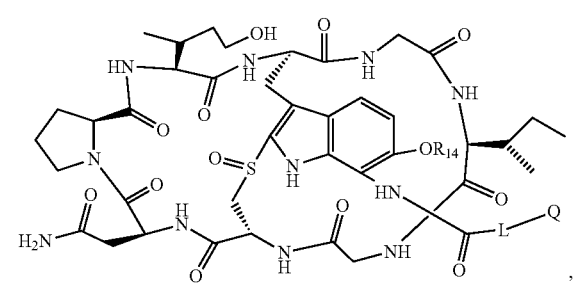

, (Id-5)

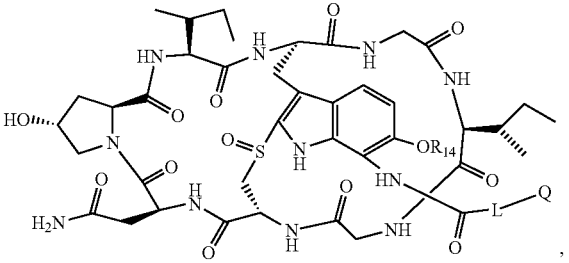

, (Id-6)

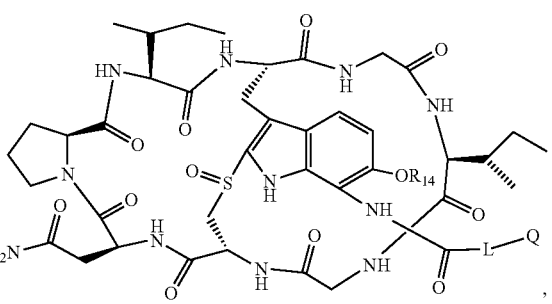

, (Id-7)

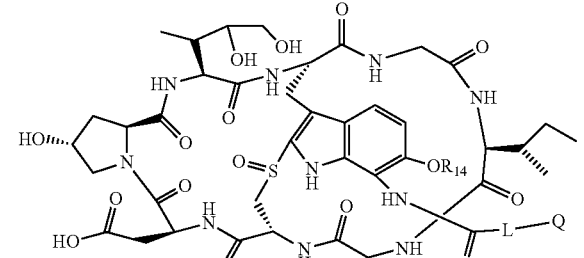

, (Id-8)

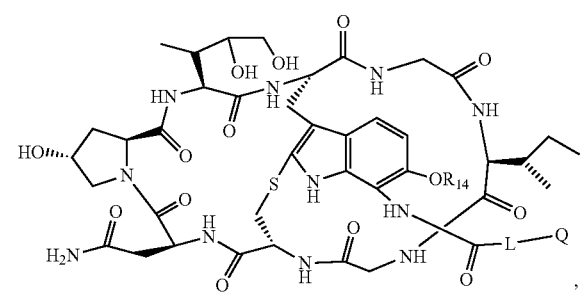

, (Id-9)

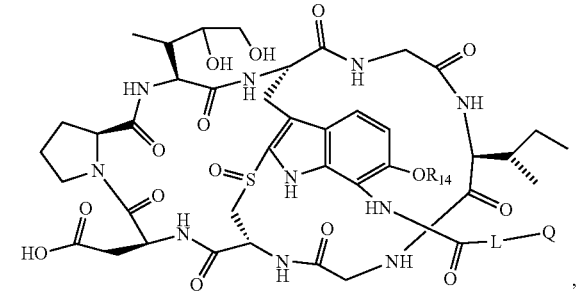

, (Id-10)
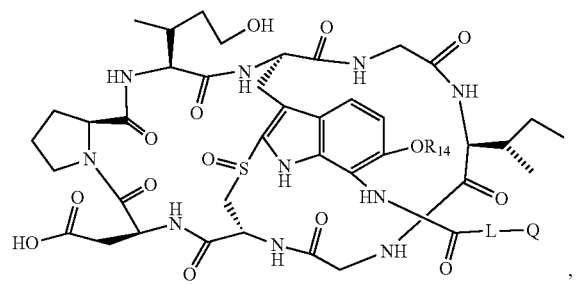
(Id-11)
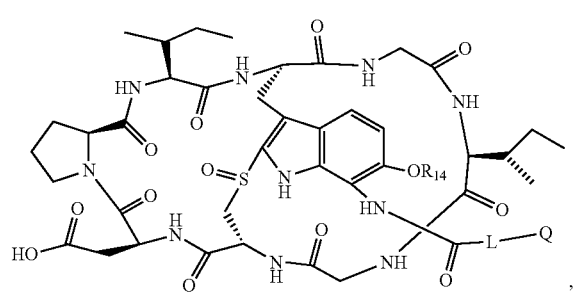
(Id-12)
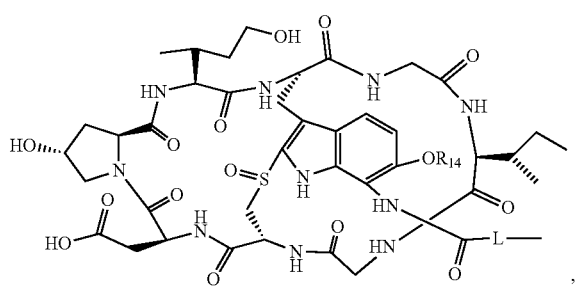
(Id-13)
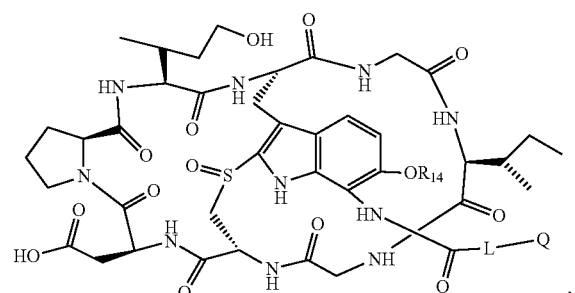
(Id-14)
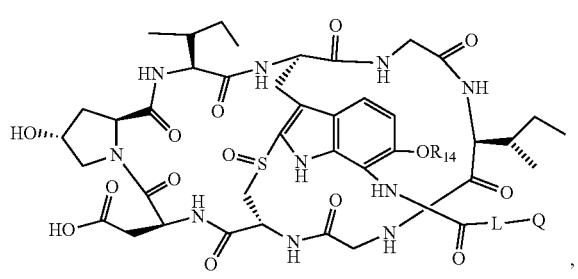
(Id-15)
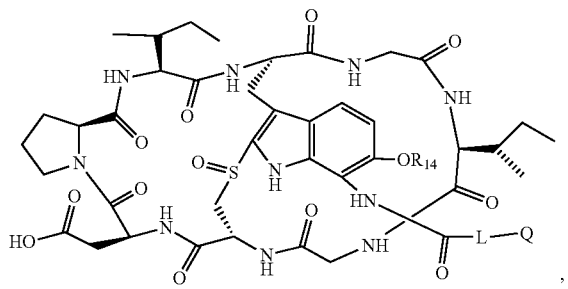
(Id-16)
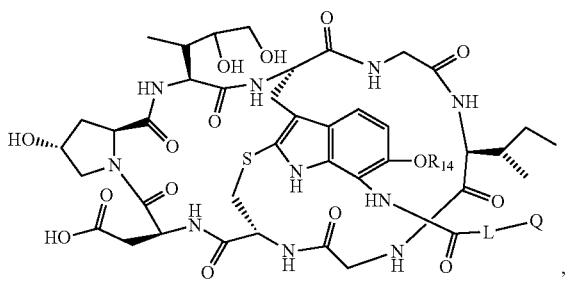
(Id-17)
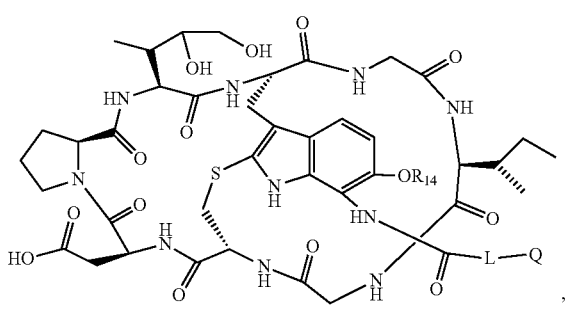
(Id-18)
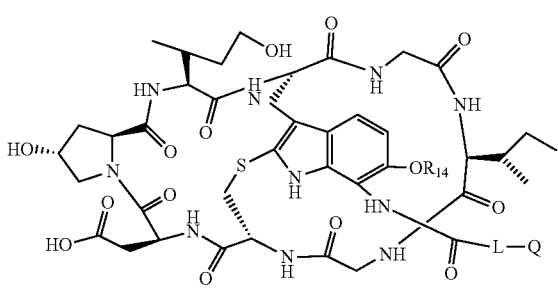
(Id-19)
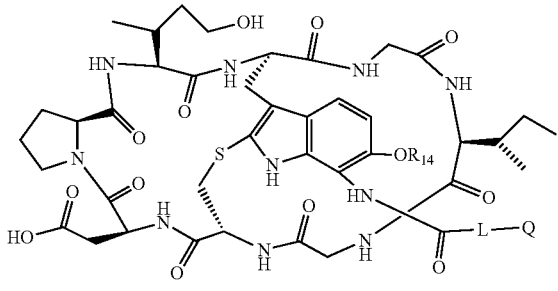

(Id-20)

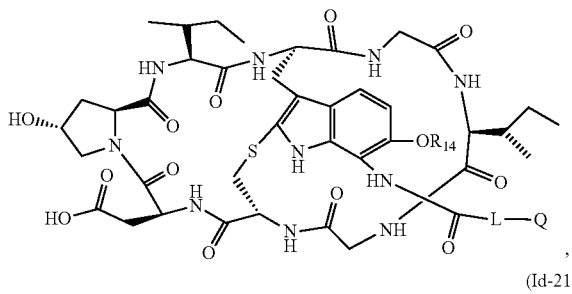

(Id-21)

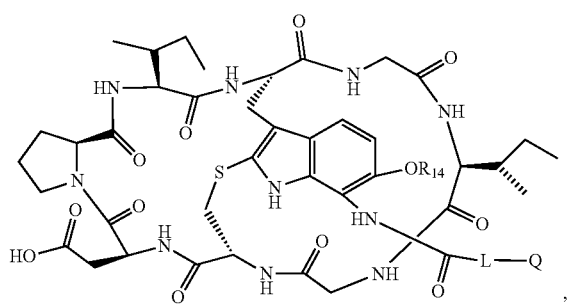

wherein L and Q are defined the same as in claim 1; $R_{14}$ is H, $PO_3^{2-}$, $SO_3^-$, $R_{12}$, —$COR_{12}$, —$COCH_3$, —$COOR_{12}$, —$CONR_{12}R_{12}'$, —$C(=O)R_{12}NH(Aa)_t$, wherein Aa is an amino acid or a polypeptide, t represents 0-100; —$CSNHR_{12}$ (thiocarbamate); —$SOR_{12}$ (sulfoxide); —$SO_2R_{12}$ (sulfone); —$SO_3^-$, $HSO_3$, $HSO_2$, or a salt of $H_5O_3^-$, $SO_3^{2-}$ or —$HSO_2^-$ (sulphite); $P(O)(OM_1)(OM_2)$, $CH_2OP(O)(OM_1)(OM_2)$, $SO_3M_1$; or glycoside (glucoside, galactoside, mannoside, glucuronoside, alloside, fructoside; $M_1$ and $M_2$ are independently H, Na, K, Ca, Mg, $NH_4$, or $NR_1'R_2'R_3'$; $R_1'$, $R_2'$ and $R_3'$ are independently H, or $C_1$~$C_8$ alkyl.

6. The compound according to claim 1 having the following Formula (I-1), (I-2), (I-3), (I-4), (I-5), (I-6), (I-7), (I-8), (I-9), (I-10), (I-11), (I-12), (I-13), (I-14), (I-15), (I-16), (I-17), (I-18), (I-19), (I-20), (I-21), (I-22), (I-23), (I-24), (I-25), (I-26), (I-27), (I-28), (I-29), (I-30), (I-31), (I-32), (I-33), (I-34), (I-35), (I-36), (I-37), (I-38), (I-39), (I-40), (I-41), (I-42), (I-43), (I-44), (I-45), (I-46), (I-47), (I-48), (I-49), (I-50), (I-51), (I-52), (I-53), (I-54), (I-55), (I-56), (I-57), (I-58), (I-69), (I-60), (I-61), (I-62), (I-63), (I-64), (I-65), (I-66), (I-67), (I-68), (I-69), (I-70), (I-71), (I-72), (I-73), (I-74), (I-75), (I-76), (I-77), (I-78), (I-79), (I-80), (I-81), (I-82), (I-83), (I-84), (I-85), (I-86), (I-87), (I-88), (I-89), (I-90), (I-91), (I-92), (I-93), (I-94), (I-95), (I-95) or (I-95):

(I-1)

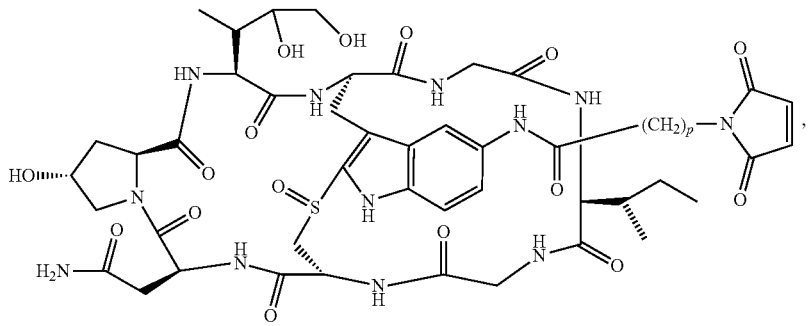

(I-2)

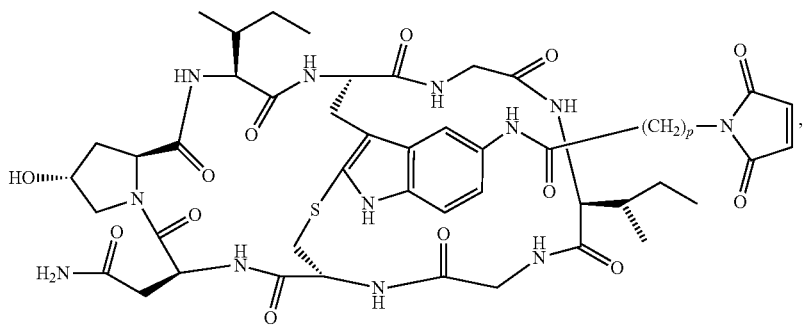

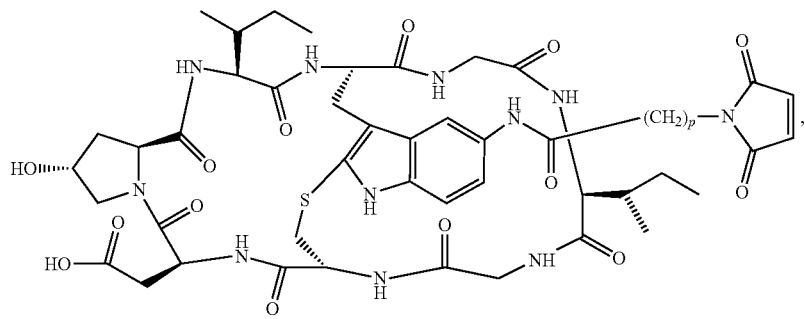
(I-3)
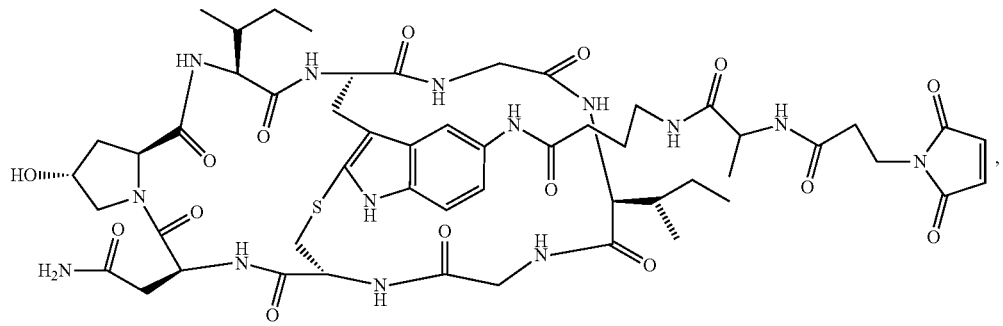
(I-4)
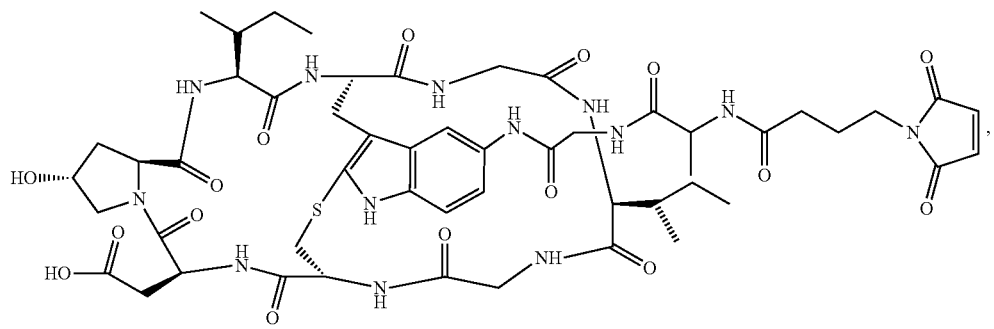
(I-5)
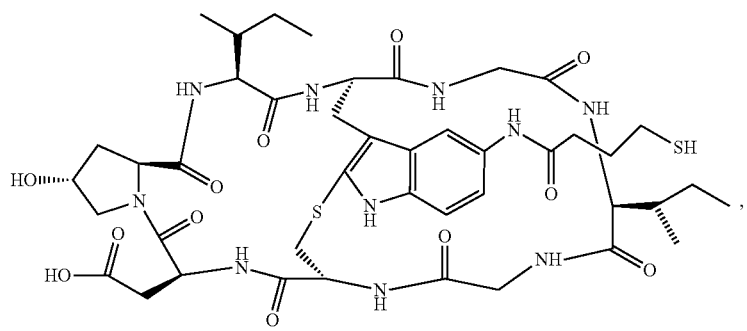
(I-6)
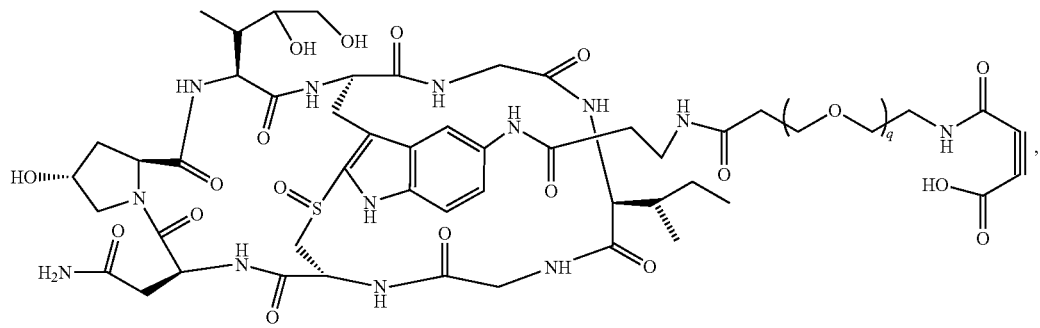
(I-7)

-continued
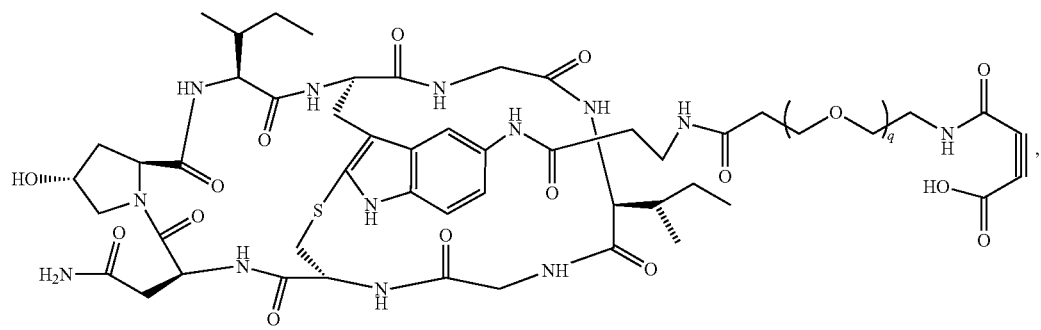
(I-8)
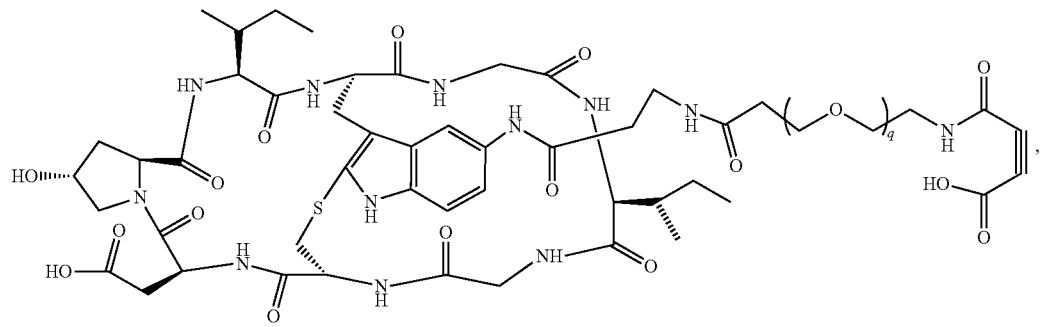
(I-9)
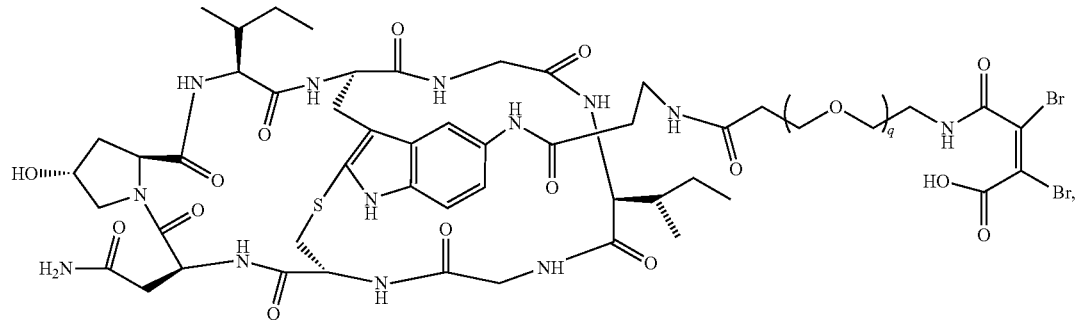
(I-10)
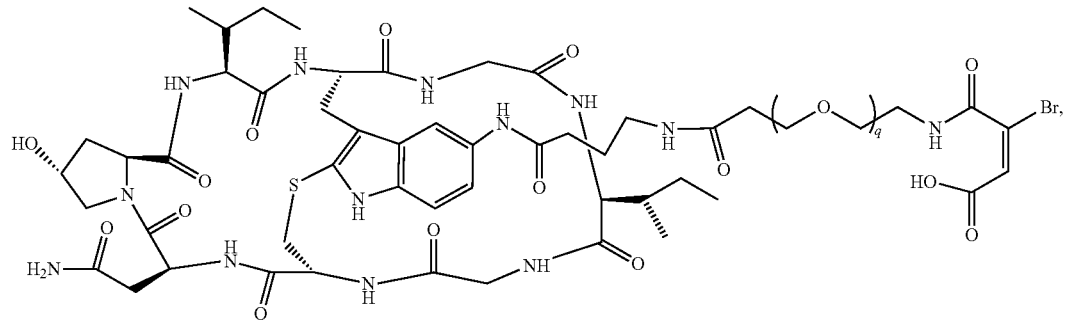
(I-11)
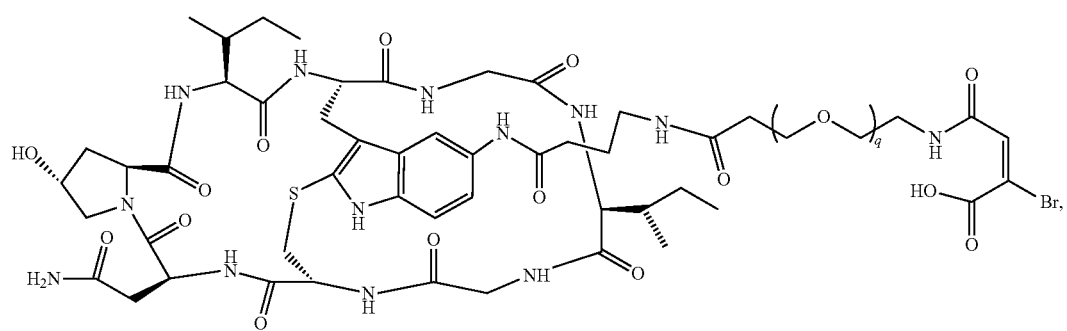
(I-12)

(I-13)
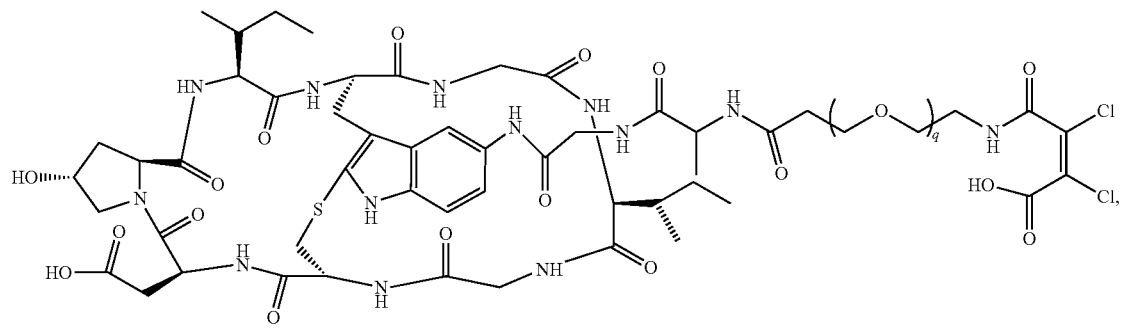
(I-14)
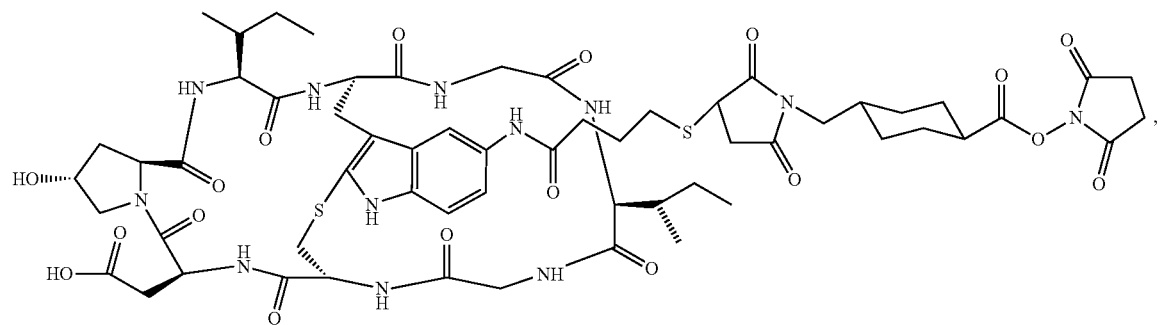
(I-15)
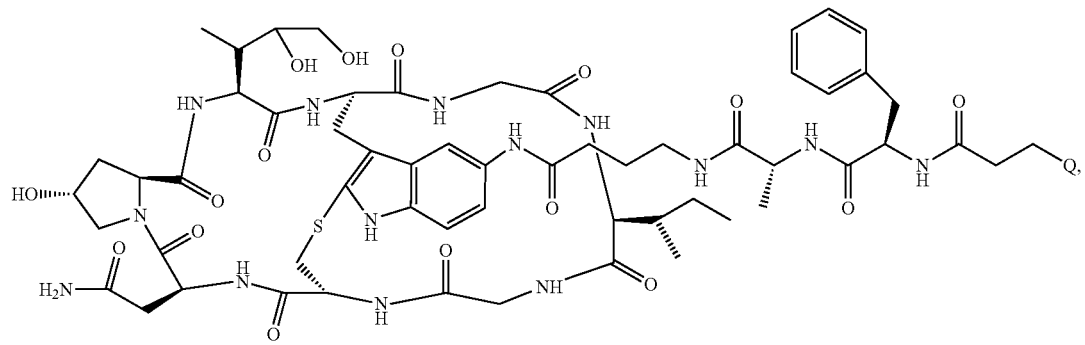
(I-16)
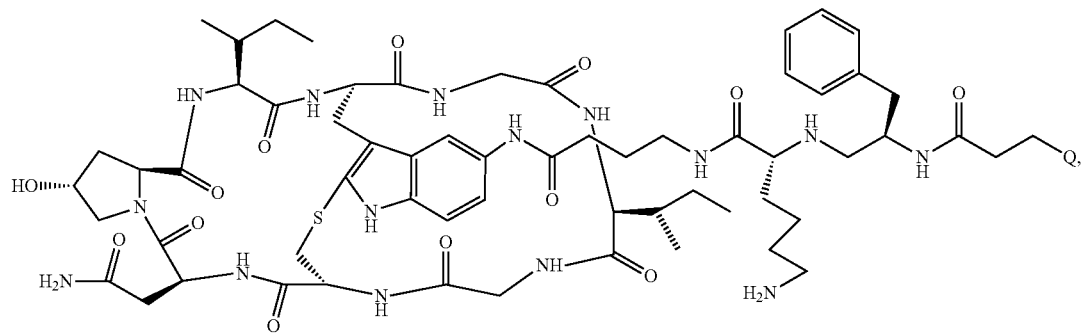

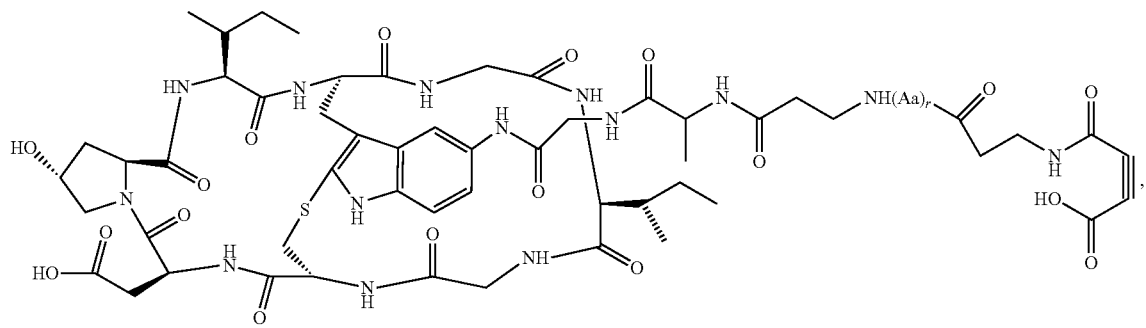
(I-17)
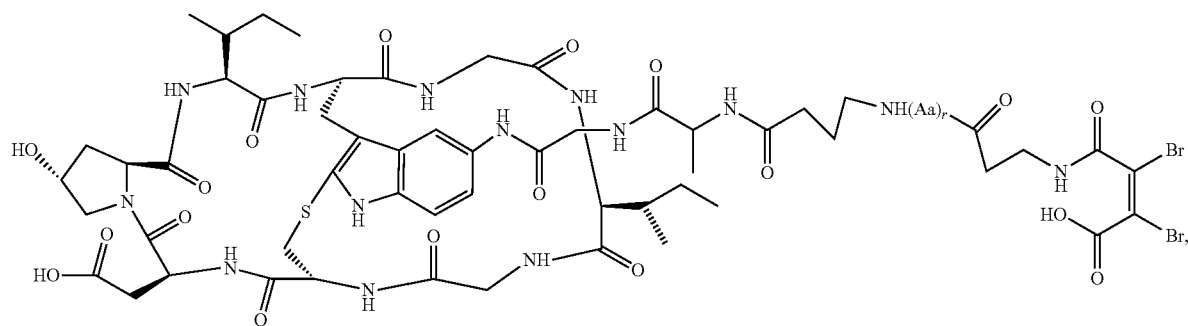
(I-18)
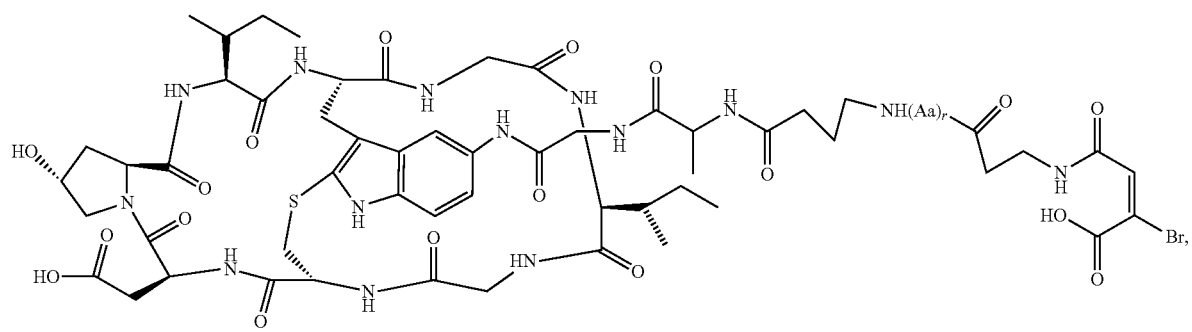
(I-19)
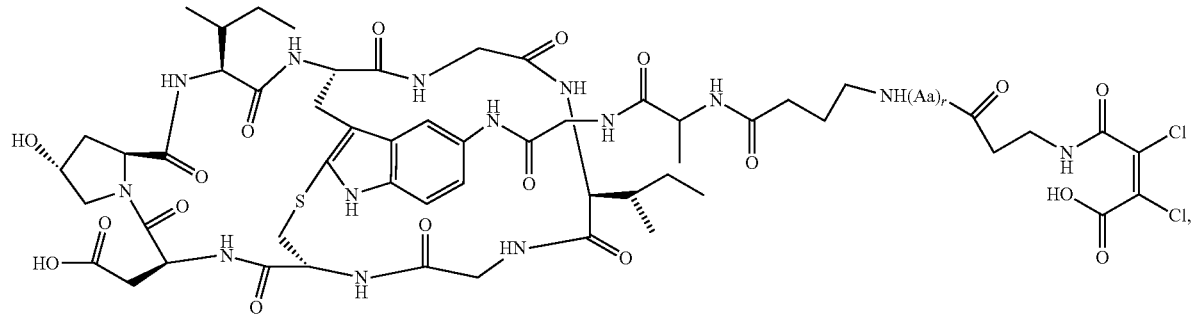
(I-20)

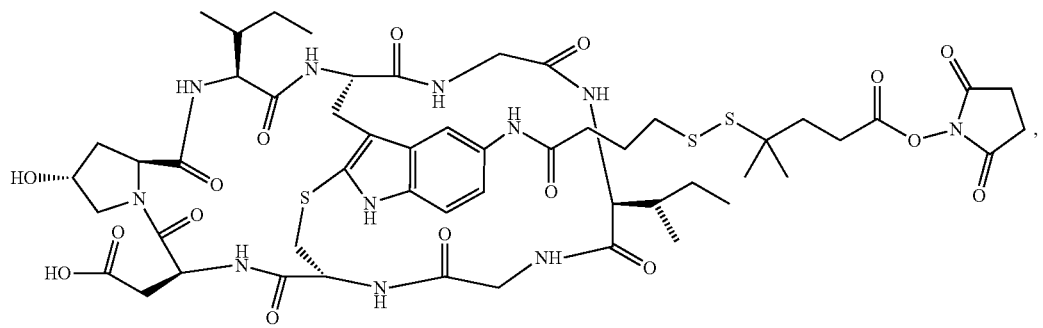
(I-21)
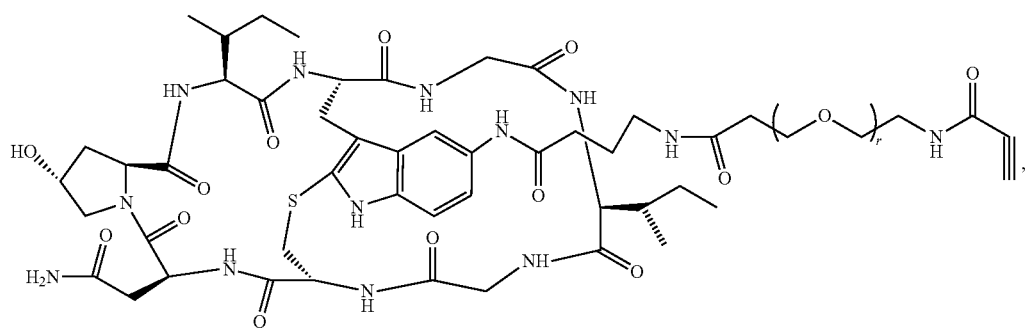
(I-22)
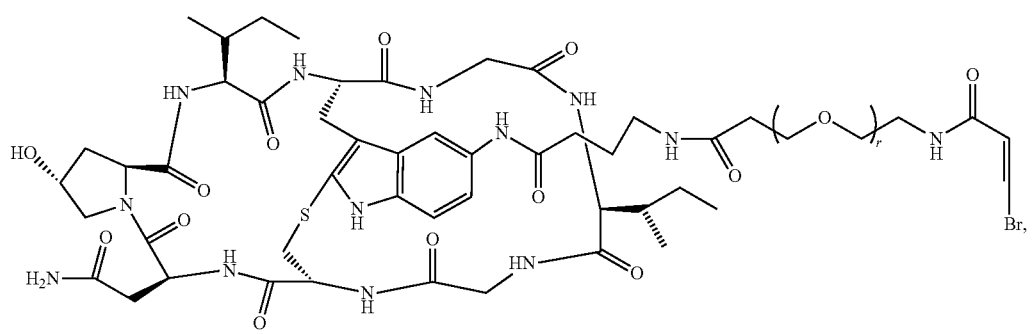
(I-23)
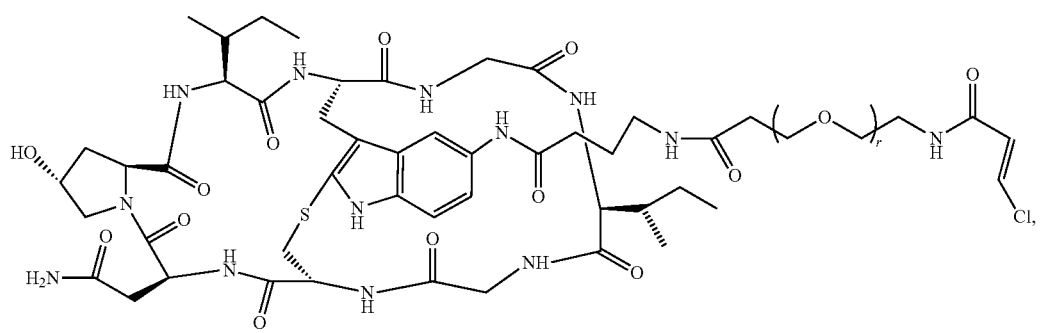
(I-24)

-continued
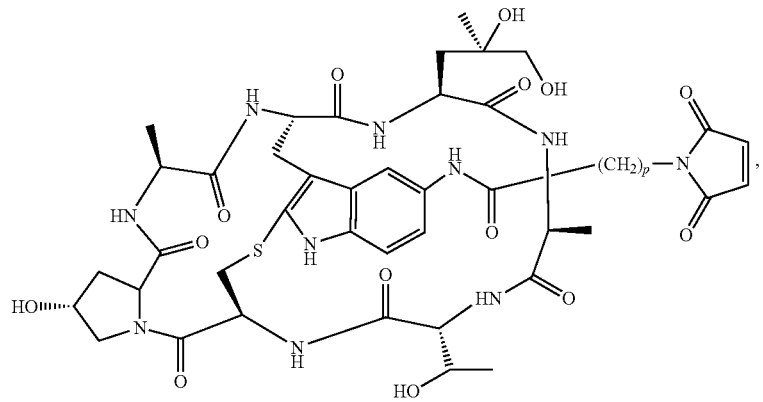
(I-25)
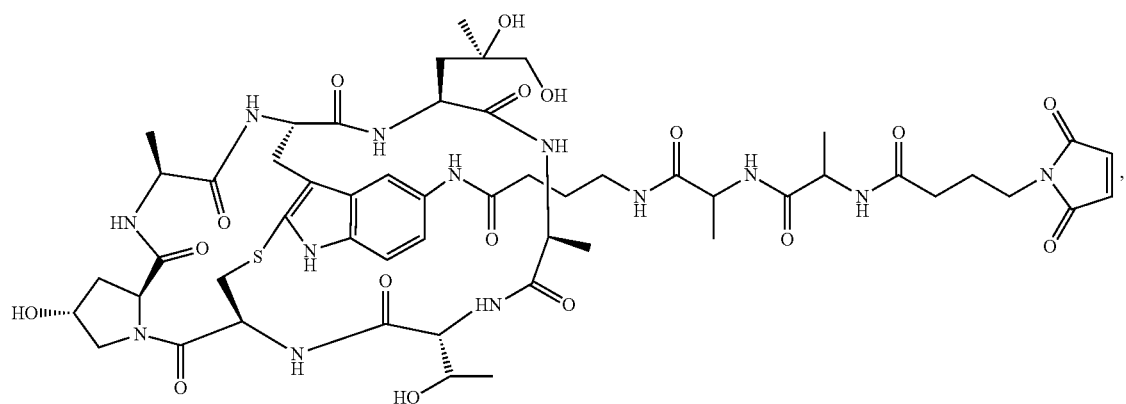
(I-26)
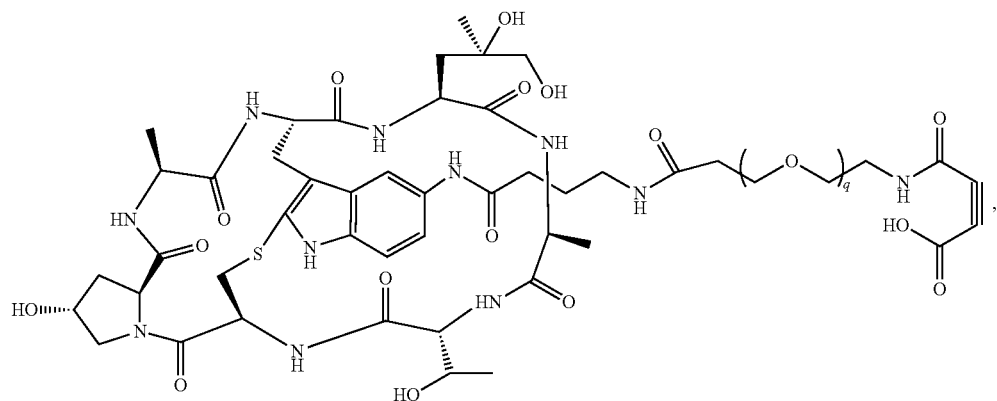
(I-27)
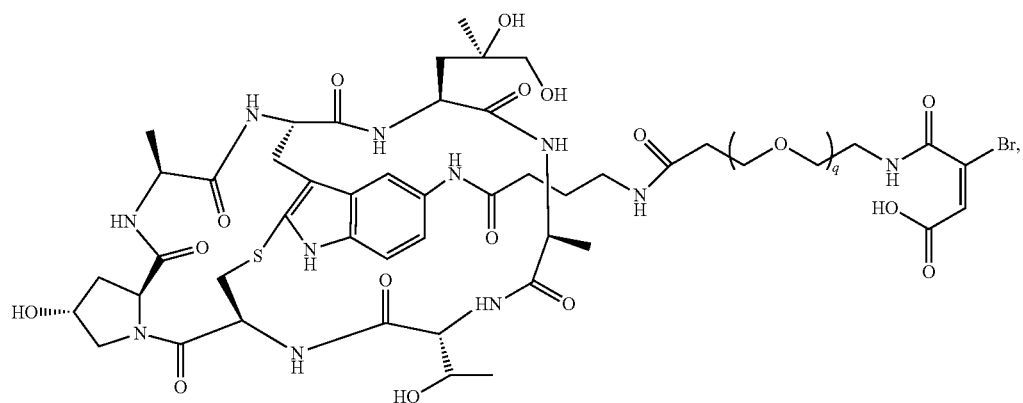
(I-28)

-continued
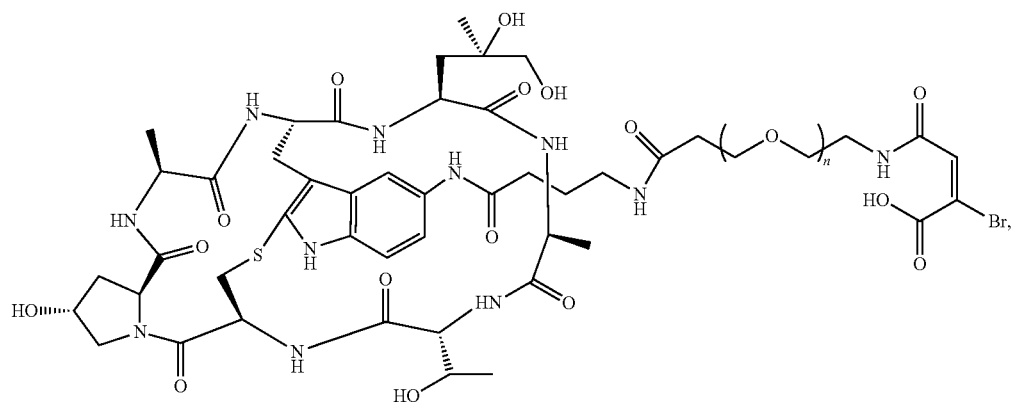
(I-29)
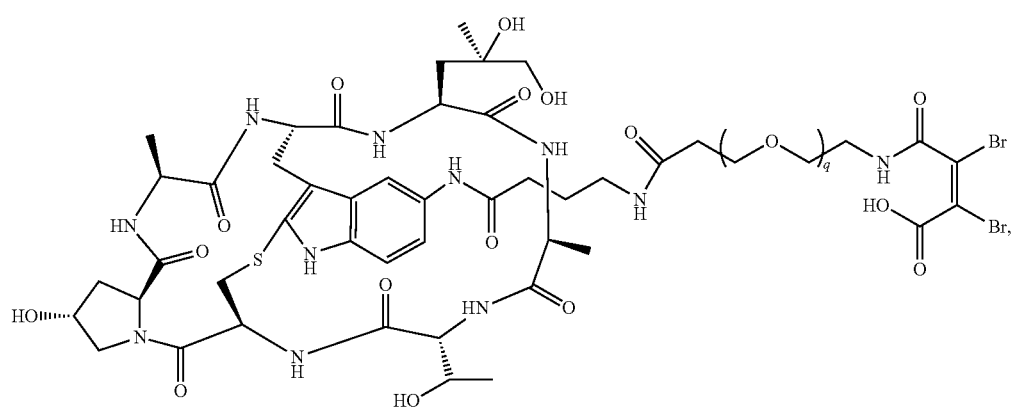
(I-30)
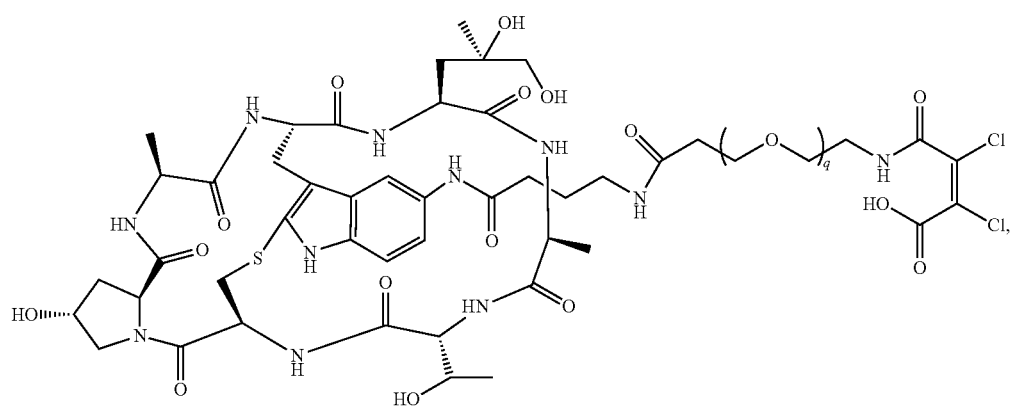
(I-31)
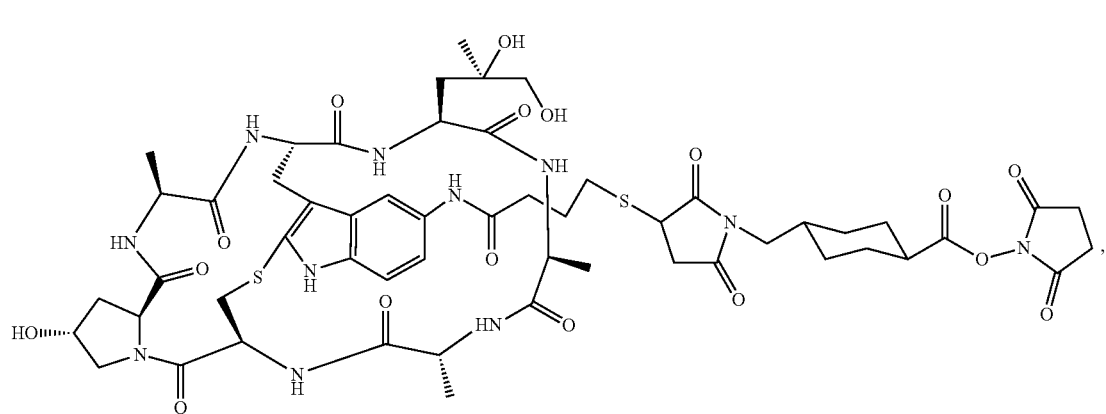
(I-32)

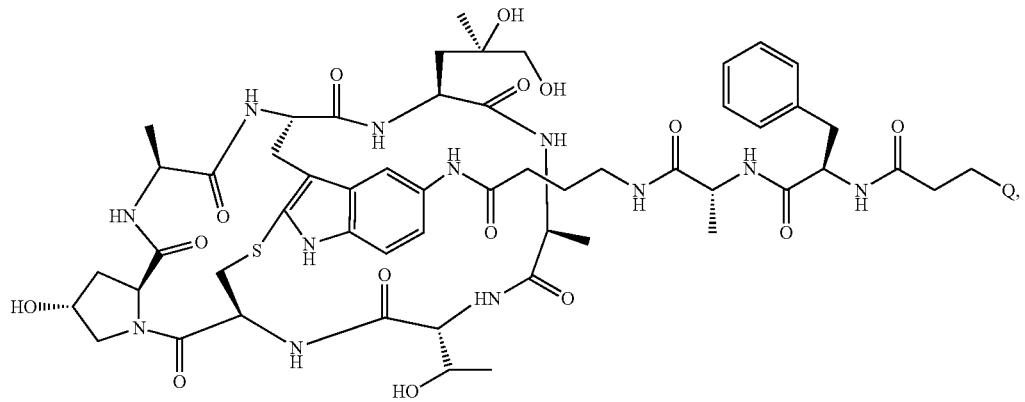
(I-33)
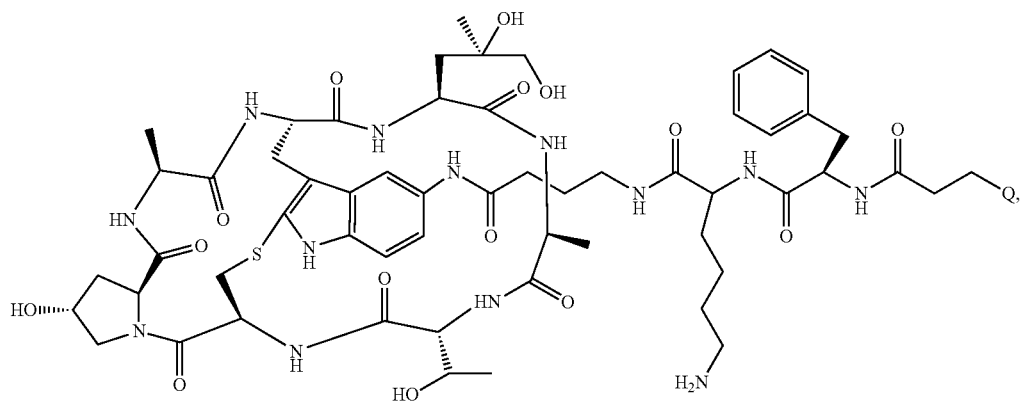
(I-34)
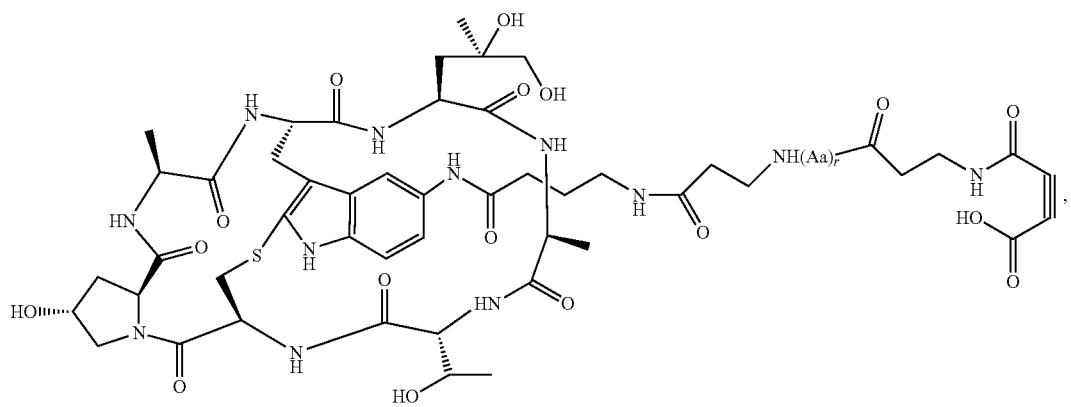
(I-35)
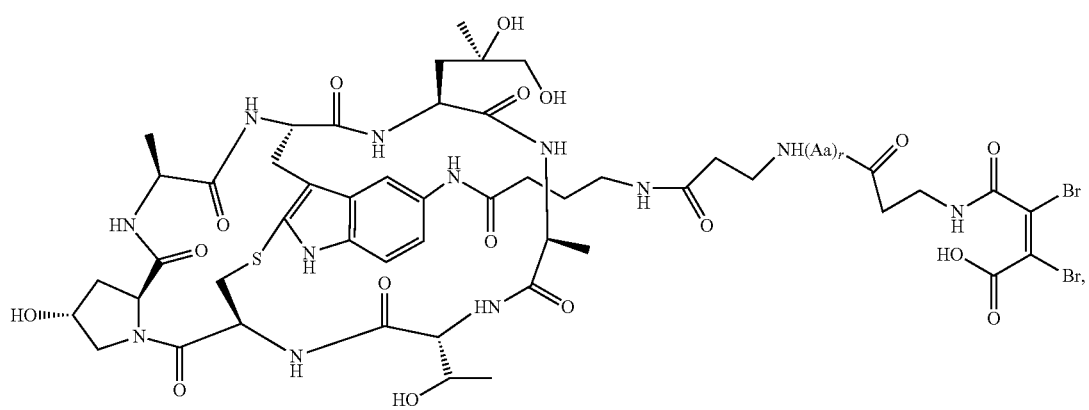
(I-36)

(I-37)
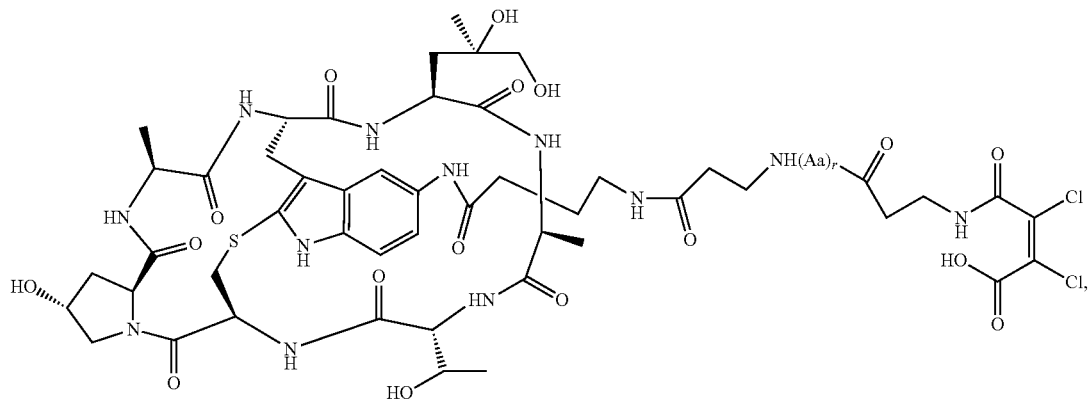
(I-38)
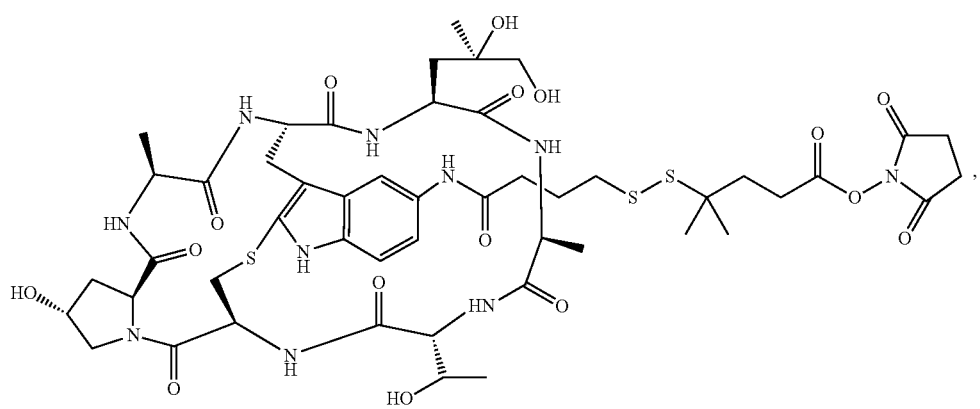
(I-39)
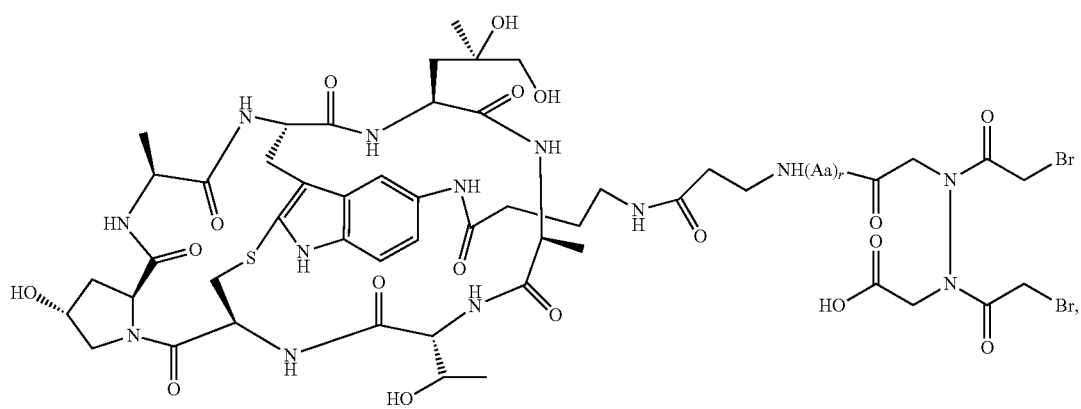
(I-40)
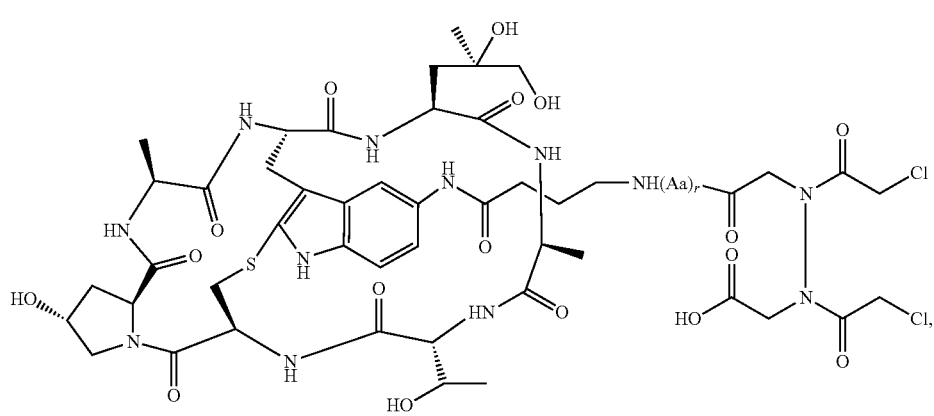

(I-41)
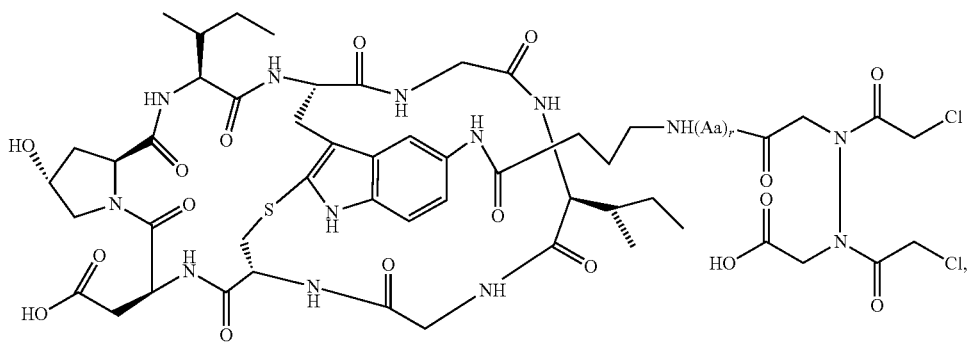
(I-42)
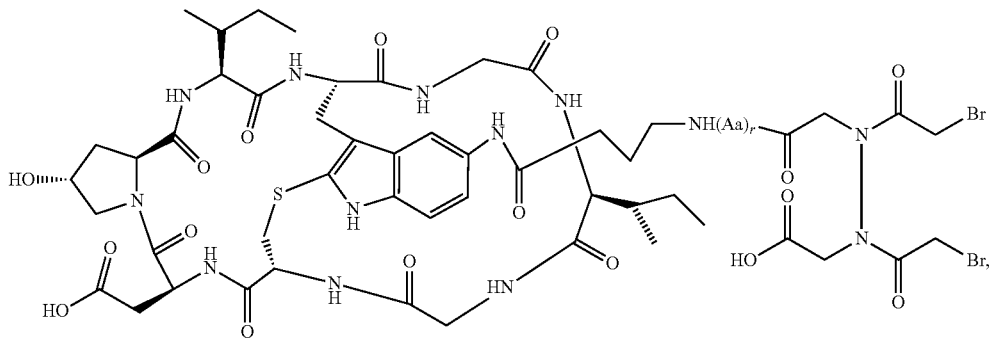
(I-43)
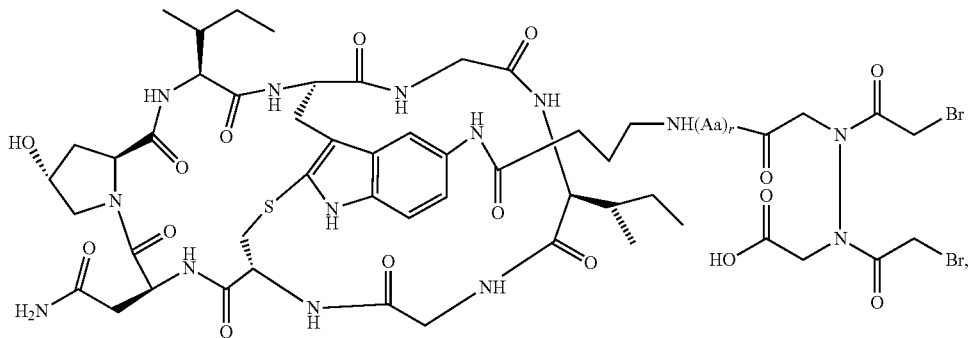
(I-44)
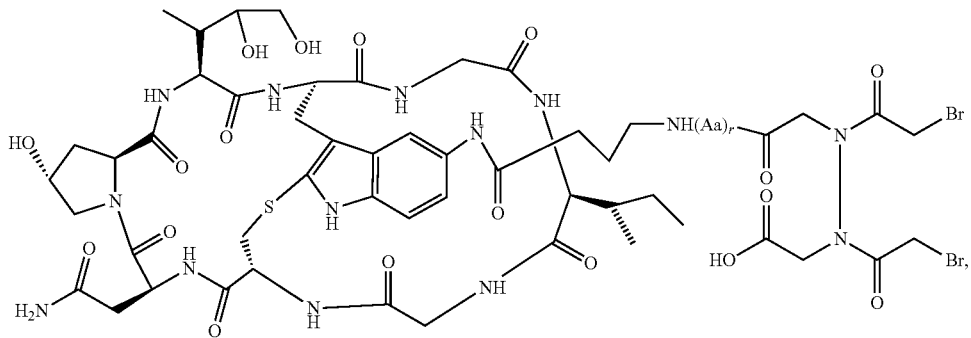

(I-45)
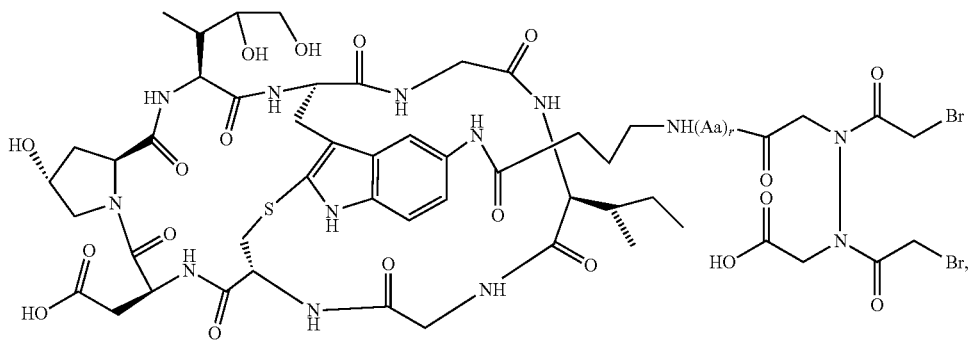
(I-46)
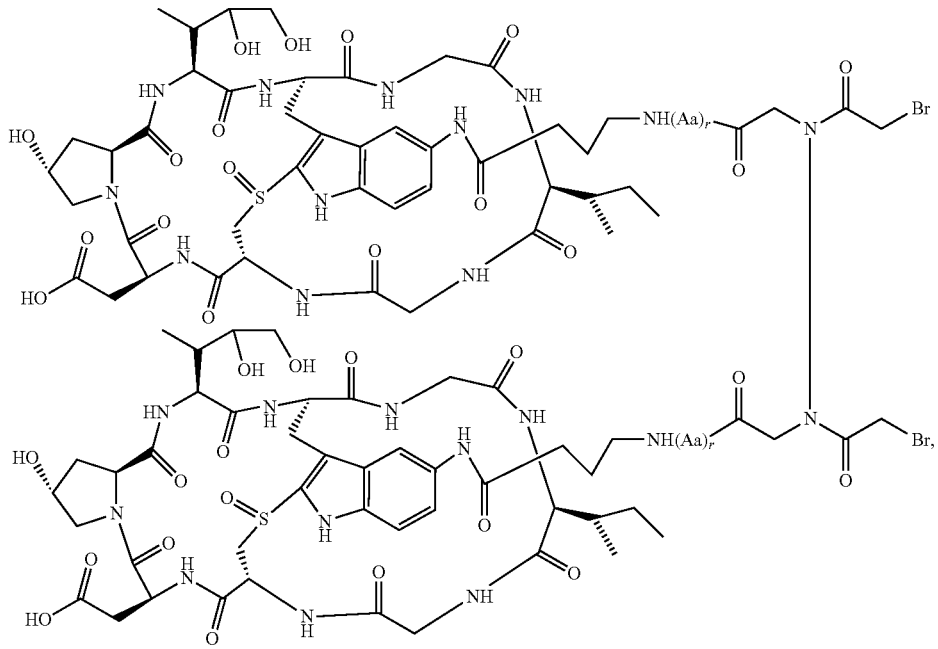
(I-47)
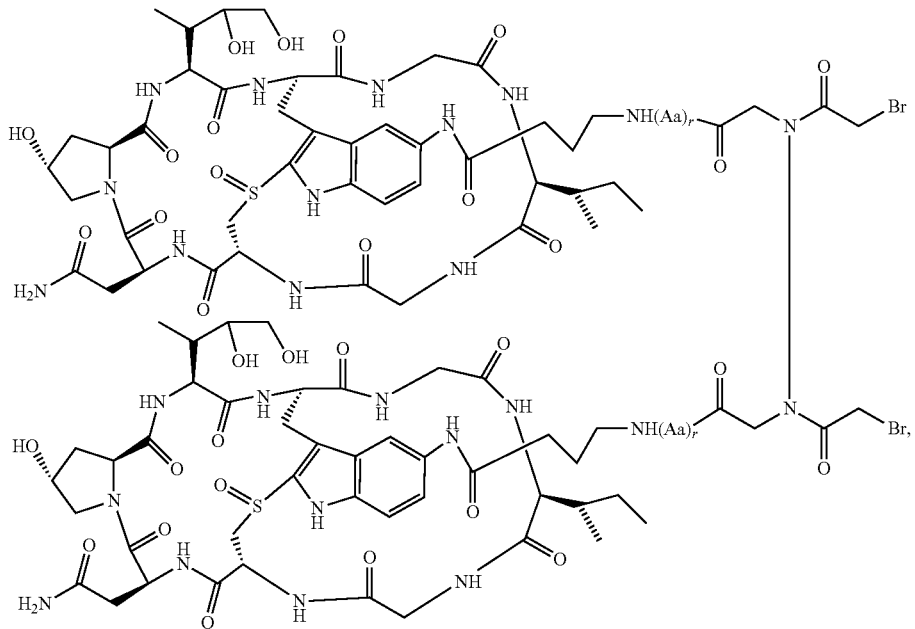

-continued
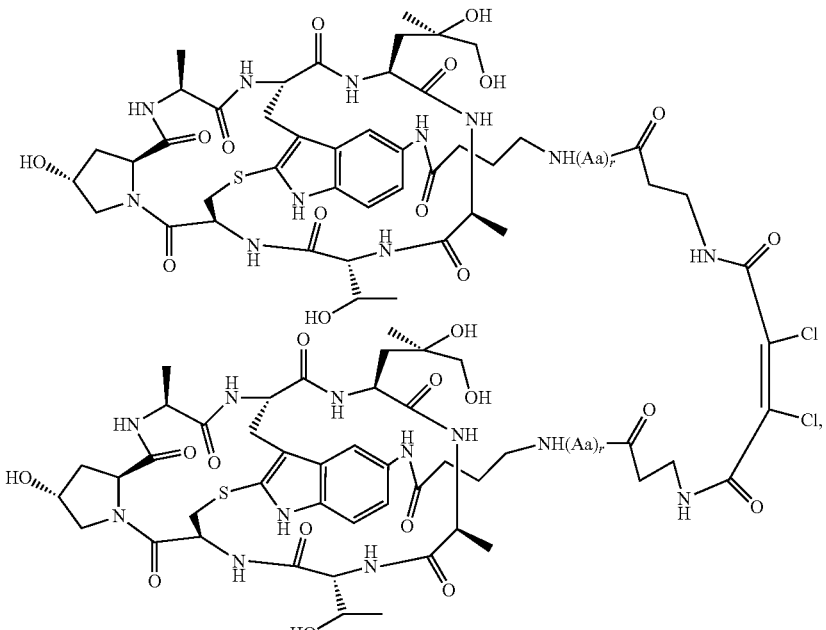
(I-48)
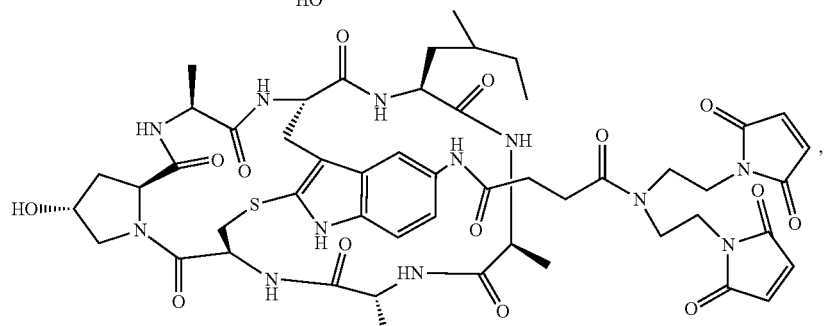
(I-49)
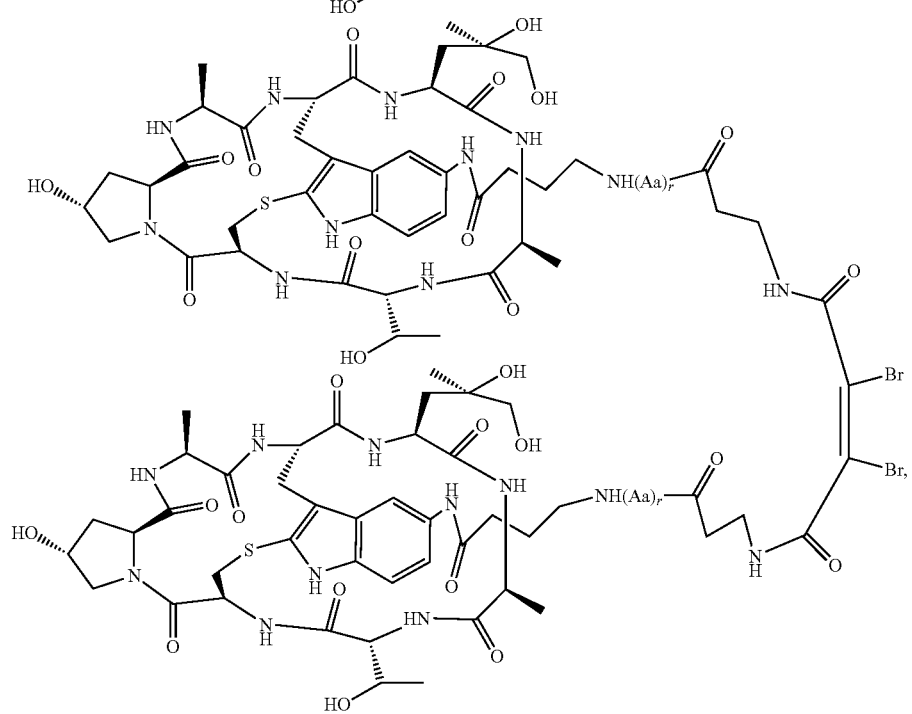
(I-50)

(I-51)
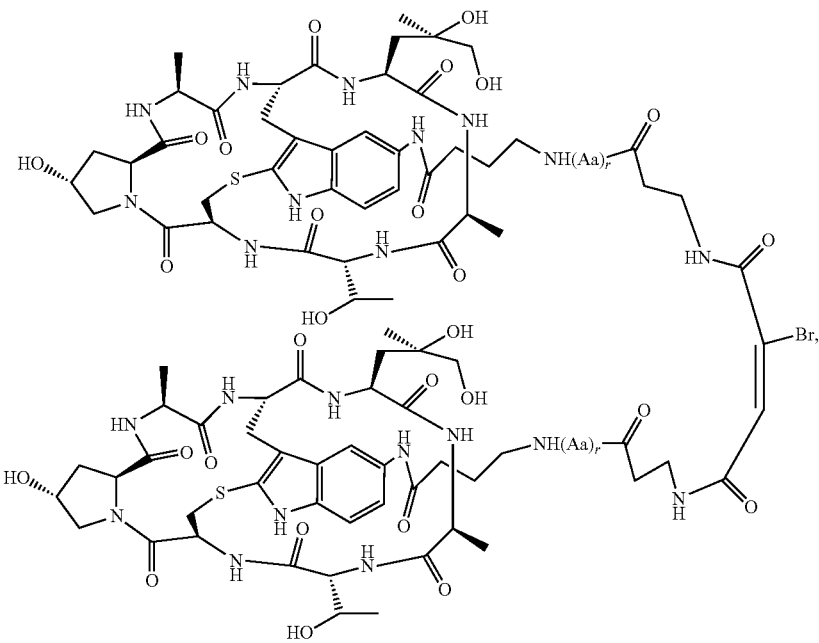
(I-52)
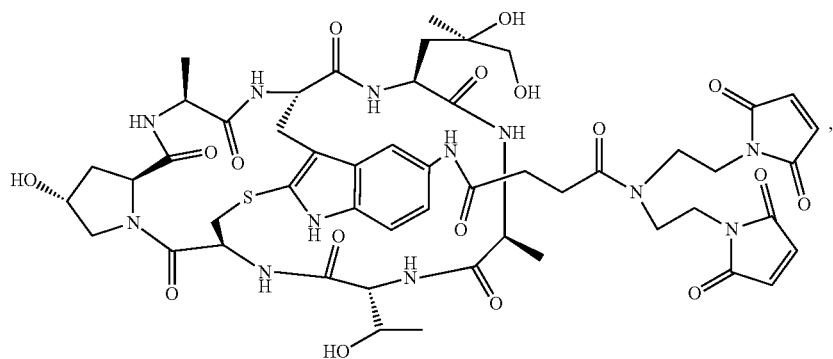
(I-53)
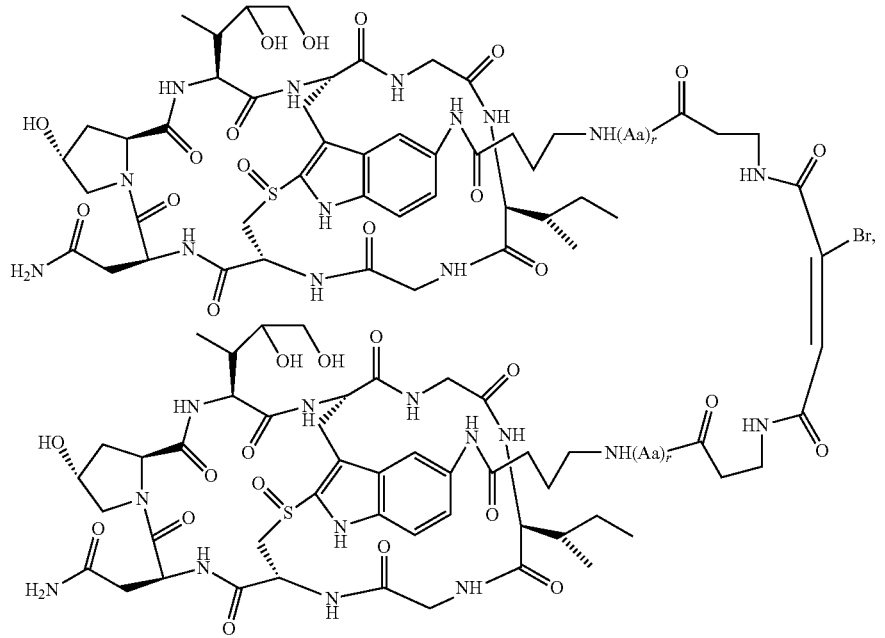

(I-54)
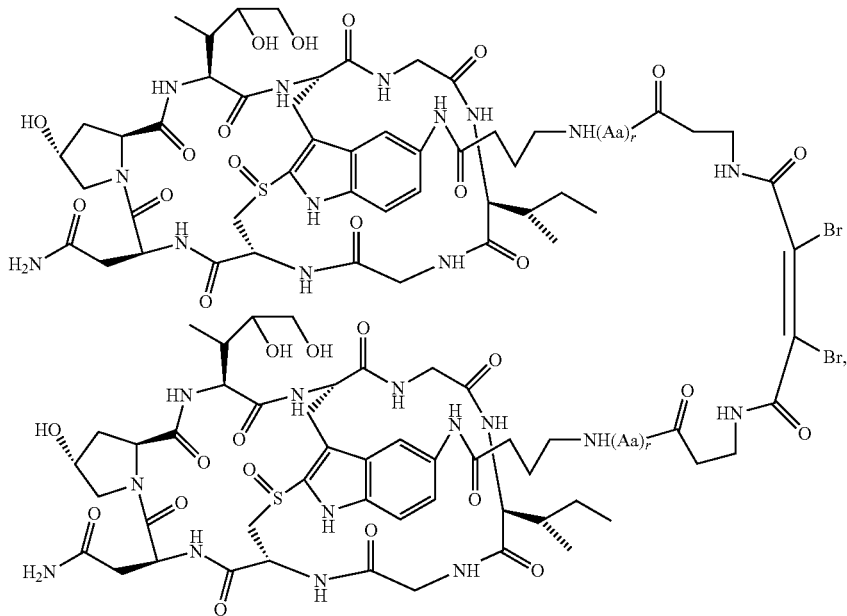
(I-55)
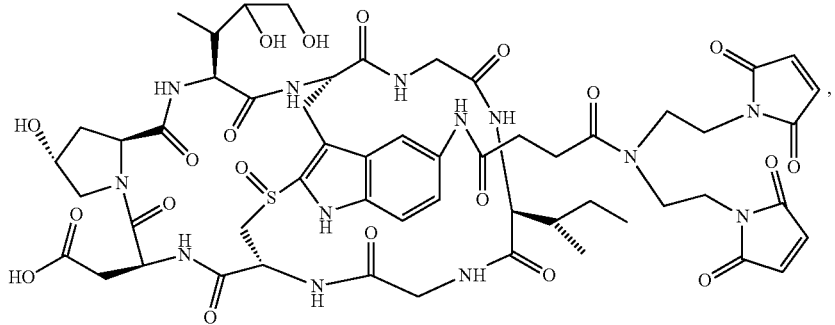
(I-56)
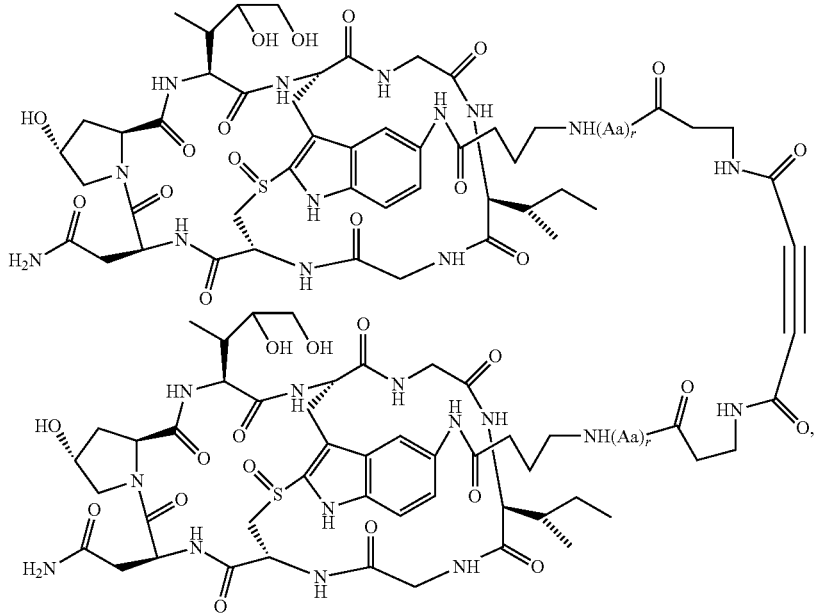

(I-57)
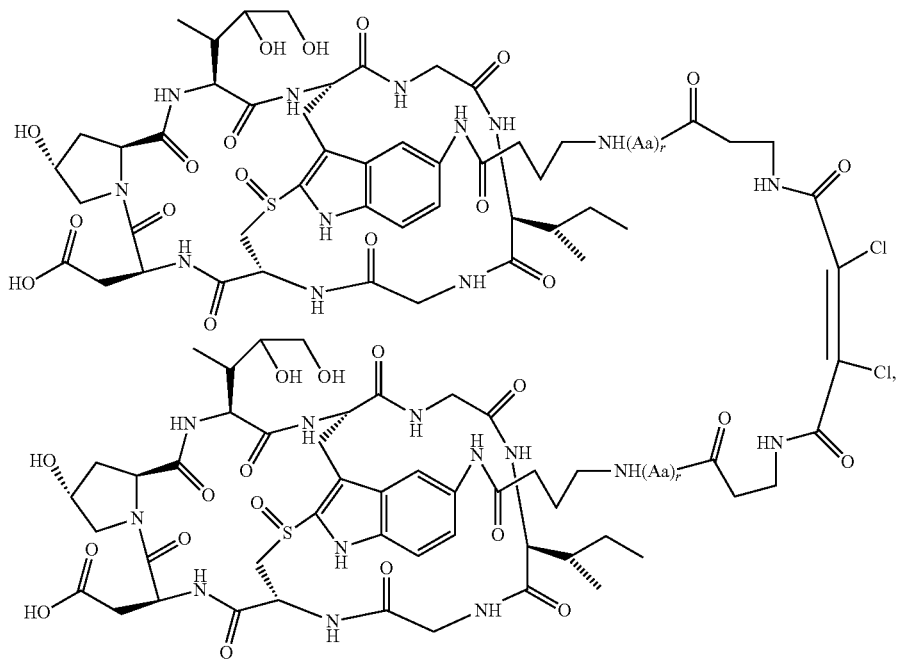
(I-58)
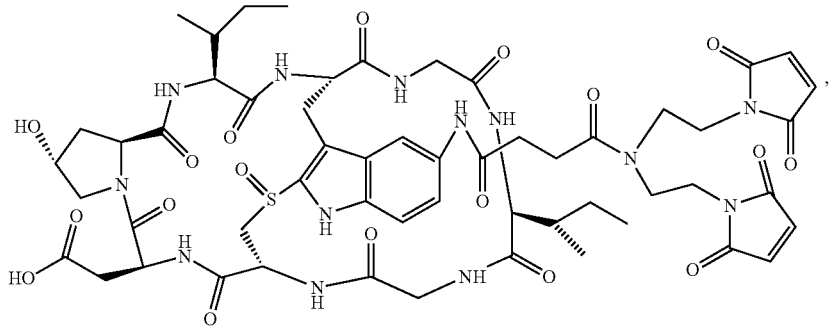
(I-59)
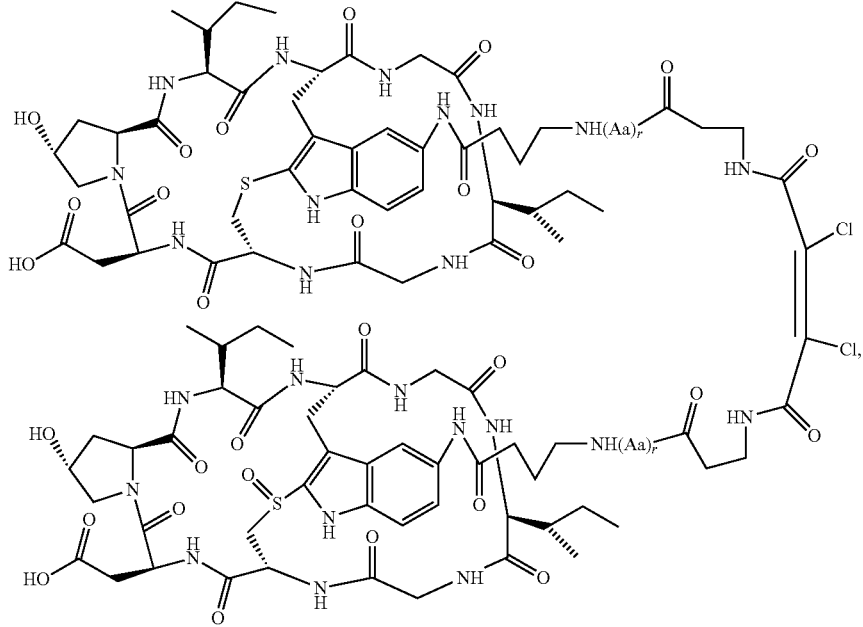

(I-60)
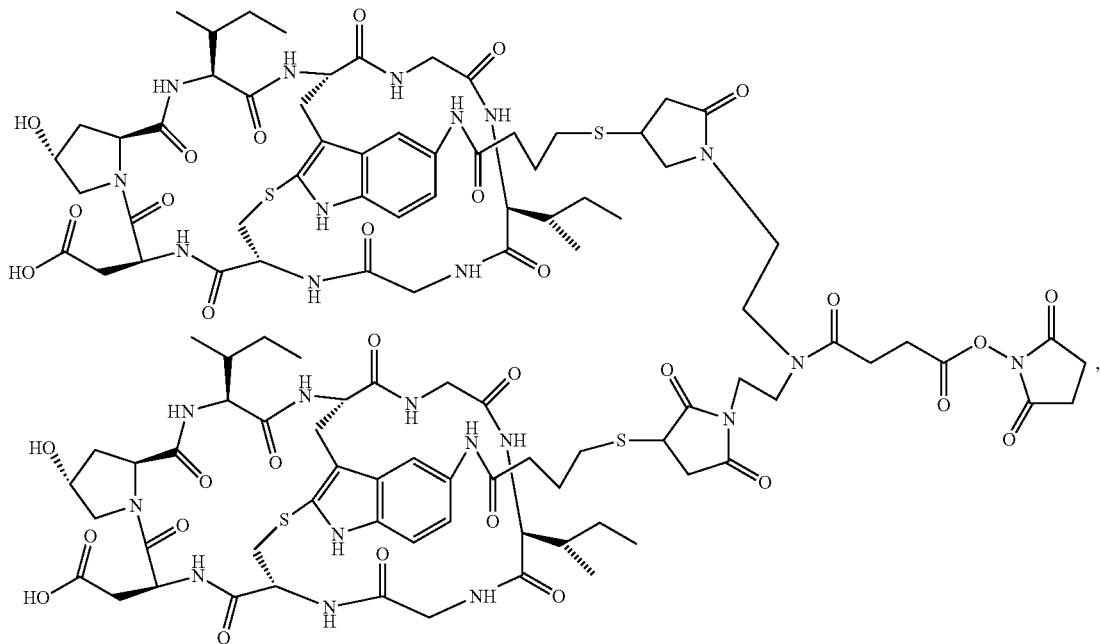
(I-61)
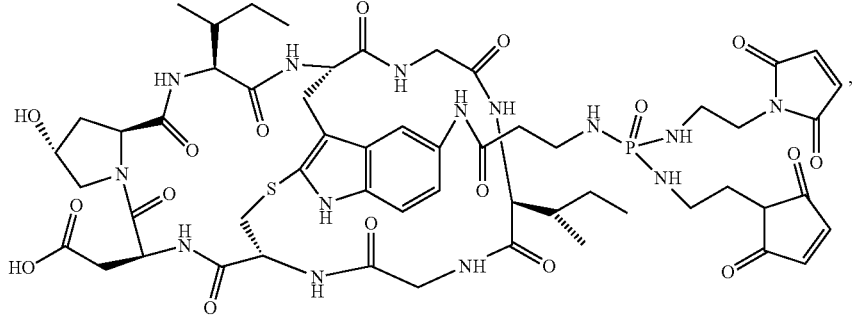
(I-62)
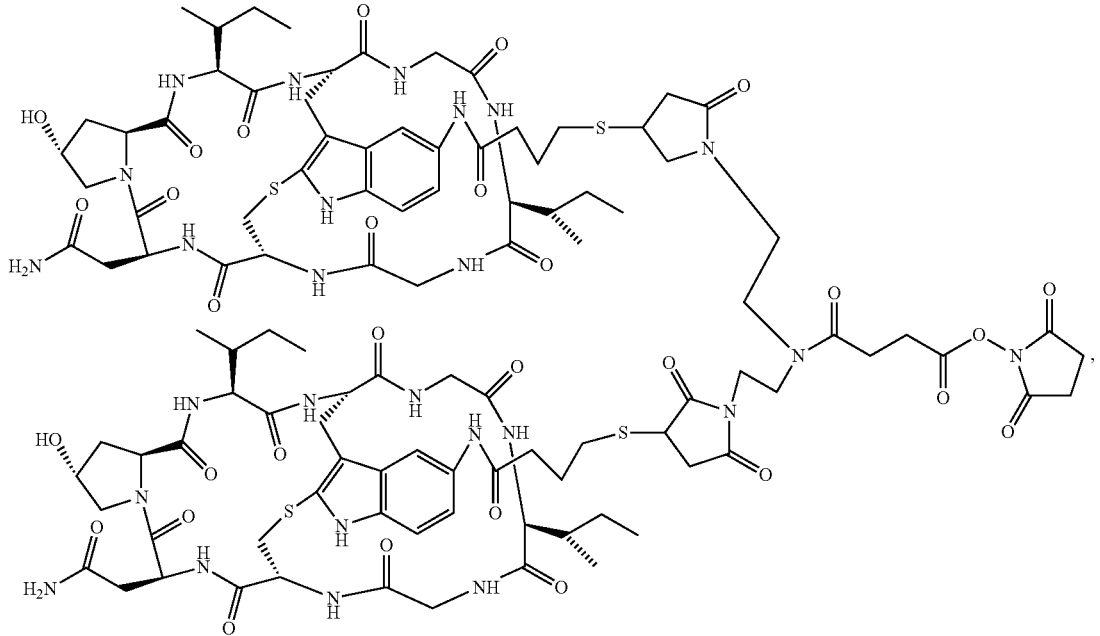

(I-63)
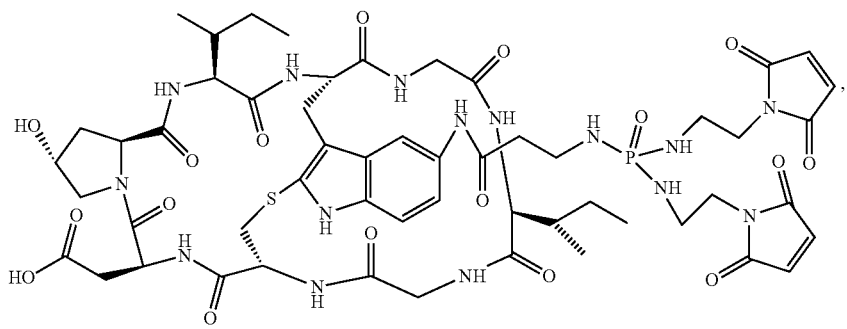
(I-64)
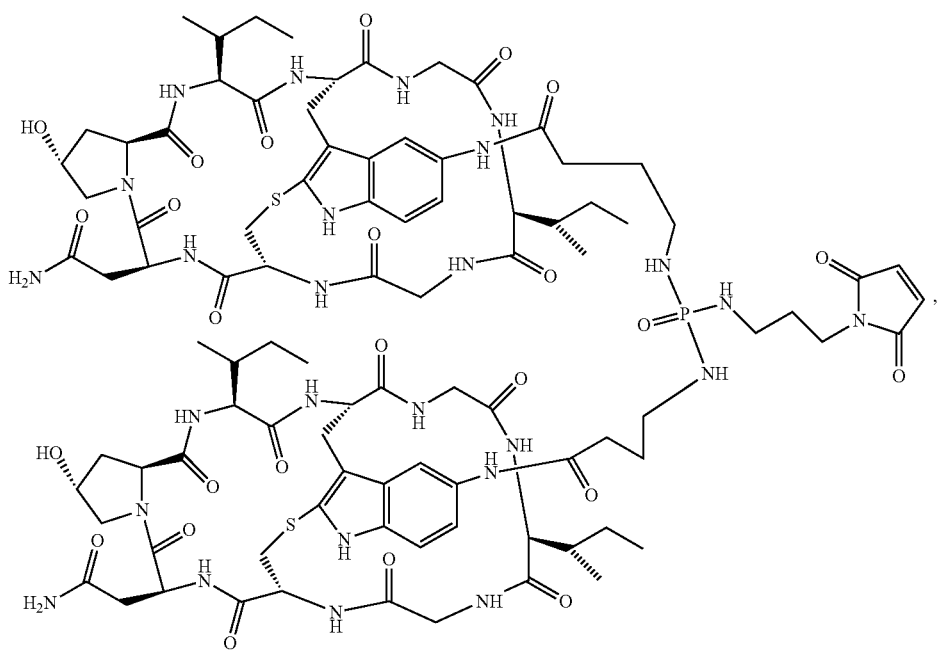
(I-65)
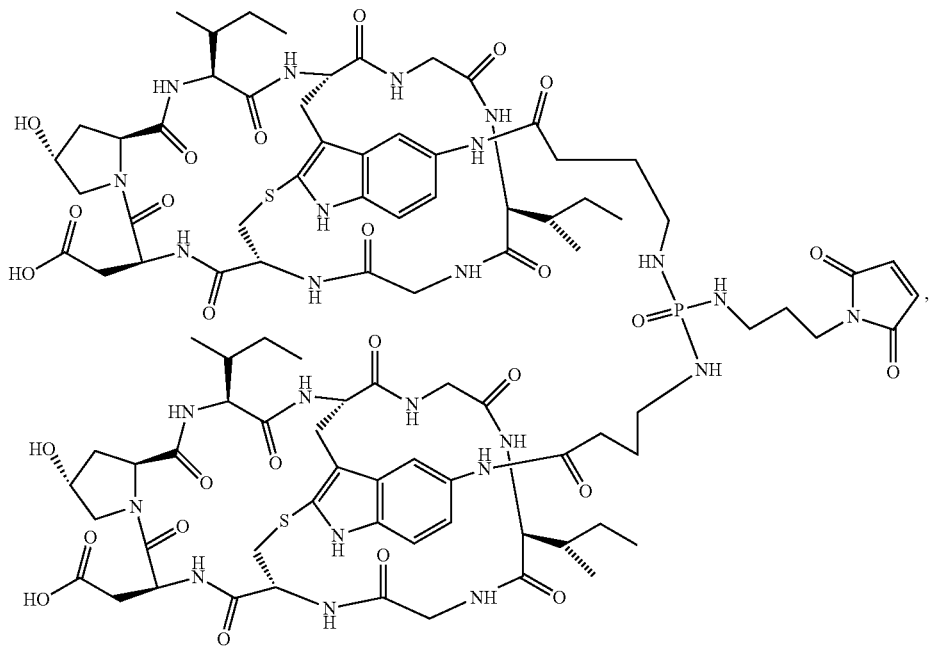

(I-66)
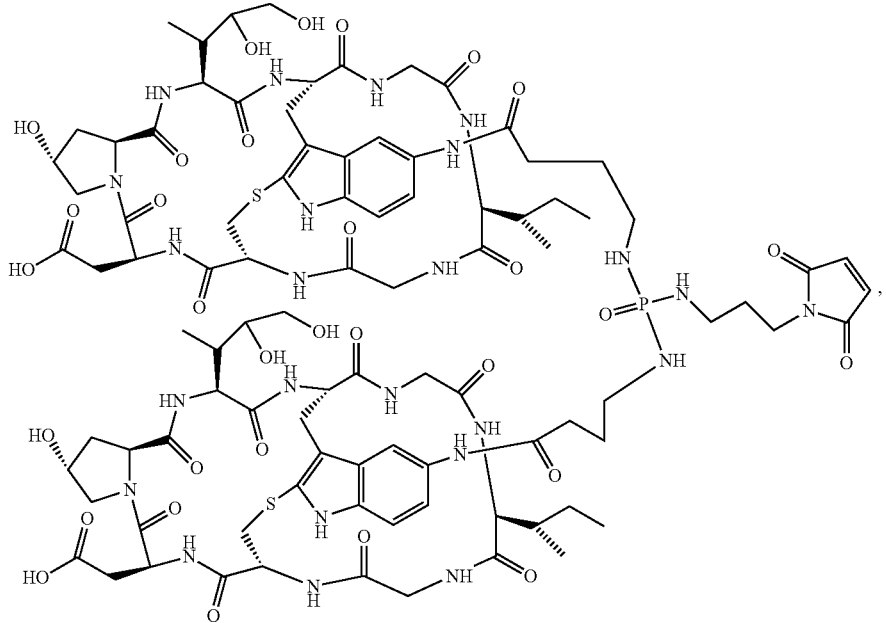
(I-67)
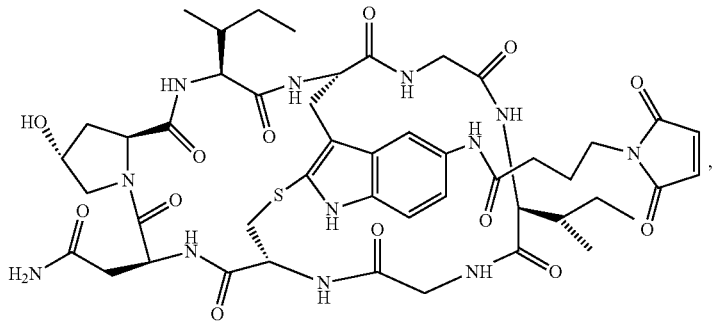
(I-68)
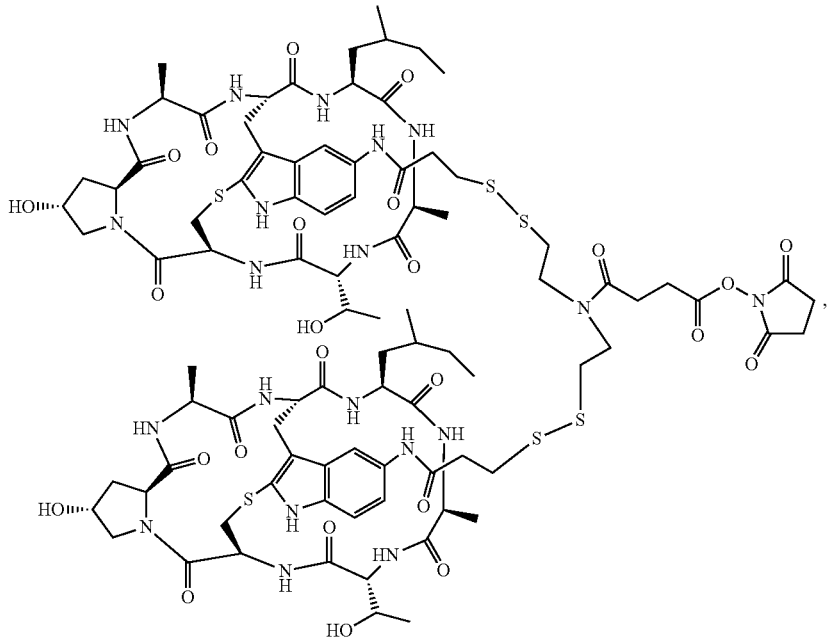

-continued
(I-69)
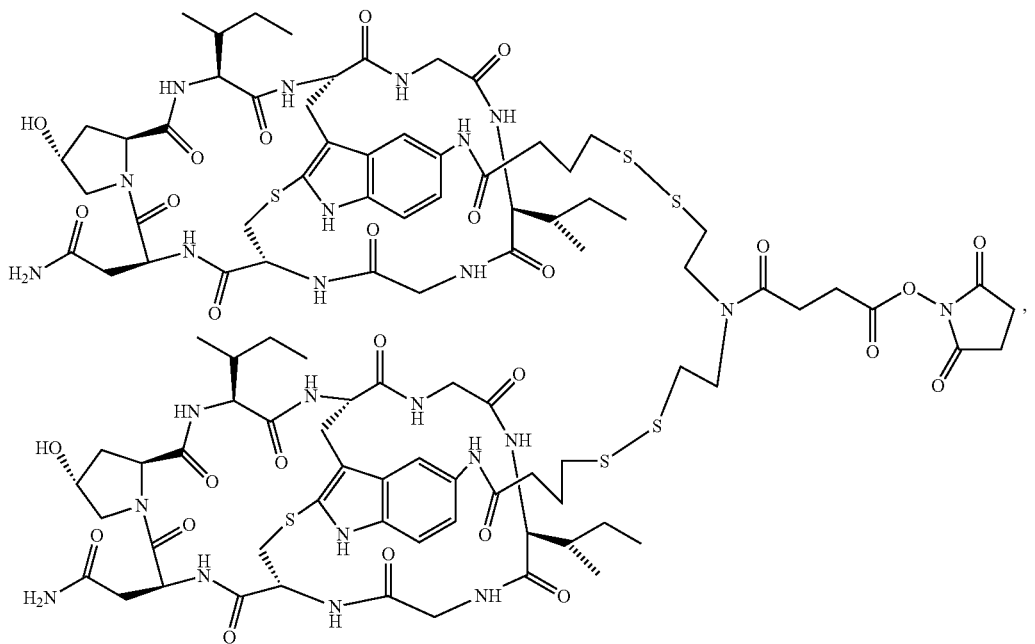
(I-70)
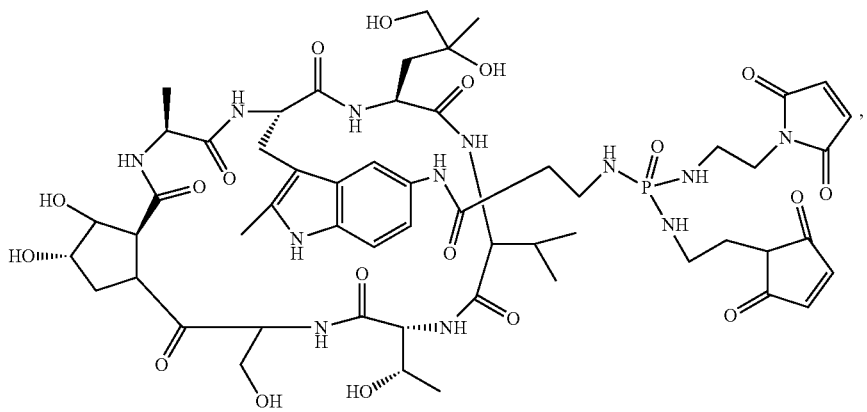
(I-71)
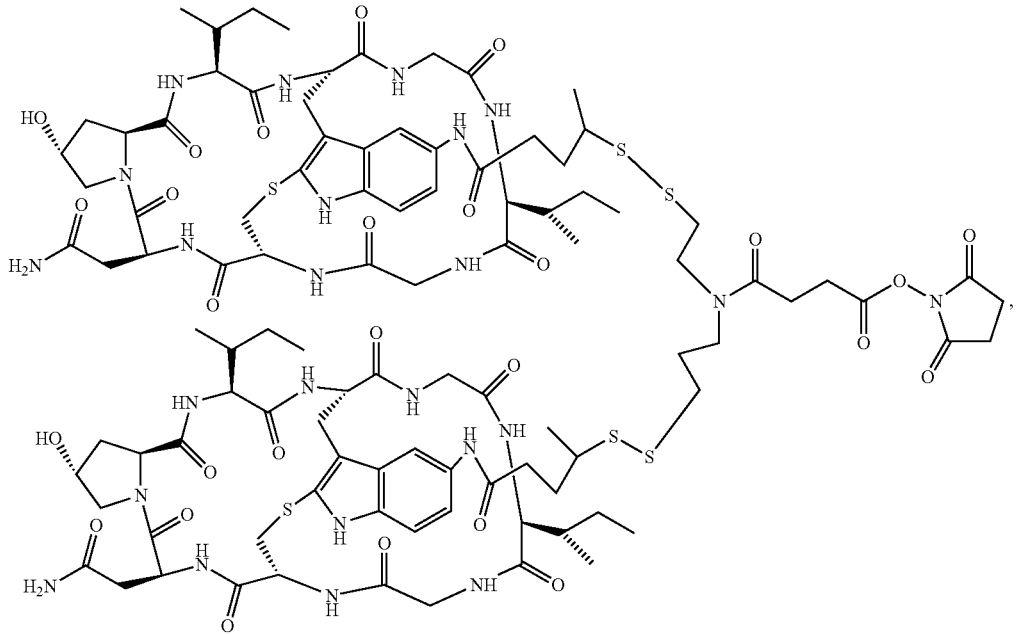

-continued
(I-72)
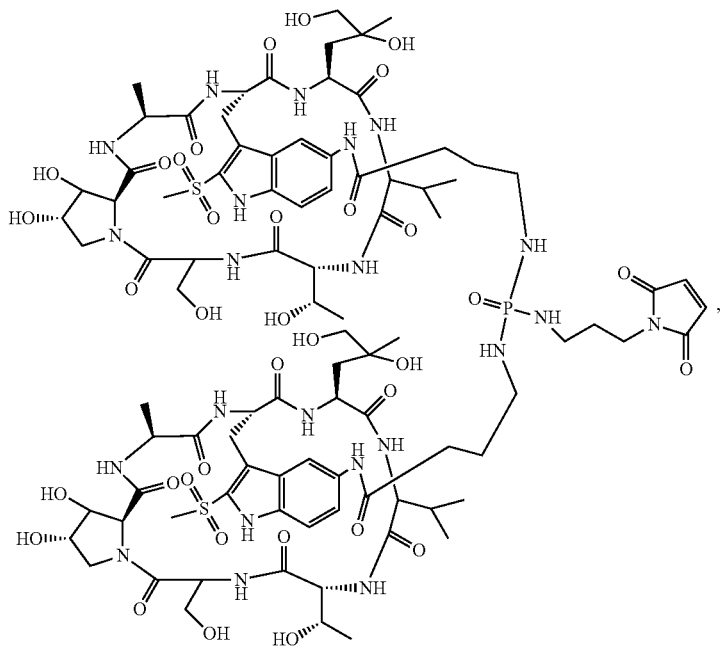
(I-73)
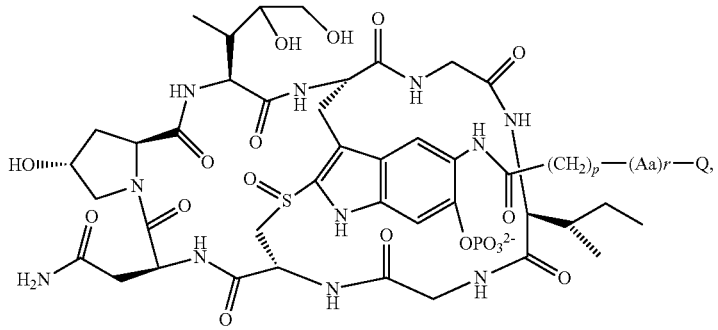
(I-74)
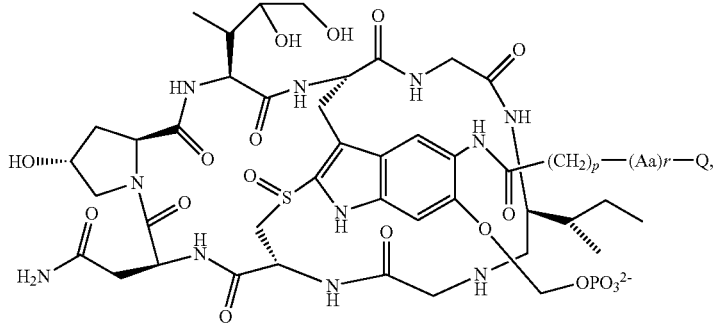
(I-75)
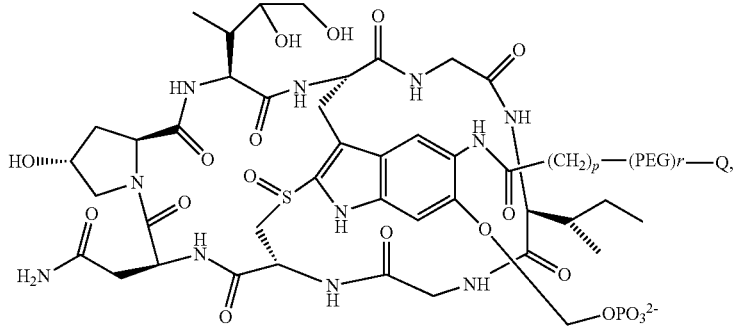

(I-76)
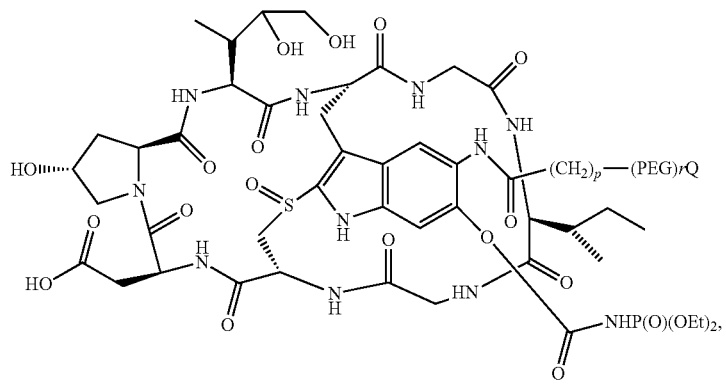
(I-77)
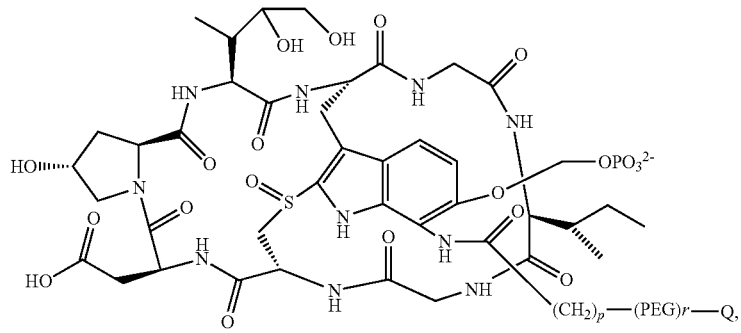
(I-78)
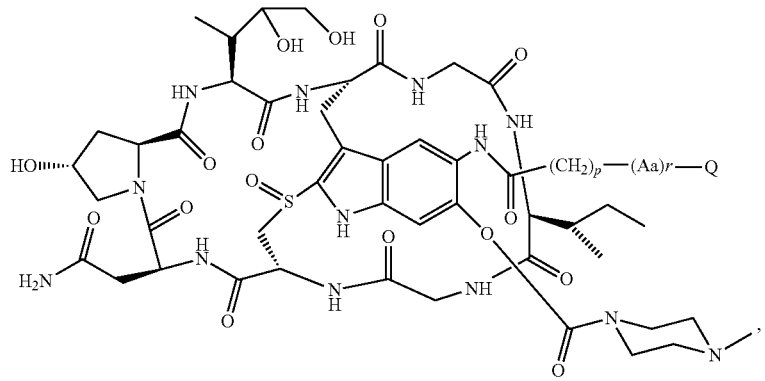
(I-79)
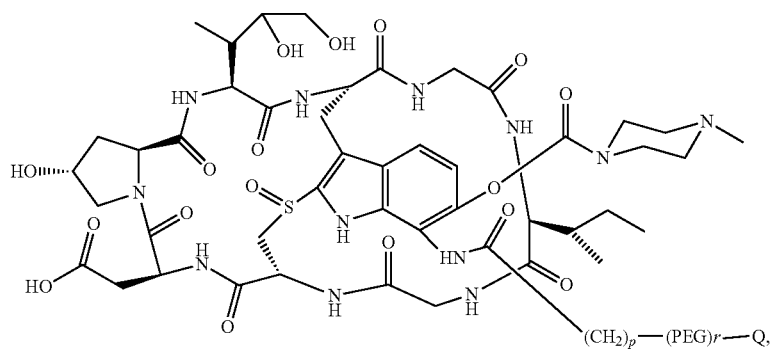

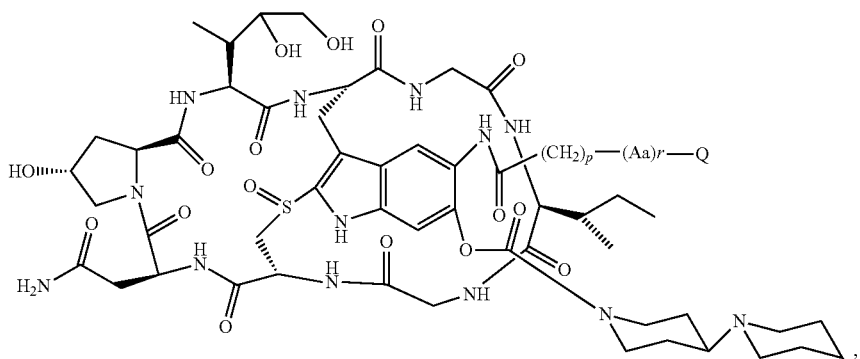
(I-80)
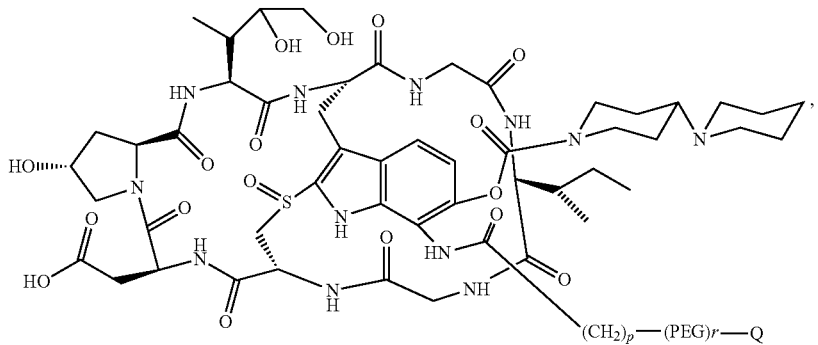
(I-81)
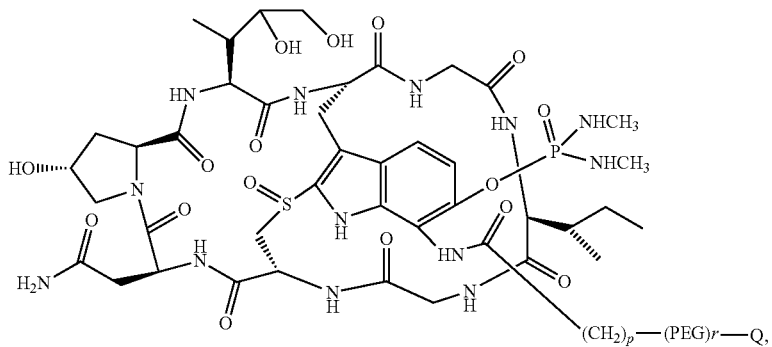
(I-82)
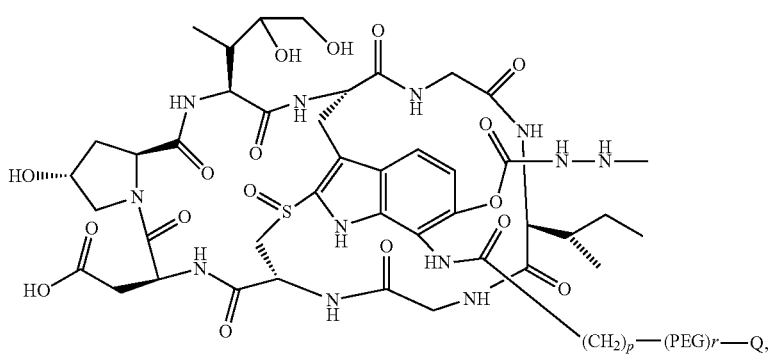
(I-83)

(I-84)
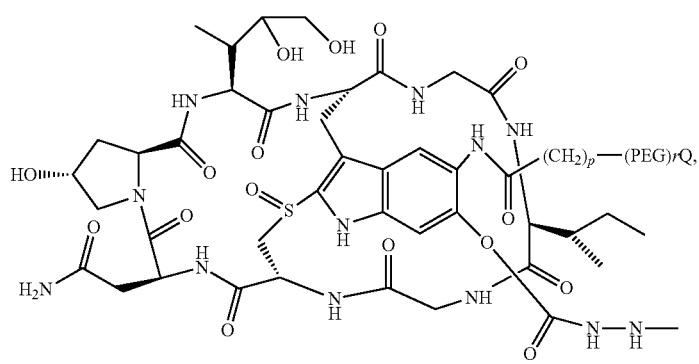
(I-85)
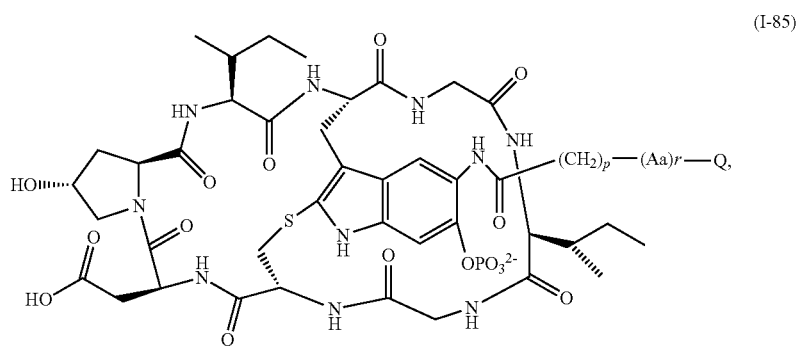
(I-86)
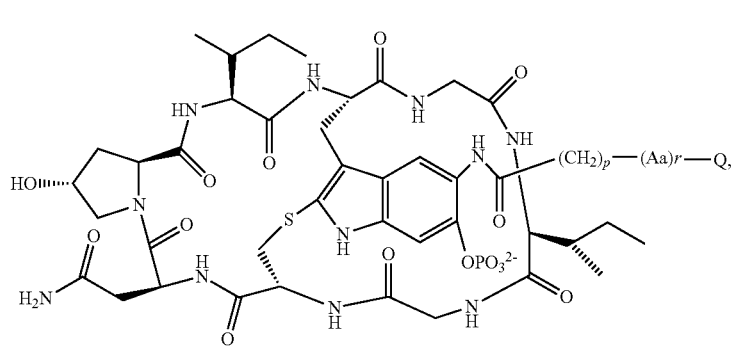
(I-87)
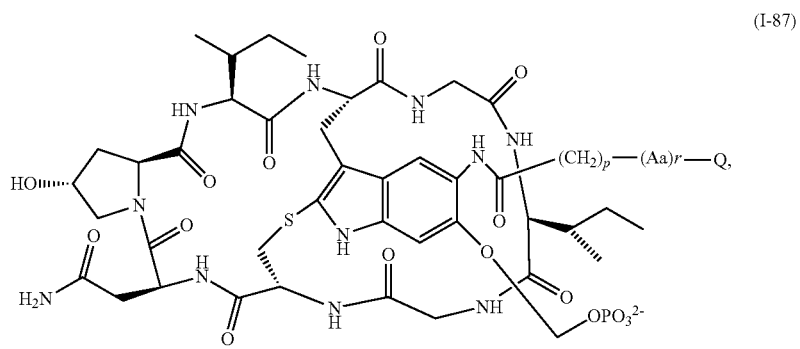

-continued
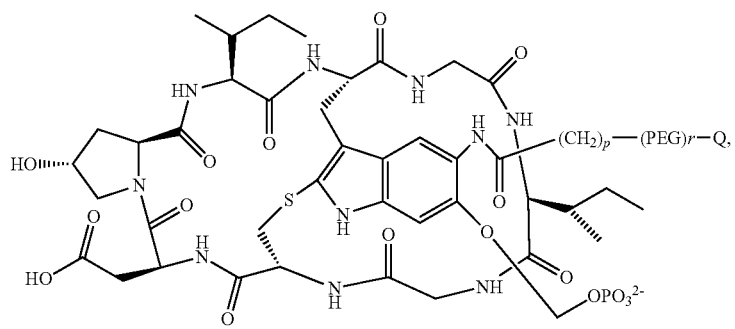
(I-88)
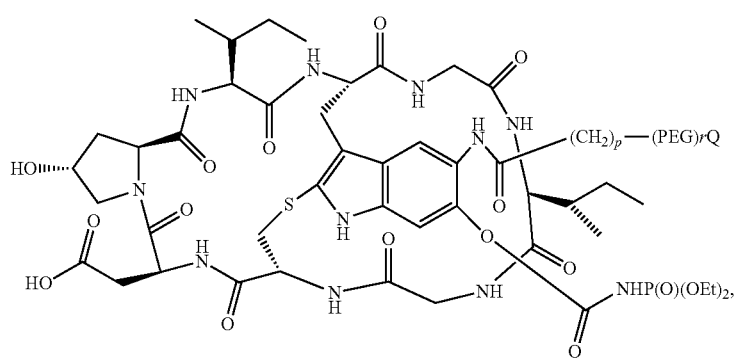
(I-89)
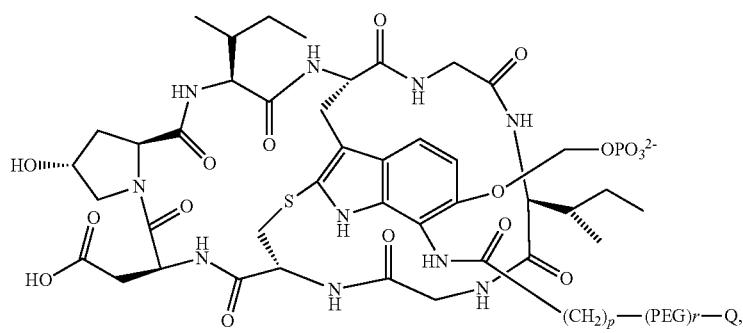
(I-90)
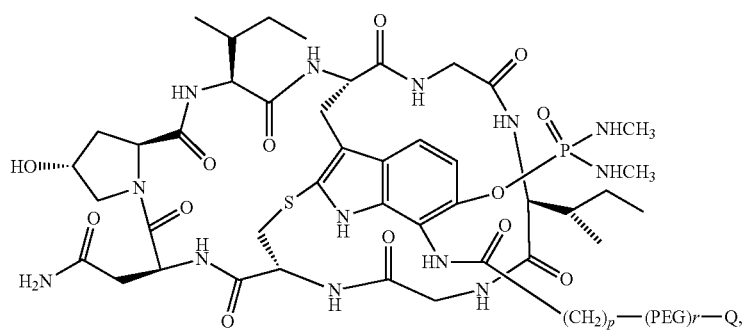
(I-91)

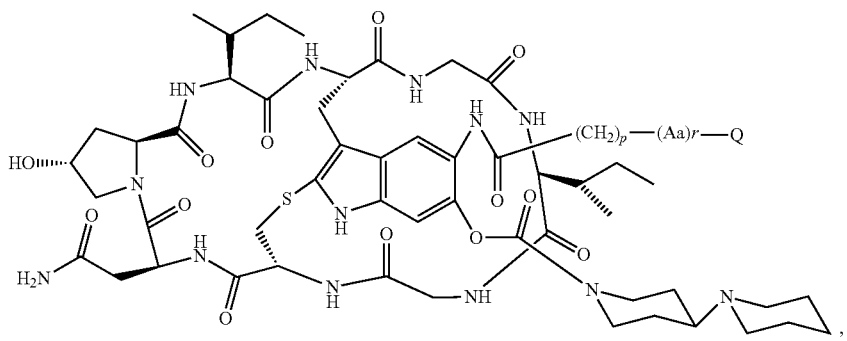
(I-92)
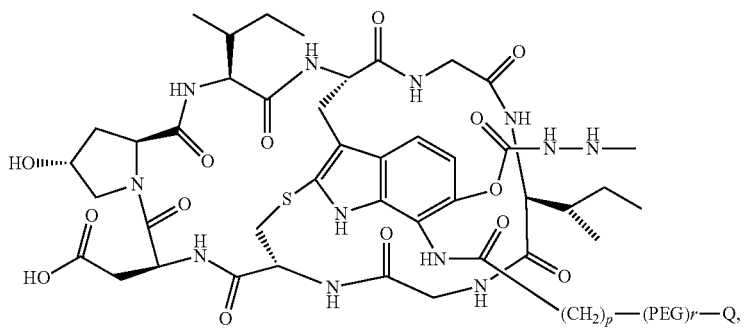
(I-93)
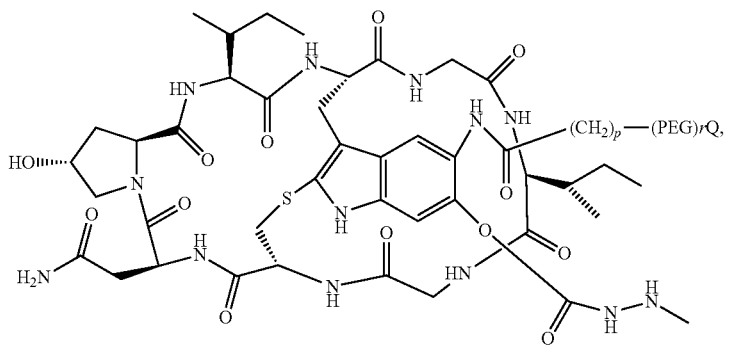
(I-94)
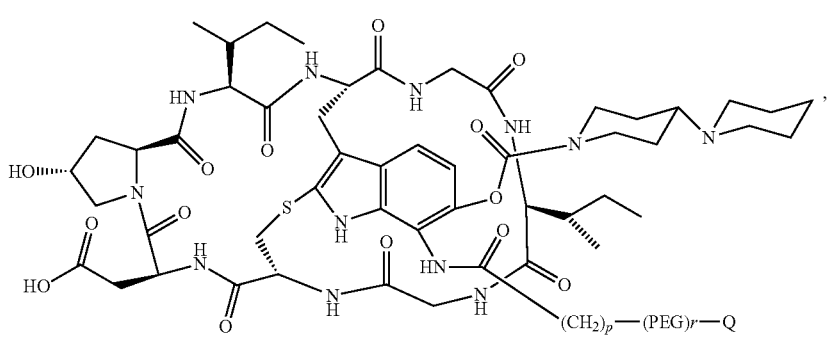
(I-95)

(I-96)

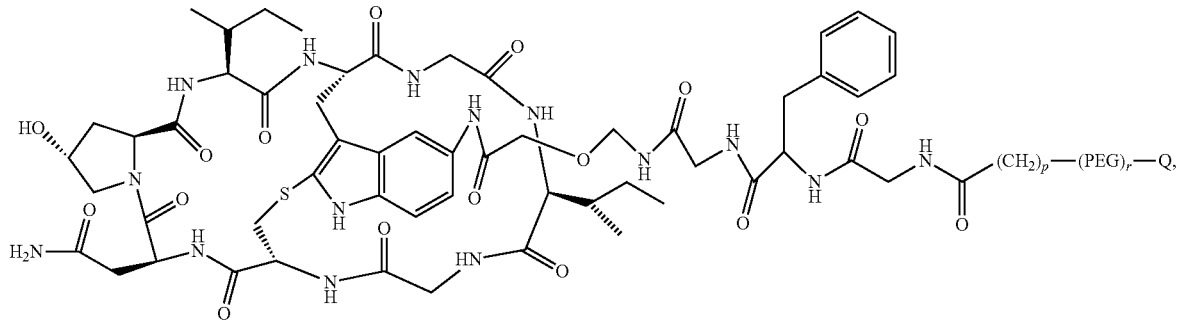

(I-97)

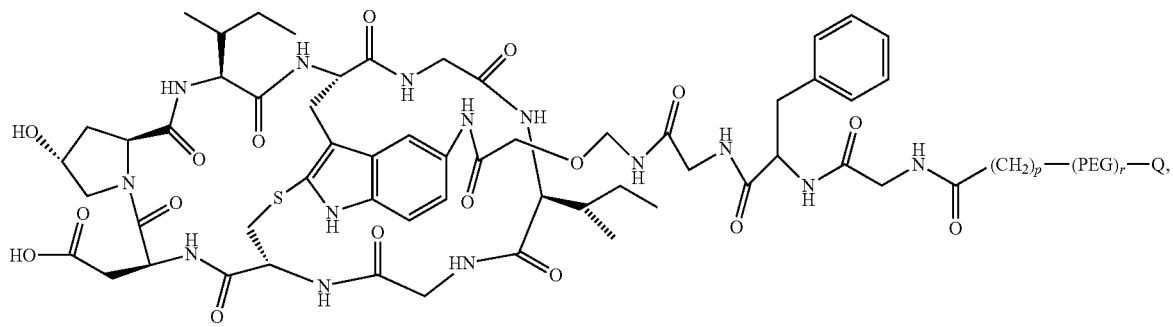

or a pharmaceutically acceptable salt, hydrate, hydrated salt, or polymorphic crystalline structure thereof, or an optical isomer, racemate, diastereomer or enantiomer thereof, wherein Aa, r, n, p, q and Q are defined the same as in the claim 1; PEG is polyethylene glycol with the formula of —(OCH$_2$CH$_2$)$_r$.

7. A method for preparing the compound according to claim 1, comprising sequentially (i) aromatic nitration of an indole unit, (ii) reduction of a nitro group on a benzene ring of the indole unit to an amine, and (iii) condensation of the produced amine compound with a linker having a reactive or a reactable carboxylic group to form an amide linkage as illustrated below:

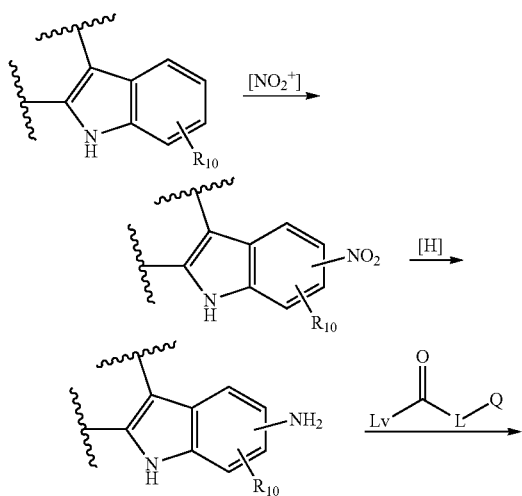

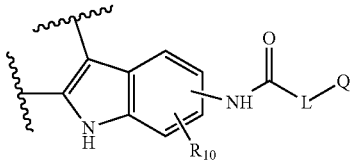

wherein R$_{10}$, L and Q are defined the same as in claim 1, wherein Lv is leaving group selected from the group consisting of OH, halogen, NHS (N-hydroxyl succinimide), nitrophenol, pentalfluorophenol, and an intermediate generated from peptide coupling and from Mitsunobu reaction.

8. The compound according to claim 1, wherein the linker L is selected from the group consisting of: R$_{12}$, OR$_{12}$, OR$_{12}$O, NHR$_{12}$, NHR$_{12}$NH, NR$_{11}$R$_{12}$, SR$_{12}$S, OR$_{12}$NH, OR$_{12}$Ar, NHR$_{12}$Ar, NR$_{11}$R$_{12}$NR$_{12}$'R$_{12}$", —(CR$_{11}$R$_{12}$)$_p$(Aa)$_r$ (CR$_{12}$'R$_{12}$")$_q$(OCH$_2$CH$_2$)$_r$, —(CR$_{11}$R$_{12}$)$_p$(CR$_{12}$'R$_{12}$")$_q$(Aa)$_r$ (OCH$_2$CH$_2$)$_r$—, -(Aa)$_r$(CR$_{11}$R$_{12}$)$_p$(CR$_{12}$'R$_{12}$")$_q$— (OCH$_2$CH$_2$)$_r$, —(CR$_{11}$R$_{12}$)$_p$(CR$_{12}$'R$_{12}$")$_n$(OCH$_2$CH$_2$)$_t$(Aa)$_r$, —(CR$_{11}$R$_{12}$)$_p$(CH=CH)(CR$_{12}$'R$_{12}$")$_q$(Aa)$_r$(OCH$_2$CH$_2$)$_r$, —(CR$_{11}$R$_{12}$)$_p$(NR$_{12}$'CO)(Aa)$_r$(CR$_{12}$'R$_{12}$'—(OCH$_2$CH$_2$)$_r$, —(CR$_{11}$R$_{12}$)$_p$(Aa)$_r$(NHCO)(CR$_{12}$'R$_{12}$")$_q$—(OCH$_2$CH$_2$)$_r$, (CR$_{11}$R$_{12}$)$_p$(OCO)(Aa)$_r$-(CR$_{12}$'R$_{12}$")$_q$—(OCH$_2$CH$_2$)$_r$, —(CR$_{11}$R$_{12}$)$_p$(OCNR$_7$)(Aa)$_r$(CR$_{12}$'R$_{12}$")$_q$(OCH$_2$CH$_2$)$_r$, —(CR$_{11}$R$_{12}$)$_p$(CO)-(Aa)$_r$(CR$_{12}$'R$_{12}$")$_q$(OCH$_2$CH$_2$)$_r$, —(CR$_{11}$R$_{12}$)$_p$(NR$_{11}$CO)(Aa)$_r$(CR$_{12}$'R$_{12}$")$_q$(OCH$_2$CH$_2$)$_r$, —(CR$_{11}$R$_{12}$)$_p$—(OCO)(Aa)$_r$(CR$_{12}$'R$_{12}$")$_q$—(OCH$_2$CH$_2$)$_r$, —(CR$_{11}$R$_{12}$)$_p$(OCNR$_7$)(Aa)$_r$(CR$_{12}$'R$_{12}$")$_q$(OCH$_2$CH$_2$)$_r$, —(CR$_{11}$R$_{12}$)$_p$(CO)(Aa)$_r$(CR$_{12}$'R$_{12}$")$_q$(OCH$_2$CH$_2$)$_r$, —(CR$_{11}$R$_{12}$)$_p$-phenyl-CO(Aa)$_r$(CR$_{12}$'R$_{12}$")$_q$, —(CR$_{11}$R$_{12}$)$_p$ —(CR$_{11}$R$_{12}$)$_p$-furyl-CO-(Aa)$_r$(CR$_{12}$'R$_{12}$")$_q$, —(CR$_{11}$R$_{12}$)$_p$- oxazolyl-CO(Aa)$_r$(CR$_{12}$'R$_{12}$")$_q$, —(CR$_{11}$R$_{12}$)$_p$-thiazolyl-CO(Aa)$_r$(CR$_{12}$'R$_{12}$")$_q$, —(CR$_{11}$R$_{12}$)$_p$-thienyl-CO (CR$_{12}$'R$_{12}$")$_q$, —(CR$_{11}$R$_{12}$)$_p$-imidazolyl-CO—

$(CR_{12}'R_{12}")_q$—, $(CR_{12}'R_{12}")_q$—, $(CR_{12}'R_{12}")_q$—, $(Aa)_r(CR_{12}'R_{12}")_q$—, —$(CR_{11}R_{12})_p$-(Aa)$_r$-furyl-, —$(CR_{11}R_{12})_p$-thiazolyl-(Aa)$_r$-, —$(CR_{11}R_{12})_p$-imidazolyl(Aa)$_r$-, —$(CR_{11}R_{12})_p$-morpholino-(Aa)$_r$-, —$(CR_{11}R_{12})_p$N-methylpiperazino-(Aa)$_r$-, —$(CR_{11}R_{12})_p$-morpholino-CO(Aa)$_r$-, —$(CR_{11}R_{12})_p$-piperazino-CO(Aa)$_r$-, —$(CR_{11}R_{12})_p$-N-methylpiperazin-CO (Aa)$_r$-phenyl-, —$(CR_{11}R_{12})_p$-oxazolyl(Aa)$_r$-, —$(CR_{11}R_{12})_p$-thienyl-(Aa)$_r$-, —$(CR_{11}R_{12})_p$N-methylpiperazino-(Aa)$_r$-, —K(CR$_{11}$R$_{12}$)$_p$-(Aa)$_r$(CR$_{12}$'R$_{12}$")$_q$ (OCH$_2$CH$_2$)$_t$, —K(CR$_{11}$R$_{12}$)$_p$(CR$_{11}$'R$_{12}$")$_q$(Aa)$_r$(OCH$_2$CH$_2$)$_t$, —K(Aa)$_r$(CR$_{11}$R$_{12}$)$_p$(CR$_{12}$'R$_{12}$")$_q$—(OCH$_2$CH$_2$)$_t$, —K(CR$_{11}$R$_{12}$)$_p$(CR$_{12}$'R$_{12}$")$_q$(OCH$_2$CH$_2$)$_t$(Aa)$_r$, —K(CR$_{11}$R$_{12}$)$_p$(CR$_7$=CR$_8$)(CR$_{12}$'R$_{12}$")$_q$-(Aa)$_r$(OCH$_2$CH$_2$)$_t$—, —K(CR$_{11}$R$_{12}$)$_p$(NR$_7$CO)(Aa)$_r$(CR$_{12}$'R$_{12}$")$_q$(OCH$_2$CH$_2$)$_t$, —K(CR$_{11}$R$_{12}$)$_p$(Aa)$_r$(NR$_7$—CO)(CR$_{12}$'R$_{12}$")$_q$(OCH$_2$CH$_2$)$_t$, —K(CR$_{11}$R$_{12}$)$_p$(OCO)(Aa)$_r$(CR$_{12}$'R$_{12}$")$_q$(OCH$_2$CH$_2$)$_t$, —K(CR$_{11}$R$_{12}$)p(OCNR$_7$)(Aa)$_r$(CR$_{12}$'R$_{12}$")$_q$(OCH$_2$CH$_2$)$_t$—, —K(CR$_{11}$R$_{12}$)$_p$(CO)(Aa)$_r$(CR$_{12}$'R$_{12}$")$_q$(OCH$_2$CH$_2$)$_t$, —K(—CR$_{11}$R$_{12}$)$_p$(NR$_{11}$CO)(Aa)$_r$(CR$_{12}$'R$_{12}$")$_q$(OCH$_2$CH$_2$)$_t$, —K(CR$_{11}$R$_{12}$)$_p$(OCO)(Aa)$_r$(CR$_{11}$'R$_{12}$")$_q$(OCH$_2$CH$_2$)$_t$, —K(CR$_{11}$R$_{12}$)$_p$(OCNR$_7$)(Aa)$_r$(CR$_{12}$'R$_{12}$")$_q$(OCH$_2$CH$_2$)$_t$, —K(CR$_{11}$R$_{12}$)$_p$(CO)(Aa)$_r$(CR$_{12}$'R$_{12}$")$_q$(OCH$_2$CH$_2$)$_r$Q, —K(CR$_{11}$R$_{12}$)$_p$-phenyl-CO-(Aa)$_r$(CR$_{12}$'R$_{12}$")$_q$—, —K(CR$_{11}$R$_{12}$)$_p$-furyl-CO(Aa)$_r$-(CR$_{12}$'R$_{12}$")$_q$, —K(CR$_{11}$R$_{12}$)$_p$-oxazolyl-CO(Aa)$_r$(CR$_{12}$'R$_{12}$")$_q$—, —K(CR$_{11}$R$_{12}$)$_p$-thiazolyl-CO(Aa)$_r$-(CR$_{12}$'R$_{12}$')$_q$, —K(CR$_{11}$R$_{12}$)$_p$-thienyl-CO(CR$_{12}$'R$_{12}$")$_q$—, —K(CR$_{11}$R$_{12}$)$_p$-thiazolyl-CO—(CR$_{12}$'R$_{12}$")$_q$, —K(CR$_{11}$R$_{12}$)$_p$-morpholino-CO(Aa)$_r$(CR$_{12}$'R$_{12}$")$_q$—, —K(CR$_{11}$R$_{12}$)$_p$-piperazino-CO-(Aa)$_r$(CR$_{12}$'R$_{12}$")$_q$—, —K(CR$_{11}$R$_{12}$)$_p$—N-methylpiperazin-CO(Aa)$_r$-(CR$_{11}$R$_{12}$")$_q$, —K(CR$_{11}$R$_{12}$)$_p$-(Aa)$_r$-phenyl-, —K(C$_{11}$R$_{12}$)$_m$-(Aa)$_r$-furyl-, —K(C$_{11}$R$_{12}$)$_p$-oxazolyl(Aa)$_r$-, —K(CR$_{11}$R$_{12}$)$_m$-thiazolyl-(Aa)$_r$-, —K(CR$_{11}$R$_{12}$)$_p$-thienyl-(Aa)$_r$, —K(CR$_{11}$R$_{12}$)$_p$-imidazolyl (Aa)$_r$, —K((CR$_{11}$R$_{12}$)$_m$-morpholino-(Aa)$_r$, —K(CR$_{11}$R$_{12}$)$_p$-piperazino-(Aa)$_r$-, and —K(CR$_{11}$R$_{12}$)$_m$N-methylpiperazino-(Aa)$_r$, wherein K is NR$_{12}$, O, S, Se, B, or C$_3$~C$_{10}$ of Ar or heterocyclic; wherein Aa, r, n, p, q, t, R$_7$, R$_{11}$, R$_{12}$, R$_{12}$', R$_{12}$" are as defined in claim 1.

9. The compound according to claim 1 having the following formula (II-1)-(II-91):

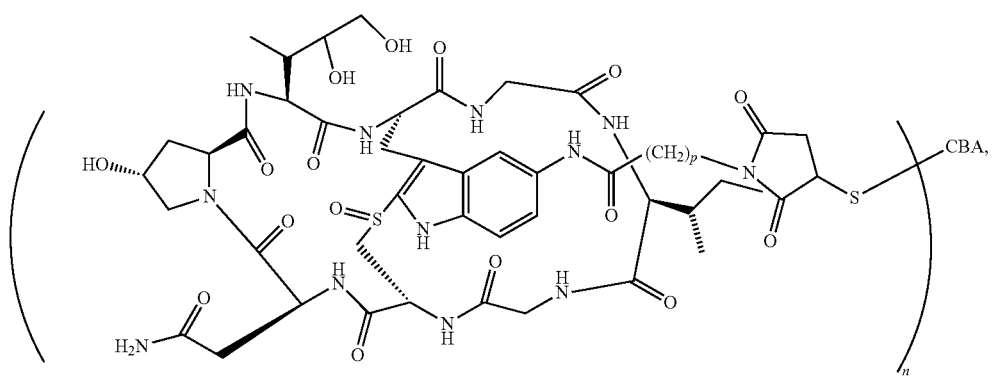

(II-1)

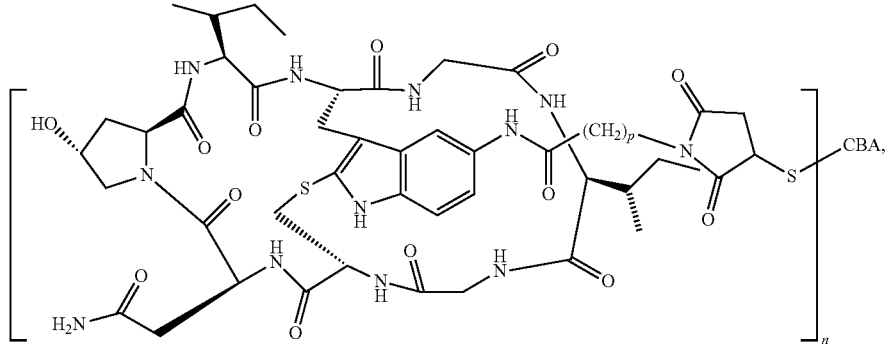

(II-2)

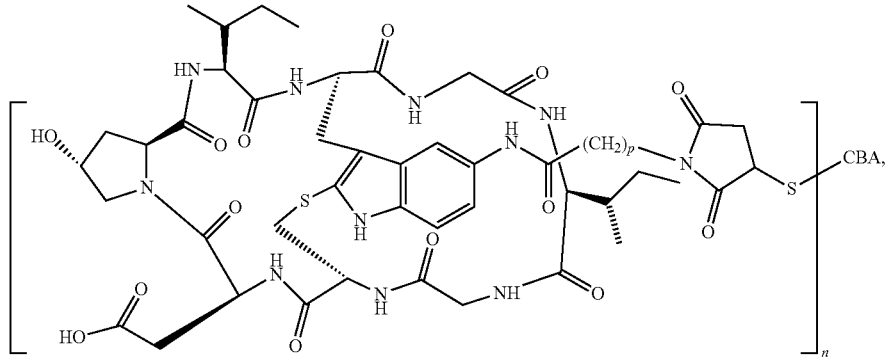

(II-3)

(II-4)
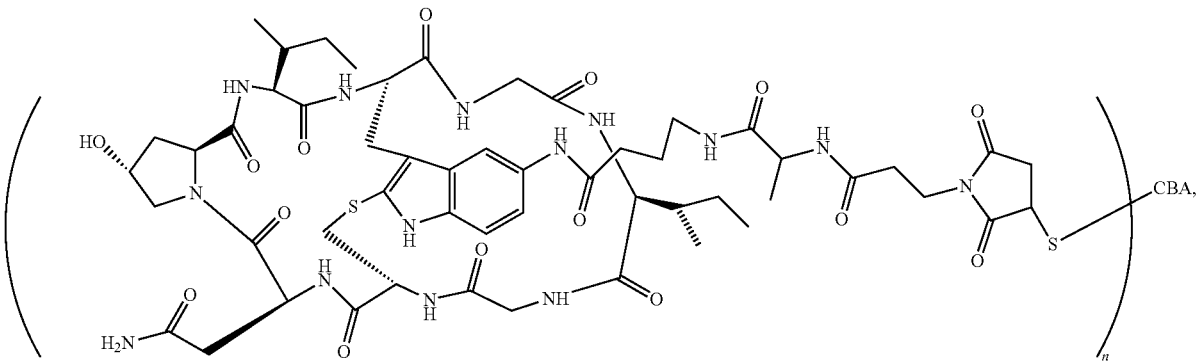
(II-5)
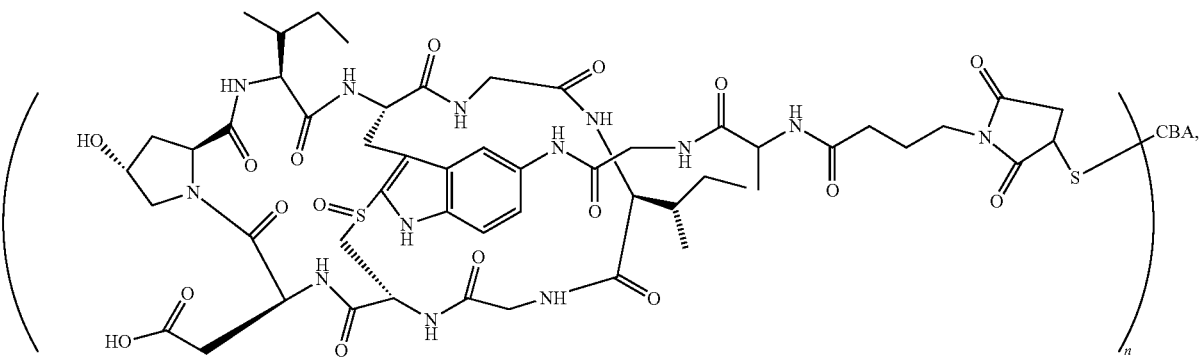
(II-6)
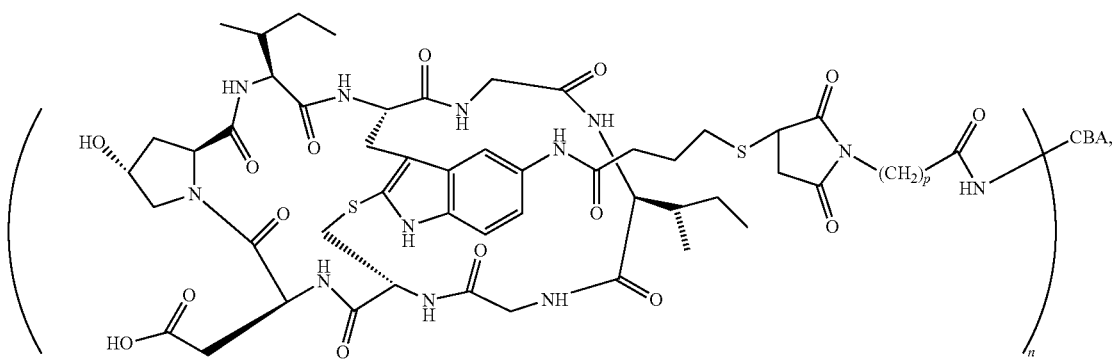
(II-7)
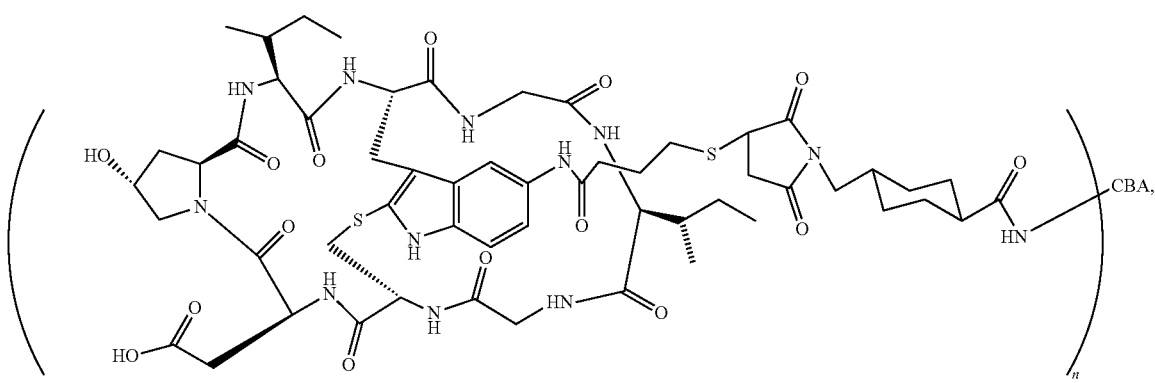

-continued
(II-8)
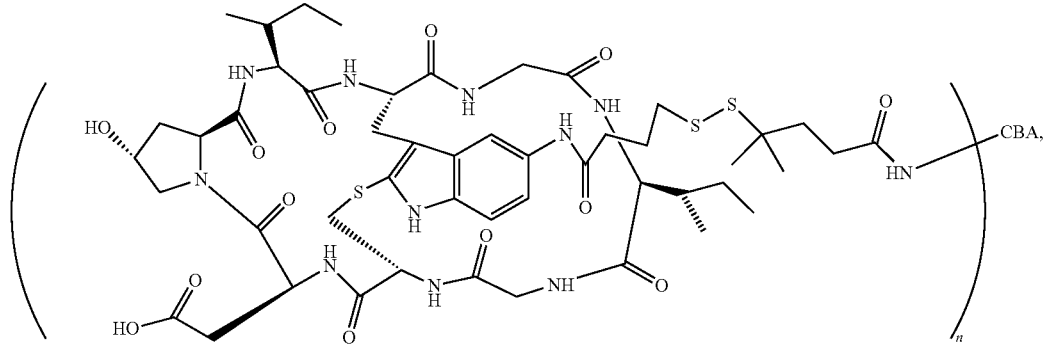
(II-9)
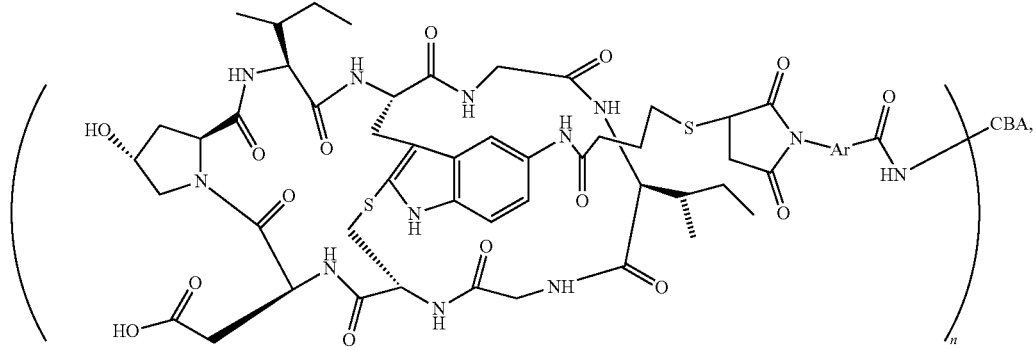
(II-10)
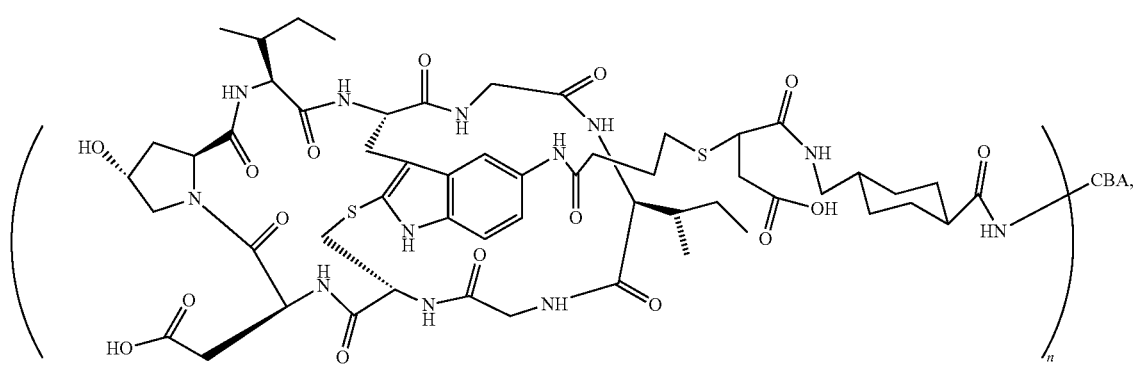
(II-11)
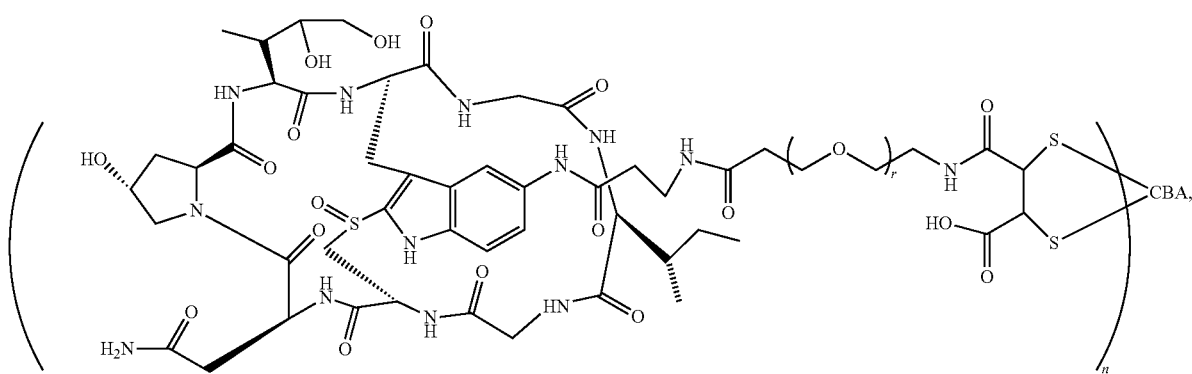

-continued
(II-12)
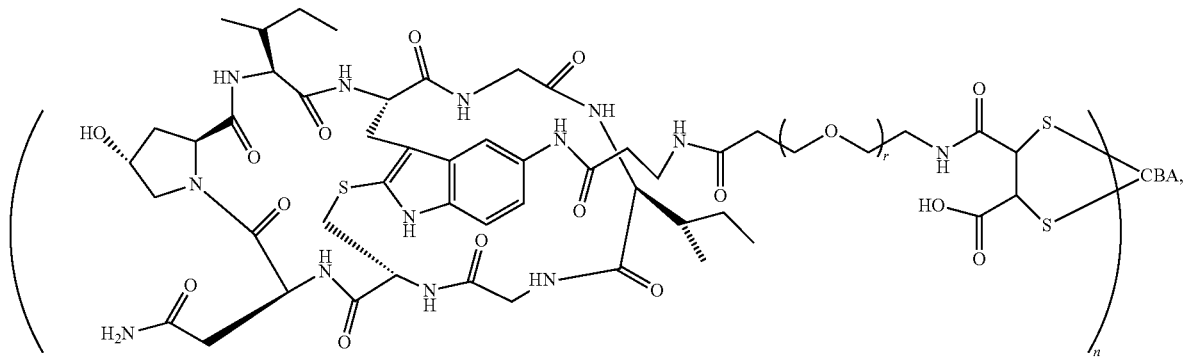
(II-13)
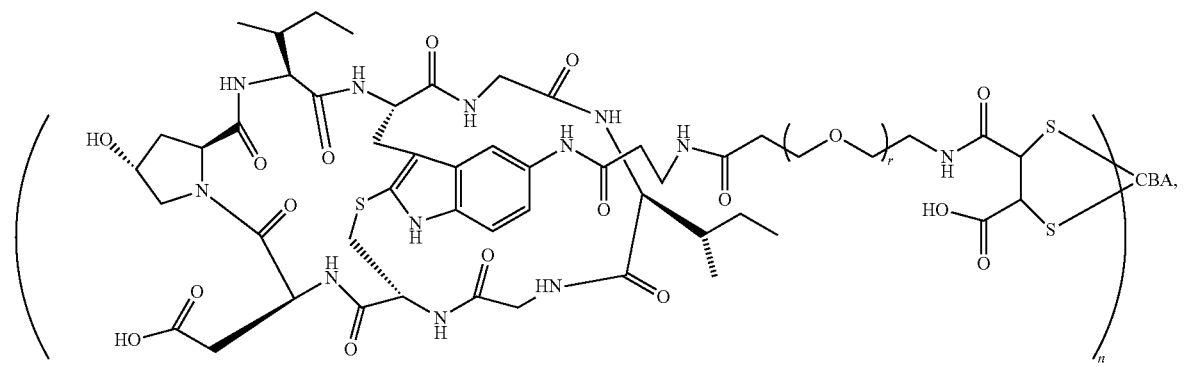
(II-14)
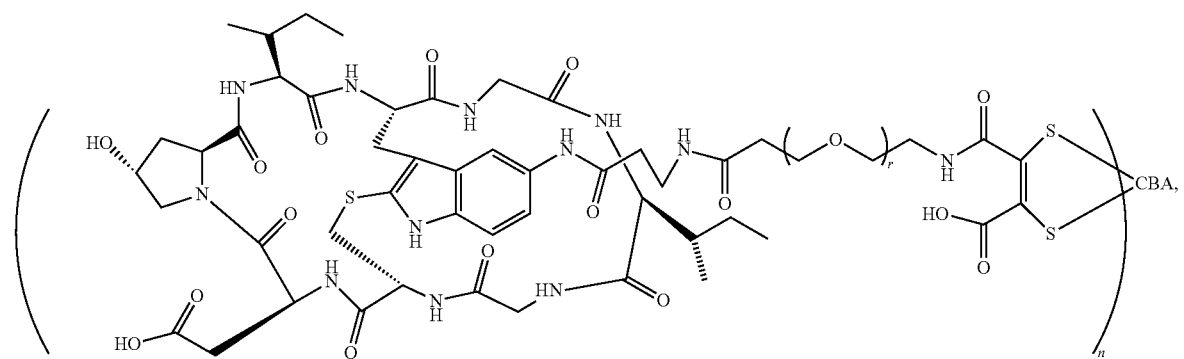
(II-15)
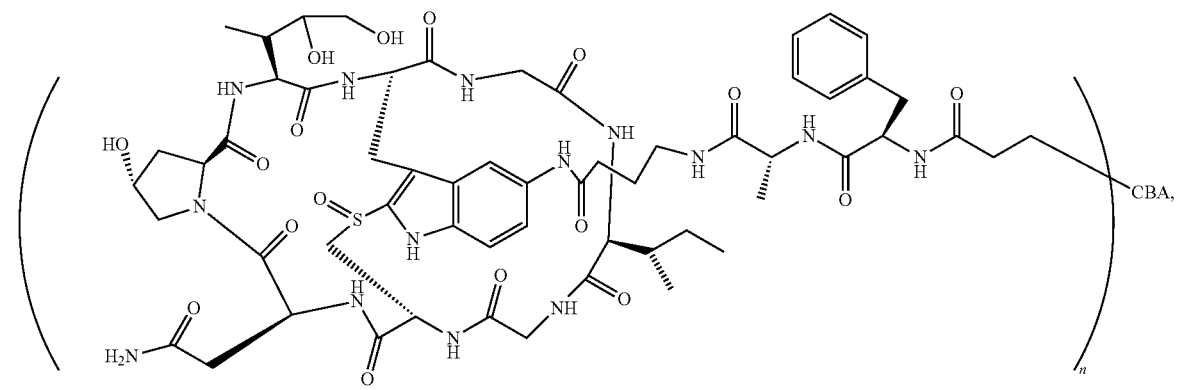

(II-16)
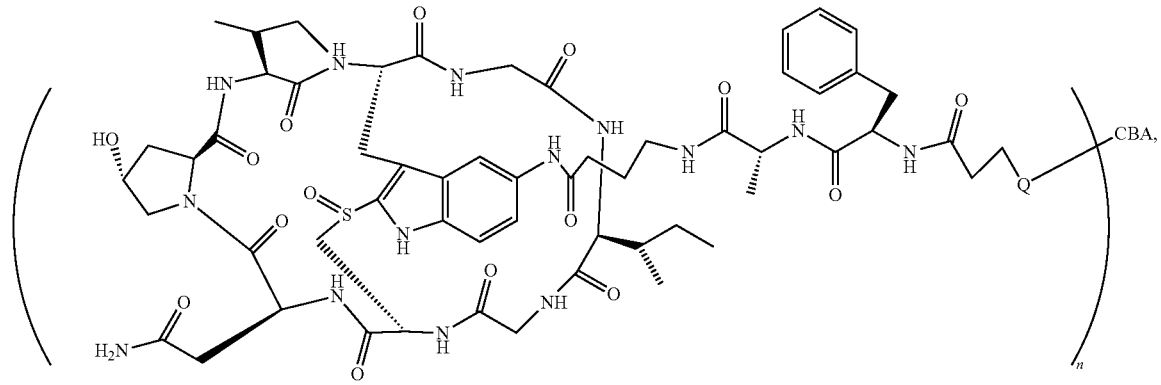
(II-16)
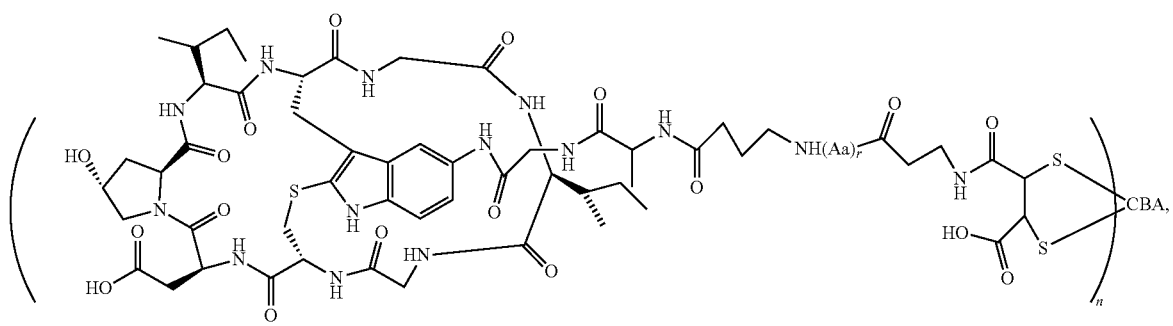
(II-17)
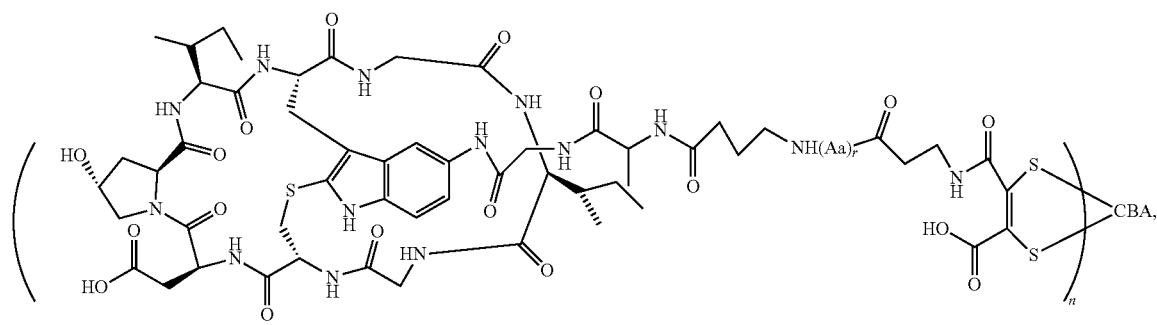
(II-18)
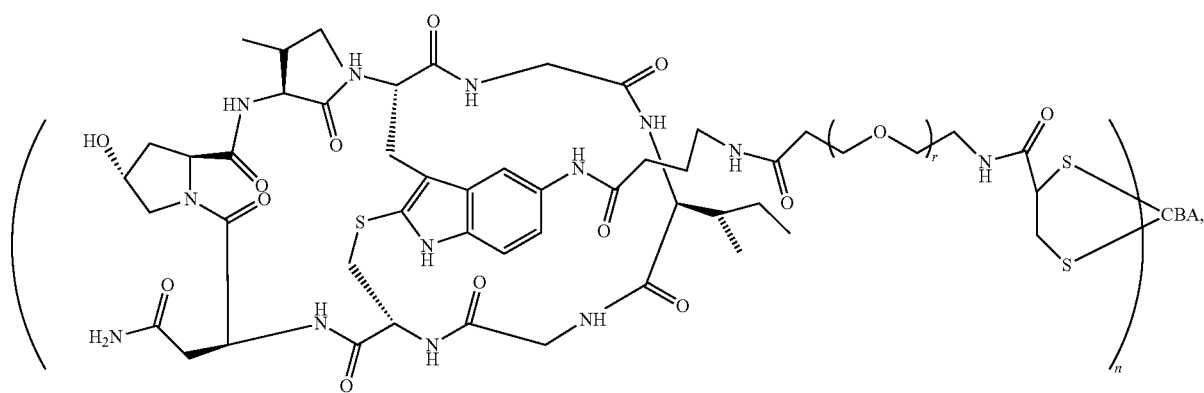

-continued
(II-19)
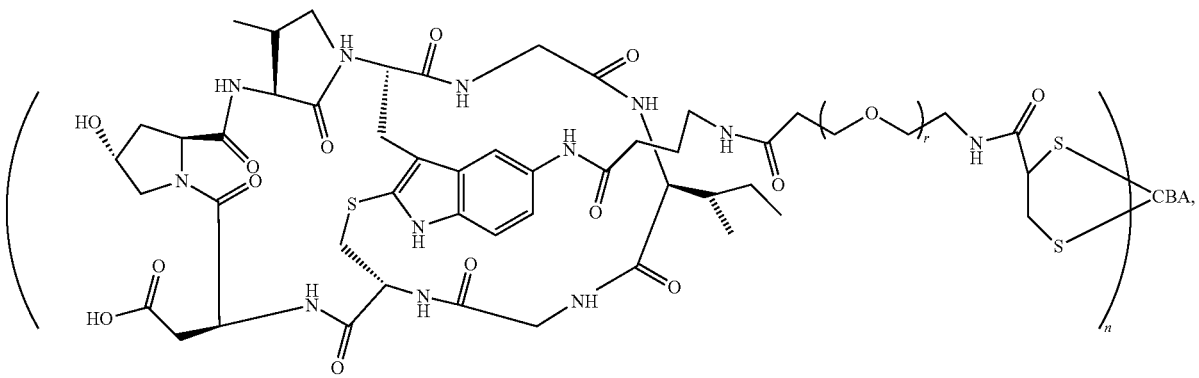
(II-21)
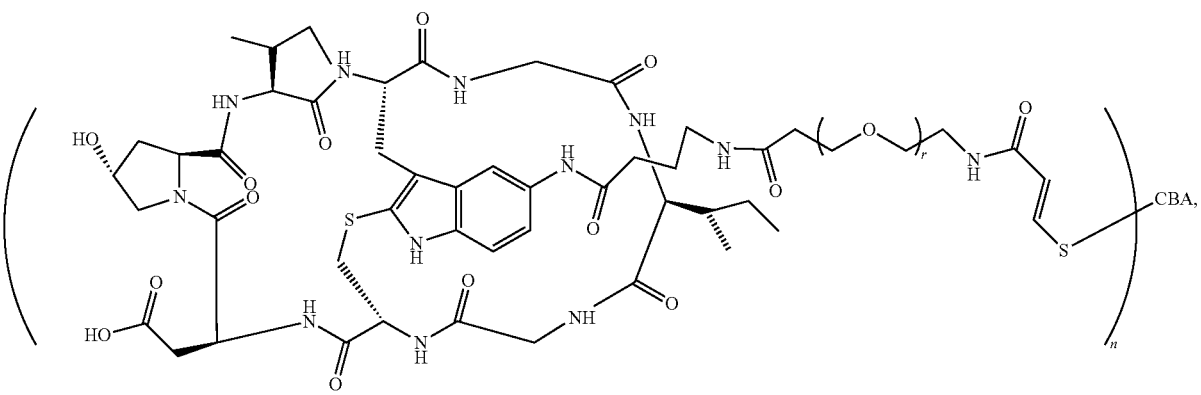
(II-22)
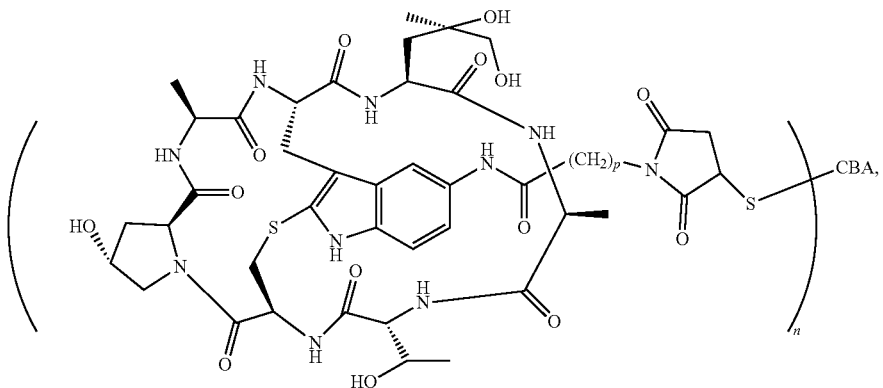
(II-23)
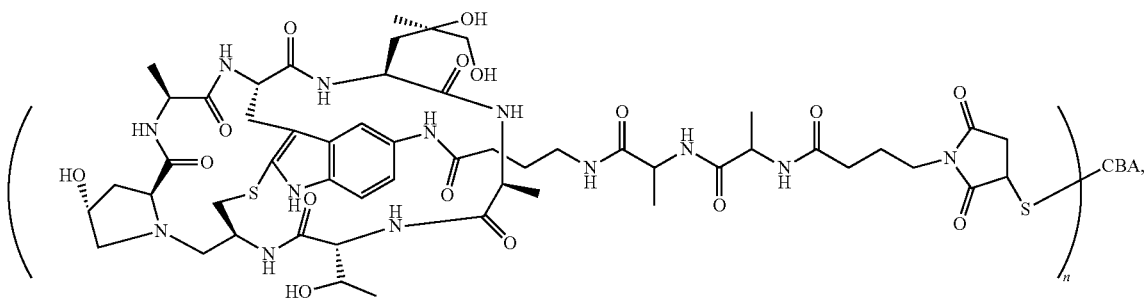

(II-24)
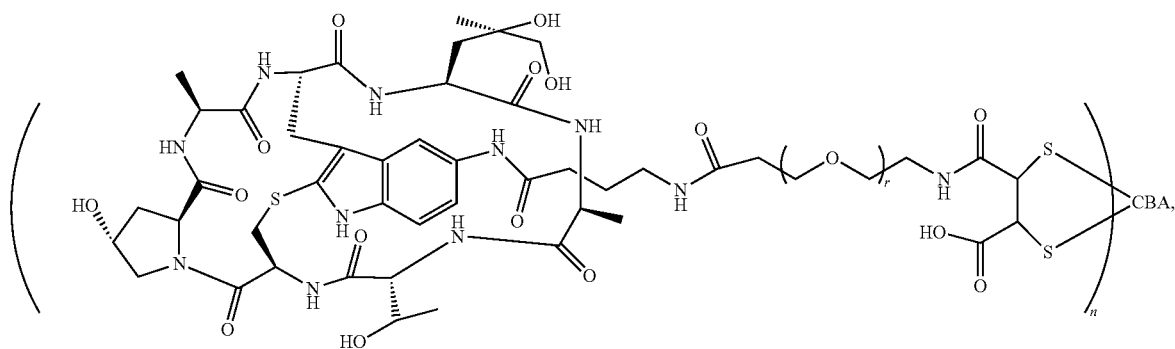
(II-25)
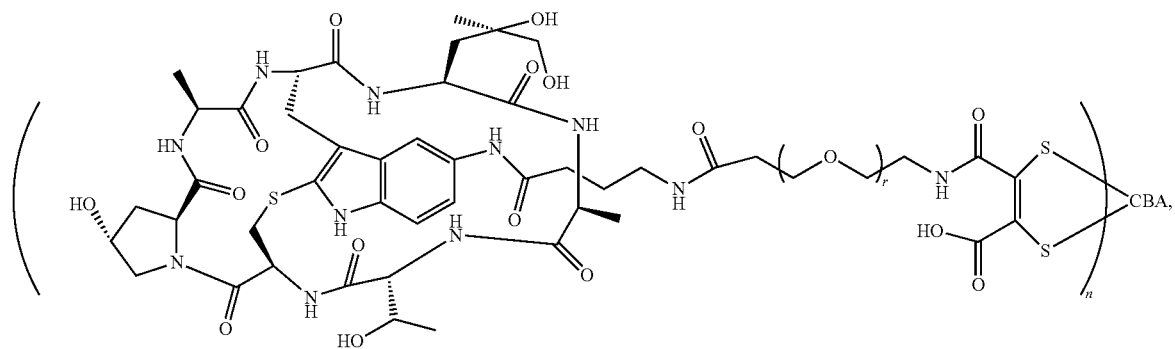
(II-26)
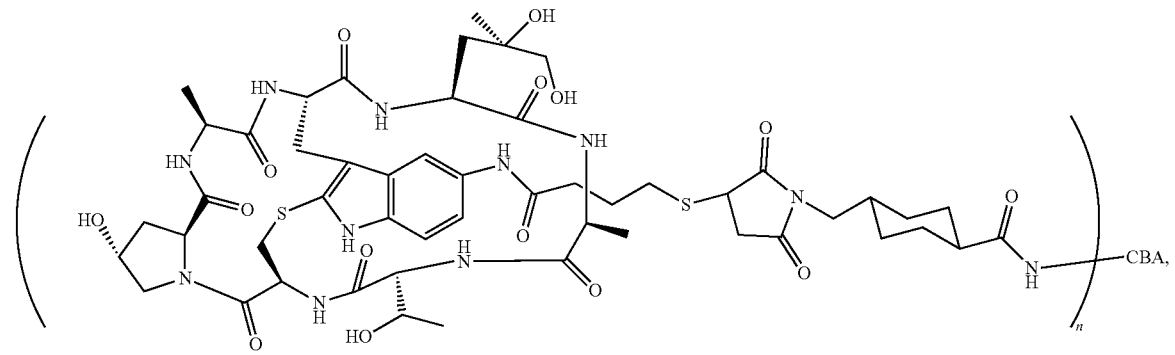
(II-27)
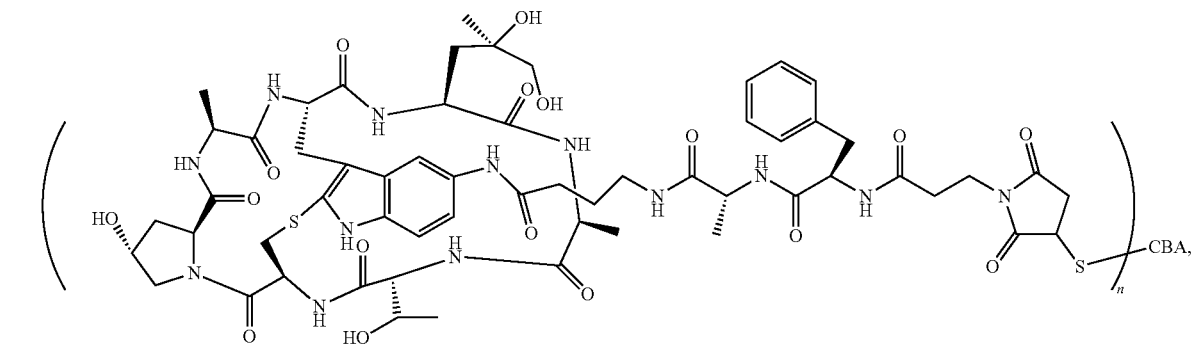

-continued
(II-28)
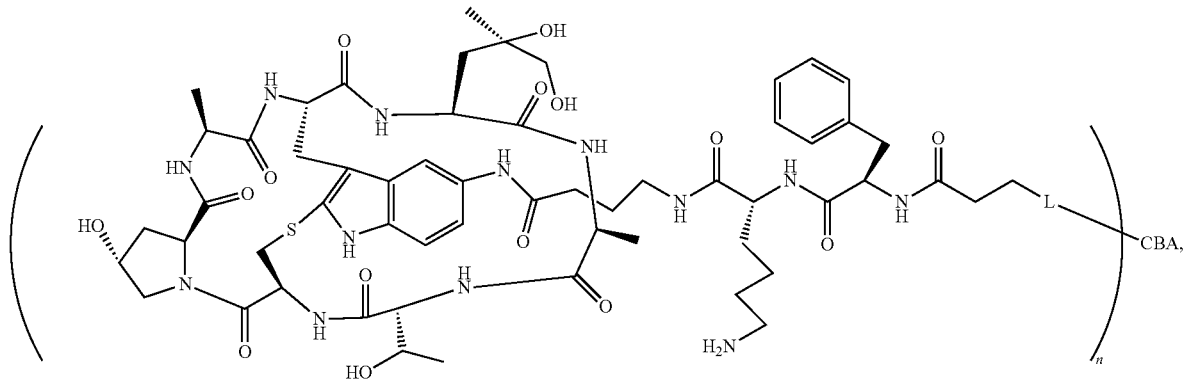
(II-29)
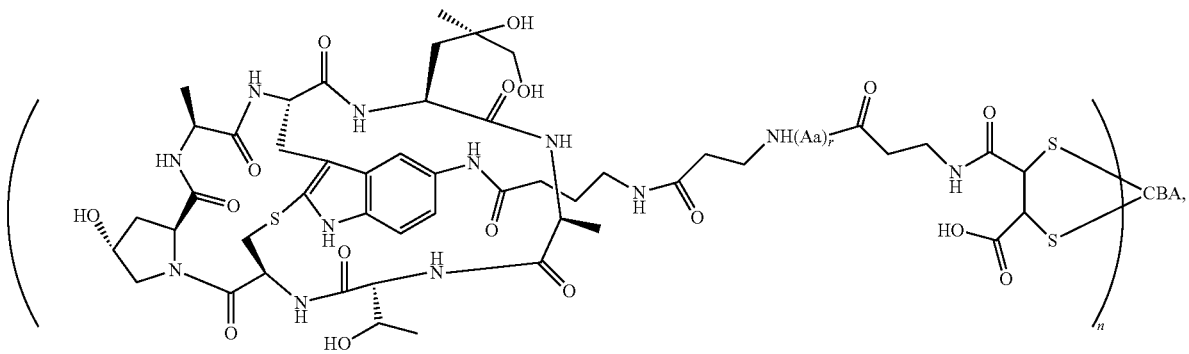
(II-30)
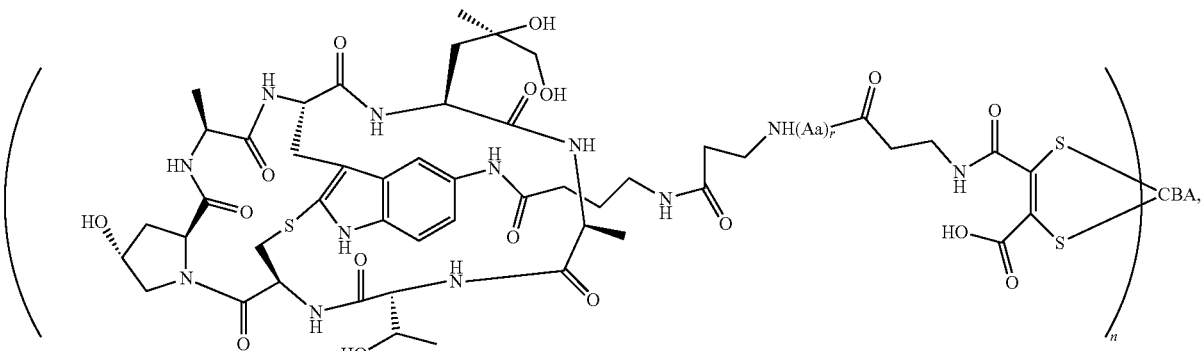
(II-31)
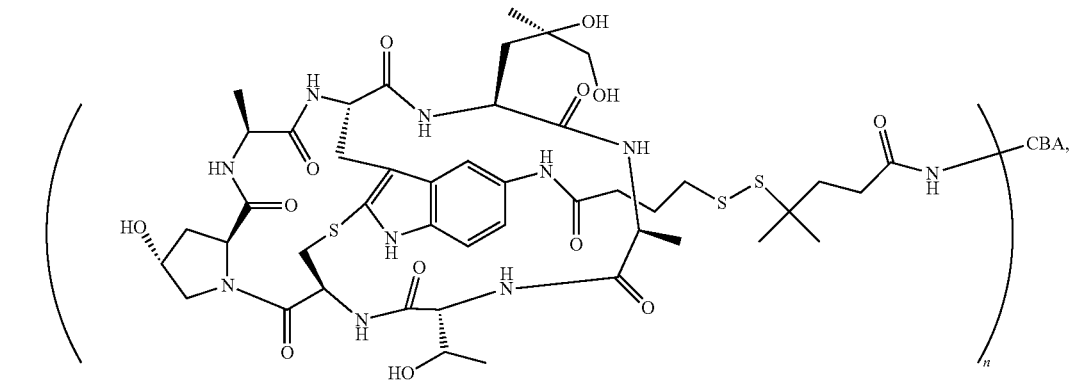

(II-32)
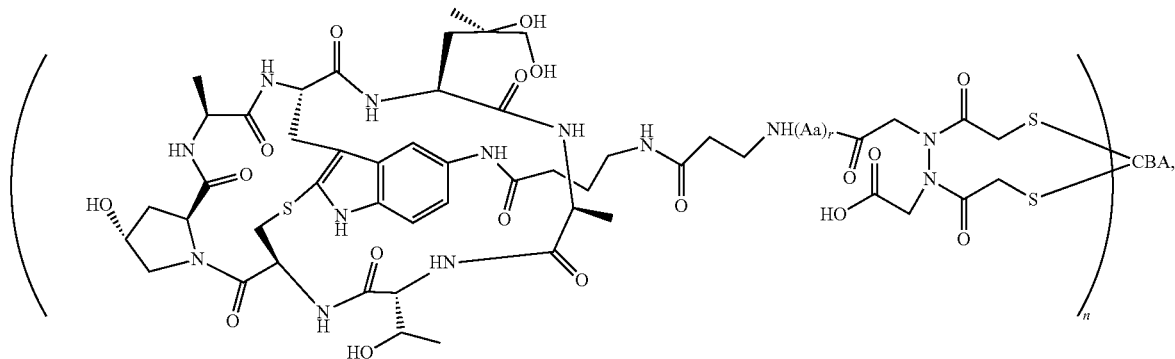
(II-33)
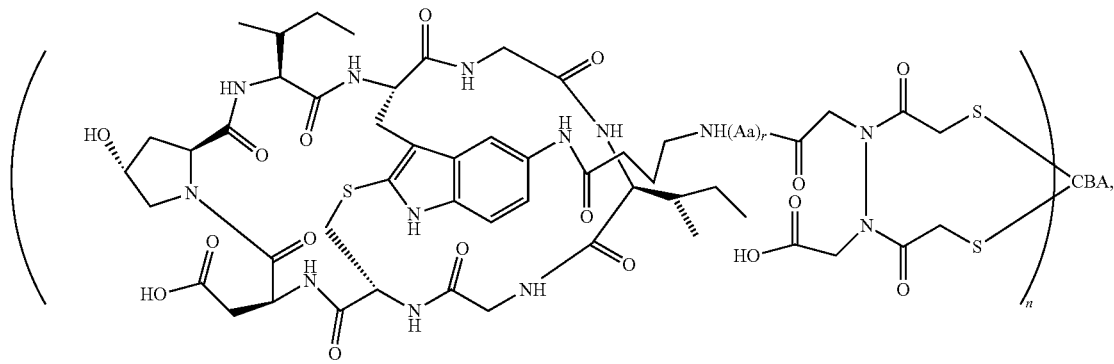
(II-34)
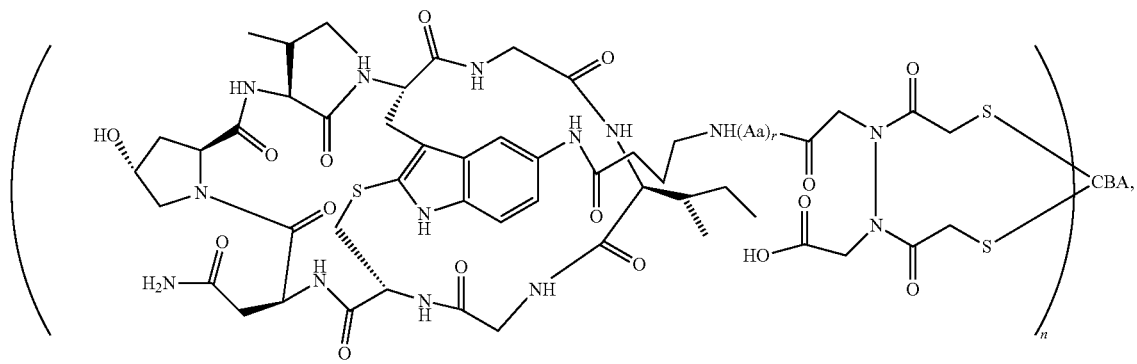
(II-35)
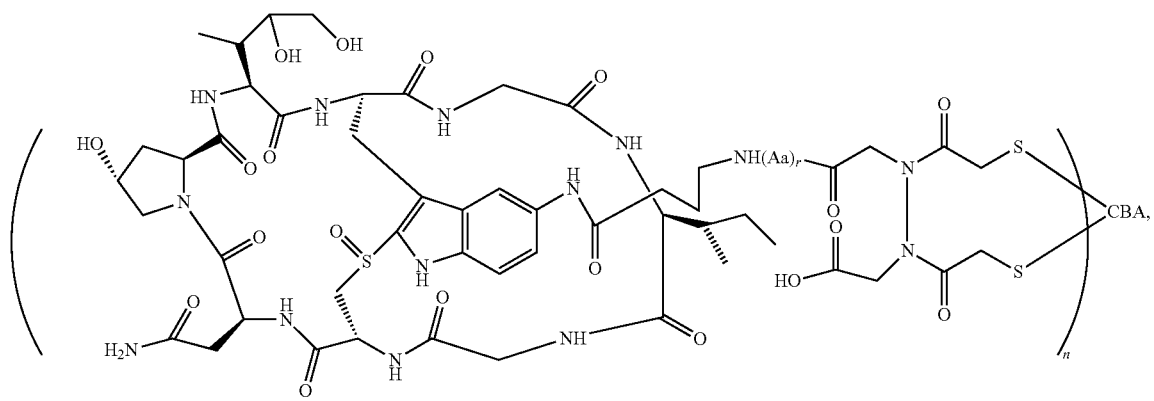

(II-36)
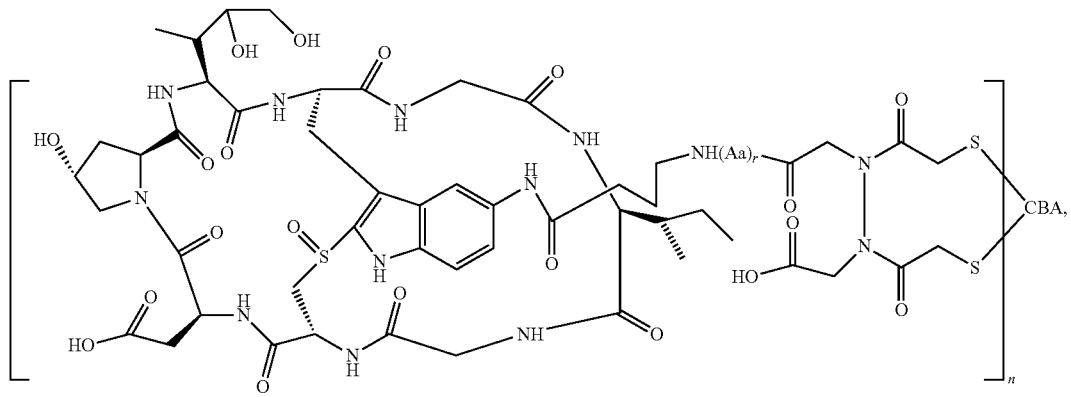
(II-37)
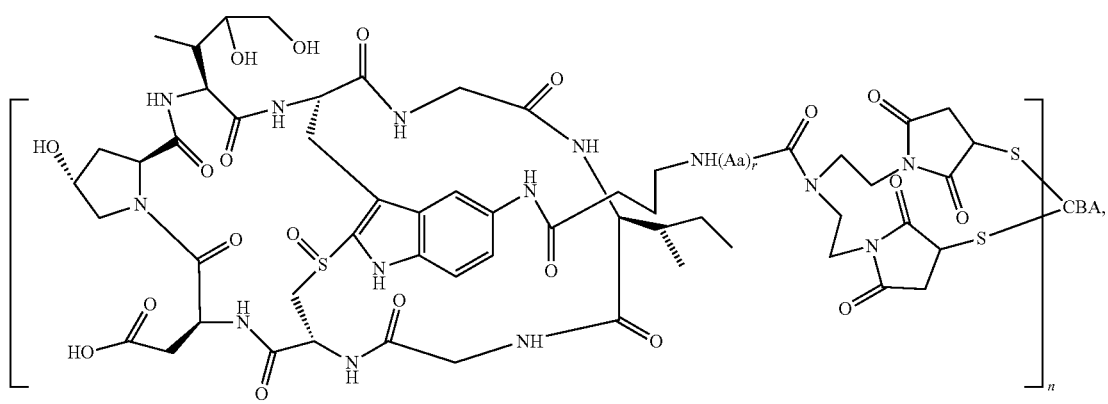
(II-38)
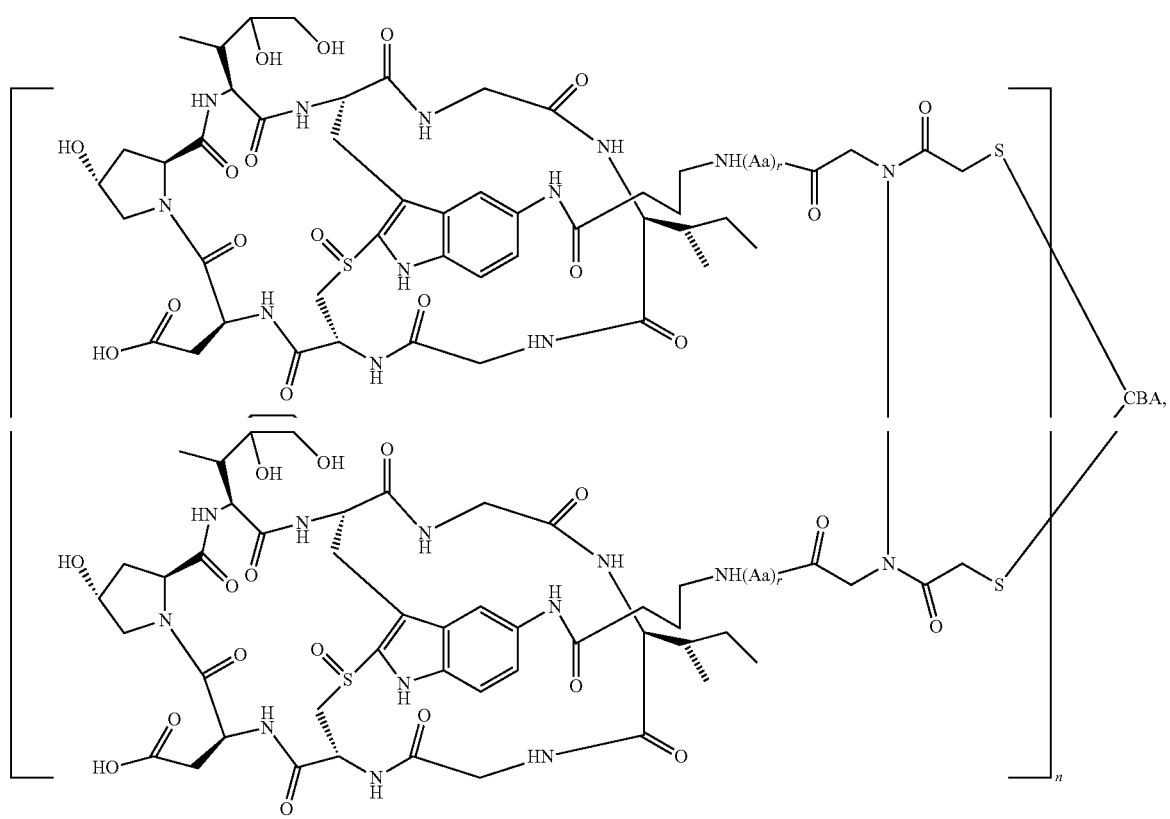

(II-39)
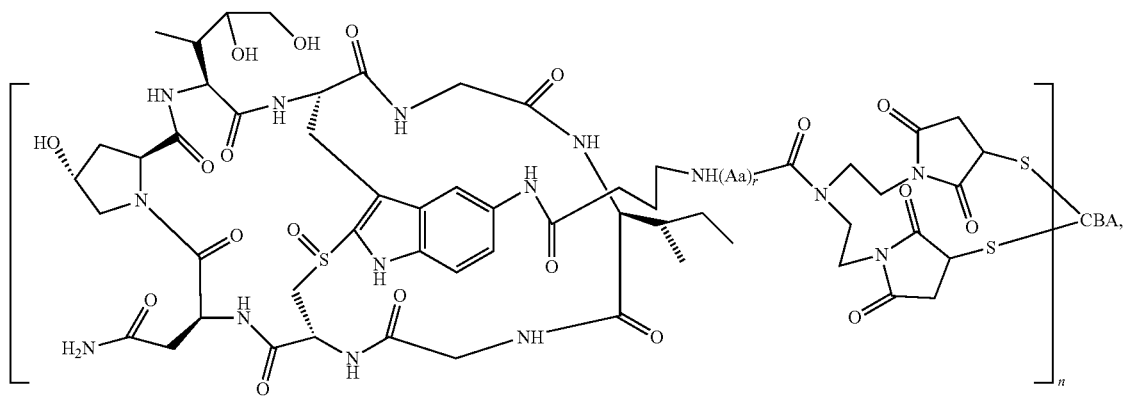
(II-40)
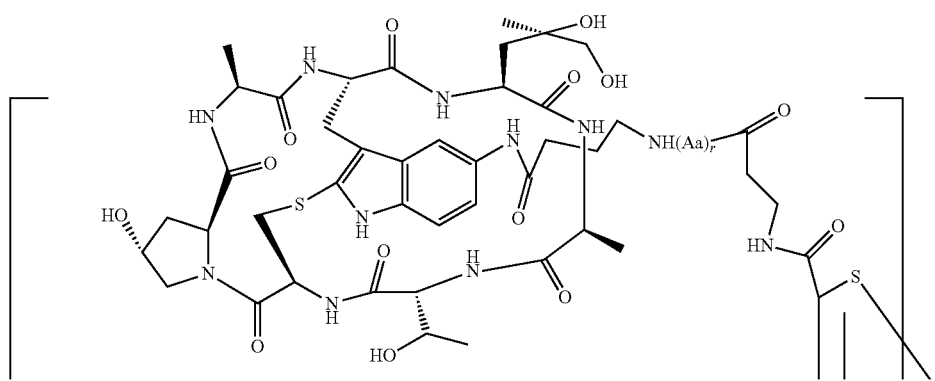
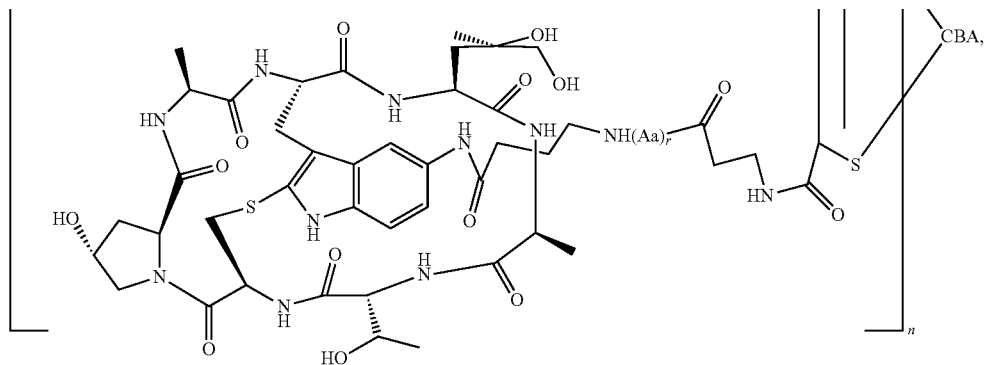
(II-41)
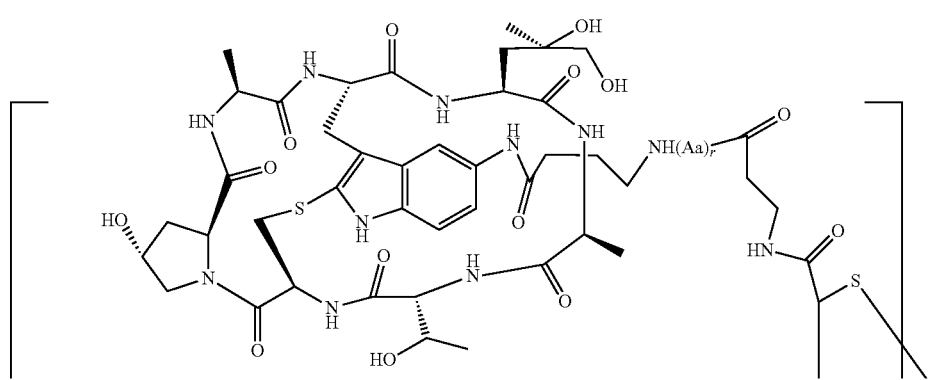

-continued
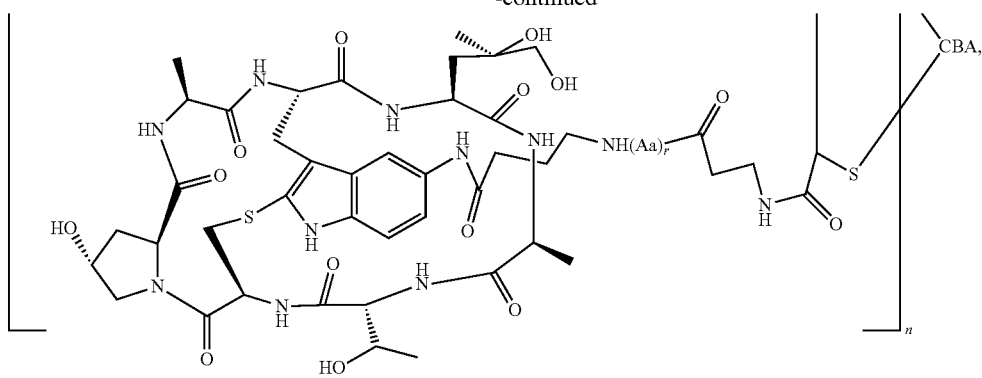
(II-42)
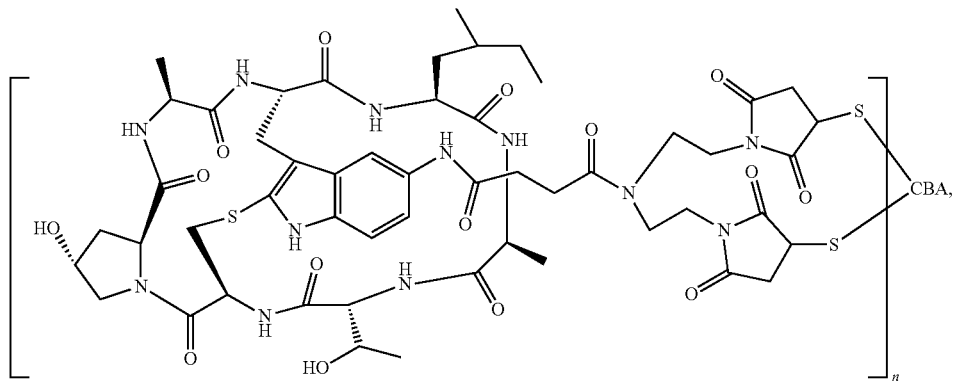
(II-43)
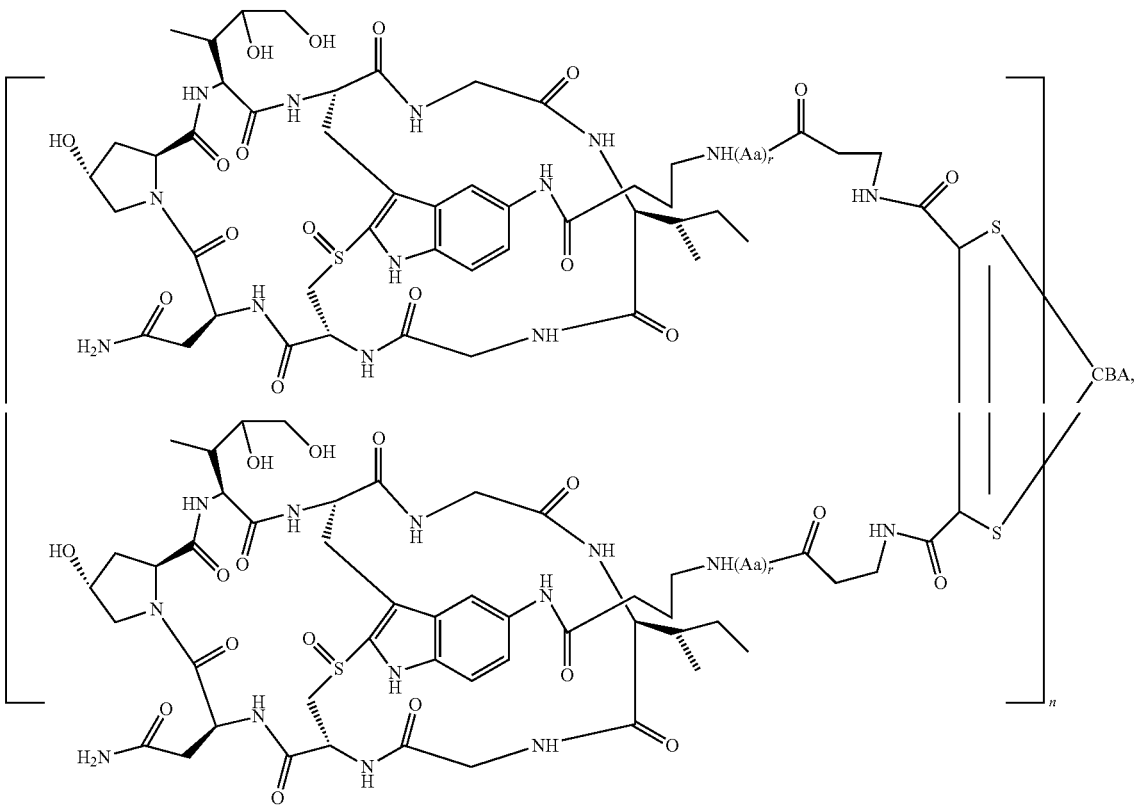

(II-44)
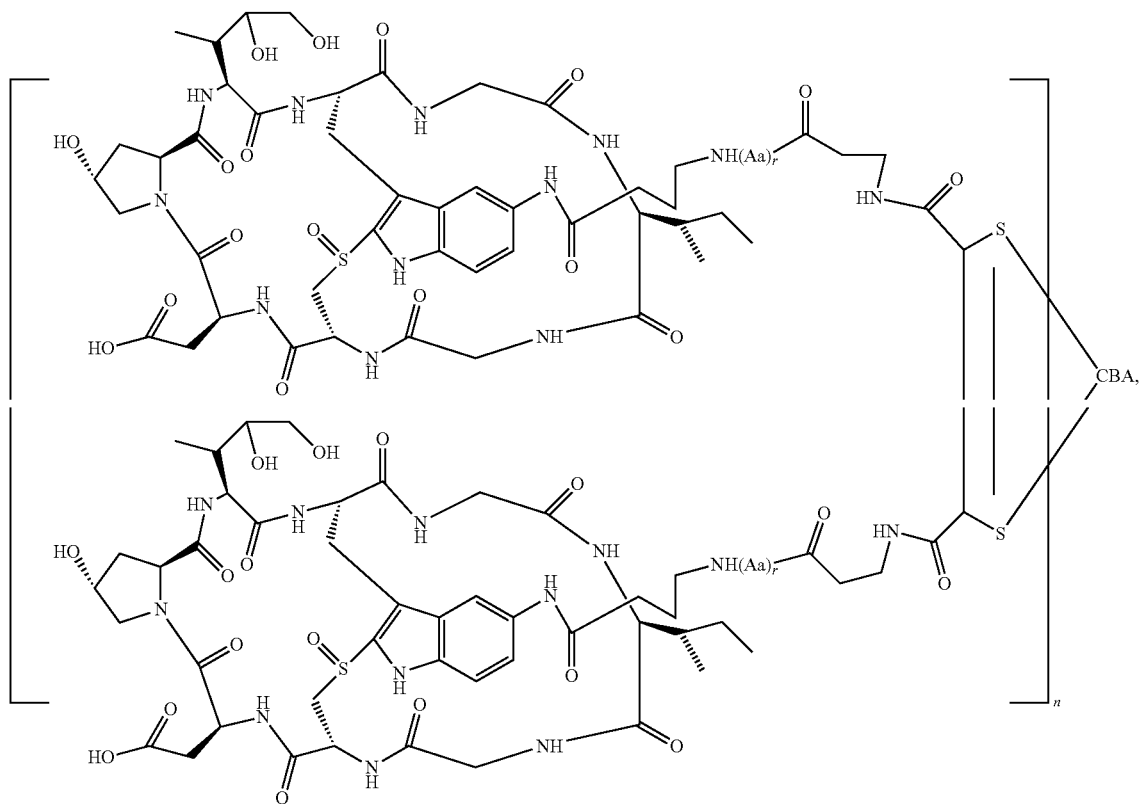
(II-45)
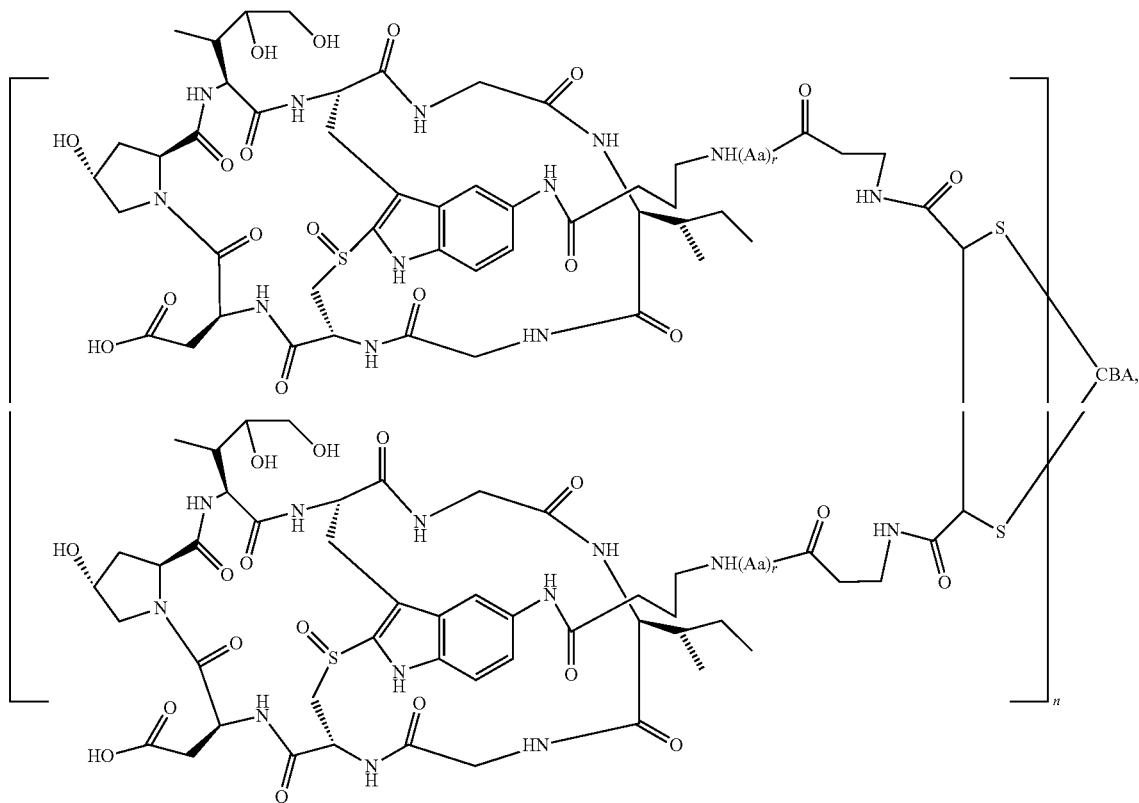

(II-46)
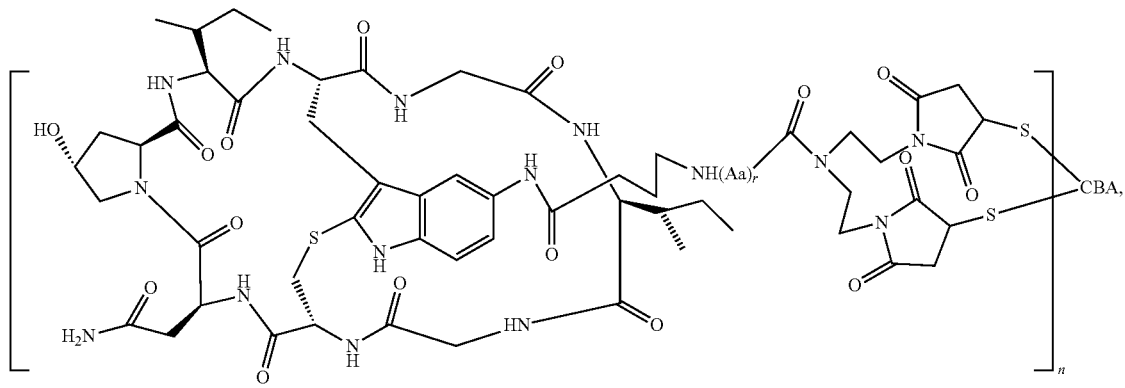
(II-47)
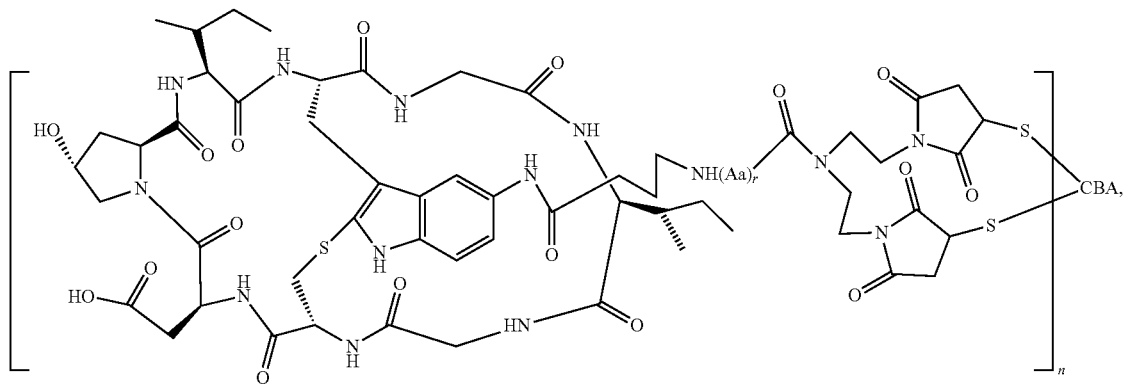
(II-48)
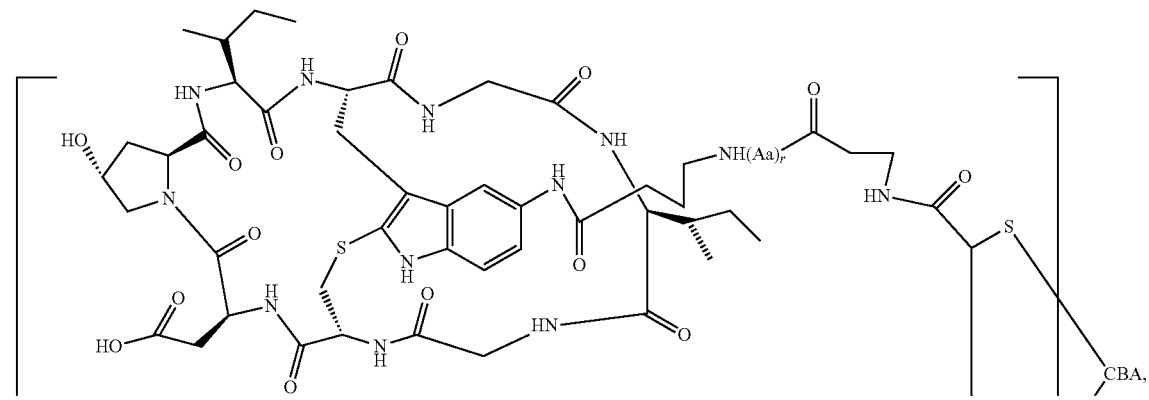
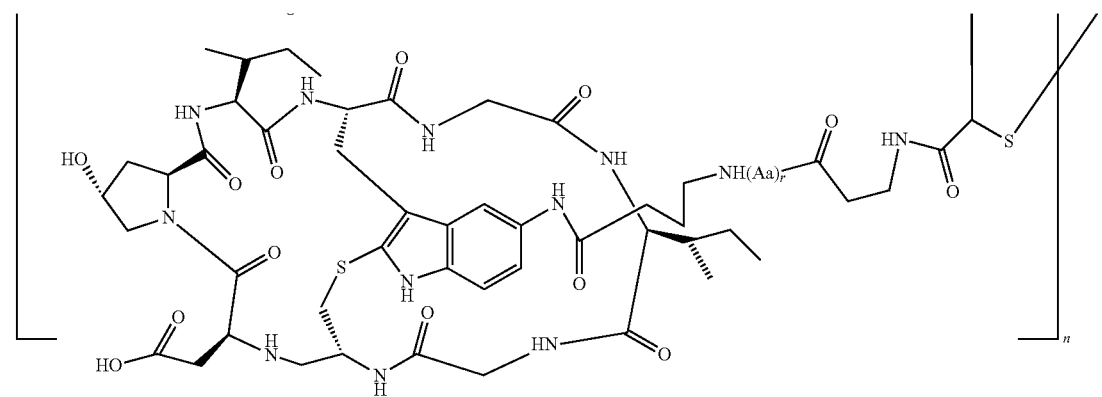

(II-49)
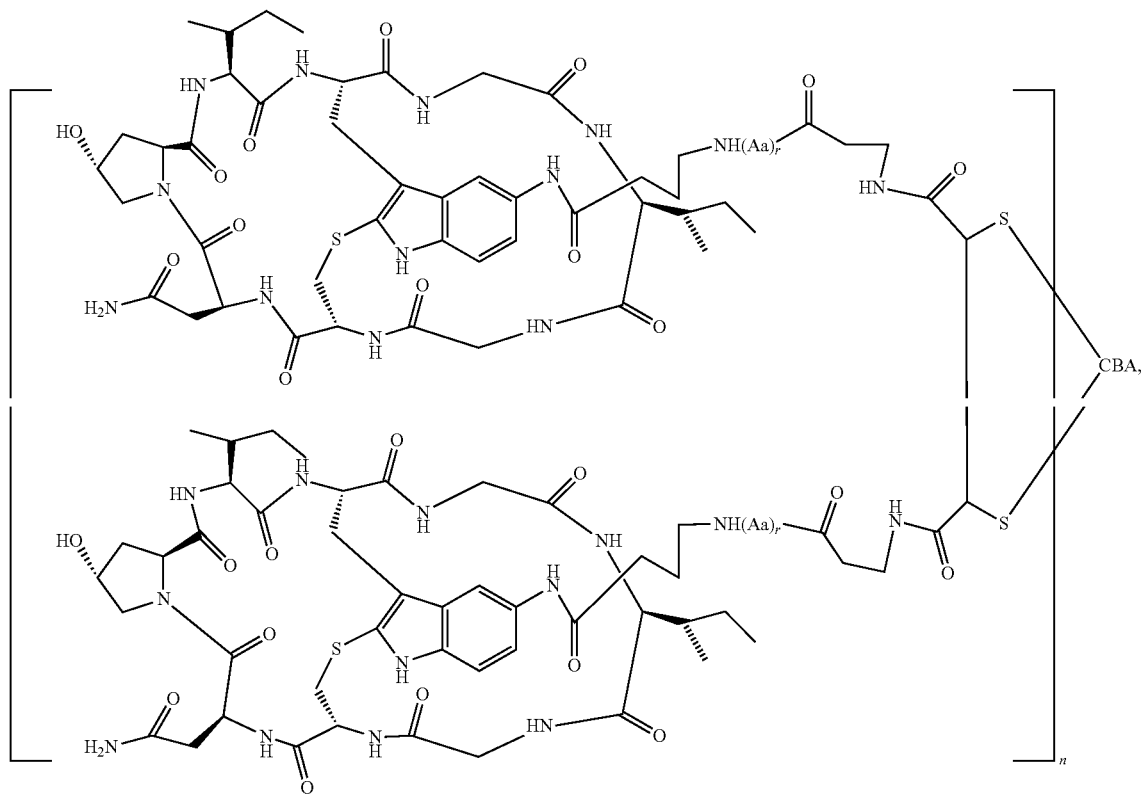
(II-50)
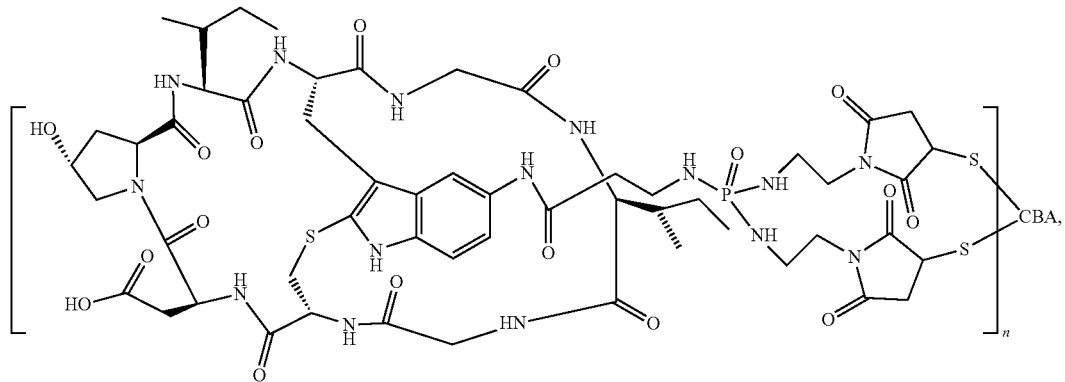
(II-51)
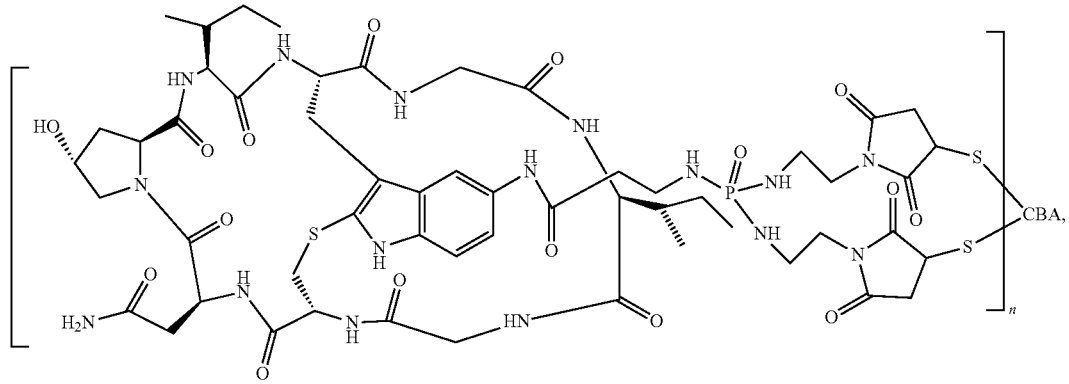

-continued
(II-52)
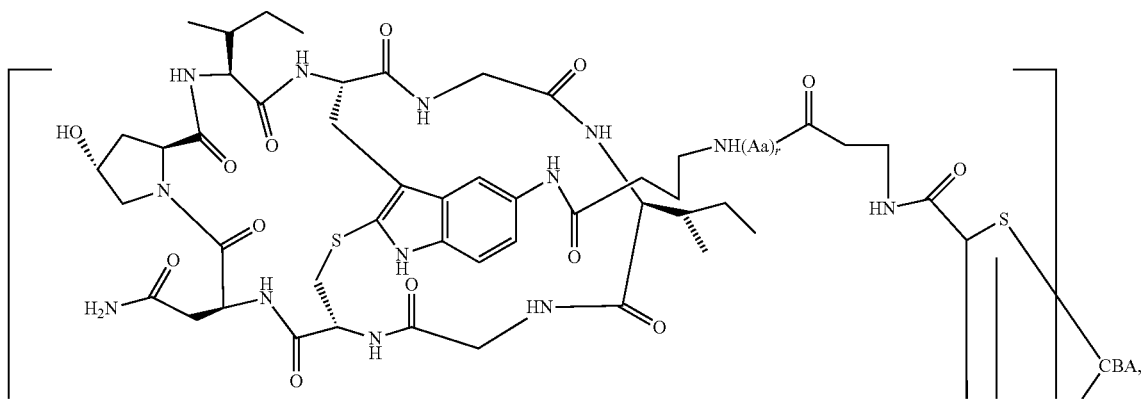
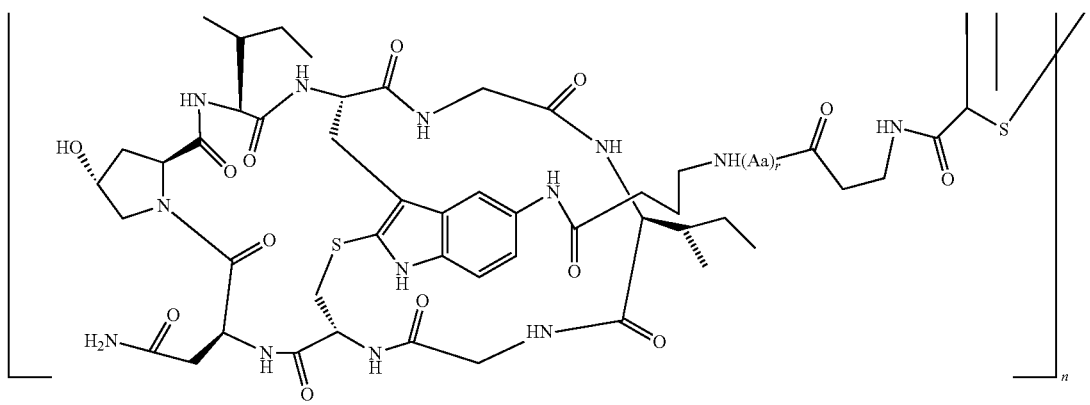
(II-53)
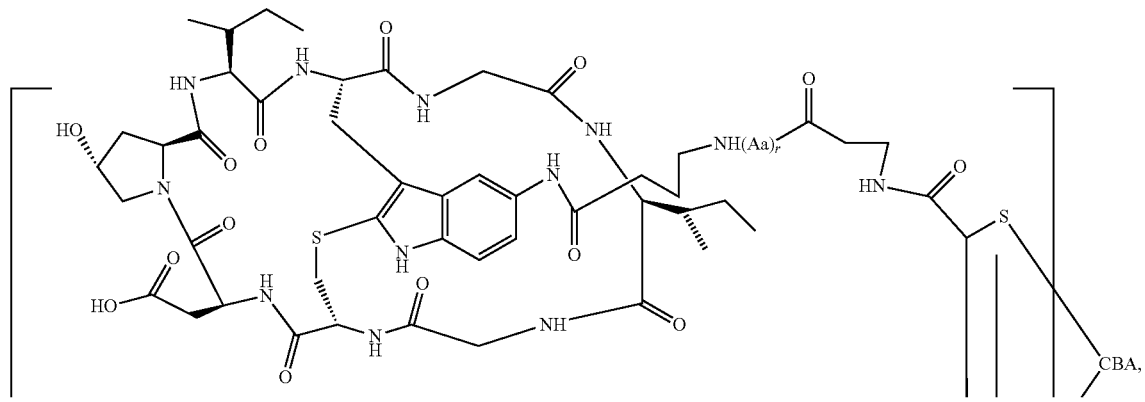
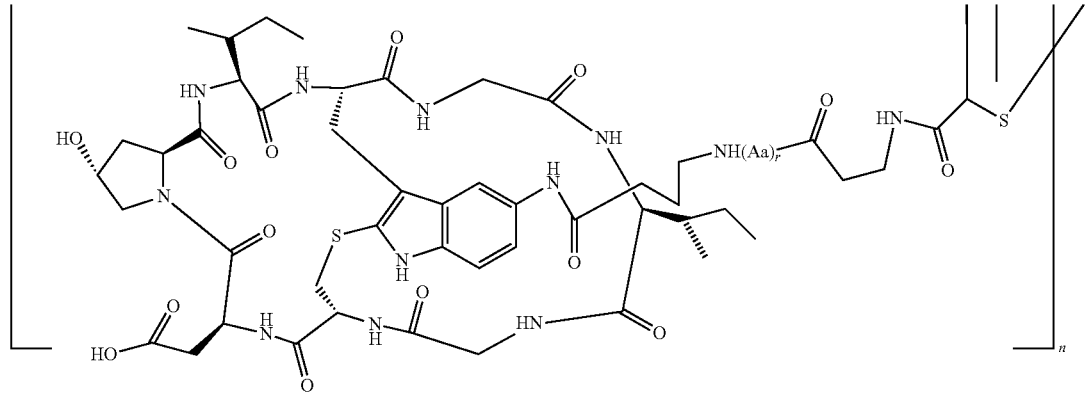

(II-54)
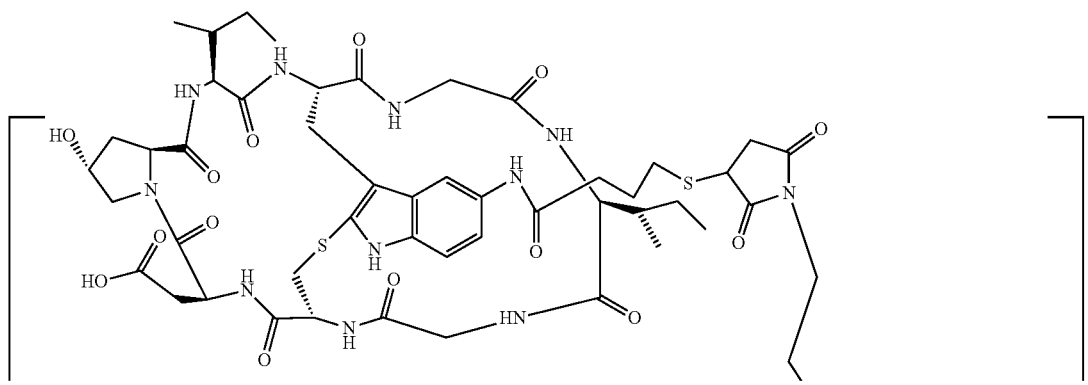
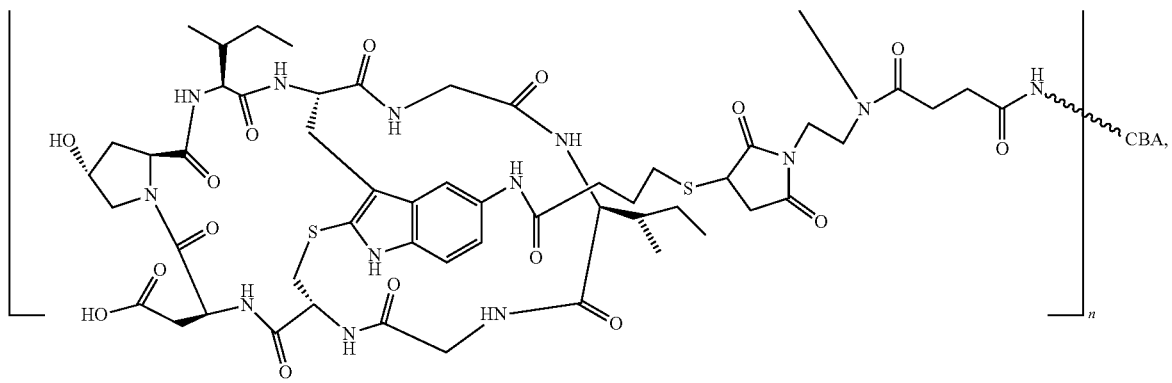
(II-55)
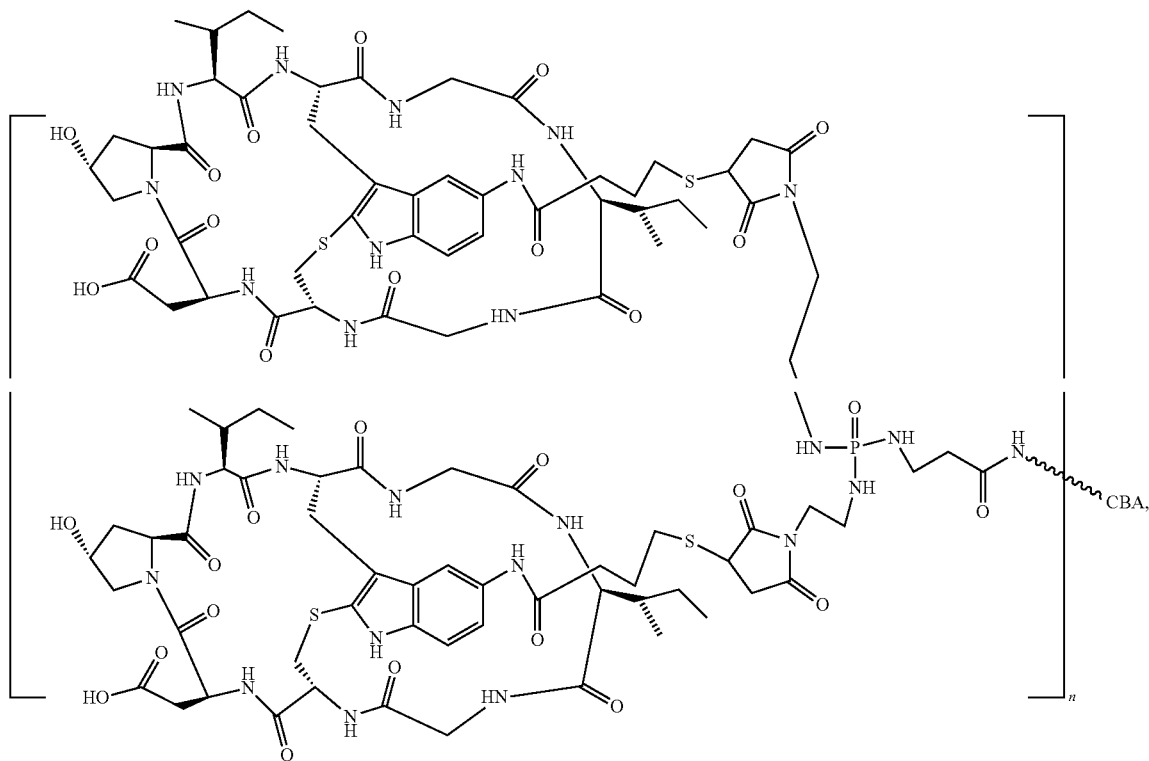

(II-56)
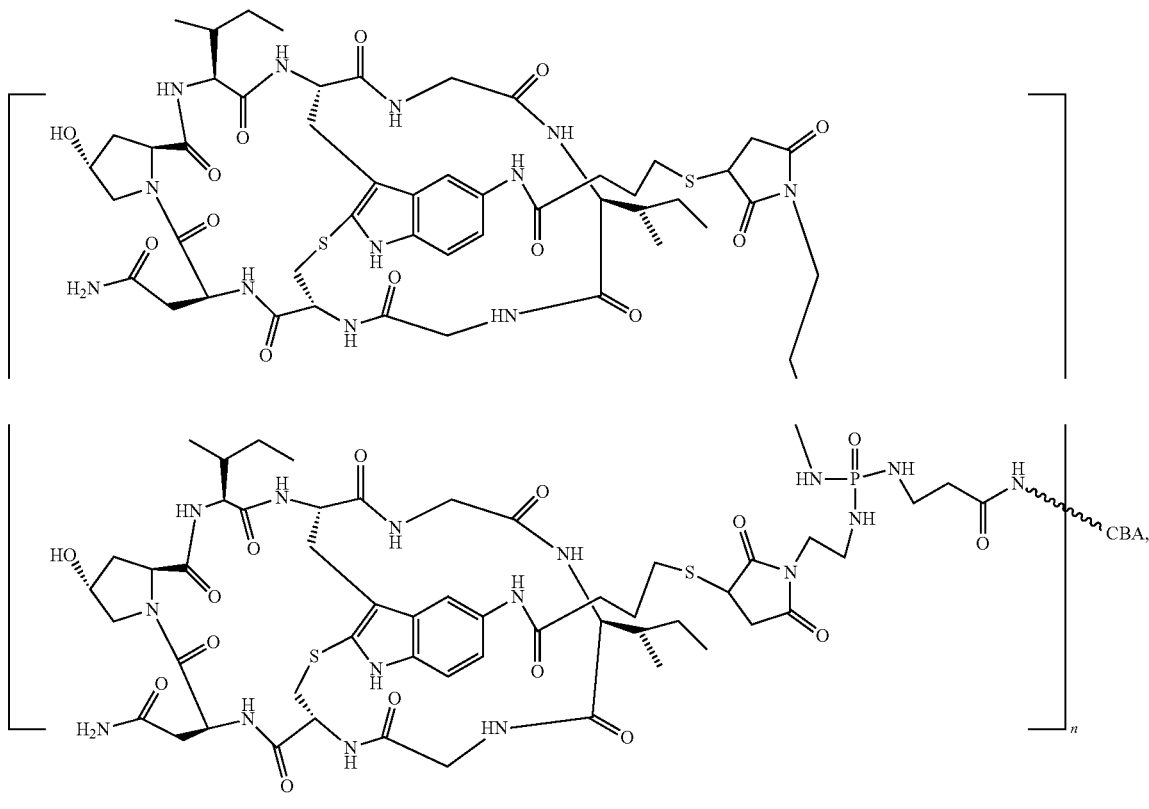
(II-57)
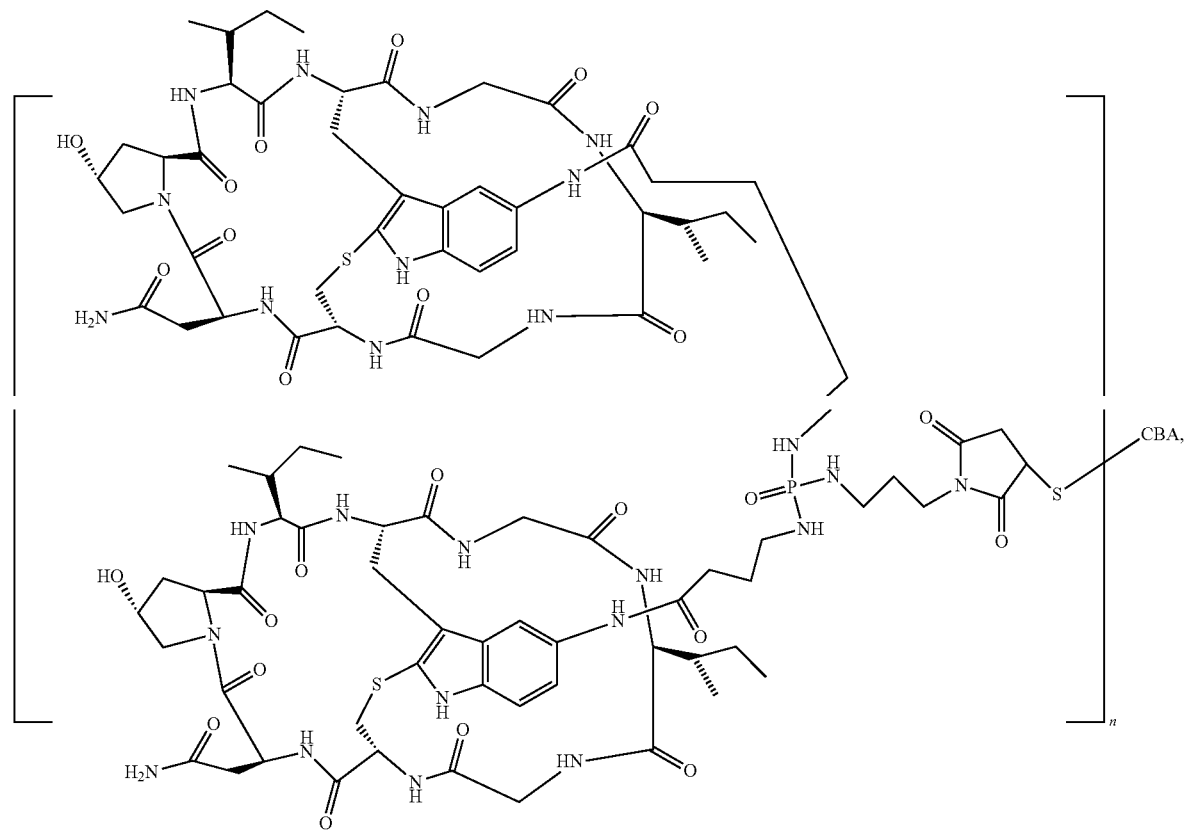

-continued
(II-58)
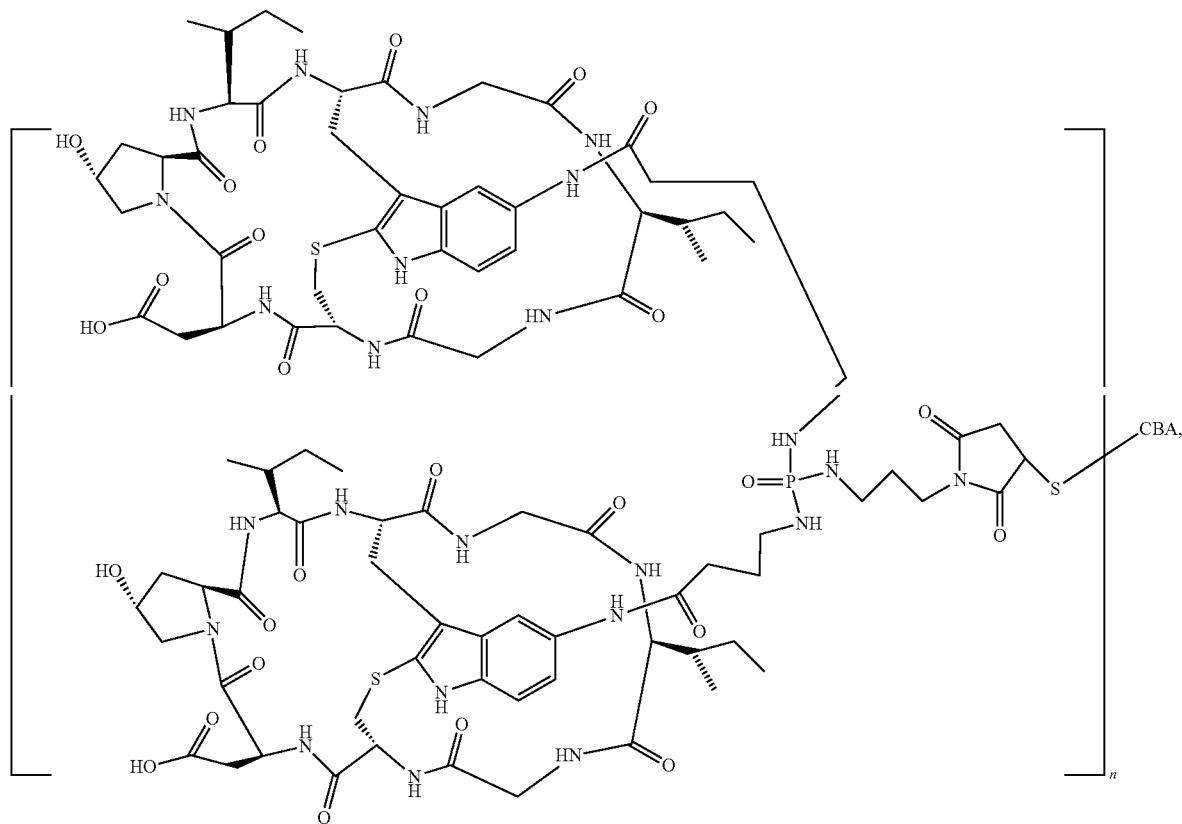
(II-59)
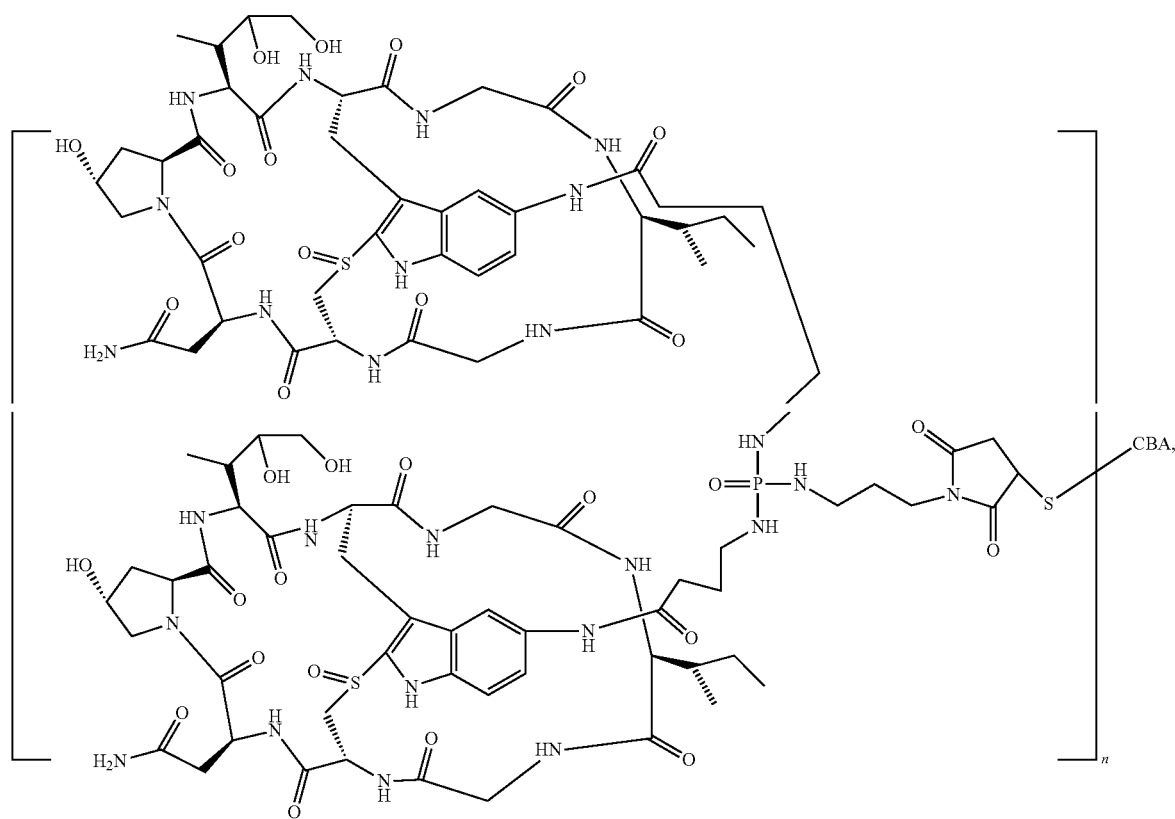

-continued
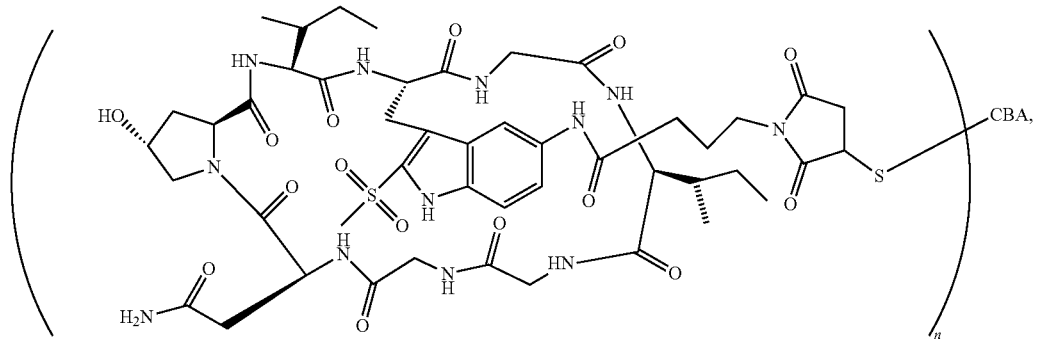
(II-60)
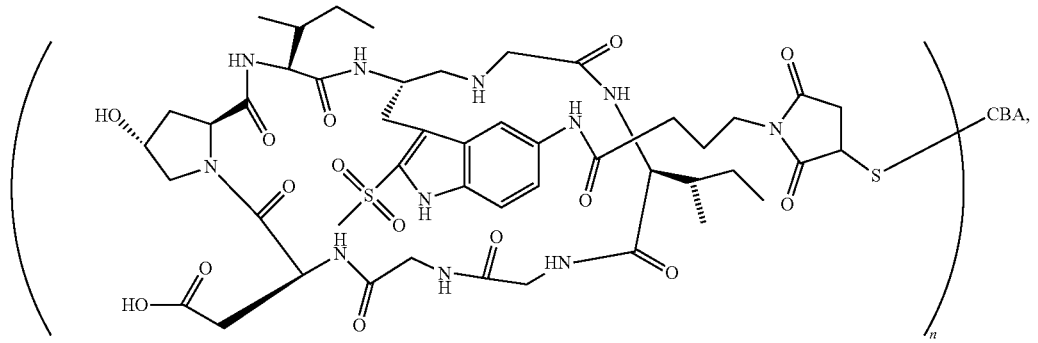
(II-61)
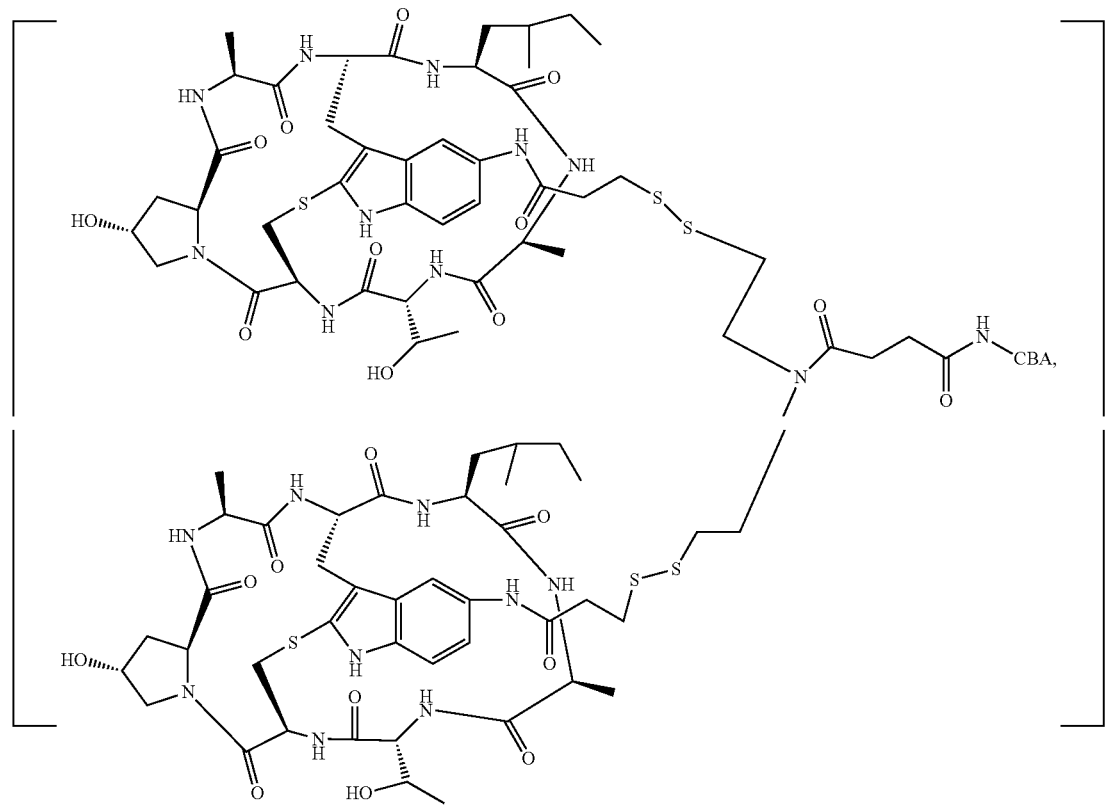
(II-62)

(II-63)
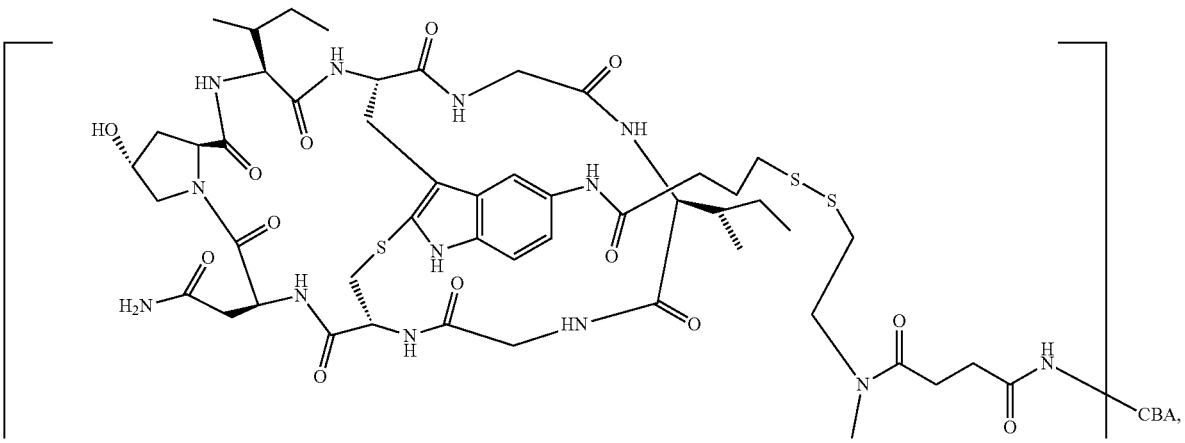
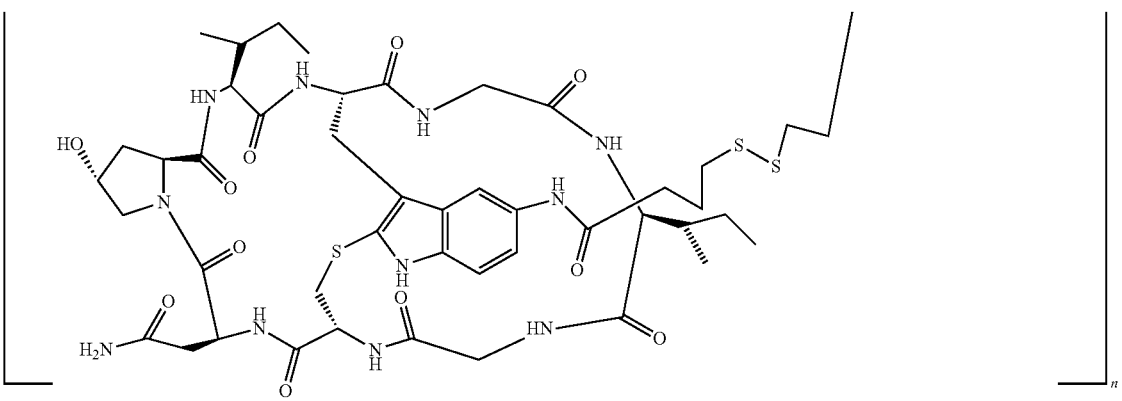
(II-64)
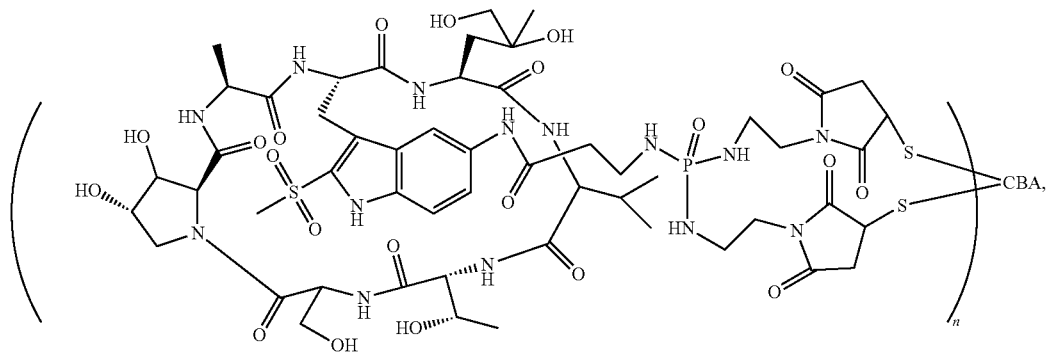
(II-65)
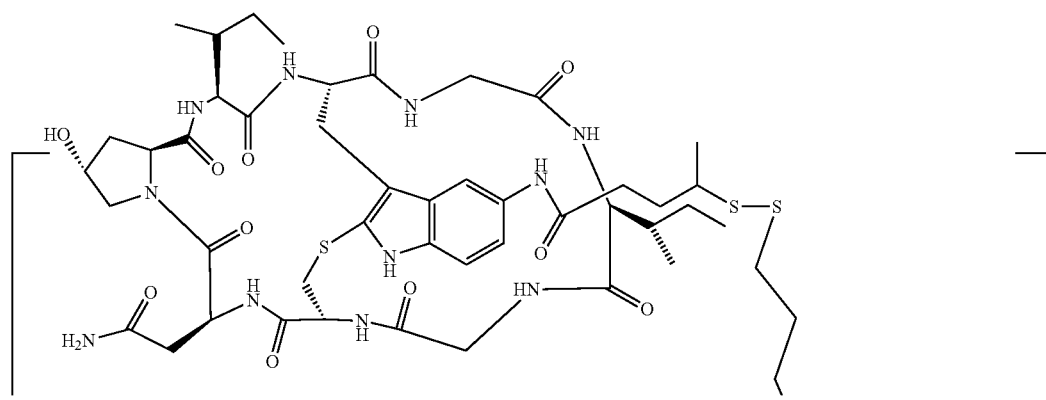

-continued
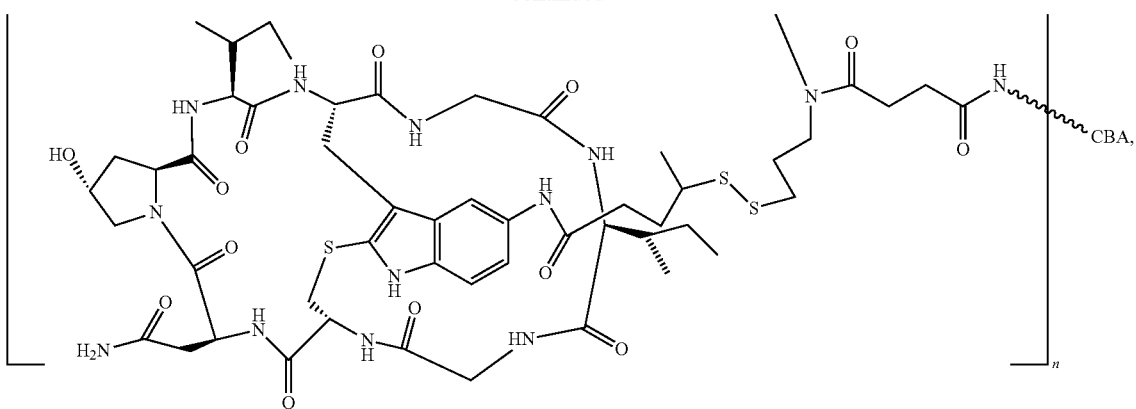
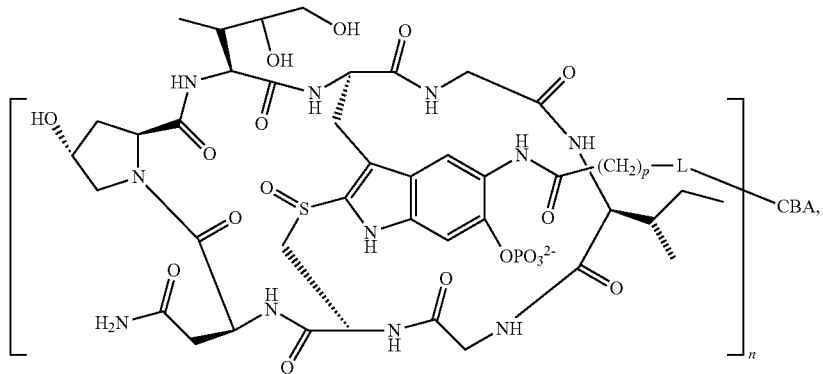
(II-66)
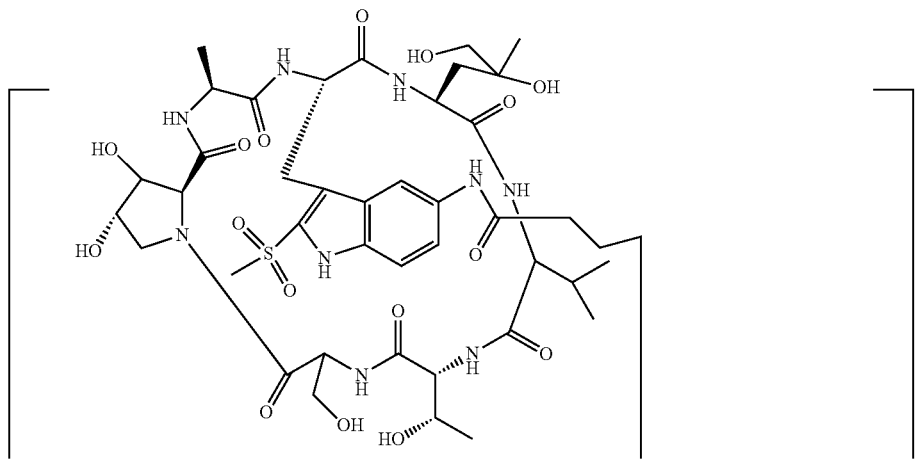
(II-67)

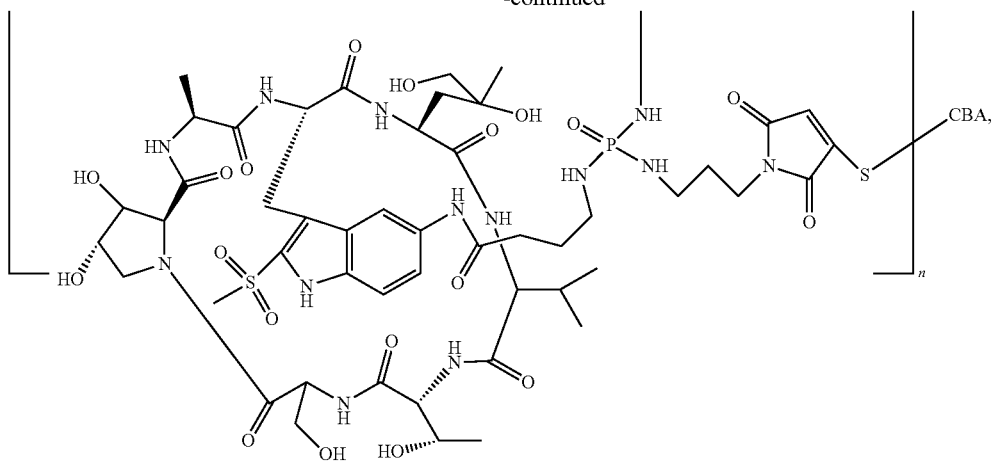
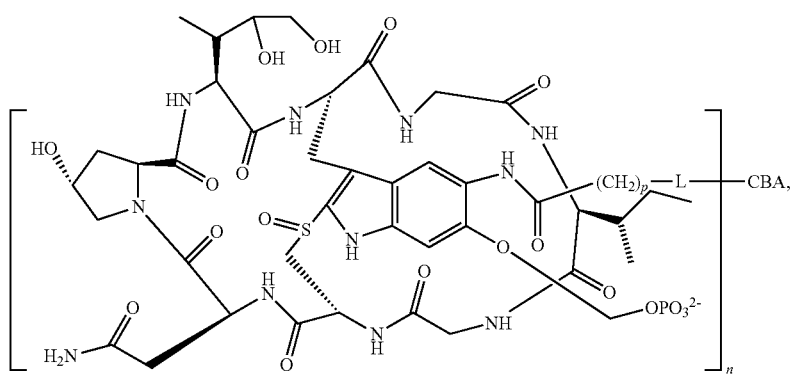
(II-68)
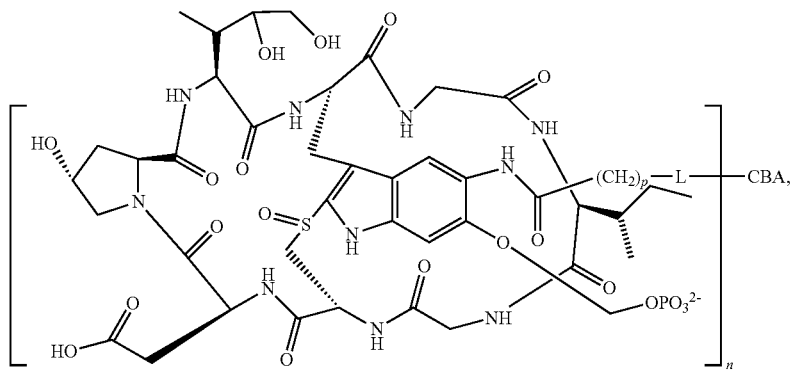
(II-69)
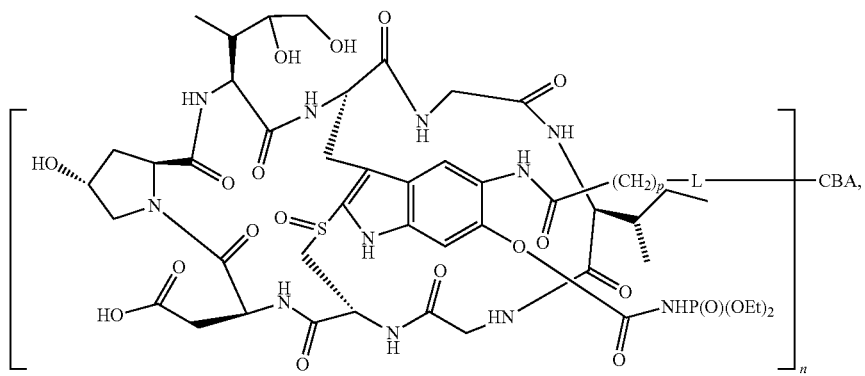
(II-70)

(II-71)
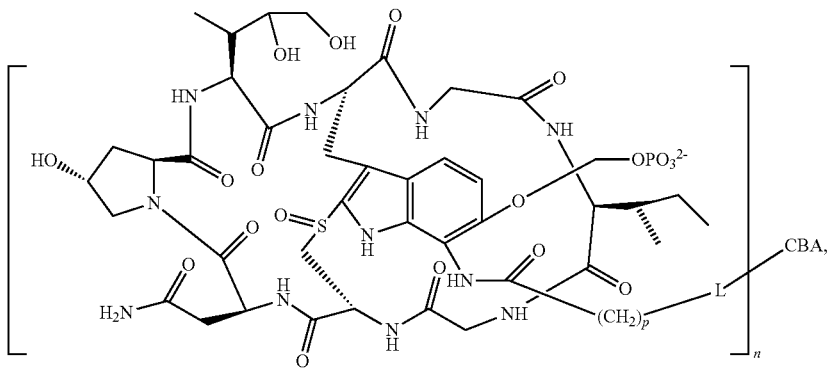
(II-72)
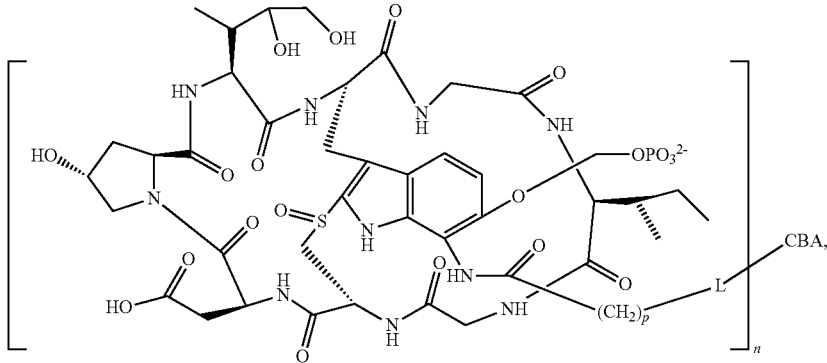
(II-73)
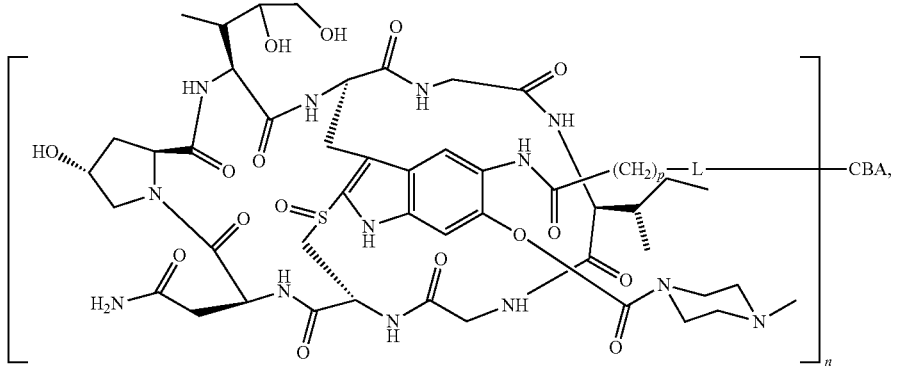
(II-74)
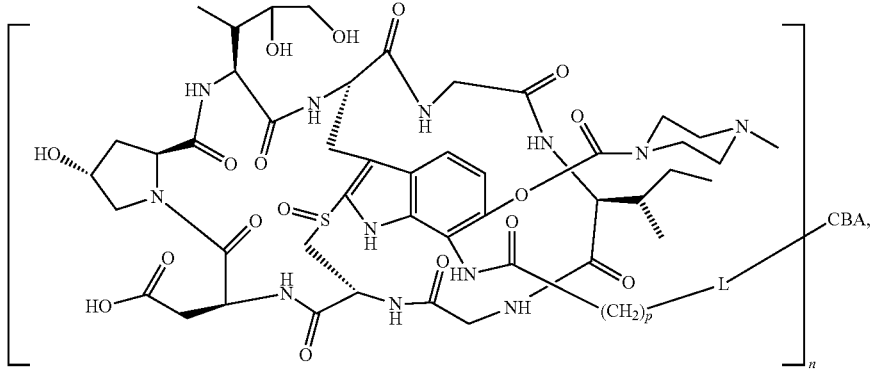

(II-75)
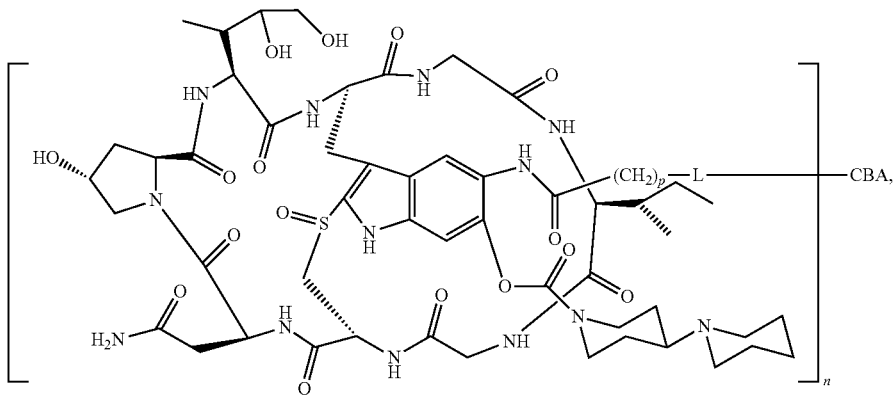
(II-76)
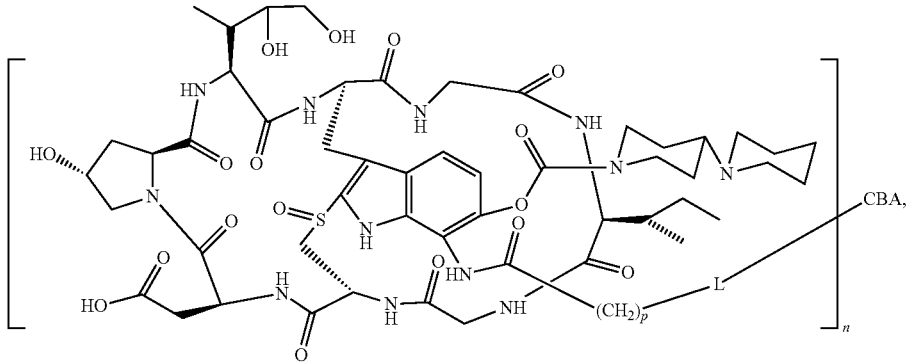
(II-77)
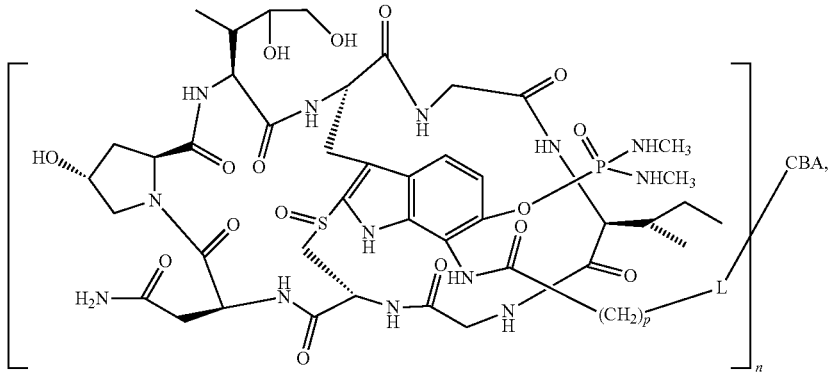
(II-78)
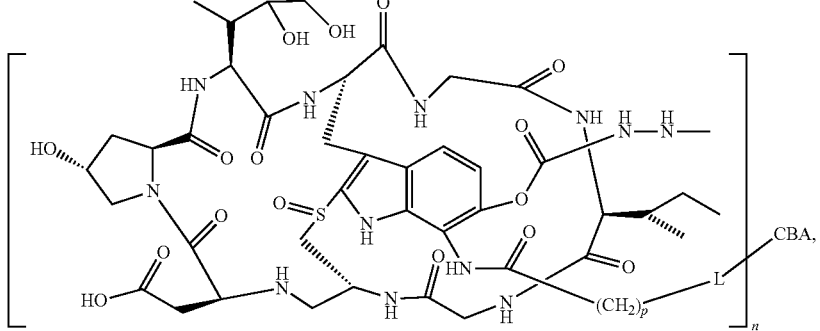

(II-79)
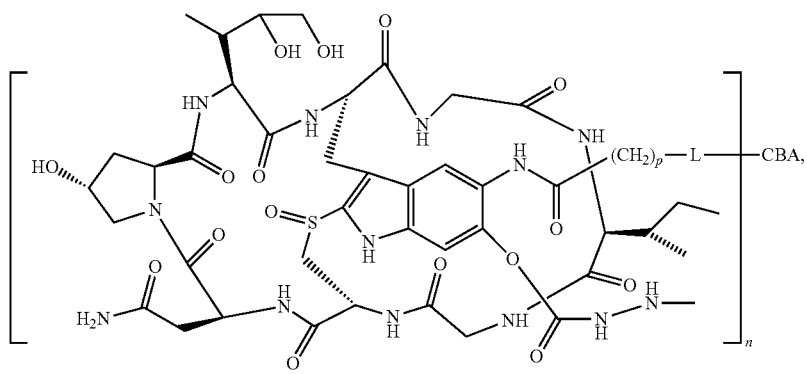
(II-80)
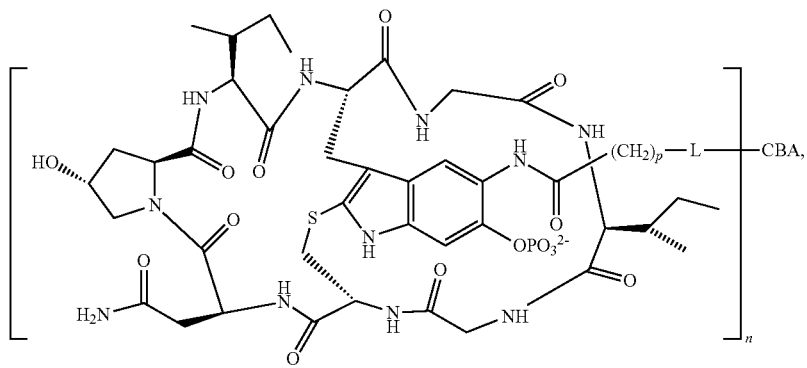
(II-81)
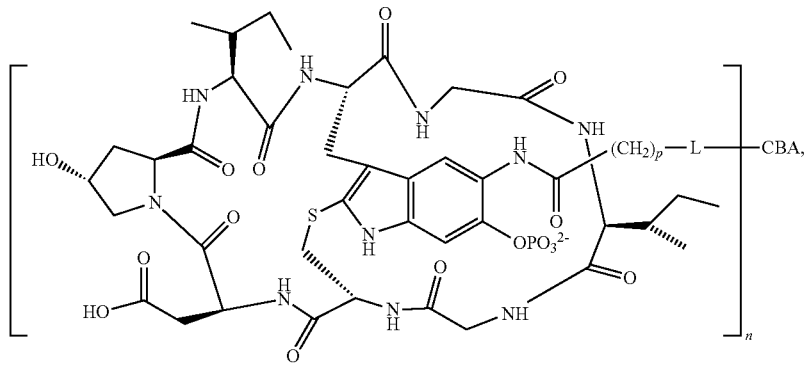
(II-82)
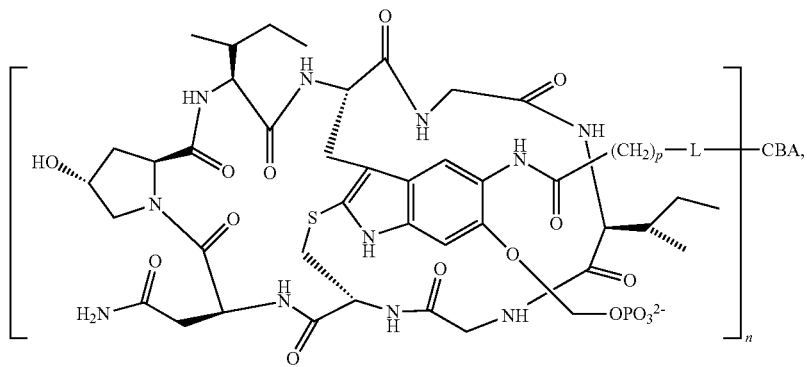

(II-83)
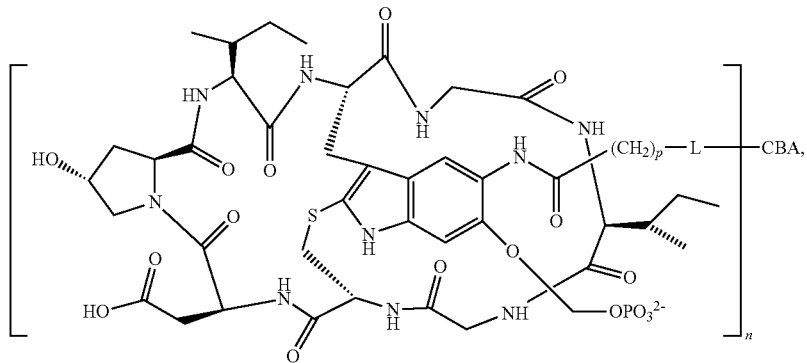
(II-84)
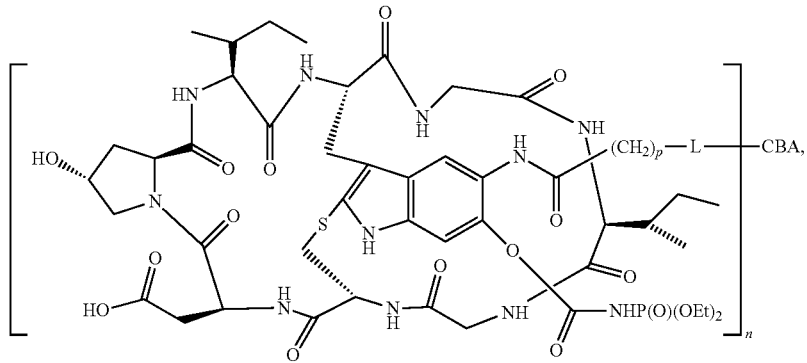
(II-85)
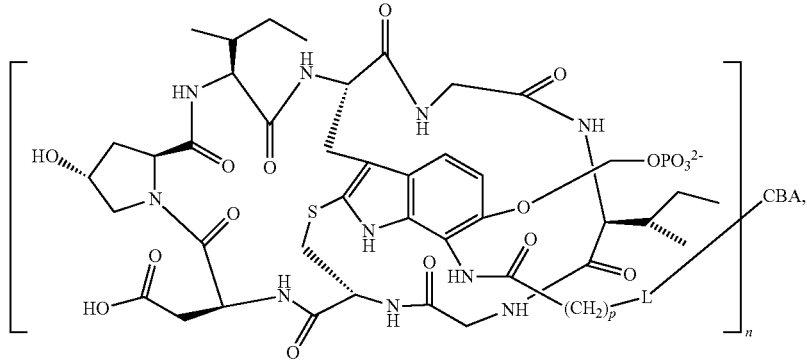
(II-86)
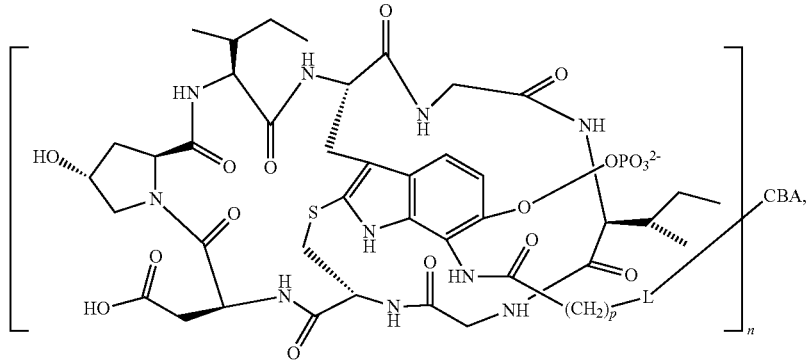

(II-87)
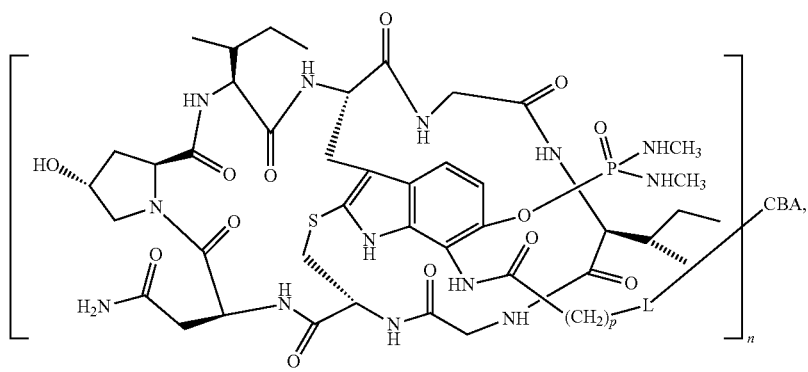
(II-88)
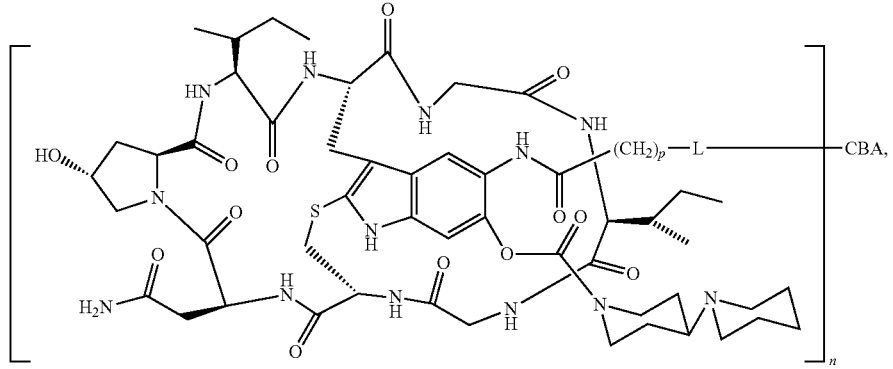
(II-89)
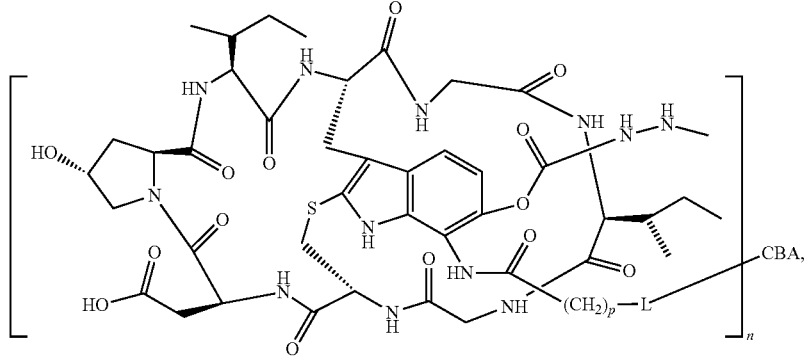
(II-90)
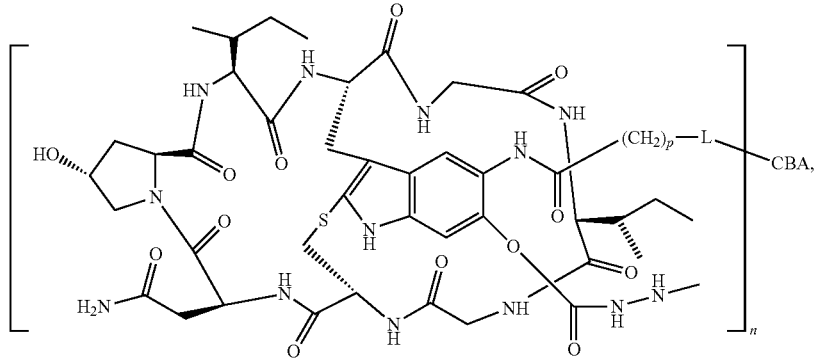

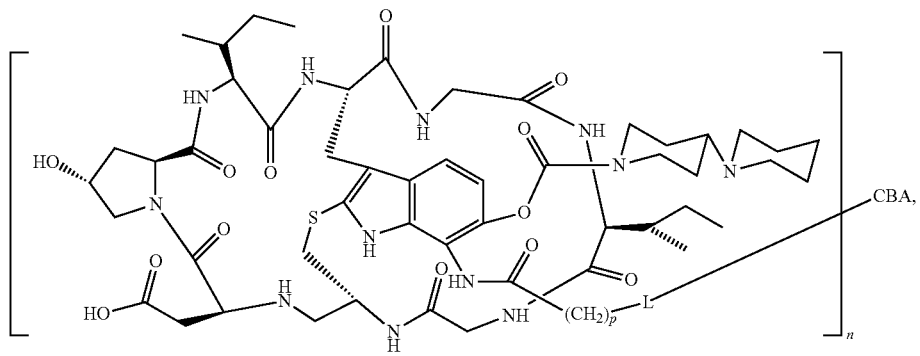

(II-91)

wherein Aa, L, m, n, p, Q, r, $R_1$, and $R_2$, are described the same as in claim 1; CBA is a cell-binding agent.

10. The compound of claim 1, wherein the cell binding agent is a full-length antibody (polyclonal and monoclonal antibody); a single chain antibody; a diabody, a triabody, a fragments of antibody (Fab, Fab', F(ab')$_2$, Fv, a fragment produced by a Fab expression library, an anti-idiotypic (anti-Id) antibody, CDR's, and an epitope-binding fragment of any of the above which immuno-specifically bind to cancer cell antigens, viral antigens or microbial antigens; interferon (type I, II, III); a peptide; a lymphokine IL-2, IL-3, IL-4, IL-6, GM-CSF, interferon-gamma (IFN-γ); a hormone, insulin, TRH (thyrotropin releasing hormone), MSH (melanocyte-stimulating hormone), a steroid hormone, androgens, estrogens, melanocyte-stimulating hormone (MSH); a growth factor and a colony-stimulating factor, an epidermal growth factors (EGF), a granulocyte-macrophage colony-stimulating factor (GM-CSF), a transforming growth factors (TGF), TGFα, TGFβ; a insulin and insulin like growth factor (IGF-I, IGF-II) G-CSF, M-CSF and GM-CSF; a vaccinia growth factor (VGF); a fibroblast growth factor (FGFs); a smaller molecular weight protein, poly-peptide, peptides and peptide hormones, bombesin, gastrin, gastrin-releasing peptide; a platelet-derived growth factor; an interleukin and a cytokine, interleukin-2 (IL-2), interleukin-6 (IL-6), a leukemia inhibitory factor, a granulocyte-macrophage colony-stimulating factor (GM-CSF); a vitamin, folate; an apoprotein and a lycoproteins; transferrin; a sugar-binding protein or a lipoproteins, a lectin; a cell nutrient-transport molecule (transferrin); and a small molecular inhibitor, prostate-specific membrane antigen (PSMA) inhibitor and small molecular tyrosine kinase inhibitors (TKI); peptides, or peptide analogs, proteins including conjugated proteins that are able to bind targeted cells; a non-peptides or any other cell binding molecule or substance in a form of bioactive polymer, bioactive dendrimer, nanoparticle, liposome, or viral capside.

11. The compound according to claim 1, wherein L is one or more linker components of 6-maleimidocaproyl ("MC"), maleimidopropanoyl ("MP"), valine-citrulline ("val-cit" or "vc"), alanine-phenylalanine ("ala-phe" or "af"), glycine-glycine, a nature peptides containing up to 6 the same or different natural amino acids (dipeptide, tripeptide, tetrapeptide, pentapeptide, hexapeptide), p-aminobenzyloxycarbonyl ("PAB"), N-succinimidyl 4-(2-pyridylthio)pentanoate ("SPP"), N-succinimidyl 4-(N-maleimidomethyl)cyclohexane-1 carboxylate ("SMCC"), N-Succinimidyl (4-iodoacetyl)aminobenzoate ("SIAB"), ethyleneoxy (—CH$_2$CH$_2$O—) as one or up to 100 repeating units ("EO" or "PEO"), or one or more components that are illustrated below:

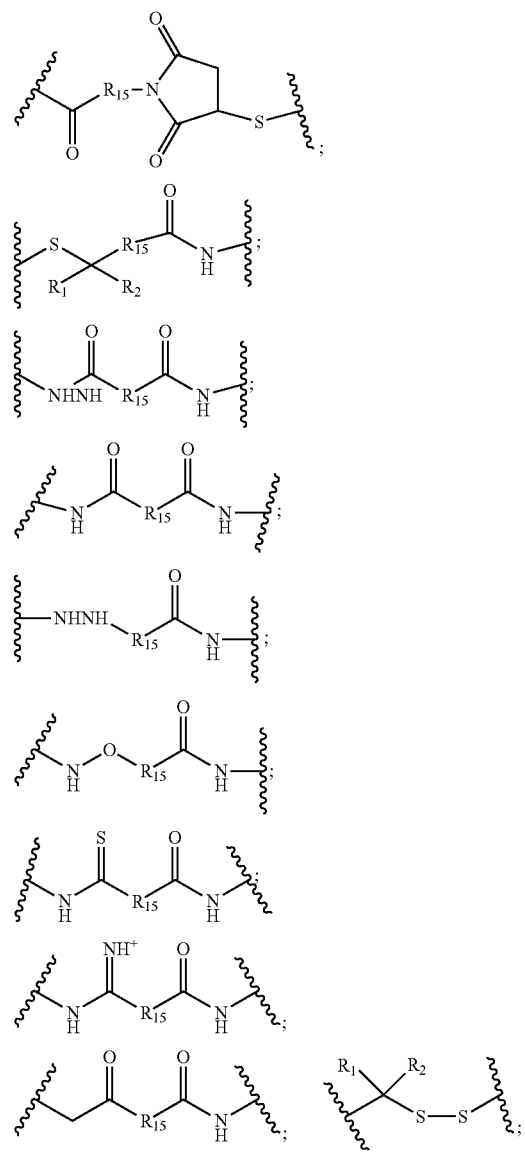

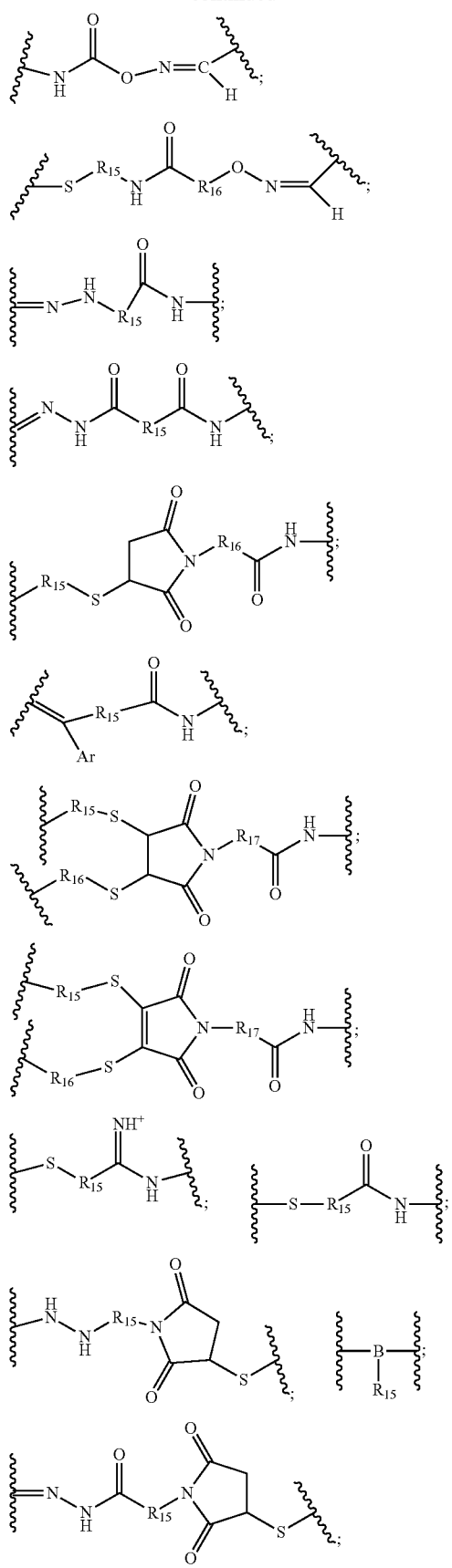

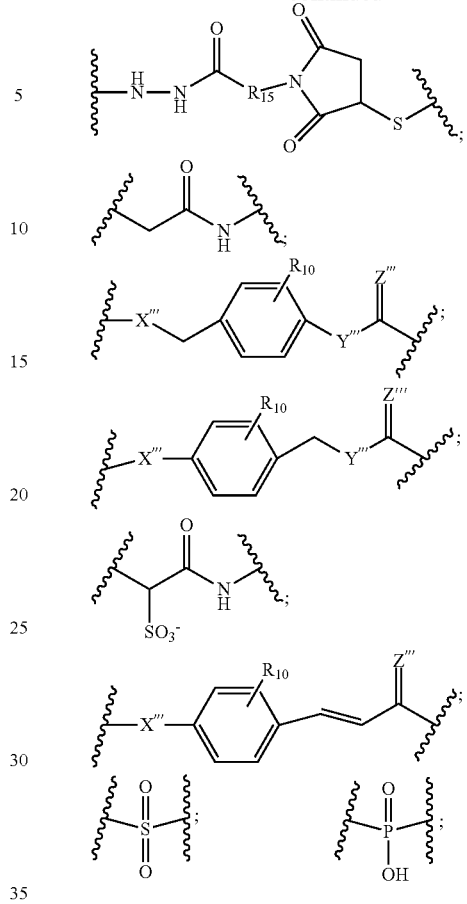

wherein $R_{10}$ is defined the same as in claim 1; $R_{15}$, $R_{16}$ and $R_{17}$ are independently selected from the group consisting of —$C_1$~$C_8$ alkyl or alkylene-, carbocyclo-, —O-($C_1$~$C_8$ alkyl)-, —NH—($C_1$~$C_8$ alkyl)-, -arylene-, —$C_1$~$C_8$ alkylene-arylene-, -arylene, —$C_1$~$C_8$alkylene-, —$C_1$~$C_8$ alkylene-($C_1$~$C_8$ carbocyclo)-, —($C_3$~$C_7$ carbocyclo)-$C_1$~$C_8$ alkylene-, —$C_3$~$C_8$ heterocyclo-, alkylene-($C_3$~$C_8$ heterocyclo)-, —($C_3$~$C_8$ heterocyclo)-$C_1$~$C_9$ alkylene-, —($CH_2CH_2O)_k$—, —($CH(CH_3)CH_2O)_k$—, and —($CH_2CH_2O)_k$—$CH_2$—; k is an integer ranging from 1-50; X''', Y''' and Z''' are independently NH, O or S.

12. The compound according to claim 1, having any one of the specific conjugation structures of (III-1), (III-2), (III-3), (III-4), (III-5), (III-6), (III-7), (III-8), (III-9), (III-10), (III-11), and (III-12) described in FIGS. 31A-31F wherein "═" represents either a single bond or a double bond; $L_1$ and $L_2$ are, the same or different, independently defined the same as L in claim 1; $X_1$ and $X_2$, are, the same or different, independently NH, N($R_1$), O, S, $CH_2$, or Ar, wherein $R_1$ is $C_1$-$C_6$ alkyl and Ar is an aromatic or heteroaromatic ring; wherein $Drug_1$ and $Drug_2$ are the same or different, independently a moiety linked to L other than Q in Formula (I) of claim 1, or one of $Drug_1$ and $Drug_2$ is the moiety linked to L other than Q in Formula (I) of claim 1, the other of $Drug_1$ and $Drug_2$ is absent, $(OCH_2CH_2)_rOR_{10}$, $(OCH_2CH(CH_3))_pOR_{10}$, $NH(CH_2CH_2O)_pR_{10}$, $NH(CH_2CH(CH_3)O)_pR_{10}$, $N[(CH_2CH_2O)_pR_{10}][(CH_2CH_2O)_rR_5]$, $(OCH_2CH_2)_pCOOR_{10}$, or $CH_2CH_2(OCH_2CH_2)_pCOOR_{10}$, wherein p, r, $R_{10}$ are described the same as in claim 1, when both $Drug_2$ and $L_2$ are absent, $X_2$ is $NH_2$ or OH.

13. The compound according to claim 1, comprising an IgG antibody linked to one of the following linkage structures of (IV-1), (IV-2), (IV-3), (IV-4), (IV-5), and (IV-6):

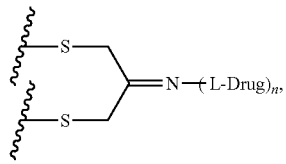
(IV-1)

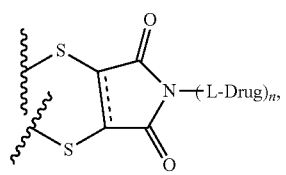
(IV-2)

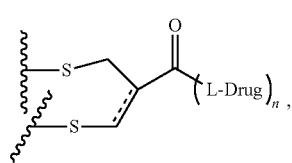
(IV-3)

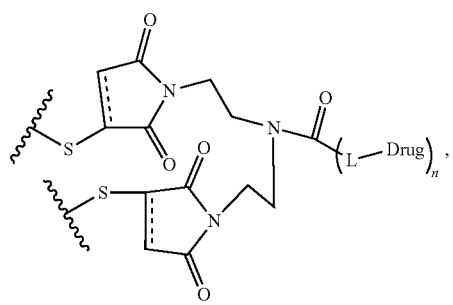
(IV-4)

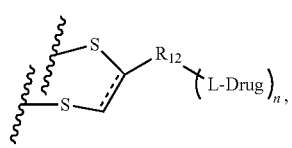
(IV-5)

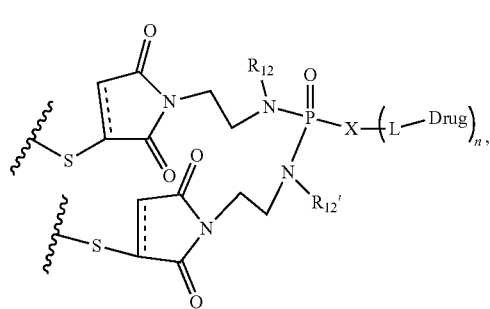
(IV-6)

wherein "=" represents either a single bond or a double bond; Drug is a moiety linked to L other than Q in Formula (I) of claim 1;

represents a site on an antibody; L, X, n and $R_{12}$ are defined the same as in claim 1.

14. A process for forming the compound according to claim 12 comprising a step of reducing a dithiol bond in an antibody with one or more reducing agent selected from the group consisting of dithiothreitol (DTT), dithioerythritol (DTE), L-glutathione (GSH), tris (2-carboxyethyl) phosphine (TCEP), 2-mercaptoethylamine (13-MEA), and beta mercaptoethanol 2-ME), the reducing agent being optionally loaded or covalently bonded to a solid polymer or a solid particle, wherein the polymer or the particle is selected from the group consisting of polyethene, polyacrylate, silica, crossed-linked silica (2-mercaptoethyl)silica, (aminoethyl) silica, (aminopropyl)silica), polyethylene terephthalate, polyethylene glycol, polystyrene, poly(isopropyl acrylate), dextrans (Sephadex, cross-linked dextran), isopropylacrylamide butyl methacrylate copolymer, and polysaccharide polymer (agarose, agar, agaropectin, Sepharose).

15. The compound according to claim 12, when one of $Drug_1$ and $Drug_2$ is a moiety linked to L other than Q in Formula (I), the other one of $Drug_1$ and $Drug_2$ is selected from the group consisting of a protein, an antibody (a monoclonal or polyclonal antibody, antibody dimers, antibody multimers, a bispecific or trispecific antibody, a single chain antibody, an antibody fragment that binds to the target cell), a chromophore molecule, a tubulysin derivative, a maytansinoid, a taxanoid (taxane), a CC-1065 analog, a daunorubicin or doxorubicin compound, a benzodiazepine dimer (dimers of pyrrolobenzodiazepine (PBD), tomaymycin, anthramycin, indolinobenzodiazepines, imidazobenzothiadiazepines, or oxazolidinobenzodiazepines), a calicheamicin, a dolastatin or auristatin derivative (monomethyl auristatin E, MMAE, MMAF, auristatin PYE, auristatin TP, Auristatins 2-AQ, 6-AQ, EB (AEB), EFP (AEFP)), a duocarmycin, a siRNA, and an enzyme.

16. A pharmaceutical composition comprising a therapeutically effective amount of the compound of claim 1, and a pharmaceutically acceptable excipient selected from the group consisting of one or more components of 0.002%~1% of polysorbate (polysorbate 20, polysorbate 40, polysorbate 60, or polysorbate 80), sodium lauryl sulfate, triton X-100; 0.01% 10% of a binder (disaccharides: sucrose, lactose, trehalose or maltose; or sugar alcohols: xylitol, sorbitol or maltitol, or polyethylene glycol), and 0.01%~10% of a pharmaceutical buffering agent (citrate, succinate acetate, phosphate, or borate) at a pH of 4.5-9.5.

17. A method for inhibiting abnormal cell growth or treating a proliferative disorder including cancers, benign or malignant tumors; leukemia and lymphoid malignancies; neuronal, glial, astrocytal, hypothalamic, glandular, macrophagal, epithelial, stromal, blastocoelic, angiogenic and immunologic disorders; inflammatory; autoimmune disorders; destructive disorders; bone disorder; infectious disease; viral disease; fibrotic disease; neurodegenerative disorder; pancreatitis or kidney disease; in a mammal, comprising administering to the mammal a pharmaceutically effective amount of the compound according to claim 1.

18. The pharmaceutical composition according to claim 16 further comprising one or more synergistic drugs of a chemotherapeutic agent, radiation therapy, immunotherapy agent, autoimmune disorder agent, or anti-infectious agent.

19. The compound according to claim 1, wherein the cell binding agent is an antibody, an antibody fragment, a diabody, a tri(a)body, an epidermal growth factor (EGF), a prostate specific membrane antigen (PSMA) inhibitor, a melanocyte stimulating hormone (MSH), a thyroid stimulating hormone (TSH), a polyclonal antibody, a somatostatin, a folate, a matriptase inhibitor, an estrogen, an estrogen analogue, a designed ankyrin repeat proteins (DARPins), an androgen, or an androgen analogue.

20. The compound according to claim 1, wherein Q targets cells selected from the group consisting of tumor cells; virus infected cells; microorganism infected cells; parasite infected cells; autoimmune cells; activated cells; myeloid cells; activated T-cells, B cells, or melanocytes; cells expressing antigen of CD3, CD4, CD5, CD6, CD7, CD8, CD9, CD10, CD11a, CD11b, CD11c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD137, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, SAC, 5T4 (Trophoblast glycoprotein, TPBG, 5T4, Wnt-Activated Inhibitory Factor 1 or WAIF1), Adenocarcinoma antigen, AGS-5, AGS-22M6, Activin receptor-like kinase 1, AFP, AKAP-4, ALK, Alpha intergrin, Alpha v beta6, Amino-peptidase N, Amyloid beta, Androgen receptor, Angiopoietin 2, Angiopoietin 3, Annexin A1, Anthrax toxin protective antigen, Anti-transferrin receptor, AOC3 (VAP-1), B7-H3, *Bacillus anthracis* anthrax, BAFF (B-cell activating factor), BCMA, B-lymphoma cell, bcr-abl, Bombesin, BORIS, C5, C242 antigen, CA125 (carbohydrate antigen 125, MUC16), CA-IX (or CAIX, carbonic anhydrase 9), CALLA, CanAg, *Canis lupus familiaris* IL31, Carbonic anhydrase IX, Cardiac myosin, CCL11(C-C motif chemokine 11), CCR4 (C-C chemokine receptor type 4, CD194), CCR5, CD3E (epsilon), CEA (Carcinoembryonic antigen), CEACAM3, CEACAM5 (carcino-embryonic antigen), CFD (Factor D), Ch4D5, Cholecystokinin 2 (CCK2R), CLDN18 (Claudin-18), Clumping factor A, cMet, CRIPTO, CSFIR (Colony stimulating factor 1 receptor, CD115), CSF2 (colony stimulating factor 2, Granulocyte-macrophage colony-stimulating factor (GM-CSF)), CSP4, CTLA4 (cytotoxic T-lymphocyte-associated protein 4), CTAA16.88 tumor antigen, CXCR4 (CD184), C—X—C chemokine receptor type 4, cyclic ADP ribose hydrolase, Cyclin B1, CYP1B1, Cytomegalovirus, Cytomegalovirus glycoprotein B, Dabigatran, DLL4 (delta-like-ligand 4), DPP4 (Dipeptidyl-peptidase 4), DR5 (Death receptor 5), *E. coli* shiga toxin type-1, *E. coli* shiga toxin type-2, ED-B, EGFL7 (EGF-like domain-containing protein 7), EGFR, EGFRII, EGFRvIII, Endoglin (CD105), Endothelin B receptor, Endotoxin, EpCAM (epithelial cell adhesion molecule), EphA2, Episialin, ERBB2 (Epidermal Growth Factor Receptor 2), ERBB3, ERG (TMPRSS2 ETS fusion gene), *Escherichia coli*, ETV6-AML, FAP (Fibroblast activation protein alpha), FCGR1, alpha-Fetoprotein, Fibrin II, beta chain, Fibronectin extra domain-B, FOLR (folate receptor), Folate receptor alpha, Folate hydrolase, Fos-related antigen 1F protein of respiratory syncytial virus, Frizzled receptor, Fucosyl GM1, GD2 ganglioside, G-28 (a cell surface antigen glyvolipid), GD3 idiotype, GloboH, Glypican 3, N-glycolylneuraminic acid, GM3, GMCSF receptor a-chain, Growth differentiation factor 8, GP100, GPNMB (Trans-membrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGFIR (IGF-1, insulin-like growth factor 1 receptor), IGHE, IFN-γ, Influenza hemagglutinin, IgE, IgE Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins ($\alpha 4$, $\alpha_{IIb}\beta_3$, $\alpha v\beta_3$, $\alpha_4\beta_7$, $\alpha_5\beta_1$, $\alpha_6\beta_4$, $\alpha_7\beta_7$, $\alpha_{11}\beta_3$, $\alpha_5\beta_5$, $\alpha v\beta_5$), Interferon gamma-induced protein, ITGA2, ITGB2, KIR2D, Kappa Ig, LCK, Le, Legumain, Lewis-Y antigen, LFA-1 (Lymphocyte function-associated antigen 1, CD11a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MARTI, MCP-1, MW (Macrophage migration inhibitory factor, or glycosylation-inhibiting factor (GIF)), MS4A1 (membrane-spanning 4-domains subfamily A member 1), MSLN (mesothelin), MUC1 (Mucin 1, cell surface associated (MUC1) or polymorphic epithelial mucin (PEM)), MUC1-KLH, MUC16 (CA125), MCP1 (monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), OY-TES1, P21, p53 nonmutant, P97, Page4, PAP, Paratope of anti-(N-glycolylneuraminic acid), PAX3, PAX5, PCSK9, PDCD1 (PD-1, Programmed cell death protein 1, CD279), PDGF-Rα (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Proteinase3 (PRI), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, ROR1, Sarcoma translocation breakpoints, SART3, Sclerostin, SLAMF7 (SLAM family member 7), Selectin P, SDCI (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF-α, TNFRSF8, TNFRSF10B (tumor necrosis factor receptor superfamily member 10B), TNFRSF-13B (tumor necrosis factor receptor superfamily member 13B), TPBG (trophoblast glycoprotein), TRAIL-R1 (Tumor necrosis apoprosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TRP-2, Tyrosinase, VCAM-1 (CD106), VEGF, VEGF-A, VEGF-2 (CD309), VEGFR-1, VEGFR2, vimentin, WT1, XAGE 1, cells expressing any insulin growth factor receptors, and epidermal growth factor receptors.

21. A method for treatment of a cancer, autoimmune disorder, infectious disease or viral disease in vitro, in vivo, or ex vivo, comprising utilizing the pharmaceutical composition according to claim 16.

22. The compound according to claim 1, wherein the self-immolative linker component has one of the following structures:

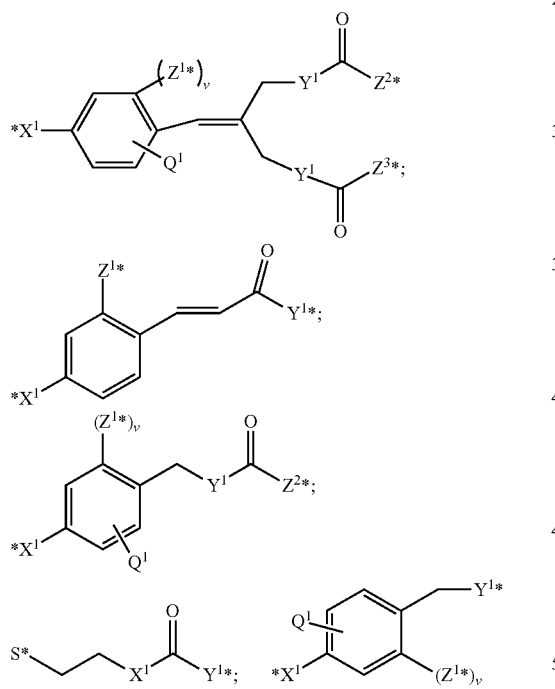

wherein the (*) atom is a point of attachment of additional spacer or releasable linker unit, or a cytotoxic agent, or the cell binding agent (CBA); $X^1$, $Y^1$, $Z^2$ and $Z^3$ are independently NH, O, or S; $Z^1$ is independently H, NH, O or S, v is 0 or 1; $Q^1$ is independently H, OH, $C_1$~$C_6$ alkyl, $(OCH_2CH_2)_n$ F, Cl, Br, I, $OR_{12}$, $SR_{12}$, $NR_{12}R_{12}'$, $N=NR_{12}$, $N=R_{12}$, $NR_{12}R_{12}'$, $NO_2$, $SOR_{12}R_{12}'$, $SO_2R_{12}$, $SO_3R_{12}$, $OSO_3R_{12}$, $PR_{12}R_{12}'$, $POR_{12}R_{12}'$, $PO_2R_{12}R_{12}'$, $OPO(OR_{12})(OR_{12}')$, or $OCH_2PO(OR_{12}'(OR_{12}')$, wherein $R_{12}$ and $R_{12}'$ are as defined the same as in claim 1.

23. The compound according to claim 22, wherein $R_{12}$ and $R_{12}'$ are independently H, $C_1$~$C_8$ alkyl; $C_2$~$C_8$ alkenyl, alkynyl, heteroalkyl; $C_3$~$C_8$ aryl, heterocyclic, carbocyclic, cycloalkyl, heterocycloalkyl, heteroaralkyl, alkylcarbonyl; or a pharmaceutical cation salt thereof.

24. The compound according to claim 1, wherein Q is one of the following formulas:

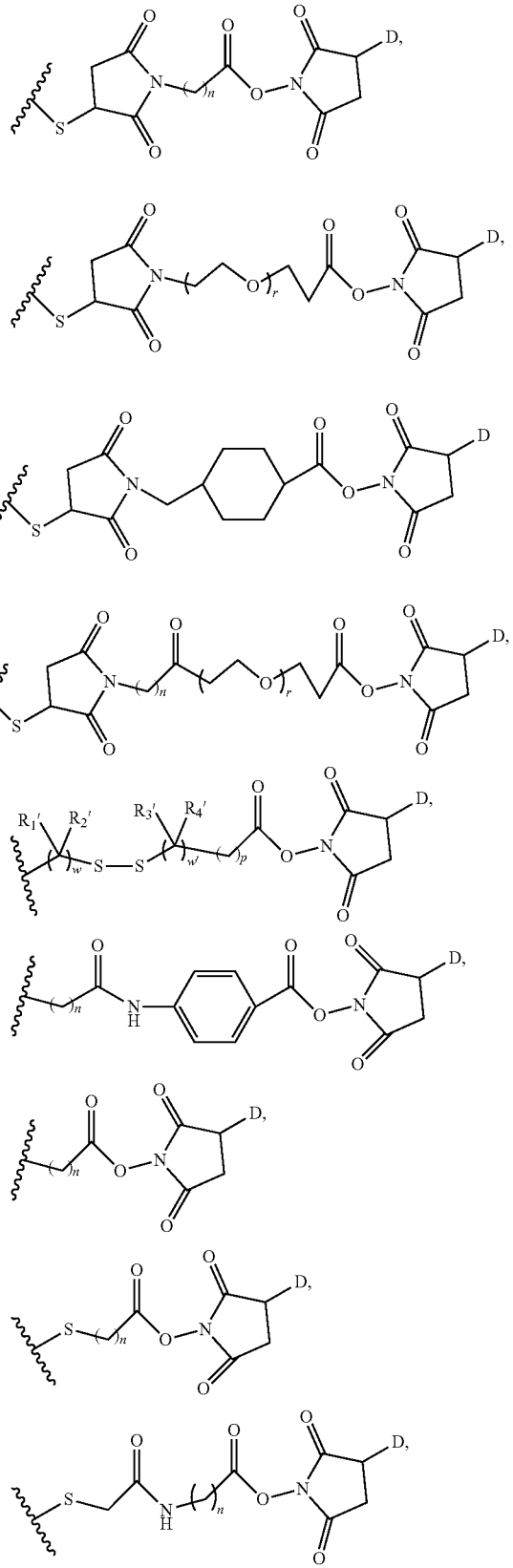

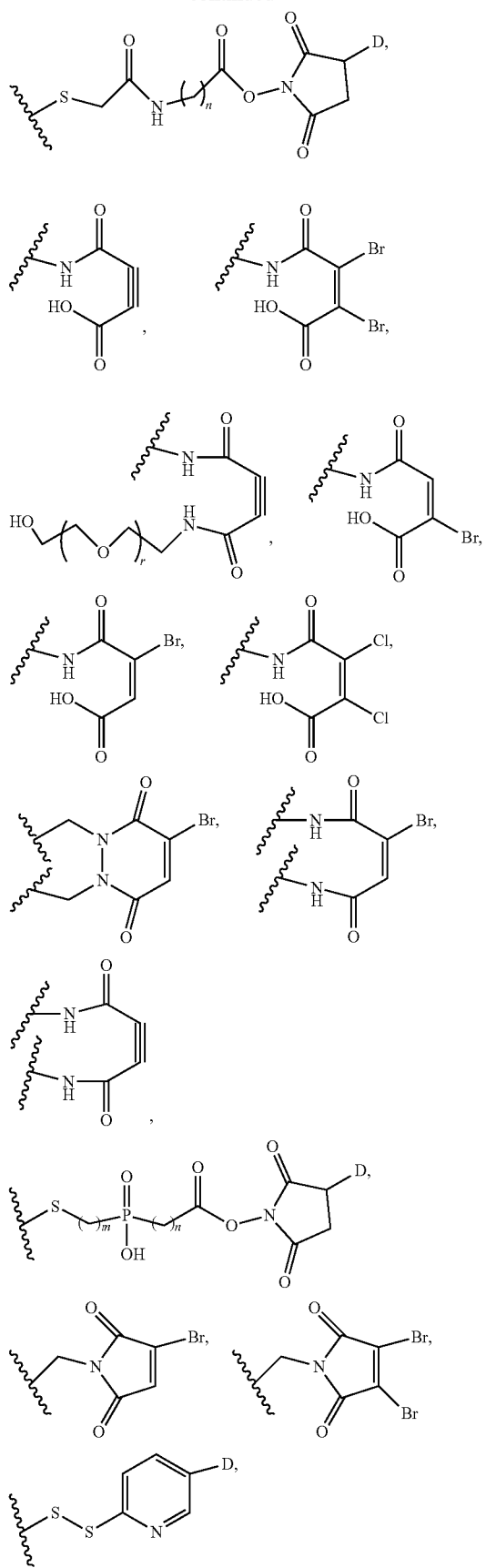
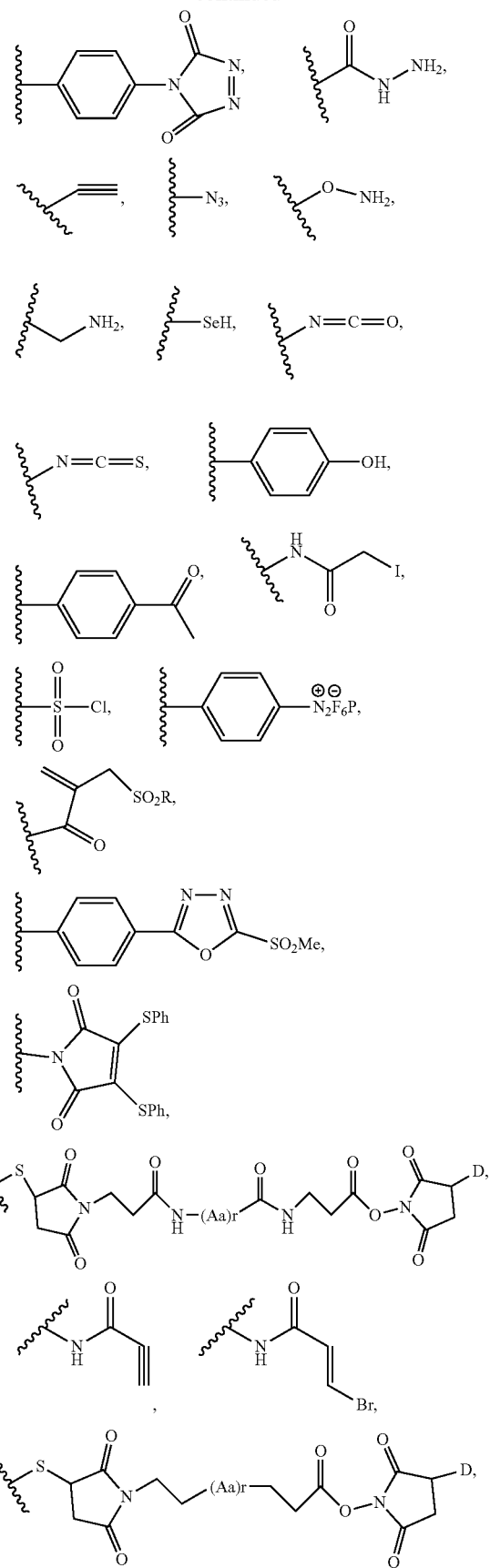

-continued

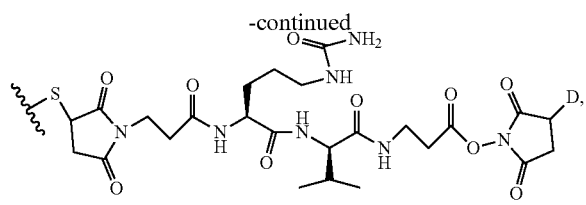

wherein D is H, —NO₂, SO₃⁻, CN, or F; Aa, r, p, q, m, and n are described the same as in claim 1; w and w' are 0 or 1 independently; $R_1'$, $R_2'$, $R_3'$, and $R_4'$ are independently H, $CH_3$, $C_2H_5$, $C_3H_7$, $CH_2OH$, or $CH_2CH_2OH$.

25. The compound according to claim 6, wherein Q is H, $C_1\sim C_8$ of alkyl, alkenyl, alkynyl, aryl, cyclic, cyclohetero, haloalkyl, alkoxy, haloalkoxy alkylamino; halogen; —NO₂; —CN; —SH; —SSCH₃; —SSAc; —SSAr; —SS-Pyridine; —SS-Ar(-NO₂); —S-cell binding agent; or a function group of NHS ester, pentafluorophenyl ester; alkyloxyamine; aldehyde; ketone; carboxyl acid; hydrazine; amine; or thiolactone; or is linked the cell binding agent via Stretcher units (Ww) or via Spacer units (Tt), wherein W, w, T, and t are defined the same as in claim 6.

26. The compound according to claim 12, wherein the IgG antibody is IgG1, IgG2, IgG3 or IgG4 antibody.

27. The compound according to claim 15, wherein the other one of Drug₁ and Drug₂ is one of structures illustrated below:

V-1, an antibody,

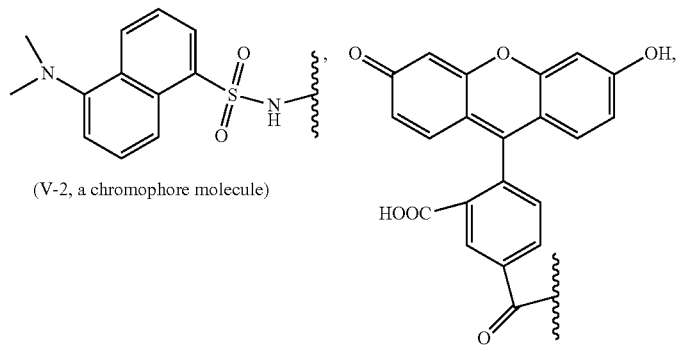

(V-2, a chromophore molecule)

(V-3, a chromophore molecule)

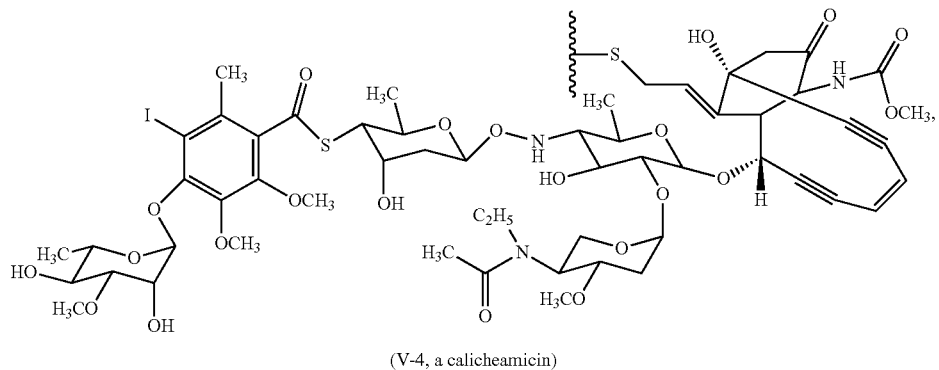

(V-4, a calicheamicin)

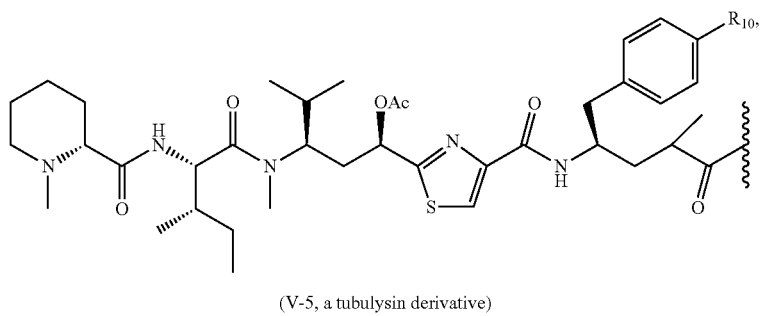

(V-5, a tubulysin derivative)

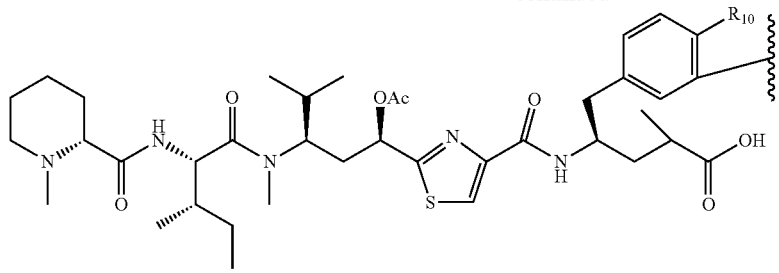
(V-6, a tubulysin derivative)
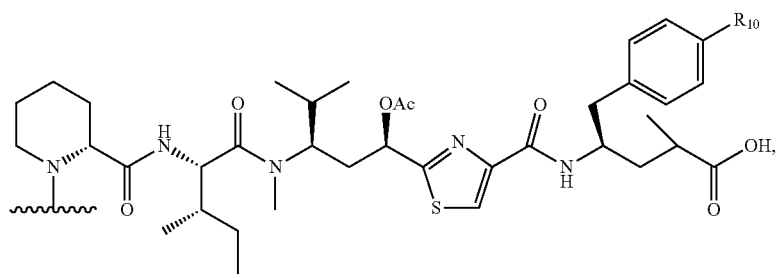
(V-7, a tubulysin derivative)
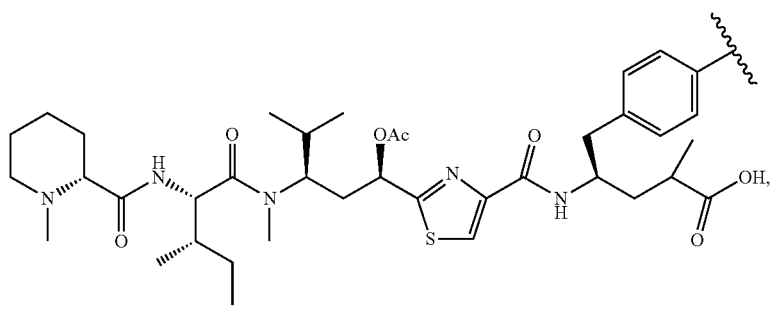
(V-8, a tubulysin derivative)
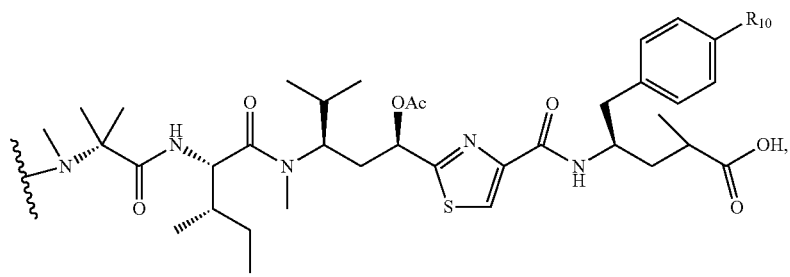
(V-9, a tubulysin derivative)
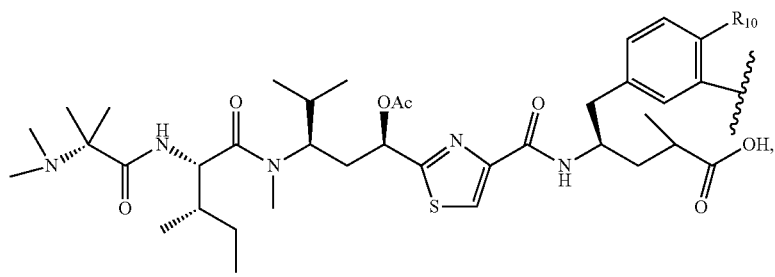
(V-10, a tubulysin derivative)

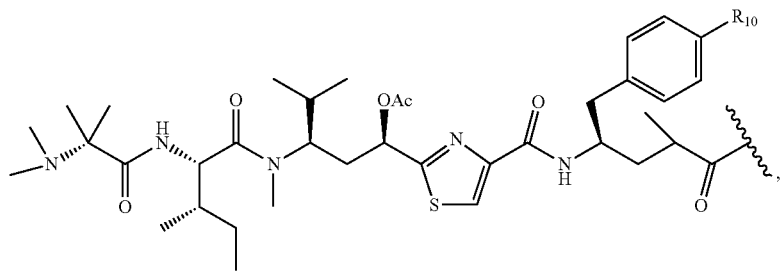
(V-11, a tubulysin derivative)
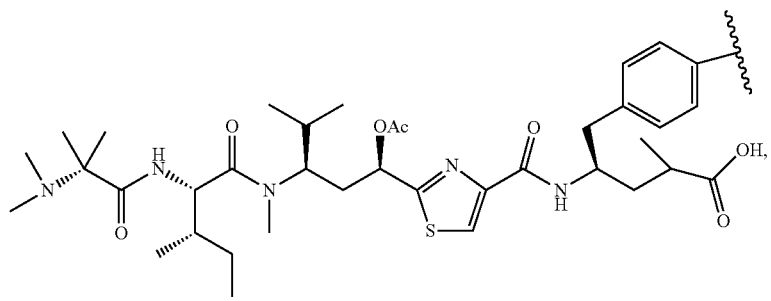
(V-12, a tubulysin derivative)
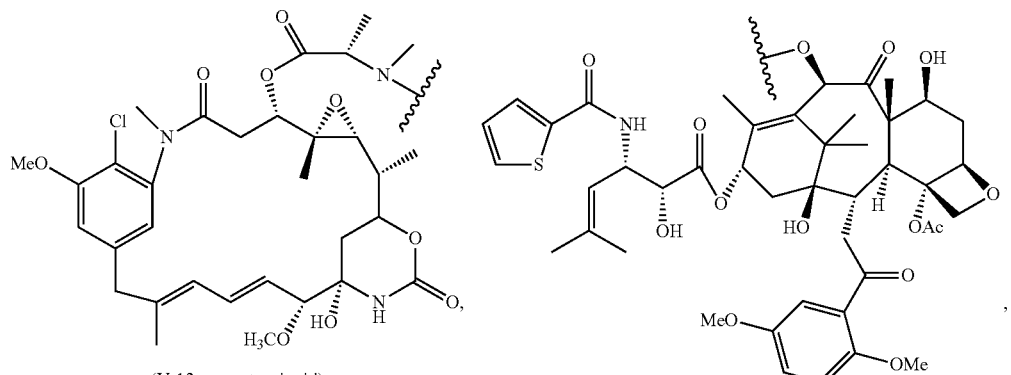
(V-13, a maytansinoid)
(V-14, a taxanoid)
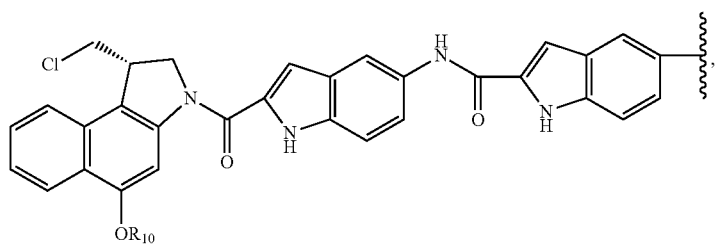
(V-15, a CC-1065 analog)
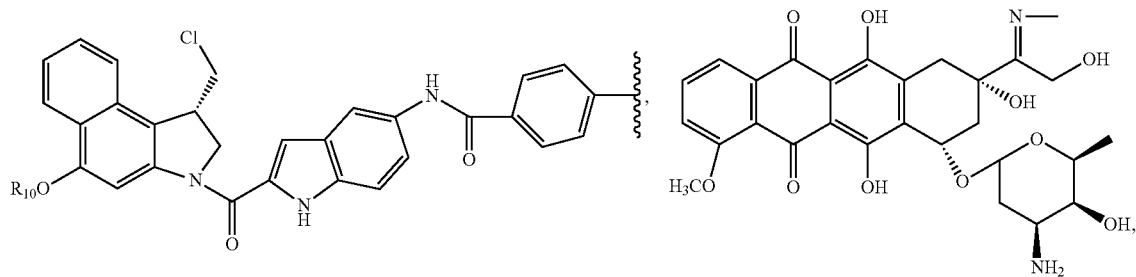
(V-16, a duocarmycin analog)
(V-17, a daunorubicin compound)

-continued
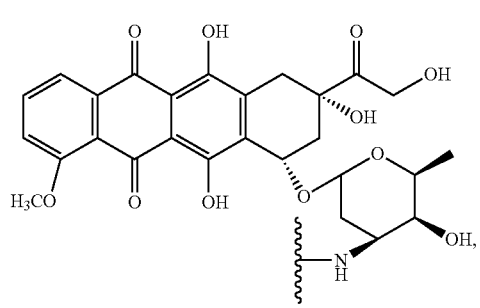
(V-18, a doxorubicin compound)
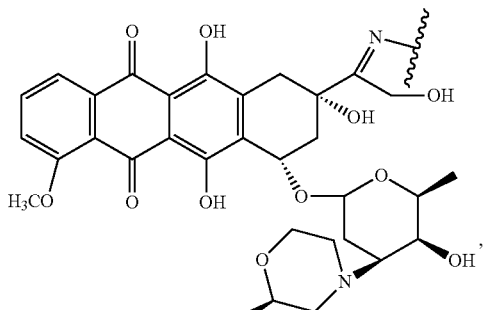
(V-19, a daunorubicin compound)
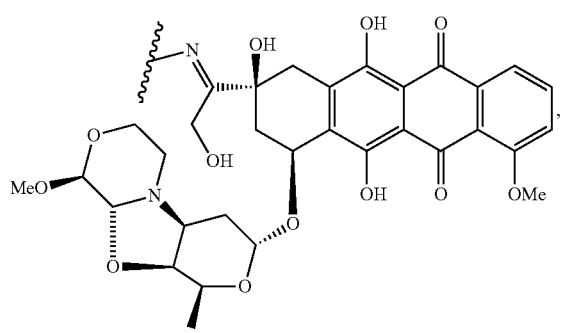
(V-20, a daunorubicin or doxorubicin compound)
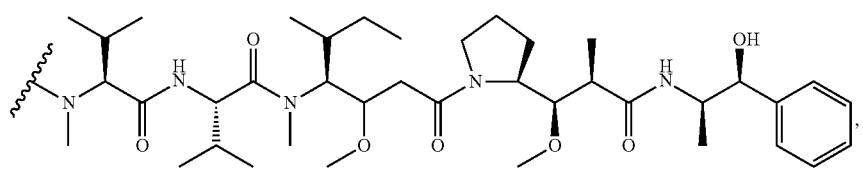
(V-21, an auristatin derivative)
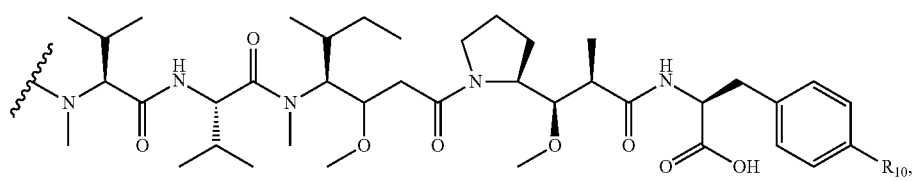
(V-22, an auristatin derivative)
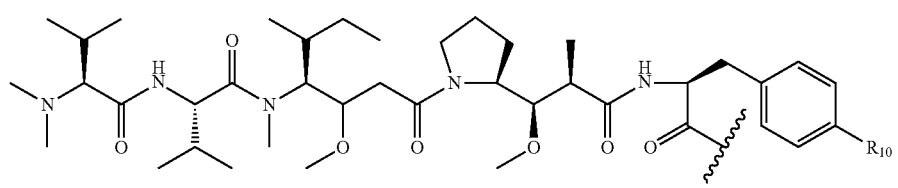
(V-23, an auristatin derivative)
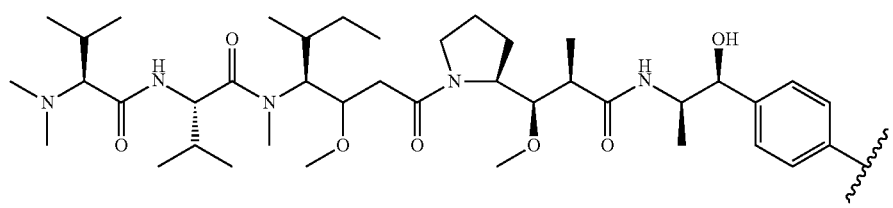
(V-24, a dolastatin or an auristatin derivative (MMAE))

-continued
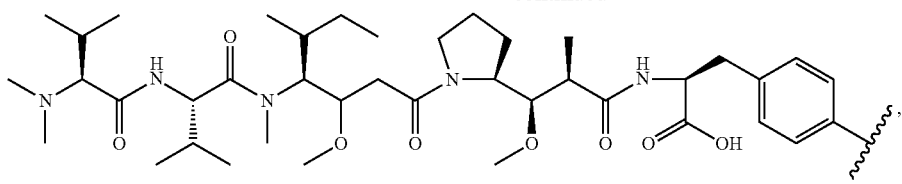
(V-25, a dolastatin or an auristatin derivative)
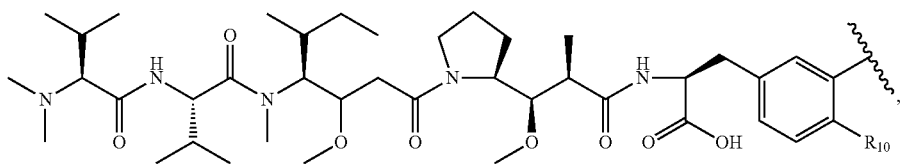
(V-26, an auristatin derivative)
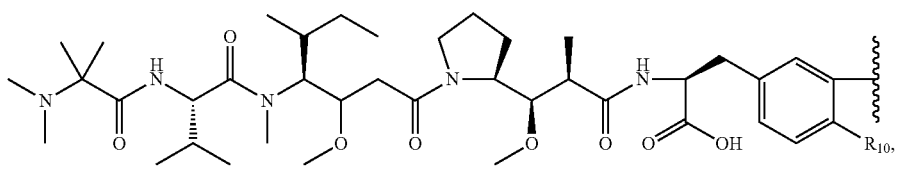
(V-27, an auristatin derivative)
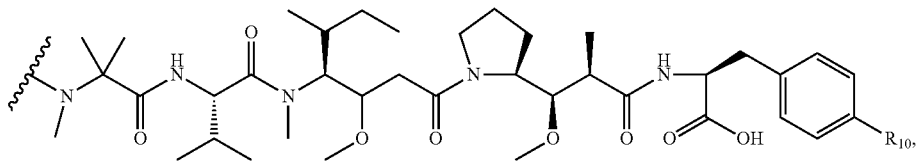
(V-28, an auristatin derivative)
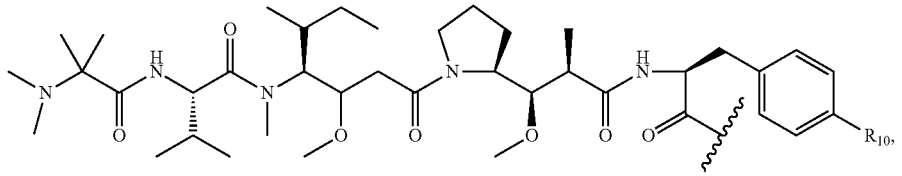
(V-29, an auristatin derivative)
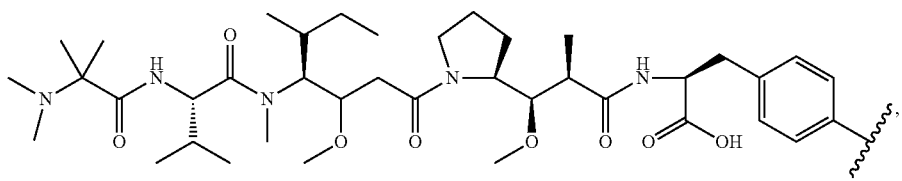
(V-30, an auristatin derivative)
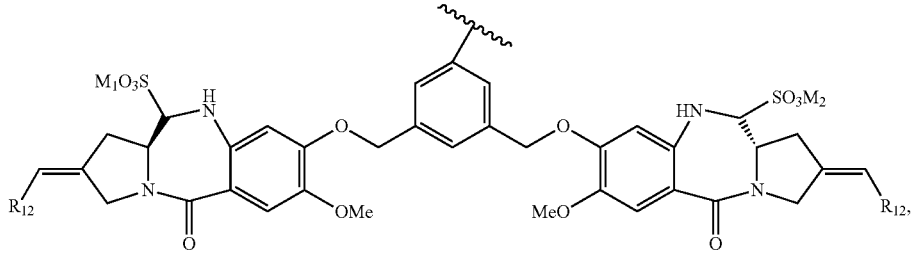
(V-31, a benzodiazepine dimer)

-continued
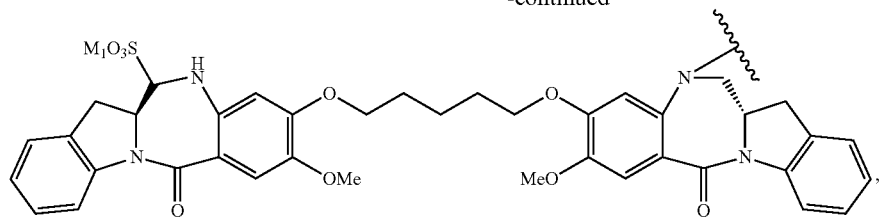
(V-32, a benzodiazepine dimer)
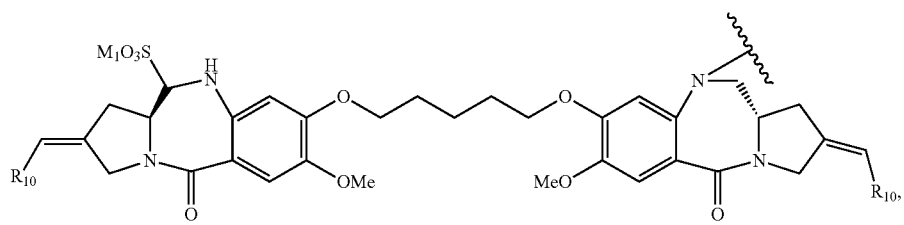
(V-33, a benzodiazepine dimer)
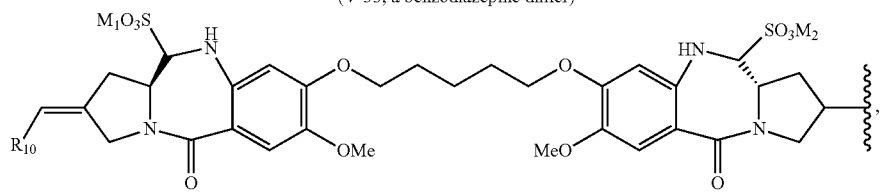
(V-34, a benzodiazepine dimer)
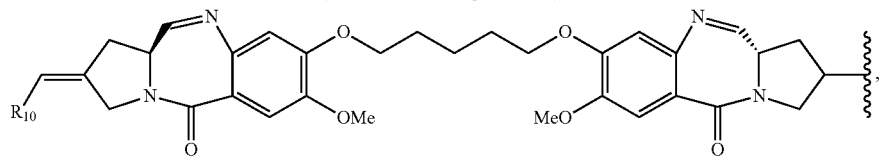
(V-35, a benzodiazepine dimer)
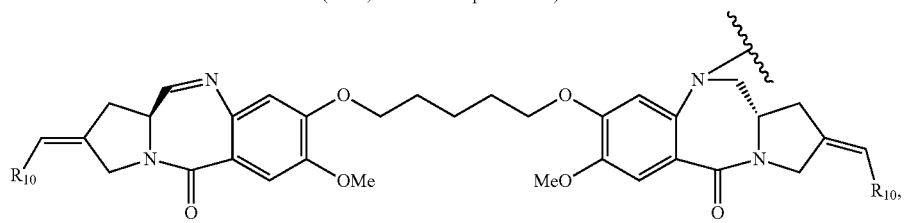
(V-36, a benzodiazepine dimer)
-V-37, a siRNA, -V-38, an enzyme or protein linked from N-terminal, -V-39, an enzyme or protein linked from C-terminal, wherein $R_{10}$ are described the same as in claim 15, and
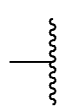
is a site of link to either linker $L_1$ or linker $L_2$.
* * * * *